US010626122B2

(12) United States Patent
Anderson et al.

(10) Patent No.: US 10,626,122 B2
(45) Date of Patent: Apr. 21, 2020

(54) HETEROAROMATIC NMDA RECEPTOR MODULATORS AND USES THEREOF

(71) Applicant: Cadent Therapeutics, Inc., Cambridge, MA (US)

(72) Inventors: David R. Anderson, Salem, CT (US); Robert A. Volkmann, Mystic, CT (US); Frank S. Menniti, Mystic, CT (US); Christopher Fanger, Bolton, MA (US)

(73) Assignee: Cadent Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/060,056

(22) PCT Filed: Dec. 9, 2016

(86) PCT No.: PCT/US2016/065852
§ 371 (c)(1),
(2) Date: Jun. 7, 2018

(87) PCT Pub. No.: WO2017/100591
PCT Pub. Date: Jun. 15, 2017

(65) Prior Publication Data
US 2018/0362541 A1 Dec. 20, 2018

Related U.S. Application Data

(60) Provisional application No. 62/265,182, filed on Dec. 9, 2015.

(51) Int. Cl.
*C07D 495/04* (2006.01)
*C07D 471/04* (2006.01)
*C07D 493/04* (2006.01)
*C07D 498/04* (2006.01)
*C07D 513/04* (2006.01)
*C07D 487/04* (2006.01)
*C07D 217/24* (2006.01)
*C07D 239/90* (2006.01)
*C07D 401/06* (2006.01)
*C07D 403/06* (2006.01)
*C07F 7/08* (2006.01)

(52) U.S. Cl.
CPC ......... *C07D 495/04* (2013.01); *C07D 217/24* (2013.01); *C07D 239/90* (2013.01); *C07D 401/06* (2013.01); *C07D 403/06* (2013.01); *C07D 471/04* (2013.01); *C07D 487/04* (2013.01); *C07D 493/04* (2013.01); *C07D 498/04* (2013.01); *C07D 513/04* (2013.01); *C07F 7/0812* (2013.01)

(58) Field of Classification Search
CPC .................................................. C07D 495/04
USPC .................................................. 514/210.16
See application file for complete search history.

(56) References Cited

U.S. PATENT DOCUMENTS

| 4,921,854 A | 5/1990 | Bozsing et al. |
|---|---|---|
| 6,852,731 B2 | 2/2005 | Larsen et al. |
| 2007/0093509 A1 | 4/2007 | Washburn et al. |
| 2008/0064678 A1 | 3/2008 | Letourneau et al. |
| 2008/0090802 A1 | 4/2008 | Letourneau et al. |
| 2008/0214553 A1 | 9/2008 | Letourneau et al. |
| 2008/0280900 A1 | 11/2008 | Pajouhesh et al. |
| 2010/0249087 A1 | 9/2010 | Wang et al. |
| 2012/0165330 A1 | 6/2012 | Vu |
| 2012/0178742 A1 | 7/2012 | Henrich et al. |
| 2013/0123231 A1 | 5/2013 | Harriman et al. |
| 2016/0222033 A1 | 8/2016 | Yu et al. |
| 2017/0305861 A1 | 10/2017 | Kim et al. |
| 2017/0313719 A1 | 11/2017 | Traynelis et al. |
| 2018/0360837 A1 | 12/2018 | Anderson et al. |
| 2018/0369245 A1 | 12/2018 | Anderson et al. |

FOREIGN PATENT DOCUMENTS

| AU | 2009243006 A1 | 11/2009 |
|---|---|---|
| AU | 2009266889 A1 | 1/2010 |
| CN | 102336768 A | 2/2012 |
| CN | 103664877 A | 3/2014 |
| WO | 9800401 A1 | 1/1998 |
| WO | 2008076883 A2 | 6/2008 |
| WO | 2008097538 A1 | 8/2008 |
| WO | 2008128982 A1 | 10/2008 |
| WO | 2009025784 A1 | 2/2009 |
| WO | 2009062930 A1 | 5/2009 |
| WO | 2009/134973 A1 | 11/2009 |
| WO | 2009146358 A1 | 12/2009 |
| WO | 2010/003048 A1 | 1/2010 |
| WO | 2010/037127 A1 | 4/2010 |
| WO | 2010037129 A1 | 4/2010 |
| WO | 2010079443 A1 | 7/2010 |
| WO | 2010/111573 A1 | 9/2010 |
| WO | 2010139483 A1 | 12/2010 |
| WO | 2011045258 A1 | 4/2011 |
| WO | 2011117381 A1 | 9/2011 |
| WO | 2011117382 A1 | 9/2011 |
| WO | 2012052540 A1 | 4/2012 |
| WO | 2012129562 A2 | 9/2012 |
| WO | 2013048928 A1 | 4/2013 |

(Continued)

OTHER PUBLICATIONS

International Search Report, Application No. PCT/US2016/065852, dated Feb. 14, 2017, 5 pages.

(Continued)

*Primary Examiner* — Kevin E Weddington
(74) *Attorney, Agent, or Firm* — McCarter & English, LLP; Steven G. Davis; Michael J. DeGrazia

(57) ABSTRACT

Disclosed herein, in part, are heteroaromatic compounds and methods of use in treating neuropsychiatric disorders, e.g., schizophrenia and major depressive disorder. Pharmaceutical compositions and methods of making heteroaromatic compounds are provided. The compounds are contemplated modulate the NMDA receptor.

16 Claims, No Drawings

(56) References Cited

FOREIGN PATENT DOCUMENTS

| WO | 2013048942 A1 | 4/2013 | |
|---|---|---|---|
| WO | 2013049104 A1 | 4/2013 | |
| WO | 2014139325 A1 | 9/2014 | |
| WO | 2014179144 A1 | 11/2014 | |
| WO | 2014206343 A1 | 12/2014 | |
| WO | 2015/007453 A1 | 1/2015 | |
| WO | WO-2015007453 A1 * | 1/2015 | ........... C07D 487/04 |
| WO | 2015/096611 A1 | 7/2015 | |
| WO | 2016034703 A1 | 3/2016 | |
| WO | 2016081649 A1 | 5/2016 | |
| WO | 2017066590 A1 | 4/2017 | |
| WO | 2017100591 A1 | 6/2017 | |
| WO | 2017100593 A1 | 6/2017 | |
| WO | 2017100599 A1 | 6/2017 | |
| WO | 2017/188694 A1 | 11/2017 | |
| WO | 2018026371 A1 | 2/2018 | |
| WO | 2018119374 A1 | 6/2018 | |

OTHER PUBLICATIONS

Susan E Napier et al: "Synthesis and SAR studies of novel 8-11, 2-(6-ami nomethyl aryl-2-aryl-4-oxo-quinazolin-3(4)-yl)acetamide Vasopressin Vreceptor antagonists", BI00RGANIC & Medicinal Chemistry Letters, Pergamon, Amsterdam, NL,vol. 21, No. 12, Apr. 6, 2011 (Apr. 6, 2011), 5 pages.

Almasi J et al: "Characterization of potential NMDA and cholecystokinin antagonists II. Lipophilicity studies on 2-methyl-4-oxo-3H-quinazoline-3-alkyl-carb oxylic acid d erivatives", International Journal of Pharmaceutics, Elsevier, Amsterdam, NL, vol. 180, No. 1, Mar. 25, 1999 (Mar. 25, 1999), pp. 13-22, XP002293777, ISSN: 0378-5173, DOI: 10.1016/50378-5173(98)00405-0.

U.S. Appl. No. 16/060,267, filed Jun. 7, 2018, U.S. Pat. No. 2018-0360837-A1.

U.S. Appl. No. 16/060,294, filed Jun. 7, 2018, U.S. Pat. No. 2018-0369245-A1.

Database Accession No. 924249-59-2 Abstract. Database Registrty [Online] Chemical Abstracts Service, Columbus, Ohio, US; Mar. 2, 2007.

International Search Report, Application No. PCT/US2016/065863, dated Feb. 22, 2017, 3 pages.

International Search Report, Application No. PCT/US2016/065855, dated Feb. 21, 2017, 4 pages.

Jia et al. Identification, design and bio-evaluation of novel Hsp90 inhibitors by ligand-based virtual screening. PLoS One. 2013;8(4):e59315.

Amit G Nerkar: "In Silico Design. Synthesis and Pharmacological Screening of Novel Mono and Di-Bromo Quinazolinone Derivatives as NMDA Receptor Antagonists for Anticonvulsant Activity". International Journal of Pharmacy and Pharmaceutical Sciences. Jan. 2013 (Jan. 2013). pp. 331-335.

Noueiry et al. Identification of Novel Small-Molecule Inhibitors of West Nile Virus Infection. J Virol. Nov. 2007; 81(21): 11992-12004.

Pubchem-CID 16957685 Create Date: Nov. 13, 2007 (Nov. 13, 2007) pp. 1-7.

Pubchem-CID 6612590 Create Date: Jun. 5, 2006 (Jun. 5, 2006) pp. 1-8.

Pubchem-CID 10587973 Create Date: Oct. 25, 2006 (Oct. 25, 2006) pp. 1-9.

Santangelo et al. Novel NMDA receptor modulators: an update. Expert Opin Ther Pat. Nov. 2012;22(11):1337-52.

U.S. Appl. No. 16/530,274, filed Aug. 2, 2019.

* cited by examiner

HETEROAROMATIC NMDA RECEPTOR MODULATORS AND USES THEREOF

CROSS REFERENCE TO RELATED APPLICATIONS

This application is a 35 U.S.C. § 371 national stage filing of International Application No. PCT/US2016/065852, filed Dec. 9, 2016, which claims priority to U.S. Provisional Patent Application No. 62/265,182, filed Dec. 9, 2015, the contents of each of which are hereby incorporated by reference in their entirety.

BACKGROUND

Diseases of the nervous system are collectively the leading cause of human disability, as measured by the global burden of disease. Even those major diseases of the nervous system for which treatments have been approved by health authorities, including psychiatric diseases such as Schizophrenia, neurological diseases such as Alzheimer's Disease, and neurodevelopmental disorders, such as Attention Deficit and Hyperactivity Disorder, are poorly managed because approved treatments have limited efficacy and serious side effects, leaving a significant burden of unmet medical need. In addition, there are many major and rare nervous system disorders for which no treatments are approved, such as the neurodevelopmental disorders of the Autism Spectrum, and many intellectual disability disorders, and which are therefore associated with profound unmet medical need.

The N-methyl-D-aspartate-(NMDA) subtype of ligand-gated ion channel receptors are a diverse family of glutamate receptors widely accepted to mediate synaptic transmission, key mechanisms of synaptic plasticity, and dynamic neuronal network connectivity required for normal nervous system development and function.

The NMDA receptor is composed of four protein subunits, two GluN1 subunits and two GluN2 subunits. The GluN1 subunit is derived from a single gene (GRIN1), is ubiquitously expressed throughout the nervous system, and is common to all NMDA receptors. Four different GluN2 subunits, GluN2A-D, are derived from separate genes (GRIN2A-D) that are differentially expressed in different regions of the nervous system and by distinct populations of neurons within a particular region. A GluN3 subunit has also been identified, but its function is less well understood. Furthermore, individual neurons may express more than one GluN2 subunit and individual NMDA receptors expressed by such neurons may contain two of the same GluN2 subunits (for example, 2GluN2B subunits) or two different subunits (one GluN2A and one GluN2B subunit). In addition, all NMDA receptor subunits are expressed as diverse mRNA splice variants. Thus, native nervous system NMDA receptors are highly diverse in their composition.

The study of the molecular basis of NMDA receptor function continues to be an area of importance. As glutamate is the major excitatory neurotransmitter, dysfunction of glutamate neurotransmission and NMDA receptor-dependent mechanisms of synaptic transmission, plasticity, and neuronal network connectivity are broadly implicated in diseases of the nervous system. Accordingly, compounds that are capable of modulating NMDA receptors may be useful for the treatment of nervous system disorders and diseases, for example, schizophrenia, Alzheimer's disease, attention deficit and hyperactivity disorder, and autism.

SUMMARY

The present disclosure provides, for example, compounds which are modulators of NMDA receptors (e.g., positive allosteric modulators of NMDA receptors) and their use as medicinal agents, processes for their preparation, and pharmaceutical compositions containing them as an active ingredient. The disclosure provides for the use of disclosed compounds as medicaments and/or in the manufacture of medicaments for the modulation of NMDA receptors in warm-blooded animals such as humans. In particular this disclosure relates to compounds useful for the treatment of psychiatric, neurological and/or neurodevelopmental disorders and/or diseases of the nervous system, for example, schizophrenia, Alzheimer's disease, attention deficit and hyperactivity, autism, and other nervous system-associated conditions. Also provided are pharmaceutical compositions comprising at least one disclosed compound and a pharmaceutically acceptable carrier.

In an embodiment, provided herein are compounds represented by Formula I:

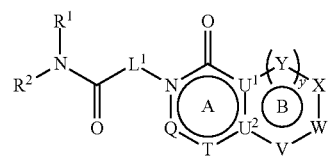

and pharmaceutically acceptable salts, stereoisomers and prodrugs thereof, where A, B, $L^1$, Q, $R^1$, $R^2$, T, $U^1$, $U^2$, V, W, X, Y, and y are as defined herein.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated, 4-10 membered ring structures, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to an OH functionality.

The term "oxo" as used herein refers to a carbonyl functionality (e.g., C=O).

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of e.g., schizophrenia desired. "Modulation" includes antagonism (e.g., inhibition), agonism, partial antagonism, partial agonism and allosteric modulation of agonists or antagonists.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in substantially relief of symptoms associated with schizophrenia.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may be chiral or exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a stereogenic center implicitly. The present invention encompasses various stereoisomers of these compounds and mixtures thereof. Mixtures of enantiomers or diastereomers may be designated "(±)" in nomenclature, but the skilled artisan will recognize that a structure may denote a stereogenic center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound of the invention contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., Molecules 2008, 13, 519 and references therein.

I. Heteroaromatic Compounds

In certain embodiments, the present disclosure provides compounds of Formula

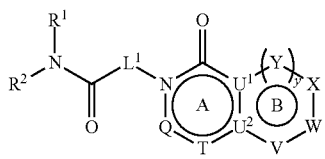

I and pharmaceutically acceptable salts, stereoisomers and prodrugs thereof, wherein:
rings A and B are a fused [5,6] or [6,6] heteroaromatic system;
Q is N or $CR^6$;
T is N or $CR^6$; and
y is 0 or 1 wherein
when y is 1, $U^1$ and $U^2$ are C; W and V are each independently selected from $CR^6$; one of Y and X is $CR^3$ and one of Y and X is $CR^6$; and
when y is 0:
X is $CR^3$ or $NR^{33}$;
W is selected from the group consisting of $CR^6$, N or S;
V is selected from the group consisting of N, $NR^7$, $CR^6$, S and O;

$U^1$ and $U^2$ may each be C or N; wherein when one of $U^1$ and $U^2$ is N the other is C; and
when Q is $CR^6$, T is N, W is $CR^6$ and X is $CR^3$; V is not S;
$L^1$ is a bond or $C_{1-4}$ alkylene optionally interrupted by O, and optionally substituted on a carbon not bound to the ring nitrogen with one, two, or three substituents each independently selected from halogen, OH, cyano or —$NR^aR^b$;
$R^1$ and $R^2$ are each independently selected from the group consisting of H, $C_{1-4}$ alkyl, $C_{3-6}$cycloalkyl, $C_{1-4}$alkoxy, and $C_{1-4}$ alkylcarbonyl (wherein $C_{1-4}$ alkyl, $C_{3-6}$cycloalkyl, $C_{1-4}$alkoxy, and $C_{1-4}$ alkylcarbonyl may be optionally substituted on a carbon not bound to the nitrogen with one, two or three substituents each independently selected from halogen, hydroxyl, cyano, and $NR^aR^b$) or
$R^1$ and $R^2$, together with the nitrogen to which they are attached, form a 3-7 membered monocyclic, bridged bicyclic, fused bicyclic or spirocyclic heterocyclic ring which may have an additional heteroatom selected from O, S, or N; and wherein the 4-6 membered monocyclic, bridged bicyclic, fused bicyclic or spirocyclic heterocyclic ring may optionally be substituted by one, two or more substituents each selected from the group consisting of: phenyl (optionally substituted by one, two or three halogens), $C_3$-$C_6$cycloalkyl (optionally substituted by one, two or three halogens), $C_{1-6}$alkoxy (optionally substituted by one, two or three halogens), and $C_{1-6}$alkyl (optionally substituted by one, two or three halogens), and on a carbon not bound to the nitrogen, by one, two or more substituents each selected from the group consisting of halogen, cyano, oxo, $NR^aR^b$ and hydroxyl; and wherein if said 4-6 membered monocyclic, bridged bicyclic, fused bicyclic or spirocyclic heterocyclic ring contains a —NH moiety that nitrogen may be optionally substituted by a substituent selected from the group consisting of hydrogen, $C_{1-6}$alkyl, $C_{1-6}$alkyl-$S(O)_2$—, $C_{1-6}$alkylcarbonyl-, and $C_{1-6}$alkoxycarbonyl-;
$R^3$ is selected from the group consisting of phenyl, naphthyl, heteroaryl, heterocyclyl and $C_{3-6}$cycloalkyl, wherein $R^3$ is optionally substituted with one, two or three substituents each independently selected from $C_{1-6}$alkyl, halogen, OH, cyano, $C_{1-4}$alkoxy, $C_{2-6}$alkenyl, $C_{2-6}$alkynyl, $C_{3-6}$cycloalkyl, $C_{1-6}$alkyl-$S(O)_2$—, $C_{1-6}$alkylcarbonyl, $R^aR^bN$—$SO_2$—, $NR^aR^b$, C(O)OH, $C_{1-4}$alkoxycarbonyl, and $NR^aR^b$-carbonyl, wherein $C_{1-6}$alkyl, $C_{2-6}$alkenyl, $C_{2-6}$alkynyl, $C_{3-6}$cycloalkyl, $C_{1-6}$alkyl-$S(O)_2$—, and $C_{1-6}$alkylcarbonyl may be optionally substituted by one or more substituents each independently selected from halogen, hydroxyl, cyano, and $NR^aR^b$;
$R^{33}$ is selected from the group consisting of phenyl, naphthyl, heteroaryl, heterocyclyl and $C_{3-6}$cycloalkyl, wherein $R^{33}$ is optionally substituted with one, two or three substituents each independently selected from $C_{1-4}$ alkyl, halogen, OH, $C_{1-4}$alkoxy, $C_{2-6}$alkenyl, $C_{2-6}$alkynyl, $C_{3-6}$cycloalkyl, $C_{1-6}$alkyl-$S(O)_2$—, $C_{1-6}$alkylcarbonyl, $R^aR^bN$—$SO_2$—, $NR^aR^b$, C(O)OH, $C_{1-4}$alkoxycarbonyl, and $NR^aR^b$-carbonyl, wherein $C_{1-6}$alkyl, $C_{2-6}$alkenyl, $C_{2-6}$alkynyl, $C_{3-6}$cycloalkyl, $C_{1-6}$alkyl-$S(O)_2$—, $C_{1-6}$alkylcarbonyl may be optionally substituted by one or more substituents each selected from halogen, hydroxyl, cyano, and $NR^aR^b$;
$R^6$ is independently selected for each occurrence from the group consisting of H, $C_{1-6}$ alkyl, $C_{1-6}$ alkoxy, halogen, cyano, $C_{2-6}$alkenyl, $C_{2-6}$alkynyl, $C_{3-6}$cycloalkyl, heteroaryl, phenyl, —C(=NH)—$NR^aR^c$, C(=N—OH)—H, C(=N—OH)—$C_{1-6}$alkyl, —$NR^aR^b$, C(O)OH, $C_{1-6}$alkylcarbonyl, $C_{1-6}$alkoxycarbonyl, $NR^aR^b$carbonyl-, and $R^aR^bN$—$SO_2$—, wherein phenyl and heteroaryl are optionally substituted by one or more substituents each selected from cyano, halogen C$_{1-4}$ alkyl (optionally substituted by halogen), cyano, C$_{1-4}$ alkoxy, NR$^a$R$^b$, =NR$^a$, —C(=NH)—NR$^a$R$^c$, and R$^a$R$^b$N—SO$_2$— and where C$_{1-6}$ alkyl, C$_{1-6}$alkyoxy, C$_{2-6}$alkenyl, C$_{2-6}$alkynyl, and C$_{3-6}$cycloalkyl are each optionally substituted by one or more substituents each selected from the group consisting of: hydroxyl, cyano, C$_{1-4}$ alkoxy, halogen, NR$^a$R$^b$, =NR$^a$, —C(=NH)—NR$^a$R$^c$, cyano, and R$^a$R$^b$N—SO$_2$—, and R$^7$ is selected from the group consisting of H, C$_{1-6}$alkyl, C$_{2-6}$alkynyl, C$_{3-6}$cycloalkyl, heterocyclyl, heteroaryl, and phenyl, wherein C$_{1-6}$alkyl, C$_{2-6}$alkenyl, C$_{3-6}$cycloalkyl may optionally be substituted by one or more substituents each selected from halogen, hydroxyl, C$_{1-4}$ alkoxy (optionally substituted by halogen or —Si(R$_s$)$_{0-3}$ (wherein R$_s$ is H or C$_{1-6}$alkyl)), cyano, —Si(R$_s$)$_{0-3}$ (wherein R$_s$ is H or C$_{1-6}$alkyl), —O—Si(R$_s$)$_{0-3}$ (wherein R$_s$ is H or C$_{1-6}$alkyl), and NR$^a$R$^b$;

R$^c$ is selected from the group consisting of hydrogen, C$_{1-3}$alkyl, and hydroxyl;

R$^a$ and R$^b$ are independently selected, for each occurrence, from the group consisting of: hydrogen, C$_{1-4}$alkylcarbonyl, —C(O)—O—C$_{1-4}$alkyl, C$_{3-6}$cycloalkyl and C$_{1-3}$alkyl; wherein C$_{1-3}$alkyl and C$_{3-6}$cycloalkyl may optionally be substituted on a carbon not bound to the nitrogen by one or more substituents selected from: fluorine, cyano, oxo and hydroxyl; or R$^a$ and R$^b$, together with the nitrogen to which they are attached, form a 4-6 membered heterocyclic ring which may have an additional heteroatom selected from O, S, or N; and wherein the 4-6 membered heterocyclic ring may optionally be substituted on a carbon not bound to the nitrogen by one or more substituents selected from the group consisting of: fluorine, methyl, cyano, oxo and hydroxyl.

In some embodiments, the fused [5,6] or [6,6] heteroaromatic system may be selected from the group consisting of:

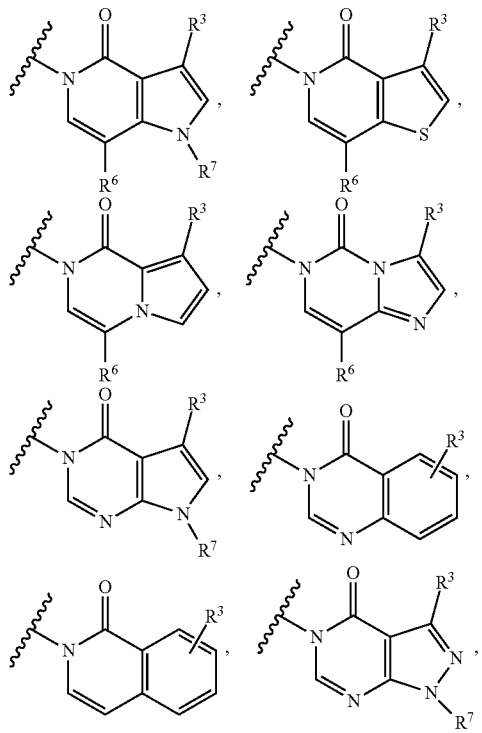

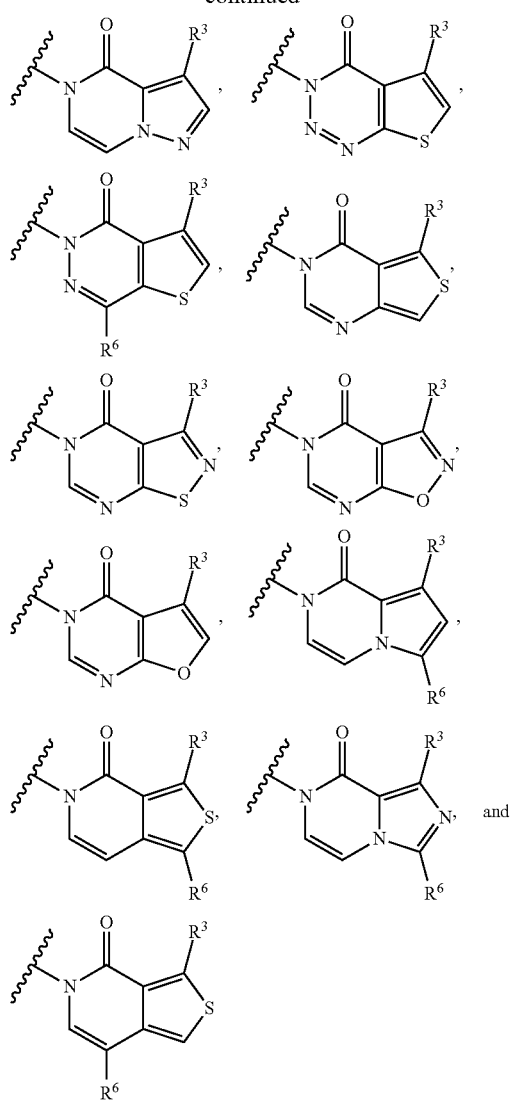

where R$^3$, R$^6$ and R$^7$ are defined above.

In certain embodiments, for example, the rings A and B may be a fused [5,6]heteroaromatic system. For example, fused [5,6] heteroaromatic system may be selected from the group consisting of:

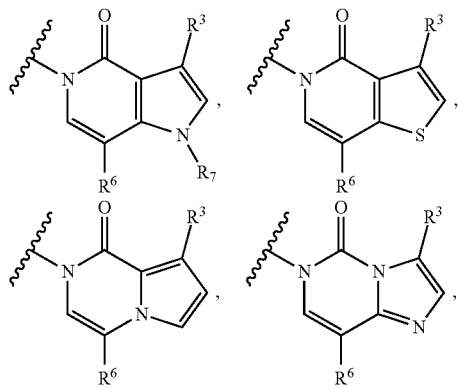

-continued

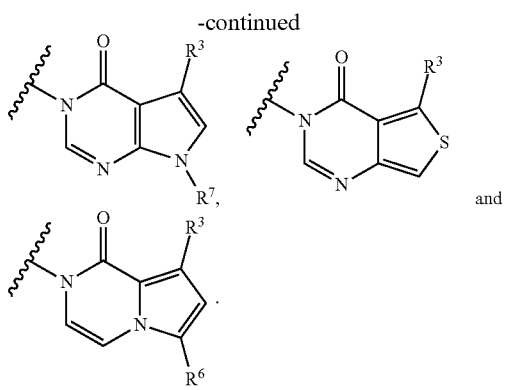

For example, the fused [5,6] heteroaromatic system may be

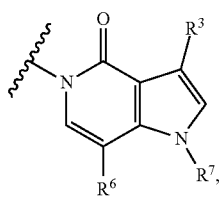

where $R^3$, $R^6$ and $R^7$ are defined above.

In some embodiments of Formula I, $L^1$ may be —CH$_2$—. In other or additional embodiments, $R^1$ and $R^2$ of Formula I, together with the nitrogen to which they are attached, may form a 4-6 membered monocyclic, bridged bicyclic, fused bicyclic or spirocyclic heterocyclic ring optionally be substituted on a carbon by one, two or more substituents each selected from the group consisting of: halogen, cyano, oxo, hydroxyl and $C_{1-6}$alkyl (optionally substituted by one, two or three halogens).

In certain embodiments, $R^3$ may be selected from the group consisting of phenyl or heteroaryl, wherein $R^3$ is optionally substituted with one, two or three substituents each independently selected from $C_{1-4}$ alkyl, halogen, OH, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, NR$^a$R$^b$, C(O)OH, $C_{1-4}$alkoxycarbonyl, and NR$^a$R$^b$carbonyl, wherein $C_{1-6}$alkyl, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and NR$^a$R$^b$.

For example, $R^3$ may be phenyl, thiophenyl, pyrimidinyl, pyrazinyl or pyridinyl, each optionally substituted by one or two substituents each independently selected from halogen and $C_{1-3}$alkyl (optionally substituted by one, two or three halogens), e.g., $R^3$ may be phenyl, optionally substituted by one or two substituents each independently selected from Cl, F, Br, and CF$_3$.

In some embodiments, $R^6$ of a disclosed formula may independently for each occurrence may be selected from H, halogen, cyano, $C_{1-4}$ alkyl (optionally substituted by one or two substituents each selected from the group consisting of —NR$^a$R$^b$, $C_{1-4}$ alkoxy, halogen, cyano, hydroxyl, C(O)H, and =NR$^a$), C(O)OH, C(O)H, —C(=NH)—NR$^a$R$^c$, phenyl (optionally substituted by one or two substituents each selected from the group consisting of NR$^a$R$^b$, $C_{1-4}$ alkoxy, halogen, cyano, hydroxyl, C(O)H, and =NR$^a$), pyridinyl and pyrimidinyl.

In other embodiments, a disclosed compound may be represented by:

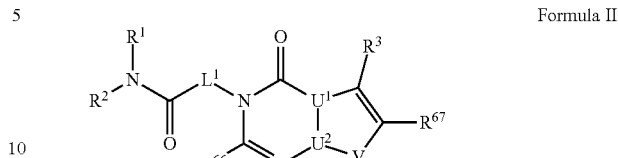

Formula II wherein $U^1$ and $U^2$ may each be C or N; wherein when one of $U^1$ and $U^2$ is N the other is C (for example, $U^1$ may N and $U^2$ may be C, or $U^1$ may be C and $U^2$ may be N);

T is N or CR$^6$;

$R^{66}$ and $R^{67}$ are each independently selected from the group consisting of halogen, $C_{1-4}$ alkyl (optionally substituted by one, two, three substituents selected from halogen, hydroxyl, cyano and NR$^a$R$^b$; and V is selected from the group consisting of N, NR$^7$, CR$^{66}$ and S, for example, V may be NR$^7$ or V may be N, and $L^1$, $R^1$, $R^2$, $R^3$, $R^6$, and $R^7$ are defined above.

In certain embodiments, a disclosed compound may be represented by:

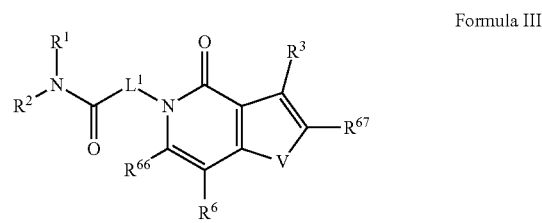

Formula III wherein V is NR$^7$ or S, and $L^1$, $R^1$, $R^2$, $R^3$, $R^{66}$, and $R^6$ are defined above. For example, provided herein are compounds represented by:

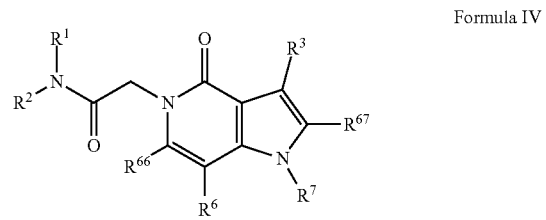

Formula IV and pharmaceutically acceptable salts, stereoisomers and prodrugs thereof, wherein:

$R^1$ and $R^2$ are each independently selected from the group consisting of H, $C_{1-4}$ alkyl, $C_{1-4}$alkoxy, and $C_{1-4}$ alkylcarbonyl or $R^1$ and $R^2$, together with the nitrogen to which they are attached, form a 3-7 membered monocyclic, bridged bicyclic, fused bicyclic or spirocyclic heterocyclic ring which may have an additional heteroatom selected from O, S, or N; and wherein the 4-6 membered monocyclic, bridged bicyclic, fused bicyclic or spirocyclic heterocyclic ring may optionally be substituted by one, two or more substituents each selected from the group consisting of: phenyl (optionally substituted by one, two or three halogens), $C_3$-$C_6$cycloalkyl (optionally substituted by one, two or three halogens), $C_{1-6}$alkoxy (optionally substituted by one, two or three halogens), and $C_{1-6}$alkyl (optionally substituted by one, two or three halogens), and on a carbon not bound to the nitrogen, by one, two or more substituents each selected from the group consisting of halogen, cyano, oxo, $NR^aR^b$ and hydroxyl; and wherein if said 4-6 membered monocyclic, bridged bicyclic, fused bicyclic or spirocyclic heterocyclic ring contains a —NH moiety that nitrogen may be optionally substituted by a substituent selected from the group consisting of hydrogen, $C_{1-6}$alkyl, $C_{1-6}$alkyl-S(O)$_2$—, $C_{1-6}$alkylcarbonyl-, and $C_{1-6}$alkoxycarbonyl-; $R^3$ is selected from the group consisting of phenyl, naphthyl, heteroaryl, heterocyclyl and $C_{3-6}$cycloalkyl, wherein $R^3$ is optionally substituted with one, two or three substituents each independently selected from $C_{1-6}$alkyl, halogen, OH, cyano, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl, wherein $C_{1-6}$alkyl, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$;

$R^6$ is independently selected for each occurrence from the group consisting of H, $C_{1-6}$ alkyl, $C_{1-6}$ alkoxy, halogen, cyano, $C_{2-6}$alkenyl, $C_{2-6}$alkynyl, $C_{3-6}$cycloalkyl, heteroaryl, phenyl, —C(=NH)—$NR^aR^c$, C(=N—OH)—H, C(=N—OH)—$C_{1-6}$alkyl, —$NR^aR^b$, C(O)OH, $C_{1-6}$alkylcarbonyl, $C_{1-6}$alkoxycarbonyl, $NR^aR^b$carbonyl-, and $R^aR^bN$—SO$_2$—, wherein phenyl and heteroaryl are optionally substituted by one or more substituents each selected from cyano, halogen $C_{1-4}$ alkyl (optionally substituted by halogen), cyano, $C_{1-4}$ alkoxy, $NR^aR^b$, =$NR^a$, —C(=NH)—$NR^aR^c$, and $R^aR^bN$—SO$_2$) and where $C_{1-6}$ alkyl, $C_{1-6}$alkyoxy, $C_{2-6}$alkenyl, $C_{2-6}$alkynyl, and $C_{3-6}$cycloalkyl are each optionally substituted by one or more substituents each selected from the group consisting of: hydroxyl, cyano, $C_{1-4}$ alkoxy, halogen, $NR^aR^b$, =$NR^a$, —C(=NH)—$NR^aR^c$, cyano, and $R^aR^bN$—SO$_2$—, $R^{66}$ and $R^{67}$ are each independently selected from the group consisting of halogen, $C_{1-4}$ alkyl (optionally substituted by one, two, three substituents selected from halogen, hydroxyl, cyano and $NR^aR^b$); and $R^7$ is selected from the group consisting of H, $C_{1-6}$alkyl, $C_{2-6}$alkynyl, $C_{3-6}$cycloalkyl, heterocyclyl, heteroaryl, and phenyl, wherein $C_{1-6}$alkyl, $C_{2-6}$alkenyl, $C_{3-6}$cycloalkyl may optionally be substituted by one or more substituents each selected from halogen, hydroxyl, $C_{1-4}$ alkoxy (optionally substituted by halogen or —Si($R_s$)$_{0-3}$ (wherein $R_s$ is H or $C_{1-6}$alkyl)), cyano, —Si($R_s$)$_{0-3}$ (wherein $R_s$ is H or $C_{1-6}$alkyl), —O—Si($R_s$)$_{0-3}$ (wherein $R_s$ is H or $C_{1-6}$alkyl), and $NR^aR^b$;

$R^c$ is selected from the group consisting of hydrogen, $C_{1-3}$alkyl, and hydroxyl;

$R^a$ and $R^b$ are independently selected, for each occurrence, from the group consisting of: hydrogen, hydroxyl, and $C_{1-3}$alkyl; wherein $C_{1-3}$alkyl may optionally be substituted by one or more substituents selected from: fluorine, cyano, oxo and hydroxyl; or $R^a$ and $R^b$, together with the nitrogen to which they are attached, form a 4-6 membered heterocyclic ring which may have an additional heteroatom selected from O, S, or N.

In some embodiments, $R^1$ and $R^2$, together with the nitrogen to which they are attached, may form a 4-6 membered monocyclic, bridged bicyclic, fused bicyclic or spirocyclic heterocyclic ring optionally substituted on a carbon not adjacent to the nitrogen by one, two or more substituents each selected from the group consisting of: halogen, cyano, oxo, hydroxyl and $C_{1-6}$alkyl (optionally substituted by one, two or three halogens).

In certain embodiments, $R^3$ may be selected from the group consisting of phenyl or heteroaryl, wherein $R^3$ is optionally substituted with one, two or three substituents each independently selected from $C_{1-4}$ alkyl, halogen, OH, $C_{1-4}$alkoxy, $C_{2-6}$alkenyl, $C_{2-6}$alkynyl, $C_{3-6}$cycloalkyl, $C_{1-6}$alkyl-S(O)$_2$—, $C_{1-6}$alkylcarbonyl, $R^aR^bN$—SO$_2$—, $NR^aR^b$, C(O)OH, $C_{1-4}$alkoxycarbonyl, and $NR^aR^b$carbonyl, wherein $C_{1-6}$alkyl, $C_{2-6}$alkenyl, $C_{2-6}$alkynyl, $C_{3-6}$cycloalkyl, $C_{1-6}$alkyl-S(O)$_2$—, and $C_{1-6}$alkylcarbonyl may be optionally substituted by one or more substituents each independently selected from halogen, hydroxyl, cyano, and $NR^aR^b$.

For example, $R^3$ may be phenyl, thiophenyl, pyrimidinyl, pyrazinyl or pyridinyl, each optionally substituted by one or two substituents each independently selected from halogen and $C_{1-3}$alkyl (optionally substituted by one, two or three halogens).

In an embodiment, $R^7$ may be selected from the group consisting of H, $C_{1-6}$alkyl, $C_{3-6}$cycloalkyl, heteroaryl, and phenyl, wherein $C_{1-6}$alkyl is optionally substituted by one or more substituents each selected from halogen, hydroxyl, $C_{1-4}$ alkoxy (optionally substituted by halogen or —Si($R_s$)$_{0-3}$ (wherein $R_s$ is H or $C_{1-6}$alkyl), cyano, and $NR^aR^b$).

Procedures for making compounds disclosed herein are provided below. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of any of Formula I, II, III, IV, as depicted above, or any of the intermediates described below, can be further derivatised by using one or more standard synthetic methods known to those skilled in the art. Such methods can involve substitution, oxidation or reduction reactions. These methods can also be used to obtain or modify compounds of Formula I or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride)

followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl suphonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid group by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or t-butyllithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis(triphenylphosphine)palladium(0), palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as tetrahydrofuran or DMF), under appropriate conditions (such as heating to, for example, 50-120° C.). In another example, a Sonogashira reaction can be used to couple such a ring system to an alkyne (which may, or may not be further substituted) by treatment with a palladium complex (such as tetrakis(triphenylphosphine)palladium(0)) and a halide salt of copper (I) (such as copper (I) iodide), in the presence of a base (such as a potassium carbonate or a tertiary amine, for example, triethylamine), in an appropriate solvent (such as tetrahydrofuran or dimethylformamide), under appropriate conditions (such as heating to, for example, 50-120° C.). In another example, a Stille reaction can be used to couple such a ring system to an alkene, by treatment with an organotin compound (such as an alkynyltin or alkenyltin reagent, for example an alkenyltributylstannane) in the presence of a palladium complex (such as tetrakis(triphenylphosphine)palladium(0)), with, or without the presence of a salt (such as a copper (I) halide), in an appropriate solvent (such as dioxane or dimethylformamide), under appropriate conditions (such as heating to, for example, 50-120° C.).

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as tetrahydrofuran). In another example, a nitro group may be reduced to an amine by catalytic hydrogenation in the presence of a metal catalyst (such as palladium on a solid support such as carbon) in a solvent (such as an ether, for example tetrahydrofuran, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (such as palladium on a solid support such as carbon), or Raney nickel in a solvent (such as tetrahydrofuran) and under suitable conditions (such as cooling to below room temperature, for example to −78° C., or heating, for example to reflux).

Salts of compounds of Formula I (e.g., Formula II, III, IV) can be prepared by the reaction of a compound of Formula I with an appropriate acid or base in a suitable solvent, or mixture of solvents (such as an ether, for example, diethyl ether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diastereomeric derivatives (such as salts) can be produced by reaction of a mixture of enantiomers of a compound of Formula I (such as a racemate) and an appropriate chiral compound (such as a chiral base). The diastereomers can then be separated by any conventional means such as crystallisation, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Steroselective Biocatalysts, Marcel Decker; New York 2000).

In another resolution process a racemate of compounds of Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the disclosure provides methods of modulating the activity of the NMDA receptor. Such methods may for example, comprise exposing said receptor to a compound described herein. In some embodiments, the compound utilized by one or more of the foregoing methods is one of the generic, subgeneric, or specific compounds described herein, such as a compound of Formula I. The ability of compounds described herein to modulate the NMDA receptor can be evaluated by procedures known in the art and/or described herein.

In certain embodiments, the present disclosure provides a method of treating and or ameliorating a disease and/or disorder of the nervous system in a patient in need thereof by administering an effective amount of a disclosed compound. Exemplary diseases and disorders of the nervous system include psychiatric diseases, neurological diseases, and neurodevelopmental disorders, further described below.

In one embodiment, an exemplary psychiatric disease is schizophrenia. Schizophrenia is a debilitating mental disorder encompassing three symptom domains: positive (psychosis, hallucination, delusions), negative (withdrawal), and cognitive (global reduction in cognitive ability). Positive symptoms of Schizophrenia typically emerge early in adulthood and are treated with antipsychotic medications. However, cognitive deficits are severe, emerge in the adolescent prodromal stage, are resistant to antipsychotic therapy, and are the leading cause of lifetime disability as measured by impaired global function (inability to live independently, unemployment, etc). NMDA receptor hypofunction is the leading hypothesis for the cause of schizophrenia. This hypothesis is supported by substantial clinical evidence including clinical pharmacology, electrophysiology, imaging, cognition, computational neuroscience, neuroanatomical studies, and genetics. In particular, several lines of evidence implicate hypofunction of GluN2B-containing NMDA receptors in schizophrenia.

The present disclosure provides herein a method of treating schizophrenia, including positive, negative, and cognitive symptoms, in a patient in need thereof, comprising administering an effective amount of a disclosed compound. For example, provided herein are methods of ameloiorating positive, negative, and cognitive symptoms of a patient not adequately treated by approved antipsychotic medications, for example the treatment of cognitive impairments in schizophrenia, by administering an effective amount of a disclosed compound to such a patient.

Also provided herein are methods to improve cognitive and global function, and/or substantially preventing the onset of schizophrenia in people at risk of developing schizophrenia, by administering an effective amount of a disclosed compound to such a patient.

Contemplated herein are methods of treating and/or ameliorating cognitive and emotional deficits and other symptoms associated with exemplary psychiatric disorders including major depressive disorder, and including but not limited to those suffering from bipolar disorder, obsessive-compulsive disorder, dysphobic disorder, dysthymic disorder, psychotic depression, post-traumatic stress disorder, and other anxiety disorders. For example, provided herein are methods of treating attention deficit disorder, ADHD (attention deficit hyperactivity disorder), schizophrenia, anxiety, amelioration of opiate, nicotine and/or ethanol addiction (e.g., method of treating such addiction or ameliorating the side effects of withdrawing from such addiction), spinal cord injury, diabetic retinopathy, traumatic brain injury, and/or post-traumatic stress syndrome in a patient in need thereof, that includes administering a disclosed compound.

In other embodiments, provided herein is a method of treating and/or ameliorating cognitive and emotional deficits and other symptoms resulting from neurological diseases, including but not limited to a patient suffering from Alzheimer's disease, Parkinson's disease, Huntington's disease, amyotrophic lateral sclerosis, multiple sclerosis, and seizure disorders comprising administering to the patient an effective amount of a disclosed compound.

The present disclosure contemplates a method of treating and/or ameliorating dysfunction caused by neurodevelopmental disorders, e.g., abnormal brain development, including but not limited to Rett Syndrome, Attention Deficit and Hyperactivity Disorder, autism and autism spectrum disorders such as Phelan-McDermid Syndrome, and other forms of intellectual disability such as Fragile X syndrome, tuberous sclerosis, Smith-Lemli-Opitz Syndrome, and Down's syndrome. A method is also provided to treat patients suffering from abnormal brain function resulting from infections of the central nervous system, exposure to toxic agents or other xenobiotics or naturally occurring toxins, and/or autoimmune disorders including, but not limited to anti-NMDA receptor encephalitis comprising administering an effective amount of a disclosed compound.

In particular, in certain embodiments, the disclosure provides a method of treating, preventing, and/or preventing the development of the above medical indications comprising administering to a subject in need thereof a therapeutically effective amount of a compound described herein, such as a compound of Formula I, II, III or IV.

In certain embodiments, the compound utilized by one or more of the foregoing methods is one of the generic, subgeneric, or specific compounds described herein, such as a compound of Formula III, III or IV.

Disclosed compounds may be administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment regimen can include a corrective phase, during which dose sufficient to maintain cognitive and/or emotional function is administered, and can be followed by a maintenance phase, during which, e.g., a a lower dose sufficient to prevent a deficit in cognitive and/or emotional function is administered. A suitable maintenance dose is likely to be found in the lower parts of the dose ranges provided herein, but corrective and maintenance doses can readily be established for individual subjects by those of skill in the art without undue experimentation, based on the disclosure herein.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of the present disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Pharmaceutical compositions of the present disclosure may also be administered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, Disclosed compounds are not covalently bound to a polymer, e.g., a polycarboxylic acid polymer, or a polyacrylate.

Advantageously, the invention also provides kits for use by, e.g., a consumer in need of a disclosed NMDA modulator. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectral chemical shifts are expressed in ppm relative to tetramethylsilane. The following abbreviations have been used: br=broad signal, s=singlet, d=doublet, dd=double doublet, ddd=double double doublet, dt=double triplet, t=triplet, td=triple doublet, q=quartet, m=multiplet.

A. PREPARATION OF THIENOPYRIDONES

Example 1: Preparation of 3-(4-chloro-3-(trifluoromethyl)phenyl)-5-(2-oxo-2-(pyrrolidin-1-yl)ethyl) thieno[3,2-c]pyridin-4(5H)-one

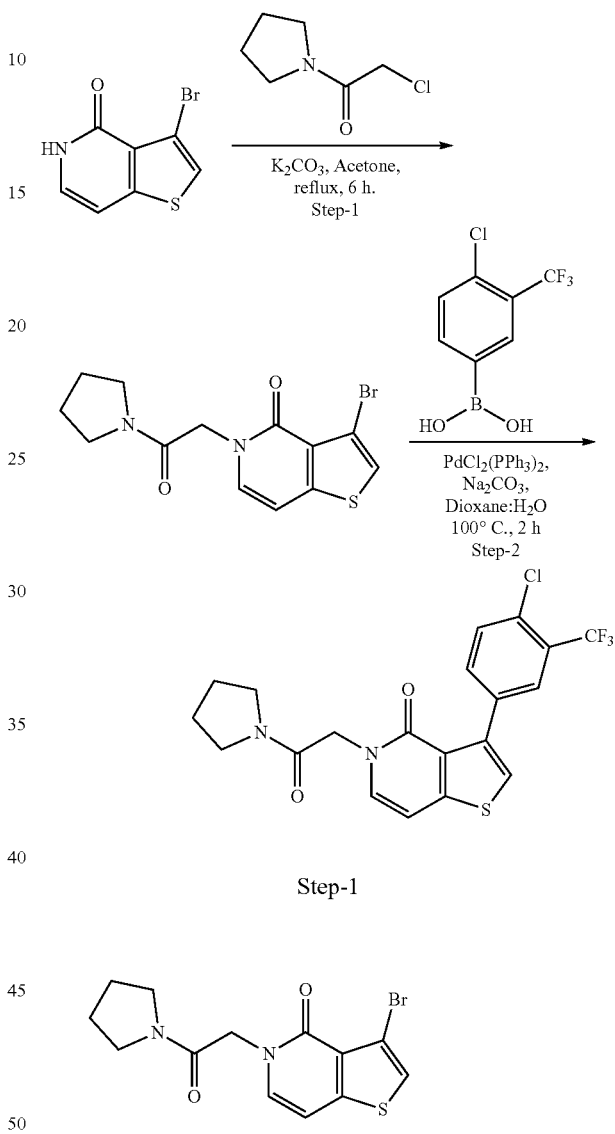

Step-1

Preparation of 3-bromo-5-(2-oxo-2-(pyrrolidin-1-yl) ethyl)thieno[3,2-c]pyridin-4(5H)-one To a stirred solution of 3-bromothieno[3,2-c]pyridin-4 (5H)-one (1 g, 4.34 mmol) in dry acetone (10 mL), potassium carbonate (1.8 g, 13.02 mmol) and 2-chloro-1-(pyrrolidin-1-yl)ethanone (0.96 g, 6.52 mmol) was added at room temperature and the reaction mixture was heated at reflux for 6 h. The reaction mixture was concentrated, the residue was diluted with water and extracted with ethyl acetate (3×10 mL). The combined organic layer was dried over sodium sulfate, filtered and concentrated to get crude compound which was washed with pentane (2×20 mL) to afford the title compound 3-bromo-5-(2-oxo-2-(pyrrolidin-1-yl)ethyl) thieno[3,2-c]pyridin-4(5H)-one (1.4 g, 94.59% yield) as off white solid. Calculated (M+H): 340.99; Found (M+H): 340.9.

Step 2

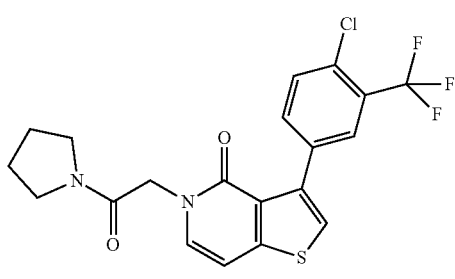 [SMILES: O=C(Cn1ccc2scc(-c3ccc(Cl)c(C(F)(F)F)c3)c2c1=O)N1CCCC1]

Preparation of 3-(4-chloro-3-(trifluoromethyl)phenyl)-5-(2-oxo-2-(pyrrolidin-1-yl)ethyl)thieno[3,2-c]pyridin-4(5H)-one To a stirred solution of 3-bromo-5-(2-oxo-2-(pyrrolidin-1-yl)ethyl)thieno[3,2-c]pyridin-4(5H)-one (0.15 g, 0.43 mmol) and 4-chloro-3-(trifluoromethyl)phenyl)boronic acid (0.145 g, 0.65 mmol) in dioxane:water (5 mL, 4:1) was added sodium carbonate (0.139 g, 1.31 mmol). The suspension was purged with argon for 15 minutes and bis(triphenylphosphine)palladium(II) dichloride (0.03 g, 0.04 mmol) was added. The reaction mixture was heated at 100° C. for 2 h. The reaction mixture was cooled to room temperature, diluted with water and extracted with ethyl acetate (2×25 mL). The combined organic layer was dried over anhydrous sodium sulfate, filtered and concentrated to get crude compound which was purified by silica gel column chromatography using 2% methanol in dichloromethane to get the title compound 3-(4-chloro-3-(trifluoromethyl)phenyl)-5-(2-oxo-2-(pyrrolidin-1-yl)ethyl)thieno[3,2-c]pyridin-4(5H)-one (0.12 g, 62.17% yield) as yellow solid. $^1$H NMR (400 MHz, DMSO-$d_6$) δ (ppm): 7.85 (s, 1H), 7.69 (d, J=4.4 Hz, 3H), 7.48 (d, J=7.2 Hz, 1H), 6.94 (d, J=7.6 Hz, 1H), 4.72 (s, 2H), 3.46 (t, J=6.6 Hz, 2H), 3.24 (s, 2H), 1.91 (t, J=6.6 Hz, 2H), 1.75 (t, J=6.6 Hz, 2H). Calculated (M+H): 441.06; Found (M+H): 441. HPLC purity: 98.36%

Example 4: Preparation of 3-(4-chloro-3-(trifluoromethyl)phenyl)-5-(2-(3-fluoropyrrolidin-1-yl)-2-oxoethyl)thieno[3,2-c]pyridin-4(5H)-one

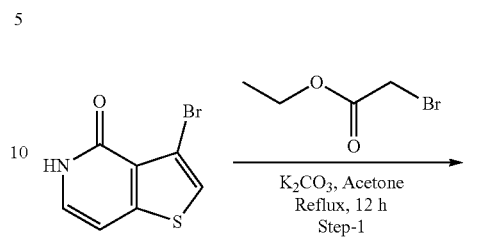

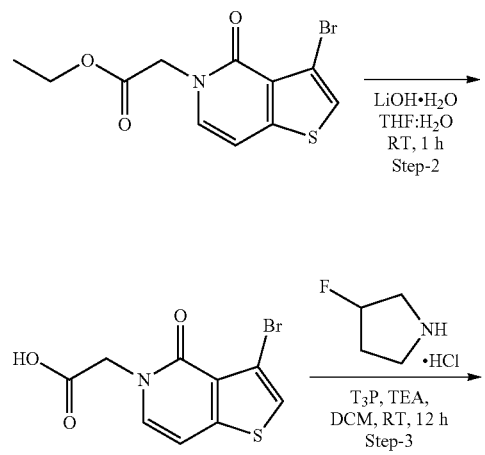

TABLE 1

The following compounds were prepared by the method described above:

| Example Number | Structure | IUPAC Name | Analytical Data |
|---|---|---|---|
| 2 | ![structure] | 3-(4-chloro-3-fluorophenyl)-5-(2-oxo-2-(pyrrolidin-1-yl)ethyl)thieno[3,2-c]pyridin-4(5H)-one | $^1$H NMR (400 MHz, DMSO-$d_6$) δ (ppm): 7.60 (s, 1H), 7.53 (t, J = 7.6 Hz, 1H), 7.48-7.44 (m, 2H), 7.28 (d, J = 8 Hz 1H), 6.93 (d, J = 6.8 Hz, 1H), 4.72 (s, 2H), 3.47 (t, J = 6.8 Hz, 2H), 3.27 (t, J = 9.6 Hz, 2H), 1.93-1.87 (m, 2H), 1.78-1.72 (m, 2H). Calculated (M + H): 391.06; Found (M + H): 391.0. HPLC purity: 99.39% |
| 3 | ![structure] | 3-(3-chloro-4-fluorophenyl)-5-(2-oxo-2-(pyrrolidin-1-yl)ethyl)thieno[3,2-c]pyridin-4(5H)-one | $^1$H NMR (400 MHz, DMSO-$d_6$) δ (ppm): 7.60 (d, J = 7.2 Hz, 1H), 7.57 (s, 1H), 7.47-7.45 (d, J = 7.6 Hz, 1H), 7.41-7.34 (m, 2H), 6.92 (d, J = 7.2 Hz, 1H), 4.72 (s, 2H), 3.47 (t, J = 6.8 Hz, 2H), 3.24 (s, 2H), 1.93-1.87 (m, 2H), 1.78-1.72 (m, 2H). Calculated (M + H): 391.8; Found (M + H): 391.0. HPLC purity: 99.87% |

-continued

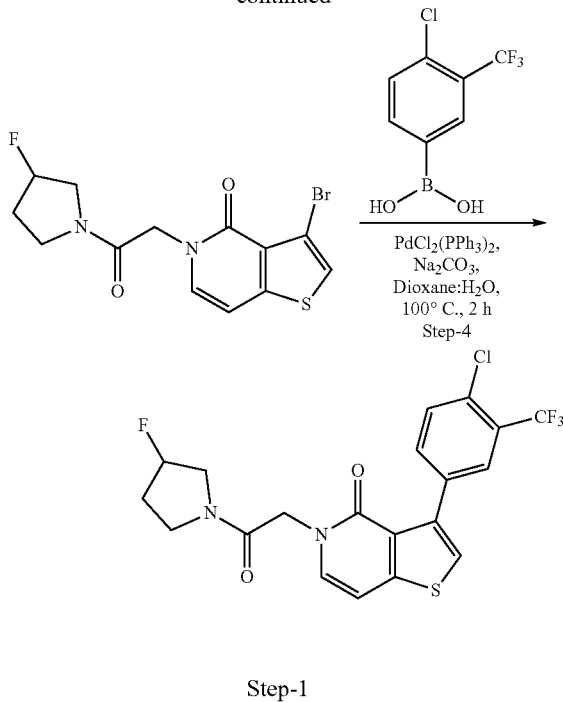

Step-1

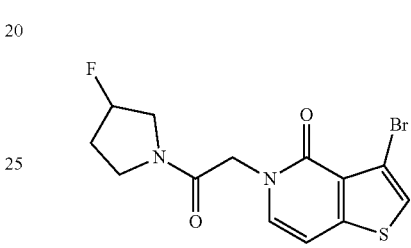

Preparation of ethyl 2-(3-bromo-4-oxothieno[3,2-c]pyridin-5(4H)-yl)acetate

To a stirred solution of 3-bromothieno[3,2-c]pyridin-4(5H)-one (1 g, 4.34 mmol) in dry acetone (20 mL) was added potassium carbonate (1.8 g, 13.04 mmol) followed by ethyl 2-bromoacetate (0.96 mL g, 8.69 mmol) at room temperature and the reaction mixture was heated at reflux for 12 h. The reaction mixture was concentrated, the residue was diluted with water (30 mL) and extracted with ethyl acetate (3×30 mL). The combined organic layer was dried over anhydrous sodium sulfate, filtered and concentrated to get crude compound which was washed with pentane (2×20 mL) to get the title compound ethyl 2-(3-bromo-4-oxothieno[3,2-c]pyridin-5(4H)-yl)acetate (1.8 g, crude) as off white solid. Calculated (M+H): 315.96; Found (M+H): 316.0.

Step-2

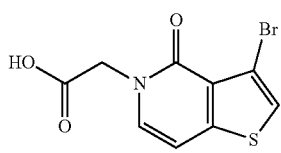 [SMILES: O=C(O)Cn1ccc2scc(Br)c2c1=O]

Preparation of 2-(3-bromo-4-oxothieno[3,2-c]pyridin-5(4H)-yl)acetic acid

To a stirred solution of ethyl 2-(3-bromo-4-oxothieno[3,2-c]pyridin-5(4H)-yl)acetate (1.8 g, 5.69 mmol) in tetrahydrofuran:water mixture (10 mL, 1:1) was added lithium hydroxide monohydrate (1.1 g, 28.48 mmol) and the reaction mixture was stirred at room temperature for 1 h. The reaction mixture was concentrated, the residue was diluted with water and the pH was adjusted to ~2 using 1.5N hydrochloric acid. The obtained solid was filtered and dried under vacuum to get the title compound 2-(3-bromo-4-oxothieno[3,2-c]pyridin-5(4H)-yl)acetic acid (1.1 g, 65.01% yield) as off white solid. Calculated (M+H): 287.93; Found (M+H): 287.9.

Step-3

Preparation 3-bromo-5-(2-(3-fluoropyrrolidin-1-yl)-2-oxoethyl)thieno[3,2-c]pyridin-4(5H)-one To a stirred solution of 2-(3-bromo-4-oxothieno[3,2-c]pyridin-5(4H)-yl)acetic acid (0.4 g, 1.38 mmol) in dichloromethane (10 mL) was added triethylamine (0.38 mL, 2.76 mmol) at room temperature and stirred for 10 minutes. 3-fluoropyrrolidine hydrochloride (0.2 g, 1.65 mmol) was added and the reaction mixture was cooled to 0° C. Then 1-propanephosphonic anhydride solution (T$_3$P) (1.3 mL, 2.07 mmol, 50% in ethyl acetate) was added and the reaction mixture was stirred at room temperature for 12 h. The solution was diluted with water and extracted with dichloromethane (3×30 mL). The combined organic layer was dried over anhydrous sodium sulfate, filtered and concentrated to get the crude compound which was washed with pentane (3×10 mL) to get title compound 3-bromo-5-(2-(3-fluoropyrrolidin-1-yl)-2-oxoethyl)thieno[3,2-c]pyridin-4(5H)-one (0.36 g, 73.46% yield) as brown solid. Calculated (M+H): 358.98; Found (M+H): 359.

Step-4

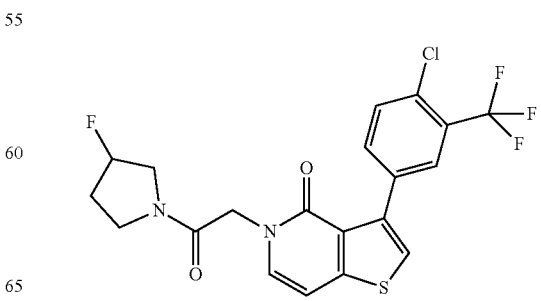

Preparation of 3-(4-chloro-3-(trifluoromethyl)phenyl)-5-(2-(3-fluoropyrrolidin-1-yl)-2-oxoethyl)thieno[3,2-c]pyridin-4(5H)-one To a stirred solution of 3-bromo-5-(2-(3-fluoropyrrolidin-1-yl)-2-oxoethyl)thieno[3,2-c]pyridin-4(5H)-one (0.12 g, 0.33 mmol) and (4-chloro-3-(trifluoromethyl)phenyl)boronic acid (0.112 g, 0.50 mmol) in dioxane:water mixture (5 mL, 4:1) was added sodium carbonate (0.106 g, 1.02 mmol) and the reaction mixture was purged with argon for 15 minutes. Then bis(triphenylphosphine)palladium(II) dichloride (0.023 g, 0.033 mmol) was added and reaction mixture was heated at 100° C. for 2 h. The reaction mixture was cooled to room temperature, diluted with water and extracted with ethyl acetate (4×25 mL). The combined organic layer was dried over anhydrous sodium sulfate, filtered and concentrated to get the crude compound which was purified by silica gel column chromatography using 2% methanol in dichloromethane to get the title compound 3-(4-chloro-3-(trifluoromethyl)phenyl)-5-(2-(3-fluoropyrrolidin-1-yl)-2-oxoethyl)thieno[3,2-c]pyridin-4(5H)-one (0.031 g, 20.3% yield) as white solid. $^1$H NMR (400 MHz, DMSO-$d_6$) δ (ppm): 7.86 (s, 1H), 7.73-7.67 (m, 3H), 7.49 (d, J=7.6 Hz, 1H), 6.97 (d, J=6.8 Hz, 1H), 5.48-5.23 (m, 1H), 4.86-4.69 (m, 2H), 3.86-3.26 (m, 4H), 2.30-1.91 (m, 2H). Calculated (M+H): 459.05; Found (M+H): 459. HPLC purity: 98.85%

TABLE 2

The following compounds were prepared by the method described above:

| Example Number | Structure | IUPAC Name | Analytical Data |
|---|---|---|---|
| 5 | 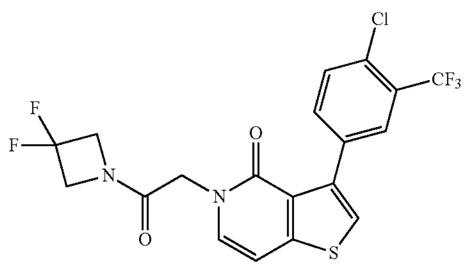 [SMILES: O=C(Cn1ccc2scc(-c3ccc(Cl)c(C(F)(F)F)c3)c2c1=O)N1CC(F)(F)C1] | 3-(4-chloro-3-(trifluoromethyl)phenyl)-5-(2-(3,3-difluoroazetidin-1-yl)-2-oxoethyl)thieno[3,2-c]pyridin-4(5H)-one | $^1$H NMR (400 MHz, DMSO-$d_6$) δ (ppm): 7.87 (s, 1H), 7.73-7.68 (m, 3H), 7.50 (d, J = 6.8 Hz, 1H), 6.98 (d, J = 7.6 Hz, 1H), 4.70-4.66 (m, 4H), 4.30 (t, J = 11.2 Hz, 2H). Calculated (M + H): 463.02; Found (M + H): 463. HPLC purity: 98.90% |
| 6 | 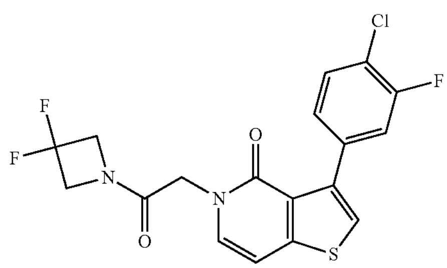 [SMILES: O=C(Cn1ccc2scc(-c3ccc(Cl)c(F)c3)c2c1=O)N1CC(F)(F)C1] | 3-(4-chloro-3-fluorophenyl)-5-(2-(3,3-difluoroazetidin-1-yl)-2-oxoethyl)thieno[3,2-c]pyridin-4(5H)-one | $^1$H NMR (400 MHz, DMSO-$d_6$) δ (ppm): 7.63 (s, 1H), 7.54 (t, J =8.4 Hz, 1H), 7.5-7.44 (m, 2H), 7.29 (d, J = 8.4 Hz, 1H), 6.96 (d, J = 7.6 Hz, 1H), 4.72-4.66 (m, 4H), 4.31 (t, J = 12 Hz, 2H). Calculated (M + H): 413.03: Found (M + H): 413.0. HPLC purity: 98.29% |
| 7 | 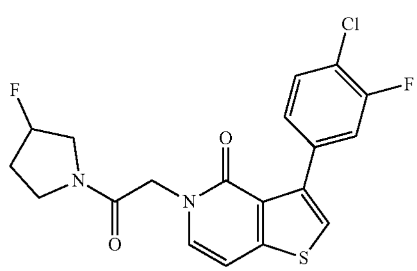 [SMILES: O=C(Cn1ccc2scc(-c3ccc(Cl)c(F)c3)c2c1=O)N1CCC(F)C1] | 3-(4-chloro-3-fluorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.61 (s, 1H), 7.55-7.43 (m, 3H), 7.29 (d, J = 8 Hz 1H), 6.94 (d, J = 6.8 Hz, 1H), 5.48-5.23 (m, 1H), 4.86-4.73 (m, 2H), 3.86-3.73 (m, 2H), 3.69-3.27 (m, 2H), 2.3-2.06 (m, 2H). Calculated (M + H): 409.05; Found (M + H): 409.0. HPLC purity: 99.72% |
| 8 | 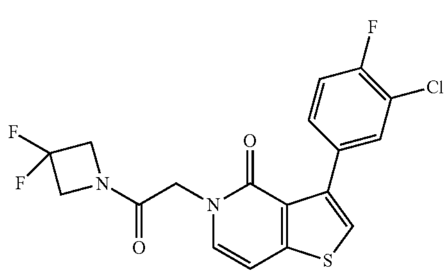 [SMILES: O=C(Cn1ccc2scc(-c3ccc(F)c(Cl)c3)c2c1=O)N1CC(F)(F)C1] | 3-(3-Chloro-4-fluorophenyl)-5-[2-(3,3-difluoroazetidin1-yl)-2-oxoethyl]-5H-thieno[3,2-c]pyridin-4-one | $^1$H NMR (400 MHz, DMSO-$d_6$) δ (ppm): 7.62-7.59 (m, 2H), 7.47 (d, J = 7.6 Hz, 1H), 7.42-7.35 (m, 2H), 6.95 (d, J = 7.6 Hz, 1H), 4.72-4.67 (m, 4H), 4.31 (t, J = 11.6 Hz, 2H). Calculated (M + H): 413.03; Found (M + H): 413.0. HPLC purity: 99.37% |

TABLE 2-continued

The following compounds were prepared by the method described above:

| Example Number | Structure | IUPAC Name | Analytical Data |
|---|---|---|---|
| 9 | 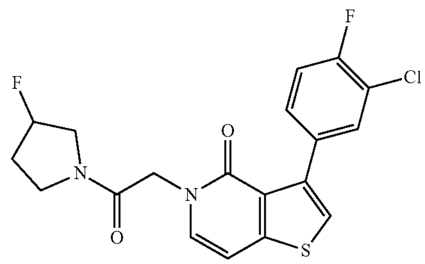 [SMILES: O=C(Cn1ccc2scc(-c3ccc(F)c(Cl)c3)c2c1=O)N1CCC(F)C1] | 3-(3-Chloro-4-fluorophenyl)-5-[2-(3-fluoro-pyrrolidin-1-yl)-2-oxo-ethyl]-5H-thieno[3,2-c]pyridin-4-one | $^1$H NMR (400 MHz, DMSO-$d_6$) δ (ppm): 7.62-7.59 (m, 1H), 7.58 (s, 1H), 7.49-7.47 (m, 1H), 7.43-7.34 (m, 2H), 6.93 (d, J = 7.2 Hz, 1H), 5.48-5.23 (m, 1H), 4.86-4.69 (m, 2H), 3.86-3.23 (m, 4H), 2.30-1.89 (m, 2H). Calculated (M + H): 409.05; Found (M + H): 409.3. HPLC purity: 99.87% |
| 10 | 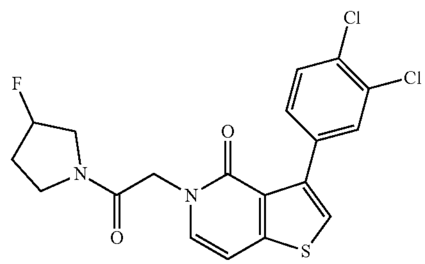 | 3-(3,4-dichlorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.66 (s, 1H), 7.62 (s, 1H), 7.58 (d, J = 8.4 Hz, 1H), 7.48 (d, J = 7.2 Hz, 1H), 7.40 (d, J = 7.2 Hz, 1H), 6.94 (d, J = 7.6 Hz, 1H), 5.48-5.23 (m, 1H), 4.86-4.69 (m, 2H), 3.83-3.27 (m, 4H), 2.24-1.94 (m, 2H). Calculated (M + H): 425.02; Found (M + H): 425.0. HPLC purity: 99.79% |
| 11 | 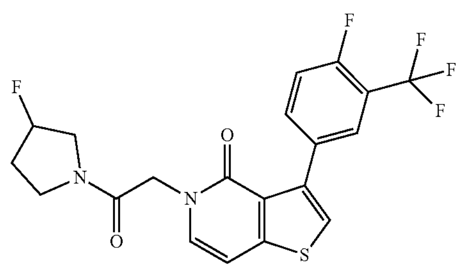 [SMILES: O=C(Cn1ccc2scc(-c3ccc(F)c(C(F)(F)F)c3)c2c1=O)N1CCC(F)C1] | 3-(4-fluoro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.78 (d, J = 6.0 Hz, 2H), 7.65 (s, 1H), 7.5-7.45 (m, 2H), 6.95 (d, J = 6.8 Hz, 1H), 5.47-5.23 (m, 1H), 4.86-4.69 (m, 2H), 3.86-3.64 (m, 2H), 3.60-3.27 (m, 2H), 2.3-1.91 (m, 2H). Calculated (M + H): 443.08; Found (M + H): 443.0. HPLC purity: 99.94%. |
| 12 | 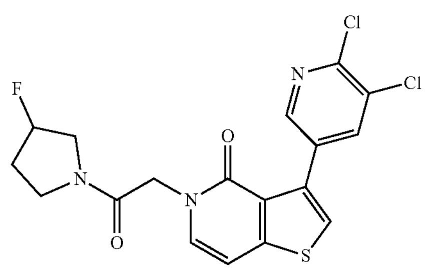 | 3-(5,6-dichloropyridin-3-yl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 8.43 (d, J = 2.0 Hz, 1H), 8.18 (d, J = 2.0 Hz, 1H), 7.79 (s, 1H), 7.51 (d, J = 7.2 Hz, 1H), 6.98 (d, J = 6.8 Hz, 1H), 5.48-5.23 (m, 1H), 4.88-4.71 (m, 2H), 3.86-3.26 (m, 4H), 2.30-1.91 (m, 2H). Calculated (M + H): 426.02; Found (M + H): 426.0. HPLC purity: 99.81%. |
| 13 | 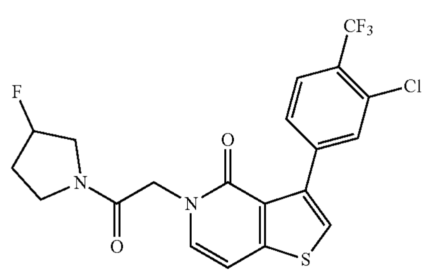 | 3-(3-chloro-4-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.81 (d, J = 8 Hz, 1H), 7.73 (d, J = 9.6 Hz, 2H), 7.60 (d, J = 10 Hz, 1H), 7.50 (d, J = 7.2 Hz, 1H), 6.96 (d, J = 7.2 Hz, 1H), 5.48-5.23 (m, 1H), 4.87-4.70 (m, 2H), 3.85-3.38 (m, 4H), 2.30-2.02 (m, 2H); Calculated (M + H): 459.05, Found (M + H): 459.0, HPLC purity: 98.67% |

TABLE 2-continued

The following compounds were prepared by the method described above:

| Example Number | Structure | IUPAC Name | Analytical Data |
|---|---|---|---|
| 14 | 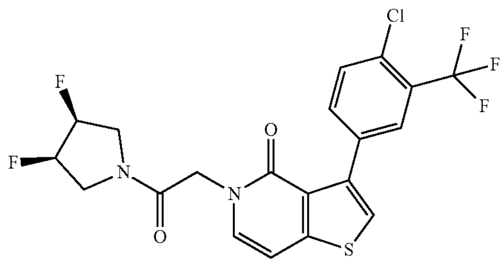 [SMILES: O=C(Cn1ccc2scc(-c3ccc(Cl)c(C(F)(F)F)c3)c2c1=O)N1C[C@@H](F)[C@@H](F)C1] | 3-(4-chloro-3-(trifluoromethyl)phenyl)-5-(2-((3S,4R)-3,4-difluoropyrrolidin-1-yl)-2-oxoethyl)thieno[3,2-c]pyridin-4(5H)-one | $^1$H NMR (400 MHz, DMSO-d$_6$) δ (ppm): 7.86 (s, 1H), 7.73-7.67 (m, 3H), 7.47 (d, J = 7.2 Hz, 1H), 6.96 (d, J = 7.2 Hz, 1H), 5.44-5.21 (m, 2H), 4.82-4.73 (m, 2H), 4.03-3.96 (m, 1H), 3.94-3.59 (m, 2H), 3.5-3.22 (m, 1H). Calculated (M + H): 477.04; Found (M + H): 477.0. HPLC purity: 99.16%. |
| 15 | 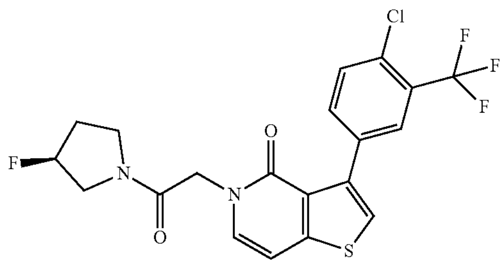 | (S)-3-(4-chloro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.86 (s, 1H), 7.72-7.69 (m, 3H), 7.49 (d, J = 6.4 Hz, 1H), 6.95 (d, J = 7.2 Hz, 1H), 5.47-5.22 (m, 1H), 4.86-4.69 (m, 2H), 3.86-3.27 (m, 4H), 2.3-1.91 (m, 2H). Calculated (M + H): 459.05; Found (M + H): 459.0. HPLC purity: 99.82%. |
| 16 | 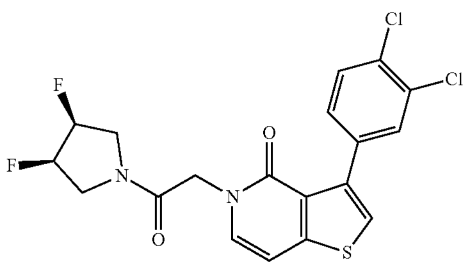 [SMILES: O=C(Cn1ccc2scc(-c3ccc(Cl)c(Cl)c3)c2c1=O)N1C[C@@H](F)[C@@H](F)C1] | 3-(3,4-dichlorophenyl)-5-(2-((3S,4R)-3,4-difluoropyrrolidin-1-yl)-2-oxoethyl)thieno[3,2-c]pyridin-4(5H)-one | $^1$H NMR (400 MHz, DMSO-d$_6$) δ (ppm): 7.66 (d, J = 2.0 Hz, 1H), 7.63 (s, 1H), 7.58 (d, J = 8.4 Hz, 1H), 7.46 (d, J = 2.0 Hz, 1H), 7.39 (dd, J$_1$ = 8.0 Hz & J$_2$ = 8.4 Hz, 1H), 6.94 (d, J = 7.2 Hz, 1H), 5.45-5.21 (m, 2H), 4.82-4.72 (m, 2H), 4.03-3.96 (m, 1H), 3.77-3.61 (m, 2H), 3.5-3.27 (m, 1H). Calculated (M + H): 443.01; Found (M + H): 443.0. HPLC purity: 98.44%. |
| 17 | 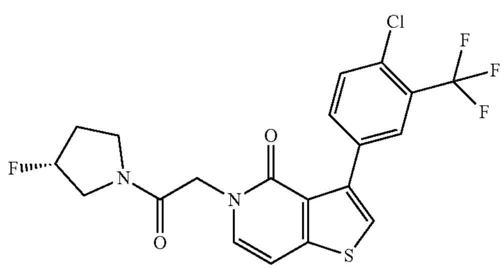 [SMILES: O=C(Cn1ccc2scc(-c3ccc(Cl)c(C(F)(F)F)c3)c2c1=O)N1CC[C@@H](F)C1] | (R)-3-(4-chloro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.86 (s, 1H), 7.73-7.67 (m, 3H), 7.49 (d, J = 6.8 Hz, 1H), 6.95 (d, J = 7.2 Hz, 1H), 5.48-5.23 (m, 1H), 4.87-4.69 (m, 2H), 3.86-3.22 (m, 4H), 2.30-1.88 (m, 2H). Calculated (M + H): 459.05; Found (M + H): 459.0. HPLC purity: 99.69%. |
| 18 | 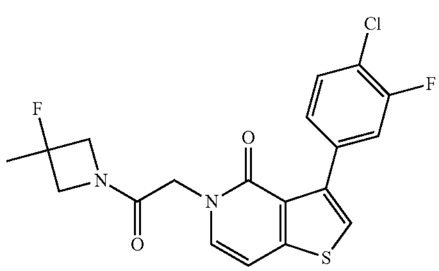 [SMILES: CC1(F)CN(C(=O)Cn2ccc3scc(-c4ccc(Cl)c(F)c4)c3c2=O)C1] | 3-(4-chloro-3-fluorophenyl)-5-(2-(3-fluoro-3-methylazetidin-1-yl)-2-oxoethyl)thieno[3,2-c]pyridin-4(5H)-one | $^1$H NMR (400 MHz, DMSO-d$_6$) δ (ppm): 7.63 (s, 1H), 7.57-7.45 (m, 3H), 7.30 (d, J = 8.4 Hz, 1H), 6.95 (d, J = 7.2 Hz, 1H), 4.61 (s, 2H), 4.38-4.25 (m, 2H), 3.96 (d, J = 19.2 Hz, 2H), 1.58 (d, J = 22 Hz, 3H). Calculated (M + H): 409.05; Found (M + 1): 409.0. HPLC purity 99.82 % |

TABLE 2-continued

The following compounds were prepared by the method described above:

| Example Number | Structure | IUPAC Name | Analytical Data |
| --- | --- | --- | --- |
| 19 | 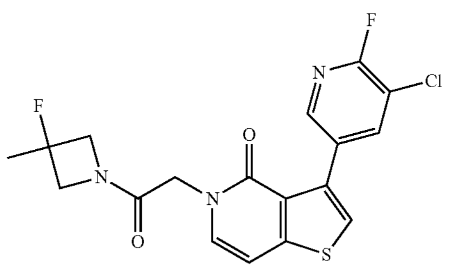 [SMILES: CC1(F)CN(C(=O)Cn2ccc3scc(-c4cnc(F)c(Cl)c4)c3c2=O)C1] | 3-(5-chloro-6-fluoropyridin-3-yl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm); 8.25-8.24 (m, 2H), 7.76 (s, 1H), 7.51 (d, J = 7.2 Hz, 1H), 6.99 (d, J = 6.8 Hz, 1H), 4.63 (s, 2H), 4.39-4.26 (m, 2H), 3.96 (d, J = 20.4 Hz, 2H), 1.58 (d, J = 22 Hz, 3H). Calculated (M + H): 410.05; Found (M + 1): 410.0. HPLC purity 99.59 % |
| 20 | 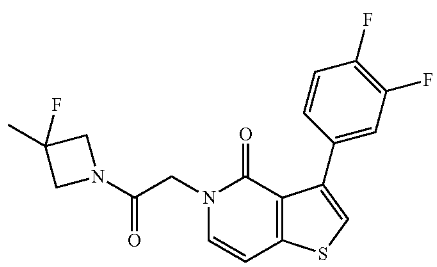 [SMILES: CC1(F)CN(C(=O)Cn2ccc3scc(-c4ccc(F)c(F)c4)c3c2=O)C1] | 3-(3,4-difluorophenyl)-5-(2-(3-fluoro-3-methylazetidin-1-yl)-2-oxoethyl)thieno[3,2-c]pyridin-4(5H)-one | $^1$H-NMR (400 MHz, DMSO-$d_6$) δ (ppm): 7.58 (s, 1H), 7.49 (d, J = 7.6 Hz, 2H), 7.45-7.36 (m, 1H), 7.27 (brs, 1H), 6.95 (d, J = 6.8 Hz, 1H), 4.61 (s, 2H), 4.38-4.25 (m, 2H), 3.98 (d, J = 19.2 Hz, 2H), 1.60 (d, J = 30 Hz, 3H), Calculated (M + H): 393.08, Found (M + H): 393.1, HPLC purity: 99.65% |
| 21 | 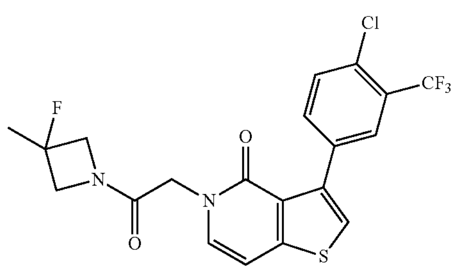 [SMILES: CC1(F)CN(C(=O)Cn2ccc3scc(-c4ccc(Cl)c(C(F)(F)F)c4)c3c2=O)C1] | 3-(4-chloro-3-(trifluoromethyl)phenyl)-5-(2-(3-fluoro-3-methylazetidin-1-yl)-2-oxoethyl)thieno[3,2-c]pyridin-4(5H)-one | $^1$H-NMR (400 MHz, DMSO-$d_6$) δ (ppm): 7.88 (s, 1H), 7.74-7.69 (m, 3H), 7.51 (d, J = 7.2 Hz, 1H), 6.98 (d, J = 7.6 Hz, 1H), 4.60 (s, 2H), 4.38-4.25 (m, 2H), 4.01-3.92 (m, 2H), 1.60 (d, J = 22.4 Hz, 3H). Calculated (M + H): 459.0, Found (M + H): 459.0, HPLC purity: 99.92% |
| 22 | 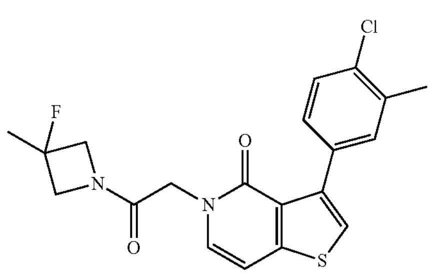 | 3-(4-chloro-3-methylphenyl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm): 7.49 (s, 1H), 4.47 (d, J = 7.2 Hz, 1H), 7.39-7.35 (m, 2H), 7.24 (d, J = 8.0 Hz, 1H), 6.93 (d, J = 7.6 Hz, 1H), 4.59 (s, 2H), 4.37-4.24 (m, 2H), 3.95 (d, J = 19.2 Hz, 2H), 2.33 (s, 3H), 1.57 (d, J = 22.4 Hz, 3H). Calculated (M + H): 405.08; Found (M + H): 405.0. HPLC Purity: 99.92% |
| 23 | 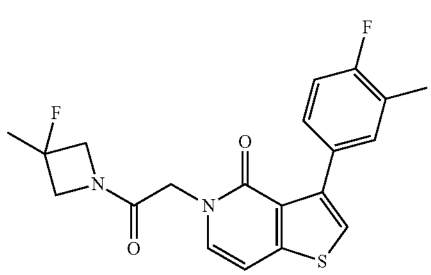 | 5-(2-(3-fluoro-3-methylazetidin-1-yl)-2-oxoethyl)-3-(4-fluoro-3-methyl-phenyl)thieno[3,2-c]pyridin-4(5H)-one | $^1$H NMR (400 MHz, DMSO-$d_6$) δ (ppm): 7.47-7.45 (m, 2H), 7.32 (d, J = 7.2 Hz, 1H), 7.24-7.23 (m, 1H), 7.08 (t, J = 9.6 Hz, 1H), 6.92 (d, J = 6.8 Hz, 1H), 4.59 (s, 2H), 4.37-4.24 (m, 2H), 3.95 (d, J = 10.8 Hz, 2H), 2.23 (s, 3H), 1.57 (d, J = 22.4 Hz, 3H). Calculated (M + H): 389.11; Found (M + H): 389.0. HPLC Purity: 99.62% |

Example 24: Preparation of 3-(4-chloro-3-(trifluoromethyl)phenyl)-5-(3-(3-fluoropyrrolidin-1-yl)-3-oxopropyl)thieno[3,2-c]pyridin-4(5H)-one

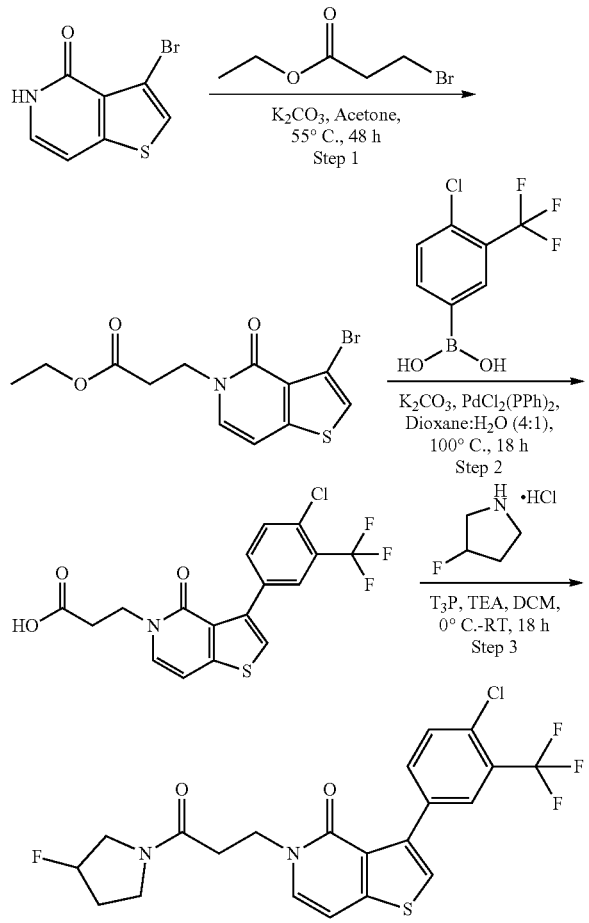

Step-1

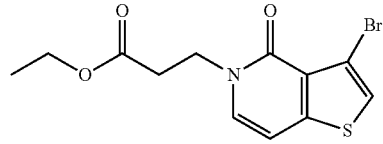 [SMILES: CCOC(=O)CCn1ccc2scc(Br)c2c1=O]

Preparation of ethyl 3-(3-bromo-4-oxothieno[3,2-c]pyridin-5(4H)-yl)propanoate

To a stirred solution of 3-bromothieno[3,2-c]pyridin-4(5H)-one (1 g, 4.34 mmol) in dry acetone (25 mL) at room temperature was added potassium carbonate (1.8 g, 13.03 mmol) followed by ethyl 3-bromopropanoate (1.1 mL, 8.69 mmol) and the reaction mixture was heated at 55° C. for 48 h. The reaction mixture was filtered and the filtrate was concentrated under vacuum. The crude product was purified by silica gel column chromatography using 1% methanol in dichloromethane to afford the title compound ethyl 3-(3-bromo-4-oxothieno[3,2-c]pyridin-5(4H)-yl)propanoate (0.14 g, 9% yield) as yellow liquid. Calculated (M+H): 329.97; Found (M+H): 330.0.

Step-2

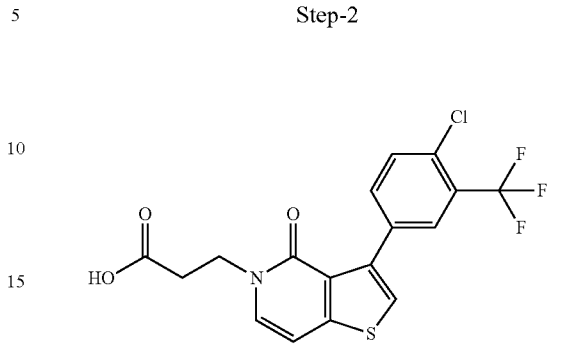

Preparation of 3-(3-(4-chloro-3-(trifluoromethyl)phenyl)-4-oxothieno[3,2-c]pyridin-5(4H)-yl)propanoic acid To a solution of ethyl 3-(3-bromo-4-oxothieno[3,2-c]pyridin-5(4H)-yl)propanoate (0.14 g, 0.42 mmol) and (4-chloro-3-(trifluoromethyl)phenyl)boronic acid (0.14 g, 0.63 mmol) in 1,4-dioxane:water mixture (10 mL, 4:1), potassium carbonate (0.176 g, 1.27 mmol) was added. Then the reaction purged with argon for 15 minutes. Then PdCl$_2$(PPh$_3$)$_2$ (0.029 g, 0.04 mmol) was added and the reaction mixture was stirred at 100° C. for 18 h. Then reaction mixture was diluted with ethyl acetate (100 mL) and washed with water (2×30 mL). The aqueous layer was separated and acidified with 1.5N hydrochloric acid at 0° C. The precipitated solid was filtered and dried under suction to afford the title compound 3-(3-(4-chloro-3-(trifluoromethyl)phenyl)-4-oxothieno[3,2-c]pyridin-5(4H)-yl)propanoic acid (0.06 g, 35% yield) as black solid. Calculated (M+H): 402.01; Found (M+H): 402.0.

Step-3

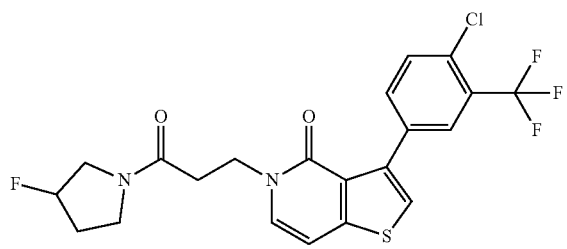 [SMILES: O=C(CCn1ccc2scc(-c3ccc(Cl)c(C(F)(F)F)c3)c2c1=O)N1CCC(F)C1]

Preparation of 3-(4-chloro-3-(trifluoromethyl)phenyl)-5-(3-(3-fluoropyrrolidin-1-yl)-3-oxopropyl)thieno[3,2-c]pyridin-4(5H)-one To a stirred solution of 3-(3-(4-chloro-3-(trifluoromethyl)phenyl)-4-oxothieno[3,2-c]pyridin-5(4H)-yl)propanoic acid (0.06 g, 0.14 mmol) and 3-fluoropyrrolidine hydrochloride (0.028 g, 0.22 mmol) in dichloromethane (12 mL) was added triethylamine (0.14 mL, 1.04 mmol) at room temperature. The reaction mixture was cooled to 0° C., 1-propanephosphonic anhydride solution (T$_3$P) (0.14 mL, 0.22 mmol, 50% in ethyl acetate) was added drop-wise and the reaction mixture was stirred at room temperature for 18 h. The reaction mixture was diluted with water (20 mL) and extracted with dichloromethane (2×60 mL). The combined organic layer was dried over anhydrous sodium sulfate, filtered and concentrated under vacuum. The crude product was purified by silica gel column chromatography using 1% methanol in dichloromethane to afford the title compound 3-(4-chloro-3-(trifluoromethyl)phenyl)-5-(3-(3-fluoropyrrolidin-1-yl)-3-oxopropyl)thieno[3,2-c]pyridin-4(5H)-one (0.03 g, 42% yield) as white solid. $^1$H NMR (400 MHz, DMSO-d$_6$) δ (ppm): 7.90 (s, 1H), 7.76 (d, J=8 Hz, 1H), 7.70-7.64 (m, 3H), 6.93 (d, J=7.2 Hz, 1H), 5.23-5.42 (m, 1H), 4.11 (brs, 2H), 3.55-3.52 (m, 2H), 3.42-3.32 (m, 1H), 3.30-3.26 (m, 1H), 2.69-2.64 (m, 2H), 2.30-2.20 (m, 2H), Calculated (M+H): 473.06, Found (M+H): 473.0, HPLC purity: 99.36%.

TABLE 3

The following compounds were prepared by the method described above:

| Ex. No. | Structure | IUPAC Name | Analytical Data |
|---|---|---|---|
| 25 | 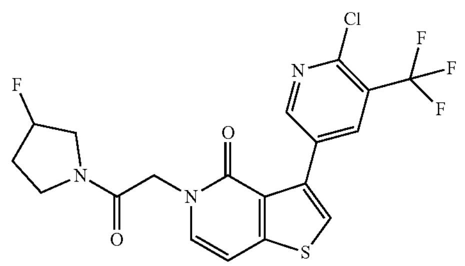 [SMILES: O=C(Cn1ccc2scc(-c3cnc(Cl)c(C(F)(F)F)c3)c2c1=O)N1CCC(F)C1] | 3-(6-chloro-5-(trifluoromethyl)pyridin-3-yl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 8.72 (d, J = 2.0 Hz, 1H), 8.36 (d, J = 2.0 Hz, 1H), 7.87 (s, 1H), 7.52 (dd, J = 1.6 Hz, 6.8 Hz, 1H), 6.99 (d, J = 7.2 Hz, 1H), 5.48-5.23 (m, 1H), 4.89-4.71 (m, 2H), 3.87-3.22 (m, 4H), 2.3-1.88 (m, 2H). Calculated (M + H): 460.04; Found (M + H): 460.0. HPLC purity: 99.2% |
| 26 | 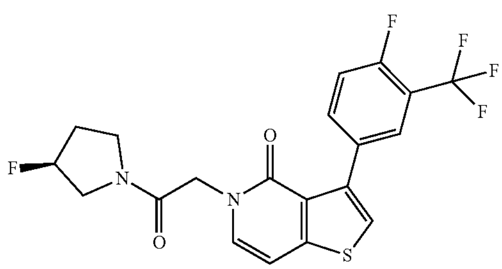 | (S)-3-(4-fluoro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.77 (d, J = 6.0 Hz, 2H), 7.49-7.45 (s, 1H), 6.94 (d, J = 7.6 Hz, 2H), 6.95 (d, J = 7.2 Hz, 1H), 5.48-5.23 (m, 1H), 4.88-4.69 (m, 2H), 3.86-3.35 (m, 4H), 2.3-1.91 (m, 2H). Calculated (M + H): 443.08; Found (M + H): 443.1; HPLC purity: 99.13% |
| 27 | 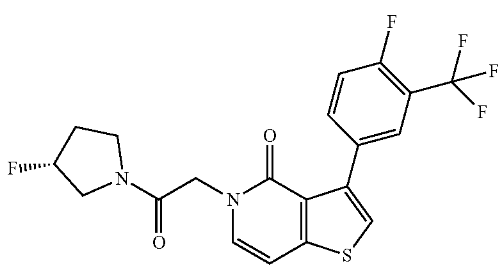 [SMILES: O=C(Cn1ccc2scc(-c3ccc(F)c(C(F)(F)F)c3)c2c1=O)N1CC[C@@H](F)C1] | (R)-3-(4-fluoro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.77 (d, J = 6.0 Hz, 2H), 7.65 (s, 1H), 7.5-7.45 (m, 2H), 6.94 (d, J = 7.2 Hz, 1H), 5.48-5.23 (m, 1H), 4.87-4.69 (m, 2H), 3.86-3.22 (m, 4H), 2.3-1.88 (m, 2H). Calculated (M + H): 443.08; Found (M + H): 443.1; HPLC purity: 99.67% |
| 28 | 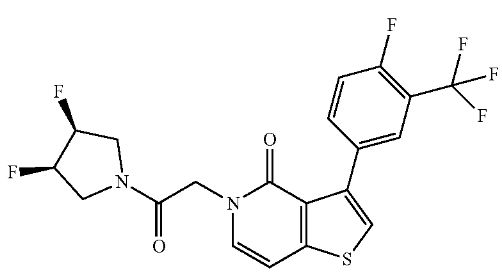 | 5-(2-((3S,4R)-3,4-difluoropyrrolidin-1-yl)-2-oxoethyl)-3-(4-fluoro-3-(trifluoromethyl)phenyl)thieno[3,2-c]pyridin-4(5H)-one | $^1$H NMR (400 MHz, DMSO-d$_6$) δ (ppm): 7.77 (d, J = 6.0 Hz, 2H), 7.66 (s, 1H), 7.5-7.46 (m, 2H), 6.95 (d, J = 7.6 Hz, 1H), 5.44-5.21 (m, 2H), 4.82-4.73 (m, 2H), 4.03-3.95 (m, 1H), 3.77-3.6 (m, 2H), 3.49-3.27 (m, 1H). Calculated (M + H): 461.07; Found (M + H): 461.1; HPLC purity: 99.82% |

TABLE 3-continued

The following compounds were prepared by the method described above:

| Ex. No. | Structure | IUPAC Name | Analytical Data |
|---|---|---|---|
| 29 | 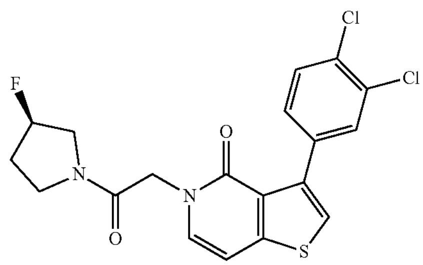 | (R)-3-(3,4-dichlorophenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.66 (s, 1H), 7.62 (s, 1H), 7.58 (d, J = 8.4 Hz, 1H), 7.48 (d, J = 7.2 Hz, 1H), 7.40 (d, J = 7.2 Hz, 1H), 6.94 (d, J = 6.8 Hz, 1H), 5.48-5.23 (m, 1H), 4.86-4.69 (m, 2H), 3.86-3.27 (m, 4H), 2.23-1.91 (m, 2H). Calculated (M + H): 425.02; Found (M + H): 425.0. HPLC purity: 98.98% |
| 30 | 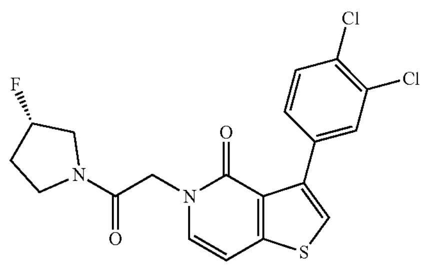 | (S)-3-(3,4-dichlorophenyl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.66 (d, J = 2 Hz, 1H), 7.62 (s, 1H), 7.58 (d, J = 8.4 Hz, 1H), 7.48 (d, J = 7.6 Hz, 1H), 7.41-7.38 (dd, J = 2.0 Hz, 8 Hz, 1H), 6.93 (d, J = 6.8 Hz, 1H), 5.48-5.23 (m, 1H),. 4.86-4.69 (m, 2H), 3.86-3.26 (m, 4H), 2.30-1.91 (m, 2H). Calculated (M + H): 425.02; Found (M + H): 425.0. HPLC purity: 97.66% |
| 31 | 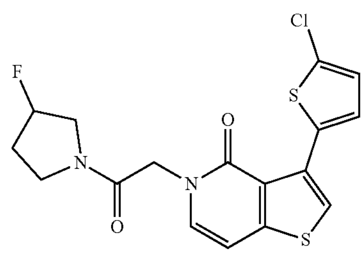 [SMILES: O=C(Cn1ccc2scc(-c3ccc(Cl)s3)c2c1=O)N1CCC(F)C1] | 3-(5-chlorothiophen-2-yl)-5-(2-(3-fluoropyrrolidin-1-yl)-2-oxoethyl)thieno[3,2-c]pyridin-4(5H)-one | $^1$H NMR (400 MHz, DMSO-d$_6$) δ (ppm): 7.73 (s, 1H), 7.49 (d, J = 7.2 Hz, 1H), 7.3 (d, J = 3.2 Hz, 1H), 7.03 (d, J = 4.0 Hz, 1H), 6.92 (d, J = 7.2 Hz, 1H), 5.50-5.25 (m, 1H), 4.88-4.71 (m, 2H), 3.88-3.27 (m, 4H), 2.26-1.96 (m, 2H). Calculated (M + H): 397.02; Found (M + H): 397.0. HPLC purity: 97.66% |
| 32 | 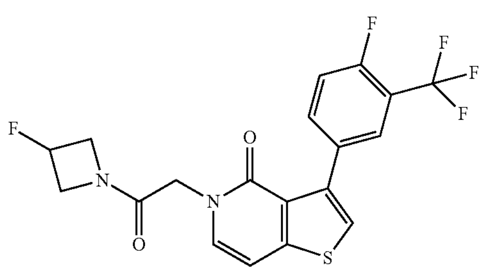 [SMILES: O=C(Cn1ccc2scc(-c3ccc(F)c(C(F)(F)F)c3)c2c1=O)N1CC(F)C1] | 3-(4-fluoro-3-(trifluoromethyl)phenyl)-5-(2-(3-fluoroazetidin-1-yl)-2-oxoethyl)thieno[3,2-c]pyridin-4(5H)-one | $^1$H NMR (400 MHz, DMSO-d$_6$) δ (ppm): 7.79-7.76 (m, 2H), 7.66 (s, 1H), 7.51-7.46 (m, 2H), 6.95 (d, J = 7.2 Hz, 1H), 5.49-5.33 (m, 1H), 4.59-4.48 (m, 3H), 4.32-4.13 (m, 2H), 3.94-3.85 (m, 1H). Calculated (M + H): 429.06; Found (M + H): 429.0; HPLC purity: 99.82%. |
| 33 | 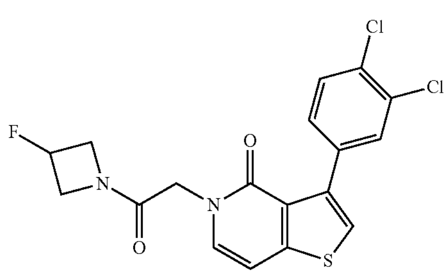 | 3-(3,4-dichlorophenyl)-5-(2-(3-fluoroazetidin-1-yl)-2-oxoethyl)thieno[3,2-c]pyridin-4(5H)-one | $^1$H NMR (400 MHz, DMSO-d$_6$) δ (ppm): 7.66 (s, 1H), 7.62 (s, 1H), 7.59 (d, J = 8.4 Hz, 1H), 7.48 (d, J = 7.6 Hz, 1H), 7.40 (d, J = 8.4 Hz, 1H), 6.94 (d, J = 7.2 Hz, 1H), 5.48-5.34 (m, 1H), 4.59-4.48 (m, 3H), 4.32-4.11 (m, 2H), 3.94-3.85 (m, 1H). Calculated (M + H): 411.01; Found (M + H): 411.0; HPLC purity: 99.21% |

TABLE 3-continued

The following compounds were prepared by the method described above:

| Ex. No. | Structure | IUPAC Name | Analytical Data |
|---|---|---|---|
| 34 | 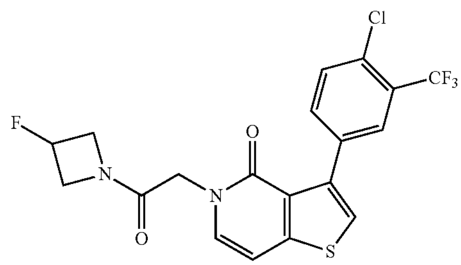 [SMILES: O=C(Cn1ccc2scc(-c3ccc(Cl)c(C(F)(F)F)c3)c2c1=O)N1CC(F)C1] | 3-(4-chloro-3-(trifluoromethyl)phenyl)-5-(2-(3-fluoroazetidin-1-yl)-2-oxoethyl)thieno[3,2-c]pyridin-4(5H)-one | $^1$H NMR (400 MHz, DMSO-d$_6$) δ (ppm): 7.86 (s, 1H), 7.73-7.68 (m, 3H), 7.49 (d, J = 7.2 Hz, 1H), 6.96 (d, J = 7.6 Hz, 1H), 5.48-5.33 (m, 1H), 4.59 (s, 2H), 4.57-4.49 (m, 1H), 4.32-4.14 (m, 2H), 3.94-3.88 (m, 1H). Calculated (M + H): 445.03; Found (M+H): 445.0; HPLC purity: 99.19% |
| 35 | 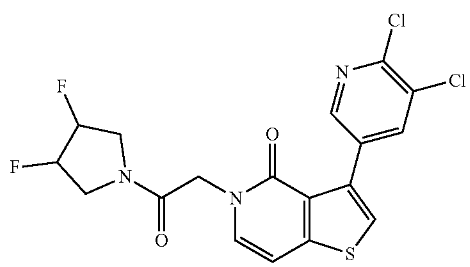 [SMILES: O=C(Cn1ccc2scc(-c3cnc(Cl)c(Cl)c3)c2c1=O)N1CC(F)C(F)C1] | 3-(5,6-dichloropyridin-3-yl)-5-(2-(3,4-difluoropyrrolidin-1-yl)-2-oxoethyl)thieno[3,2-c]pyridin-4(5H)-one | $^1$H-NMR (DMSO-d$_6$, 400 MHz) δ (ppm): 8.43 (s, 1H), 8.19 (s, 1H), 7.79 (s, 1H), 7.49 (d, J = 7.2 Hz, 1H), 6.99 (d, J = 7.2 Hz, 1H), 5.45-5.22 (m, 2H), 4.84-4.74 (m, 2H), 4.04-3.78 (m, 1H), 3.74-3.61 (m, 2H), 3.50-3.27 (m, 1H). Calculated (M + H): 444.01, Found (M + H): 444.0. HPLC purity: 99.56% |
| 36 | 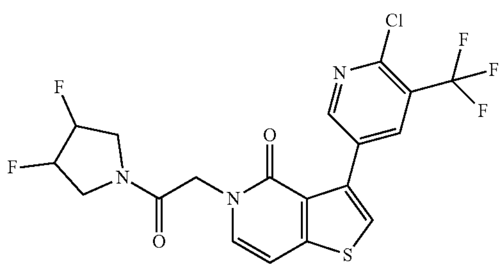 [SMILES: O=C(Cn1ccc2scc(-c3cnc(Cl)c(C(F)(F)F)c3)c2c1=O)N1CC(F)C(F)C1] | 3-(6-chloro-5-(trifluoromethyl)pyridin-3-yl)-5-(2-(3,4-difluoro-pyrrolidin-1-yl)-2-oxoethyl)thieno[3,2-c]pyridin-4(5H)-one | $^1$H-NMR (DMSO-d$_6$, 400 MHz) δ (ppm): 8.73 (s, 1H), 8.36 (s, 1H), 7.87 (s, 1H), 7.50 (d, J = 6.8 Hz, 1H), 7.00 (d, J = 6.8 Hz, 1H), 5.45-5.22 (m, 2H), 4.84-4.74 (m, 2H), 4.04-3.96 (m, 1H), 3.78-3.61 (m, 2H), 3.60-3.27 (m, 1H). Calculated (M + H): 478.03, Found (M + H): 478.0. HPLC purity: 99.62% |
| 37 | 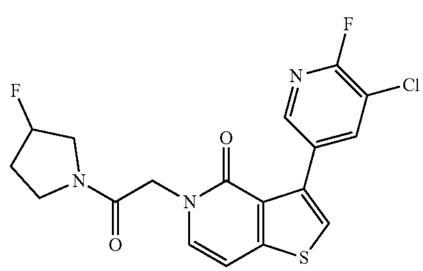 [SMILES: O=C(Cn1ccc2scc(-c3cnc(F)c(Cl)c3)c2c1=O)N1CCC(F)C1] | 3-(5-chloro-6-fluoropyridin-3-yl)-5-(2-(3-fluoropyrrolidin-1-yl)-2-oxoethyl)thieno[3,2-c]pyridin-4(5H)-one | $^1$H-NMR (DMSO-d$_6$, 400 MHz) δ (ppm): 8.25-8.23 (m, 2H), 7.75 (s, 1H), 7.51 (d, J = 7.2 Hz, 1H), 6.98 (d, J = 7.6 Hz, 1H), 5.49-5.24 (m, 1H), 4.89-4.71 (m, 2H), 3.87-3.39 (m, 4H), 2.30-1.90 (m, 2H). Calculated (M + H): 410.05, Found (M + H): 410.2. HPLC purity: 99.69% |
| 38 | 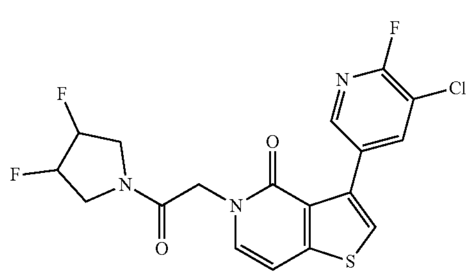 [SMILES: O=C(Cn1ccc2scc(-c3cnc(F)c(Cl)c3)c2c1=O)N1CC(F)C(F)C1] | 3-(5-chloro-6-fluoropyridin-3-yl)-5-(2-(3,4-difluoropyrrolidin-1-yl)-2-oxoethyl)thieno[3,2-c]pyridin-4(5H)-one | $^1$H-NMR (DMSO-d$_6$, 400 MHz) δ (ppm): 8.25-8.23 (m, 2H), 7.76 (s, 1H), 7.49 (d, J = 7.6 Hz, 1H), 6.98 (d, J = 6.8 Hz, 1H), 5.45-5.22 (m, 2H), 4.85-4.75 (m, 2H), 4.05-3.96 (m, 1H), 3.78-3.61 (m, 2H), 3.51-3.42 (m, 1H). Calculated (M + H): 428.04, Found (M + H): 428.0. HPLC purity: 99.14% |

TABLE 3-continued

The following compounds were prepared by the method described above:

| Ex. No. | Structure | IUPAC Name | Analytical Data |
|---|---|---|---|
| 39 | 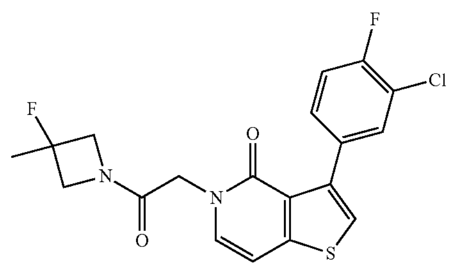 [SMILES: CC1(F)CN(C(=O)Cn2ccc3scc(-c4ccc(F)c(Cl)c4)c3c2=O)C1] | 3-(3-chloro-4-fluorophenyl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm): 7.62-7.59 (m, 2H), 7.48 (d, J = 6.8 Hz, 1H), 7.44-7.35 (m, 2H), 6.94 (d, J = 6.8 Hz, 1H), 4.61 (s, 2H), 4.38-4.25 (m, 2H), 3.95 (d, J = 18.8 Hz, 2H), 1.57 (d, J = 21.6 Hz, 3H). Calculated (M + H): 409.05; Found (M + H): 409.0. HPLC purity: 98.35% |
| 40 | 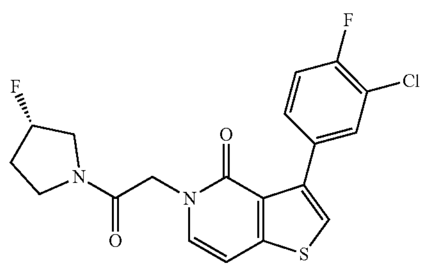 [SMILES: O=C(Cn1ccc2scc(-c3ccc(F)c(Cl)c3)c2c1=O)N1CC[C@H](F)C1] | (S)-3-(3-chloro-4-fluorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.62-7.58 (m, 2H), 7.48 (s, J = 7.2 Hz, 1H), 7.43-7.35 (m, 2H), 6.93 (d, J = 7.2 Hz, 1H), 5.48-5.24 (m, 1H), 4.87-4.70 (m, 2H), 3.83-3.27 (m, 4H), 2.30-2.05 (m, 2H). Calculated (M + H): 409.05; Found (M + H): 409.0. HPLC purity: 98.01% |
| 41 | 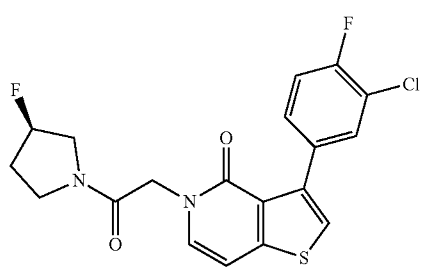 [SMILES: O=C(Cn1ccc2scc(-c3ccc(F)c(Cl)c3)c2c1=O)N1CC[C@@H](F)C1] | (R)-3-(3-chloro-4-fluorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.62-7.58 (m, 2H), 7.48 (s, J = 7.2 Hz, 1H), 7.43-7.35 (m, 2H), 6.94 (d, J = 6.8 Hz, 1H), 5.49-5.24 (m, 1H), 4.87-4.70 (m, 2H), 3.83-3.27 (m, 4H), 2.30-2.07 (m, 2H). Calculated (M + H): 409.05; Found (M + H): 409.0. HPLC purity: 98.53% |
| 42 | 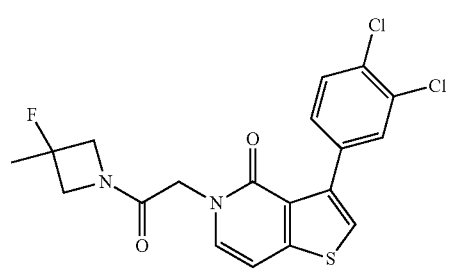 [SMILES: CC1(F)CN(C(=O)Cn2ccc3scc(-c4ccc(Cl)c(Cl)c4)c3c2=O)C1] | 3-(3,4-dichlorophenyl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm): 7.67 (s, 1H), 7.64 (s, 1H), 7.60 (d, J = 8.4 Hz, 1H), 7.49 (d, J = 6 Hz, 1H), 7.40 (d, J = 8 Hz, 1H), 6.96 (d, J = 6.8 Hz, 1H), 4.61 (s, 2H), 4.38-4.25 (m, 2H), 3.95 (d, J = 19.6 Hz, 2H), 1.57 (d, J = 22 Hz, 3H). Calculated (M + H): 425.02; Found (M + H): 425.0. HPLC purity: 98.33% |
| 43 | 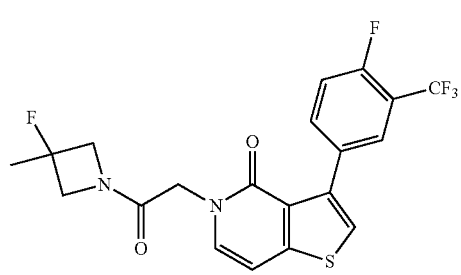 [SMILES: CC1(F)CN(C(=O)Cn2ccc3scc(-c4ccc(F)c(C(F)(F)F)c4)c3c2=O)C1] | 3-(4-fluoro-3-(trifluoromethyl)phenyl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm): 7.80-7.78 (m, 2H), 7.67 (s, 1H), 7.51-7.47 (m, 2H), 6.97 (d, J = 6.8 Hz, 1H), 4.60 (s, 2H), 4.38-4.25 (m, 2H), 4.00-3.92 (m, 2H), 1.56 (d, J = 22 Hz, 3H). Calculated (M + H): 443.08; Found (M + H): 443.1. HPLC purity: 99.55% |

TABLE 3-continued

The following compounds were prepared by the method described above:

| Ex. No. | Structure | IUPAC Name | Analytical Data |
|---|---|---|---|
| 44 | 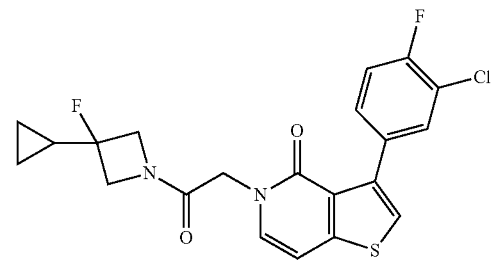 [SMILES: O=C(Cn1ccc2scc(-c3ccc(F)c(Cl)c3)c2c1=O)N1CC(F)(C2CC2)C1] | 3-(3-chloro-4-fluorophenyl)-5-(2-(3-cyclopropyl-3-fluoroazetidin-1-yl)-2-oxoethyl)thieno[3,2-c]pyridin-4(5H)-one | $^1$H NMR (400 MHz, DMSO-$d_6$) δ (ppm); 7.62-7.59 (m, 2H), 7.49 (d, J = 6.8 Hz, 1H), 7.42-7.35 (m, 2H), 6.94 (d, J = 7.2 Hz, 1H), 4.60-4.58 (m, 2H), 4.25-4.18 (m, 2H), 3.89-3.84 (m, 2H), 1.37 (s, 1H), 0.58 (d, J = 7.6 Hz, 2H), 0.48 (s, 1H), 0.39 (s, 1H). Calculated (M + H): 435.07; Found (M + H): 435.1. HPLC purity 98.81% |
| 45 | 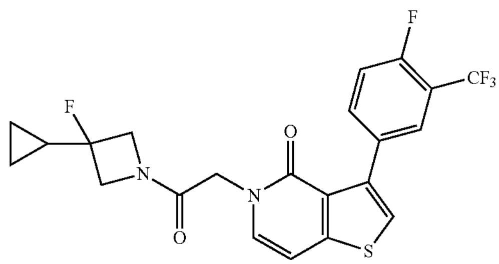 [SMILES: O=C(Cn1ccc2scc(-c3ccc(F)c(C(F)(F)F)c3)c2c1=O)N1CC(F)(C2CC2)C1] | 5-(2-(3-cyclopropyl-3-fluoroazetidin-1-yl)-2-oxoethyl)-3-(4-fluoro-3-(trifluoromethyl)phenyl)thieno[3,2-c]pyridin-4(5H)-one | $^1$H NMR (400 MHz, DMSO-$d_6$) δ (ppm); 7.80-7.78 (m, 2H), 7.66 (s, 1H), 7.51-7.46 (m, 2H), 6.96 (d, J = 7.2 Hz, 1H), 4.63-4.54 (m, 2H), 4.27-4.15 (m, 2H), 3.91-3.79 (m, 2H), 1.36 (s, 1H), 0.57 (d, J = 7.2 Hz, 2H), 0.47 (s, 1H), 0.38 (s, 1H). Calculated (M + H): 469.09; Found (M + H): 469.1. HPLC purity 99.54% |
| 46 | 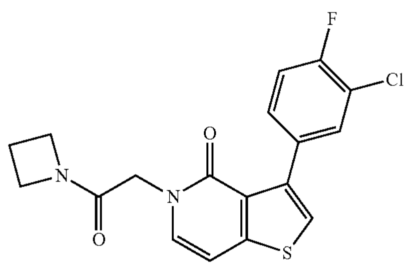 [SMILES: O=C(Cn1ccc2scc(-c3ccc(F)c(Cl)c3)c2c1=O)N1CCC1] | 5-(2-(azetidin-1-yl)-2-oxoethyl)-3-(3-chloro-4-fluoro-phenyl)thieno[3,2-c]pyridin-4(5H)-one | $^1$H NMR (400 MHz, DMSO-$d_6$) δ (ppm): 7.61 (d, J = 7.2 Hz, 1H), 7.58 (s, 1H), 7.47 (d, J = 7.2 Hz, 1H), 7.40-7.36 (m, 2H), 6.93 (d, J = 7.2 Hz, 1H), 4.53 (s, 2H), 4.18 (t, J = 7.6 Hz, 2H), 3.85 (t, J = 7.2 Hz, 2H), 2.25-2.21 (m, 2H). Calculated (M + H): 377.04, Found (M + H): 377.0, HPLC purity: 97.0% |
| 47 | 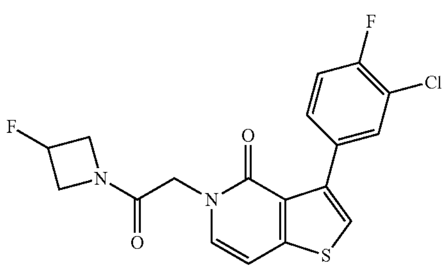 [SMILES: O=C(Cn1ccc2scc(-c3ccc(F)c(Cl)c3)c2c1=O)N1CC(F)C1] | 3-(3-chloro-4-fluorophenyl)-5-(2-(3-fluoroazetidin-1-yl)-2-oxoethyl)thieno[3,2-c]pyridin-4(5H)-one | $^1$H NMR (400 MHz, DMSO-$d_6$) δ (ppm): 7.62-7.60 (m, 1H), 7.59 (s, 1H), 7.48 (d, J = 7.2 Hz, 1H), 7.44-7.35 (m, 2H), 6.94 (d, J = 7.2 Hz, 1H), 5.50-5.34 (m, 1H), 4.602 (s, 2H), 4.55-4.32 (m, 1H), 4.30-4.15 (m, 2H), 3.95-3.86 (m, 1H); Calculated (M + H): 395.04, Found (M + H): 395.0, HPLC purity: 98.2% |
| 48 | 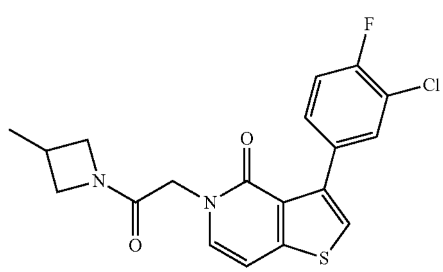 [SMILES: CC1CN(C(=O)Cn2ccc3scc(-c4ccc(F)c(Cl)c4)c3c2=O)C1] | 3-(3-chloro-4-fluorophenyl)-5-(2-(3-methylazetidin-1-yl)-2-oxoethyl)thieno[3,2-c]pyridin-4(5H)-one | $^1$H NMR (400 MHz, DMSO-$d_6$) δ (ppm): 7.61 (d, J = 7.2 Hz, 1H), 7.58 (s, 1H), 7.47 (d, J = 6.8 Hz, 1H), 7.41-7.35 (m, 2H), 6.93 (d, J = 6.8 Hz, 1H), 4.54 (s, 2H), 4.28 (t, J = 8.4 Hz, 1H), 3.95 (t, J = 8.8 Hz, 1H), 3.74 (t, J = 5.6 Hz, 1H), 3.41 (t, J = 6.0 Hz, 1H), 2.70-2.65 (m, 1H), 1.18 (d, J = 7.2 Hz, 3H). Calculated (M + H): 391.06, Found (M + H): 391.1, HPLC purity: 97.84% |

TABLE 3-continued

The following compounds were prepared by the method described above:

| Ex. No. | Structure | IUPAC Name | Analytical Data |
|---|---|---|---|
| 49 | 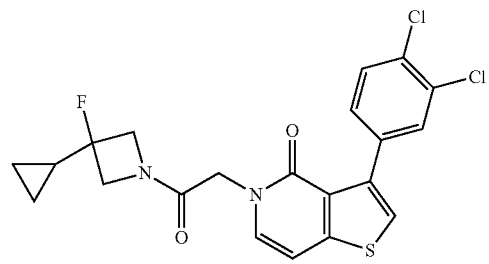 [SMILES: O=C(Cn1ccc2scc(-c3ccc(Cl)c(Cl)c3)c2c1=O)N1CC(F)(C2CC2)C1] | 5-(2-(3-cyclopropyl-3-fluoroazetidin-1-yl)-2-oxoethyl)-3-(3,4-dichlorophenyl)thieno[3,2-c]pyridin-4(5H)-one | $^1$H NMR (400 MHz, DMSO-d$_6$) δ (ppm): 7.67 (d, J = 2.0 Hz, 1H), 7.63 (s, 1H), 7.59 (d, J = 8 Hz, 1H), 7.50 (d, J = 7.6 Hz, 1H), 7.40 (dd, J = 2.4 Hz, 8.4 Hz, 1H), 6.95 (d, J = 7.2 Hz, 1H), 4.64-4.55 (m, 2H), 4.28-4.16 (m, 2H), 3.89-3.80 (m, 2H), 1.42-1.33 (m, 1H), 0.59-0.39 (m, 4H). Calculated (M + H): 451.04, Found (M + H): 451.0, HPLC purity: 98.27% |
| 50 | 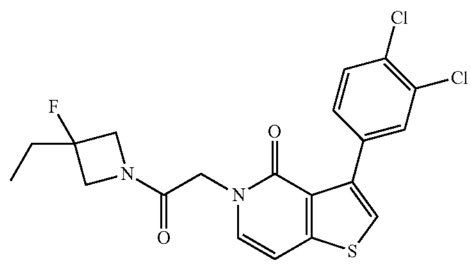 | 3-(3,4-dichlorophenyl)-5-(2-(3-ethyl-3-fluoroazetidin-1-yl)-2-oxoethyl)thieno[3,2-c]pyridin-4(5H)-one | $^1$H NMR (400 MHz, DMSO-d$_6$) δ (ppm): 7.67-7.58 (m, 3H), 7.49 (d, J = 9.6 Hz, 1H), 7.41 (d, J = 8.4 Hz, 1H), 6.95 (d, J = 7.2 Hz, 1H), 4.61 (s, 2H), 4.36-4.24 (m, 2H), 4.00-3.86 (m, 2H), 1.91-1.80 (m, 2H), 0.90 (t, J = 7.2 Hz, 3H). Calculated (M + H): 438.04; Found (M + H): 438.0. HPLC purity: 98.83% |
| 51 | 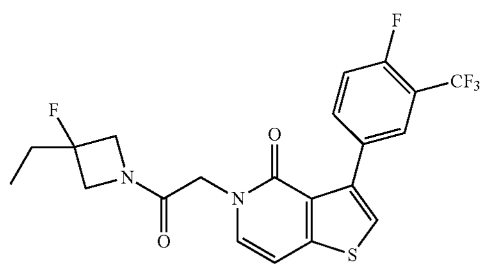 [SMILES: CCC1(F)CN(C(=O)Cn2ccc3scc(-c4ccc(F)c(C(F)(F)F)c4)c3c2=O)C1] | 5-(2-(3-ethyl-3-fluoroazetidin-1-yl)-2-oxoethyl)-3-(4-fluoro-3-(trifluoromethyl)phenyl)thieno[3,2-c]pyridin-4(5H)-one | $^1$H NMR (400 MHz, DMSO-d$_6$) δ (ppm): 7.78 (s, 2H), 7.66 (s, 1H), 7.49 (t, J = 7.6 Hz, 2H), 7.96 (d, J = 7.6 Hz, 1H), 4.60 (s, 2H), 4.36-4.24 (m, 2H), 3.90-3.74 (m, 2H), 1.90-1.79 (m, 2H), 0.89 (t, J = 7.6 Hz, 3H). Calculated (M + H): 457.09; Found (M + H): 457.1. HPLC purity: 99.01% |
| 52 | 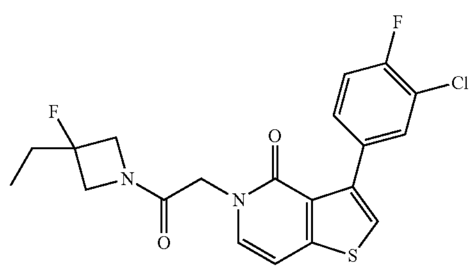 [SMILES: CCC1(F)CN(C(=O)Cn2ccc3scc(-c4ccc(F)c(Cl)c4)c3c2=O)C1] | 3-(3-chloro-4-fluorophenyl)-5-(2-(3-ethyl-3-fluoroazetidin-1-yl)-2-oxoethyl)thieno[3,2-c]pyridin-4(5H)-one | $^1$H NMR (400 MHz, DMSO-d$_6$) δ (ppm): 7.62-7.59 (m, 2H), 7.48 (d, J = 7.2 Hz, 1H), 7.41-7.35 (m, 2H), 6.94 (d, J = 7.2 Hz, 1H), 4.61 (s, 2H), 4.40-4.24 (m, 2H), 4.00-3.86 (m, 2H), 1.91-1.80 (m, 2H), 0.92-0.88 (m, 3H). Calculated (M + H): 423.07; Found (M + H): 423.0. HPLC purity: 99.94% |
| 53 | 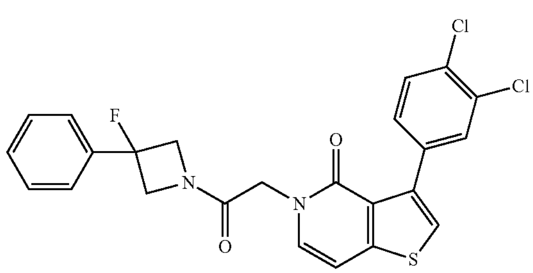 [SMILES: O=C(Cn1ccc2scc(-c3ccc(Cl)c(Cl)c3)c2c1=O)N1CC(F)(c2ccccc2)C1] | 3-(3,4-dichlorophenyl)-5-(2-(3-fluoro-3-phenylazetidin-1-yl)-2-oxoethyl)thieno[3,2-c]pyridin-4(5H)-one | $^1$H NMR (400 MHz, DMSO-d$_6$) δ (ppm): 7.68 (s, 1H), 7.65 (s, 1H), 7.60 (d, J = 8.0 Hz, 1H), 7.55-7.51 (m, 3H), 7.42 (d, J = 6.4 Hz, 4H), 6.97 (d, J = 7.2 Hz, 1H), 4.82-4.68 (m, 4H), 4.33 (d, J = 21.2 Hz, 2H). Calculated (M + H): 487.04; Found (M + 1): 487.0. HPLC purity 98.15% |

TABLE 3-continued

The following compounds were prepared by the method described above:

| Ex. No. | IUPAC Name | Analytical Data |
|---|---|---|
| 54 | 3-(4-fluoro-3-(trifluoromethyl)phenyl)-5-(2-(3-fluoro-3-phenyl-azetidin-1-yl)-2-oxoethyl)thieno[3,2-c]pyridin-4(5H)-one | $^1$H NMR (400 MHz, DMSO-d$_6$) δ (ppm); 7.81-7.79 (m, 2H), 7.67 (s, 1H), 7.54-7.41 (m, 7H), 6.98 (d, J = 7.6 Hz, 1H), 4.80-4.69 (m, 4H), 4.33 (d, J = 21.6 Hz, 2H). Calculated (M + H): 505.09; Found (M +1): 505.1. HPLC purity 99.91% |
| 55 | 3-(4-fluoro-3-(trifluoromethyl)phenyl)-5-(2-(3-hydroxy-3-methylazetidin-1-yl)-2-oxoethyl)thieno[3,2-c]pyridin-4(5H)-one | $^1$H NMR (400 MHz, DMSO-d$_6$) δ (ppm): 7.78 (d, J = 6.0 Hz, 2H), 7.65 (s, 1H), 7.48 (s, 2H), 6.95 (d, J = 7.2 Hz, 1H), 5.66 (s, 1H), 4.57 (s, 2H), 4.04-4.00 (m, 2H), 3.71-3.68 (m, 2H), 1.35 (s, 3H). Calculated (M + H): 441.08; Found (M + H): 441.1. HPLC purity: 99.91% |
| 56 | 2-(3-(3-chloro-4-fluorophenyl)-4-oxothieno[3,2-c]pyridin-5(4H)-yl)-N-(2,2,2-trifluoro-ethyl)acetamide | $^1$H NMR (400 MHz, DMSO-d$_6$) δ (ppm): 8.81 (t, J = 6.4 Hz, 1H), 7.63-7.54 (m, 3H), 7.48-7.35 (m, 2H), 6.94 (d, J = 7.2 Hz, 1H), 4.65 (s, 2H), 3.94-3.85 (m, 2H). Calculated (M + H): 419.02; Found (M + H): 419.0. HPLC Purity: 98.32% |
| 57 | 3-(3-chloro-4-fluorophenyl)-5-(2-(3-fluoro-3-phenylazetidin-1-yl)-2-oxoethyl)thieno[3,2-c]pyridin-4(5H)-one | $^1$H NMR (400 MHz, DMSO-d$_6$) δ (ppm); 7.64-7.60 (m, 2H), 7.53-7.51 (m, 3H), 7.43-7.36 (m, 5H), 6.96 (d, J = 7.2 Hz, 1H), 4.81-4.69 (m, 4H), 4.33 (d, J = 21.2 Hz, 2H). Calculated (M + H): 471.07; Found (M + 1): 471.2. HPLC purity 99.72% |
| 58 | 3-(3-chloro-4-fluorophenyl)-5-(2-(3-hydroxy-3-methylazetidin-1-yl)-2-oxoethyl)thieno[3,2-c]pyridin-4(5H)-one | $^1$H NMR (400 MHz, DMSO-d$_6$) δ (ppm); 7.61 (d, J = 7.6 Hz, 1H), 7.58 (s, 1H), 7.48 (d, J = 7.6 Hz, 1H), 7.41-7.35 (m, 2H), 6.93 (d, J = 7.2 Hz, 1H), 5.67 (s, 1H), 4.57 (s, 2H), 4.04-3.99 (m, 2H), 3.72-3.66 (m, 2H), 1.36 (s, 3H). Calculated (M + H): 407.06; Found (M + 1): 407.0. HPLC purity 98.70% |

TABLE 3-continued

The following compounds were prepared by the method described above:

| Ex. No. | Structure | IUPAC Name | Analytical Data |
|---|---|---|---|
| 59 | 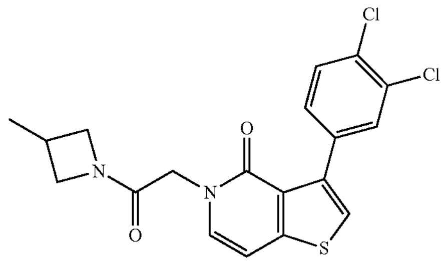 | 3-(3,4-dichlorophenyl)-5-(2-(3-methylazetidin-1-yl)-2-oxoethyl)thieno[3,2-c]pyridin-4(5H)-one | $^1$H NMR (400 MHz, DMSO-$d_6$) δ (ppm): 7.66 (d, J = 2 Hz, 1H), 7.62 (s, 1H), 7.60 (d, J = 8.4 Hz, 1H), 7.48 (d, J = 12 Hz, 1H), 7.41-7.39 (m, 1H), 6.93 (d, J = 7.2 Hz, 1H), 4.54 (t, J = 16.4 Hz, 2H), 4.28 (t, J = 8.4 Hz, 1H), 3.95 (t, J = 8.8 Hz, 1H), 3.75-3.72 (m, 1H), 3.42-3.38 (m, 1H), 2.74-2.65 (m, 1H), 1.17 (d, J = 6.8 Hz, 3H). Calculated (M + H): 407.03; Found (M + H): 407.0. HPLC purity: 99.10% |
| 60 | 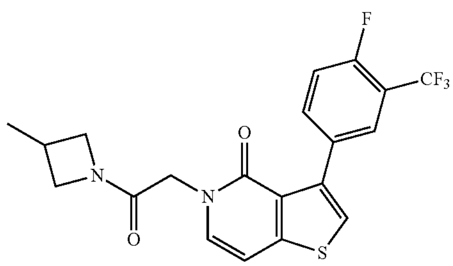 | 3-(4-fluoro-3-(trifluoromethyl)phenyl)-5-(2-(3-methylazetidin-1-yl)-2-oxoethyl)thieno[3,2-c]pyridin-4(5H)-one | $^1$H NMR (400 MHz, DMSO-$d_6$) δ (ppm): 7.79-7.78 (m, 2H), 7.65 (s, 1H), 7.51-7.47 (m, 2H), 6.95 (d, J = 6.8 Hz, 1H), 4.54 (s, 2H), 4.28 (t, J = 8.4 Hz, 1H), 3.95 (t, J = 8.8 Hz, 1H), 3.74 (t, J = 6 Hz, 1H), 3.42-3.38 (m, 1H), 2.70-2.65 (m, 1H), 1.17 (d, J = 6.4 Hz, 3H). Calculated (M + H): 425.09; Found (M + H): 425.1. HPLC purity: 99.44% |
| 61 | 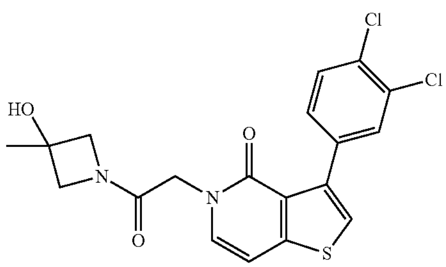 | 3-(3,4-dichlorophenyl)-5-(2-(3-hydroxy-3-methylazetidin-1-yl)-2-oxoethyl)thieno[3,2-c]pyridin-4(5H)-one | $^1$H NMR (400 MHz, DMSO-$d_6$) δ (ppm): 7.66-7.58 (m, 3H), 7.48 (d, J = 7.2 Hz, 1H), 7.40 (d, J = 6.4 Hz, 1H), 6.94 (d, J = 7.2 Hz, 1H), 5.67 (s, 1H), 4.57 (s, 2H), 4.04-3.98 (m, 2H), 3.72-3.66 (m, 2H), 1.36 (s, 3H). Calculated (M + H): 423.03; Found (M + H): 423.0. HPLC purity: 99.64% |
| 62 | 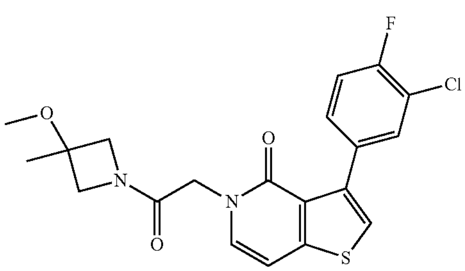 [SMILES: COC1(C)CN(C(=O)Cn2ccc3scc(-c4ccc(F)c(Cl)c4)c3c2=O)C1] | 3-(3-chloro-4-fluorophenyl)-5-(2-(3-methoxy-3-methylazetidin-1-yl)-2-oxoethyl)thieno[3,2-c]pyridin-4(5H)-one | $^1$H NMR (400 MHz, DMSO-$d_6$) δ (ppm): 7.62-7.58 (m, 2H), 7.48 (s, J = 6.8 Hz, 1H), 7.41-7.35 (m, 2H), 6.93 (d, J = 7.2 Hz, 1H), 4.59 (s, 2H), 4.13 (d, J = 7.2 Hz, 1H), 3.99 (d, J = 8.8 Hz, 1H), 3.77 (d, J = 9.6 Hz, 1H), 3.64 (d, J = 10.0 Hz, 1H), 3.15 (s, 3H), 1.40 (s, 3H). Calculated (M + H): 421.07; Found (M + H): 421.1. HPLC purity: 99.86% |
| 63 | 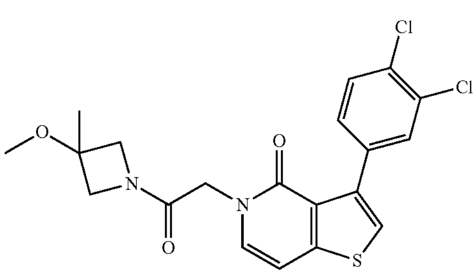 [SMILES: COC1(C)CN(C(=O)Cn2ccc3scc(-c4ccc(Cl)c(Cl)c4)c3c2=O)C1] | 3-(3,4-dichlorophenyl)-5-(2-(3-methoxy-3-methylazetidin-1-yl)-2-oxoethyl)thieno[3,2-c]pyridin-4(5H)-one | $^1$H NMR (400 MHz, DMSO-$d_6$) δ (ppm): 7.67 (s, 1H), 7.63 (s, 1H), 7.60 (d, J = 8.4 Hz, 1H), 7.49 (d, J = 6.8 Hz, 1H), 7.41 (d, J = 7.6 Hz, 1H), 6.95 (d, J = 7.2 Hz, 1H), 4.59 (s, 2H), 4.13 (d, J = 8.8 Hz, 1H), 4.99 (d, J = 8.8 Hz, 1H), 3.78 (d, J = 9.6 Hz, 1H), 3.65 (d, J = 9.6 Hz, 1H), 3.16 (s, 3H), 1.40 (s, 3H). Calculated (M + H): 437.04; Found (M + H): 437.0. HPLC Purity: 98.42% |

TABLE 3-continued

The following compounds were prepared by the method described above:

| Ex. No. | Structure | IUPAC Name | Analytical Data |
|---|---|---|---|
| 64 | 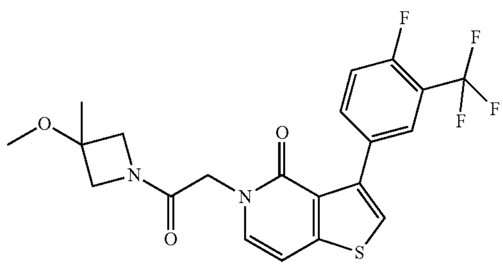 [SMILES: COC1(C)CN(C(=O)Cn2ccc3scc(-c4ccc(F)c(C(F)(F)F)c4)c3c2=O)C1] | 3-(4-fluoro-3-(tri-fluoromethyl)phenyl)-5-(2-(3-methoxy-3-methylazetidin-1-yl)-2-oxoethyl)thieno[3,2-c]pyridin-4(5H)-one | $^1$H NMR (400 MHz, DMSO-d$_6$) δ (ppm): 7.80-7.78 (m, 2H), 7.66 (s, 1H), 7.51-7.47 (m, 2H), 6.96 (d, J = 7.2 Hz, 1H), 4.59 (s, 2H), 4.13 (d, J = 8.8 Hz, 1H), 3.99 (d, J = 8.8 Hz, 1H), 3.78 (d, J = 9.6 Hz, 1H), 3.64 (d, J = 10.0 Hz, 1H), 3.15 (s, 3H), 1.39 (s, 3H). Calculated (M + H): 455.1; Found (M + H): 455.1. HPLC Purity: 98.94% |
| 65 | 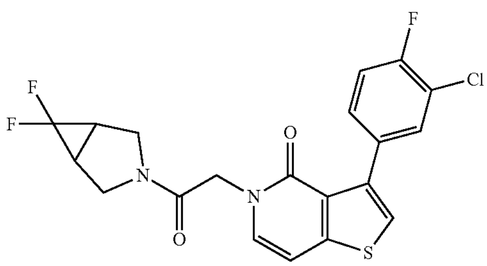 [SMILES: O=C(Cn1ccc2scc(-c3ccc(F)c(Cl)c3)c2c1=O)N1CC2C(C1)C2(F)F] | 3-(3-chloro-4-fluorophenyl)-5-(2-(6,6-difluoro-3-azabicyclo[3.1.0]hexan-3-yl)-2-oxoethyl)thieno[3,2-c]pyridin-4(5H)-one | $^1$H NMR (400 MHz, DMSO-d$_6$) δ (ppm); 7.62-7.58 (m, 2H), 7.46-7.35 (m, 3H), 6.92 (d, J = 7.2 Hz, 1H), 4.72 (s, 2H), 3.88 (s, 2H), 3.68-3.57 (m, 2H), 2.71-2.53 (m, 2H). Calculated (M + H): 439.04; Found (M + 1): 439.0. HPLC purity 99.01% |
| 66 | 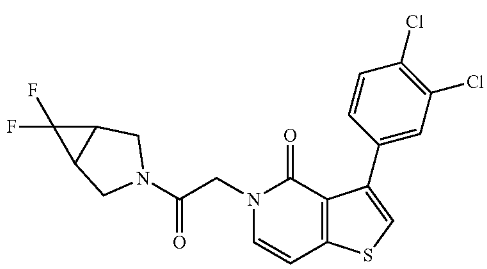 [SMILES: O=C(Cn1ccc2scc(-c3ccc(Cl)c(Cl)c3)c2c1=O)N1CC2C(C1)C2(F)F] | 3-(3,4-dichlorophenyl)-5-(2-(6,6-difluoro-3-azabicyclo[3.1.0]hexan-3-yl)-2-oxoethyl)thieno[3,2-c]pyridin-4(5H)-one | $^1$H NMR (400 MHz, DMSO-d$_6$) δ (ppm); 7.63-7.58 (m, 3H), 7.50-7.38 (m, 2H), 6.93 (d, J = 7.6 Hz, 1H), 4.72 (s, 2H), 3.88 (s, 2H), 3.68-3.57 (m, 2H), 2.68-2.51 (m, 2H). Calculated (M + H): 455.01; Found (M + 1): 455.0. HPLC purity 95.52% |
| 67 | 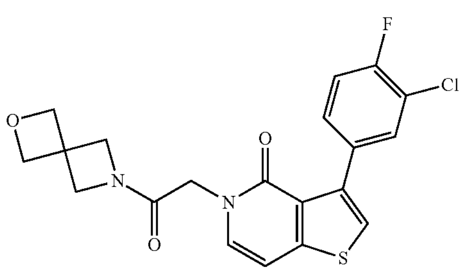 [SMILES: O=C(Cn1ccc2scc(-c3ccc(F)c(Cl)c3)c2c1=O)N1CC2(COC2)C1] | 3-(3-chloro-4-fluorophenyl)-5-(2-oxo-2-(2-oxa-6-azaspiro[3.3]heptan-6-yl)ethyl)thieno[3,2-c]pyridin-4(5H)-one | $^1$H NMR (400 MHz, DMSO-d$_6$) δ (ppm): 7.61-7.58 (m, 2H), 7.45-7.35 (m, 3H), 6.93 (d, J = 6.8 Hz, 1H), 4.65 (d, J = 4 Hz, 4H), 4.53 (s, 2H), 4.36 (s, 2H), 4.03 (s, 2H). Calculated (M + H): 419.06; Found (M + H): 419.0. HPLC purity: 99.37% |
| 68 | 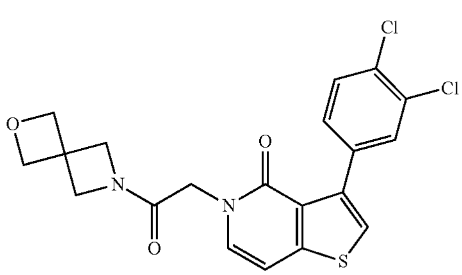 [SMILES: O=C(Cn1ccc2scc(-c3ccc(Cl)c(Cl)c3)c2c1=O)N1CC2(COC2)C1] | 3-(3,4-dichlorophenyl)-5-(2-oxo-2-(2-oxa-6-azaspiro[3.3]heptan-6-yl)ethyl)thieno[3,2-c]pyridin-4(5H)-one | $^1$H NMR (400 MHz, DMSO-d$_6$) δ (ppm): 7.66 (s, 1H), 7.62 (s, 1H), 7.59 (d, J = 8.4 Hz, 1H), 7.45 (d, J = 7.2 Hz, 1H), 7.40 (d, J = 8.4 Hz, 1H), 6.93 (d, J = 7.2 Hz, 1H), 4.66-4.63 (m, 4H), 4.53 (s, 2H), 4.36 (s, 2H), 4.03 (s, 2H). Calculated (M + H): 435.03; Found (M + H): 435.0. HPLC purity: 99.00% |

TABLE 3-continued

The following compounds were prepared by the method described above:

| Ex. No. | Structure | IUPAC Name | Analytical Data |
|---|---|---|---|
| 69 | 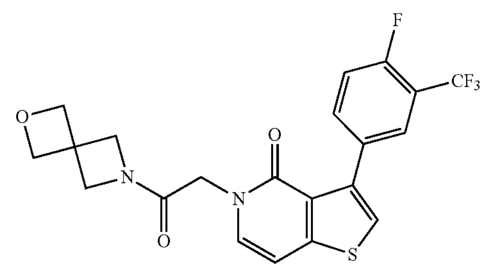 [SMILES: O=C(Cn1ccc2scc(-c3ccc(F)c(C(F)(F)F)c3)c2c1=O)N1CC2(COC2)C1] | 3-(4-fluoro-3-(trifluoromethyl)phenyl)-5-(2-oxo-2-(2-oxa-6-azaspiro[3.3]heptan-6-yl)ethyl)thieno[3,2-c]pyridin-4(5H)-one | $^1$H NMR (400 MHz, DMSO-d$_6$) δ (ppm): 7.79-7.75 (m, 2H), 7.65 (s, 1H), 7.51-7.45 (m, 2H), 6.94 (d, J = 6.8 Hz, 1H), 4.67-4.63 (m, 4H), 4.53 (s, 2H), 4.36 (s, 2H), 4.03 (s, 2H). Calculated (M + H): 453.08; Found (M + H): 453.1. HPLC purity: 99.56% |
| 70 | 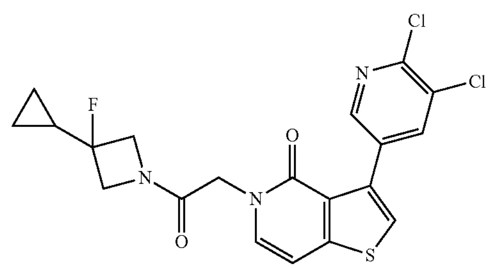 [SMILES: O=C(Cn1ccc2scc(-c3cnc(Cl)c(Cl)c3)c2c1=O)N1CC(F)(C2CC2)C1] | 5-(2-(3-cyclopropyl-3-fluoroazetidin-1-yl)-2-oxoethyl)-3-(5,6-dichloropyridin-3-yl)thieno[3,2-c]pyridin-4(5H)-one | $^1$H NMR (400 MHz, DMSO-d$_6$) δ (ppm): 8.44 (s, 1H), 8.20 (d, J = 1.6 Hz, 1H), 7.81 (s, 1H), 7.53 (d, J = 7.2 Hz, 1H), 7.00 (d, J = 7.2 Hz, 1H), 4.66-4.56 (m, 2H), 4.29-4.17 (m, 2H), 3.92-3.80 (m, 2H), 1.39-1.36 (m, 1H), 0.59-0.400 (m, 4H). Calculated (M + H): 452.03; Found (M + H): 452.0. HPLC purity: 98.05% |
| 71 | 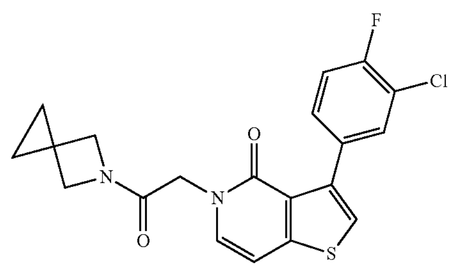 [SMILES: O=C(Cn1ccc2scc(-c3ccc(F)c(Cl)c3)c2c1=O)N1CC2(CC2)C1] | 3-(3-chloro-4-fluorophenyl)-5-(2-oxo-2-(5-azaspiro[2.3]hexan-5-yl)ethyl)thieno[3,2-c]pyridin-4(5H)-one | $^1$H NMR (400 MHz, DMSO-d$_6$) δ (ppm): 7.62-7.58 (m, 2H), 7.50 (d, J = 6.8 Hz, 1H), 7.42-7.36 (m, 2H), 6.94 (d, J = 7.2 Hz, 1H), 4.59 (s, 2H), 4.24 (s, 2H), 3.91 (s, 2H), 0.63 (d, J = 7.2 Hz, 4H). Calculated (M + H): 403.6; Found (M + H): 403.1. HPLC purity: 95.22% |
| 72 | 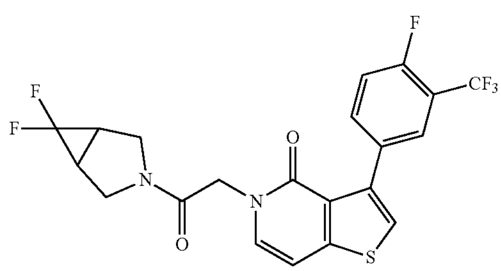 [SMILES: O=C(Cn1ccc2scc(-c3ccc(F)c(C(F)(F)F)c3)c2c1=O)N1CC2C(C1)C2(F)F] | 5-(2-(6,6-difluoro-3-azabicyclo[3.1.0]hexan-3-yl)-2-oxoethyl)-3-(4-fluoro-3-(trifluoromethyl)phenyl)thieno[3,2-c]pyridin-4(5H)-one | $^1$H NMR (400 MHz, DMSO-d$_6$) δ (ppm); 7.87-7.77 (m, 2H), 7.65 (s, 1H), 7.50-7.45 (m, 2H), 6.94 (d, J = 7.2 Hz, 1H), 4.72 (s, 2H), 3.87 (s, 2H), 3.67-3.59 (m, 2H), 2.68-2.48 (m, 2H). Calculated (M + H): 473.07; Found (M + 1): 473.1. HPLC purity 99.36% |
| 73 | 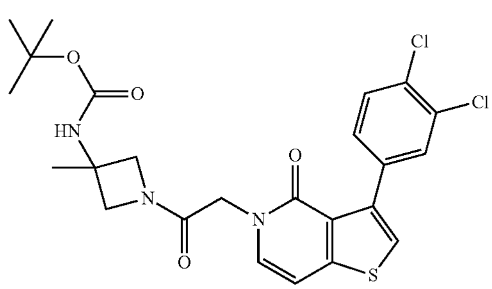 [SMILES: CC1(NC(=O)OC(C)(C)C)CN(C(=O)Cn2ccc3scc(-c4ccc(Cl)c(Cl)c4)c3c2=O)C1] | tert-butyl (1-(2-(3-(3,4-dichlorophenyl)-4-oxothieno[3,2-c]pyridin-5(4H)-yl)acetyl)-3-methylazetidin-3-yl)carbamate | $^1$H NMR (400 MHz, DMSO-d$_6$) δ (ppm): 7.67 (s, 1H), 7.63 (s, 1H), 7.59 (d, J = 8.4 Hz, 1H), 7.49 (d, J = 7.2 Hz, 1H), 7.4 (d, J = 6.8 Hz, 2H), 6.94 (d, J = 6.8 Hz, 1H), 4.57 (s, 2H), 4.2 (d, J = 7.2 Hz, 1H) 3.98 (d, J = 8.8 Hz, 1H), 3.89 (d, J = 9.6 Hz, 1H), 3.62 (d, J = 9.6 Hz, 1H), 1.39 (d, J = 18.8 Hz, 3H), 1.37 (s, 9H). Calculated (M + H): 522.1, Found (M + H): 522.1, HPLC purity: 94.32% |

TABLE 3-continued

The following compounds were prepared by the method described above:

| Ex. No. | IUPAC Name | Analytical Data |
|---|---|---|
| 74 | tert-butyl (1-(2-(3-(3-chloro-4-fluorophenyl)-4-oxothieno[3,2-c]pyridin-5(4H)-yl)acetyl)-3-methylazetidin-3-yl)carbamate | ¹H NMR (400 MHz, DMSO-d₆) δ (ppm): 7.61 (d, J = 7.2 Hz, 1H), 7.59 (s, 1H), 7.48 (d, J = 6.8 Hz, 1H), 7.41-7.35 (m, 3H), 6.93 (d, J = 7.6 Hz, 1H), 4.57 (s, 2H), 4.20 (d, J = 8.0 Hz, 1H), 3.98 (d, J = 8.4 Hz, 1H), 3.89 (d, J = 9.6 Hz, 1H), 3.62 (d, J = 9.6 Hz, 1H), 1.42 (s, 3H), 1.37 (s, 9H). Calculated (M + H): 506.12, Found (M + H): 506.1. HPLC purity: 95.02% |
| 75 | 3-(5,6-dichloropyridin-3-yl)-5-(2-(3-ethyl-3-fluoroazetidin-1-yl)-2-oxoethyl)thieno[3,2-c]pyridin-4(5H)-one | ¹H NMR (400 MHz, DMSO-d₆) δ (ppm): 8.44 (d, J = 1.6 Hz, 1H), 8.20 (d, J = 1.2 Hz, 1H), 7.81 (s, 1H), 7.52 (d, J = 7.6 Hz, 1H), 7.00 (d, J = 6.8 Hz, 1H), 4.63 (s, 2H), 4.35-4.28 (m, 2H), 3.98-3.89 (m, 2H), 1.90-1.82 (m, 2H), 0.90 (t, J = 7.2 Hz, 3H). Calculated (M + H): 440.03; Found (M + H): 440.0. HPLC Purity: 99.54% |
| 76 | 3-(5,6-dichloropyridin-3-yl)-5-(2-(3-fluoro-3-methylazetidin-1-yl)-2-oxoethyl)thieno[3,2-c]pyridin-4(5H)-one | ¹H NMR (400 MHz, DMSO-d₆) δ (ppm): 8.44 (d, 1.6 Hz, 1H), 8.20 (d, J = 2.4 Hz, 1H), 7.81 (s, 1H), 7.52 (d, J = 6.8 Hz, 1H), 7.10 (d, J = 7.2 Hz, 1H), 4.62 (s, 2H), 4.39-4.26 (m, 2H), 3.98-3.90 (m, 2H), 1.58 (d, J = 22.0 Hz, 3H). Calculated (M + H): 426.02; Found (M + H): 426.2. HPLC Purity: 98.19% |
| 77 | tert-butyl (1-(2-(3-(4-fluoro-3-(trifluoromethyl)phenyl)-4-oxothieno[3,2-c]pyridin-5(4H)-yl)acetyl)-3-methylazetidin-3-yl)carbamate | ¹H NMR (400 MHz, DMSO-d₆) δ (ppm): 7.80-7.76 (m, 2H), 7.66 (s, 1H), 7.51-7.46 (m, 2H), 7.39 (brs, 1H), 6.96 (d, J = 7.2 Hz, 1H), 4.57 (s, 2H), 4.20-3.90 (m, 3H), 3.61 (d, J = 10.0 Hz, 1H), 1.41 (s, 3H), 1.37 (s, 9H). Calculated (M + H): 540.15; Found (M + H): 540.0. HPLC Purity: 99.07% |
| 78 | 3-(3,4-dichlorophenyl)-5-(2-oxo-2-(5-azaspiro[2.3]hexan-5-yl)ethyl)thieno[3,2-c]pyridin-4(5H)-one | ¹H NMR (400 MHz, DMSO-d₆) δ (ppm): 7.67 (d, J = 1.6 Hz, 1H), 7.63 (m, 2H), 7.50 (d, J = 7.2 Hz, 1H), 7.41 (dd, J = 1.6 Hz, 8.4 Hz, 1H), 6.95 (d, J = 6.8 Hz, 1H), 4.59 (s, 2H), 4.24 (s, 2H), 3.91 (s, 2H), 0.63 (d, J = 7.2 Hz, 4H). Calculated (M + H): 419.03; Found (M + H): 419.0. HPLC purity: 98.35% |

TABLE 3-continued

The following compounds were prepared by the method described above:

| Ex. No. | Structure | IUPAC Name | Analytical Data |
|---|---|---|---|
| 79 | 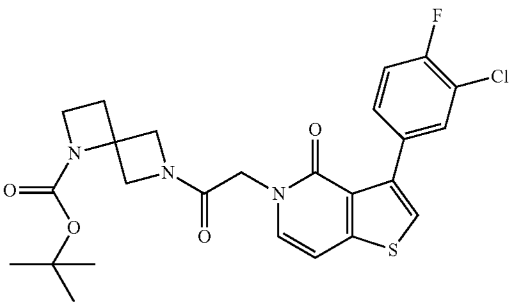 [SMILES: CC(C)(C)OC(=O)N1CCC12CN(C(=O)Cn1ccc3scc(-c4ccc(F)c(Cl)c4)c3c1=O)C2] | tert-butyl 6-(2-(3-(3-chloro-4-fluorophenyl)-4-oxothieno[3,2-c]pyridin-5(4H)-yl)acetyl)-1,6-diazaspiro[3.3]heptane-1-carboxylate | $^1$H NMR (400 MHz, DMSO-d$_6$) δ (ppm); 7.62 (d, J = 7.2 Hz, 1H), 7.58 (s, 1H), 7.47-7.35 (m, 3H), 6.93 (d, J = 6.8 Hz, 1H), 4.60-4.53 (s, 3H), 4.30-4.23 (m, 2H), 3.93 (d, J = 10 Hz, 1H), 3.71-3.63 (m, 2H), 2.40-2.39 (m, 2H), 1.38-1.32 (m, 9H). Calculated (M + H): 518.12; Found (M + 1): 518.1. HPLC purity 98.54% |
| 80 | 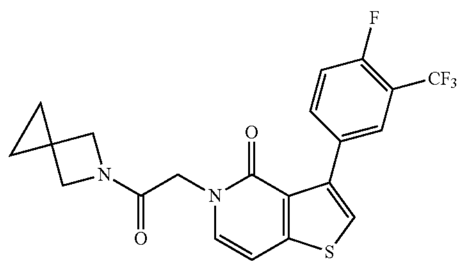 [SMILES: O=C(Cn1ccc2scc(-c3ccc(F)c(C(F)(F)F)c3)c2c1=O)N1CC2(CC2)C1] | 3-(4-fluoro-3-(trifluoromethyl)phenyl)-5-(2-oxo-2-(5-azaspiro[2.3]hexan-5-yl)ethyl)thieno[3,2-c]pyridin-4(5H)-one | $^1$H NMR (400 MHz, DMSO-d$_6$) δ (ppm); 7.80-7.78 (m, 2H), 7.66 (s, 1H), 7.52-7.47 (m, 2H), 6.96 (d, J = 7.2 Hz, 1H), 4.60 (s, 2H), 4.24 (s, 2H), 3.91 (s, 2H), 0.63 (d, J = 6 Hz, 4H). Calculated (M + H): 437.09; Found (M + H): 437.1. HPLC purity: 99.84% |
| 81 | 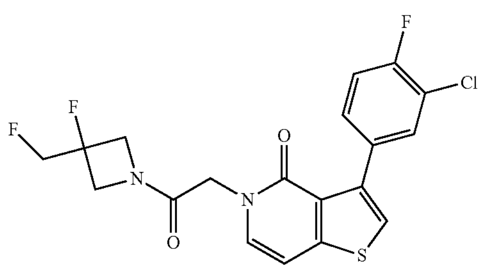 | 3-(3-chloro-4-fluorophenyl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-d$_6$) δ (ppm); 7.63-7.60 (m, 2H), 8.48 (d, J = 7.2 Hz, 1H), 7.42-7.35 (m, 2H), 6.95 (d, J = 7.2 Hz, 1H), 4.87-4.69 (m, 2H), 4.62 (s, 2H), 4.49-4.34 (m, 2H), 4.12-3.95 (m, 2H). Calculated (M + H): 427.04; Found (M + 1): 427.0. HPLC purity 98.33% |
| 82 | 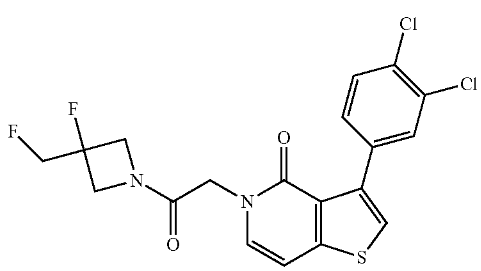 [SMILES: O=C(Cn1ccc2scc(-c3ccc(F)c(Cl)c3)c2c1=O)N1CC(F)(CF)C1] | 3-(3,4-dichlorophenyl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-d$_6$) δ (ppm); 7.67 (d, J = 1.6 Hz, 1H), 7.64 (s, 1H), 7.59 (d, J = 8.0 Hz, 1H), 7.48 (d, J = 7.2 Hz, 1H), 7.42-7.40 (dd, J = 2.0 Hz, 8.4 Hz, 1H), 6.96 (d, J = 7.2 Hz, 1H), 4.87-4.69 (m, 2H), 4.63 (s, 2H), 4.49-4.34 (m, 2H), 4.12-3.95 (m, 2H). Calculated (M + H): 443.03; Found (M + 1): 443.0. HPLC purity 99.75% |
| 83 | 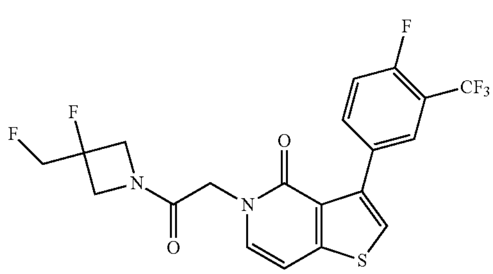 [SMILES: O=C(Cn1ccc2scc(-c3ccc(F)c(C(F)(F)F)c3)c2c1=O)N1CC(F)(CF)C1] | 5-(2-(3-fluoro-3-(fluoromethyl)azetidin-1-yl)-2-oxoethyl)-3-(4-fluoro-3-(trifluoromethyl)phenyl)thieno[3,2-c]pyridin-4(5H)-one | $^1$H NMR (400 MHz, DMSO-d$_6$) δ (ppm); 7.78 (brs, 2H), 7.67 (s, 1H), 7.75-7.46 (m, 2H), 6.97 (d, J = 6.8 Hz, 1H), 4.86-4.68 (m, 2H), 4.62 (s, 2H), 4.48-4.34 (m, 2H), 4.11-3.94 (m, 2H). Calculated (M + H): 461.07; Found (M + 1): 461.1. HPLC purity 98.26% |

TABLE 3-continued

The following compounds were prepared by the method described above:

| Ex. No. | Structure | IUPAC Name | Analytical Data |
|---|---|---|---|
| 84 | 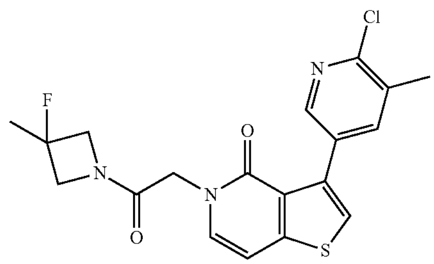 | 3-(6-chloro-5-methylpyridin-3-yl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm); 8.25 (s, 1H), 7.84 (s, 1H), 7.66 (s, 1H), 7.49 (d, J = 7.6 Hz, 1H), 6.97 (d, J = 6.8 Hz, 1H), 4.60 (s, 2H), 4.37-4.24 (m, 2H), 3.97-3.92 (m, 2H), 2.34 (s, 3H), 1.57 (d, J = 22.4 Hz, 3H). Calculated (M + H): 406.07; Found (M + 1): 406.0. HPLC purity 99.43% |
| 85 | 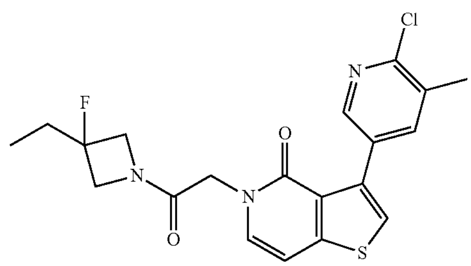 [SMILES: CCC1(F)CN(C(=O)Cn2ccc3scc(-c4cnc(Cl)c(C)c4)c3c2=O)C1] | 3-(6-chloro-5-methylpyridin-3-yl)-5-(2-(3-ethyl-3-fluoroazetidin-1-yl)-2-oxoethyl)thieno[3,2-c]pyridin-4(5H)-one | $^1$H NMR (400 MHz, DMSO-$d_6$) δ (ppm); 8.25 (s, 1H), 7.84 (s, 1H), 7.66 (s, 1H), 7.50 (d, J = 7.2 Hz, 1H), 6.97 (d, J = 7.6 Hz, 1H), 4.61 (s, 2H), 4.33-4.24 (m, 2H), 4.00-3.86 (m, 2H), 2.34 (s, 3H), 1.91-1.80 (m, 2H), 0.90 (t, J = 7.2 Hz, 3H). Calculated (M + H): 420.09; Found (M + 1): 420.1. HPLC purity 99.25% |
| 86 | 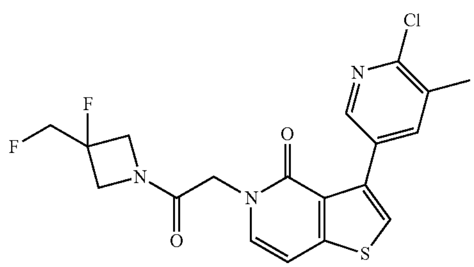 | 3-(6-chloro-5-methylpyridin-3-yl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-$d_6$) δ (ppm); 8.26 (s, 1H), 7.85 (s, 1H), 7.67 (s, 1H), 7.49 (d, J = 7.2 Hz, 1H), 6.97 (d, J = 7.2 Hz, 1H), 4.87-4.69 (m, 2H), 4.62 (s, 2H), 4.48-4.36 (m, 2H), 4.12-3.97 (m, 2H), 2.34 (s, 3H). Calculated (M + H): 424.06; Found (M + 1): 424.0. HPLC purity 99.25% |
| 87 | 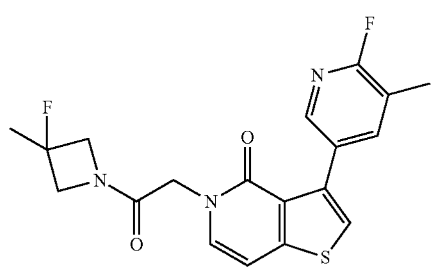 | 5-(2-(3-fluoro-3-methylazetidin-1-yl)-2-oxoethyl)-3-(6-fluoro-5-methylpyridin-3-yl)thieno[3,2-c]pyridin-4(5H)-one | $^1$H NMR (400 MHz, DMSO-$d_6$) δ (ppm); 8.05 (s, 1H), 7.87 (d, J = 10.0 Hz, 1H), 7.62 (s, 1H), 7.49 (d, J = 7.2 Hz, 1H), 6.96 (d, J = 7.2 Hz, 1H), 4.60 (s, 2H), 4.37-4.25 (m, 2H), 3.97-3.92 (m, 2H), 2.55 (s, 3H), 1.57 (d, J = 22.4 Hz, 3H). Calculated (M + H): 390.10; Found (M + 1): 390.1. HPLC purity 99.21% |
| 88 | 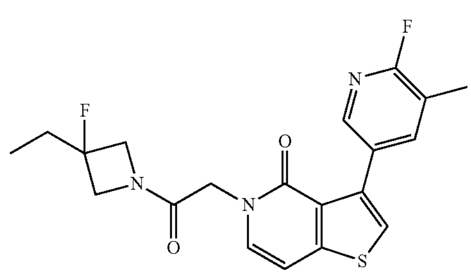 | 5-(2-(3-ethyl-3-fluoroazetidin-1-yl)-2-oxoethyl)-3-(6-fluoro-5-methylpyridin-3-yl)thieno[3,2-c]pyridin-4(5H)-one | $^1$H NMR (400 MHz, DMSO-$d_6$) δ (ppm); 8.05 (s, 1H), 7.87 (d, J = 9.2 Hz, 1H), 7.62 (s, 1H), 7.49 (d, J = 7.2 Hz, 1H), 6.96 (d, J = 6.8 Hz, 1H), 4.61 (s, 2H), 4.36-4.24 (m, 2H), 4.00-3.86 (m, 2H), 2.25 (s, 3H), 1.98-1.80 (m, 2H), 0.90 (t, J = 7.2 Hz, 3H). Calculated (M + H): 404.12; Found (M + 1): 404.1. HPLC purity 98.16% |

TABLE 3-continued

The following compounds were prepared by the method described above:

| Ex. No. | Structure | IUPAC Name | Analytical Data |
|---|---|---|---|
| 89 | 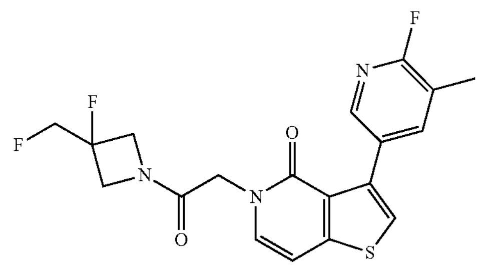 [SMILES: Cc1cc(-c2csc3ccn(CC(=O)N4CC(F)(CF)C4)c(=O)c23)cnc1F] | 5-(2-(3-fluoro-3-(fluoromethyl)azetidin-1-yl)-2-oxoethyl)-3-(6-fluoro-5-methylpyridin-3-yl)thieno[3,2-c]pyridin-4(5H)-one | $^1$H NMR (400 MHz, DMSO-d$_6$) δ (ppm); 8.05 (s, 1H), 7.87 (d, J = 8.4 Hz, 1H), 7.62 (s, 1H), 7.48 (d, J = 7.6 Hz, 1H), 6.97 (d, J = 7.6 Hz, 1H), 4.87-4.69 (m, 2H), 4.62 (s, 2H), 4.49-4.34 (m, 2H), 4.12-3.95 (m, 2H), 2.25 (s, 3H). Calculated (M + H): 408.09; Found (M + 1): 408.1. HPLC purity 98.65% |
| 90 | 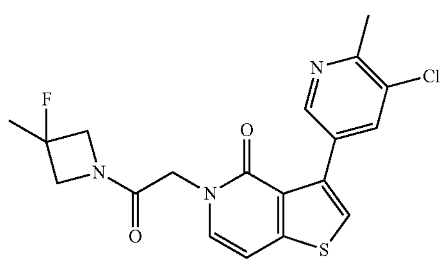 [SMILES: Cc1ncc(-c2csc3ccn(CC(=O)N4CC(C)(F)C4)c(=O)c23)cc1Cl] | 3-(5-chloro-6-methylpyridin-3-yl)-5-(2-(3-fluoro-3-methylazetidin-1-yl)-2-oxoethyl)thieno[3,2-c]pyridin-4(5H)-one | $^1$H NMR (400 MHz, DMSO-d$_6$) δ (ppm); 8.44 (s, 1H), 7.90 (s, 1H), 7.70 (s, 1H), 7.50 (d, J = 7.2 Hz, 1H), 6.97 (d, J = 6.8 Hz, 1H), 4.61 (s, 2H), 4.35-4.28 (m, 2H), 3.97-3.93 (m, 2H), 2.55 (s, 3H), 1.57 (d, J = 21.6 Hz, 3H). Calculated (M + H): 406.07; Found (M + 1): 406.1. HPLC purity 99.70% |
| 91 | 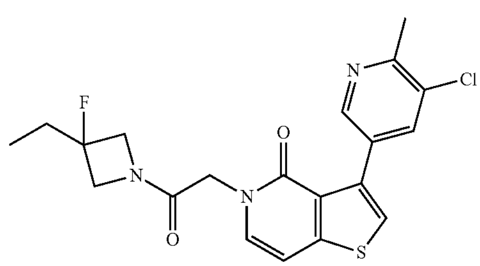 [SMILES: CCC1(F)CN(C(=O)Cn2ccc3scc(-c4cnc(C)c(Cl)c4)c3c2=O)C1] | 3-(5-chloro-6-methylpyridin-3-yl)-5-(2-(3-ethyl-3-fluoroazetidin-1-yl)-2-oxoethyl)thieno[3,2-c]pyridin-4(5H)-one | $^1$H NMR (400 MHz, DMSO-d$_6$) δ (ppm); 8.44 (d, J = 1.6 Hz, 1H), 7.90 (d, J = 1.2 Hz, 1H), 7.70 (s, 1H), 7.50 (d, J = 7.2 Hz, 1H), 6.97 (d, J = 7.6 Hz, 1H), 4.61 (s, 2H), 4.34-4.27 (m, 2H), 3.98-3.89 (m, 2H), 2.56 (s, 3H), 1.90-1.82 (m, 2H), 0.90 (t, J = 7.6 Hz, 3H). Calculated (M + H): 420.09; Found (M + 1): 420.1. HPLC purity 99.47% |
| 92 | 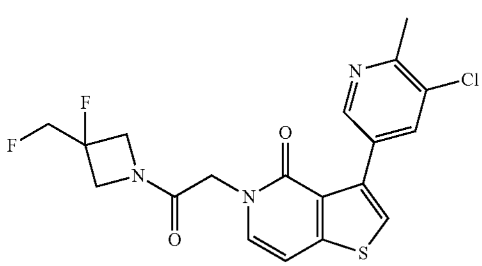 [SMILES: Cc1ncc(-c2csc3ccn(CC(=O)N4CC(F)(CF)C4)c(=O)c23)cc1Cl] | 3-(5-chloro-6-methylpyridin-3-yl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-d$_6$) δ (ppm); 8.45 (s, 1H), 7.91 (s, 1H), 7.71 (s, 1H), 7.49 (d, J = 6.8 Hz, 1H), 6.97 (d, J = 7.2 Hz, 1H), 4.87-4.70 (m, 2H), 4.63 (s, 2H), 4.46-4.37 (m, 2H), 4.09-3.98 (m, 2H), 2.56 (s, 3H). Calculated (M + H): 424.06; Found (M + 1): 424.1. HPLC purity 99.72% |

Example 93: Preparation of 2-(3-(3-chloro-4-fluorophenyl)-4-oxothieno[3,2-c]pyridin-5(4H)-yl)-N-methyl-N-(2,2,2-trifluoroethyl)acetamide

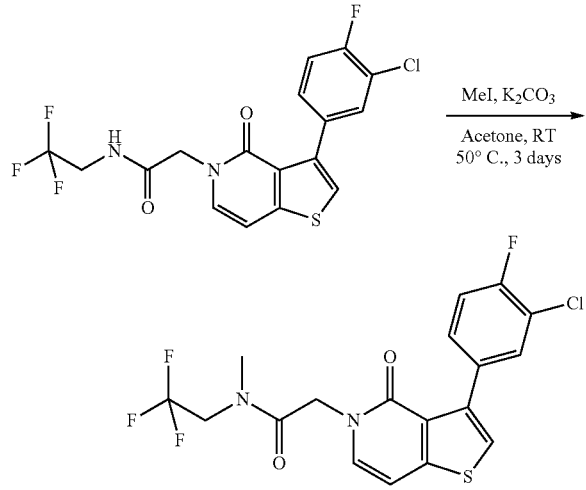

To a stirred solution of 2-(3-(3-chloro-4-fluorophenyl)-4-oxothieno[3,2-c]pyridin-5(4H)-yl)-N-(2,2,2-trifluoroethyl)acetamide (0.04 g, 0.09 mmol) in acetone (5 mL) was added potassium carbonate (0.04 g, 028 mmol) followed by methyl iodide (0.06 mL, 0.95 mmol). The reaction mixture was heated at 50° C. for 3 days. The reaction mixture was filtered and the filtrate was concentrated. The crude material was purified by column chromatography, followed by preparative HPLC (analysis method: Kinetex C18 (100 mm×4.6 mm×2.6 m), mobile phase (A): water, mobile phase (B): acetonitrile, Flow rate: 0.75 mL/min) to afford the title compound 2-(3-(3-chloro-4-fluorophenyl)-4-oxothieno[3,2-c]pyridin-5(4H)-yl)-N-methyl-N-(2,2,2-trifluoroethyl)acetamide (0.01 g, 24% yield) as off white solid. $^1$H NMR (400 MHz, DMSO-$d_6$) δ (ppm): 7.62-7.60 (m, 2H), 7.51-7.35 (m, 3H), 6.96-6.32 (m, 1H), 4.94 (s, 2H), 4.18-4.11 (m, 2H), 3.17 (s, 3H). Calculated (M+H): 433.03; Found (M+H): 433.0. HPLC purity: 99.55%.

Example 94: Preparation of 5-(2-(3-amino-3-methylazetidin-1-yl)-2-oxoethyl)-3-(3,4-dichlorophenyl)thieno[3,2-c]pyridin-4(5H)-one

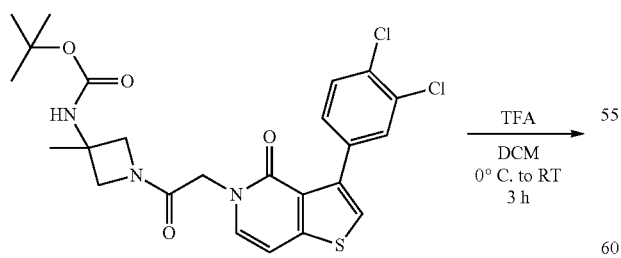

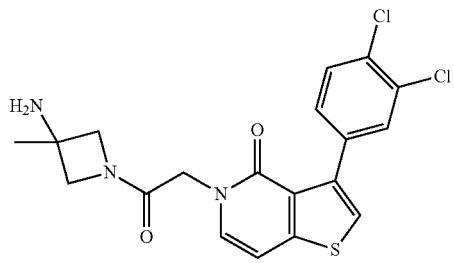

To a solution of tert-butyl (1-(2-(3-(3,4-dichlorophenyl)-4-oxothieno[3,2-c]pyridin-5(4H)-yl)acetyl)-3-methylazetidin-3-yl)carbamate (0.13 g, 0.24 mmol) in dichloromethane (10 mL) cooled to 0° C., was added trifluoroacetic acid (0.2 mL, 2.49 mmol) and the reaction mixture was stirred at room temperature for 3 h. After completion of the reaction (as monitored by TLC), the reaction mixture was concentrated, the residue was basified with saturated sodium bicarbonate solution (30 mL) and extracted with dichloromethane (2×50 mL). The combined organic layer was dried over anhydrous sodium sulphate, filtered and concentrated. The crude product was purified by silica gel column chromatography using 5% methanol in dichloromethane to afford the title compound 5-(2-(3-amino-3-methylazetidin-1-yl)-2-oxoethyl)-3-(3,4-dichlorophenyl)thieno[3,2-c]pyridin-4(5H)-one (0.033 g, 33% yield) as white solid. $^1$H NMR (400 MHz, DMSO-$d_6$) δ (ppm): 7.67 (s, 1H), 7.63 (s, 1H), 7.59 (d, J=8.4 Hz, 1H), 7.47 (d, J=7.2 Hz, 1H), 7.4 (d, J=6.8 Hz, 1H), 6.93 (d, J=6.8 Hz, 1H), 4.56 (s, 2H), 3.94 (d, J=8 Hz, 1H) 3.88 (d, J=7.6 Hz, 1H), 3.63 (d, J=9.2 Hz, 1H), 3.57 (d, J=9.2 Hz, 1H), 2.37 (brs, 2H), 1.29 (s, 3H). Calculated (M+H): 422.05, Found (M+H): 422.0, HPLC purity: 96.09%.

TABLE 4

The following compounds were prepared by the method described above:

| Ex. No. | Structure | IUPAC Name | Analytical Data |
|---|---|---|---|
| 95 | 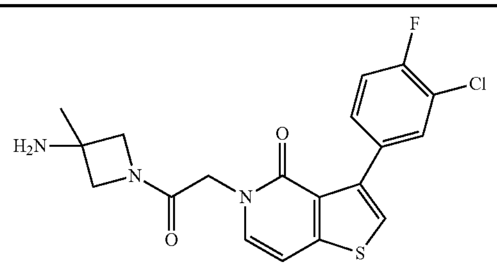 | 5-(2-(3-amino-3-methylazetidin-1-yl)-2-oxoethyl)-3-(3-chloro-4-fluorophenyl)thieno[3,2-c]pyridin-4(5H)-one | $^1$H NMR (400 MHz, DMSO-$d_6$) δ (ppm): 7.61 (d, J = 7.6 Hz, 1H), 7.58 (s, 1H), 7.47 (d, J = 7.6 Hz, 1H), 7.44-7.36 (m, 2H), 6.93 (d, J = 7.2 Hz, 1H), 4.56 (s, 2H), 3.95 (d, J = 8.0 Hz, 1H), 3.88 (d, J = 8.0 Hz, 1H), 3.63 (d, J = 9.2 Hz, 1H), 3.57 (d, J = 9.2 Hz, 1H), 2.14 (s, 2H), 1.29 (s, 3H). Calculated (M + H): 406.07, Found (M + H): 406.0. HPLC purity: 99.21% |
| 96 | 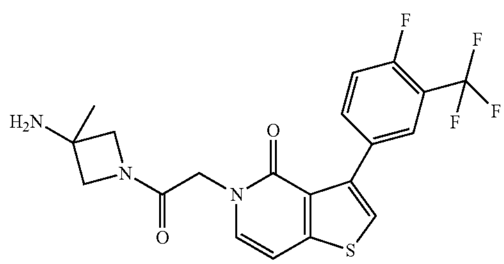 [SMILES: CC1(N)CN(C(=O)Cn2ccc3scc(-c4ccc(F)c(C(F)(F)F)c4)c3c2=O)C1] | 5-(2-(3-amino-3-methylazetidin-1-yl)-2-oxoethyl)-3-(4-fluoro-3-(trifluoromethyl)phenyl)thieno[3,2-c]pyridin-4(5H)-one | $^1$H NMR (400 MHz, DMSO-$d_6$) δ (ppm): 7.80-7.76 (m, 2H), 7.66 (s, 1H), 7.51-7.47 (m, 2H), 6.95 (d, J = 7.2 Hz, 1H), 4.56 (s, 2H), 3.95 (d, J = 8.0 Hz, 1H), 3.87 (d, J = 8.4 Hz, 1H), 3.63 (d, J = 9.2 Hz, 1H), 3.57 (d, J = 9.2 Hz, 1H), 2.22 (brs, 2H), 1.29 (s, 3H). Calculated (M + H): 440.1; Found (M + H): 440.1. HPLC Purity: 99.74% |
| 97 | 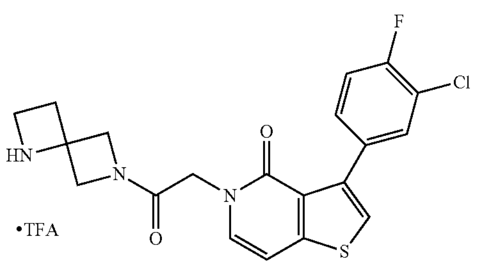 [SMILES: O=C(Cn1ccc2scc(-c3ccc(F)c(Cl)c3)c2c1=O)N1CC2(CCN2)C1] | 3-(3-chloro-4-fluorophenyl)-5-(2-oxo-2-(1,6-diazaspiro[3.3]heptan-6-yl)ethyl)thieno[3,2-c]pyridin-4(5H)-one 2,2,2-trifluoroacetate | $^1$H NMR (400 MHz, DMSO-$d_6$) δ (ppm); 9.15 (brs, 2H), 7.63-7.60 (m, 2H), 7.48-7.36 (m, 3H), 6.96 (d, J = 7.2 Hz, 1H), 4.63-4.46 (m, 4H), 4.33 (d, J = 11.2 Hz, 1H), 4.15 (d, J = 11.6 Hz, 1H), 3.76 (brs, 2H), 2.68 (brs, 2H). Calculated (M + H): 418.07; Found (M + H): 418.2. HPLC purity: 99.66% |

Examples 98 and 99: Preparation of 7-bromo-3-(4-chloro-3-(trifluoromethyl)phenyl)-5-(2-oxo-2-(pyrrolidin-1-yl)ethyl)thieno[3,2-c]pyridin-4(5H)-one & 3-(4-chloro-3-(trifluoromethyl)phenyl)-4-oxo-5-(2-oxo-2-(pyrrolidin-1-yl)ethyl)-4,5-dihydrothieno[3,2-c]pyridine-7-carbonitrile

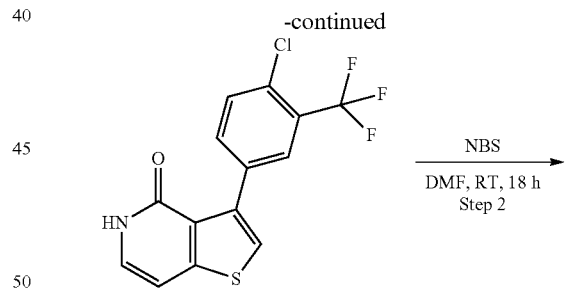

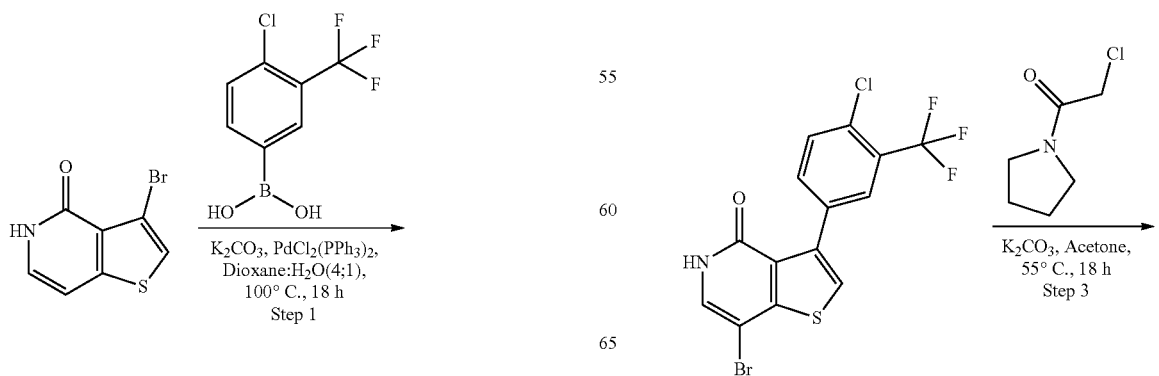

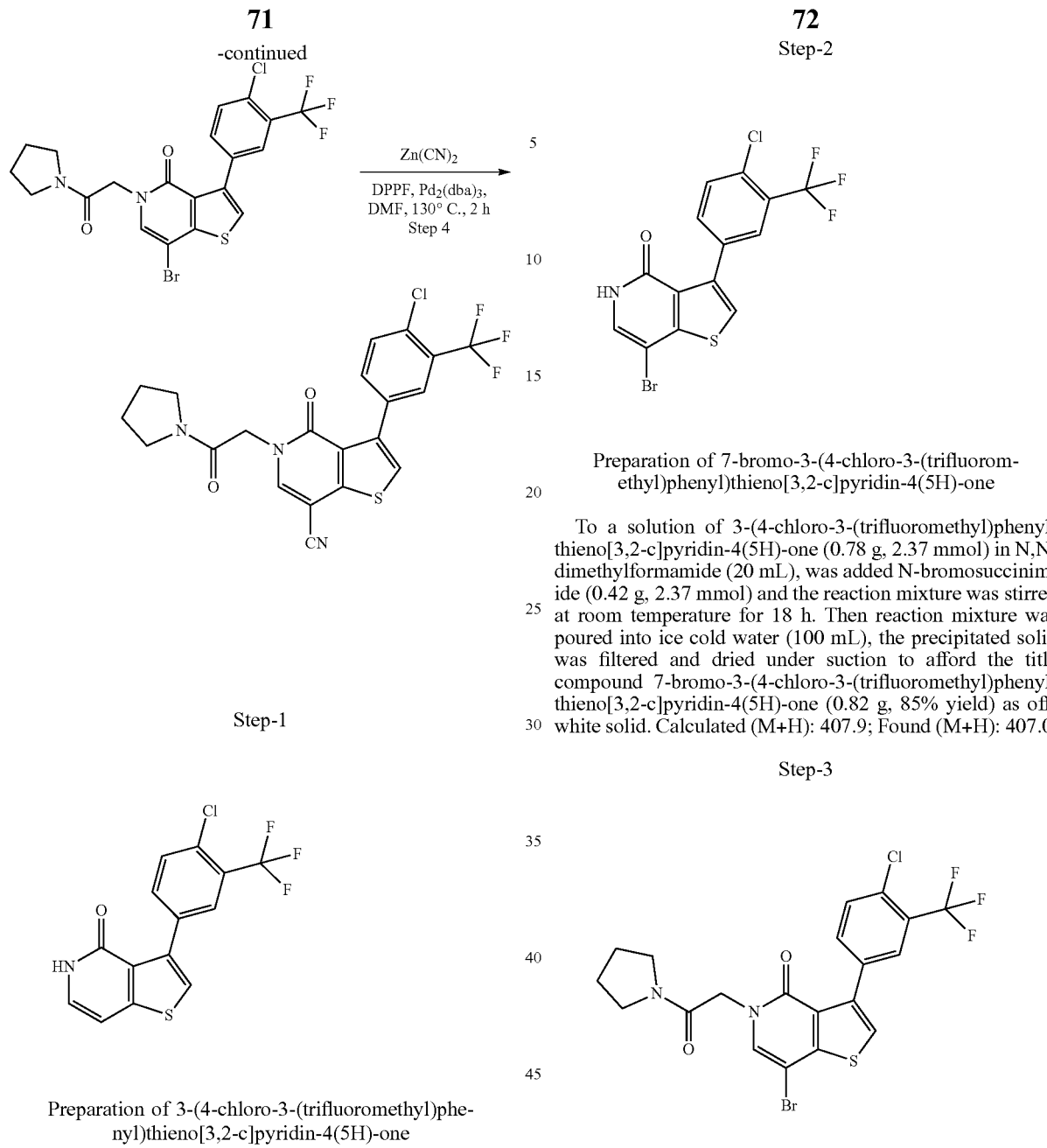

Step-1

Preparation of 3-(4-chloro-3-(trifluoromethyl)phenyl)thieno[3,2-c]pyridin-4(5H)-one To a solution of 3-bromothieno[3,2-c]pyridin-4(5H)-one (0.55 g, 2.17 mmol) and (4-chloro-3-(trifluoromethyl)phenyl)boronic acid (0.73 g, 3.25 mmol) in 1,4-dioxane:water mixture (20 mL, 4:1), potassium carbonate (0.9 g, 6.51 mmol) was added. The reaction mixture was purged with argon for 15 minutes and PdCl$_2$(PPh$_3$)$_2$ (0.15 g, 0.21 mmol) was added. Then the reaction mixture was stirred at 100° C. for 18 h. The reaction mixture was diluted with water (50 mL) and extracted with ethyl acetate (3×100 mL). The combined organic layer was dried over anhydrous sodium sulphate, filtered and concentrated. The crude product was purified by silica gel column chromatography using 30% ethyl acetate in hexane to afford the title compound 3-(4-chloro-3-(trifluoromethyl)phenyl)thieno[3,2-c]pyridin-4(5H)-one (0.74 g, 94% yield) as off-white solid. Calculated (M+H): 330; Found (M+H): 330.0.

Step-2

Preparation of 7-bromo-3-(4-chloro-3-(trifluoromethyl)phenyl)thieno[3,2-c]pyridin-4(5H)-one To a solution of 3-(4-chloro-3-(trifluoromethyl)phenyl)thieno[3,2-c]pyridin-4(5H)-one (0.78 g, 2.37 mmol) in N,N-dimethylformamide (20 mL), was added N-bromosuccinimide (0.42 g, 2.37 mmol) and the reaction mixture was stirred at room temperature for 18 h. Then reaction mixture was poured into ice cold water (100 mL), the precipitated solid was filtered and dried under suction to afford the title compound 7-bromo-3-(4-chloro-3-(trifluoromethyl)phenyl)thieno[3,2-c]pyridin-4(5H)-one (0.82 g, 85% yield) as off-white solid. Calculated (M+H): 407.9; Found (M+H): 407.0.

Step-3

Preparation of 7-bromo-3-(4-chloro-3-(trifluoromethyl)phenyl)-5-(2-oxo-2-(pyrrolidin-1-yl)ethyl)thieno[3,2-c]pyridin-4(5H)-one To a stirred solution of 7-bromo-3-(4-chloro-3-(trifluoromethyl)phenyl)thieno[3,2-c]pyridin-4(5H)-one (1.5 g, 3.68 mmol) in dry acetone (80 mL) was added potassium carbonate (1.52 g, 11.05 mmol) followed by 2-chloro-1-(pyrrolidin-1-yl)ethanone (0.65 g, 4.42 mmol) at room temperature and the reaction mixture was heated at 55° C. for 18 h. The reaction mixture was filtered through the celite, washed with acetone and the filtrate was concentrated under vacuum. The crude product was purified by silica gel column chromatography using 40% ethyl acetate in hexane to afford the title compound 7-bromo-3-(4-chloro-3-(trifluoromethyl)phenyl)-5-(2-oxo-2-(pyrrolidin-1-yl)ethyl)thieno[3,2-c]pyridin-4(5H)-one (1.2 g, 63% yield) as white solid. $^1$H NMR (400 MHz, DMSO-d$_6$) δ (ppm): 7.89 (s, 1H), 7.86 (s, 1H), 7.82 (s, 1H), 7.71 (brs, 2H), 4.73 (s, 2H), 3.45 (t, J=6.4 Hz, 2H); 3.273.24 (m, 2H), 1.93-1.86 (m, 2H), 1.78-1.71 (m, 2H). Calculated (M+H): 519.0, Found (M+H): 519.0, HPLC purity: 99.04%.

Step-4

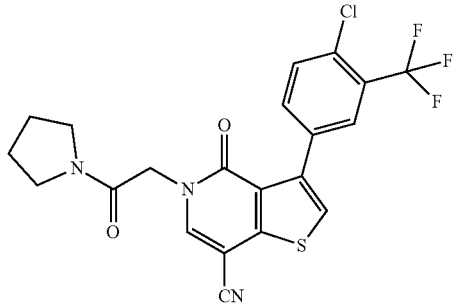 [SMILES: N#Cc1cn(CC(=O)N2CCCC2)c(=O)c2c(-c3ccc(Cl)c(C(F)(F)F)c3)csc12]

Preparation of 3-(4-chloro-3-(trifluoromethyl)phenyl)-4-oxo-5-(2-oxo-2-(pyrrolidin-1-yl)ethyl)-4,5-dihydrothieno[3,2-c]pyridine-7-carbonitrile A solution of 7-bromo-3-(4-chloro-3-(trifluoromethyl)phenyl)-5-(2-oxo-2-(pyrrolidin-1-yl)ethyl)thieno[3,2-c]pyridin-4(5H)-one (0.2 g, 0.38 mmol) in N,N-dimethylformamide (10 mL) was degassed with argon for 10 min. Then zinc cyanide (0.04 g, 0.34 mmol), Pd$_2$(dba)$_3$ (0.007 g, 0.008 mmol) and 1,1'-bis(diphenylphosphino)ferrocene (DPPF) (0.009 g, 0.0169 mmol) were added and the resulting mixture was stirred at 130° C. for 2 h. After completion of reaction (monitored by TLC), the reaction mixture was cooled to room temperature, diluted with water (50 mL) and extracted with ethyl acetate (3×80 mL). The combined organic layer was dried over anhydrous sodium sulfate, filtered and concentrated under vacuum. The crude product was purified by silica gel column chromatography using 40% ethyl acetate in hexane to afford the title compound 3-(4-chloro-3-(trifluoromethyl)phenyl)-4-oxo-5-(2-oxo-2-(pyrrolidin-1-yl)ethyl)-4,5-dihydrothieno[3,2-c]pyridine-7-carbonitrile (0.1 g, 55% yield) as white solid. $^1$H NMR (400 MHz, DMSO-d$_6$) δ (ppm): 8.51 (s, 1H), 7.90 (s, 1H), 7.86 (s, 1H), 7.74-7.72 (m, 2H), 4.79 (s, 2H), 3.46 (t, J=6.4 Hz, 2H), 3.27-3.24 (m, 2H), 1.96-1.86 (m, 2H), 1.78-1.73 (m, 2H) Calculated (M+H): 466.05, Found (M+H): 466.0, HPLC purity: 99.46%.

Example 101: Preparation of 3-(4-chloro-3-(trifluoromethyl)phenyl)-7-cyclopropyl-5-(2-oxo-2-(pyrrolidin-1-yl)ethyl)thieno[3,2-c]pyridin-4(5H)-one

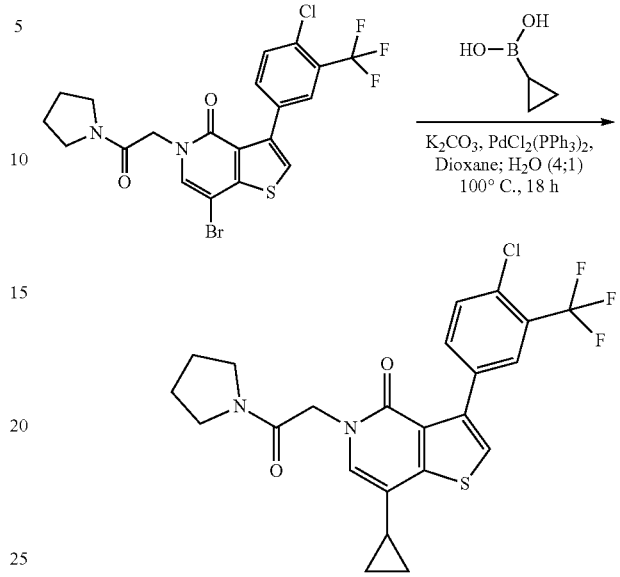

To a solution of 7-bromo-3-(4-chloro-3-(trifluoromethyl)phenyl)-5-(2-oxo-2-(pyrrolidin-1-yl)ethyl)thieno[3,2-c]pyridin-4(5H)-one (0.15 g, 0.28 mmol), potassium carbonate (0.11 g, 0.86 mmol) and cyclopropylboronic acid (0.037 g, 0.43 mmol) in dioxane:water mixture (8 mL, 4:1) argon was purged for 10 min. Then PdCl$_2$(PPh$_3$)$_2$ (0.02 g, 0.02 mmol) was added and the resulting mixture was stirred at 100° C. for 18 h. After completion of reaction (monitored by TLC), reaction mixture was cooled to room temperature and filtered through celite. The filtrate was concentrated under vacuum and the crude product was purified by prep HPLC (analytical conditions: column: chemsil C18 (250 mm×4.6 mm×5µ), mobile phase (A): 0.01% ammonia in water, mobile phase (B): acetonitrile, flow rate: 1.0 mL/min, T/% B: 0/20, 10/80, 25/80, 27/20, 30/20, wavelength: 220 nm) to afford the title compound 3-(4-chloro-3-(trifluoromethyl)phenyl)-7-cyclopropyl-5-(2-oxo-2-(pyrrolidin-1-yl)ethyl)thieno[3,2-c]pyridin-4(5H)-one (0.018 g, 12% yield) as

TABLE 5

The following compound was prepared by the method described above:

| Ex. No. | Structure | IUPAC Name | Analytical Data |
|---|---|---|---|
| 100 |  | 3-(4-fluoro-3-(trifluoromethyl)phenyl)-4-oxo-5-(2-oxo-2-(pyrrolidin-1-yl)ethyl)-4,5-dihydrothieno[3,2-c]pyridine-7-carbonitrile | $^1$H NMR (400 MHz, DMSO-d$_6$) δ (ppm): 8.50 (s, 1H), 7.87 (s, 1H), 7.79-7.75 (m, 2H), 7.51 (t, J = 10.8 Hz, 1H), 4.79 (s, 2H), 3.46 (t, J = 6.8 Hz, 2 H), 1.91-1.86 (m, 2 H), 1.79-1.72 (m, 2H). 2H are merged with DMSO water peak. Calculated (M + H): 450.08; Found (M + H): 450.1. HPLC purity: 98.53% | white solid. ¹H NMR (400 MHz, DMSO-d₆) δ (ppm): 7.86 (s, 1H), 7.72-7.67 (m, 3H), 7.31 (s, 1H), 4.68 (s, 2H), 3.45 (t, J=6.4 Hz, 2H), 3.25 (s, 2H), 1.92-1.82 (m, 3H), 1.81-1.71 (m, 2H), 0.91-0.86 (m, 2H), 0.62-0.58 (m, 2H). Calculated (M+H): 481.09, Found (M+H): 481.1. HPLC purity: 99.94%.

TABLE 6

The following compounds were prepared by the method described above:

| Ex. No. | Structure | IUPAC Name | Analytical Data |
|---|---|---|---|
| 102 | 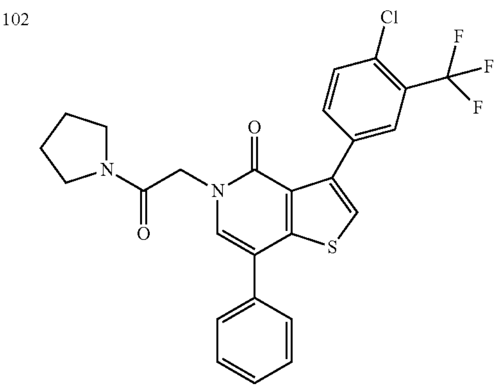 | 3-(4-chloro-3-(trifluoromethyl)phenyl)-5-(2-oxo-2-(pyrrolidin-1-yl)ethyl)-7-phenylthieno[3,2-c]pyridin-4(5H)-one | ¹H NMR (400 MHz, DMSO-d₆) δ (ppm): 7.88 (s, 1H), 7.75 (s, 1H), 7.72 (d, J = 2.8 Hz, 2H), 7.66 (s, 1H), 7.60 (d, J = 7.6 Hz, 2H); 7.52-7.42 (t, J = 8 Hz, 2H), 7.44 (d, J = 7.2 Hz, 1H), 4.81 (s, 2H), 3.48 (t, J = 6.8 Hz, 2H), 3.28 (s, 2H), 1.92-1.87 (m, 2H), 1.79-1.72 (m, 2H), Calculated (M + H): 517.09, Found (M + H): 517.1, HPLC purity: 99.90% |
| 103 | 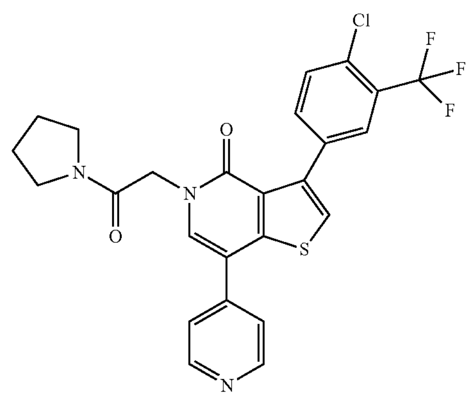 | 3-(4-chloro-3-(trifluoromethyl)phenyl)-5-(2-oxo-2-(pyrrolidin-1-yl)ethyl)-7-(pyridin-4-yl)thieno[3,2-c]pyridin-4(5H)-one | ¹H NMR (400 MHz, DMSO-d₆) δ (ppm): 8.69 (d, J = 5.6 Hz, 2H), 7.92 (s, 1H), 7.87 (s, 1H), 7.80 (s, 1H), 7.72 (s, 2H); 7.64 (d, J = 6 Hz, 2H), 4.82 (s, 2H), 3.48 (t, J = 6.4 Hz, 2H), 3.289 (s, 2H), 1.94-1.894 (m, 2H), 1.87-1.72 (m, 2H), Calculated (M + H): 518.08, Found (M + H): 518.1, HPLC purity: 99.87% |
| 104 | 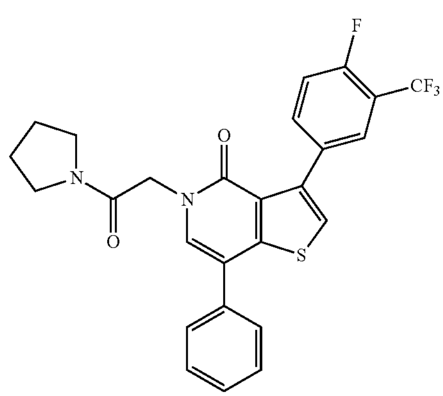 [SMILES: O=C(Cn1cc(-c2ccccc2)c2scc(-c3ccc(F)c(C(F)(F)F)c3)c2c1=O)N1CCCC1] | 3-(4-fluoro-3-(trifluoromethyl)phenyl)-5-(2-oxo-2-(pyrrolidin-1-yl)ethyl)-7-phenylthieno[3,2-c]pyridin-4(5H)-one | ¹H NMR (400 MHz, DMSO-d₆) δ (ppm): 7.80-7.77 (m, 2H), 7.70 (s, 1H), 7.65 (s, 1H), 7.60 (d, J = 7.6 Hz, 2H), 7.54-7.47 (m, 3H), 7.43 (t, J = 7.2 Hz, 1H), 4.81 (s, 2H), 3.47 (t, J = 6.8 Hz, 2H), 3.35-3.26 (m, 2H), 1.94-1.87 (m, 2H), 1.79-1.72 (m, 2H). Calculated (M + H): 501.12; Found (M + H): 501.1. HPLC purity: 99.77% |

TABLE 6-continued

The following compounds were prepared by the method described above:

| Ex. No. | Structure | IUPAC Name | Analytical Data |
|---|---|---|---|
| 105 | 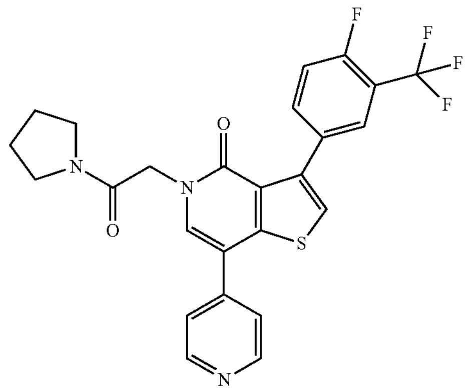 [SMILES: O=C(Cn1cc(-c2ccncc2)c2scc(-c3ccc(F)c(C(F)(F)F)c3)c2c1=O)N1CCCC1] | 3-(4-fluoro-3-(trifluoromethyl)phenyl)-5-(2-oxo-2-(pyrrolidin-1-yl)ethyl)-7-(pyridin-4-yl)thieno[3,2-c]pyridin-4(5H)-one | $^1$H NMR (400 MHz, DMSO-d$_6$) δ (ppm): 8.80 (d, J = 6.4 Hz, 2H), 8.08 (s, 1H), 7.90 (d, J = 5.2 Hz, 2H), 7.80-7.76 (m, 3H), 7.51 (t, J = 10 Hz, 1H), 4.84 (s, 2H), 3.50-3.47 (m, 2H), 3.27 (t, J = 6.8 Hz, 2H), 1.93-1.88 (m, 2H), 1.79-1.73 (m, 2H). Calculated (M + H): 502.11, Found (M + H): 502.1. HPLC purity: 99.82% |

Example 106: Preparation of 3-(4-chloro-3-(trifluoromethyl)phenyl)-7-methyl-5-(2-oxo-2-(pyrrolidin-1-yl)ethyl)thieno[3,2-c]pyridin-4(5H)-one

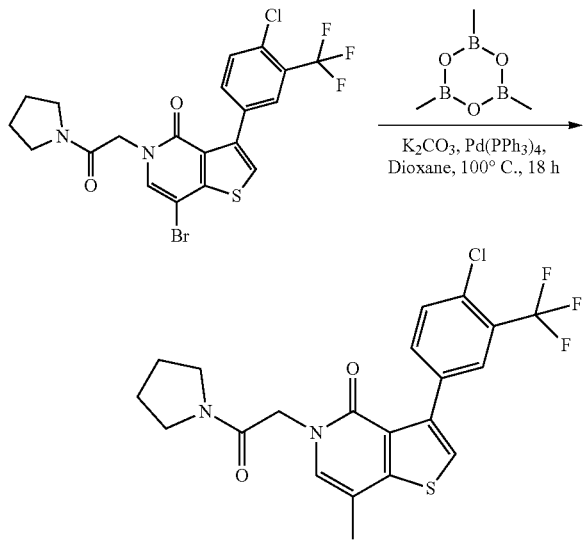

To a solution of 7-bromo-3-(4-chloro-3-(trifluoromethyl)phenyl)-5-(2-oxo-2-(pyrrolidin-1-yl)ethyl)thieno[3,2-c]pyridin-4(5H)-one (0.15 g, 0.28 mmol) and potassium carbonate (0.199 g, 1.44 mmol) in dioxane (12 mL) argon was purged for 10 minutes. Then trimethylboroxine (0.04 mL, 0.28 mmol), Pd(PPh$_3$)$_4$ (0.05 g, 0.04 mmol) were added and the resulting mixture was stirred at 100° C. for 18 h. After completion of reaction (monitored by TLC), the reaction mixture was cooled to room temperature and filtered through celite. The filtrate was concentrated under vacuum and the crude product was purified by prep HPLC (analytical conditions: column chemsil C18 (250 mm×4.6 mm×5µ), mobile phase (A): 0.01% ammonia in water, mobile phase (B): acetonitrile, flow rate: 1.0 mL/min, T/% B: 0/20, 12/80, 25/80, 27/20, 30/20, wavelength: 220 nm) to afford the title compound 3-(4-chloro-3-(trifluoromethyl)phenyl)-7-methyl-5-(2-oxo-2-(pyrrolidin-1-yl)ethyl)thieno[3,2-c]pyridin-4(5H)-one (0.033 g, 25% yield) as white solid. $^1$H NMR (400 MHz, DMSO-d$_6$) δ (ppm): 7.86 (s, 1H), 7.73-7.67 (m, 3H), 7.33 (s, 1H), 4.69 (s, 2H), 3.46 (t, J=6.4 Hz, 2H); 3.27 (s, 2H), 2.22 (s, 3H), 1.92-1.86 (m, 2H), 1.78-1.71 (m, 2H). Calculated (M+H): 455.07, Found (M+H): 455.1, HPLC purity: 99.85%.

TABLE 7

The following compound was prepared by the method described above:

| Ex. No. | Structure | IUPAC Name | Analytical Data |
|---|---|---|---|
| 107 | 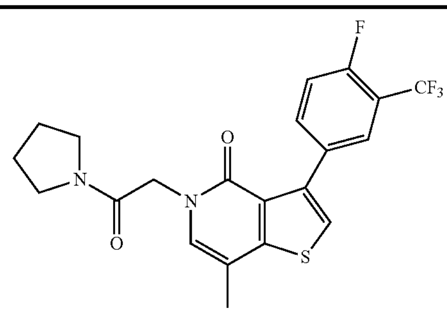 | 3-(4-fluoro-3-(trifluoromethyl)phenyl)-7-methyl-5-(2-oxo-2-(pyrrolidin-1-yl)ethyl)thieno[3,2-c]pyridin-4(5H)-one | $^1$H NMR (400 MHz, DMSO-d$_6$) δ (ppm): 7.79-7.75 (m, 2H), 7.68 (s, 1H), 7.48 (t, J = 10 Hz, 1H), 7.33 (s, 1H), 4.69 (s, 2H), 3.46 (t, J = 6.4 Hz, 2H), 3.27-3.24 (m, 2H), 2.22 (s, 3H), 1.89 (t, J = 6.8 Hz, 2H), 1.75 (t, J = 6.4 Hz, 2H). Calculated (M + H): 439.10; Found (M + H): 439.1. HPLC purity: 99.71% |

Examples 108 and 109: Preparation of 3-(4-fluoro-3-(trifluoromethyl)phenyl)-N-hydroxy-4-oxo-5-(2-oxo-2-(pyrrolidin-1-yl)ethyl)-4,5-dihydrothieno[3,2-c]pyridine-7-carboximidamide & 3-(4-fluoro-3-(trifluoromethyl)phenyl)-7-(1,2,4-oxadiazol-3-yl)-5-(2-oxo-2-(pyrrolidin-1-yl)ethyl)thieno[3,2-c]pyridin-4(5H)-one

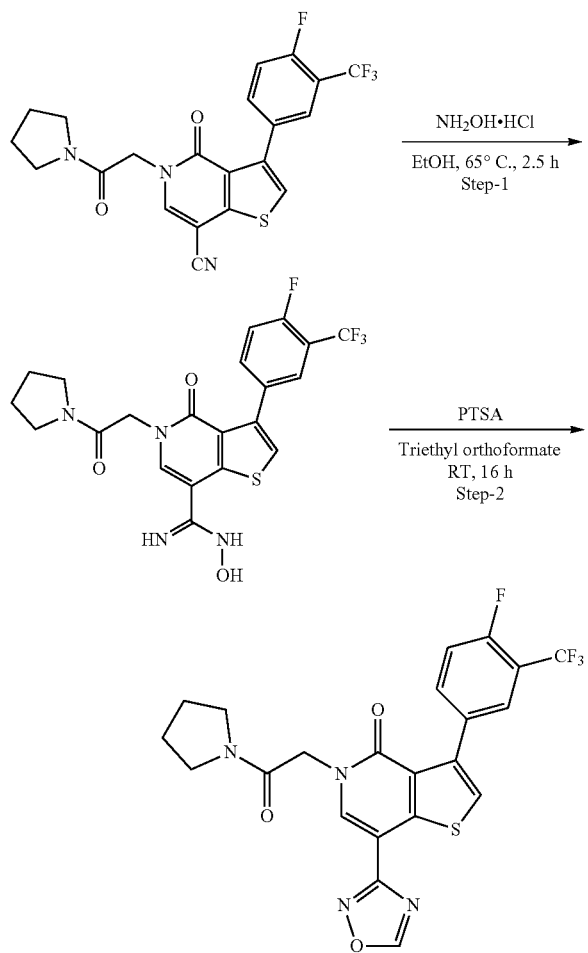

Step-1

Preparation of 3-(4-fluoro-3-(trifluoromethyl)phenyl)-N-hydroxy-4-oxo-5-(2-oxo-2-(pyrrolidin-1-yl)ethyl)-4,5-dihydrothieno[3,2-c]pyridine-7-carboximidamide To a stirred solution of hydroxylamine hydrochloride (0.23 g, 3.33 mmol) in ethanol (20 mL) was added triethylamine (0.9 mL, 6.67 mmol) and stirred for 10 minutes. Then 3-(4-fluoro-3-(trifluoromethyl)phenyl)-4-oxo-5-(2-oxo-2-(pyrrolidin-1-yl)ethyl)-4,5-dihydrothieno[3,2-c]pyridine-7-carbonitrile (1.0 g, 2.22 mmol) was added and the reaction mixture was stirred at 65° C. for 2 h. The reaction mixture was concentrated and the residue was washed with hexane followed by 5% methanol in dichloromethane and dried under vacuum to afford the title compound 3-(4-fluoro-3-(trifluoromethyl)phenyl)-N-hydroxy-4-oxo-5-(2-oxo-2-(pyrrolidin-1-yl)ethyl)-4,5-dihydrothieno[3,2-c]pyridine-7-carboximidamide (0.9 g, 83% yield) as white solid. $^1$H NMR (400 MHz, DMSO-$d_6$) δ (ppm): 9.91 (s, 1H), 7.96 (s, 1H), 7.73 (d, J=6 Hz, 2H), 7.64 (s, 1H), 7.46 (t, J=10 Hz, 1H), 5.77 (s, 2H), 4.72 (s, 2H), 3.48 (t, J=6.4 Hz, 2H), 3.32-3.27 (m, 2H), 1.96-1.87 (m, 2H), 1.79-1.74 (m, 2H). Calculated (M+H): 483.10; Found (M+H): 483.1. HPLC purity: 99.02%.

Step-2

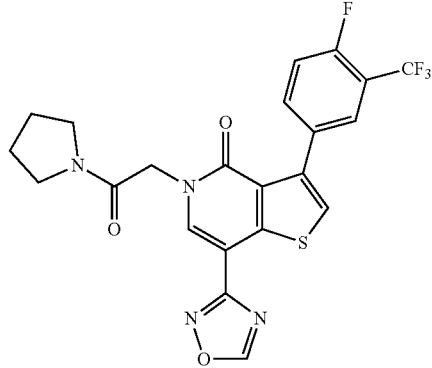 [SMILES: O=C(Cn1cc(-c2ncon2)c2scc(-c3ccc(F)c(C(F)(F)F)c3)c2c1=O)N1CCCC1]

Preparation of 3-(4-fluoro-3-(trifluoromethyl)phenyl)-7-(1,2,4-oxadiazol-3-yl)-5-(2-oxo-2-(pyrrolidin-1-yl)ethyl)thieno[3,2-c]pyridin-4(5H)-one To a stirred solution of 3-(4-fluoro-3-(trifluoromethyl)phenyl)-N-hydroxy-4-oxo-5-(2-oxo-2-(pyrrolidin-1-yl)ethyl)-4,5-dihydrothieno[3,2-c]pyridine-7-carboximidamide (0.1 g, 0.20 mmol) in triethylorthoformate (5 mL) was added p-toluenesulfonic acid (0.017 g, 0.10 mmol) and the reaction mixture was stirred at room temperature for 16 h. The reaction mixture was concentrated and the residue was purified by silica gel column chromatography using 5% methanol in dichloromethane. The obtained material was again washed with water, hexane and dried under high vacuum to get the title compound 3-(4-fluoro-3-(trifluoromethyl)phenyl)-7-(1,2,4-oxadiazol-3-yl)-5-(2-oxo-2-(pyrrolidin-1-yl)ethyl)thieno[3,2-c]pyridin-4(5H)-one (0.075 g, 74% yield) as white solid. $^1$H NMR (400 MHz, DMSO-$d_6$) δ (ppm): 9.74 (s, 1H), 8.50 (s, 1H), 7.87 (s, 1H), 7.85-7.77 (m, 2H), 7.50 (t, J=8.8 Hz, 1H), 4.94 (s, 2H), 3.48 (t, J=6.4 Hz, 2H), 3.32-3.22 (m, 2H), 1.94-1.88 (m, 2H), 1.86-1.73 (m, 2H). Calculated (M+H): 393.09; Found (M+H): 393.1. HPLC purity: 99.84%.

TABLE 8

The following compound was prepared by the method described above:

| Ex. No. | Structure | IUPAC Name | Analytical Data |
|---|---|---|---|
| 110 | 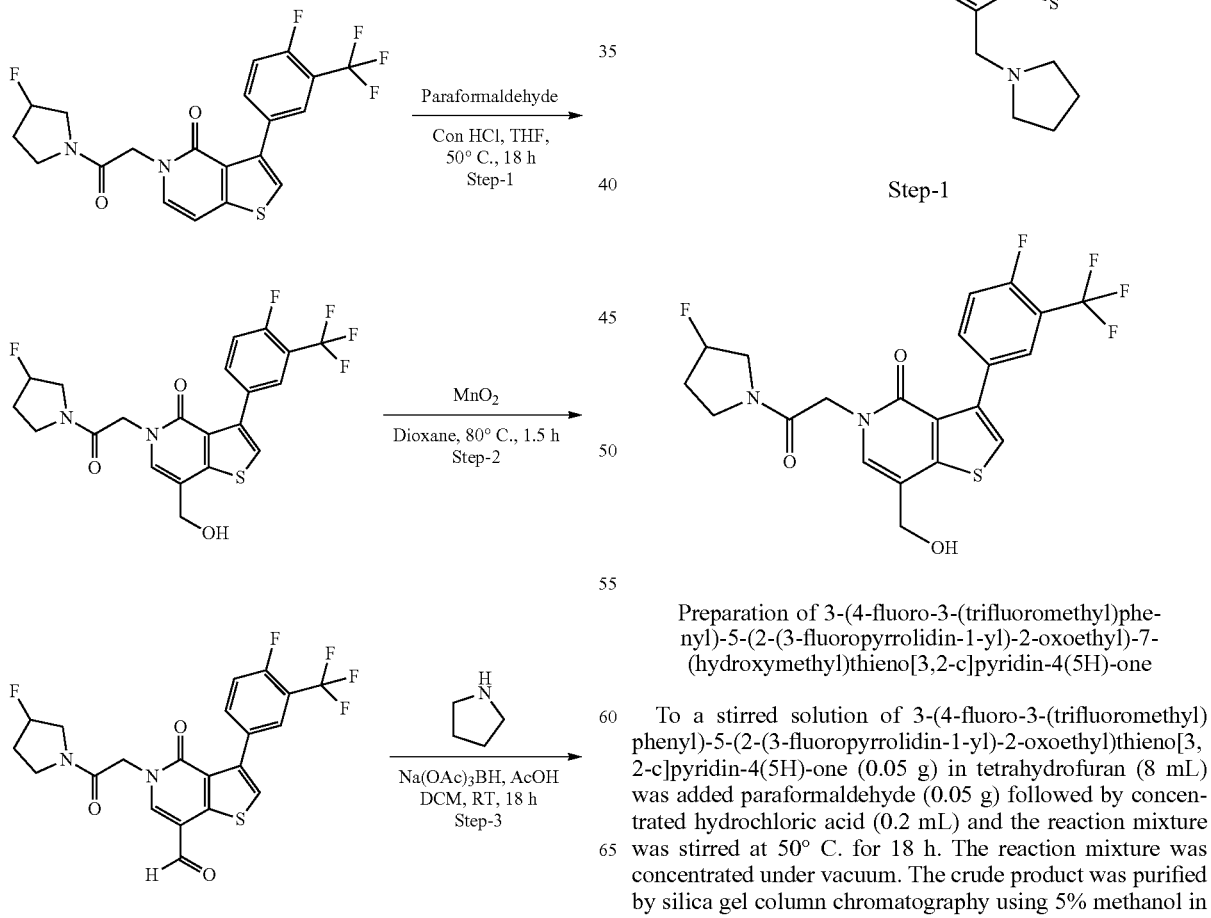 | 3-(4-fluoro-3-(trifluoromethyl)phenyl)-5-(2-(3-fluoropyrrolidin-1-yl)-2-oxoethyl)-N-hydroxy-4-oxo-4,5-dihydrothieno[3,2-c]pyridine-7-carboximidamide | $^1$H NMR (400 MHz, DMSO-$d_6$) δ (ppm): 9.91 (s, 1H), 7.98 (s, 1H), 7.74 (d, J = 6.8 Hz, 2H), 7.65 (s, 1H), 7.46 (t, J = 10 Hz, 1H), 5.77 (s, 2H), 5.5-5.2 (m, 1H), 4.89-4.69 m, 2H), 3.80-3.32 (m, 4H), 2.30-2.21 (m, 2H). Calculated (M + H): 501.09; Found (M + H): 501.1. HPLC purity: 97.01% |

Examples 111 and 112: Preparation 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one & 3-(4-fluoro-3-(trifluoromethyl)phenyl)-5-(2-(3-fluoropyrrolidin-1-yl)-2-oxoethyl)-7-(pyrrolidin-1-ylmethyl)thieno[3,2-c]pyridin-4(5H)-one Preparation of 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one To a stirred solution of 3-(4-fluoro-3-(trifluoromethyl)phenyl)-5-(2-(3-fluoropyrrolidin-1-yl)-2-oxoethyl)thieno[3,2-c]pyridin-4(5H)-one (0.05 g) in tetrahydrofuran (8 mL) was added paraformaldehyde (0.05 g) followed by concentrated hydrochloric acid (0.2 mL) and the reaction mixture was stirred at 50° C. for 18 h. The reaction mixture was concentrated under vacuum. The crude product was purified by silica gel column chromatography using 5% methanol in dichloromethane to afford the title compound 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (0.012 g, 22% yield) as off-white solid. $^1$H NMR (400 MHz, DMSO-$d_6$) δ (ppm): 7.78-7.76 (m, 2H), 7.68 (s, 1H), 7.50-7.45 (m, 2H), 5.47-5.23 (m, 2H), 4.87-4.68 (m, 2H), 4.48 (d, J=4.4 Hz, 2H); 3.86-3.27 (m, 4H), 2.30-1.90 (m, 2H), Calculated (M+H): 473.09, Found (M+H): 473.2. HPLC purity: 98.14%.

Step-2

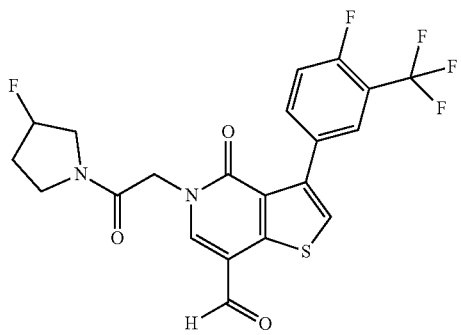 [SMILES: O=Cc1cn(CC(=O)N2CCC(F)C2)c(=O)c2c(-c3ccc(F)c(C(F)(F)F)c3)csc12]

Preparation of 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde To a stirred solution of 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (0.045 g, 0.09 mmol) in dioxane (8 mL) was added manganese dioxide (0.082 g, 0.95 mmol) and the reaction mixture was stirred at 80° C. for 1.5 h. The reaction mixture was filtered through celite, washed with ethyl acetate and the filtrate was concentrated under vacuum. The crude product was purified by silica gel column chromatography using 5% methanol in dichloromethane to afford the title compound 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde (0.035 g, 79% yield) as a yellow solid. Calculated (M+H): 471.07, Found (M+H): 471.1.

Step-3

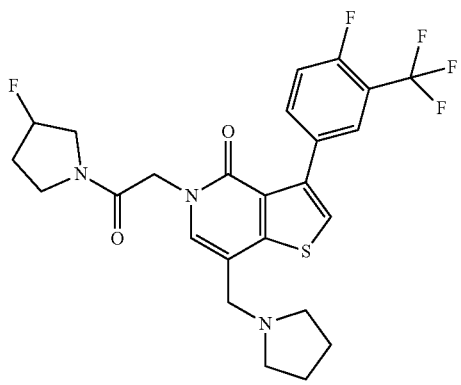 [SMILES: O=C(Cn1cc(CN2CCCC2)c2scc(-c3ccc(F)c(C(F)(F)F)c3)c2c1=O)N1CCC(F)C1]

Preparation of 3-(4-fluoro-3-(trifluoromethyl)phenyl)-5-(2-(3-fluoropyrrolidin-1-yl)-2-oxoethyl)-7-(pyrrolidin-1-ylmethyl)thieno[3,2-c]pyridin-4(5H)-one To a stirred solution 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde (0.1 g, 0.21 mmol) in dichloromethane (20 mL) was added acetic acid (0.06 mL, 10.63 mmol) followed by pyrrolidine (0.1 mL, 1.27 mmol) and the reaction mixture was stirred at room temperature for 30 minutes. Sodium triacetoxyborohydride (0.225 g, 10.63 mmol) was added and the reaction mixture was stirred at room temperature for 18 h. The reaction mixture was diluted with saturated sodium bicarbonate solution (30 mL) and extracted with dichloromethane (3×60 mL). The combined organic layer was dried over anhydrous sodium sulfate, filtered and evaporated to afford the crude product, which was purified by prep HPLC (analytical conditions: column: chemsil C18 (250 mm×4.6 mm×5μ), mobile phase (A): 0.01% ammonia in water, mobile phase (B): acetonitrile, flow rate: 1.0 mL/min, T/% B: 0/20, 10/80, 25/80, 27/20, 30/20, wavelength: 220 nm) to afford the title compound 3-(4-fluoro-3-(trifluoromethyl)phenyl)-5-(2-(3-fluoropyrrolidin-1-yl)-2-oxoethyl)-7-(pyrrolidin-1-ylmethyl)thieno[3,2-c]pyridin-4(5H)-one (0.024 g, 21% yield) as a white solid. $^1$H-NMR (CDCl$_3$, 400 MHz) δ (ppm): 7.70 (d, J=6.4 Hz, 2H), 7.20-7.15 (m, 3H), 5.39-5.17 (m, 1H), 5.00-4.91 (m, 1H), 4.49-4.37 (m, 1H); 3.92-3.79 (m, 2H), 3.77-3.49 (m, 4H), 2.58 (s, 4H), 2.40-2.03 (m, 2H), 1.80 (s, 4H). Calculated (M+H): 526.15; Found (M+1): 526.3. HPLC purity: 99.93%.

Example 113: Preparation of 3-(4-fluoro-3-(trifluoromethyl)phenyl)-4-oxo-5-(2-oxo-2-(pyrrolidin-1-yl)ethyl)-4,5-dihydrothieno[3,2-c]pyridine-7-carboximidamide

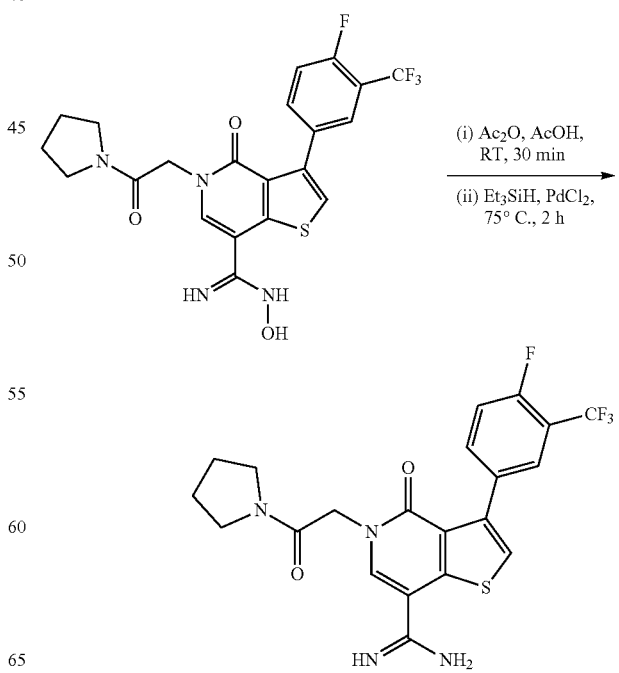

To a stirred solution of 3-(4-fluoro-3-(trifluoromethyl)phenyl)-N-hydroxy-4-oxo-5-(2-oxo-2-(pyrrolidin-1-yl)ethyl)-4,5-dihydrothieno[3,2-c]pyridine-7-carboximidamide (0.3 g, 0.62 mmol) in acetic acid (20 mL) was added acetic anhydride (0.06 mL, 0.68 mmol) and the reaction mixture was stirred at room temperature for 30 min. Then triethyl silane (0.02 mL, 0.13 mmol), palladium chloride (0.01 g, 0.0001 mmol) were added and the reaction mixture was stirred at 75° C. for 2 h. The reaction mixture was cooled to room temperature and the pH was adjusted to 7 by adding saturated sodium bicarbonate solution. The precipitated solid was filtered. The solid was dissolved in 5% methanol in dichloromethane, dried over anhydrous sodium sulfate and filtered through celite bed. The filtrate was evaporated to get the crude compound which was washed with n-pentane and diethyl ether and dried under vacuum to get the title compound 3-(4-fluoro-3-(trifluoromethyl)phenyl)-4-oxo-5-(2-oxo-2-(pyrrolidin-1-yl)ethyl)-4,5-dihydrothieno[3,2-c]pyridine-7-carboximidamide (0.038 g, 13% yield) as brown solid. $^1$H NMR (400 MHz, DMSO-$d_6$) δ (ppm): 8.08 (s, 1H), 7.73 (d, J=7.2 Hz, 2H), 7.62 (s, 1H), 7.45 (t, J=10.4 Hz, 1H), 7.06 (brs, 1H), 6.14 (brs, 2H), 4.72 (s, 2H), 3.49 (t, J=6.8 Hz, 2H), 1.94-1.87 (m, 2H), 1.79-1.74 (m, 2H). 2H are merged with DMSO water peak. Calculated (M+H): 467.11; Found (M+H): 467.1. HPLC purity: 98.81%.

Example 114: Preparation of 3-(4-fluoro-3-(trifluoromethyl)phenyl)-5-(2-oxo-2-(pyrrolidin-1-yl)ethyl)-7-(pyrrolidin-1-yl)thieno[3,2-c]pyridin-4(5H)-one

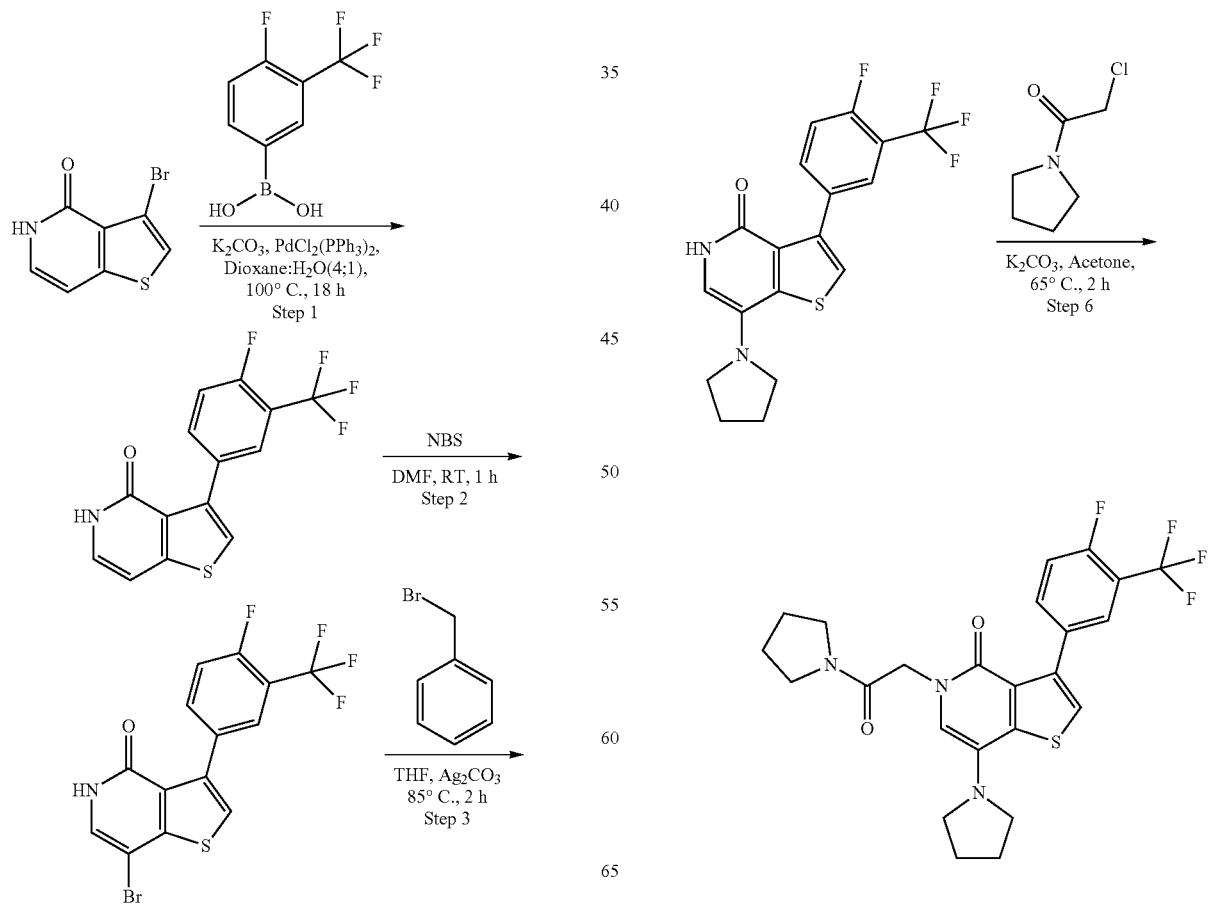

Step-1

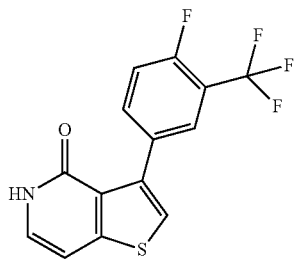 [SMILES: O=c1[nH]ccc2scc(-c3ccc(F)c(C(F)(F)F)c3)c12]

Preparation of 3-(4-fluoro-3-(trifluoromethyl)phenyl)thieno[3,2-c]pyridin-4(5H)-one To a solution of 3-bromothieno[3,2-c]pyridin-4(5H)-one (0.55 g, 2.17 mmol) and (4-chloro-3-(trifluoromethyl)phenyl)boronic acid (0.73 g, 3.25 mmol) in 1,4-dioxane:water mixture (20 mL, 4:1), potassium carbonate (0.9 g, 6.51 mmol) was added. The reaction mixture was purged with argon for 15 min and bis(triphenylphosphine)palladium chloride [PdCl$_2$(PPh$_3$)$_2$] (0.15 g, 0.21 mmol) was added. Then the reaction mixture was stirred at 100° C. for 18 h. The reaction mixture was diluted with water (50 mL) and extracted with ethyl acetate (3×100 mL). The combined organic layer was dried over anhydrous sodium sulphate, filtered and concentrated. The crude product was purified by silica gel column chromatography using 30% ethyl acetate in hexane to afford the title compound 3-(4-chloro-3-(trifluoromethyl)phenyl)thieno[3,2-c]pyridin-4(5H)-one (0.74 g, 94% yield) as off-white solid. Calculated (M+H): 330; Found (M+H): 330.0.

Step-2

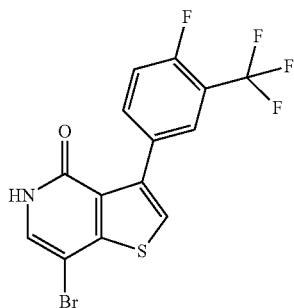 [SMILES: O=c1[nH]cc(Br)c2scc(-c3ccc(F)c(C(F)(F)F)c3)c12]

Preparation of 7-bromo-3-(4-chloro-3-(trifluoromethyl)phenyl)thieno[3,2-c]pyridin-4(5H)-one To a solution of 3-(4-chloro-3-(trifluoromethyl)phenyl)thieno[3,2-c]pyridin-4(5H)-one (4.23 g, 13.51 mmol) in N,N-dimethylformamide (60 mL), was added N-bromosuccinimide (2.39 g, 13.51 mmol) and the reaction mixture was stirred at room temperature for 1 h. Then reaction mixture was poured into ice cold water (100 mL), the precipitated solid was filtered and dried under suction to afford the title compound 7-bromo-3-(4-chloro-3-(trifluoromethyl)phenyl) thieno[3,2-c]pyridin-4(5H)-one (0.82 g, 85% yield) as off-white solid. Calculated (M+H): 391.93; Found (M+H): 391.9.

Step-3

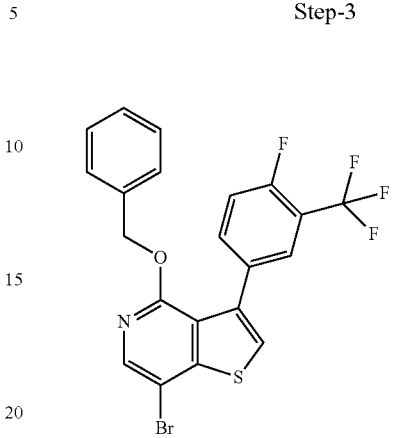

Preparation of 4-(benzyloxy)-7-bromo-3-(4-fluoro-3-(trifluoromethyl)phenyl)thieno[3,2-c]pyridine To a solution of 3-(4-chloro-3-(trifluoromethyl)phenyl) thieno[3,2-c]pyridin-4(5H)-one (4.1 g, 10.73 mmol) in tetrahydrofuran (50 mL) were added silver carbonate (3.88 g, 13.98 mmol), benzyl bromide (1.6 mL, 12.87 mmol) and the reaction mixture was stirred at 85° C. for 2 h. The reaction mixture was diluted with water (50 mL) and extracted with ethyl acetate (3×100 mL). The combined organic layer was dried over anhydrous sodium sulphate, filtered and concentrated to afford the title compound 4-(benzyloxy)-7-bromo-3-(4-fluoro-3-(trifluoromethyl)phenyl)thieno[3,2-c]pyridine (0.7 g, 72.0% yield) as pale yellow solid. Calculated (M+H): 481.98; Found (M+H): 482.0.

Step-4

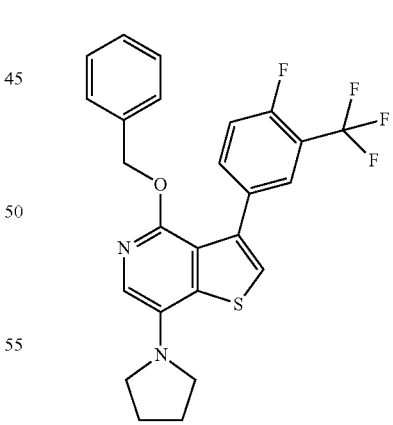

Preparation of 4-(benzyloxy)-3-(4-fluoro-3-(trifluoromethyl)phenyl)-7-(pyrrolidin-1-yl)thieno[3,2-c]pyridine To a solution of 4-(benzyloxy)-7-bromo-3-(4-fluoro-3-(trifluoromethyl)phenyl)thieno[3,2-c]pyridine (0.75 g, 1.43 mmol) in toluene (20 mL), was added sodium tertiary butoxide (0.44 g, 4.61 mmol) and the solution was purged with argon for 10 min. Then pyrrolidine (0.3 mL, 3.58 mmol), 2,2'-bis(diphenylphosphino)-1,1'-binaphthyl (0.093 g, 0.073 mmol) and tris(dibenzylideneacetone)dipalladium (0) [Pd₂(dba)₃] (0.07 g, 0.076 mmol) were added and the resulting mixture was stirred at 120° C. for 18 h. The reaction mixture was cooled to room temperature, diluted with water (50 mL) and extracted with ethyl acetate (3×100 mL). The combined organic layer was dried over anhydrous sodium sulphate, filtered and concentrated under vacuum. The crude product was purified by silica gel column chromatography using 10% ethyl acetate in hexane to afford the title compound 4-(benzyloxy)-3-(4-fluoro-3-(trifluoromethyl)phenyl)-7-(pyrrolidin-1-yl)thieno[3,2-c]pyridine (0.55 g, 75% yield) as pale yellow solid. Calculated (M+H): 473.12; Found (M+H): 473.1.

Step-5

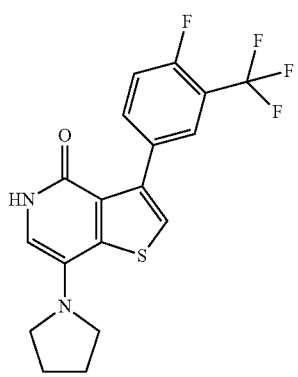 [SMILES: O=c1[nH]cc(N2CCCC2)c2scc(-c3ccc(F)c(C(F)(F)F)c3)c12]

Preparation of 3-(4-fluoro-3-(trifluoromethyl)phenyl)-7-(pyrrolidin-1-yl)thieno[3,2-c]pyridin-4(5H)-one To 4-(benzyloxy)-3-(4-fluoro-3-(trifluoromethyl)phenyl)-7-(pyrrolidin-1-yl)thieno[3,2-c]pyridine (0.15 g, 0.31 mmol)trifluoroaceticacid (5 mL) was added at 0° C. and the reaction mixture was stirred at room temperature for 30 min. The reaction mixture was diluted with ice water (20 mL) and extracted with ethyl acetate (3×50 mL). The combined organic layer was dried over anhydrous sodium sulphate, filtered and concentrated to afford the title compound 3-(4-fluoro-3-(trifluoromethyl)phenyl)-7-(pyrrolidin-1-yl)thieno[3,2-c]pyridin-4(5H)-one (0.13 g, 99.0% yield) as purple solid. Calculated (M+H): 383.08; Found (M+H): 383.1.

Step-6

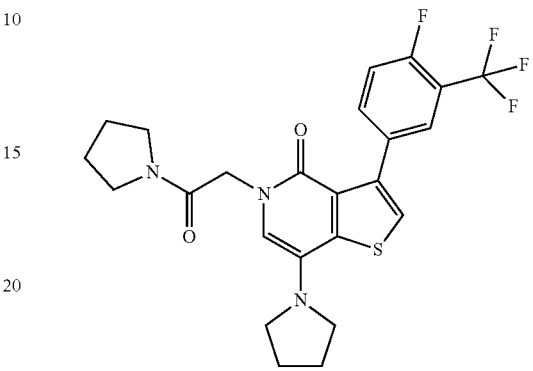

Preparation of 3-(4-fluoro-3-(trifluoromethyl)phenyl)-5-(2-oxo-2-(pyrrolidin-1-yl)ethyl)-7-(pyrrolidin-1-yl)thieno[3,2-c]pyridin-4(5H)-one To a stirred solution of 3-(4-fluoro-3-(trifluoromethyl)phenyl)-7-(pyrrolidin-1-yl)thieno[3,2-c]pyridin-4(5H)-one (0.13 g, 0.34 mmol) in dry acetone (20 mL) was added potassium carbonate (0.23 g, 1.67 mmol) followed by 2-chloro-1-(pyrrolidin-1-yl)ethanone (0.075 g, 0.51 mmol) at room temperature. The reaction mixture was heated at 65° C. for 2 h. The reaction mixture was filtered and the filtrate was concentrated under vacuum. The crude product was purified by silica gel column chromatography using 5% methanol in dichloromethane to afford the title compound 3-(4-fluoro-3-(trifluoromethyl)phenyl)-5-(2-oxo-2-(pyrrolidin-1-yl)ethyl)-7-(pyrrolidin-1-yl)thieno[3,2-c]pyridin-4(5H)-one (0.006 g, 4.0% yield) as white solid. ¹H NMR (400 MHz, DMSO-d₆) δ (ppm): 7.75 (d, J=5.6 Hz, 2H), 7.69 (s, 1H), 7.47 (t, J=9.2 Hz, 1H), 7.04 (s, 1H), 4.68 (s, 2H), 3.45 (t, J=6.8 Hz, 2H), 3.11 (s, 4H), 1.89 (t, J=6.4 Hz, 6H), 1.78-1.73 (q, 2H). 2H merged with DMSO water. Calculated (M+H): 494.14, Found (M+H): 494.1. HPLC purity: 99.80%.

TABLE 9

The following compound was prepared by the method described above:

| Ex. No. | Structure | IUPAC Name | Analytical Data |
|---|---|---|---|
| 115 | 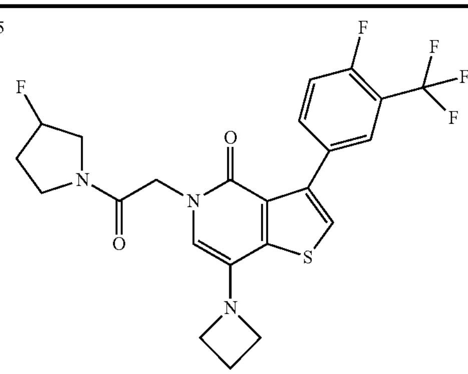 | 7-(azetidin-1-yl)-3-(4-fluoro-3-(trifluoromethyl)phenyl)-5-(2-(3-fluoropyrrolidin-1-yl)-2-oxoethyl)thieno[3,2-c]pyridin-4(5H)-one | ¹H NMR (400 MHz, DMSO-d₆) δ (ppm): 7.77 (d, J = 6.4 Hz, 2H), 7.7 (s, 1H), 7.46 (t, J = 9.2 Hz, 1H), 6.82 (s, 1H), 5.48-5.23 (m, 1H), 4.83-4.66 (m, 2H), 3.84-3.20 (m, 8H), 2.30-1.85 (m, 4H). Calculated (M + H): 498.12, Found (M + H): 498.1, HPLC purity: 99.09% |

Example 116: Preparation of 7-((dimethylamino)methyl)-3-(4-fluoro-3-(trifluoromethyl)phenyl)-5-(2-(3-fluoropyrrolidin-1-yl)-2-oxoethyl)thieno[3,2-c]pyridin-4(5H)-one

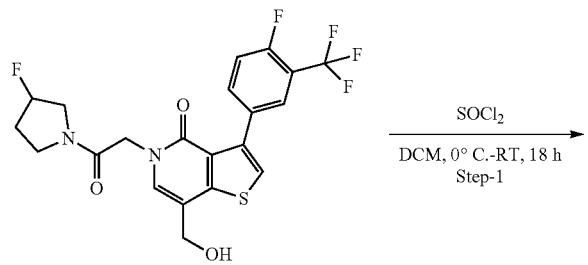

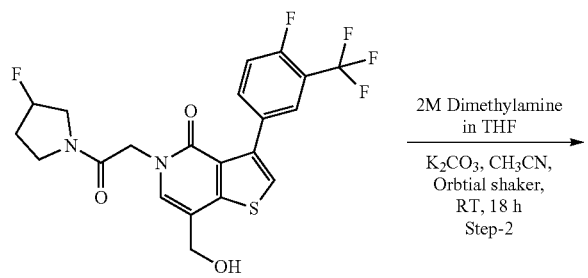

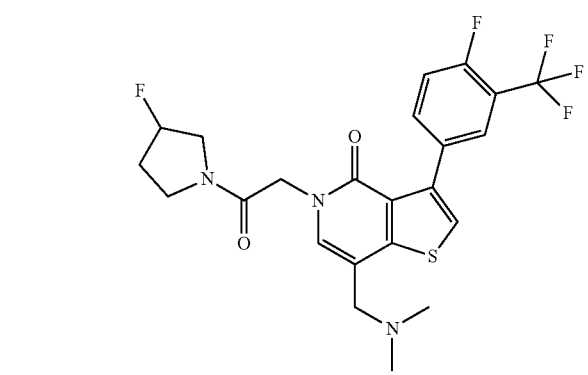

Step-1

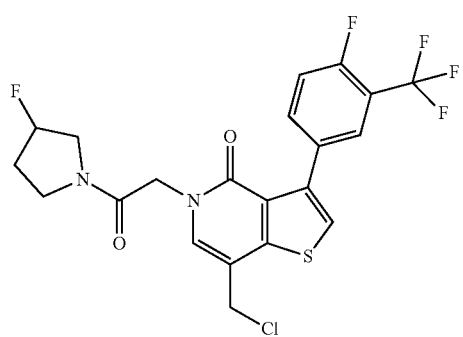 [SMILES: O=C(Cn1cc(CCl)c2scc(-c3ccc(F)c(C(F)(F)F)c3)c2c1=O)N1CCC(F)C1]

Preparation of 7-(chloromethyl)-3-(4-fluoro-3-(trifluoromethyl)phenyl)-5-(2-(3-fluoropyrrolidin-1-yl)-2-oxoethyl)thieno[3,2-c]pyridin-4(5H)-one To a stirred solution of 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (0.1 g) in dichloromethane (10 mL) was added thionyl chloride (3 mL) at 0° C. and the reaction mixture was stirred at room temperature for 18 h. The reaction mixture was concentrated under vacuum to afford the title compound 7-(chloromethyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.12 g, crude) as a colourless liquid. The crude was as such taken for the next step without purification.

Step-2

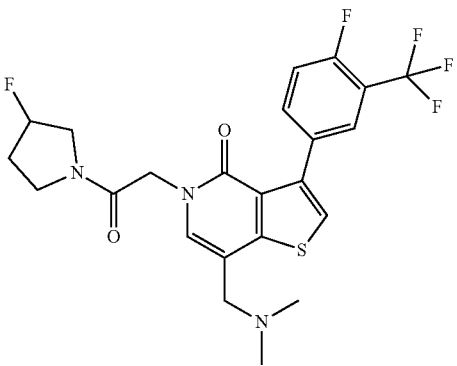 [SMILES: CN(C)Cc1cn(CC(=O)N2CCC(F)C2)c(=O)c2c(-c3ccc(F)c(C(F)(F)F)c3)csc12]

Preparation of 7-((dimethylamino)methyl)-3-(4-fluoro-3-(trifluoromethyl)phenyl)-5-(2-(3-fluoropyrrolidin-1-yl)-2-oxoethyl)thieno[3,2-c]pyridin-4(5H)-one To a stirred suspension of potassium carbonate (0.10 g, 0.732 mmol) in acetonitrile (5 mL) was added 2M dimethylamine in tetrahydrofuran (1.2 mL, 2.44 mmol) and the reaction mixture was stirred at room temperature for 10 min. Then a solution of 7-(chloromethyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.12 g, 0.244 mmol, crude) in acetonitrile (5 mL) was added and the reaction mixture was stirred in orbital shaker at room temperature for 18 h. The reaction mixture was filtered, the filtrate was concentrated and the crude product was purified by silica gel column chromatography using 6% methanol in dichloromethane to afford the title compound 7-((dimethylamino)methyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.009 g, 7% yield) as a green solid. $^1$H NMR (400 MHz, DMSO-$d_6$) δ (ppm): 7.76 (t, J=6.4 Hz, 2H), 7.64 (s, 1H), 7.47 (t, J=10 Hz, 1H), 7.42 (s, 1H), 5.48-5.23 (m, 1H); 4.86-4.68 (m, 2H), 3.82-3.47 (m, 4H), 3.44 (s, 2H), 2.47-2.19 (m, 2H), 2.16 (s, 6H), Calculated (M+H): 500.1, Found (M+H): 500.1. HPLC purity: 96.29%.

Example 117: Preparation of 7-((diethylamino)methyl)-3-(4-fluoro-3-(trifluoromethyl)phenyl)-5-(2-(3-fluoropyrrolidin-1-yl)-2-oxoethyl)thieno[3,2-c]pyridin-4(5H)-one 2,2,2-trifluoroacetate

Example 118: Preparation of 7-(azetidin-1-ylmethyl)-3-(4-fluoro-3-(trifluoromethyl)phenyl)-5-(2-(3-fluoropyrrolidin-1-yl)-2-oxoethyl)thieno[3,2-c]pyridin-4(5H)-one

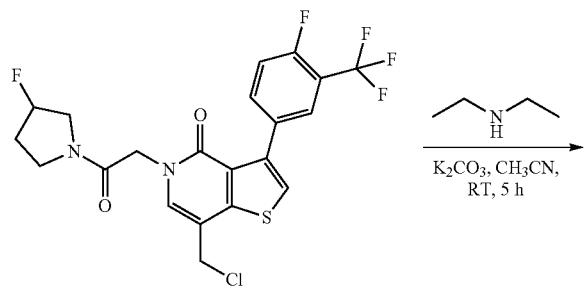
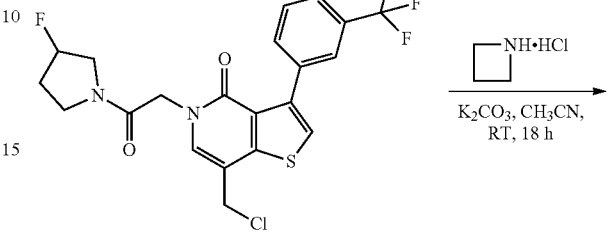

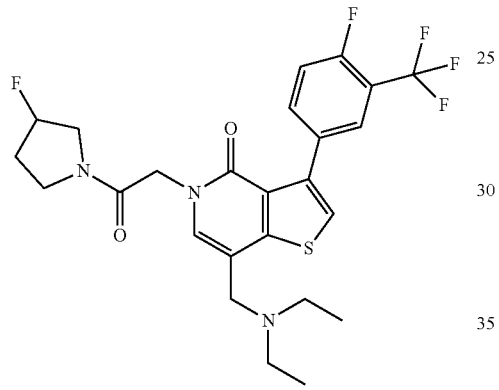
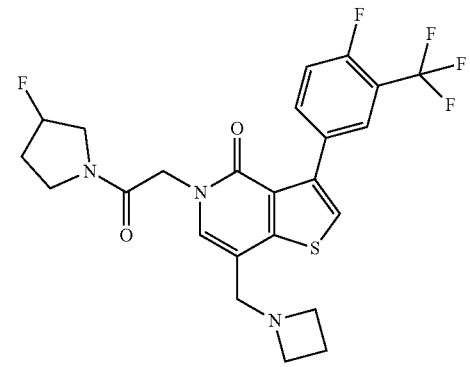

To a stirred solution of potassium carbonate (0.033 g, 0.24 mmol) in acetonitrile (8 mL) was added diethyl amine (1.2 mL, 2.44 mmol) and the reaction mixture was stirred at room temperature for 10 min. Then a solution of 7-(chloromethyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.06 g, crude) in acetonitrile (5 mL) was added and the reaction mixture was stirred at room temperature for 5 h. The reaction mixture was filtered, the filtrate was concentrated and the crude product was purified by preparative HPLC (analysis method: kinetex C18 (100 mm×4.6 mm×2.6 m), mobile phase (A): 0.01% TFA in water, mobile phase (B): acetonitrile, flow rate: 0.75 ml/min) to afford the title compound 7-((diethylamino)methyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.007 g, 10% yield) as a white solid. $^1$H NMR (400 MHz, DMSO-$d_6$) δ (ppm): 9.42 (brs, 1H), 7.81-7.76 (m, 4H), 7.50 (t, J=10 Hz, 1H), 5.49-5.24 (m, 1H); 4.94-4.76 (m, 2H), 4.35 (s, 2H), 3.89-3.59 (m, 4H), 3.20 (brs, 4H), 2.30-1.952 (m, 2H), 1.28 (s, 6H). Calculated (M+H): 528.1, Found (M+H): 528.2. HPLC purity: 99.52%.

To a stirred solution of potassium carbonate (0.084 g, 0.61 mmol) in acetonitrile (10 mL) was added azetidine hydrochloride (0.095, 1.02 mmol) and the reaction mixture was stirred at room temperature for 10 min. Then a solution of 7-(chloromethyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.1 g, 0.204 mmol, crude) in acetonitrile (5 mL) was added and the reaction mixture was stirred at room temperature for 18 h. The reaction mixture was filtered, the filtrate was concentrated and the crude product was purified by silica gel column chromatography using 5% methanol in dichloromethane to afford the title compound 7-(azetidin-1-ylmethyl)-3-(4-fluoro-3-(trifluoromethyl)phenyl)-5-(2-(3-fluoropyrrolidin-1-yl)-2-oxoethyl)thieno[3,2-c]pyridin-4(5H)-one (0.006 g, 5% yield) as a brown solid. $^1$H NMR (400 MHz, DMSO-$d_6$) δ (ppm): 7.77 (d, J=6 Hz, 2H), 7.64 (s, 1H), 7.46 (t, J=9.6 Hz, 1H), 7.40 (s, 1H); 5.48-5.23 (m, 1H), 4.86-4.68 (m, 2H), 3.85-3.77 (m, 2H), 3.74-3.54 (m, 2H), 3.50 (s, 2H), 3.15 (s, 4H), 2.30-2.05 (m, 2H), 2.05 (t, J=6 Hz, 2H). Calculated (M+H): 512.1, Found (M+H): 512.1. HPLC purity: 98.64%.

TABLE 10

The following compound was prepared by the method described above:

| Ex. No. | Structure | IUPAC Name | Analytical Data |
|---|---|---|---|
| 119 | 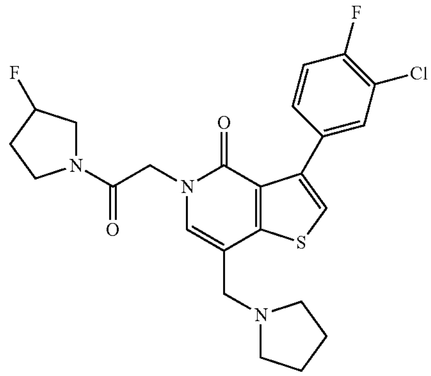 [SMILES: O=C(Cn1cc(CN2CCCC2)c2scc(-c3ccc(F)c(Cl)c3)c2c1=O)N1CCC(F)C1] | 3-(3-chloro-4-fluorophenyl)-5-(2-(3-fluoropyrrolidin-1-yl)-2-oxoethyl)-7-(pyrrolidin-1-ylmethyl)thieno[3,2-c]pyridin-4(5H)-one | $^1$H NMR (400 MHz, DMSO-$d_6$) δ (ppm): 7.76 (d, J = 14.4 Hz, 2H), 7.60 (d, J = 7.2 Hz, 1H), 7.41-7.37 (m, 2H), 5.49-5.25 (m, 1H), 4.94-4.76 (m, 2H), 4.43-4.29 (m, 2H), 4.07-3.71 (m, 3H), 3.66-3.25 (m, 7H), 2.31-1.86 (m, 4H). Calculated (M + H): 492.12; Found (M + H): 492.1; HPLC purity: 99.42% |
| 120 | 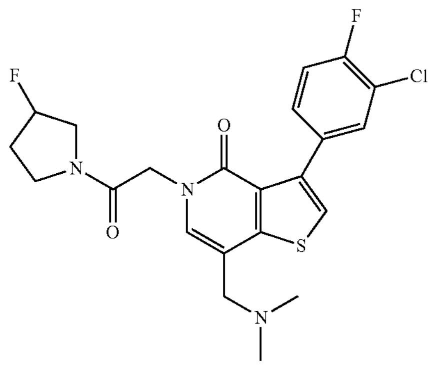 [SMILES: CN(C)Cc1cn(CC(=O)N2CCC(F)C2)c(=O)c2c(-c3ccc(F)c(Cl)c3)csc12] | 3-(3-chloro-4-fluorophenyl)-7-((dimethylamino)methyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.60 (d, J = 6.8 Hz, 1H), 7.57 (s, 1H), 7.41-7.34 (m, 3H), 5.50-5.22 (m, 1H), 4.82-4.73 (m, 2H), 3.86-3.45 (m, 4H), 3.37 (s, 2H), 2.25-2.02 (m, 8H). Calculated (M + H): 466.11; Found (M + H): 466.2; HPLC purity: 98.92% |
| 121 | 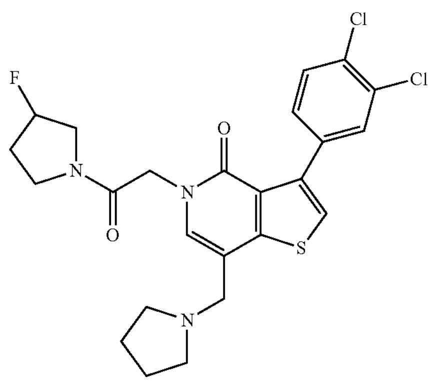 [SMILES: O=C(Cn1cc(CN2CCCC2)c2scc(-c3ccc(Cl)c(Cl)c3)c2c1=O)N1CCC(F)C1] | 3-(3,4-dichlorophenyl)-5-(2-(3-fluoropyrrolidin-1-yl)-2-oxoethyl)-7-(pyrrolidin-1-ylmethyl)thieno[3,2-c]pyridin-4(5H)-one | $^1$H NMR (400 MHz, DMSO-$d_6$) δ (ppm): 9.77 (brs, 1 H), 7.78 (s, 2H), 7.62 (t, J = 8.4 Hz, 2H), 7.39 (d, J = 7.6 Hz, 1H), 5.49-5.24 (m, 1H), 4.94-4.75 (m, 2H), 4.42 (d, J = 4.4 Hz, 2H), 3.87-3.19 (m, 8H), 2.30-1.86 (m, 6H): Calculated (M + H): 508.1, Found (M + H): 508.1, HPLC purity: 99.74% |
| 122 | 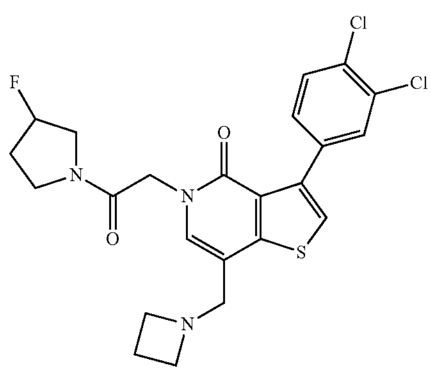 [SMILES: O=C(Cn1cc(CN2CCC2)c2scc(-c3ccc(Cl)c(Cl)c3)c2c1=O)N1CCC(F)C1] | 7-(azetidin-1-ylmethyl)-3-(3,4-dichlorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.65 (s, 1H), 7.62 (s, 1H), 7.58 (d, J = 8.4 Hz, 1H), 7.40 (s, 2 H), 5.35-5.23 (m, 1H), 4.86-4.72 (m, 2H), 3.75 (s, 2H), 3.60-3.49 (m, 4H), 3.16-3.12 (m, 6H), 2.30-1.98 (m, 2H). Calculated (M + H): 494.08, Found (M + H): 494.2, HPLC purity: 97.48% |

TABLE 10-continued

The following compound was prepared by the method described above:

| Ex. No. | Structure | IUPAC Name | Analytical Data |
|---|---|---|---|
| 123 | 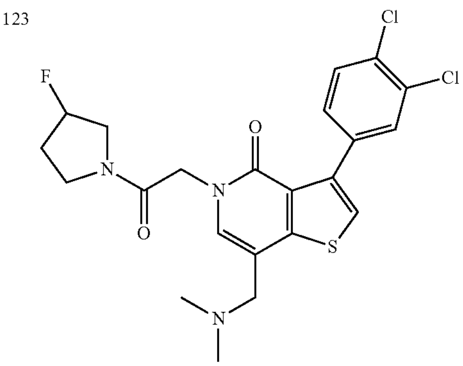 | 3-(3,4-dichlorophenyl)-7-((dimethylamino)methyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 9.70 (brs, 1H), 7.75 (d, J = 12.0 Hz, 2H), 7.65 (s, 1H), 7.61 (d, J = 8.4 Hz, 1H), 7.39 (d, J = 8.0 Hz, 1H), 5.49-5.24 (m, 1H), 4.94-4.76 (m, 2H), 4.34 (s, 2H), 3.90-3.11 (m, 4H), 2.82 (brs, 6H), 2.30-1.95 (m, 2H). Calculated (M + H): 482.08, Found (M + H): 482.3, HPLC purity: 99.17% |
| 124 | 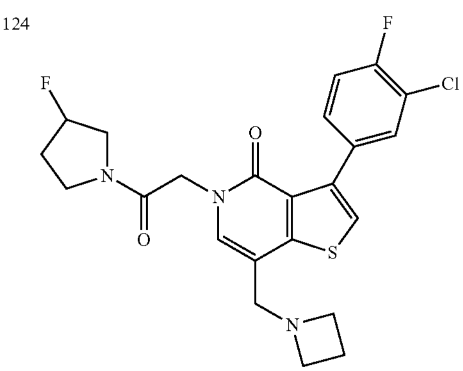 | 7-(azetidin-1-ylmethyl)-3-(3-chloro-4-fluorophenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.61-7.58 (m, 2H), 7.39-7.34 (m, 3H), 5.48-5.23 (m, 1H), 4.86-4.69 (m, 2H), 3.86-3.3 (m, 6H), 3.14 (t, J = 7.2 Hz, 4H), 2.3-1.9 (m, 4H). Calculated (M + H): 478.11, Found (M + H): 478.1. HPLC purity: 99.82% |
| 125 | 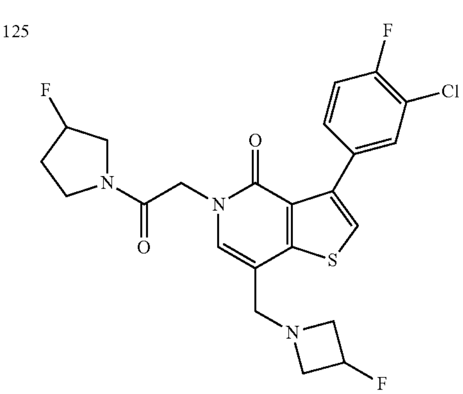 | 3-(3-chloro-4-fluorophenyl)-7-((3-fluoroazetidin-1-yl)methyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.61-7.59 (m, 2H), 7.43-7.34 (m, 3H), 5.49-5.10 (m, 2H), 4.87-4.69 (m, 2H), 3.86-3.65 (m, 1H), 3.62-3.49 (m, 6H), 3.46-3.36 (m, 1H), 3.28-3.14 (m, 2H), 2.24-2.21 (m, 1H), 2.10-2.06 (m, 1H). Calculated (M + H): 496.10, Found (M + H): 496.1. HPLC purity: 99.39% |

Example 126: Preparation of 3-(4-fluoro-3-(trifluoromethyl)phenyl)-5-(2-(3-fluoropyrrolidin-1-yl)-2-oxoethyl)-7-(methoxymethyl)thieno[3,2-c]pyridin-4(5H)-one

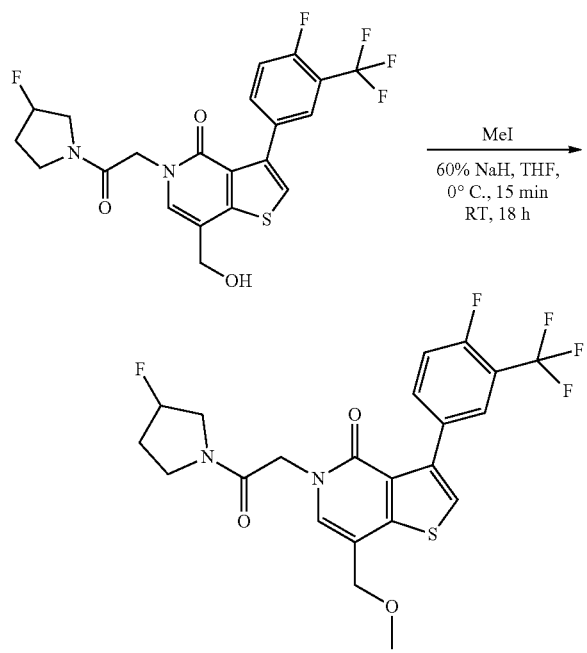

To a suspension of sodium hydride (60% dispersion in oil) (0.06 g, 0.67 mmol) in tetrahydrofuran cooled to 0° C., was added 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (0.08 g, 0.16 mmol) portion wise and the reaction mixture stirred at 0° C. for 15 min. Then methyl iodide (0.1 mL, 1.69 mmol) was added drop wise and the reaction mixture was stirred at room temperature for 18 h. The reaction mixture was quenched with cold water (20 mL) and extracted with ethyl acetate (3×50 mL). The combined organic layer was dried over anhydrous sodium sulfate, filtered and evaporated to afford the crude product which was purified by silica gel column chromatography using 3% methanol in dichloromethane to afford 3-(4-fluoro-3-(trifluoromethyl)phenyl)-5-(2-(3-fluoropyrrolidin-1-yl)-2-oxoethyl)-7-(methoxymethyl)thieno[3,2-c]pyridin-4(5H)-one (0.022 g, 26% yield) as a white solid. $^1$H-NMR (400 MHz, DMSO-$d_6$) δ (ppm): 7.69 (brs, 2H), 7.25-7.17 (m, 3H), 5.3-5.18 (m, 1H), 4.97-4.91 (m, 1H), 4.49-4.38 (m, 3H), 3.89-3.49 (m, 4H), 3.42 (s, 3H), 2.37-2.10 (m, 2H). Calculated (M+H): 487.1, Found (M+H): 487.1, HPLC purity: 99.86%.

TABLE 11

The following compound was prepared by the method described above:

| Ex. No. | Structure | IUPAC Name | Analytical Data |
|---|---|---|---|
| 127 | (structure) | 7-(ethoxymethyl)-3-(4-fluoro-3-(trifluoromethyl)phenyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.79-7.77 (m, 2H), 7.69 (s, 1H), 7.53-7.46 (m, 2H), 5.48-5.23 (m, 1H), 4.87-4.69 (m, 2H), 4.47 (s, 2H), 3.86-3.27 (m, 6H), 2.30-1.91 (m, 2H), 1.15 (t, J = 7.2 Hz, 3H). Calculated (M + H): 501.12; Found (M + H): 501.2. HPLC purity: 98.45% |

TABLE 11-continued

The following compound was prepared by the method described above:

| Ex. No. | Structure | IUPAC Name | Analytical Data |
|---|---|---|---|
| 128 | 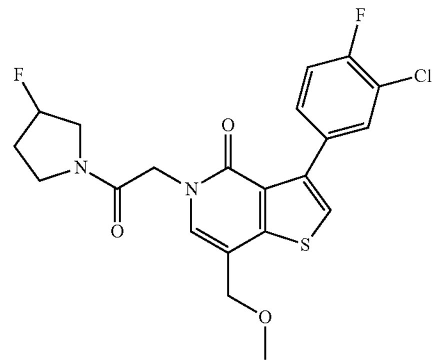 [SMILES: COCc1cn(CC(=O)N2CCC(F)C2)c(=O)c2c(-c3ccc(F)c(Cl)c3)csc12] | 3-(3-chloro-4-fluorophenyl)-5-(2-(3-fluoropyrrolidin-1-yl)-2-oxoethyl)-7-(methoxymethyl)thieno[3,2-c]pyridin-4(5H)-one | $^1$H NMR (400 MHz, DMSO-$d_6$) δ (ppm): 7.51 (d, J = 6.0 Hz, 1H), 7.36 (brs, 1H), 7.21 (brs, 1H), 7.16-7.11 (m, 2 H), 5.38-5.17 (m, 1H), 5.01-4.91 (m, 1H), 4.48-4.38 (m, 3H), 3.92-3.41 (m, 7H), 2.36-2.26 (m, 1H), 2.03-1.99 (m, 1H). Calculated (M + H): 453.08, Found (M + H): 453.1, HPLC purity: 98.28% |
| 129 | 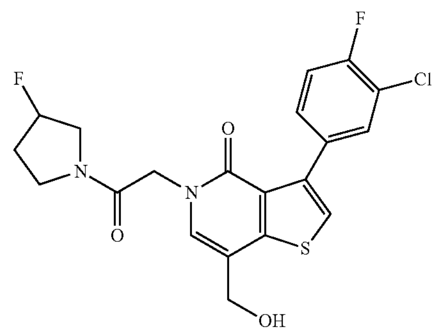 [SMILES: O=C(Cn1cc(CO)c2scc(-c3ccc(F)c(Cl)c3)c2c1=O)N1CCC(F)C1] | 3-(3-chloro-4-fluorophenyl)-5-(2-(3-fluoropyrrolidin-1-yl)-2-oxoethyl)-7-(hydroxymethyl)thieno[3,2-c]pyridin-4(5H)-one | $^1$H NMR (400 MHz, DMSO-$d_6$) δ (ppm): 7.61-7.59 (m, 2H), 7.44-7.34 (m, 3H), 5.48-5.35 (m, 2H), 4.87-4.69 (m, 2H), 4.48 (d, J = 5.2 Hz, 2H), 3.86-3.27 (m, 4H), 2.24-1.94 (m, 2H). Calculated (M + H): 439.06, Found (M + H): 439.0. HPLC purity: 96.17% |
| 130 | 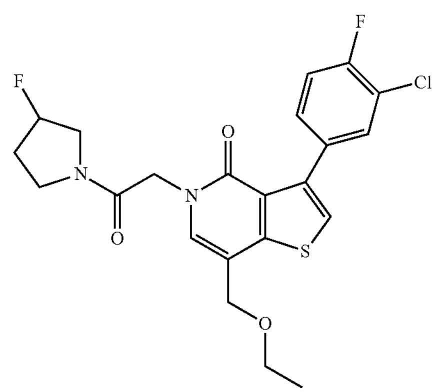 [SMILES: CCOCc1cn(CC(=O)N2CCC(F)C2)c(=O)c2c(-c3ccc(F)c(Cl)c3)csc12] | 3-(3-chloro-4-fluorophenyl)-7-(ethoxymethyl)-5-(2-(3-fluoropyrrolidin-1-yl)-2-oxoethyl)thieno[3,2-c]pyridin-4(5H)-one | $^1$H NMR (400 MHz, DMSO-$d_6$) δ (ppm): 7.62-7.60 (m, 2H), 7.52 (s, 1H), 7.43-7.34 (m, 2H), 5.48-5.23 (m, 1H), 4.87-4.69 (m, 2H), 4.45 (s, 2H), 3.86-3.27 (m, 6H), 2.24-1.94 (m, 2H), 1.14 (t, J = 7.2 Hz, 3H). Calculated (M + H): 467.09, Found (M + H): 467.1. HPLC purity: 99.1% |
| 131 | 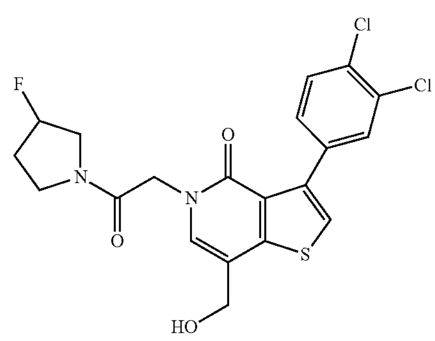 [SMILES: O=C(Cn1cc(CO)c2scc(-c3ccc(Cl)c(Cl)c3)c2c1=O)N1CCC(F)C1] | 3-(3,4-dichlorophenyl)-5-(2-(3-fluoropyrrolidin-1-yl)-2-oxoethyl)-7-(hydroxymethyl)thieno[3,2-c]pyridin-4(5H)-one | $^1$H NMR (400 MHz, DMSO-$d_6$) δ (ppm): 7.65 (s, 2H), 7.59 (d, J = 8.4 Hz, 1H), 7.45 (s, 1H), 7.40 (d, J = 8.4 Hz, 1H), 5.48-5.34 (m, 2H), 4.87-4.69 (m, 2H), 4.48 (d, J = 4.8 Hz, 2H), 3.86-3.32 (m, 4H), 2.24-1.94 (m, 2H). Calculated (M + H): 455.03, Found (M + H): 455.2, HPLC purity: 99.15% |

TABLE 11-continued

The following compound was prepared by the method described above:

| Ex. No. | Structure | IUPAC Name | Analytical Data |
|---|---|---|---|
| 132 | 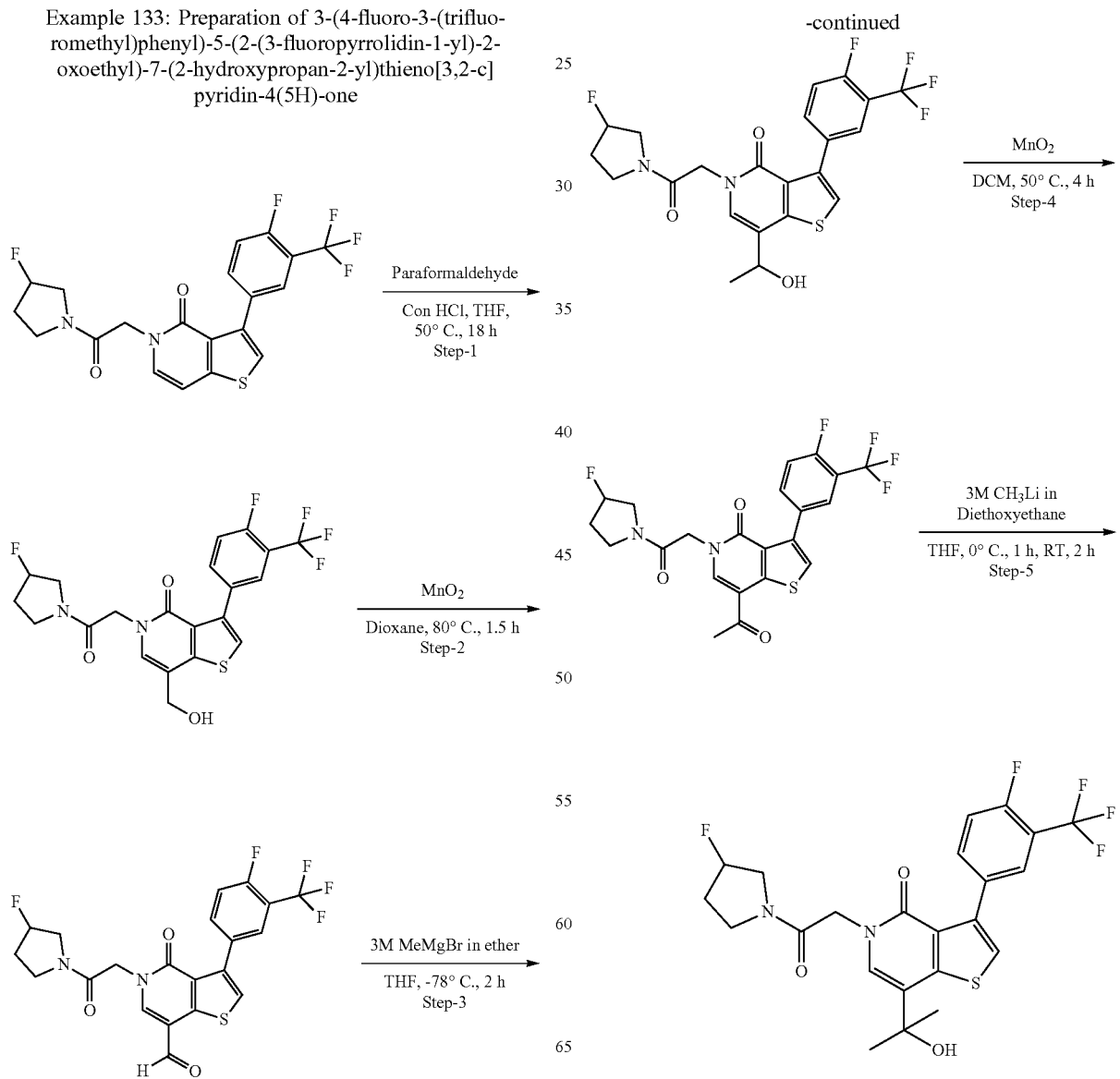 | 3-(3,4-dichlorophenyl)-5-(2-(3-fluoropyrrolidin-1-yl)-2-oxoethyl)-7-(methoxymethyl)thieno[3,2-c]pyridin-4(5H)-one | $^1$H NMR (400 MHz, DMSO-$d_6$) δ (ppm): 7.57 (s, 1H), 7.43 (d, J = 8.0 Hz, 1H), 7.34 (d, J = 8.0 Hz, 1H), 7.23 (d, J = 6.0 Hz, 1H), 7.18 (s. 1H), 5.30-5.17 (m, 1H), 5.02-4.93 (m, 1H), 4.48-4.37 (m, 3H), 3.88-3.41 (m, 6H), 2.4-2.0 (m, 2H). Calculated (M + H): 469.05, Found (M + H): 469.0, HPLC purity: 99.17% |

Example 133: Preparation of 3-(4-fluoro-3-(trifluoromethyl)phenyl)-5-(2-(3-fluoropyrrolidin-1-yl)-2-oxoethyl)-7-(2-hydroxypropan-2-yl)thieno[3,2-c]pyridin-4(5H)-one Step-1

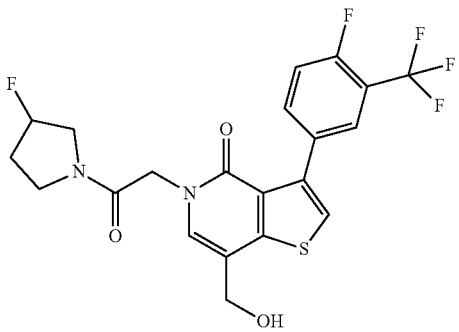 [SMILES: O=C(Cn1cc(CO)c2scc(-c3ccc(F)c(C(F)(F)F)c3)c2c1=O)N1CCC(F)C1]

Preparation of 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one To a stirred solution of 3-(4-fluoro-3-(trifluoromethyl)phenyl)-5-(2-(3-fluoropyrrolidin-1-yl)-2-oxoethyl)thieno[3,2-c]pyridin-4(5H)-one (0.05 g) in tetrahydrofuran (8 mL), was added paraformaldehyde (0.05 g) followed by concentrated hydrochloric acid (0.2 mL) and the reaction mixture was stirred at 50° C. for 18 h. The reaction mixture was concentrated under vacuum. The crude product was purified by silica gel column chromatography using 5% methanol in dichloromethane to afford the title compound 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (0.012 g, 22% yield) as off-white solid. $^1$H NMR (400 MHz, DMSO-$d_6$) δ (ppm): 7.78-7.76 (m, 2H), 7.68 (s, 1H), 7.50-7.45 (m, 2H), 5.47-5.23 (m, 2H), 4.87-4.68 (m, 2H), 4.48 (d, J=4.4 Hz, 2H); 3.86-3.27 (m, 4H), 2.30-1.90 (m, 2H), Calculated (M+H): 473.09, Found (M+H): 473.2. HPLC purity: 98.14%.

Step-2

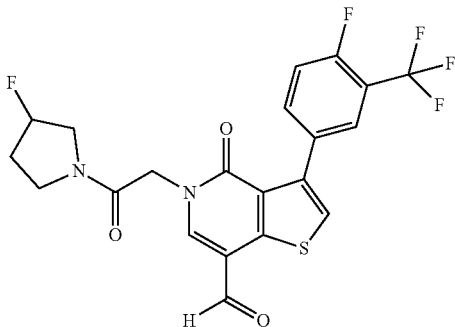 [SMILES: O=Cc1cn(CC(=O)N2CCC(F)C2)c(=O)c2c(-c3ccc(F)c(C(F)(F)F)c3)csc12]

Preparation of 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde To a stirred solution of 3-(4-fluoro-3-(trifluoromethyl)phenyl)-5-(2-(3-fluoropyrrolidin-1-yl)-2-oxoethyl)-7-(hydroxymethyl)thieno[3,2-c]pyridin-4(5H)-one (1.82 g, 3.85 mmol) in dioxane (50 mL) was added manganese dioxide (3.35 g, 38.55 mmol) and the reaction mixture was stirred at 80° C. for 1.5 h. The reaction mixture was filtered through celite, washed with ethyl acetate and the filtrate was concentrated under vacuum. The crude product was purified by silica gel column chromatography using 5% methanol in dichloromethane to afford the title compound 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde (1.53 g, 84% yield) as a yellow solid. $^1$H-NMR (400 MHz, DMSO-$d_6$) δ (ppm): 9.78 (s, 1H), 8.58 (d, J=2.4 Hz, 1H), 7.82 (s, 1H), 7.79-7.75 (m, 2H), 7.50 (t, J=9.2 Hz, 1H); 5.7-5.24 (m, 1H), 5.04-4.86 (m, 2H), 3.90-3.79 (m, 2H); 3.77-3.62 (m, 2H), 2.47-2.07 (m, 2H), Calculated (M+H): 471.0; Found (M+1): 471.0. HPLC purity: 98.87%.

Step-3

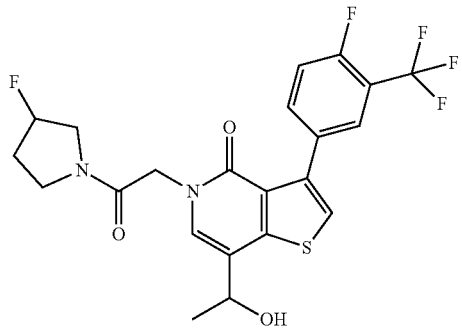 [SMILES: CC(O)c1cn(CC(=O)N2CCC(F)C2)c(=O)c2c(-c3ccc(F)c(C(F)(F)F)c3)csc12]

Preparation of 3-(4-fluoro-3-(trifluoromethyl)phenyl)-5-(2-(3-fluoropyrrolidin-1-yl)-2-oxoethyl)-7-(1-hydroxyethyl)thieno[3,2-c]pyridin-4(5H)-one To a stirred solution 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde (0.1 g, 0.21 mmol) in tetrahydrofuran (8 mL), was added 3M methyl magnesium bromide in ether (0.13 mL, 0.42 mmol) at −78° C. drop wise and the reaction mixture was stirred at −78° C. for 2 h. The reaction mixture was quenched with saturated ammonium chloride solution (15 mL) and extracted with ethyl acetate (3×60 mL). The combined organic layer was dried over anhydrous sodium sulfate, filtered and evaporated to afford the crude product, which was purified by silica gel column chromatography using 4% methanol in dichloromethane to afford the title compound 3-(4-fluoro-3-(trifluoromethyl)phenyl)-5-(2-(3-fluoropyrrolidin-1-yl)-2-oxoethyl)-7-(1hydroxyethyl)thieno[3,2-c]pyridin-4(5H)-one (0.06 g, 60% yield) as a white solid. $^1$H-NMR (400 MHz, DMSO-$d_6$) δ (ppm): 7.70 (d, J=6 Hz, 2H), 7.66 (s, 1H), 7.49-7.43 (m, 2H), 5.49-5.23 (m, 2H), 4.88-4.68 (m, 3H); 3.82-3.48 (m, 4H), 2.30-2.05 (m, 2H), 1.44 (d, J=6.8 Hz, 3H). Calculated (M+H): 487.1; Found (M+1): 487.3. HPLC purity: 99.41%.

Step-4

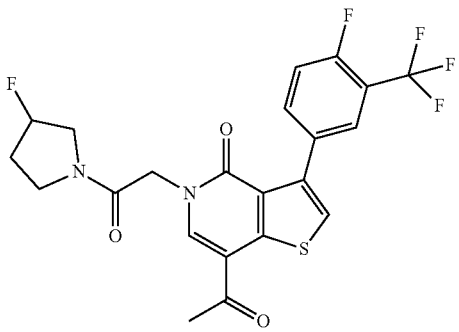 [SMILES: CC(=O)c1cn(CC(=O)N2CCC(F)C2)c(=O)c2c(-c3ccc(F)c(C(F)(F)F)c3)csc12]

Preparation of 7-acetyl-3-(4-fluoro-3-(trifluoromethyl)phenyl)-5-(2-(3-fluoropyrrolidin-1-yl)-2-oxoethyl)thieno[3,2-c]pyridin-4(5H)-one To a stirred solution of 3-(4-fluoro-3-(trifluoromethyl)phenyl)-5-(2-(3-fluoropyrrolidin-1-yl)-2-oxoethyl)-7-(hydroxyethyl)thieno[3,2-c]pyridin-4(5H)-one (0.05 g, 0.10 mmol) in dichloromethane (8 mL), was added manganese dioxide (0.089 g, 1.02 mmol) and the reaction mixture was stirred at 50° C. for 30 minutes. The reaction mixture was filtered through celite, washed with ethyl acetate and the filtrate was concentrated under vacuum. The crude product was purified by silica gel column chromatography using 5% methanol in dichloromethane to afford the title compound 7-acetyl-3-(4-fluoro-3-(trifluoromethyl)phenyl)-5-(2-(3-fluoropyrrolidin-1-yl)-2-oxoethyl)thieno[3,2-c]pyridin-4(5H)-one (0.045 g, 91% yield) as a white solid. $^1$H-NMR (400 MHz, DMSO-d$_6$) δ (ppm): 8.74 (s, 1H), 7.76 (d, J=4.4 Hz, 3H), 7.48 (t, J=9.6 Hz, 1H); 5.38-5.03 (m, 1H), 4.99-4.85 (m, 2H), 3.85-3.76 (m, 2H), 3.63-3.27 (m, 2H), 2.47 (s, 3H) 2.30-2.09 (m, 2H). Calculated (M+H): 485.0; Found (M+1): 485.1. HPLC purity: 99.65%.

Step-5

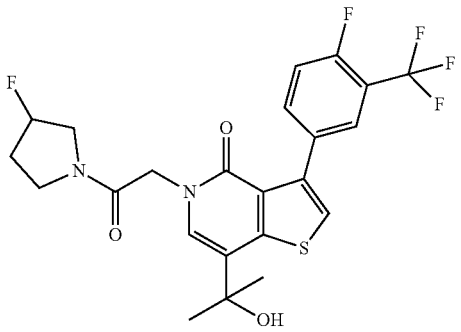 [SMILES: CC(C)(O)c1cn(CC(=O)N2CCC(F)C2)c(=O)c2c(-c3ccc(F)c(C(F)(F)F)c3)csc12]

Preparation of 3-(4-fluoro-3-(trifluoromethyl)phenyl)-5-(2-(3-fluoropyrrolidin-1-yl)-2-oxoethyl)-7-(2-hydroxypropan-2-yl)thieno[3,2-c]pyridin-4(5H)-one To a stirred solution 7-acetyl-3-(4-fluoro-3-(trifluoromethyl)phenyl)-5-(2-(3-fluoropyrrolidin-1-yl)-2-oxoethyl)thieno[3,2-c]pyridin-4(5H)-one (0.21 g, 0.43 mmol) in tetrahydrofuran (15 mL), was added 3M methyl lithium in diethoxyethane (0.57 mL, 1.73 mmol) at 0° C. drop wise and the reaction mixture was stirred at room temperature for 2 h. The reaction mixture was quenched with saturated ammonium chloride solution (30 mL) and extracted with ethyl acetate (3×80 mL). The combined organic layer was dried over anhydrous sodium sulfate, filtered and evaporated to afford the crude product, which was purified by prep HPLC (analytical conditions: column: chemsil C$_{18}$ (250 mm×4.6 mm×5μ), mobile phase (A): 0.1% ammonia in water, mobile phase (B): acetonitrile, flow rate: 1.0 mL/min, T/% B: 0/20, 10/80, 25/80, 27/20, 30/20) to afford the title compound 3-(4-fluoro-3-(trifluoromethyl)phenyl)-5-(2-(3-fluoropyrrolidin-1-yl)-2-oxoethyl)-7-(2-hydroxypropan-2-yl)thieno[3,2-c]pyridin-4(5H)-one (0.23 g, 10% yield) as a white solid. $^1$H-NMR (400 MHz, DMSO-d$_6$) δ (ppm): 7.74 (d, J=5.6 Hz, 2H), 7.65 (s, 1H), 7.45 (t, J=10 Hz, 1H), 7.39 (s, 1H), 5.48-5.36 (m, 1H), 5.23 (s, 1H), 4.86-4.68 (m, 2H); 3.84-3.483.51 (m, 4H), 2.47-2.07 (m, 2H). 1.52 (s, 6H), Calculated (M+H): 501.1; Found (M+1): 501.1. HPLC purity: 99.40%.

Example 134: Preparation of (E)-3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde oxime

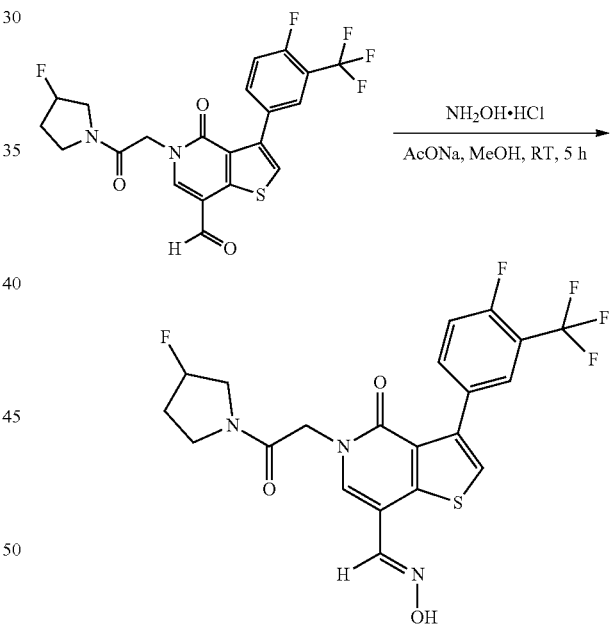

To a stirred solution of 3-(4-fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde (0.1 g, 0.21 mmol) in methanol (10 mL) were added hydroxylamine hydrochloride (0.073 g, 1.06 mmol), sodium acetate (0.139 g, 1.70 mmol) and the reaction mixture was stirred at room temperature for 5 h. The reaction mixture was concentrated under vacuum. The residue was diluted with dichloromethane (100 mL) and washed with water (30 mL). The organic layer was dried over anhydrous sodium sulfate, filtered and evaporated to afford the crude product which was purified by silica gel column chromatography using 5% methanol in dichloromethane to afford the title compound (E)-3-(4- fluoro-3-(trifluoromethyl)phenyl)-5-(2-(3-fluoropyrrolidin-1-yl)-2-oxoethyl)-4-oxo-4,5-dihydrothieno[3,2-c]pyridine-7-carbaldehyde oxime (0.05 g, 48% yield) as a white solid. $^1$H NMR (400 MHz, DMSO-$d_6$) δ (ppm): 11.31 (s, 1H), 8.16 (s, 1H), 7.84 (d, J=4 Hz, 1H), 7.77 (d, J=8.8 Hz, 3H), 7.48 (t, J=9.6 Hz, 1H), 5.48-5.23 (m, 1H); 4.92-4.76 (m, 2H), 3.88-3.46 (m, 4H), 2.30-2.06 (m, 2H), Calculated (M+H): 486.0, Found (M+H): 486.1. HPLC purity: 98.19%.

Example 135: Preparation of (Z)-3-(4-fluoro-3-(trifluoromethyl)phenyl)-5-(2-(3-fluoropyrrolidin-1-yl)-2-oxoethyl)-7-(1-(hydroxyimino)ethyl)thieno[3,2-c]pyridin-4(5H)-one

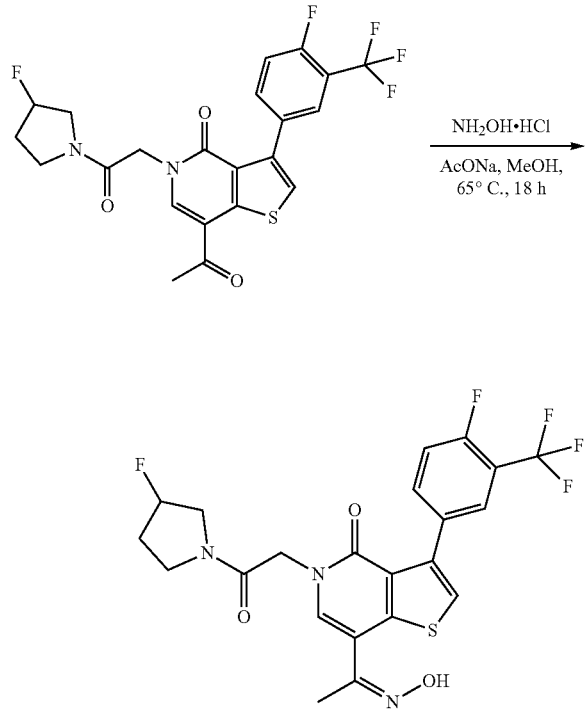

To a stirred solution of 7-acetyl-3-(4-fluoro-3-(trifluoromethyl)phenyl)-5-(2-(3-fluoropyrrolidin-1-yl)-2-oxoethyl)thieno[3,2-c]pyridin-4(5H)-one (0.1 g, 0.20 mmol) in methanol (10 mL) were added hydroxylamine hydrochloride (0.143 g, 2.06 mmol), sodium acetate (0.135 g, 1.64 mmol) and the reaction mixture was stirred at 65° C. for 18 h. The reaction mixture was concentrated under vacuum. The residue was diluted with dichloromethane (100 mL) and washed with water (30 ml). The organic layer was dried over anhydrous sodium sulfate, filtered and evaporated to afford the crude product which was purified by silica gel column chromatography using 4% methanol in dichloromethane to afford the title compound Z)-3-(4-fluoro-3-(trifluoromethyl)phenyl)-5-(2-(3-fluoropyrrolidin-1-yl)-2-oxoethyl)-7-(1-(hydroxyimino)ethyl)thieno[3,2-c]pyridin-4(5H)-one (0.022 g, 16% yield) as a white solid. $^1$H NMR (400 MHz, DMSO-$d_6$) δ (ppm): 11.36 (s, 1H), 7.95 (s, 1H), 7.75 (d, J=6.8 Hz, 2H), 7.69 (s, 1H), 7.46 (t, J=10 Hz, 1H), 5.49-5.24 (m, 1H); 4.96-4.4.79 (m, 2H), 3.83-3.56 (m, 4H), 2.30-1.9 (m, 5H). Calculated (M+H): 500.1, Found (M+H): 500.1. HPLC purity: 96.72%.

Example 136: Preparation of 3-chloro-5-(5-(2-(3-fluoro-3-methylazetidin-1-yl)-2-oxoethyl)-4-oxo-4,5-dihydrothieno[3,2-c]pyridin-3-yl)picolinonitrile

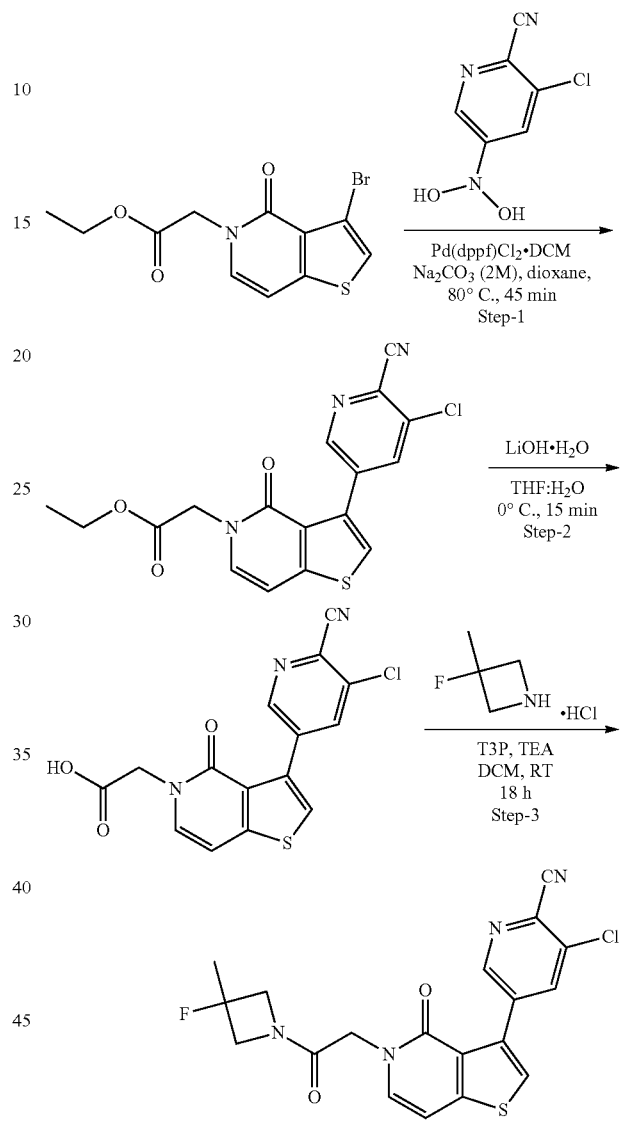

Step-1

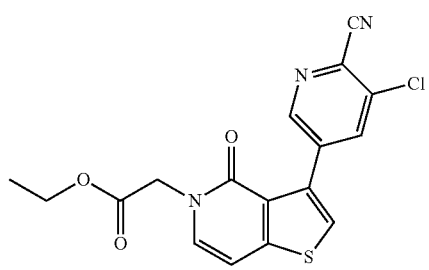 [SMILES: CCOC(=O)Cn1ccc2scc(-c3cnc(C#N)c(Cl)c3)c2c1=O]

Preparation of ethyl 2-(3-(5-chloro-6-cyanopyridin-3-yl)-4-oxothieno[3,2-c]pyridin-5(4H)-yl)acetate To a solution of ethyl 2-(3-bromo-4-oxothieno[3,2-c]pyridin-5(4H)-yl)acetate (0.1 g, 0.31 mmol) and (5-chloro-6-cyanopyridin-3-yl)boronic acid (0.105 g, 0.39 mmol) in 1,4-dioxane (10 mL), sodium carbonate (0.101 g, 0.95 mmol, 2M in water) was added. Then the reaction purged with argon for 15 minutes. Then Pd(dppf)Cl$_2$.DCM (0.013 g, 0.015 mmol) was added and the reaction mixture was stirred at 80° C. for 45 minutes. Then reaction mixture was filtered through celite, the filtrate was diluted with ethyl acetate (100 mL) and washed with water (2×30 mL). The organic layer was concentrated to afford the crude product which was purified by silica gel column chromatography using 65% ethyl acetate in hexane to afford title compound ethyl 2-(3-(5-chloro-6-cyanopyridin-3-yl)-4-oxothieno[3,2-c]pyridin-5(4H)-yl)acetate (0.1 g, 84% yield) as brownish solid. Calculated (M+H): 374.03; Found (M+H): 374.0.

Step-2

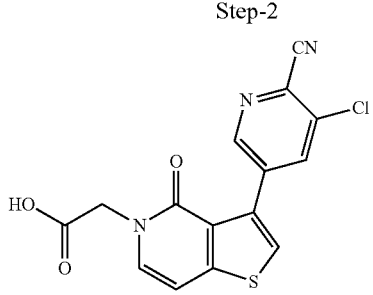

Preparation of 2-(3-(5-chloro-6-cyanopyridin-3-yl)-4-oxothieno[3,2-c]pyridin-5(4H)-yl)acetic acid To a stirred solution of ethyl 2-(3-(5-chloro-6-cyanopyridin-3-yl)-4-oxothieno[3,2-c]pyridin-5(4H)-yl)acetate (0.1 g, 0.26 mmol) in tetrahydrofuran:water mixture (10 mL, 1:1) was added lithium hydroxide monohydrate (0.056 g, 1.34 mmol) at 0° C. and the reaction mixture was stirred at 0° C. for 15 minutes. The reaction mixture was acidified using 1.5N hydrochloric acid and extracted with ethyl acetate (2×50 mL). The combined organic layer was dried over anhydrous sodium sulphate, filtered and concentrated to afford the title compound 2-(3-(5-chloro-6-cyanopyridin-3-yl)-4-oxothieno[3,2-c]pyridin-5(4H)-yl)acetic acid (0.08 g, 87% yield) as brownish solid. Calculated (M+H): 346.00; Found (M+H): 346.0.

Step-3

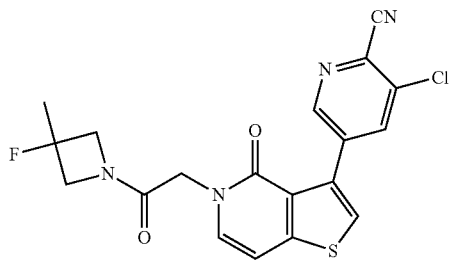 [SMILES: CC1(F)CN(C(=O)Cn2ccc3scc(-c4cnc(C#N)c(Cl)c4)c3c2=O)C1]

Preparation of 3-chloro-5-(5-(2-(3-fluoro-3-methylazetidin-1-yl)-2-oxoethyl)-4-oxo-4,5-dihydrothieno[3,2-c]pyridin-3-yl)picolinonitrile To a stirred solution of 2-(3-(5-chloro-6-cyanopyridin-3-yl)-4-oxothieno[3,2-c]pyridin-5(4H)-yl)acetic acid (0.08 g, 0.23 mmol) and 3-fluoro-3-methylazetidine hydrochloride (0.057 g, 0.46 mmol) in dichloromethane (20 mL) was added triethylamine (0.26 mL, 1.85 mmol) at room temperature. The reaction mixture was cooled to 0° C., 1-propanephosphonic anhydride solution (T$_3$P) (0.26 mL, 0.40 mmol, 50% in ethyl acetate) was added drop-wise and the reaction mixture was stirred at room temperature for 18 h. The reaction mixture was diluted with water (20 mL) and extracted with dichloromethane (2×60 mL). The combined organic layer was dried over anhydrous sodium sulfate, filtered and concentrated under vacuum. The crude product was purified by silica gel column chromatography followed by preparative HPLC [analytical conditions: column: Inertsil ODS 3V (250 mm×4.6 mm×5), mobile phase (A): 0.1% ammonia in water, mobile phase (B): acetonitrile, flow rate: 1.0 mL/min, isocratic: (50:50)] to afford the title compound 3-chloro-5-(5-(2-(3-fluoro-3-methylazetidin-1-yl)-2-oxoethyl)-4-oxo-4,5-dihydrothieno[3,2-c]pyridin-3-yl)picolinonitrile (0.03 g, 31% yield) as white solid. $^1$H NMR (400 MHz, DMSO-d$_6$) δ (ppm); 8.77 (d, J=1.2 Hz, 1H), 8.34 (d, J=1.2 Hz, 1H), 7.94 (s, 1H), 7.54 (d, J=7.6 Hz, 1H), 7.02 (d, J=7.2 Hz, 1H), 4.63 (s, 2H), 4.36-4.28 (m, 2H), 3.97-3.93 (m, 2H), 1.57 (d, J=22 Hz, 3H). Calculated (M+H): 417.05; Found (M+1): 417.1. HPLC purity 99.47%.

TABLE 12

The following compound was prepared by the method described above:

| Ex. No. | Structure | IUPAC Name | Analytical Data |
|---|---|---|---|
| 137 | 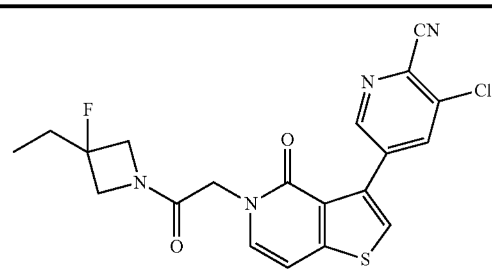 | 3-chloro-5-(5-(2-(3-ethyl-3-fluoroazetidin-1-yl)-2-oxoethyl)-4-oxo-4,5-dihydrothieno[3,2-c]pyridin-3-yl)picolinonitrile | $^1$H NMR (400 MHz, DMSO-d$_6$) δ (ppm); 8.77 (d, J = 1.2 Hz, 1H), 8.34 (s, 1H), 7.93 (s, 1H), 7.54 (d, J = 7.6 Hz, 1H), 7.02 (d, J = 7.2 Hz, 1H), 4.64 (s, 2H), 4.37-4.25 (m, 2H), 4.00-3.86 (m, 2H), 1.92-1.80 (m, 2H), 0.90 (t, J = 7.6 Hz, 3H). Calculated (M + H): 431.07; Found (M + 1): 431.2. HPLC purity 99.82% |

TABLE 12-continued

The following compound was prepared by the method described above:

| Ex. No. | Structure | IUPAC Name | Analytical Data |
|---|---|---|---|
| 138 | 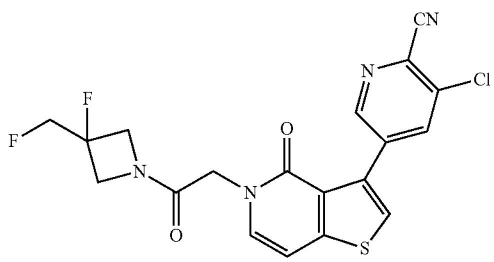 [SMILES: N#Cc1ncc(-c2csc3ccn(CC(=O)N4CC(F)(CF)C4)c(=O)c23)cc1Cl] | 3-chloro-5-(5-(2-(3-fluoro-3-(fluoromethyl)azetidin-1-yl)-2-oxoethyl)-4-oxo-4,5-dihydrothieno[3,2-c]pyridin-3-yl)picolinonitrile | $^1$H NMR (400 MHz, DMSO-$d_6$) δ (ppm); 8.77 (d, J = 1.2 Hz, 1H), 8.34 (d, J = 0.8 Hz, 1H), 7.94 (s, 1H), 7.53 (d, J = 6.8 Hz, 1H), 7.03 (d, J = 7.2 Hz, 1H), 4.87-4.70 (m, 2H), 4.66 (s, 2H), 4.47-4.35 (m, 2H), 4.12-3.95 (m, 2H). Calculated (M + H): 435.04; Found (M + 1): 435.2. HPLC purity 99.89% |
| 139 | 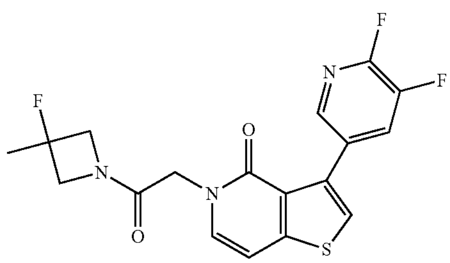 [SMILES: CC1(F)CN(C(=O)Cn2ccc3scc(-c4cnc(F)c(F)c4)c3c2=O)C1] | 3-(5,6-difluoropyridin-3-yl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm); 8.12 (m, 2H), 7.75 (s, 1H), 7.51 (d, J = 7.2 Hz, 1H), 6.99 (d, J = 7.2 Hz, 1H), 4.62 (s, 2H), 4.38-4.25 (m, 2H), 3.98-3.93 (m, 2H), 1.57 (d, J = 22 Hz, 3H). Calculated (M + H): 394.08; Found (M + 1): 394.1. HPLC purity 98.32% |
| 140 | 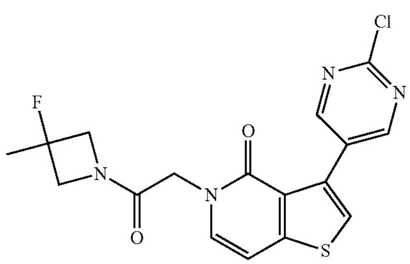 [SMILES: CC1(F)CN(C(=O)Cn2ccc3scc(-c4cnc(Cl)nc4)c3c2=O)C1] | 3-(2-chloropyrimidin-5-yl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm); 8.82 (s, 2H), 7.86 (s, 1H), 7.53 (d, J = 7.6 Hz, 1H), 7.01 (d, J = 7.6 Hz, 1H), 4.62 (s, 2H), 4.38-4.25 (m, 2H), 3.98-3.93 (m, 2H), 1.57 (d, J = 22 Hz, 3H). Calculated (M + H): 393.05; Found (M + 1): 393.0. HPLC purity 99.94% |
| 141 | 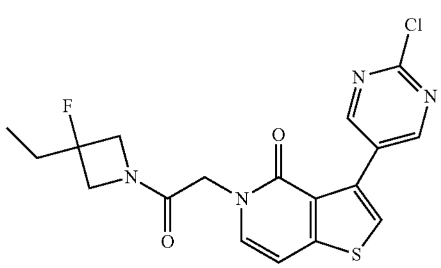 [SMILES: CCC1(F)CN(C(=O)Cn2ccc3scc(-c4cnc(Cl)nc4)c3c2=O)C1] | 3-(2-chloropyrimidin-5-yl)-5-(2-(3-ethyl-3-fluoroazetidin-1-yl)-2-oxoethyl)thieno[3,2-c]pyridin-4(5H)-one | $^1$H NMR (400 MHz, DMSO-$d_6$) δ (ppm); 8.82 (s, 2H), 7.86 (s, 1H), 7.53 (d, J = 7.2 Hz, 1H), 7.01 (d, J = 7.2 Hz, 1H), 4.63 (s, 2H), 4.37-4.25 (m, 2H), 4.00-3.86 (m, 2H), 1.92-1.80 (m, 2H), 0.90 (t, J = 7.2 Hz, 3H). Calculated (M + H): 407.07; Found (M + 1): 407.1. HPLC purity 99.67% |
| 142 | 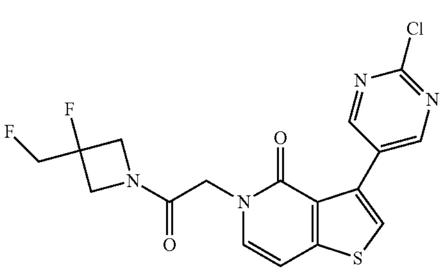 [SMILES: O=C(Cn1ccc2scc(-c3cnc(Cl)nc3)c2c1=O)N1CC(F)(CF)C1] | 3-(2-chloropyrimidin-5-yl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-$d_6$) δ (ppm); 8.83 (s, 2H), 7.86 (s, 1H), 7.52 (d, J = 7.2 Hz, 1H), 7.02 (d, J = 7.6 Hz, 1H), 4.87-4.70 (m, 2H), 4.64 (s, 2H), 4.49-4.34 (m, 2H), 4.12-3.95 (m, 2H). Calculated (M + H): 411.04; Found (M + 1): 411.0. HPLC purity 99.73% |

TABLE 12-continued

The following compound was prepared by the method described above:

| Ex. No. | Structure | IUPAC Name | Analytical Data |
|---|---|---|---|
| 143 | 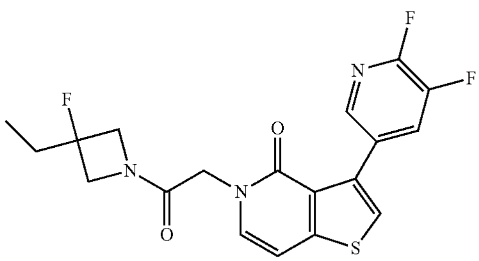 [SMILES: CCC1(F)CN(C(=O)Cn2ccc3scc(-c4cnc(F)c(F)c4)c3c2=O)C1] | 3-(5,6-difluoropyridin-3-yl)-5-(2-(3-ethyl-3-fluoroazetidin-1-yl)-2-oxoethyl)thieno[3,2-c]pyridin-4(5H)-one | $^1$H NMR (400 MHz, DMSO-$d_6$) δ (ppm); 8.12-8.07 (m, 2H), 7.75 (s, 1H), 7.51 (d, J = 7.6 Hz, 1H), 6.98 (d, J = 7.2 Hz, 1H), 4.62 (s, 2H), 4.37-4.25 (m, 2H), 4.00-3.86 (m, 2H), 1.91-1.80 (m, 2H), 0.90 (t, J = 7.2 Hz, 3H). Calculated (M + H): 408.09; Found (M + 1): 408.1. HPLC purity 99.88% |
| 144 | 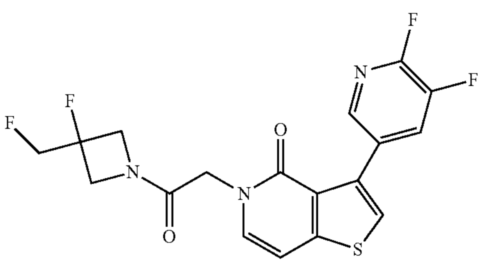 [SMILES: O=C(Cn1ccc2scc(-c3cnc(F)c(F)c3)c2c1=O)N1CC(F)(CF)C1] | 3-(5,6-difluoropyridin-3-yl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-$d_6$) δ (ppm); 8.13-8.08 (m, 2H), 7.76 (s, 1H), 7.50 (d, J = 6.8 Hz, 1H), 6.99 (d, J = 6.8 Hz, 1H), 4.87-4.69 (m, 2H), 4.64 (s, 2H), 4.49-4.34 (m, 2H), 4.12-3.95 (m, 2H). Calculated (M + H): 412.07; Found (M + 1): 412.1. HPLC purity 99.62% |
| 145 | 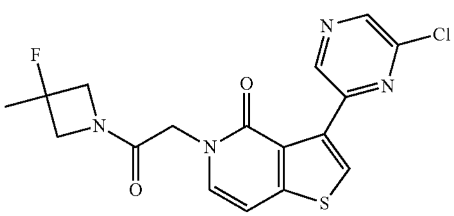 [SMILES: CC1(F)CN(C(=O)Cn2ccc3scc(-c4cncc(Cl)n4)c3c2=O)C1] | 3-(6-chloropyrazin-2-yl)-5-(2-(3-fluoro-3-methylazetidin-1-yl)-2-oxoethyl)thieno[3,2-c]pyridin-4(5H)-one | $^1$H NMR (400 MHz, DMSO-$d_6$) δ (ppm); 8.85 (s, 1H), 8.71 (s, 1H), 7.97 (s, 1H), 7.54 (d, J = 7.2 Hz, 1H), 7.02 (d, J = 7.6 Hz, 1H), 4.63 (s, 2H), 4.38-4.25 (m, 2H), 3.98-3.93 (m, 2H), 1.57 (d, J = 22 Hz, 3H). Calculated (M + H): 393.05; Found (M + 1): 393.0. HPLC purity 99.36% |
| 146 | 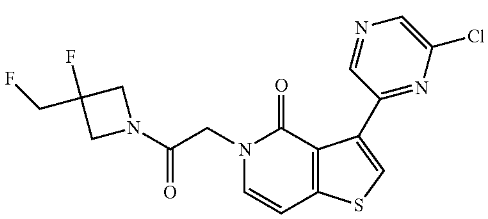 [SMILES: O=C(Cn1ccc2scc(-c3cncc(Cl)n3)c2c1=O)N1CC(F)(CF)C1] | 3-(6-chloropyrazin-2-yl)-5-(2-(3-fluoro-3-(fluoromethyl)azetidin-1-yl)-2-oxoethyl)thieno[3,2-c]pyridin-4(5H)-one | $^1$H NMR (400 MHz, DMSO-$d_6$) δ (ppm); 8.85 (s, 1H), 8.71 (s, 1H), 7.98 (s, 1H), 7.53 (d, J = 7.2 Hz, 1H), 7.03 (d, J = 6.8 Hz, 1H), 4.87-4.69 (m, 2H), 4.66 (s, 2H), 4.49-4.35 (m, 2H), 4.12-3.95 (m, 2H). Calculated (M + H): 411.04; Found (M + 1): 411.0. HPLC purity 99.88% |
| 147 | 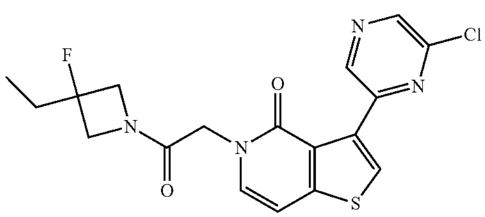 [SMILES: CCC1(F)CN(C(=O)Cn2ccc3scc(-c4cncc(Cl)n4)c3c2=O)C1] | 3-(6-chloropyrazin-2-yl)-5-(2-(3-ethyl-3-fluoroazetidin-1-yl)-2-oxoethyl)thieno[3,2-c]pyridin-4(5H)-one | $^1$H NMR (400 MHz, DMSO-$d_6$) δ (ppm); 8.85 (s, 1H), 8.71 (s, 1H), 7.97 (s, 1H), 7.54 (d, J = 7.6 Hz, 1H), 7.02 (d, J = 7.6 Hz, 1H), 4.64 (s, 2H), 4.34-4.27 (m, 2H), 3.98-3.90 (m, 2H), 1.90-1.82 (m, 2H), 0.90 (t, J = 7.2 Hz, 3H). Calculated (M + H): 407.07; Found (M + 1): 407.1. HPLC purity 99.64% |

B. PREPARATION OF PYRROLOPYRIMIDINONES

Examples 148 and 149: Preparation of 5-(4-chloro-3-(trifluoromethyl)phenyl)-3-(2-oxo-2-(pyrrolidin-1-yl)ethyl)-3H-pyrrolo[2,3-d]pyrimidin-4(7H)-one & 5-(4-chloro-3-(trifluoromethyl)phenyl)-7-(2-fluoroethyl)-3-(2-oxo-2-(pyrrolidin-1-yl)ethyl)-3H-pyrrolo[2,3-d]pyrimidin-4(7H)-one

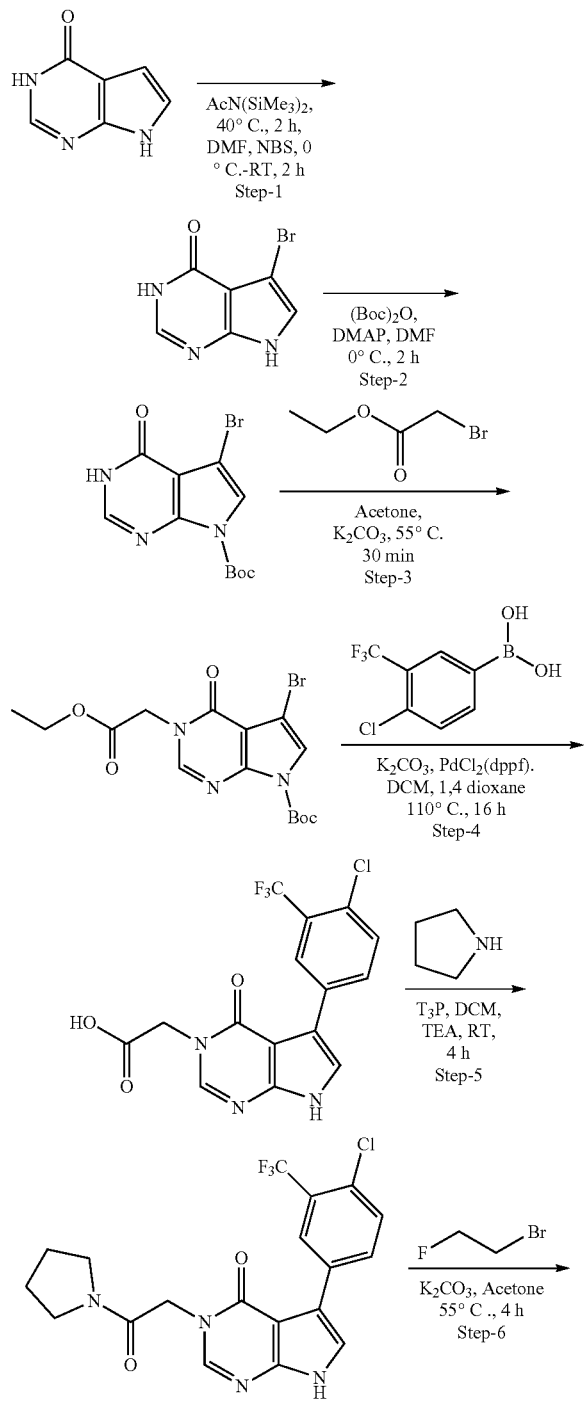

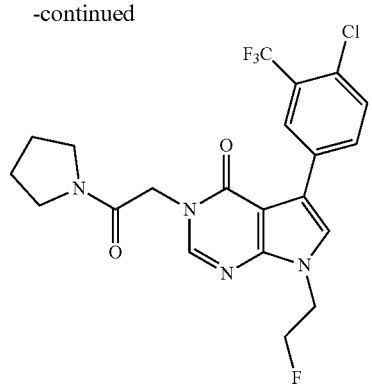

Step 1

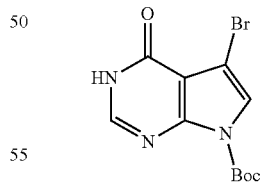

Preparation of 5-bromo-3H-pyrrolo[2,3-d]pyrimidin-4(7H)-one

To a stirred solution of 3H-pyrrolo[2,3-d]pyrimidin-4(7H)-one (5.5 g, 40.7 mmol) in N,N-dimethyl formamide (100 mL), N-(bis-trimethylsilyl)acetonitrile (18.22 g, 89.55 mmol) and N-bromo succinimide (7.24 g, 40.7 mmol) were added and the reaction mixture was stirred at room temperature for 2 h. The reaction mixture was quenched with cold water (1000 mL) and stirred for 30 minutes. The precipitated solid was filtered and dried under suction to afford title compound 5-bromo-3H-pyrrolo[2,3-d]pyrimidin-4(7H)-one (6.26 g, crude) as brown solid. Calculated (M+H): 213.9; Found (M+H): 214.0.

Step 2

Preparation of tert-butyl 5-bromo-4-oxo-3H-pyrrolo[2,3-d]pyrimidine-7(4H)-carboxylate To a solution of 5-bromo-3H-pyrrolo[2,3-d]pyrimidin-4(7H)-one (7.1 g, 33.17 mmol) in N,N-dimethyl formamide (150 mL) were added 4-dimethylaminopyridine (DMAP) (0.406 mL, 3.31 mmol)) and di-tert-butyl dicarbonate [(Boc)₂O] (6.46 mL, 28.19 mmol) at 0° C. The reaction mixture was stirred at 0° C. for 2 h. The reaction mixture was quenched with cold water (1000 mL) and stirred for 30 minutes. The precipitated solid was filtered and dried under suction to afford the title compound tert-butyl 5-bromo-4-oxo-3H-pyrrolo[2,3-d]pyrimidine-7(4H)-carboxylate as off white solid (8.1 g, crude). Calculated (M+H): 314.1; Found (M+H): 314.0.

Step 3

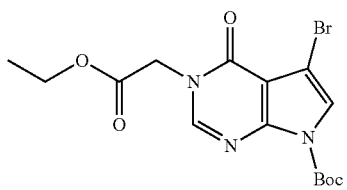

Preparation of tert-butyl 5-bromo-3-(2-ethoxy-2-oxoethyl)-4-oxo-3H-pyrrolo[2,3-d]pyrimidine-7(4H)-carboxylate To a solution of tert-butyl 5-bromo-4-oxo-3H-pyrrolo[2,3-d]pyrimidine-7(4H)-carboxylate (4.0 g, 12.73 mmol) in acetone (100 mL) were added ethyl 2-bromoacetate (4.25 g, 25.47 mmol) and potassium carbonate (5.28 g, 38.19 mmol) at room temperature and the reaction mixture was stirred at 55° C. for 30 minutes. The reaction mixture was cooled and filtered. The solid was washed with ethyl acetate (100 mL) and the combined filtrate was evaporated to get crude product, which was purified by silica gel column chromatography using 50% ethyl acetate in hexane to afford tert-butyl 5-bromo-3-(2-ethoxy-2-oxoethyl)-4-oxo-3H-pyrrolo[2,3-d]pyrimidine-7(4H)-carboxylate (3.49 g, 66.7% yield) as off-white solid. Calculated (M+H): 400.04; Found (M+H): 400.0.

Step 4

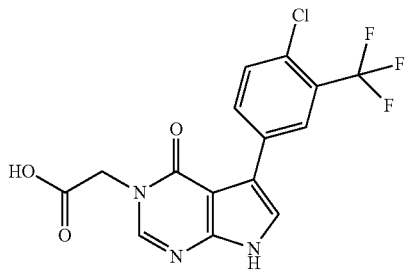 [SMILES: O=C(O)Cn1cnc2[nH]cc(-c3ccc(Cl)c(C(F)(F)F)c3)c2c1=O]

Preparation of 2-(5-(4-chloro-3-(trifluoromethyl)phenyl)-4-oxo-4,7-dihydro-3H-pyrrolo[2,3-d]pyrimidin-3-yl)acetic acid To a solution of tert-butyl 5-bromo-3-(2-ethoxy-2-oxoethyl)-4-oxo-3H-pyrrolo[2,3-d]pyrimidine-7(4H)-carboxylate (1.5 g, 3.88 mmol) and (4-chloro-3-(trifluoromethyl)phenyl)boronic acid (1.2 g, 5.82 mmol) in 1,4-dioxane:water mixture (32 mL, 4:1), potassium carbonate (1.63 g, 11.68 mmol) was added. The reaction mixture was purged with argon for 30 minutes. Then Pd(dppf)Cl$_2$.DCM complex (0.167 g, 0.19 mmol) was added and the reaction mixture was stirred at 100° C. for 16 h. The reaction mixture was cooled, diluted with water (150 mL), extracted with ethyl acetate (150 mL) and the organic layer was discarded. The aqueous layer was acidified using 1.5N hydrochloric acid at 0° C., the obtained precipitate was filtered and dried under suction to afford the title compound 2-(5-(4-chloro-3-(trifluoromethyl)phenyl)-4-oxo-4,7-dihydro-3H-pyrrolo[2,3-d]pyrimidin-3-yl)acetic acid (1.1 g, crude) as off-white solid. Calculated (M+H): 372.02; Found (M+H): 372.0.

Step 5

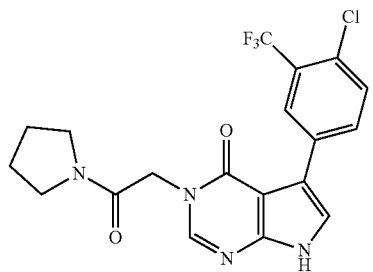 [SMILES: O=C(Cn1cnc2[nH]cc(-c3ccc(Cl)c(C(F)(F)F)c3)c2c1=O)N1CCCC1]

Preparation of 5-(4-chloro-3-(trifluoromethyl)phenyl)-3-(2-oxo-2-(pyrrolidin-1-yl)ethyl)-3H-pyrrolo[2,3-d]pyrimidin-4(7H)-one To a stirred solution of 2-(5-(4-chloro-3-(trifluoromethyl)phenyl)-4-oxo-4,7-dihydro-3H-pyrrolo[2,3-d]pyrimidin-3-yl)acetic acid (0.5 g, 1.34 mmol) in dichloromethane (30 mL) were added triethylamine (0.94 mL, 2.69 mmol) and pyrrolidine (0.21 mL, 2.69 mmol) at room temperature. The reaction mixture was stirred for 10 minutes, then propylphosphonic anhydride solution (T$_3$P) (0.60 mL, 2.69 mmol, 50% in ethyl acetate) was added at 0° C. and reaction mixture was stirred at room temperature for 16 h. The reaction mixture was diluted with water (50 mL) and extracted with dichloromethane (3×70 mL). The combined organic extract was dried over anhydrous sodium sulfate, filtered and evaporated to get crude product, which was purified by silica gel column chromatography using 2% methanol in dichloromethane to afford the title compound 5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.23 g, 40.3% yield) as off-white. $^1$H NMR (400 MHz, DMSO-d$_6$) δ (ppm): 12.31 (s, 1H), 8.60 (s, 1H), 8.19 (d, J=8.4 Hz, 1H), 8.07 (s, 1H), 7.69 (s, 1H), 7.63 (d, J=8.4 Hz, 1H), 4.79 (s, 2H), 3.53 (t, J=6 Hz, 2H), 3.30-3.26 (m, 2H), 1.94-1.91 (m, 2H), 1.79-1.76 (m, 2H). Calculated M+H: 425.09; Found M+H: 425.1. HPLC purity: 98.55%.

Step 6

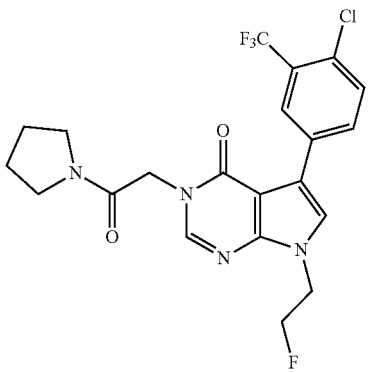 [SMILES: O=C(Cn1cnc2c(c(-c3ccc(Cl)c(C(F)(F)F)c3)cn2CCF)c1=O)N1CCCC1]

Preparation of 5-(4-chloro-3-(trifluoromethyl)phenyl)-7-(2-fluoroethyl)-3-(2-oxo-2-(pyrrolidin-1-yl)ethyl)-3H-pyrrolo[2,3-d]pyrimidin-4(7H)-one To a solution 5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.08 g, 0.19 mmol) in acetone (15 mL) were added 1-bromo-2-fluoro-ethane (0.07 mL, 0.95 mmol) followed by potassium carbonate (0.78 g, 0.57 mmol) at 0° C. and the reaction mixture was heated at 55° C. for 4 h. The reaction mixture was cooled, filtered and the solid was washed with acetone. The combined filtrate was concentrated to get the crude product, which was purified by silica gel column chromatography using 1.5% methanol in dichloromethane to afford the title compound 5-(4-chloro-3-(trifluoromethyl)phenyl)-7-(2-fluoroethyl)-3-(2-oxo-2-(pyrrolidin-1-yl)ethyl)-3H-pyrrolo[2,3-d]pyrimidin-4(7H)-one (0.011 g, 12% yield) as white solid. $^1$H NMR (400 MHz, DMSO-$d_6$) δ (ppm): 8.56 (s, 1H), 8.19-8.16 (m, 2H), 7.83 (s, 1H), 7.68-7.66 (d, J=8.4 Hz, 1H), 4.87-4.85 (m, 1H), 4.82 (s, 2H), 4.76-4.73 (m, 1H), 4.53-4.51 (m, 1H), 4.46-4.45 (m, 1H), 3.55-3.51 (m, 2H), 3.31-3.27 (m, 2H), 1.95-1.90 (m, 2H), 1.82-1.76 (m, 2H). Calculated M+H: 471.11; Found M+H: 471.0. HPLC purity: 95.02%.

TABLE 13

The following compounds were prepared by the method described above:

| Ex. No. | Structure | Name | Analytical data |
|---|---|---|---|
| 150 | 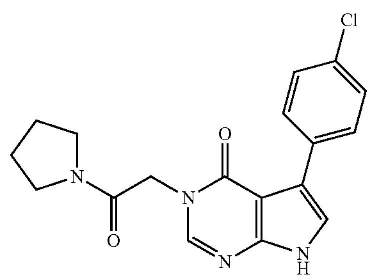 [SMILES: O=C(Cn1cnc2[nH]cc(-c3ccc(Cl)cc3)c2c1=O)N1CCCC1] | 5-(4-chlorophenyl)-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 12.15 (s, 1H), 8.05 (s, 1H), 7.95 (d, J = 8.4 Hz, 2H), 7.46 (d, J = 2.0 Hz, 1H), 7.34 (d, J = 8.4 Hz, 2H), 4.76 (s, 2H), 3.54-3.50 (m, 2H), 3.31-3.27 (m, 2H), 1.95-1.89 (m, 2H), 1.81-1.74 (m, 2H); Calculated (M + H): 357.10, Found (M + H): 357.1. HPLC purity: 98.65% |
| 151 | 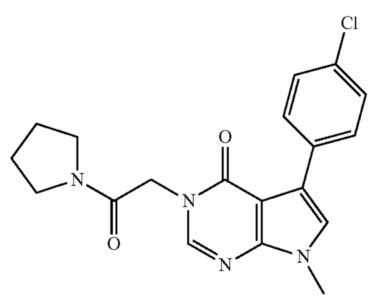 [SMILES: Cn1cc(-c2ccc(Cl)cc2)c2c(=O)n(CC(=O)N3CCCC3)cnc21] | 5-(4-chlorophenyl)-7-methyl-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.12 (s, 1H), 7.92 (d, J = 8.4 Hz, 2H), 7.54 (s, 1H), 7.35 (d, J = 8.4 Hz, 2H), 4.77 (s, 2H), 3.73 (s, 3H), 3.53-3.50 (m, 2H), 3.30-3.27 (m, 2H), 1.94-1.89 (m, 2H), 1.81-1.76 (m, 2H). Calculated (M + H): 371.12, Found (M + H): 371.3. HPLC purity: 99.39% |
| 152 | 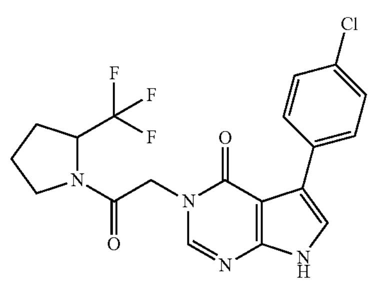 [SMILES: O=C(Cn1cnc2[nH]cc(-c3ccc(Cl)cc3)c2c1=O)N1CCCC1C(F)(F)F] | 5-(4-chlorophenyl)-3-(2-oxo-2-(2-(trifluoromethyl)pyrrolidin-1-yl)ethyl)-3H-pyrrolo[2,3-d]pyrimidin-4(7H)-one | $^1$H NMR (400 MHz, DMSO-$d_6$) δ (ppm): 12.18 (s, 1H), 8.10-8.04 (m, 1H), 7.95-7.91 (m, 2H), 7.48 (d, J = 2.0 Hz, 1H), 7.34 (d, J = 8.4 Hz, 2H), 5.11-4.70 (m, 3H), 3.73-3.60 (m, 2H), 2.17-1.91 (m, 4H); Calculated (M + H): 425.09, Found (M + H): 425.0. HPLC purity: 97.51% |

TABLE 13-continued

The following compounds were prepared by the method described above:

| Ex. No. | Structure | Name | Analytical data |
|---|---|---|---|
| 153 | 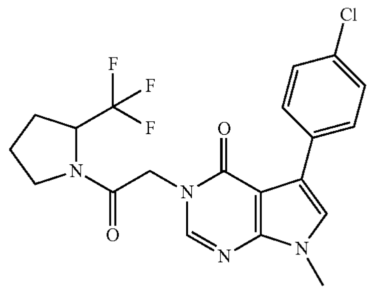 [SMILES: Cn1cc(-c2ccc(Cl)cc2)c2c(=O)n(CC(=O)N3CCCC3C(F)(F)F)cnc21] | 5-(4-chlorophenyl)-7-methyl-3-(2-oxo-2-(2-(trifluoromethyl)pyrrolidin-1-yl)ethyl)-3H-pyrrolo[2,3-d]pyrimidin-4(7H)-one | $^1$H NMR (400 MHz, DMSO-d$_6$) δ (ppm): 8.17-8.14 (m, 1H), 8.91 (d, J = 8.0 Hz, 2H), 7.55 (s, 1H), 7.36 (d, J = 7.6 Hz, 2H), 5.08-4.72 (m, 3H), 3.73 (s, 3H), 3.70 (brs, 2H), 2.08-2.04 (m, 4H); Calculated (M + H): 439.11, Found (M + H): 439.1, HPLC purity: 98.23% |
| 154 | 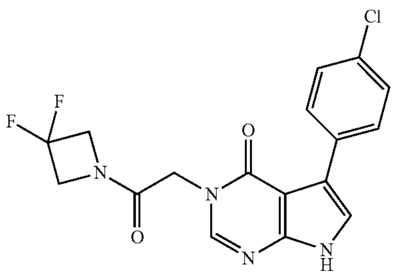 [SMILES: O=C(Cn1cnc2[nH]cc(-c3ccc(Cl)cc3)c2c1=O)N1CC(F)(F)C1] | 5-(4-chlorophenyl)-3-(2-(3,3-difluoroazetidin-1-yl)-2-oxoethyl)-3H-pyrrolo[2,3-d]pyrimidin-4(7H)-one | $^1$H NMR (400 MHz, DMSO-d$_6$) δ (ppm): 12.20 (s, 1H), 8.08 (s, 1H), 7.93 (d, J = 8.4 Hz, 2H), 7.48 (d, J = 2.4 Hz, 1H), 7.35 (d, J = 8.8 Hz, 2H), 4.76 (t, J = 12.0 Hz, 2H), 4.69 (s, 2H), 4.34 (t, J = 12.0 Hz, 2H); Calculated (M + H): 379.07, Found (M + H): 379.1. HPLC purity: 99.49% |
| 155 | 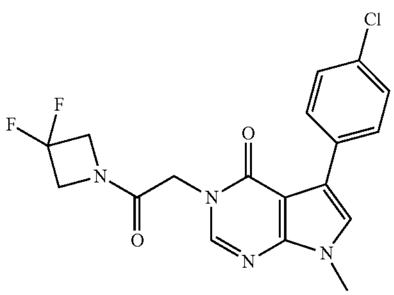 [SMILES: Cn1cc(-c2ccc(Cl)cc2)c2c(=O)n(CC(=O)N3CC(F)(F)C3)cnc21] | 5-(4-chlorophenyl)-3-(2-(3,3-difluoroazetidin-1-yl)-2-oxoethyl)-7-methyl-3H-pyrrolo[2,3-d]pyrimidin-4(7H)-one | $^1$H NMR (400 MHz, DMSO-d$_6$) δ (ppm): 8.15 (s, 1H), 7.90 (d, J = 8.4 Hz, 2H), 7.55 (s, 1H), 7.36 (d, J= 8.4 Hz, 2H), 4.75 (t, J = 12.4 Hz, 2H), 4.70 (s, 2H), 4.34 (t, J = 12.4 Hz, 2H), 3.73 (s, 3H); Calculated (M + H): 393.09, Found (M + H): 393.1. HPLC purity: 99.59% |
| 156 | 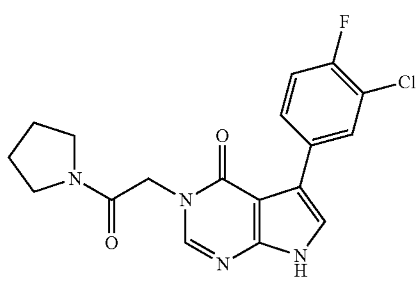 [SMILES: O=C(Cn1cnc2[nH]cc(-c3ccc(F)c(Cl)c3)c2c1=O)N1CCCC1] | 5-(3-chloro-4-fluorophenyl)-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 12.19 (s, 1H), 8.29-8.27 (dd, J = 2 Hz, 7.2 Hz, 1H), 8.05 (s, 1H), 7.92-7.89 (m, 1H), 7.55 (s, 1H), 7.33 (t, J = 9.2 Hz, 1H), 4.78 (s, 2H), 3.53 (t, J = 6.8 Hz, 2H), 3.31-3.27 (m, 2H), 1.97-1.90 (m, 2H), 1.82-1.75 (m, 2H). Calculated (M + H): 375.09, Found (M + H): 375.1. HPLC purity: 99.72% |
| 157 | 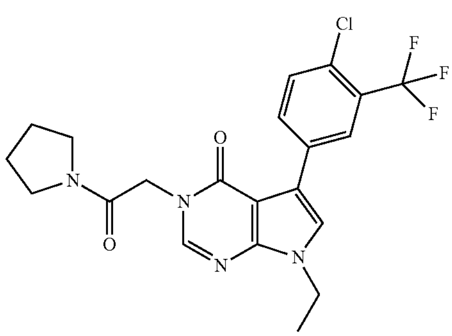 [SMILES: CCn1cc(-c2ccc(Cl)c(C(F)(F)F)c2)c2c(=O)n(CC(=O)N3CCCC3)cnc21] | 5-(4-chloro-3-(trifluoromethyl)phenyl)-7-ethyl-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.57 (d, J = 1.6 Hz, 1H), 8.21-8.18 (m, 1H), 8.14 (s, 1H), 7.85 (s, 1H), 6.65 (d, J = 8.4 Hz, 1H), 4.81 (s, 2H), 4.18 (q, J = 7.2 Hz, 2H), 3.53 (t, J = 6.4 Hz, 2H), 3.29 (t, J = 6.4 Hz, 2H), 1.97-1.90 (m, 2H), 1.81-1.75 (m, 2H), 1.39 (t, J = 7.2 Hz, 3H). Calculated (M + H): 453.12, Found (M + H): 453.2. HPLC purity: 99.25% |

TABLE 13-continued

The following compounds were prepared by the method described above:

| Ex. No. | Structure | Name | Analytical data |
|---|---|---|---|
| 158 | 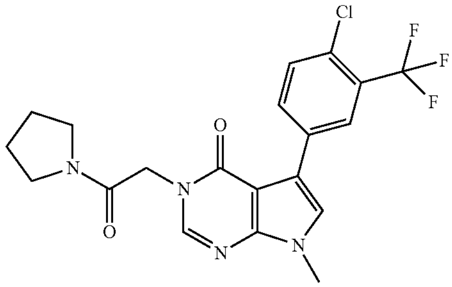 [SMILES: Cn1cc(-c2ccc(Cl)c(C(F)(F)F)c2)c2c(=O)n(CC(=O)N3CCCC3)cnc21] | 5-(4-chloro-3-(trifluoromethyl)phenyl)-7-methyl-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.57 (d, J = 2.0 Hz, 1H), 8.18-8.15 (m, 2H), 7.77 (s, 1H), 7.65 (d, J = 8.4 Hz, 1H), 4.81 (s, 2H), 3.75 (s, 3H), 3.534 (t, J = 6.4 Hz, 2H), 3.29 (t, J = 6.4 Hz, 2H), 1.95-1.90 (m, 2H), 1.81-1.76 (m, 2H); Calculated (M + H): 439.11, Found (M + H): 439.1. HPLC purity: 99.76% |
| 159 | 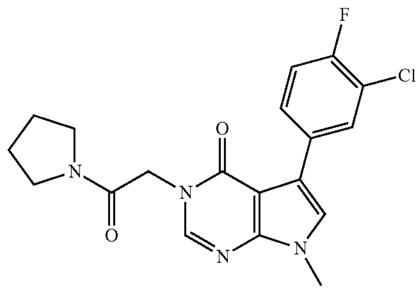 [SMILES: Cn1cc(-c2ccc(F)c(Cl)c2)c2c(=O)n(CC(=O)N3CCCC3)cnc21] | 5-(3-chloro-4-fluorophenyl)-7-methyl-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.27-8.25 (dd, J = 2.4 Hz, 7.6 Hz, 1H), 8.13 (s, 1H), 7.88-7.84 (m, 1H), 7.62 (s, 1H), 7.37-7.32 (t, J = 9.2 Hz, 1 H), 4.79 (s, 2H), 3.73 (s 3H), 3.54-3.51 (t, J = 7.2 Hz, 2H), 3.31-3.28 (t, J = 7.6 Hz, 2H), 1.97-1.90 (m, 2H), 1.82-1.76 (m, 2H), Calculated (M + H): 389.11, Found (M + H): 389.3. HPLC purity: 99.75% |
| 160 | 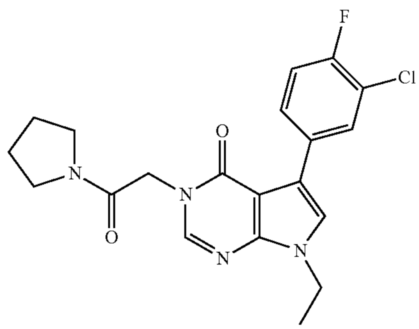 [SMILES: CCn1cc(-c2ccc(F)c(Cl)c2)c2c(=O)n(CC(=O)N3CCCC3)cnc21] | 5-(3-chloro-4-fluorophenyl)-7-ethyl-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.27-8.25 (m, 1H), 8.12 (s, 1H), 7.91-7.88 (m, 1H), 7.7 (s, 1H), 7.37-7.33 (t, J = 8.8 Hz, 1 H), 4.79 (s, 2H), 4.19-4.14 (q, J = 7.2 Hz, 2H), 3.54-3.51 (t, J = 6.8 Hz, 2H), 3.31-3.27 (t, J = 11.6 Hz, 2H), 1.95-1.90 (m, 2H), 1.82-1.77 (m, 2H), 1.40-1.36 (t, J = 7.2 Hz, 3H). Calculated (M + H): 403.13, Found (M + H): 403.4. HPLC purity: 99.70% |
| 161 | 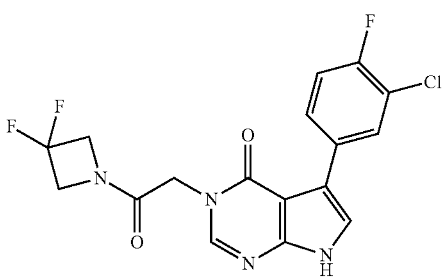 [SMILES: O=C(Cn1cnc2[nH]cc(-c3ccc(F)c(Cl)c3)c2c1=O)N1CC(F)(F)C1] | 5-(3-chloro-4-fluorophenyl)-3-(2-(3,3-difluoroazetidin-1-yl)-2-oxoethyl)-3H-pyrrolo[2,3-d]pyrimidin-4(7H)-onepyrrolo[2,3-d]pyrimidin-4(7H)-one | $^1$H NMR (400 MHz, DMSO-d$_6$) δ (ppm): 12.25 (s, 1H), 8.28-8.26 (dd, J = 1.6 Hz, 7.2 Hz, 1H), 8.08 (s, 1H), 7.91-7.89 (m, 1H), 7.56 (s, 1H), 7.36-7.32 (t, J = 9.2 Hz, 1H), 4.8-4.71 (m, 4H), 4.38-4.32 (t, J = 12.4 Hz, 2H); Calculated (M + H): 397.06, Found (M + H): 397.0. HPLC purity: 99.55% |
| 162 | 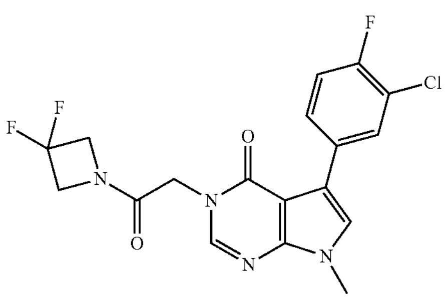 [SMILES: Cn1cc(-c2ccc(F)c(Cl)c2)c2c(=O)n(CC(=O)N3CC(F)(F)C3)cnc21] | 5-(3-chloro-4-fluorophenyl)-3-(2-(3,3-difluoroazetidin-1-yl)-2-oxoethyl)-7-methyl-3H-pyrrolo[2,3-d]pyrimidin-4(7H)-one | $^1$H NMR (400 MHz, DMSO-d$_6$) δ (ppm): 8.24 (d, J = 5.6 Hz, 1H), 8.14 (s, 1H), 7.85 (s, 1H), 7.63 (s, 1H), 7.38-7.33 (t, J = 9.2 Hz, 1H), 4.79-4.73 (m, 4H), 4.38-4.32 (t, J = 24.4 Hz, 2H), 3.73 (s, 3H); Calculated (M + H): 411.08, Found (M + H): 411.0, HPLC purity: 99.13% |

TABLE 13-continued

The following compounds were prepared by the method described above:

| Ex. No. | Structure | Name | Analytical data |
|---|---|---|---|
| 163 | 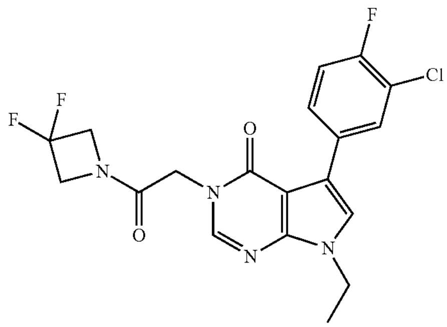 [SMILES: CCn1cc(-c2ccc(F)c(Cl)c2)c2c(=O)n(CC(=O)N3CC(F)(F)C3)cnc21] | 5-(3-chloro-4-fluorophenyl)-3-(2-(3,3-difluoroazetidin-1-yl)-2-oxoethyl)-7-ethyl-3H-pyrrolo[2,3-d]pyrimidin-4(7H)-one | $^1$H NMR (400 MHz, DMSO-$d_6$) δ (ppm): 8.26-8.24 (dd, J = 2 Hz, 7.6 Hz, 1H), 8.14 (s, 1H), 7.90-7.87 (m, 1H), 7.71 (s, 1H), 7.38-7.34 (t, J = 9.2 Hz, 1H), 4.80-4.73 (m, 4H), 4.35 (t, J = 12.4 Hz, 2H), 4.19-4.14 (m, 2H), 1.38 (t, J = 7.6 Hz, 3H), Calculated (M + H): 425.09, Found (M + H): 425.0. HPLC purity: 98.83% |
| 164 | 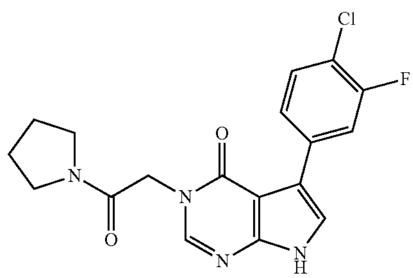 [SMILES: O=C(Cn1cnc2[nH]cc(-c3ccc(Cl)c(F)c3)c2c1=O)N1CCCC1] | 5-(4-chloro-3-fluorophenyl)-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 12.20 (s, 1H), 8.28 (dd, J = 2.0 Hz, 6.8 Hz, 1H), 8.06 (s, 1H), 7.93-7.89 (m, 1H), 7.55 (d, J = 2.0 Hz, 1H), 7.33 (t, J = 8.8 Hz, 1H), 4.78 (s, 2H), 3.53 (t, J = 7.2 Hz, 2H), 3.29 (t, J = 7.2 Hz, 2H), 2.04-1.90 (m, 2H), 1.82-1.75 (m, 2H); Calculated (M + H): 375.09, Found (M + H): 375.0. HPLC purity: 99.55% |
| 165 | 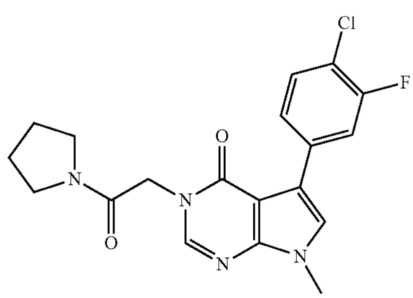 [SMILES: Cn1cc(-c2ccc(Cl)c(F)c2)c2c(=O)n(CC(=O)N3CCCC3)cnc21] | 5-(4-chloro-3-fluorophenyl)-7-methyl-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.26 (dd, J = 2.4 Hz, 7.2 Hz, 1H), 8.13 (s, 1H), 7.88-7.84 (m, 1H), 7.63 (s, 1H), 7.35 (t, J = 8.8 Hz, 1H), 4.80 (s, 2H), 3.73 (s, 3H), 3.53 (t, J = 6.8 Hz, 2H), 3.29 (t, J = 7.2 Hz, 2H), 1.95-1.90 (m, 2H), 1.82-1.76 (m, 2H); Calculated (M + H): 389.11, Found (M + H): 389.1, HPLC purity(%): 99.312. |
| 166 | 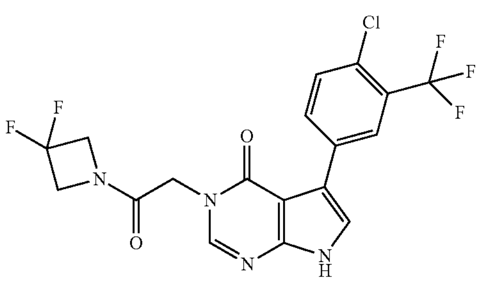 [SMILES: O=C(Cn1cnc2[nH]cc(-c3ccc(Cl)c(C(F)(F)F)c3)c2c1=O)N1CC(F)(F)C1] | 5-(4-chloro-3-(trifluoromethyl)phenyl)-3-(2-(3,3-difluoroazetidin-1-yl)-2-oxoethyl)-3H-pyrrolo[2,3-d]pyrimidin-4(7H)-one | $^1$H NMR (400 MHz, DMSO-$d_6$) δ (ppm): 12.36 (s, 1H), 8.63 (d, J = 1.6 Hz, 1H), 8.17 (d, J = 8.4 Hz, 1H), 8.10 (s, 1H), 7.71 (d, J = 2.0 Hz, 1H), 7.64 (d, J = 8.0 Hz, 1H), 4.77 (t, J = 12.0 Hz, 2H), 4.73 (s, 2H), 4.34 (t, J = 12.0 Hz, 2H); Calculated (M + H): 447.06, Found (M + H): 447.0. HPLC purity: 99.32% |
| 167 | 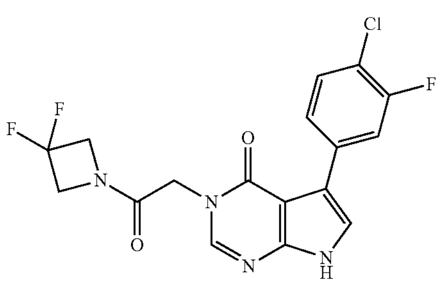 | 5-(4-chloro-3-fluorophenyl)-3-(2-(3,3-difluoroazetidin-1-yl)-2-oxoethyl)-3H-pyrrolo[2,3-d]pyrimidin-4(7H)-one | $^1$H NMR (400 MHz, DMSO-$d_6$) δ (ppm): 12.25 (brs, 1H), 8.17 (dd, J = 1.6 Hz, 12.0 Hz, 1H), 8.08 (s, 1H), 7.82 (dd, J = 2.0 Hz, 9.2 Hz, 1H), 7.64 (s, 1H), 7.47 (t, J = 8.4 Hz, 1H), 4.77 (t, J = 12.0 Hz, 2H), 4.70 (s, 2H), 4.35 (t, J = 12.0 Hz, 2H); Calculated (M + H): 397.06, Found (M + H): 397.0. HPLC purity: 98.90% |

TABLE 13-continued

The following compounds were prepared by the method described above:

| Ex. No. | Structure | Name | Analytical data |
|---|---|---|---|
| 168 | 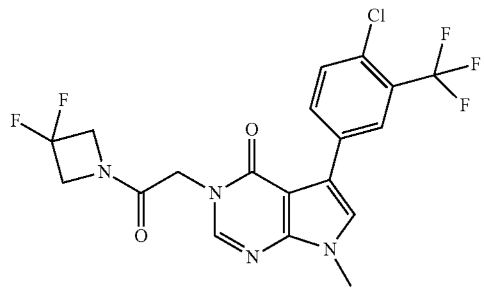 [SMILES: Cn1cc(-c2ccc(Cl)c(C(F)(F)F)c2)c2c(=O)n(CC(=O)N3CC(F)(F)C3)cnc21] | 5-(4-chloro-3-(trifluoromethyl)phenyl)-3-(2-(3,3-difluoroazetidin-1-yl)-2-oxoethyl)-7-methyl-3H-pyrrolo[2,3-d]pyrimidin-4(7H)-one | $^1$H NMR (400 MHz, DMSO-d$_6$) δ (ppm): 8.59 (s, 1H), 8.15 (d, J = 12.8 Hz, 2H), 7.79 (s, 1H), 7.66 (d, J = 8.4 Hz, 1H), 4.77 (t, J = 12.0 Hz, 2H), 4.74 (s, 2H), 4.35 (t, J = 12.4 Hz, 2H), 3.75 (s, 3H); Calculated (M + H): 461.07, Found (M + H): 461.0. HPLC purity: 99.48% |
| 169 | 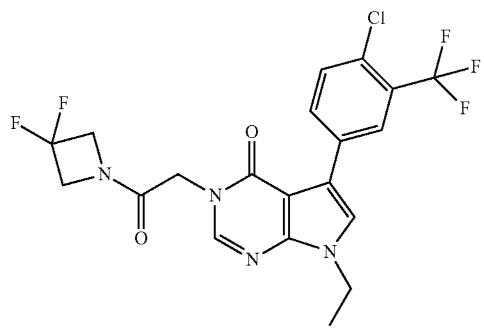 [SMILES: CCn1cc(-c2ccc(Cl)c(C(F)(F)F)c2)c2c(=O)n(CC(=O)N3CC(F)(F)C3)cnc21] | 5-(4-chloro-3-(trifluoromethyl)phenyl)-3-(2-(3,3-difluoroazetidin-1-yl)-2-oxoethyl)-7-ethyl-3H-pyrrolo[2,3-d]pyrimidin-4(7H)-one | $^1$H NMR (400 MHz, DMSO-d$_6$) δ (ppm): 8.60 (d, J = 2.0 Hz, 1H), 8.19 (d, J = 1.6 Hz, 1H), 8.16 (s, 1H), 7.86 (s, 1H), 7.66 (d, J = 8.8 Hz, 1H), 4.77 (t, J = 12.0 Hz, 2H), 4.74 (s, 2H), 4.35 (t, J = 12.4 Hz, 2H), 4.18 (q, J = 7.2 Hz, 2H), 1.39 (t, J = 7.2 Hz, 3H); Calculated (M + H): 475.09, Found (M + H): 475.0. HPLC purity: 98.79% |
| 170 | 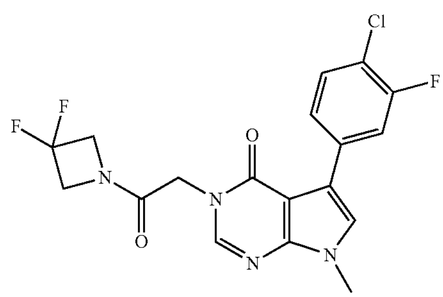 [SMILES: Cn1cc(-c2ccc(Cl)c(F)c2)c2c(=O)n(CC(=O)N3CC(F)(F)C3)cnc21] | 5-(4-chloro-3-fluorophenyl)-3-(2-(3,3-difluoroazetidin-1-yl)-2-oxoethyl)-7-methyl-3H-pyrrolo[2,3-d]pyrimidin-4(7H)-one | $^1$H NMR (400 MHz, DMSO-d$_6$) δ (ppm): 8.16-8.12 (m, 2H), 7.76 (dd, J = 1.6 Hz, 8.4 Hz, 1H), 7.71 (s, 1H), 7.51 (t, J = 8.4 Hz, 1H), 4.77 (t, J = 12.0 Hz, 2H), 4.73 (s, 2H), 4.35 (t, J = 12.0 Hz, 2H), 3.73 (s, 3H); Calculated (M + H): 411.08, Found (M + H): 411.0. HPLC purity: 99.78% |
| 171 | 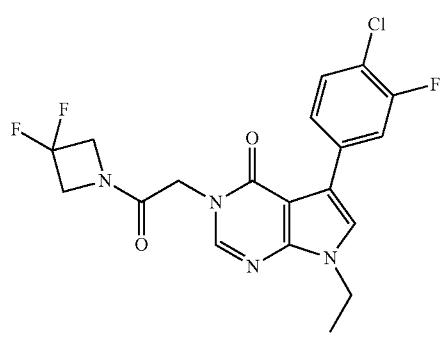 [SMILES: CCn1cc(-c2ccc(Cl)c(F)c2)c2c(=O)n(CC(=O)N3CC(F)(F)C3)cnc21] | 5-(4-chloro-3-fluorophenyl)-3-(2-(3,3-difluoroazetidin-1-yl)-2-oxoethyl)-7-ethyl-3H-pyrrolo[2,3-d]pyrimidin-4(7H)-one | $^1$H NMR (400 MHz, DMSO-d$_6$) δ (ppm): 8.15-8.13 (m, 2H), 7.79 (brs, 2H), 7.50 (t, J = 8.0 Hz, 1H), 4.80-4.72 (m, 4H), 4.35 (t, J = 12.0 Hz, 2H), 4.20-4.14 (m, 2H), 1.38 (t, J = 7.2 Hz, 3H); Calculated (M + H): 425.09, Found (M + H): 425.0, HPLC purity(%): 98.557. |

TABLE 13-continued

The following compounds were prepared by the method described above:

| Ex. No. | Structure | Name | Analytical data |
|---|---|---|---|
| 172 | 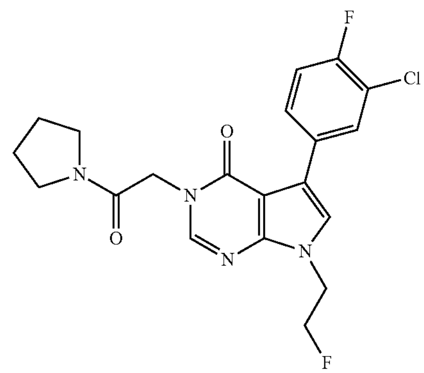 [SMILES: O=C(Cn1cnc2c(c(-c3ccc(F)c(Cl)c3)cn2CCF)c1=O)N1CCCC1] | 5-(3-chloro-4-fluorophenyl)-7-(2-fluoroethyl)-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.25 (d, J = 5.6 Hz, 1H), 8.14 (s, 1H), 7.89-7.86 (m, 1H), 7.69 (s, 1H), 7.36 (t, J = 9.2 Hz, 1H), 4.85 (t, J = 4.4 Hz, 1H), 4.80 (s, 2H), 4.73 (t, J = 4.4 Hz, 1H), 4.50 (t, J = 4.4 Hz, 1H), 4.44 (t, J = 4.4 Hz, 1H), 3.53 (t, J = 6.4 Hz, 2H), 3.30 (t, J = 6.4 Hz, 2H), 1.95-1.90 (m, 2H), 1.82-1.77 (m, 2H). Calculated M + H: 421.12; Found M + H: 421.0. HPLC purity: 98.11%. |
| 173 | 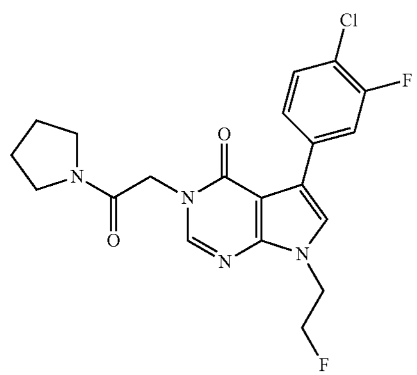 [SMILES: O=C(Cn1cnc2c(c(-c3ccc(Cl)c(F)c3)cn2CCF)c1=O)N1CCCC1] | 5-(4-chloro-3-fluorophenyl)-7-(2-fluoroethyl)-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.17-8.15 (m, 2H), 7.79-7.77 (m, 2H), 7.53-7.49 (m, 1H), 4.85 (t, J = 4.4 Hz, 1H), 4.80 (s, 2H), 4.74 (t, J = 4.4 Hz, 1H), 4.52 (t, J = 4.4 Hz, 1H), 4.45 (t, J = 5.2 Hz, 1H), 3.53 (t, J = 6.8 Hz, 2H), 3.30 (t, J = 7.2 Hz, 2H), 1.95-1.90 (m, 2H), 1.82-1.77 (3, 2H). Calculated M + H: 421.12; Found M + H: 421.1, HPLC: 99.92% |
| 174 | 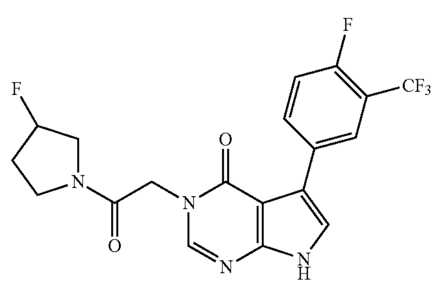 [SMILES: O=C(Cn1cnc2[nH]cc(-c3ccc(F)c(C(F)(F)F)c3)c2c1=O)N1CCC(F)C1] | 5-(4-fluoro-3-(trifluoromethyl)phenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.26 (s, 1H), 8.47 (d, J = 6.4 Hz, 1H), 8.22 (brs, 1H), 8.08 (d, J = 2 Hz, 1H), 7.62 (s, 1H), 7.44 (t, J = 10 Hz, 1H), 5.51-5.25 (m, 1H), 4.93-4.75 (m, 2H), 3.92-3.39 (m, 4H), 2.27-2.10 (m, 2H). Calculated (M + H): 427.11, Found (M + H): 427.1, HPLC purity 98.85%. |
| 175 | 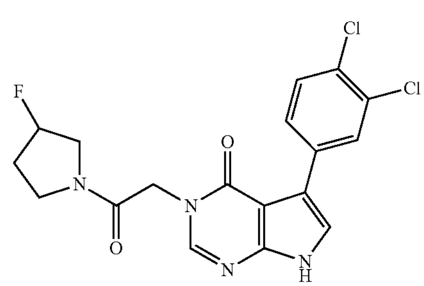 [SMILES: O=C(Cn1cnc2[nH]cc(-c3ccc(Cl)c(Cl)c3)c2c1=O)N1CCC(F)C1] | 5-(3,4-dichlorophenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.28 (s, 1H), 8.39 (d, J = 2.0 Hz, 1H), 8.09 (d, J = 2.0 Hz, 1H), 7.93 (d, J = 8.0 Hz, 1H), 7.64 (s, 1H), 7.53 (d, J = 8.4 Hz, 1H), 5.51-5.26 (m, 1H), 4.93-4.75 (m, 2H), 3.92-3.39 (m, 4H), 2.27-2.08 (m, 2H). Calculated (M + H): 409.06, Found (M + H): 409.0, HPLC purity 99.65%. |

TABLE 13-continued

The following compounds were prepared by the method described above:

| Ex. No. | Structure | Name | Analytical data |
|---|---|---|---|
| 176 | 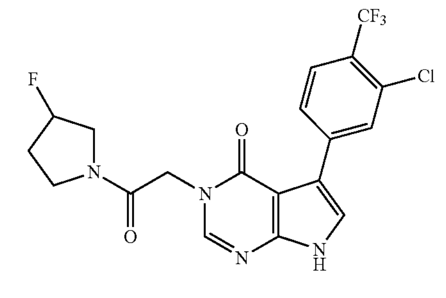 [SMILES: O=C(Cn1cnc2[nH]cc(-c3ccc(C(F)(F)F)c(Cl)c3)c2c1=O)N1CCC(F)C1] | 5-(3-chloro-4-(trifluoromethyl)phenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.42 (s, 1H), 8.49 (s, 1H), 8.12-8.11 (m, 2H), 7.79 (s, 1H), 7.74 (d, J = 8.4 Hz, 1H), 5.51-5.26 (m, 1H), 4.94-4.77 (m, 2H), 3.93-3.40 (m, 4H), 2.27-2.10 (m, 2H). Calculated (M + H): 443.08, Found (M + H): 443.0, HPLC purity 99.25%. |
| 177 | 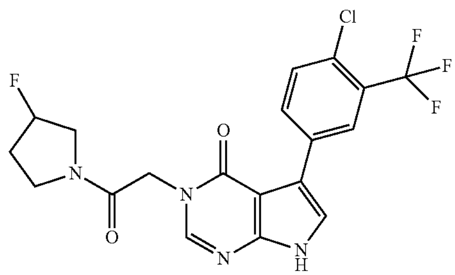 [SMILES: O=C(Cn1cnc2[nH]cc(-c3ccc(Cl)c(C(F)(F)F)c3)c2c1=O)N1CCC(F)C1] | 5-(4-chloro-3-(trifluoromethyl)phenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.32 (s, 1H), 8.61 (s, 1H), 8.19 (d, J = 8.4 Hz, 1H), 8.10 (s, 1H), 7.70 (s, 1H), 7.63 (d, J = 8.8 Hz, 1H), 5.51-5.25 (m, 1H), 4.94-4.76 (m, 2H), 3.89-3.75 (m, 2H); 3.67-3.52 (m, 2H); 2.30-2.13 (m, 2H); Calculated (M + H): 443.08, Found (M + H): 443.0, HPLC purity: 99.18%. |
| 178 | 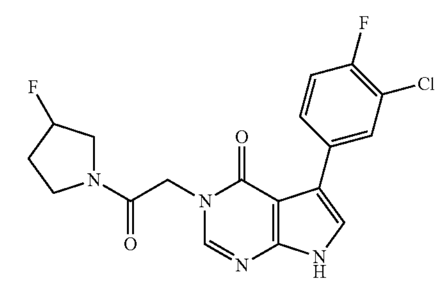 [SMILES: O=C(Cn1cnc2[nH]cc(-c3ccc(F)c(Cl)c3)c2c1=O)N1CCC(F)C1] | 5-(3-chloro-4-fluorophenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.22 (s, 1H), 8.29-8.27 (dd, J = 2 Hz, 7.2 Hz, 1H), 8.08 (d, J = 2.0 Hz, 1H), 7.912 (s, 1H), 7.55 (d, J = 2.4 Hz, 1H), 7.33 (t, J = 9.6 Hz, 1H), 5.51-5.25 (m, 1H), 4.92-4.78 (m, 2H), 3.89-3.79 (m, 2H); 3.64-3.42 (m, 2H); 2.30-2.10 (m, 2H); Calculated (M + H): 393.09, Found (M + H): 393.0, HPLC purity: 97.11%. |
| 179 | 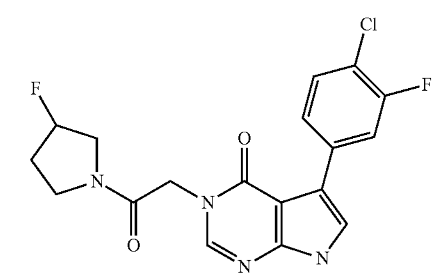 [SMILES: O=C(Cn1cnc2[nH]cc(-c3ccc(Cl)c(F)c3)c2c1=O)N1CCC(F)C1] | 5-(4-Chloro-3-fluoro-phenyl)-3-[2-(3-fluoro-pyrrolidin-1-yl)-2-oxo-ethyl]-3,7-dihydro-pyrrolo[2,3-d]pyrimidin-4-one | $^1$H NMR (400 MHz, DMSO-d$_6$) δ (ppm): 12.27 (s, 1H), 8.20-8.17 (dd, J = 1.2 Hz, 12 Hz, 1H), 8.09 (brs, 1H), 7.84 (d, J = 8.4 Hz, 1H), 7.64 (d, J = 2.4 Hz, 1H), 7.47 (t, J = 8 Hz, 1H), 5.51-5.26 (m, 1H), 4.91-4.74 (m, 2H), 3.99-3.34 (m, 4H), 2.29-1.93 (m, 2H). Calculated M + H: 393.09; Found M + H: 393.4, HPLC purity: 98.36% |
| 180 | 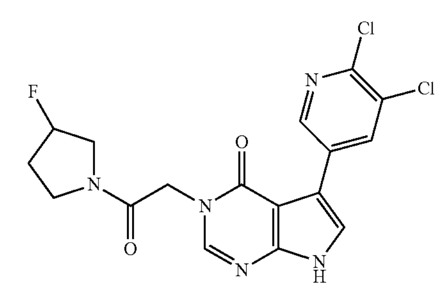 [SMILES: O=C(Cn1cnc2[nH]cc(-c3cnc(Cl)c(Cl)c3)c2c1=O)N1CCC(F)C1] | 5-(5,6-dichloropyridin-3-yl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 12.44 (s, 1H), 8.93 (d, J = 1.2 Hz, 1H), 8.86 (s, 1H), 8.12 (s, 1H), 7.81 (s, 1H), 5.51-5.25 (t, J = 50.8 Hz, 1H), 4.94-4.76 (m, 2H), 3.92-3.42 (m, 4H), 2.29-2.10 (m, 2H). Calculated (M + H): 410.05, Found (M + H): 410.0, HPLC purity 99.35% |

TABLE 13-continued

The following compounds were prepared by the method described above:

| Ex. No. | Structure | Name | Analytical data |
|---|---|---|---|
| 181 | 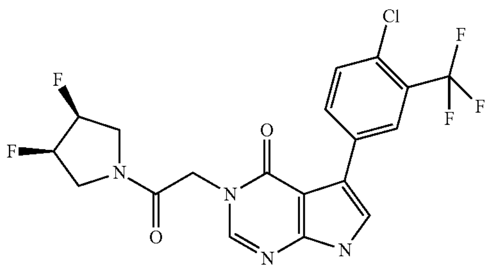 [SMILES: O=C(Cn1cnc2[nH]cc(-c3ccc(Cl)c(C(F)(F)F)c3)c2c1=O)N1C[C@@H](F)[C@@H](F)C1] | 5-(4-Chloro-3-trifluoromethyl-phenyl)-3-[2-((3R,4S)-3,4-difluoro-pyrrolidin-1-yl)-2-oxo-ethyl]-3,7-dihydro-pyrrolo[2,3-d]pyrimidin-4-one-d]pyrimidin-4-one | 1H NMR (400 MHz, DMSO-$d_6$) δ (ppm): 12.34 (s, 1H), 8.61 (s, 1H), 8.18 (d, J = 8.4 Hz, 1H), 8.08 (s, 1H), 7.70 (s, 1H), 7.63 (d, J = 8.4 Hz, 1H), 5.24-5.48 (m, 2H), 4.89-4.80 (m, 2H), 4.06-3.48 (m, 4H). Calculated M + H: 461.07; Found M + H: 461.1. HPLC purity: 96.10%. |
| 182 | 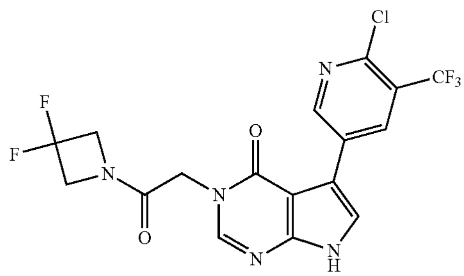 [SMILES: O=C(Cn1cnc2[nH]cc(-c3cnc(Cl)c(C(F)(F)F)c3)c2c1=O)N1CC(F)(F)C1] | 5-(6-chloro-5-(trifluoromethyl)pyridin-3-yl)-3-(2-(3,3-difluoroazetidin-1-yl)-2-oxoethyl)-3H-pyrrolo[2,3-d]pyrimidin-4(7H)-one | $^1$H NMR (400 MHz, DMSO-$d_6$) δ (ppm): 12.52 (s, 1H), 9.18 (s, 1H), 9.10 (s, 1H), 8.13 (s, 1H), 7.90 (s, 1H), 4.81-4.74 (m, 4H), 4.35 (t, J = 11.2 Hz, 2H). Calculated M + H: 448.05; Found M + H: 448.1, HPLC purity: 97.97% |
| 183 | 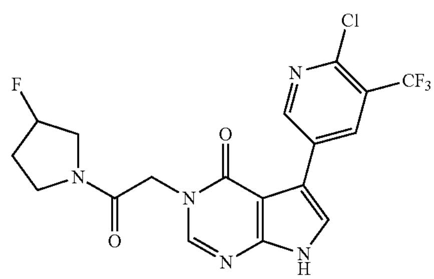 [SMILES: O=C(Cn1cnc2[nH]cc(-c3cnc(Cl)c(C(F)(F)F)c3)c2c1=O)N1CCC(F)C1] | 5-(6-chloro-5-(trifluoromethyl)pyridin-3-yl)-3-(2-(3-fluoropyrrolidin-1-yl)-2-oxoethyl)-3H-pyrrolo[2,3-d]pyrimidin-4(7H)-one | $^1$H NMR (400 MHz, DMSO-$d_6$) δ (ppm): 12.47 (s, 1H), 9.18 (s, 1H), 9.09 (s, 1H), 8.13 (s, 1H), 7.89 (s, 1H), 5.51-5.25 (m, 1H), 4.96-4.82 (m, 2H), 3.84-3.58 (m, 4H), 2.30-2.13 (m, 2H). Calculated M + H: 444.08; Found M + H: 444.1, HPLC: 99.87% |
| 184 | 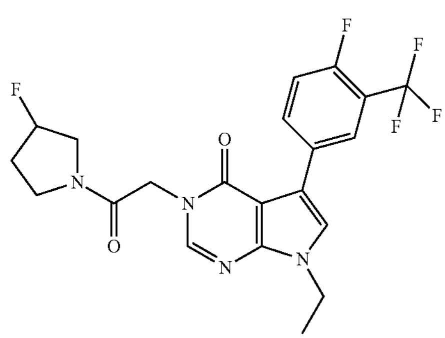 [SMILES: CCn1cc(-c2ccc(F)c(C(F)(F)F)c2)c2c(=O)n(CC(=O)N3CCC(F)C3)cnc21] | 1-Ethyl-5-[2-(3-fluoro-pyrrolidin-1-yl)-2-oxo-ethyl]-3-(4-fluoro-3-trifluoromethyl-phenyl)-1,5-dihydro-pyrrolo[3,2-c]pyridin-4-one | $^1$H NMR (400 MHz, DMSO-$d_6$) δ (ppm): 8.44 (d, J = 6 Hz, 1H), 8.22 (brs, 1H), 8.15 (s, 1H), 7.77 (s, 1H), 7.45 (t, J = 10 Hz, 1H), 5.51-5.25 (m, 1H), 4.94-4.76 (m, 2H), 4.19-4.15 (m, 2H), 3.92-3.26 (m, 4H), 2.30-1.95 (m, 2H), 1.39 (t, J = 7.6 Hz, 3H). Calculated M + H: 455.14; Found M + H: 455.1. HPLC: 99.50% |

Example 185: Preparation of 5-(4-chloro-3-(trifluoromethyl)phenyl)-7-(2-methoxyethyl)-3-(2-oxo-2-(pyrrolidin-1-yl)ethyl)-3H-pyrrolo[2,3-d]pyrimidin-4(7H)-one

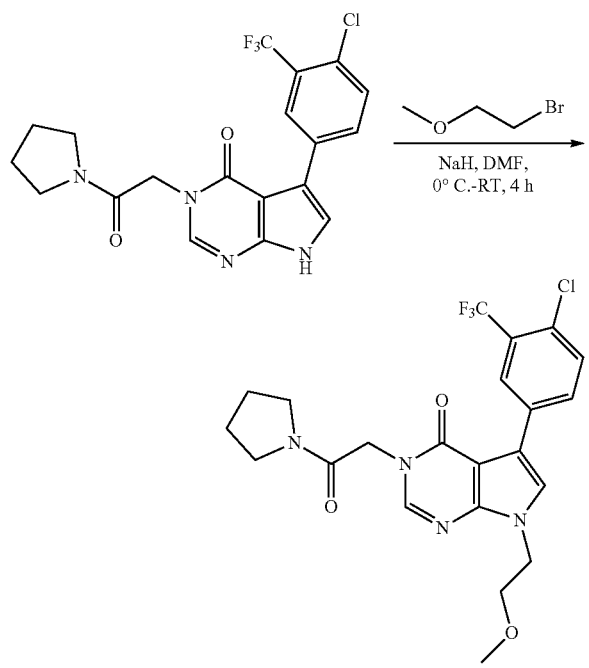

To a solution 5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.08 g, 0.19 mmol) in N,N-dimethylformamide (10 mL), sodium hydride (0.018 g, 0.38 mmol) was added at 0° C. and the reaction mixture was stirred at room temperature for 30 minutes. Then 1-bromo-2-methoxy-ethane (0.068 mL, 0.57 mmol) was added at 0° C. and the reaction mixture was stirred at room temperature for 4 h. The reaction mixture was quenched with cold water (20 mL) and stirred for 30 minutes to get precipitation. The precipitated solid was filtered, washed with pentane and dried under vacuum. The crude product was purified by silica gel column chromatography using 1.5% methanol in dichloromethane to afford the title compound 5-(4-chloro-3-(trifluoromethyl)phenyl)-7-(2-methoxyethyl)-3-(2-oxo-2-(pyrrolidin-1-yl)ethyl)-3H-pyrrolo[2,3-d]pyrimidin-4(7H)-one (0.028 g, 30% yield) as white solid. $^1$H NMR (400 MHz, DMSO-$d_6$) δ (ppm): 8.56 (s, 1H), 8.18-8.14 (m, 2H), 7.79 (s, 1H), 7.66 (d, J=8.4 Hz, 1H), 4.81 (s, 2H), 4.32 (brs, 2H), 3.75-3.71 (m, 2H), 3.53 (t, J=6.8 Hz 2H), 3.31-3.27 (m, 2H), 3.23 (s, 3H), 1.93 (t, J=6.8 Hz, 2H), 1.78 (t, J=6.8 Hz, 2H). Calculated M+H: 483.13; Found M+H: 483.3. HPLC: 97.24%.

TABLE 14

The following compounds were prepared by the method described above:

| Ex. No. | Structure | Name | Analytical data |
|---|---|---|---|
| 186 | 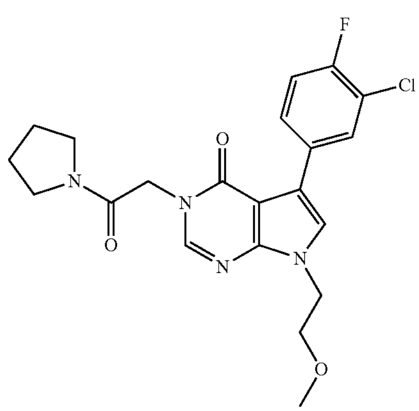 [SMILES: COCCn1cc(-c2ccc(F)c(Cl)c2)c2c(=O)n(CC(=O)N3CCCC3)cnc21] | 5-(3-chloro-4-fluorophenyl)-7-(2-methoxyethyl)-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.27-8.24 (dd, J = 2 Hz, 7.2 Hz, 1H), 8.12 (s, 1H), 7.89-7.85 (m, 1H), 7.64 (s, 1H), 7.35 (t, J = 9.6 Hz, 1H), 4.79 (s, 2H), 4.30 (t, J = 5.2 Hz, 2H), 3.73-3.69 (m, 2H), 3.53 (t, J = 6.4 Hz, 2H), 3.31-3.21 (m, 5H), 1.97-1.90, ( m, 2H), 1.82-1.76 (m, 2H). Calculated M + H: 433.14; Found M + H: 433.3. HPLC: 97.92% |

TABLE 14-continued

The following compounds were prepared by the method described above:

| Ex. No. | Structure | Name | Analytical data |
|---|---|---|---|
| 187 | 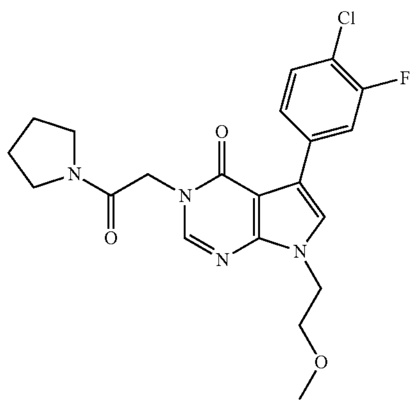 [SMILES: COCCn1cc(-c2ccc(Cl)c(F)c2)c2c(=O)n(CC(=O)N3CCCC3)cnc21] | 5-(4-chloro-3-fluorophenyl)-7-(2-methoxyethyl)-3-(2-oxo-2-(pyrrolidin-1-yl)ethyl)-3H-pyrrolo[2,3-d]pyrimidin-4(7H)-one | $^1$H NMR (400 MHz, DMSO-d$_6$) δ (ppm): 8.18 (s, 1H), 8.14 (m, 1H), 7.78 (d, J = 8.4 Hz, 1H), 7.72 (s, 1H), 7.50 (t, J = 8.4 Hz, 1H), 4.79 (s, 2H), 4.30 (t, J = 4.8 Hz, 2 H), 3.70 (t, J = 5.2 Hz, 2H), 3.53 (t, J = 6.8 Hz, 2H), 3.31-3.23 (m, 5H), 1.93 (t, J = 6.8 Hz, 2H), 1.82-1.77 (m, 2H). Calculated M + H: 433.14; Found M + H: 433.1, HPLC: 99.97% |
| 188 | 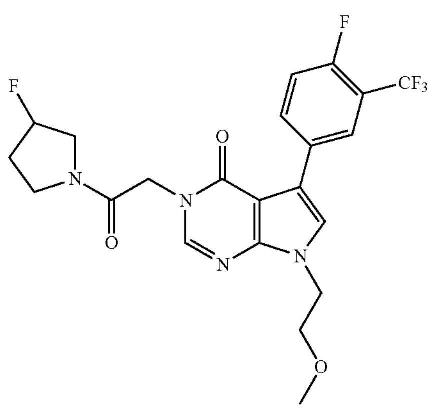 [SMILES: COCCn1cc(-c2ccc(F)c(C(F)(F)F)c2)c2c(=O)n(CC(=O)N3CCC(F)C3)cnc21] | 5-(4-fluoro-3-(trifluoromethyl)phenyl)-3-(2-(3-fluoropyrrolidin-1-yl)-2-oxoethyl)-7-(2-methoxyethyl)-3H-pyrrolo[2,3-d]pyrimidin-4(7H)-one | $^1$H NMR (400 MHz, DMSO-d$_6$) δ (ppm): 8.42 (d, J = 6 Hz, 1H), 8.20 (brs, 1H), 8.15 (s, 1H), 7.71 (s, 1H), 7.45 (t, J = 10 Hz, 1H), 5.51-5.25 (m, 1H), 4.94-4.80 (m, 2H), 4.31 (t, J = 5.2 Hz, 2H), 3.89-3.27 (m, 6H), 3.237 (s, 3H), 2.30-2.10 (m, 2H). Calculated M + H: 485.15; Found M + H: 485.1. HPLC: 99.27% |
| 189 | 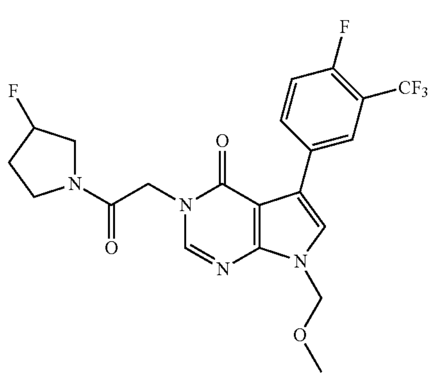 [SMILES: COCn1cc(-c2ccc(F)c(C(F)(F)F)c2)c2c(=O)n(CC(=O)N3CCC(F)C3)cnc21] | 5-(4-fluoro-3-(trifluoromethyl)phenyl)-3-(2-(3-fluoropyrrolidin-1-yl)-2-oxoethyl)-7-(methoxymethyl)-3H-pyrrolo[2,3-d]pyrimidin-4(7H)-one | $^1$H NMR (400 MHz, CDCl$_3$) δ (ppm): 8.04-7.99 (m, 2H), 7.96 (d, J = 3.2 Hz, 1H), 7.19 (t, J = 9.6 Hz, 1H), 7.15 (s, 1H), 5.52 (s, 2H), 5.45-5.2 (m, 1H), 5.02-4.92 (m, 1H), 4.54-4.44 (m, 1H), 4.0-3.5 (m, 4H), 3.35 (s, 3H), 2.45-1.9 (m, 2H). Calculated M + H: 471.14; Found M + H: 471.3. HPLC: 99.38% |

Example 190: Preparation of 5-(4-chloro-3-(trifluoromethyl)phenyl)-7-cyclopropyl-3-(2-oxo-2-(pyrrolidin-1-yl)ethyl)-3H-pyrrolo[2,3-d]pyrimidin-4(7H)-one

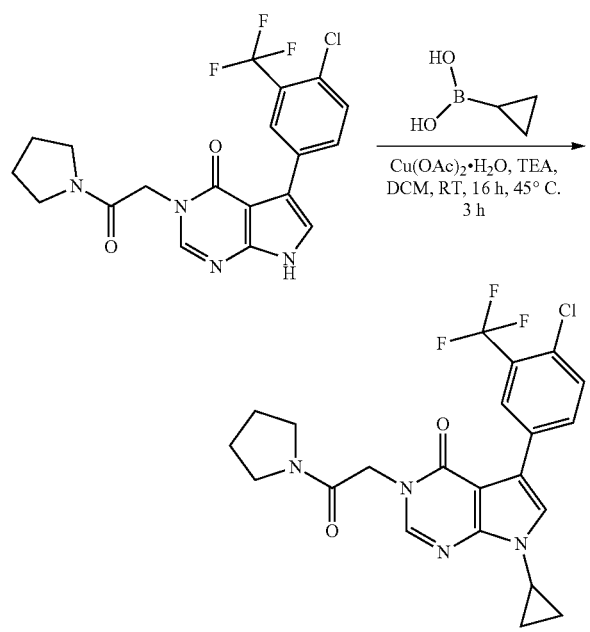

To a solution of 5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.08 g, 0.188 mmol) in dichloromethane (10 mL), triethylamine (0.13 mL, 0.943 mmol) and copper (II)acetate mono hydrate (0.112 g, 0.565 mmol) were added and the reaction mixture was stirred at room temperature for 16 h under air. Then the reaction mixture heated at 45° C. for 3 h. The reaction mixture was quenched with cold water (20 mL) and extracted with dichloromethane (3×30 mL). The combined organic layer was dried over anhydrous sodium sulphate, filtered and concentrated. The crude compound was purified by silica gel column chromatography using 1% methanol in dichloromethane to afford 5-(4-chloro-3-(trifluoromethyl)phenyl)-7-cyclopropyl-3-(2-oxo-2-(pyrrolidin-1-yl)ethyl)-3H-pyrrolo[2,3-d]pyrimidin-4(7H)-one (0.011 g, 12.8% yield) as white solid. $^1$H NMR (400 MHz, DMSO-$d_6$) δ (ppm): 8.57 (s, 1H), 8.21 (d, J=8 Hz, 1H), 8.15 (s, 1H), 7.72 (s, 1H), 7.64 (d, J=8.4 Hz, 1H), 4.81 (s, 2H), 3.63-3.62 (m, 1H), 3.53 (t, J=6.8 Hz, 2H), 1.93 (t, J=6.4 Hz, 2H), 1.78 (t, J=6.8 Hz, 2H), 1.09-1.03 (m, 4H); 2H are merged in DMSO water. Calculated M+H: 465.12; Found M+H: 465.0. HPLC purity: 98.22%.

TABLE 15

The following compounds were prepared by the method described above:

| Ex. No. | Structure | Name | Analytical data |
|---|---|---|---|
| 191 | 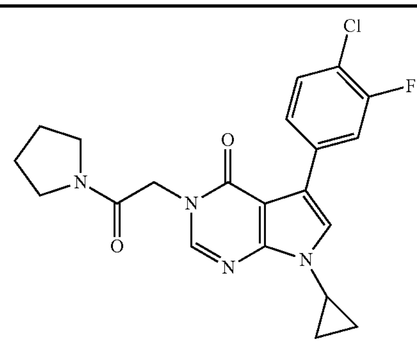 | 5-(4-chloro-3-fluorophenyl)-7-cyclopropyl-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.16 (d, J = 11.6 Hz, 2H), 7.84 (d, J = 8.4 Hz, 1H), 7.65 (s, 1H), 7.48 (t, J = 8.4 Hz, 1H), 4.80 (s, 2H), 3.62 (d, J = 4 Hz, 1H), 3.53 (t, J = 6.4 Hz, 2H), 3.29 (t, J = 7.2 Hz, 2H), 1.93 (t, 6.8 Hz, 2H), 1.78 (t, J = 6.8 Hz, 2H), 1.07-1.02 (m, 4H). Calculated M + H: 415.13; Found M + H: 415.1. HPLC purity: 99.7% |
| 192 | 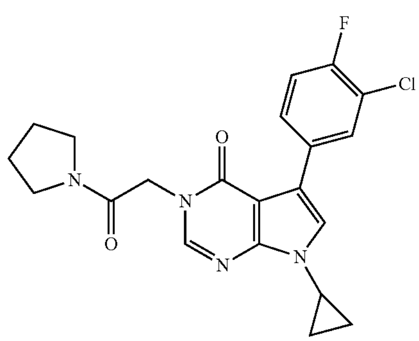 [SMILES: O=C(Cn1cnc2c(c(-c3ccc(F)c(Cl)c3)cn2C2CC2)c1=O)N1CCCC1] | 5-(3-chloro-4-fluorophenyl)-7-cyclopropyl-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.25 (d, J = 5.6 Hz, 1H), 8.13 (s, 1H), 7.94-7.91 (m, 1H), 7.57 (s, 1H), 7.33 (t, J = 8.8 Hz, 1H), 4.80 (s, 2H), 3.63-3.58 (m, 1H), 3.53 (t, J = 6.4 Hz, 2H), 3.29 (t, J = 6.8 Hz, 2H), 1.95-1.90 (m, 2H), 1.82-1.75 (m, 2H), 1.07-1.00 (m, 4H). Calculated M + H: 415.13; Found M + H: 415.1. HPLC: 99.20% |

TABLE 15-continued

The following compounds were prepared by the method described above:

| Ex. No. | Structure | Name | Analytical data |
|---|---|---|---|
| 193 | 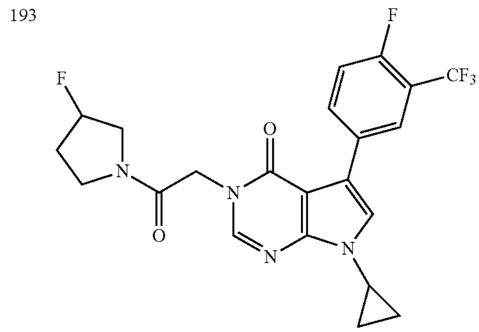 | 7-cyclopropyl-5-(4-fluoro-3-(trifluoromethyl)phenyl)-3-(2-(3-fluoropyrrolidin-1-yl)-2-oxoethyl)-3H-pyrrolo[2,3-d]pyrimidin-4(7H)-one | $^1$H NMR (400 MHz, DMSO-d$_6$) δ (ppm): 8.43 (d, J = 5.6 Hz, 1H), 8.23 (brs, 1H), 8.16 (d, J = 2.4 Hz, 1H), 7.64 (s, 1H), 7.44 (t, J = 10 Hz, 1H), 5.51-5.25 (m, 1H), 4.94-4.76 (m, 2H), 3.927-3.31 (m, 5H), 2.30-1.952 (m, 2H), 1.21-1.01 (m, 4H), Calculated M + H: 467.14; Found M + H: 467.1. HPLC purity: 99.76% |

Example 194: Preparation of 5-(4-chloro-3-(trifluoromethyl)phenyl)-7-(2-hydroxyethyl)-3-(2-oxo-2-(pyrrolidin-1-yl)ethyl)-3H-pyrrolo[2,3-d]pyrimidin-4(7H)-one

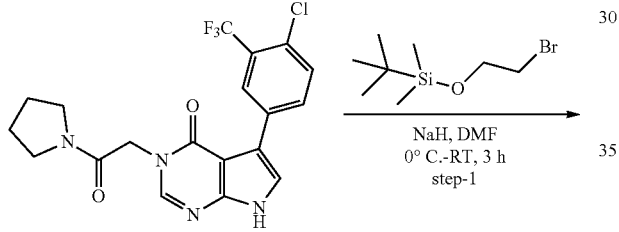

-continued

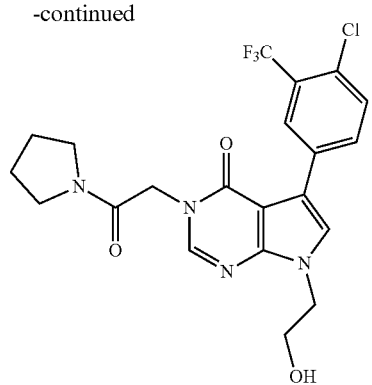

Step-1

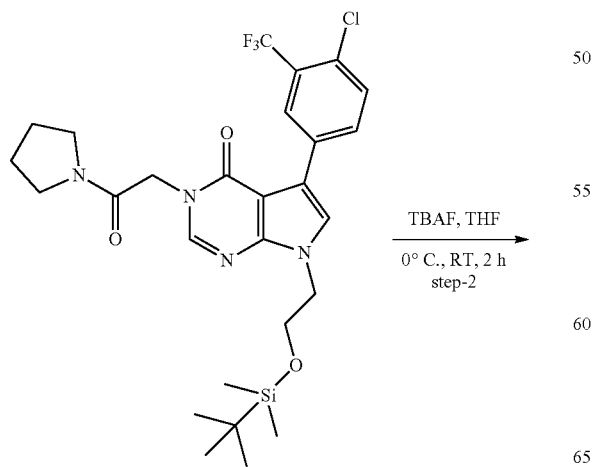

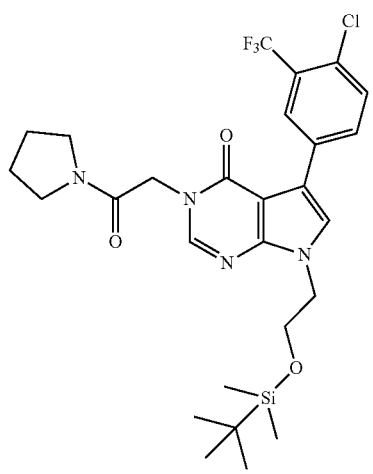 [SMILES: CC(C)(C)[Si](C)(C)OCCn1cc(-c2ccc(Cl)c(C(F)(F)F)c2)c2c(=O)n(CC(=O)N3CCCC3)cnc21]

145

Preparation of 7-(2-((tert-butyldimethylsilyl)oxy)ethyl)-5-(4-chloro-3-(trifluoromethyl)phenyl)-3-(2-oxo-2-(pyrrolidin-1-yl)ethyl)-3H-pyrrolo[2,3-d]pyrimidin-4(7H)-one To a solution 5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.07 g, 0.166 mmol) in N,N-dimethylformamide (8 mL), sodium hydride (0.018 g, 0.332 mmol) was added at 0° C. Then the reaction mixture was stirred at room temperature for 30 minutes. Then (2-Bromo-ethoxy)-tert-butyl-dimethyl-silane (0.119 g, 0.498 mmol) was added at 0° C. and the reaction mixture was stirred at room temperature for 3 h. The reaction mixture was quenched with cold water (20 mL) and extracted with ethyl acetate (3×30 mL). The combined organic layer was dried over anhydrous sodium sulphate, filtered and concentrated to afford the title compound 7-(2-((tert-butyldimethylsilyl)oxy)ethyl)-5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.221 g, crude) as gummy liquid. The crude product was as such taken for next step without further purification.

Step-2

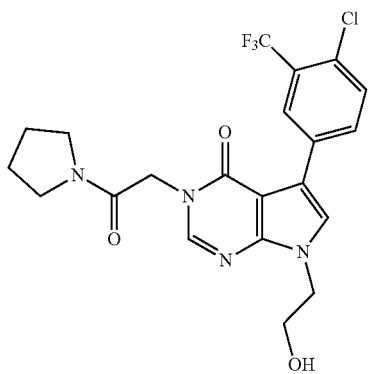 [SMILES: O=C(Cn1cnc2c(c(-c3ccc(Cl)c(C(F)(F)F)c3)cn2CCO)c1=O)N1CCCC1]

146

Preparation of 5-(4-chloro-3-(trifluoromethyl)phenyl)-7-(2-hydroxyethyl)-3-(2-oxo-2-(pyrrolidin-1-yl)ethyl)-3H-pyrrolo[2,3-d]pyrimidin-4(7H)-one To a solution 7-(2-((tert-butyldimethylsilyl)oxy)ethyl)-5-(4-chloro-3-(trifluoromethyl)phenyl)-3-(2-oxo-2-(pyrrolidin-1-yl)ethyl)-3H-pyrrolo[2,3-d]pyrimidin-4(7H)-one (0.220 g, 0.377 mmol) in tetrahydrofuran (30 mL), tetra butyl ammonium fluoride (0.32 mL, 1.13 mmol) was added at 0° C. and the solution was stirred at room temperature for 2 h. The reaction mixture was quenched with cold water (20 mL) and extracted with ethyl acetate (3×30 mL). The combined organic layer was dried over anhydrous sodium sulphate, filtered and concentrated. The crude compound was purified by preparative HPLC (column: chemsil C18 (250 mm×4.6 mm×5μ), mobile phase (A): 0.01% ammonia in water, mobile phase (B): acetonitrile, flow rate: 1.0 mL/min, T/% B: 0/20, 5/80, 25/90, 27/20, 30/20, wavelength: 254 nm) to afford the title compound 5-(4-chloro-3-(trifluoromethyl)phenyl)-7-(2-hydroxyethyl)-3-(2-oxo-2-(pyrrolidin-1-yl)ethyl)-3H-pyrrolo[2,3-d]pyrimidin-4(7H)-one (0.020 g, 2.8% yield) as white solid. $^1$H NMR (400 MHz, DMSO-$d_6$) δ (ppm): 8.57 (s, 1H), 8.18 (d, J=8.4 Hz, 1H), 8.13 (s, 1H), 7.78 (s, 1H), 7.65 (d, J=8.4 Hz, 1H), 4.95 (s, 1H), 4.81 (s, 2H), 4.20 (s, 2H), 3.76-3.74 (m, 2H), 3.53 (t, J=6.8 Hz, 2H), 1.93 (t, J=6.8 Hz, 2H), 1.78 (t, J=6.8 Hz, 2H). 2H are merged in DMSO water peak. Calculated M+H: 469.12; Found M+H: 469.2. HPLC purity: 99.87%.

TABLE 16

The following compounds were prepared by the method described above:

| Ex. No. | Structure | Name | Analytical data |
|---|---|---|---|
| 195 | 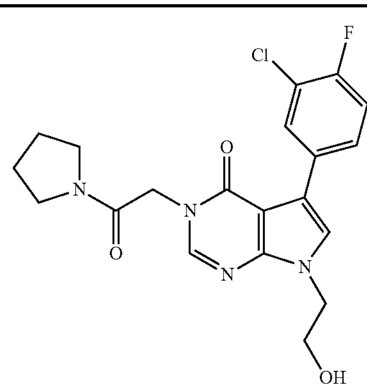 | 5-(3-chloro-4-fluorophenyl)-7-(2-hydroxyethyl)-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.26 (d, J = 7.2 Hz, 1H), 8.11 (s, 1H), 7.873 (brs, 1H), 7.63 (s, 1H), 7.35 (t, J = 8.8 Hz, 1H), 4.94 (s, 1H), 4.79 (s, 2H), 4.18 (bs, 2H), 3.74 (d, J = 4.4 Hz, 2H), 3.53 (t, J = 6 Hz, 2H), 3.29-3.27 (m, 2H), 1.93 (t, J = 6.4 Hz, 2H), 1.78 (t, J = 6.4 Hz, 2H). Calculated M + H: 419.12; Found M + H: 419.1. HPLC purity: 99.94% |

TABLE 16-continued

The following compounds were prepared by the method described above:

| Ex. No. | Structure | Name | Analytical data |
|---|---|---|---|
| 196 | 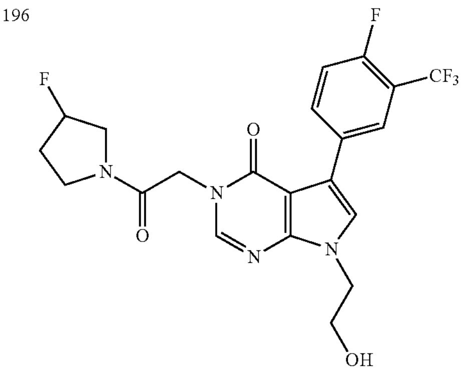 | 5-(4-fluoro-3-(trifluoromethyl)phenyl)-3-(2-(3-fluoropyrrolidin-1-yl)-2-oxoethyl)-7-(2-hydroxyethyl)-3H-pyrrolo[2,3-d]pyrimidin-4(7H)-one | $^1$H NMR (400 MHz, DMSO-$d_6$) δ (ppm): 8.43 (d, J = 6.8 Hz, 1H), 8.20 (brs, 1H), 8.14 (s, 1H), 7.70 (s, 1H), 7.45 (t, J = 9.6 Hz, 1H), 5.51-5.25 (m, 1H), 4.96-4.77 (m, 3H), 4.21-4.19 (t, J = 5.2 Hz, 2H), 3.89-3.31(m, 6H), 2.30-1.95 (m, 2H), Calculated M + H: 471.14; Found M + H: 471.3. HPLC purity: 99.58% |
| 197 | 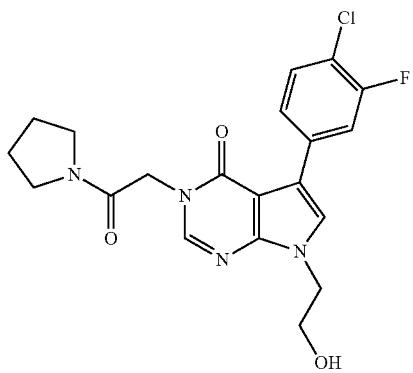 [SMILES: O=C(Cn1cnc2c(c(-c3ccc(Cl)c(F)c3)cn2CCO)c1=O)N1CCCC1] | 5-(4-chloro-3-fluorophenyl)-7-(2-hydroxyethyl)-3-(2-oxo-2-(pyrrolidin-1-yl)ethyl)-3H-pyrrolo[2,3-d]pyrimidin-4(7H)-one | $^1$H NMR (400 MHz, DMSO-$d_6$) δ (ppm): 8.18-8.13 (m, 2H), 7.78 (d, J = 8.0 Hz, 1H), 7.71(s, 1H), 7.49 (t, J = 8.4 Hz, 1H), 4.95 (s, 1H), 4.79 (s, 2H), 4.19 (t, d = 5.2 Hz, 2H), 3.74 (d, J = 4 Hz, 2H), 3.53 (t, J = 6.8 Hz, 2H), 3.29 (m, 2H), 1.93 (t, J = 6.8 Hz, 2H), 1.78 (t, J = 6.8 Hz, 2H). Calculated M + H: 419.12; Found M + H: 419.2, HPLC purity: 99.85% |

C. PREPARATION OF PYRROLOPYRIDONES

Example 198: Preparation of 3-(4-chloro-3-(trifluoromethyl)phenyl)-5-(2-(3-fluoropyrrolidin-1-yl)-2-oxoethyl)-1H-pyrrolo[3,2-c]pyridin-4(5H)-one

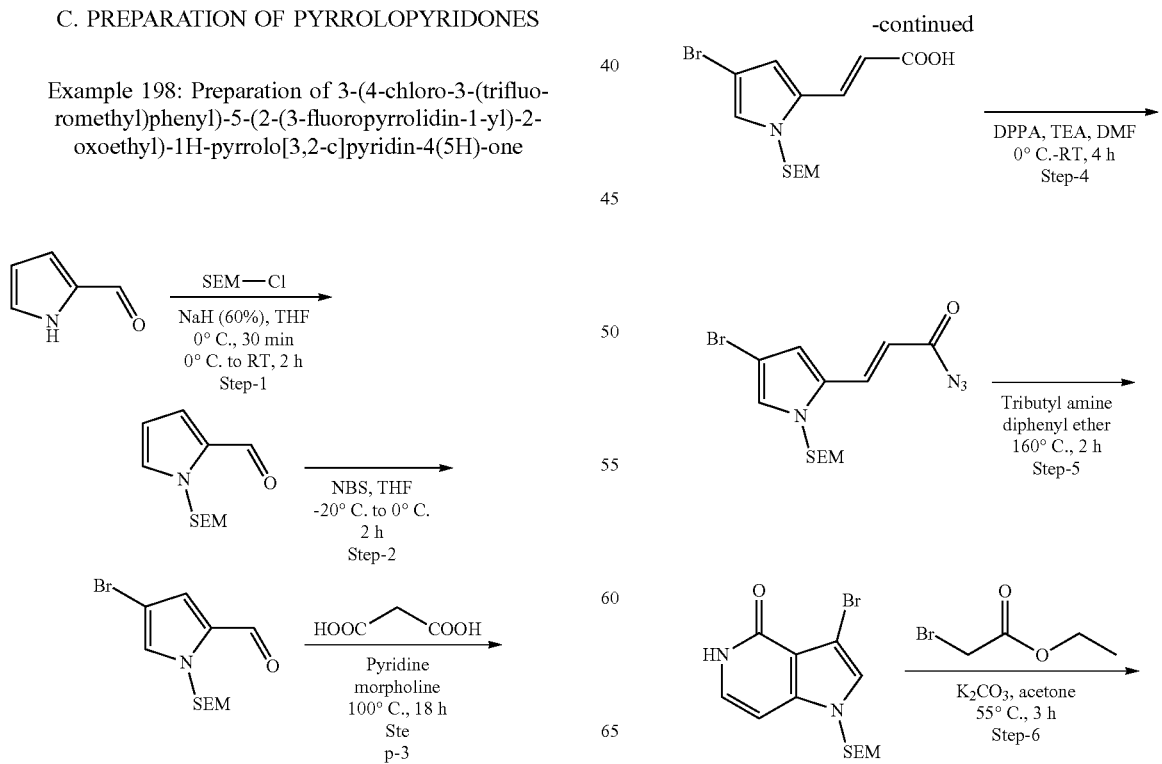

-continued

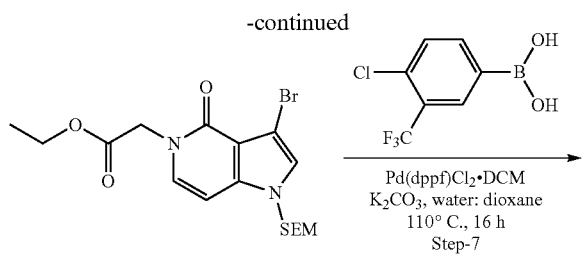

Pd(dppf)Cl$_2$·DCM
K$_2$CO$_3$, water: dioxane
110° C., 16 h
Step-7

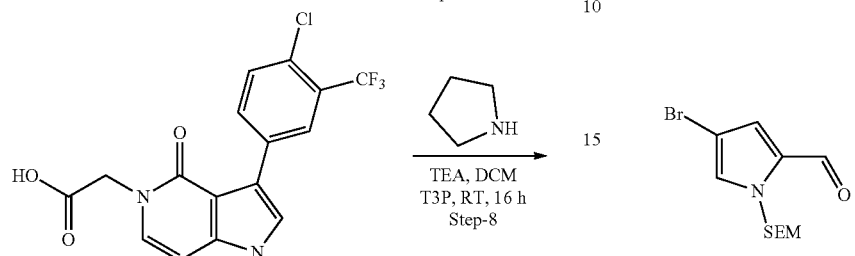

TEA, DCM
T3P, RT, 16 h
Step-8

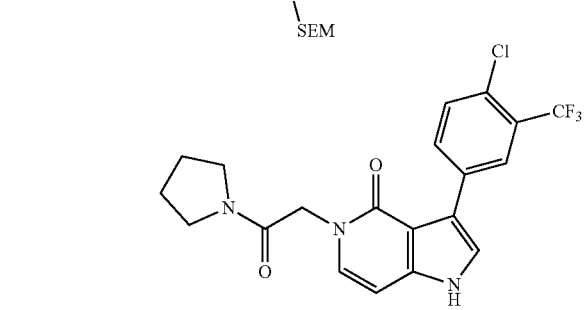

Triethyl silane
TFA, RT, 1 h
Step-9

Step 1

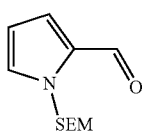

Preparation of 1-((2-(trimethylsilyl)ethoxy)methyl)-1H-pyrrole-2-carbaldehyde

To a stirred suspension of sodium hydride (60% dispersion in mineral oil) (9.16 g, 228.70 mmol) in tetrahydrofuran was added a solution of 1H-pyrrole-2-carbaldehyde (14.5 g, 152.47 mmol) in tetrahydrofuran at 0° C. and stirred for 30 min. Then, (2-(chloromethoxy)ethyl)trimethylsilane (SEMCl) (40.6 mL, 228.70 mmol) was added at 0° C. portion wise (15 min time interval) and stirred at room temperature for 2 h. After completion of reaction (monitored by TLC), mixture was quenched with ice cold water (100 mL), extracted with ethyl acetate (3×500 mL). The combined organic layers were dried over anhydrous sodium sulfate, filtered and evaporated under vacuum to afford crude product, which was purified by silica gel (60-120) column chromatography using 5% ethyl acetate in hexane to afford title compound 1-((2-(trimethylsilyl)ethoxy)methyl)-1H-pyrrole-2-carbaldehyde (25.9 g, 75.5% yield) as a yellow liquid. Calculated (M+H): 226.12, Found (M+H): 226.1.

Step 2

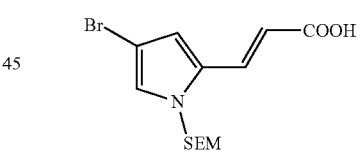

Preparation of 4-bromo-1-((2-(trimethylsilyl)ethoxy)methyl)-1H-pyrrole-2-carbaldehyde To a solution of 1-((2-(trimethylsilyl)ethoxy)methyl)-1H-pyrrole-2-carbaldehyde (25.9 g, 114.93 mmol) in tetrahydrofuran (200 mL) was added N-bromosuccinimide (21.5 g, 120.80 mmol) at −20° C. and stirred at 0° C. for 2 h. After completion of reaction, the reaction mixture was poured on to hexane (200 mL), solid suspension was filtered off, the filtrate was concentrated under vacuum to afford crude product, which was purified by silica gel (60-120) column chromatography using 10% ethyl acetate in hexane to afford title compound 4-bromo-1-((2-(trimethylsilyl)ethoxy)methyl)-1H-pyrrole-2-carbaldehyde (26.33 g, crude) as a yellow liquid. Calculated (M+H): 304.03, Found (M+H): 304.0.

Step 3

Preparation of (E)-3-(4-bromo-1-((2-(trimethylsilyl)ethoxy)methyl)-1H-pyrrol-2-yl)acrylic acid To a mixture of 4-bromo-1-((2-(trimethylsilyl)ethoxy)methyl)-1H-pyrrole-2-carbaldehyde (26.33 g, 86.54 mmol) and malonic acid (10.81 g, 103.84 mmol) in pyridine (50 mL), was added morpholine (0.73 g, 8.65 mmol) at room temperature and stirred at 120° C. for 18 h. After completion of reaction, the reaction mixture was cooled to room temperature and concentrated under vacuum to afford crude product, which was purified by silica gel (60-120) column chromatography using 30% ethyl acetate in hexane to afford title compound (E)-3-(4-bromo-1-((2-(trimethylsilyl) ethoxy)methyl)-1H-pyrrol-2-yl)acrylic acid (18.0 g, 60.2% Yield) as brown solid. Calculated (M+H): 346.04; Found (M+H): 346.0.

Step 4

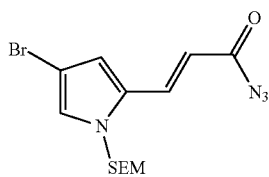 [SMILES: C[Si](C)(C)CCOCn1cc(Br)cc1/C=C/C(=O)N=[N+]=[N-]]

Preparation of (E)-3-(4-bromo-1-((2-(trimethylsilyl)ethoxy)methyl)-1H-pyrrol-2-yl)acryloyl azide To a stirred solution of (E)-3-(4-bromo-1-((2-(trimethylsilyl)ethoxy)methyl)-1H-pyrrol-2-yl)acrylic acid (18.0 g, 51.98 mmol) in N,N-dimethylformamide (30 mL), was added triethylamine (7.98 mL, 57.18 mmol) and diphenylphosphorylazide (12.32 mL, 57.18 mmol) at 0° C. and stirred at room temperature for 4 h. After completion of reaction mixture, the mixture was poured on to 500 mL of ice cold water, extracted with ethyl acetate (2×500 mL). The combined organic layer was concentrated under vacuum to afford title compound (E)-3-(4-bromo-1-((2-(trimethylsilyl)ethoxy)methyl)-1H-pyrrol-2-yl)acryloyl azide (24.0 g, crude) as brown liquid. $^1$H NMR (400 MHz, CDCl$_3$) δ (ppm): 7.64 (d, J=15.6 Hz, 1H), 6.89 (s, 1H), 6.72 (s, 1H), 6.19-6.14 (m, 1H), 5.24 (s, 2H), 3.48 (t, J=8.0 Hz, 2H), 1.25 (s, 1H), 0.88 (t, J=8.0 Hz, 2H), −0.022 (s, 9H).

Step 5

Preparation of 3-bromo-1-((2-(trimethylsilyl)ethoxy)methyl)-1H-pyrrolo[3,2-c]pyridin-4(5H)-one To a stirred solution of (E)-3-(4-bromo-1-((2-(trimethylsilyl)ethoxy)methyl)-1H-pyrrol-2-yl)acryloyl azide (24.0 g, 64.64 mmol) in diphenyl ether (50 mL), was added tributylamine (16.9 mL, 71.10 mmol) at room temperature and stirred at 100° C. for 10 min, the temperature was raised to 160° C. and stirred for 16 h. After completion of the reaction, mixture was allowed to cool to room temperature and loaded to silica gel (60-120) column directly. Initially the column was eluted with hexane to remove diphenyl ether, then eluted with 5% methanol in dichloromethane to afford 3-bromo-1-((2-(trimethylsilyl)ethoxy)methyl)-1H-pyrrolo[3,2-c]pyridin-4(5H)-one (6.0 g, 27% yield) as brown solid. Calculated (M+H): 343.04, Found (M+H): 343.0.

Step 6

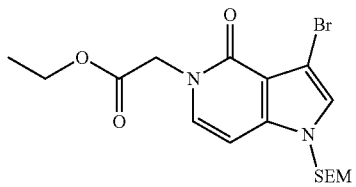 [SMILES: CCOC(=O)Cn1ccc2c(c(Br)cn2COCC[Si](C)(C)C)c1=O]

Preparation of ethyl ethyl 2-(3-bromo-4-oxo-1-((2-(trimethylsilyl)ethoxy)methyl)-1H-pyrrolo[3,2-c]pyridin-5(4H)-yl)acetate To a stirred suspension of 3-bromo-1-((2-(trimethylsilyl)ethoxy)methyl)-1H-pyrrolo[3,2-c]pyridin-4(5H)-one (6.0 g, 17.48 mmol) in acetone (200 mL), was added potassium carbonate (7.24 g, 52.43 mmol) and ethyl 2-bromoacetate (3.88 mL, 34.96 mmol) at room temperature, stirred at 55° C. for 2 h. After completion of reaction, the reaction mixture cooled to room temperature, filtered and washed with acetone. The filtrate was concentrated under vacuum to afford crude product, which was purified by silica gel column chromatography using 50% ethyl acetate in hexane to afford ethyl 2-(3-bromo-4-oxo-1-((2-(trimethylsilyl)ethoxy)methyl)-1H-pyrrolo[3,2-c]pyridin-5(4H)-yl)acetate (4.7 g, 62.8% yield) as brown solid. Calculated (M+H): 429.08, Found (M+H): 429.10.

Step 7

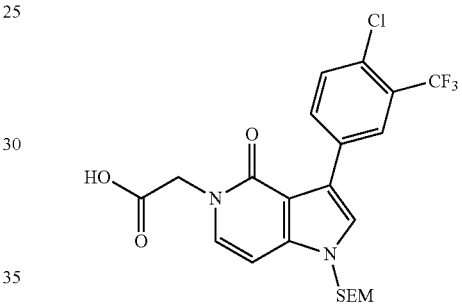

Preparation of 2-(3-(4-chloro-3-(trifluoromethyl)phenyl)-4-oxo-1-((2-(trimethylsilyl)ethoxy)methyl)-1H-pyrrolo[3,2-c]pyridin-5(4H)-yl)acetic acid To a stirred suspension of ethyl 2-(3-bromo-4-oxo-1-((2-(trimethylsilyl)ethoxy)methyl)-1H-pyrrolo[3,2-c]pyridin-5(4H)-yl)acetate (2.0 g, 4.66 mmol) in a mixture of 1,4-dioxane:water (50 mL, 4:1) was added (4-chloro-3-(trifluoromethyl)phenyl)boronic acid (1.57 g, 6.99 mmol) at room temperature and the resulting mixture was purged with nitrogen for 10 min. To the above mixture was added[1,1'-Bis(diphenylphosphino)ferrocene]dichloropalladium(II) dichloromethane complex (0.19 g, 0.23 mmol) and potassium carbonate (1.93 g, 13.97 mmol) under nitrogen, the reaction mixture was stirred at 110° C. for 16 h. After completion of reaction, the mixture was cooled to room temperature, diluted with water (30 mL), acidified with 2N hydrochloric acid and extracted with ethyl acetate (3×500 mL). The combined organic layers were dried over anhydrous sodium sulfate, filtered and concentrated under vacuum to afford crude product, which was purified by silica gel column chromatography using 15% methanol in dichloromethane to afford 2-(3-(4-chloro-3-(trifluoromethyl)phenyl)-4-oxo-1-((2-(trimethylsilyl)ethoxy)methyl)-1H-pyrrolo[3,2-c]pyridin-5(4H)-yl)acetic acid (2.26 g, crude) as brown solid. Calculated (M+H): 501.11, Found (M+H): 501.10.

Step 8

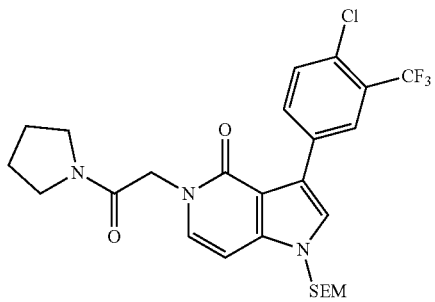 [SMILES: C[Si](C)(C)CCOCn1cc(-c2ccc(Cl)c(C(F)(F)F)c2)c2c(=O)n(CC(=O)N3CCCC3)ccc21]

Preparation of 3-(4-chloro-3-(trifluoromethyl)phenyl)-5-(2-oxo-2-(pyrrolidin-1-yl)ethyl)-1-((2-(trimethylsilyl)ethoxy)methyl)-1H-pyrrolo[3,2-c]pyridin-4(5H)-one To the stirred suspension of 2-(3-(4-chloro-3-(trifluoromethyl)phenyl)-4-oxo-1-((2-(trimethylsilyl)ethoxy)methyl)-1H-pyrrolo[3,2-c]pyridin-5(4H)-yl)acetic acid (0.25 g, 0.50 mmol) and pyrrolidine (0.071 g, 1.02 mmol) in dichloromethane (10 mL), was added triethylamine (0.3 g, 3.08 mmol). The reaction mixture was cooled to 0° C., was added 1-propylphosphonic anhydride (50% solution in ethyl acetate) (0.44 mL, 0.75 mmol), and stirred at room temperature for 4 h. The reaction mixture was diluted with dichloromethane (50 mL), washed with water, brine, dried over anhydrous sodium sulfate, filtered and concentrated under vacuum to afford crude product, which was purified by silica gel column chromatography using 5% methanol in dichloromethane to afford title compound 3-(4-chloro-3-(trifluoromethyl)phenyl)-5-(2-oxo-2-(pyrrolidin-1-yl) ethyl)-1-((2-(trimethylsilyl)ethoxy)methyl)-1H-pyrrolo[3,2-c]pyridin-4(5H)-one (0.1 g, crude). Calculated (M+H): 554.18, Found (M+H): 554.1.

Step 9

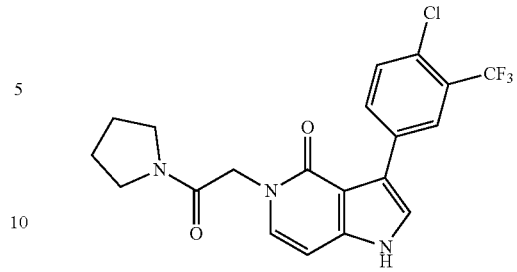

Preparation of 3-(4-chloro-3-(trifluoromethyl)phenyl)-5-(2-oxo-2-(pyrrolidin-1-yl)ethyl)-1H-pyrrolo[3,2-c]pyridin-4(5H)-one To a stirred suspension of 3-(4-chloro-3-(trifluoromethyl)phenyl)-5-(2-oxo-2-(pyrrolidin-1-yl)ethyl)-1-((2-(trimethylsilyl)ethoxy)methyl)-1H-pyrrolo[3,2-c]pyridin-4(5H)-one (0.1 g, 0.18 mmol) in triethylsilane (0.058 mL, 0.36 mmol), was added trifluoroaceticacid (0.55 mL, 7.21 mmol) at room temperature and stirred for 1 h. After completion of reaction, reaction mixture was evaporated under vacuum and the residue was diluted with 1 mL of acetonitrile and 3 mL of ammonium hydroxide. The resulting mixture was stirred for 2 h at room temperature, and acidified with 2N hydrochloric acid at 0° C. The precipitated product was filtered and dried to afford the crude product, which was purified by preparative HPLC method (column: chemsil, C18 (250 mm×4.6 mm×5μ), mobile phase (A): 0.01% ammonia in water, mobile phase (B): acetonitrile, flow rate: 1.0 mL/min, T/% B: 0/20, 10/80, 25/80, 27/20, 30/20, at 254 nm) to afford title compound 3-(4-chloro-3-(trifluoromethyl)phenyl)-5-(2-oxo-2-(pyrrolidin-1-yl)ethyl)-1H-pyrrolo[3,2-c]pyridin-4 (5H)-one (0.02 g, 26.3% yield) as off white solid. $^1$H-NMR (DMSO-$d_6$, 400 MHz) δ (ppm): 11.90 (brs, 1H), 8.49 (d, J=1.6 Hz, 1H), 8.11 (dd, J=1.6 Hz, J=8.0 Hz, 1H), 7.59 (d, J=8.4 Hz, 1H), 7.57 (s, 1H), 7.21 (d, J=7.2 Hz, 1H), 6.44 (d, J=7.6 Hz, 1H), 4.72 (s, 2H), 3.52-3.49 (m, 2H), 3.29-3.26 (m, 2H), 1.95-1.88 (m, 2H), 1.80-1.73 (m, 2H). Calculated (M+H): 424.10, Found (M+H): 424.0, HPLC purity: 99.79%.

TABLE 17

The following compounds were prepared by the method described above:

| Ex. No. | Structure | Name | Analytical data |
|---|---|---|---|
| 199 | ![structure] | 3-(4-chloro-3-(trifluoromethyl)phenyl)-5-(2-(3-fluoropyrrolidin-1-yl)-2-oxoethyl)-1-((2-(trimethylsilyl)ethoxy)methyl)-1H-pyrrolo[3,2-c]pyridin-4(5H)-one | $^1$H-NMR (DMSO-$d_6$, 400 MHz) δ (ppm): 8.40 (s, 1H), 8.08 (d, J = 8.4 Hz, 1H), 7.75 (s, 1H), 7.64 (d, J = 8.4 Hz, 1H), 7.36 (d, J = 7.2 Hz, 1H), 6.67 (d, J = 7.2 Hz, 1H), 5.47-5.24 (m, 3H), 4.84-4.72 (m, 2H) 3.81-3.49 (m, 6H), 2.32-1.95 (m, 2H), 0.83 (t, J = 8.0 Hz, 2H), −0.073 (s, 9H). Calculated (M + H): 572.17, Found (M + H): 572.3, HPLC purity: 99.70% |

TABLE 17-continued

The following compounds were prepared by the method described above:

| Ex. No. | Structure | Name | Analytical data |
|---|---|---|---|
| 200 | 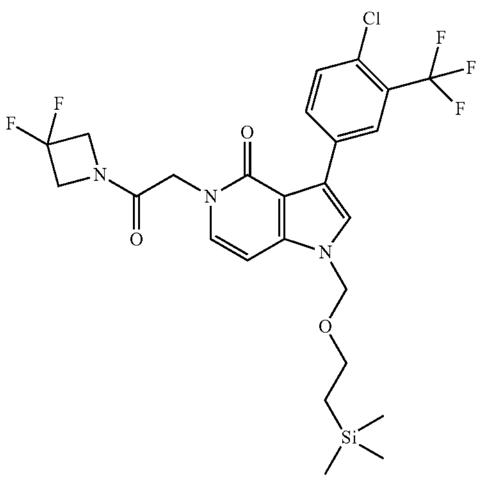 [SMILES: C[Si](C)(C)CCOCn1cc(-c2ccc(Cl)c(C(F)(F)F)c2)c2c(=O)n(CC(=O)N3CC(F)(F)C3)ccc21] | 3-(4-chloro-3-(trifluoromethyl)phenyl)-5-(2-(3,3-difluoroazetidin-1-yl)-2-oxoethyl)-1-((2-(trimethylsilyl)ethoxy)methyl)-1H-pyrrolo[3,2-c]pyridin-4(5H)-one | $^1$H-NMR (DMSO-$d_6$, 400 MHz) δ (ppm): 8.45 (d, J = 1.2 Hz, 1H), 8.06 (d, J = 8.4 Hz, 1H), 7.77 (s, 1H), 7.65 (d, J = 8.4 Hz, 1H), 7.38 (d, J = 7.6 Hz, 1H), 6.70 (d, J = 7.6 Hz, 1H), 5.47 (s, 2H), 4.72 (t, J = 12.0 Hz, 2H), 4.66 (s, 2H), 4.31 (t, J = 12.0 Hz, 2H), 3.51 (t, J = 8.0 Hz, 2H), 0.83 (t, J = 8.0 Hz, 2H), −0.080 (s, 9H); Calculated (M + H): 576.14, Found (M + H): 576.0, HPLC purity: 99.90% |
| 201 | 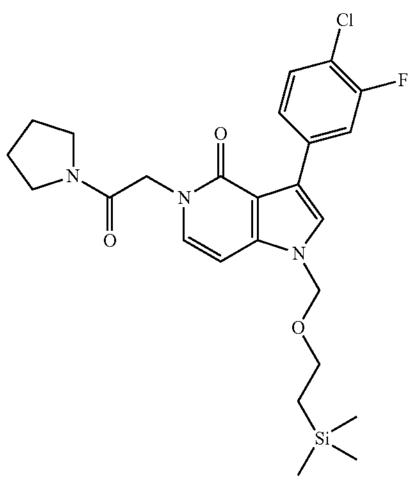 [SMILES: C[Si](C)(C)CCOCn1cc(-c2ccc(Cl)c(F)c2)c2c(=O)n(CC(=O)N3CCCC3)ccc21] | 3-(4-chloro-3-fluorophenyl)-5-(2-oxo-2-(pyrrolidin-1-yl)ethyl)-1-((2-(trimethylsilyl)ethoxy)methyl)-1H-pyrrolo[3,2-c]pyridin-4(5H)-one | $^1$H-NMR (DMSO-$d_6$, 400 MHz) δ (ppm): 8.07 (d, J = 12.0 Hz, 1H), 7.69-7.67 (m, 2H), 7.48 (t, J = 8.4 Hz, 1H), 7.34 (d, J = 7.6 Hz, 1H), 6.64 (d, J = 7.6 Hz, 1H), 5.46 (s, 2H), 4.72 (s, 2H), 3.53-3.49 (m, 4H), 3.30-3.27 (m, 2H), 1.95-1.88 (m, 2H), 1.80-1.74 (m, 2H), 0.83 (t, J = 8.0 Hz, 2H), −0.075 (s, 9H); Calculated (M + H): 504.18, Found (M + H): 504.5, HPLC purity: 99.69% |
| 202 | 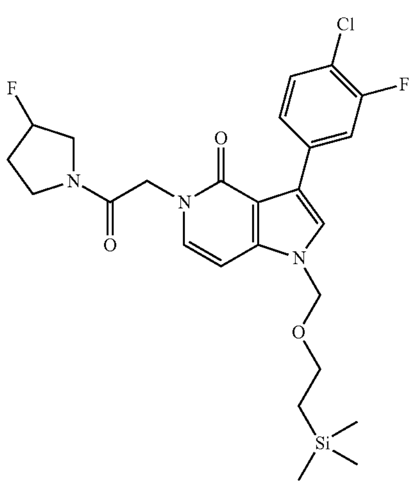 [SMILES: C[Si](C)(C)CCOCn1cc(-c2ccc(Cl)c(F)c2)c2c(=O)n(CC(=O)N3CCC(F)C3)ccc21] | 3-(4-chloro-3-fluorophenyl)-5-(2-(3-fluoropyrrolidin-1-yl)-2-oxoethyl)-1-((2-(trimethylsilyl)ethoxy)methyl)-1H-pyrrolo[3,2-c]pyridin-4(5H)-one | $^1$H-NMR (DMSO-$d_6$, 400 MHz) δ (ppm): 8.06 (d, J = 12.0 Hz, 1H), 7.68 (m, 2H), 7.48 (t, J = 8.4 Hz, 1H), 7.36 (d, J = 7.2 Hz, 1H), 6.65 (d, J = 7.2 Hz, 1H), 5.49-5.24 (m, 3H), 4.86-4.72 (m, 2H), 3.86-3.32 (m, 6H), 2.30-2.09 (m, 2H), 0.83 (t, J = 12.0 Hz, 2H), −0.07 (s, 9H); Calculated (M + H): 522.17, Found (M + H): 522.1, HPLC purity: 99.72% |

TABLE 17-continued

The following compounds were prepared by the method described above:

| Ex. No. | Structure | Name | Analytical data |
|---|---|---|---|
| 203 | 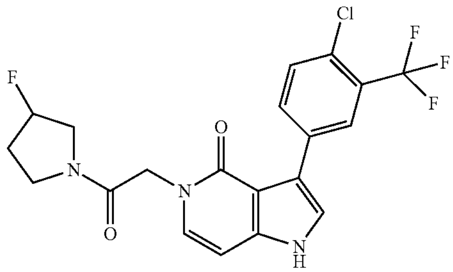 [SMILES: O=C(Cn1ccc2[nH]cc(-c3ccc(Cl)c(C(F)(F)F)c3)c2c1=O)N1CCC(F)C1] | 3-(4-chloro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-d$_6$, 400 MHz) δ (ppm): 11.80 (s, 1H), 8.48 (s, 1H), 8.11 (d, J = 8.0 Hz, 1H), 7.60 (m 2H), 7.24 (d, J = 6.8 Hz, 1H), 7.44 (d, J = 7.2 Hz, 1H), 5.49-5.24 (m, 1H), 4.86-4.71 (m, 2H), 3.90-3.36 (m, 4H), 2.30-1.93 (m, 2H). Calculated (M + H): 442.09, Found (M + H): 442.0, HPLC purity: 96.92% |
| 204 | 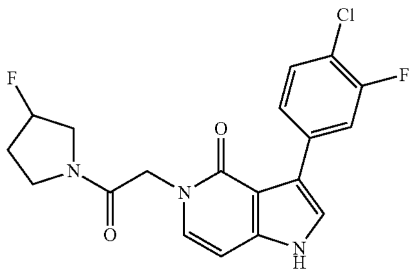 [SMILES: O=C(Cn1ccc2[nH]cc(-c3ccc(Cl)c(F)c3)c2c1=O)N1CCC(F)C1] | 3-(4-chloro-3-fluorophenyl)-5-(2-(3-fluoropyrrolidin-1-yl)-2-oxoethyl)-1H-pyrrolo[3,2-c]pyridin-4(5H)-one | $^1$H-NMR (DMSO-d$_6$, 400 MHz) δ (ppm): 11.75 (s, 1H), 8.13-8.10 (m, 1H), 7.73 (d, J = 8.4 Hz, 1H), 7.53 (s, 1H), 7.44 (t, J = 8.4 Hz, 1H), 7.24 (d, J = 7.2 Hz, 1H), 6.43 (d, J = 7.6 Hz, 1H), 5.49-5.24 (m, 1H), 4.84-4.68 (m, 2H), 3.89-3.37 (m, 4H), 2.47-1.96 (m, 2H); Calculated (M + H): 392.09, Found (M + H): 392.0, HPLC purity: 98.62% |
| 205 | 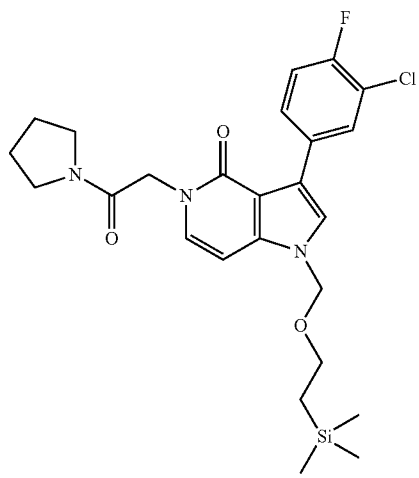 [SMILES: C[Si](C)(C)CCOCn1cc(-c2ccc(F)c(Cl)c2)c2c(=O)n(CC(=O)N3CCCC3)ccc21] | 3-(3-chloro-4-fluorophenyl)-5-(2-oxo-2-(pyrrolidin-1-yl)ethyl)-1-((2-(trimethylsilyl)ethoxy)methyl)-1H-pyrrolo[3,2-c]pyridin-4(5H)-one | $^1$H-NMR (DMSO-d$_6$, 400 MHz) δ (ppm): 8.13 (dd, J = 1.6 Hz, J = 5.2 Hz, 1H), 7.78-7.75 (m, 1H), 7.61 (s, 1H), 7.36-7.31 (m, 2H), 6.63 (d, J = 7.2 Hz, 1H), 5.45 (s, 2H), 4.72 (s, 2H), 3.53-3.49 (m, 4H), 3.39-3.27 (m, 2H), 1.93-1.90 (m, 2H), 1.80-1.77 (m, 2H), 0.83 (t, 8.0 Hz, 2H), 0.10 (s, 9H). Calculated (M + H): 504.18, found (M + H): 504.1, HPLC purity: 99.2% |
| 206 | 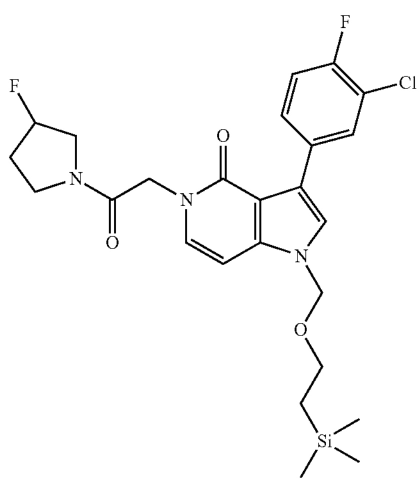 [SMILES: C[Si](C)(C)CCOCn1cc(-c2ccc(F)c(Cl)c2)c2c(=O)n(CC(=O)N3CCC(F)C3)ccc21] | 3-(3-chloro-4-fluorophenyl)-5-(2-(3-fluoropyrrolidin-1-yl)-2-oxoethyl)-1-((2-(trimethylsilyl)ethoxy)methyl)-1H-pyrrolo[3,2-c]pyridin-4(5H)-one | $^1$H-NMR (DMSO-d$_6$, 400 MHz) δ (ppm): 8.13 (dd, J = 1.6 Hz, J = 6.0 Hz, 1H), 7.77 (s, 1H), 7.61 (s, 1H), 7.36-7.32 (m, 2H), 6.64 (d, J = 7.6 Hz, 1H), 5.49-5.24 (m, 3H), 4.86-4.71 (m, 2H), 3.86-3.37 (m, 6H), 2.25-2.08 (m, 2H), 0.83 (t, J = 8.0 Hz, 2H), 0.10 (s, 9H). Calculated (M + H): 522.17, found (M + H): 522.5, HPLC purity: 98.91% |

TABLE 17-continued

The following compounds were prepared by the method described above:

| Ex. No. | Structure | Name | Analytical data |
|---|---|---|---|
| 207 | 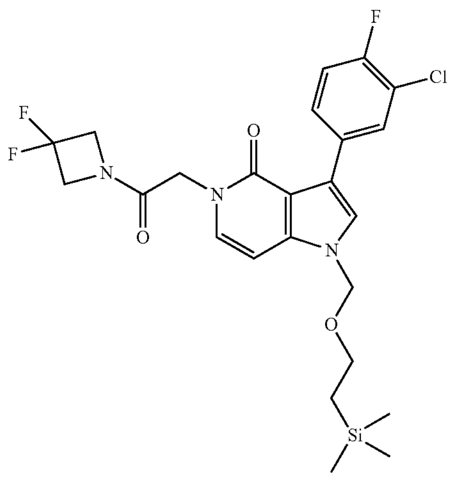 [SMILES: C[Si](C)(C)CCOCn1cc(-c2ccc(F)c(Cl)c2)c2c(=O)n(CC(=O)N3CC(F)(F)C3)ccc21] | 3-(3-chloro-4-fluorophenyl)-5-(2-(3,3-difluoroazetidin-1-yl)-2-oxoethyl)-1-((2-(trimethylsilyl)ethoxy)methyl)-1H-pyrrolo[3,2-c]pyridin-4(5H)-one | $^1$H-NMR (DMSO-$d_6$, 400 MHz) δ (ppm): 8.12 (d, J = 6.4 Hz, 1H), 7.76 (s, 1H), 7.61 (s, 1H), 7.36-7.32 (m, 2H), 6.67 (d, J = 7.2 Hz, 1H), 5.45 (s, 2H), 4.71-4.65 (m, 4H), 4.32 (s, 2H), 3.50 (t, J = 7.6 Hz, 2H), 082 (t, J = 8.0 Hz, 2H), 0.001 (s, 9H). Calculated (M + H): 526.15, found (M + H): 526.2, HPLC purity: 98.47% |
| 208 | 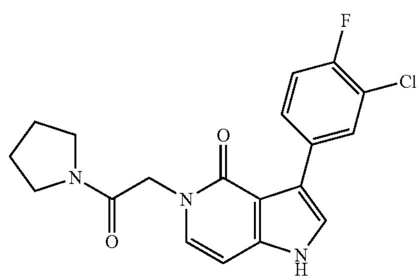 [SMILES: O=C(Cn1ccc2[nH]cc(-c3ccc(F)c(Cl)c3)c2c1=O)N1CCCC1] | 3-(3-chloro-4-fluorophenyl)-5-(2-oxo-2-(pyrrolidin-1-yl)ethyl)-1H-pyrrolo[3,2-c]pyridin-4(5H)-one | $^1$H-NMR (DMSO-$d_6$, 400 MHz) δ (ppm): 11.67 (s, 1H), 8.18 (d, J = 6.8 Hz, 1H), 7.80 (s, 1H), 7.44 (s, 1H), 7.30 (t, J = 9.2 Hz, 1H), 7.21 (d, J = 7.2 Hz, 1H), 6.41 (d, J = 7.6 Hz, 1H), 4.71 (s, 2H), 3.50 (t, J = 6.8 Hz, 2H), 3.28 (d, J = 11.6 Hz, 2H), 1.92 (t, J = 6.4 Hz, 2H), 1.77 (d, J = 6.4 Hz, 2H). Calculated (M + H): 374.10, found (M + H): 374.4, HPLC purity: 98.20% |
| 209 | 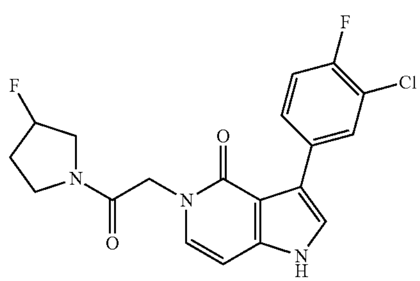 [SMILES: O=C(Cn1ccc2[nH]cc(-c3ccc(F)c(Cl)c3)c2c1=O)N1CCC(F)C1] | 3-(3-chloro-4-fluorophenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 11.69 (s, 1H), 8.17 (t, J = 7.6 Hz, 1H), 7.80 (s, 1H), 7.45 (s, 1H), 7.30 (t, J = 8.8 Hz, 1H), 7.22 (d, J = 6.8 Hz, 1H), 6.42 (d, J = 7.2 Hz, 1H), 5.49-5.24 (m, 1H), 4.85-4.70 (m, 2H), 3.86-3.79 (m, 1H), 3.77-3.66 (m, 2H), 3.62-3.50 (m, 1H), 2.30-2.22 (m, 1H), 2.11-2.08 (m, 1H). Calculated (M + H): 392.09, found (M + H): 392.0, HPLC purity: 98.05% |
| 210 | 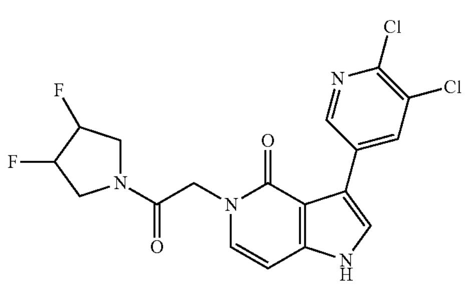 [SMILES: O=C(Cn1ccc2[nH]cc(-c3cnc(Cl)c(Cl)c3)c2c1=O)N1CC(F)C(F)C1] | 3-(5,6-dichloropyridin-3-yl)-5-(2-(3,4-difluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 11.93 (s, 1H), 8.82 (d, J = 7.2 Hz, 2H), 7.71 (s, 1H), 7.26 (d, J = 7.2 Hz, 1H), 6.47 (d, J = 7.2 Hz, 1H), 5.5-5.2 (m, 2H), 4.84-4.76 (m, 2H), 4.08-4.01 (m, 1H), 3.78-3.69 (m, 2H), 3.66-3.63 (m, 1H). Calculated (M + H): 428.23, Found (M + H): 427.2. HPLC purity: 99.66% |

Example 211: Preparation of 3-(4-chloro-3-fluorophenyl)-5-(2-oxo-2-(pyrrolidin-1-yl)ethyl)-1H-pyrrolo[3,2-c]pyridin-4(5H)-one

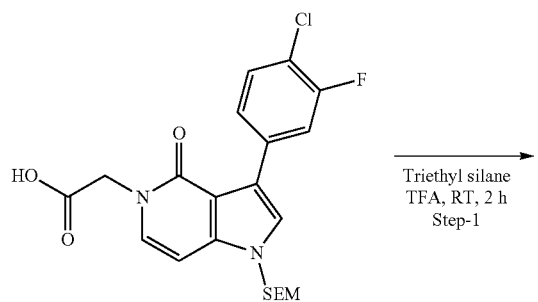

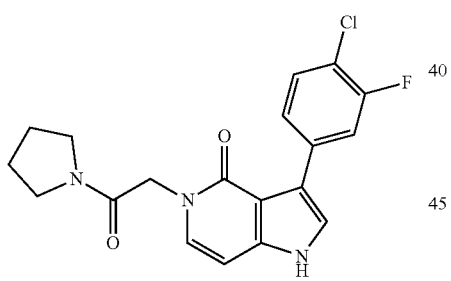

Step 1

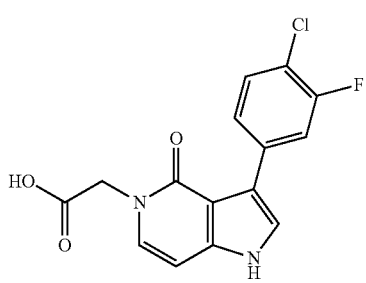 [SMILES: O=C(O)Cn1ccc2[nH]cc(-c3ccc(Cl)c(F)c3)c2c1=O]

Preparation of 2-(3-(4-chloro-3-fluorophenyl)-4-oxo-1H-pyrrolo[3,2-c]pyridin-5(4H)-yl)acetic acid To a stirred suspension of 2-(3-(4-chloro-3-fluorophenyl)-4-oxo-1-((2-(trimethylsilyl)ethoxy)methyl)-1H-pyrrolo[3,2-c]pyridin-5(4H)-yl)acetic acid (0.1 g, 0.22 mmol) in triethylsilane (0.12 mL, 0.44 mmol), was added trifluro acetic acid (0.85 mL, 11.10 mmol) at room temperature and stirred for 1 h. After completion of reaction, reaction mixture was evaporated under vacuum and the residue was diluted with 1 mL of acetonitrile and 3 mL of ammonium hydroxide. The resulting mixture was stirred for 2 h at room temperature, and acidified with 2N hydrochloric acid at 0° C. The precipitated product was filtered and dried to afford the title compound 2-(3-(4-chloro-3-fluorophenyl)-4-oxo-1H-pyrrolo[3,2-c]pyridin-5(4H)-yl)acetic acid (0.05 g, 70.4% yield) as off white solid. Calculated (M+H): 321.04, Found (M+H): 321.0.

Step 2

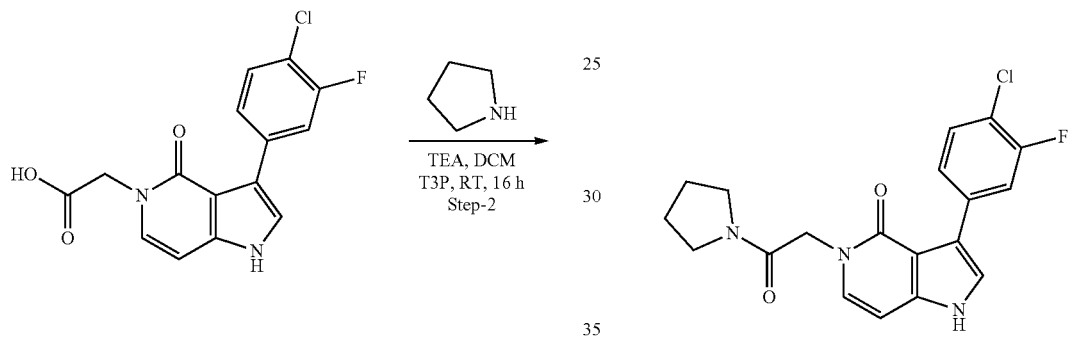

Preparation of 3-(4-chloro-3-fluorophenyl)-5-(2-oxo-2-(pyrrolidin-1-yl)ethyl)-1H-pyrrolo[3,2-c]pyridin-4(5H)-one To the stirred suspension of 22-(3-(4-chloro-3-fluorophenyl)-4-oxo-1H-pyrrolo[3,2-c]pyridin-5(4H)-yl)acetic acid (0.05 g, 0.15 mmol) and pyrrolidine (0.022 g, 0.31 mmol) in dichloromethane (10 mL), was added triethylamine (0.1 g, 0.94 mmol). The reaction mixture was cooled to 0° C., was added 1-propylphosphonic anhydride (50% solution in ethyl acetate) (0.074 g, 0.23 mmol), and stirred at room temperature for 4 h. The reaction mixture was diluted with dichloromethane (25 mL), washed with water, brine, dried over anhydrous sodium sulfate, filtered and concentrated under vacuum to afford crude product, which was purified by silica gel (60-120) column chromatography using 5% methanol in dichloromethane to afford title compound 3-(4-chloro-3-fluorophenyl)-5-(2-oxo-2-(pyrrolidin-1-yl)ethyl)-1H-pyrrolo[3,2-c]pyridin-4(5H)-one (0.02 g, 34.5% yield). $^1$H-NMR (DMSO-$d_6$, 400 MHz) δ (ppm): 11.73 (s, 1H), 8.13 (d, J=12.0 Hz, 1H), 7.73 (d, J=8.4 Hz, 1H), 7.53 (s, 1H), 7.48 (t, J=8.4 Hz, 1H), 7.22 (d, J=6.8 Hz, 1H), 6.42 (d, J=7.6 Hz, 1H), 4.71 (s, 2H), 3.52-3.49 (m, 2H), 3.30-3.27 (m, 2H), 1.94-1.89 (m, 2H), 1.80-1.75 (m, 2H). Calculated (M+H): 374.10, found (M+H): 374.1, HPLC purity: 98.55%.

TABLE 18

The following compounds were prepared by the method described above:

| Ex. No. | Structure | Name | Analytical data |
|---|---|---|---|
| 212 | 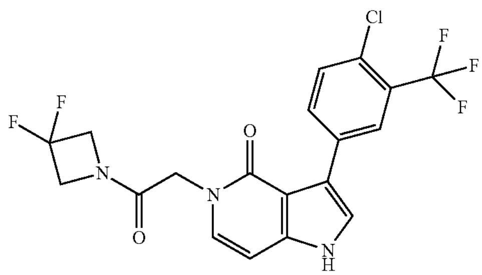 | 3-(4-chloro-3-(trifluoromethyl)phenyl)-5-(2-(3,3-difluoroazetidin-1-yl)-2-oxoethyl)-1H-pyrrolo[3,2-c]pyridin-4(5H)-one | $^1$H-NMR (DMSO-$d_6$, 400 MHz) δ (ppm): 11.84 (s, 1H), 8.53 (s, 1H), 8.08 (d, J = 8.4 Hz, 1H), 7.61 (d, J = 8.0 Hz, 2H), 7.27 (d, J = 6.8 Hz, 1H), 6.47 (d, J = 6.8 Hz, 1H), 4.73 (t, J = 11.6 Hz, 2H), 4.64 (s, 2H), 4.31 (t, J = 11.6 Hz, 2H). Calculated (M + H): 446.06, found (M + H): 446.0, HPLC purity: 98.52%. |
| 213 | 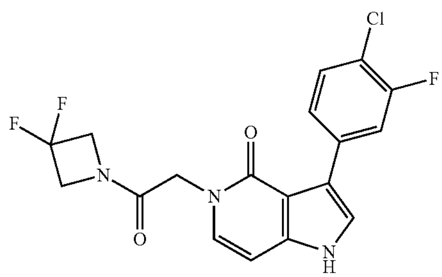 [SMILES: O=C(Cn1ccc2[nH]cc(-c3ccc(Cl)c(F)c3)c2c1=O)N1CC(F)(F)C1] | 3-(4-chloro-3-fluorophenyl)-5-(2-(3,3-difluoroazetidin-1-yl)-2-oxoethyl)-1H-pyrrolo[3,2-c]pyridin-4(5H)-one | $^1$H-NMR (DMSO-$d_6$, 400 MHz) δ (ppm): 11.78 (s, 1H), 8.11 (d, J = 11.2 Hz, 1H), 7.72 (d, J = 8.4 Hz, 1H), 7.55 (d, J = 1.6 Hz, 1H), 7.45 (t, J = 8.4 Hz, 1H), 7.25 (d, J = 6.8 Hz, 1H), 6.45 (d, J = 7.2 Hz, 1H), 4.41 (t, J = 11.6 Hz, 2H), 4.63 (s, 2H), 4.32 (t, J = 12.0 Hz, 2H), Calculated (M + H): 396.06, found (M + H): 396.0, HPLC purity: 98.29% |
| 214 | 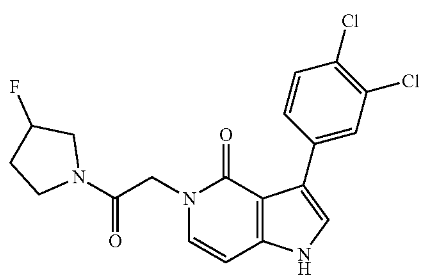 [SMILES: O=C(Cn1ccc2[nH]cc(-c3ccc(Cl)c(Cl)c3)c2c1=O)N1CCC(F)C1] | 3-(3,4-dichlorophenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 11.75 (s, 1H), 8.30 (s, 1H), 7.83 (d, J = 8.4 Hz, 1H), 7.53-7.49 (m, 2H), 7.24 (d, J = 7.2 Hz, 1H), 6.42 (d, J = 7.2 Hz, 1H), 5.49-5.24 (m, 1H), 4.85-4.70 (m, 2H), 3.89-3.81 (m, 1H), 3.77-3.66 (m, 2H), 3.62-3.50 (m, 1H), 2.30-2.22 (m, 1H), 2.11-2.08 (m, 1H); Calculated (M + H): 408.06, found (M + H): 408.0, HPLC purity: 99.68% |
| 215 | 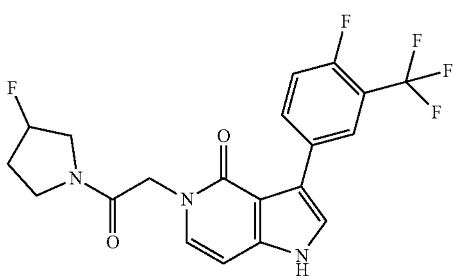 [SMILES: O=C(Cn1ccc2[nH]cc(-c3ccc(F)c(C(F)(F)F)c3)c2c1=O)N1CCC(F)C1] | 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 11.74 (s, 1H), 8.34 (d, J = 7.2 Hz, 1H), 8.12 (brs, 1H), 7.50 (s, 1H), 7.41 (t, J = 9.6 Hz, 1H), 7.23 (d, J = 7.2 Hz, 1H), 6.43 (d, J = 7.2 Hz, 1H), 5.49-5.24 (m, 1H), 4.84-4.68 (m, 2H), 3.89-3.36 (m, 4H), 2.30-1.92 (m, 2H). Calculated (M + H): 426.12, found (M + H): 426.2, HPLC purity: 98.13% |
| 216 | 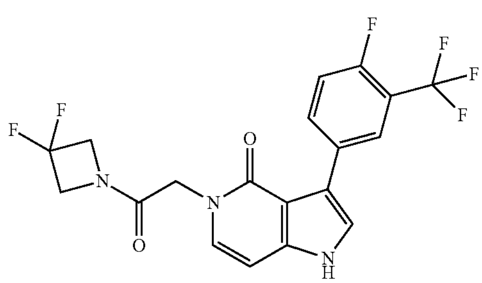 | 5-(2-(3,3-difluoroazetidin-1-yl)-2-oxoethyl)-3-(4-fluoro-3-(trifluoromethyl)phenyl)-1H-pyrrolo[3,2-c]pyridin-4(5H)-one | $^1$H-NMR (DMSO-$d_6$, 400 MHz) δ (ppm): 11.78 (s, 1H), 7.38 (d, J = 6.4 Hz, 1H), 8.11 (brs, 1H), 7.53 (s, 1H), 7.41 (t, J = 9.6 Hz, 1H), 7.25 (d, J = 7.2 Hz, 1H), 6.46 (d, J = 7.2 Hz, 1H), 4.72 (t, J = 12.0 Hz, 2H), 4.63 (s, 2H), 4.31 (t, J = 12.0 Hz, 2H). Calculated (M + H): 430.09, found (M + H): 430.2, HPLC purity: 99.46% |

TABLE 18-continued

The following compounds were prepared by the method described above:

| Ex. No. | Structure | Name | Analytical data |
|---|---|---|---|
| 217 | 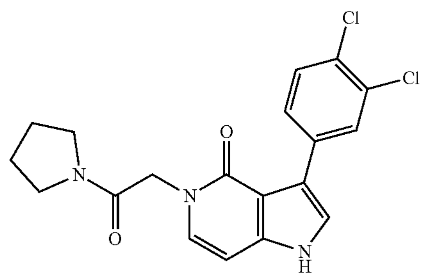 [SMILES: O=C(Cn1ccc2[nH]cc(-c3ccc(Cl)c(Cl)c3)c2c1=O)N1CCCC1] | 3-(3,4-dichlorophenyl)-5-(2-oxo-2-(pyrrolidin-1-yl)ethyl)-1H-pyrrolo[3,2-c]pyridin-4(5H)-one | $^1$H-NMR (DMSO-$d_6$, 400 MHz) δ (ppm): 11.74 (s, 1H), 8.30 (s, 1H), 7.83 (d, J = 6.8 Hz, 1H), 7.52-7.49 (m, 2H), 7.22 (d, J = 7.6 Hz, 1H), 6.41 (d, J = 7.2 Hz, 1H), 4.71 (s, 2H), 3.50 (t, J = 6.4 Hz, 2H), 3.26 (s, 2H), 1.92 (t, J = 6.4 Hz, 2H), 1.77 (t, J = 6.4 Hz, 2H). Calculated (M + H): 390.07, found (M + H): 390.1, HPLC purity: 99.30% |
| 218 | 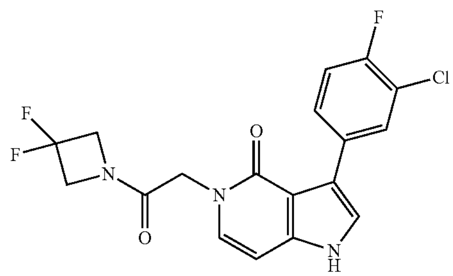 [SMILES: O=C(Cn1ccc2[nH]cc(-c3ccc(F)c(Cl)c3)c2c1=O)N1CC(F)(F)C1] | 3-(3-chloro-4-fluorophenyl)-5-(2-(3,3-difluoroazetidin-1-yl)-2-oxoethyl)-1H-pyrrolo[3,2-c]pyridin-4(5H)-one | $^1$H-NMR (DMSO-$d_6$, 400 MHz) δ (ppm): 11.73 (s, 1H), 8.18 (dd, J = 2.0 Hz, J = 5.6 Hz, 1H), 7.80-7.78 (m, 1H), 7.47 (s, 1H), 7.31 (t, J = 9.2 Hz, 1H), 7.24 (d, J = 7.6 Hz, 1H), 6.45 (d, J = 6.8 Hz, 1H), 4.71 (s, 2H), 4.64 (s, 2H), 4.32 (s, 2H); Calculated (M + H): 396.06, found (M + H): 396.1, HPLC purity: 98.01% |
| 219 | 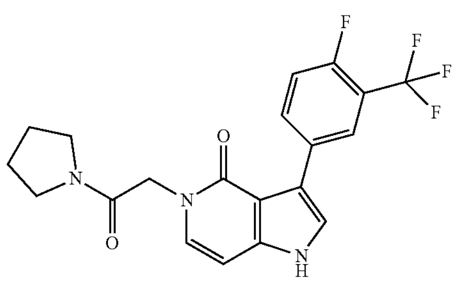 [SMILES: O=C(Cn1ccc2[nH]cc(-c3ccc(F)c(C(F)(F)F)c3)c2c1=O)N1CCCC1] | 3-(4-fluoro-3-(trifluoromethyl)phenyl)-5-(2-oxo-2-(pyrrolidin-1-yl)ethyl)-1H-pyrrolo[3,2-c]pyridin-4(5H)-one | $^1$H-NMR (DMSO-$d_6$, 400 MHz) δ (ppm): 11.72 (s, 1H), 8.34 (d, J = 6.0 Hz, 1H), 8.12 (t, J = 5.6 Hz, 1H), 7.50 (s, 1H), 7.41 (t, J = 6.0 Hz, 1H), 7.21 (d, J = 7.2 Hz, 1H), 6.42 (d, J = 7.6 Hz, 1H), 4.71 (s, 2H), 3.52-3.48 (m, 2H), 3.29-3.27 (m, 2H), 1.94-1.88 (m, 2H), 1.80-1.73 (m, 2H). Calculated (M + H): 408.13, found (M + H): 408.1, HPLC purity: 99.35% |
| 220 | 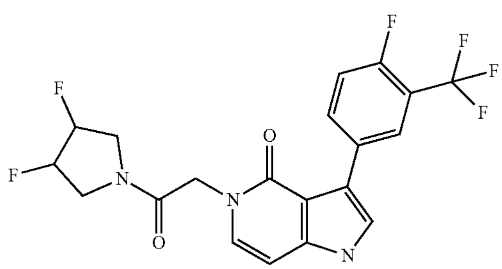 [SMILES: O=C(Cn1ccc2[nH]cc(-c3ccc(F)c(C(F)(F)F)c3)c2c1=O)N1CC(F)C(F)C1] | 5-(2-(3,4-difluoropyrrolidin-1-yl)-2-oxoethyl)-3-(4-fluoro-3-(trifluoromethyl)phenyl)-1H-pyrrolo[3,2-c]pyridin-4(5H)-one | $^1$H-NMR (DMSO-$d_6$, 400 MHz) δ (ppm): 11.7 (s, 1H), 8.34 (d, J = 6.4 Hz, 1H), 8.13 (brs, 1H), 7.51 (s, 1H), 7.41 (t, J = 9.2 Hz, 1H), 7.22 (d, J = 7.2 Hz, 1H), 6.44 (d, J = 7.6 Hz, 1H), 5.46-5.23 (m, 2H), 4.82-4.71 (m, 2H), 4.08-3.27 (m, 4H). Calculated (M + H): 444.11, Found (M + H): 444.2, HPLC purity: 99.28% |
| 221 | 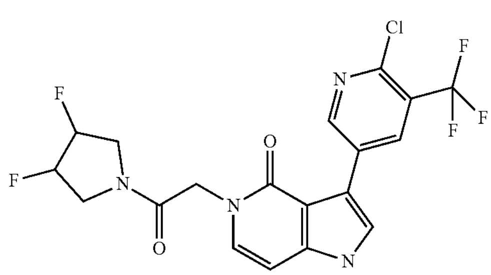 [SMILES: O=C(Cn1ccc2[nH]cc(-c3cnc(Cl)c(C(F)(F)F)c3)c2c1=O)N1CC(F)C(F)C1] | 3-(6-chloro-5-(trifluoromethyl)pyridin-3-yl)-5-(2-(3,4-difluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 11.97 (s, 1H), 9.08 (s, 1H), 9.02 (s, 1H), 7.78 (s, 1H), 7.27 (d, J = 6.8 Hz, 1H), 6.49 (d, J = 6.8 Hz, 1H), 5.47-5.23 (m, 2H), 4.85-4.73 (m, 2H), 4.08-4.00 (m, 1H), 3.82-3.63 (m, 2H), 3.62-3.27 (m, 1H); Calculated (M + H): 461.07, Found (M + H): 461.0, HPLC purity: 99.2% |

TABLE 18-continued

The following compounds were prepared by the method described above:

| Ex. No. | Structure | Name | Analytical data |
|---|---|---|---|
| 222 | 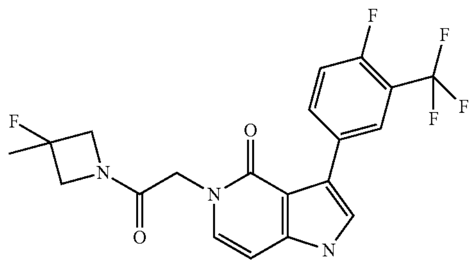 [SMILES: CC1(F)CN(C(=O)Cn2ccc3[nH]cc(-c4ccc(F)c(C(F)(F)F)c4)c3c2=O)C1] | 3-(4-fluoro-3-(trifluoromethyl)phenyl)-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 11.76 (s, 1H), 8.38 (d, J = 5.6 Hz, 1H), 8.12-8.1 (m, 1H), 7.52 (d, J = 2.4 Hz, 1H), 7.42 (t, J = 9.2 Hz, 1H), 7.25 (d, J = 7.2 Hz, 1H), 6.45 (d, J = 7.2 Hz, 1H), 4.57 (s, 2H), 4.44-4.28 (m, 2H), 3.98-3.93 (m, 2H), 1.58 (d, J = 22 Hz, 3H). Calculated (M + H): 426.12, Found (M + H): 426.3, HPLC purity: 96.35% |
| 223 | 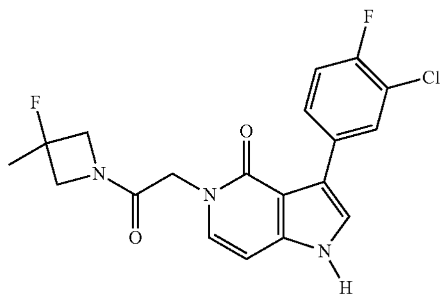 [SMILES: CC1(F)CN(C(=O)Cn2ccc3[nH]cc(-c4ccc(F)c(Cl)c4)c3c2=O)C1] | 3-(3-chloro-4-fluorophenyl)-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 11.72 (brs, 1H), 8.19 (d, J = 5.6 Hz, 1H), 7.81-7.79 (m, 1H), 7.64 (s, 1H), 7.31 (t, J = 9.2 Hz, 1H), 7.23 (d, J = 6.8 Hz, 1H), 6.44 (d, J = 7.6 Hz, 1H), 4.58 (s, 2H), 4.39-4.27 (m, 2H), 3.98-3.94 (m, 2H), 1.59 (d, J = 22.4 Hz, 3H). Calculated (M − H): 392.09, found (M − H): 392.3, HPLC purity: 99.97% |

Example 224: Preparation of 3-(4-chloro-3-(trifluoromethyl)phenyl)-5-(2-(3-fluoropyrrolidin-1-yl)-2-oxoethyl)-1-(pyridin-2-yl)-1H-pyrrolo[3,2-c]pyridin-4(5H)-one

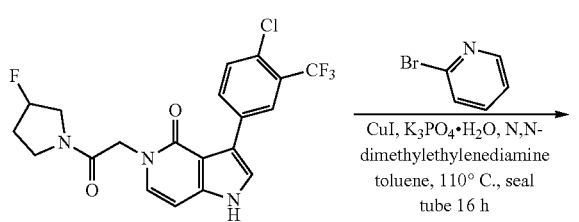

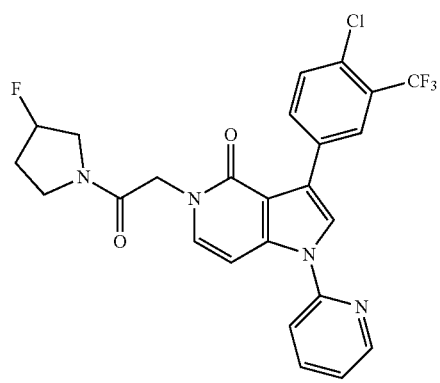

In a seal tube, a stirred suspension of 3-(4-chloro-3-(trifluoromethyl)phenyl)-5-(2-(3-fluoropyrrolidin-1-yl)-2-oxoethyl)-1H-pyrrolo[3,2-c]pyridin-4(5H)-one (0.075 g, 0.17 mmol) in toluene (2 mL), was added 2-bromopyridine (0.032 mL, 0.34 mmol), N,N-dimethylethylenediamine (0.037 mL, 0.34 mmol) and potassium phosphate tribasic monohydrate (0.117 g, 0.51 mmol) at room temperature and resulting mixture was purged with argon for 15 min. Then copper(I)iodide was added at room temperature and stirred at 110° C. for 16 h. The reaction mixture was cooled to room temperature, diluted with dichloromethane (10 mL), filtered and washed with ethyl acetate (20 mL), the filtrate was concentrated under vacuum to afford the crude product, which was purified by silica gel (60-120) column chromatography using 2% methanol in dichloromethane to afford title compound 3-(4-chloro-3-(trifluoromethyl)phenyl)-5-(2-(3-fluoropyrrolidin-1-yl)-2-oxoethyl)-1-(pyridin-2-yl)-1H-pyrrolo[3,2-c]pyridin-4(5H)-one (0.05 g, 56.8% yield) as off-white solid. $^1$H-NMR (DMSO-$d_6$, 400 MHz) δ (ppm): 8.61 (d, J=3.2 Hz, 1H), 8.43 (d, J=2.0 Hz, 1H), 8.15 (d, J=7.6 Hz, 2H), 8.09-8.04 (m, 1H), 7.86 (d, J=8.4 Hz, 1H), 7.69 (d, J=8.4 Hz, 1H), 7.46-7.40 (m, 2H), 7.26 (d, J=7.2 Hz, 1H), 5.50-5.25 (m, 1H), 4.92-4.74 (m, 2H), 3.91-3.32 (m, 4H), 2.30-1.93 (m, 2H). Calculated (M+H): 519.11, found (M+H): 519.1, HPLC purity: 99.62%

TABLE 19

The following compounds were prepared by the method described above:

| Ex. No. | Structure | Name | Analytical data |
|---|---|---|---|
| 225 | 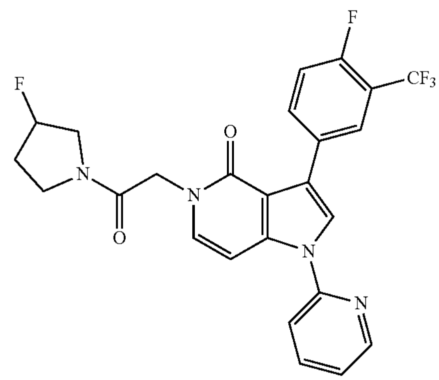 [SMILES: O=C(Cn1ccc2c(c(-c3ccc(F)c(C(F)(F)F)c3)cn2-c2ccccn2)c1=O)N1CCC(F)C1] | 3-(4-fluoro-3-(trifluoromethyl)phenyl)-5-(2-(3-fluoropyrrolidin-1-yl)-2-oxoethyl)-1-(pyridin-2-yl)-1H-pyrrolo[3,2-c]pyridin-4(5H)-one | $^1$H-NMR (DMSO-$d_6$, 400 MHz) δ (ppm): 8.60 (d, J = 4.0 Hz, 1H), 8.30 (d, J = 6.4 Hz, 1H), 8.18 (brs, 1H), 8.10 (s, 1H), 8.06 (t, J = 8.0 Hz, 1H), 7.85 (d, J = 8.4 Hz, 1H), 7.51-7.39 (m, 3H), 7.26 (d, J = 7.6 Hz, 1H), 5.50-5.24 (m, 1H), 4.91-4.74 (m, 2H), 3.90-3.82 (m, 1H), 3.80-3.66 (m, 2H), 3.66-3.57 (m, 1H), 2.30-2.22 (m, 1H), 2.09-2.07 (m, 1H). Calculated (M + H): 503.14, Found (M + H): 503.1, HPLC purity: 99.32% |
| 226 | 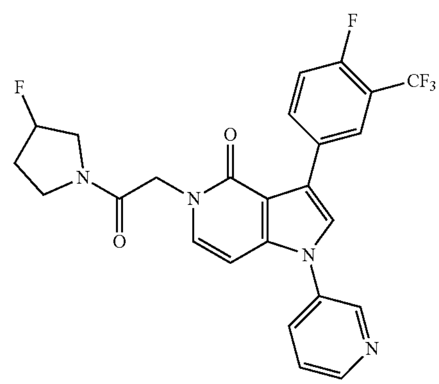 [SMILES: O=C(Cn1ccc2c(c(-c3ccc(F)c(C(F)(F)F)c3)cn2-c2cccnc2)c1=O)N1CCC(F)C1] | 3-(4-fluoro-3-(trifluoromethyl)phenyl)-5-(2-(3-fluoropyrrolidin-1-yl)-2-oxoethyl)-1-(pyridin-3-yl)-1H-pyrrolo[3,2-c]pyridin-4(5H)-one | $^1$H-NMR (DMSO-$d_6$, 400 MHz) δ (ppm): 8.88 (s, 1H), 8.69 (s, 1H), 8.33 (d, J = 6.4 Hz, 1H), 8.19 (s, 1H), 8.09 (d, J = 7.6 Hz, 1H), 7.91 (s, 1H), 7.65 (t, J = 4.4 Hz, 1H), 7.48 (t, J = 10 Hz, 1H), 7.39 (d, J = 7.2 Hz, 1H), 6.52 (d, J = 7.6 Hz, 1H), 5.50-5.24 (m, 1H), 4.92-4.76 (m, 2H), 3.87-3.80 (m, 1H), 3.63-3.50 (m, 2H), 3.40-3.26 (m, 1H), 2.25-2.22 (m, 1H), 2.12-2.09 (m, 1H); Calculated (M + H): 503.14, Found (M + H): 503.1, HPLC purity: 99.74% |
| 227 | 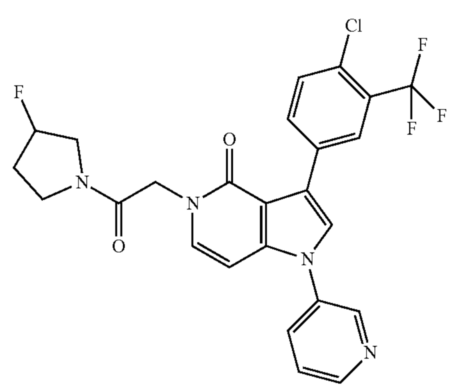 [SMILES: O=C(Cn1ccc2c(c(-c3ccc(Cl)c(C(F)(F)F)c3)cn2-c2cccnc2)c1=O)N1CCC(F)C1] | 3-(4-chloro-3-(trifluoromethyl)phenyl)-5-(2-(3-fluoropyrrolidin-1-yl)-2-oxoethyl)-1-(pyridin-3-yl)-1H-pyrrolo[3,2-c]pyridin-4(5H)-one | $^1$H NMR (400 MHz, DMSO-$d_6$) δ (ppm): 8.88 (d, J = 1.6 Hz, 1H), 8.69 (d, J = 4.4 Hz, 1H), 8.45 (s, 1H), 8.17 (d, J = 8.4 Hz, 1H), 8.10 (d, J = 7.6 Hz, 1H), 7.98 (s, 1H), 7.70-7.64 (m, 2H), 7.40 (d, J = 7.2 Hz, 1H), 6.52 (d, J = 7.2 Hz, 1H), 5.50-2.25 (m, 1H), 4.93-4.75 (m, 2H), 3.91-3.38 (m, 4H), 2.26-1.94 (m, 2H). Calculated (M + H): 519.11; Found (M + H): 519.1. HPLC Purity: 97.6% |

TABLE 19-continued

The following compounds were prepared by the method described above:

| Ex. No. | Structure | Name | Analytical data |
|---|---|---|---|
| 228 | 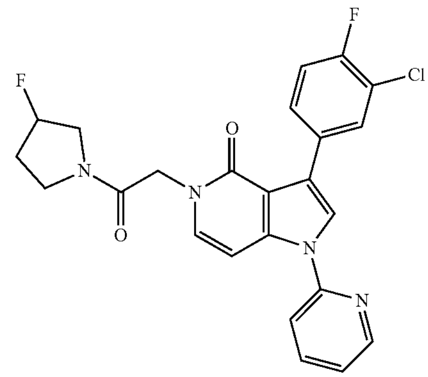 [SMILES: O=C(Cn1ccc2c(c(-c3ccc(F)c(Cl)c3)cn2-c2ccccn2)c1=O)N1CCC(F)C1] | 3-(3-chloro-4-fluorophenyl)-5-(2-(3-fluoropyrrolidin-1-yl)-2-oxoethyl)-1-(pyridin-2-yl)-1H-pyrrolo[3,2-c]pyridin-4(5H)-one | $^1$H NMR (400 MHz, DMSO-$d_6$) δ (ppm): 8.62 (brs, 1H), 7.89 (t, J = 7.6 Hz, 1H), 7.79 (d, J = 7.2 Hz, 1H), 7.68 (brs, 1H), 7.45 (brs, 2H), 7.31-7.13 (m, 4H), 5.41-5.27 (m, 1H), 5.18-5.03 (m, 1H), 4.55-4.41 (m, 1H), 3.96- 3.84 (m, 2H), 3.74-3.53 (m, 2H), 2.38-1.94 (m, 2H). Calculated (M + H): 469.12; Found (M + H): 469.1. HPLC Purity: 99.82% |
| 229 | 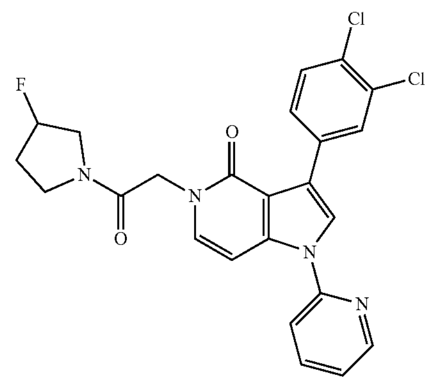 | 3-(3,4-dichlorophenyl)-5-(2-(3-fluoropyrrolidin-1-yl)-2-oxoethyl)-1-(pyridin-2-yl)-1H-pyrrolo[3,2-c]pyridin-4(5H)-one | $^1$H-NMR (DMSO-$d_6$, 400 MHz) δ (ppm): 8.60 (d, J = 4.4 Hz, 1H), 8.25 (d, J = 2.0 Hz, 1H), 8.11 (s, 1H), 8.06 (t, J = 7.2 Hz, 1H), 7.90-7.84 (m, 2H), 7.59 (d, J = 8.4 Hz, 1H), 7.45-7.40 (m, 2H), 7.25 (d, J = 7.2 Hz, 1H), 5.50-5.25 (m, 1H), 4.92-4.74 (m, 2H), 3.91-3.3 (m, 4H), 2.26-2.08 (m, 2H); Calculated (M + H): 485.09, Found (M + H): 485.1, HPLC purity: 99.7% |

Example 230: Preparation of 3-(4-fluoro-3-(trifluoromethyl)phenyl)-5-(2-(3-fluoropyrrolidin-1-yl)-2-oxoethyl)-1-phenyl-1H-pyrrolo[3,2-c]pyridin-4(5H)-one

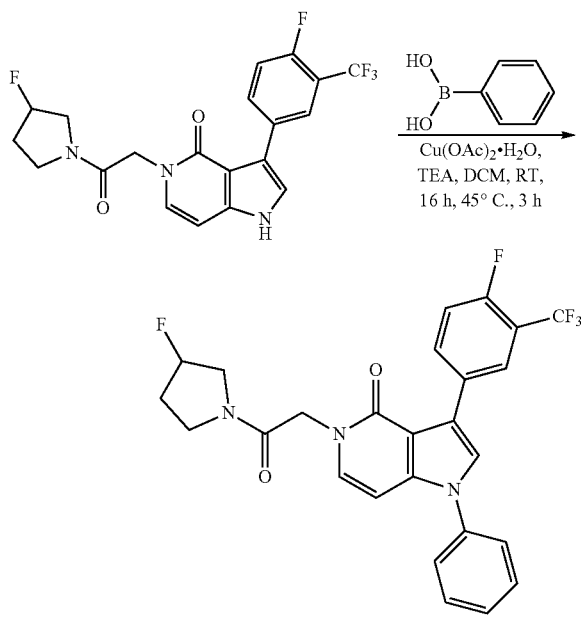

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.12 g, 0.28 mmol) in dichloromethane (5 mL), triethylamine (0.08 mL, 0.56 mmol) and copper (II)acetate mono hydrate (0.084 g, 0.42 mmol) were added and the reaction mixture was purged with air for 10 min. Then phenyl boronic acid (0.051 g, 0.42 mmol) was added and the reaction mixture was stirred at room temperature for 16 h and then at 45° C. for 3 h in the presence of air. The reaction mixture was diluted with dichloromethane, washed with water, dried over anhydrous sodium sulfate, filtered and concentrated under vacuum to afford the crude product, which was purified by silica gel column chromatography using 5% methanol in dichloromethane. Again it was purified by preparative HPLC(Column: Chemsil C18 (250 mm×4.6 mm×5µ), mobile phase (A): 0.01% ammonia in water, mobile phase (B): acetonitrile, flow rate: 1.0 mL/min, T/% B: 0/20, 12/80, 25/80, 27/20, 30/20 at 220 nm) to afford 3-(4-fluoro-3-(trifluoromethyl)phenyl)-5-(2-(3-fluoropyrrolidin-1-yl)-2-oxoethyl)-1-phenyl-1H-pyrrolo[3,2-c]pyridin-4(5H)-one (0.035 g, 25% yield) as white solid. $^1$H-NMR (DMSO-$d_6$, 400 MHz) δ (ppm): 8.34 (d, J=5.6 Hz, 1H), 8.19 (s, 1H), 7.83 (s, 1H), 7.61-7.58 (m, 4H), 7.49-7.44 (m, 2H), 7.35 (d, J=5.6 Hz, 1H), 6.48 (d, J=7.6 Hz, 1H), 5.50-5.24 (m, 1H), 4.91-4.74 (m, 2H), 3.90-3.80 (m, 3H), 3.72-3.32 (m, 1H), 2.47-2.12 (m, 1H), 2.09-2.04 (m, 1H). Calculated (M+H): 502.15, Found (M+H): 502.1, HPLC purity 99.9%.

TABLE 20

The following compounds were prepared by the method described above:

| Ex. No. | Structure | Name | Analytical data |
| --- | --- | --- | --- |
| 231 | 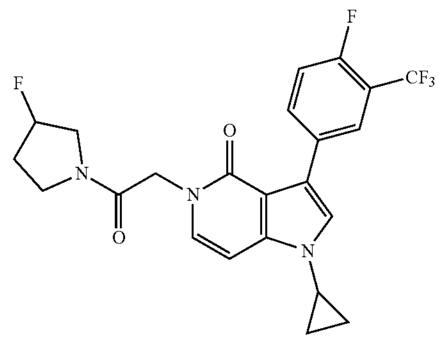 [SMILES: O=C(Cn1ccc2c(c(-c3ccc(F)c(C(F)(F)F)c3)cn2C2CC2)c1=O)N1CCC(F)C1] | 1-cyclopropyl-3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.30 (d, J = 6.4 Hz, 1H), 8.13 (s, 1H), 7.52 (s, 1H), 7.41 (t, J = 9.6 Hz, 1H), 7.34 (d, J = 6.8 Hz, 1H), 6.65 (d, J = 7.6 Hz, 1H), 5.49-5.24 (m, 1H), 4.87-4.72 (m, 2H), 3.86-3.40 (m, 5H), 2.30-1.96 (m, 2H), 1.04-1.01 (m, 4H). Calculated (M + H): 466.15, Found (M + H): 466.1. HPLC purity: 99.57% |
| 232 | 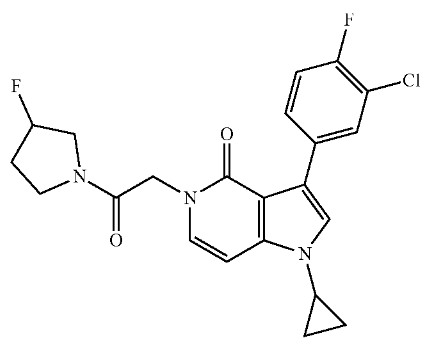 [SMILES: O=C(Cn1ccc2c(c(-c3ccc(F)c(Cl)c3)cn2C2CC2)c1=O)N1CCC(F)C1] | 3-(3-chloro-4-fluorophenyl)-1-cyclopropyl-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.15 (d, J = 7.6 Hz, 1H), 7.81 (s, 1H), 7.46 (s, 1H), 7.35-7.28 (m, 2H), 6.63 (d, J = 6.8 Hz, 1H), 5.49-5.25 (m, 1H), 4.87-4.72 (m, 2H), 3.89-3.28 (m, 5H), 2.3-2.08 (m, 2H), 1.01 (d, J = 12.4 Hz, 4H). Calculated (M + H): 432.12, Found (M + H): 432.1, HPLC purity: 98.69% |
| 233 | 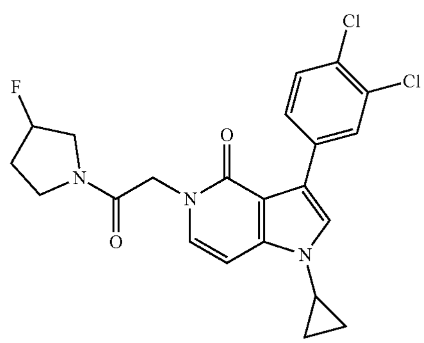 [SMILES: O=C(Cn1ccc2c(c(-c3ccc(Cl)c(Cl)c3)cn2C2CC2)c1=O)N1CCC(F)C1] | 1-cyclopropyl-3-(3,4-dichlorophenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.26 (d, J = 1.6 Hz, 1H), 7.85 (d, J = 8.8 Hz, 1H), 7.54 (s, 1H), 7.51 (d, J = 8.4 Hz, 1H), 7.35 (d, J = 7.6 Hz, 1H), 6.65 (d, J = 7.2 Hz, 1H), 5.50-5.24 (m, 1H), 4.87-4.70 (m, 2H), 3.9-3.55 (m, 5H), 2.30-1.96 (m, 2H), 1.08-0.98 (m, 4H); Calculated (M + H): 448.09, Found (M + H): 448.4, HPLC purity: 99.9% |
| 234 | 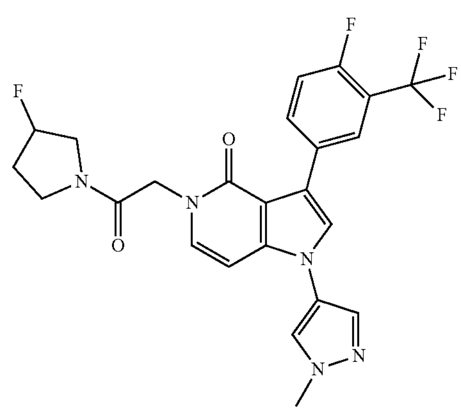 [SMILES: Cn1cc(-n2cc(-c3ccc(F)c(C(F)(F)F)c3)c3c(=O)n(CC(=O)N4CCC(F)C4)ccc32)cn1] | 3-(4-fluoro-3-(trifluoromethyl)phenyl)-5-(2-(3-fluoropyrrolidin-1-yl)-2-oxoethyl)-1-(1-methyl-1H-1,2,4-triazol-3-yl)-1H-pyrrolo[3,2-c]pyridin-4(5H)-one | $^1$H-NMR (DMSO-$d_6$, 400 MHz) δ (ppm): 8.31 (d, J = 6.4 Hz, 1H), 8.25 (s, 1H), 8.16 (brs, 1H), 7.84 (s, 1H), 7.72 (s, 1H), 7.46 (t, J = 9.6 Hz, 1H), 7.37 (d, J = 6.8 Hz, 1H), 6.52 (d, J = 7.2 Hz, 1H), 5.5-5.25 (m, 1H), 4.91-4.75 (m, 2H), 3.91 (s, 3H), 3.88-3.27 (m, 4H), 2.31-2.08 (m, 2H). Calculated (M + H): 506.15, Found (M + H): 506.1, HPLC purity: 99.57% |

TABLE 20-continued

The following compounds were prepared by the method described above:

| Ex. No. | Structure | Name | Analytical data |
|---|---|---|---|
| 235 | 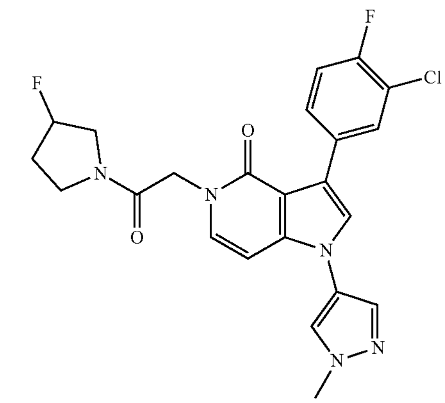 [SMILES: Cn1cc(-n2cc(-c3ccc(F)c(Cl)c3)c3c(=O)n(CC(=O)N4CCC(F)C4)ccc32)cn1] | 3-(3-chloro-4-fluorophenyl)-5-(2-(3-fluoropyrrolidin-1-yl)-2-oxoethyl)-1-(1-methyl-1H-pyrazol-4-yl)-1H-pyrrolo[3,2-c]pyridin-4(5H)-one | $^1$H-NMR (DMSO-d$_6$, 400 MHz) δ (ppm): 8.25 (s, 1H), 8.17 (d, J = 7.2 Hz, 1H), 7.84 (brs, 2H), 7.67 (s, 1H), 7.38-7.29 (m, 2H), 6.51 (d, J = 6.8 Hz, 1H), 5.51-5.25 (m, 1H), 4.9-4.75 (m, 2H), 3.91 (s, 3H), 3.87-3.31 (m, 4H), 2.31-2.1 (m, 2H). Calculated (M + H): 472.13, Found (M + H): 472.1, HPLC purity: 97.09% |
| 236 | 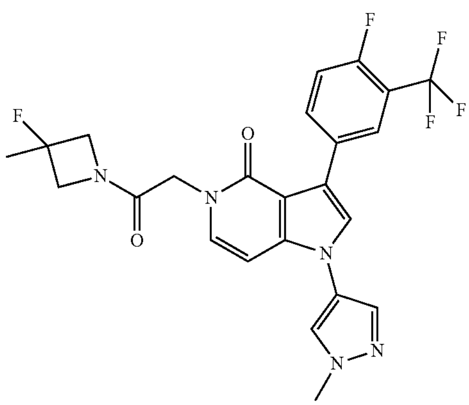 [SMILES: Cn1cc(-n2cc(-c3ccc(F)c(C(F)(F)F)c3)c3c(=O)n(CC(=O)N4CC(C)(F)C4)ccc32)cn1] | 3-(4-fluoro-3-(trifluoromethyl)phenyl)-5-(2-(3-fluoro-3-methylazetidin-1-yl)-2-oxoethyl)-1-(1-methyl-1H-pyrazol-4-yl)-1H-pyrrolo[3,2-c]pyridin-4(5H)-one | $^1$H-NMR (DMSO-d$_6$, 400 MHz) δ (ppm): 8.35 (d, J = 6 Hz, 1H), 8.25 (s, 1H), 8.15 (s, 1H), 7.84 (s, 1H), 7.73 (s, 1H), 7.6 (d, J = 7.6 Hz, 1H), 6.53 (d, J = 7.6 Hz, 1H), 4.62 (s, 2H), 4.41-4.29 (m, 2H), 3.99-3.91 (m, 5H) 1.59 (d, J = 22 Hz, 3H). Calculated (M + H): 406.45, Found (M + H): 406.1, HPLC purity: 96.11% |
| 237 | 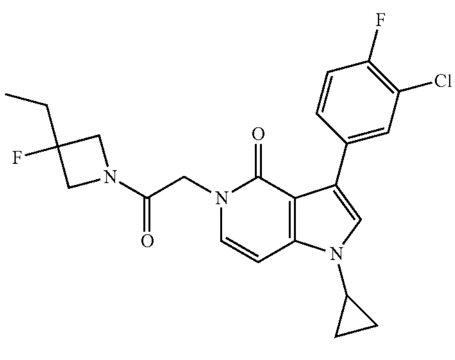 [SMILES: CCC1(F)CN(C(=O)Cn2ccc3c(c(-c4ccc(F)c(Cl)c4)cn3C3CC3)c2=O)C1] | 3-(3-chloro-4-fluorophenyl)-1-cyclopropyl-5-(2-(3-ethyl-3-fluoroazetidin-1-yl)-2-oxoethyl)-1H-pyrrolo[3,2-c]pyridin-4(5H)-one | $^1$H-NMR (DMSO-d$_6$, 400 MHz) δ (ppm): 8.16 (d, J = 7.2 Hz 1H), 7.83-7.79 (m, 1H), 7.47 (s, 1H), 7.36-7.29 (m, 2H), 6.65 (d, J = 7.2 Hz, 1H), 4.6 (s, 2H), 4.37-4.29 (m, 2H), 3.99-3.9 (m, 2H), 3.48-3.47 (m, 1H), 1.92-1.84 (m, 2H), 1.08-1.01 (m, 4H), 0.92 (t, J = 7.2 Hz, 3H). Calculated (M + H): 446.14, Found (M + H): 446.0, HPLC purity: 97.32% |

Example 238: Preparation of 3-(4-fluoro-3-(trifluoromethyl)phenyl)-5-(2-(3-fluoropyrrolidin-1-yl)-2-oxoethyl)-1-(methoxymethyl)-1H-pyrrolo[3,2-c]pyridin-4(5H)-one

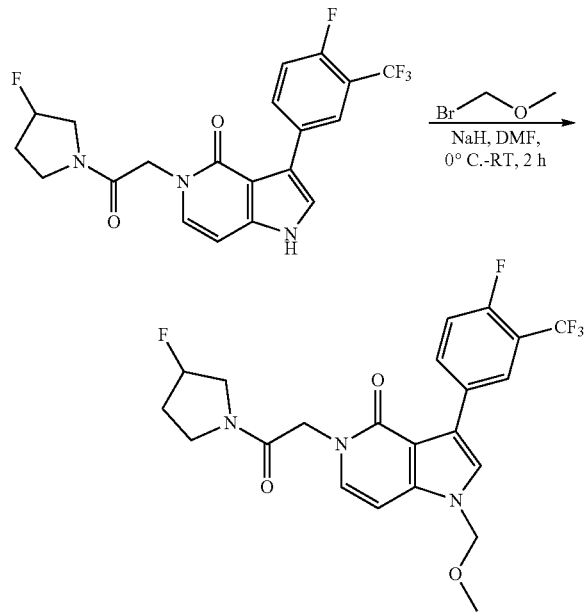

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.1 g, 0.24 mmol) in N,N-dimethylformamide (2 mL), was added sodium hydride (60% dispersion in oil)(0.019 g, 0.47 mmol), at 0° C. and stirred at room temperature for 20 min, The reaction mixture was cooled to 0° C. and was added bromo(methoxy)methane (0.058 g, 0.47 mmol) at 0° C. The reaction mixture was allowed to warm to room temperature and stirred for 2 h. The reaction mixture was quenched with cold water (20 mL), the precipitated product was filtered, washed thoroughly with water, dried to afford crude product which was purified by preparative HPLC (column: chemsil C18 (250 mm×4.6 mm×5μ), mobile phase (A): 0.01% ammonia in water, mobile phase (B): acetonitrile, flow rate: 1.0 mL/min, T/% B: 0/20, 10/80, 25/80, 27/20, 30/20 at 254 nm) to afford 3-(4-fluoro-3-(trifluoromethyl)phenyl)-5-(2-(3-fluoropyrrolidin-1-yl)-2-oxoethyl)-1-(methoxymethyl)-1H-pyrrolo[3,2-c]pyridin-4(5H)-one (0.07 g, 25% yield) as white solid. $^1$H-NMR (DMSO-$d_6$, 400 MHz) δ (ppm): 8.28 (d, J=7.2 Hz, 1H), 8.12 (s, 1H), 7.68 (s, 1H), 7.44 (t, J=10.0 Hz, 1H), 7.35 (d, J=7.2 Hz, 1H), 6.67 (d, J=7.6 Hz, 1H), 5.45-5.23 (m, 3H), 4.88-4.72 (m, 2H), 3.81-3.79 (m, 1H), 3.62-3.42 (m, 3H), 3.23 (s, 3H), 2.37-2.12 (m, 1H), 2.09-2.04 (m, 1H). Calculated (M+H): 470.14, Found (M+H): 470.1, HPLC purity: 99.05%

TABLE 21

The following compounds were prepared by the method described above:

| Ex. No. | Structure | Name | Analytical data |
|---|---|---|---|
| 239 | 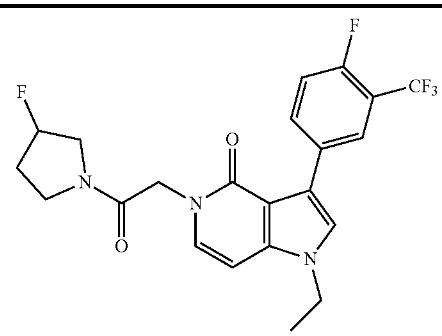 | 1-ethyl-3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.29 (d, J = 5.6 Hz, 1H), 8.12 (brs, 1H), 7.59 (s, 1H), 7.44-7.39 (m, 1H), 7.30 (d, J = 7.2 Hz, 1H), 6.62 (d, J = 7.2 Hz, 1H), 5.49-5.24 (m, 1H), 4.86-4.69 (m, 2H), 4.15-4.10 (m, 2H), 3.86-3.37 (m, 4H), 2.30-1.96 (m, 2H), 1.36 (t, J = 7.6 Hz, 3H). Calculated (M + H): 454.15, Found (M + H): 454.2, HPLC purity: 99.70%. |
| 240 | 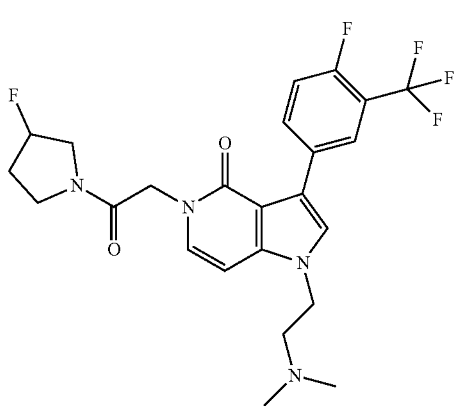 [SMILES: CN(C)CCn1cc(-c2ccc(F)c(C(F)(F)F)c2)c2c(=O)n(CC(=O)N3CCC(F)C3)ccc21] | 1-(2-(dimethylamino)ethyl)-3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.27 (d, J = 6.8 Hz, 1H), 8.11 (brs, 1H), 7.58 (s, 1H), 7.43 (t, J = 9.6 Hz, 1H), 7.29 (d, J = 7.2 Hz, 1H), 6.63 (d, J = 7.2 Hz, 1H), 5.5-5.25 (m, 1H), 4.8-4.73 (m, 2H), 4.16-4.15 (m, 2H), 3.9-3.5 (m, 4H), 2.61 (t, J = 6.4 Hz, 2H), 2.23-2 (s, 8H). Calculated (M + H): 497.19, Found (M + H): 497.0, HPLC purity: 98.73% |

TABLE 21-continued

The following compounds were prepared by the method described above:

| Ex. No. | Structure | Name | Analytical data |
|---|---|---|---|
| 241 | 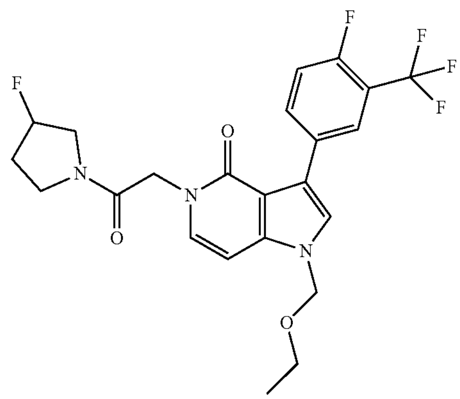 [SMILES: CCOCn1cc(-c2ccc(F)c(C(F)(F)F)c2)c2c(=O)n(CC(=O)N3CCC(F)C3)ccc21] | 1-(ethoxymethyl)-3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.28 (d, J = 6.4 Hz, 1H), 8.13 (brs, 1H), 7.68 (s, 1H), 7.44 (t, J = 9.2 Hz, 1H), 7.35 (d, J = 7.2 Hz, 1H), 6.67 (d, J = 7.6 Hz, 1H), 5.48-5.25 (m, 3H), 4.88-4.69 (m, 2H), 3.9-3.27 (m, 6H), 2.31-2.07 (m, 2H), 1.07 (t, J = 7.2 Hz, 3H). Calculated (M + H): 484.16, Found (M + H): 484.0. HPLC purity: 99.68% |
| 242 | 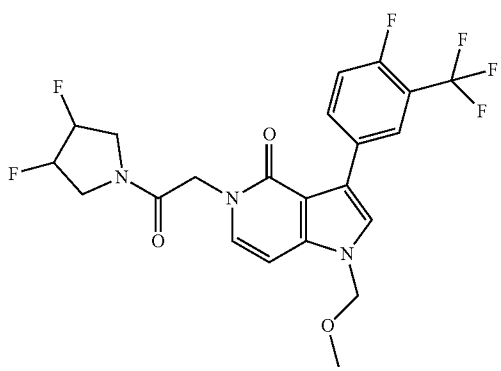 [SMILES: COCn1cc(-c2ccc(F)c(C(F)(F)F)c2)c2c(=O)n(CC(=O)N3CC(F)C(F)C3)ccc21] | 5-(2-(3,4-difluoropyrrolidin-1-yl)-2-oxoethyl)-3-(4-fluoro-3-(trifluoromethyl)phenyl)-1-(methoxymethyl)-1H-pyrrolo[3,2-c]pyridin-4(5H)-one | $^1$H-NMR (DMSO-$d_6$, 400 MHz) δ (ppm): 8.29 (d, J = 6.4 Hz, 1H), 8.12 (brs, 1H), 7.69 (s, 1H), 7.45 (t, J = 9.2 Hz, 1H), 7.34 (d, J = 7.6 Hz, 1H), 6.68 (d, J = 7.2 Hz, 1H), 5.45-5.24 (m, 4H), 4.84-4.73 (m, 2H), 4.08-3.44 (m, 4H), 3.23 (s, 3H). Calculated (M + H): 488.13, Found (M + H): 488.1. HPLC purity: 99.74% |
| 243 | 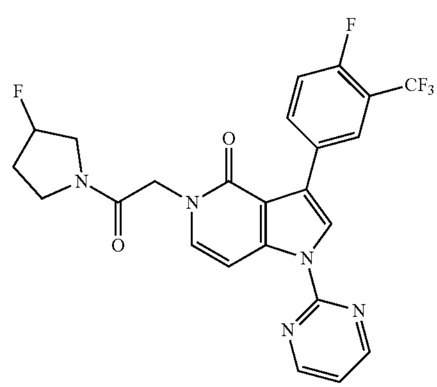 [SMILES: O=C(Cn1ccc2c(c(-c3ccc(F)c(C(F)(F)F)c3)cn2-c2ncccn2)c1=O)N1CCC(F)C1] | 3-(4-fluoro-3-(trifluoromethyl)phenyl)-5-(2-(3-fluoropyrrolidin-1-yl)-2-oxoethyl)-1-(pyrimidin-2-yl)-1H-pyrrolo[3,2-c]pyridin-4(5H)-one | $^1$H-NMR (DMSO-$d_6$, 400 MHz) δ (ppm): 8.92 (d, J = 4.8 Hz, 2H), 8.28 (s, 1H), 8.23 (d, J = 6.0 Hz, 1H), 8.11 (s, 1H), 7.72 (d, J = 7.6 Hz, 1H), 7.50-7.45 (m, 3H), 5.50-5.25 (m, 1H), 4.93-4.76 (m, 2H), 3.91-3.41 (m, 4H), 2.30-1.93 (m, 2H). Calculated (M + H): 504.14, Found (M + H): 504.10. HPLC purity: 99.61% |
| 244 | 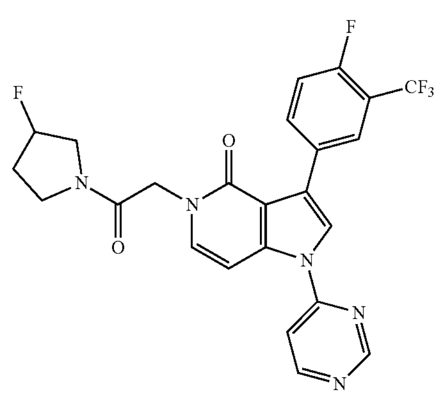 [SMILES: O=C(Cn1ccc2c(c(-c3ccc(F)c(C(F)(F)F)c3)cn2-c2ccncn2)c1=O)N1CCC(F)C1] | 3-(4-fluoro-3-(trifluoromethyl)phenyl)-5-(2-(3-fluoropyrrolidin-1-yl)-2-oxoethyl)-1-(pyrimidin-4-yl)-1H-pyrrolo[3,2-c]pyridin-4(5H)-one | $^1$H-NMR (DMSO-$d_6$, 400 MHz) δ (ppm): 9.18 (s, 1H), 8.95 (d, J = 5.6, 1H), 8.28 (s, 2H), 8.17 (s, 1H), 8.02 (d, J = 5.2 Hz, 1H), 7.63 ( d, J = 7.6 Hz, 1H), 7.50 (t, J = 6.4 Hz, 2H), 5.50-5.25 (m, 1H), 4.93-4.75 (m, 2H), 4.03-3.72 (m, 2H), 3.69-3.27 (m, 2H), 2.20-1.96 (m, 2H); Calculated (M + H): 504.14, Found (M + H): 504.1, HPLC purity: 98.50% |

TABLE 21-continued

The following compounds were prepared by the method described above:

| Ex. No. | Structure | Name | Analytical data |
|---|---|---|---|
| 245 | 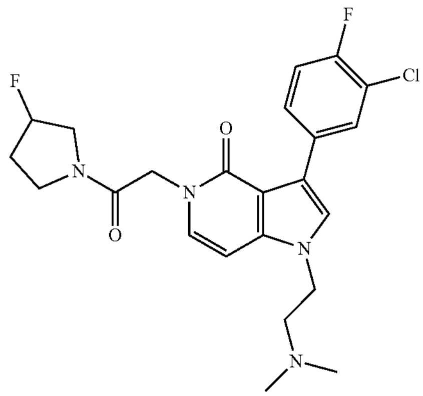 [SMILES: CN(C)CCn1cc(-c2ccc(F)c(Cl)c2)c2c(=O)n(CC(=O)N3CCC(F)C3)ccc21] | 3-(3-chloro-4-fluorophenyl)-1-(2-(dimethylamino)ethyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.14 (d, J = 6 Hz, 1H), 7.78 (bs, 1H), 7.52 (s, 1H), 7.34-7.27 (m, 2H), 6.61 (d, J = 7.2 Hz, 1H), 5-5.25 (m, 1H), 4.82-4.73 (m, 2H), 4.15 (t, J = 6.4 Hz, 2H), 3.79-3.57 (m, 4H), 2.61 (t, J = 6 Hz, 2H), 2.22-2.12 (s, 8H). Calculated (M + H): 463.16, Found (M + H): 463.1, HPLC purity: 99.2% |
| 246 | 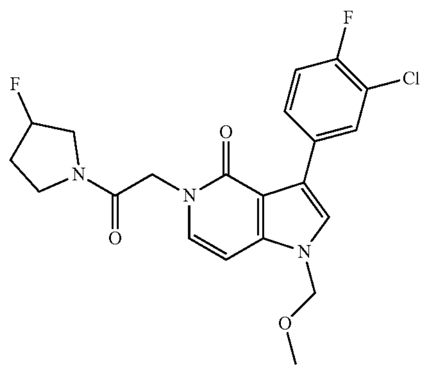 [SMILES: COCn1cc(-c2ccc(F)c(Cl)c2)c2c(=O)n(CC(=O)N3CCC(F)C3)ccc21] | 3-(3-chloro-4-fluorophenyl)-5-(2-(3-fluoropyrrolidin-1-yl)-2-oxoethyl)-1-(methoxymethyl)-1H-pyrrolo[3,2-c]pyridin-4(5H)-one | $^1$H-NMR (DMSO-$d_6$, 400 MHz) δ (ppm): 8.15-8.13 (m, 1H), 7.78 (brs, 1H), 7.62 (s, 1H), 7.36-7.32 (m, 2H), 6.66 (d, J = 7.6 Hz, 1H), 5.5-5.25 (m, 3H), 4.87-4.73 (m, 2H), 3.81-3.4 (m, 4H), 3.23 (s, 3H), 2.31-2.09 (m, 2H). Calculated (M + H): 436.12, Found (M + H): 436.1, HPLC purity: 98.18% |
| 247 | 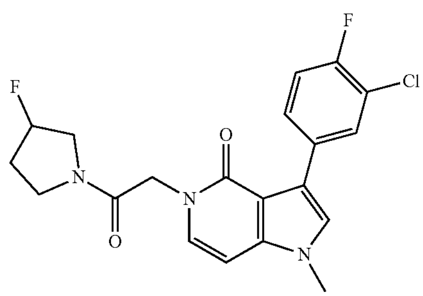 [SMILES: Cn1cc(-c2ccc(F)c(Cl)c2)c2c(=O)n(CC(=O)N3CCC(F)C3)ccc21] | 3-(3-chloro-4-fluorophenyl)-5-(2-(3-fluoropyrrolidin-1-yl)-2-oxoethyl)-1-methyl-1H-pyrrolo[3,2-c]pyridin-4(5H)-one | $^1$H-NMR (DMSO-$d_6$, 400 MHz) δ (ppm): 8.12 (dd, J = 2 Hz, 7.6 Hz, 1H), 7.77 (brs, 1H), 7.46 (s, 1H), 7.43-7.3 (m, 2H), 6.57 (d, J = 7.2 Hz, 1H), 5.5-5.25 (m, 1H), 4.82-4.74 (m, 2H), 3.9.3.75 (m, 2H), 3.73 (s, 3H), 3.63-3.3 (m, 2H), 2.38-2.01 (m, 2H). Calculated (M + H): 406.11, Found (M + H): 406.1, HPLC purity: 92.56% |
| 248 | 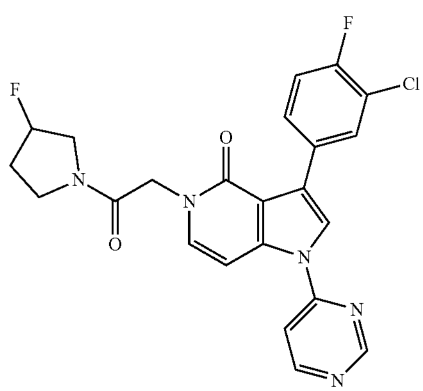 [SMILES: O=C(Cn1ccc2c(c(-c3ccc(F)c(Cl)c3)cn2-c2ccncn2)c1=O)N1CCC(F)C1] | 3-(3-chloro-4-fluorophenyl)-5-(2-(3-fluoropyrrolidin-1-yl)-2-oxoethyl)-1-(pyrimidin-4-yl)-1H-pyrrolo[3,2-c]pyridin-4(5H)-one | $^1$H-NMR (400 MHz, DMSO-$d_6$) δ (ppm): 9.17 (s, 1H), 8.95 (d, J = 5.6 Hz, 1H), 8.22 (s, 1H), 8.12 (d, J = 5.6 Hz, 1H), 8.03 (d, J = 6 Hz, 1H), 7.85 (brs, 1H), 7.63 (d, J = 7.6 Hz, 1H), 7.50 (d, J = 7.6 Hz, 1H), 7.41 (t, J = 8.8 Hz, 1H), 5.72-5.25 (m, 1H), 4.92-4.75 (m, 2H), 3.9-3.22 (m, 4H), 2.30-1.94 (m, 2H), Calculated (M + H): 470.1, Found (M + H): 470.1, HPLC purity: 98.05% |

TABLE 21-continued

The following compounds were prepared by the method described above:

| Ex. No. | Structure | Name | Analytical data |
|---|---|---|---|
| 249 | 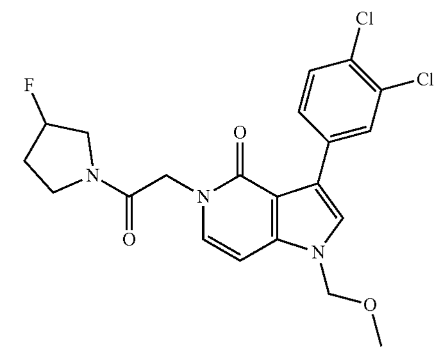 [SMILES: COCn1cc(-c2ccc(Cl)c(Cl)c2)c2c(=O)n(CC(=O)N3CCC(F)C3)ccc21] | 3-(3,4-dichlorophenyl)-5-(2-(3-fluoropyrrolidin-1-yl)-2-oxoethyl)-1-(methoxymethyl)-1H-pyrrolo[3,2-c]pyridin-4(5H)-one | $^1$H-NMR (DMSO-d$_6$, 400 MHz) δ (ppm): 8.24 (s, 1H), 7.81 (d, J = 8.4 Hz, 1H), 7.70 (s, 1H), 7.55 (d, J = 8.4 Hz, 1H), 7.36 (d, J = 7.6 Hz, 1H), 6.67 (d, J = 6.8 Hz, 1H), 5.50-5.25 (m, 3H), 4.88-4.73 (m, 2H), 3.87-3.41 (m, 4H), 3.27 (s, 3H), 2.26-1.97 (m, 2H); Calculated (M + H): 452.09, Found (M + H): 452.1, HPLC purity: 100% |
| 250 | 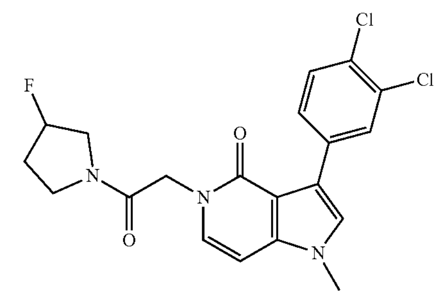 | 3-(3,4-dichlorophenyl)-5-(2-(3-fluoropyrrolidin-1-yl)-2-oxoethyl)-1-methyl-1H-pyrrolo[3,2-c]pyridin-4(5H)-one | $^1$H-NMR (DMSO-d$_6$, 400 MHz) δ (ppm): 8.26 (d, J = 1.6 Hz, 1H), 7.8 (d, J = 8.4 Hz, 1H), 7.55-7.51 (m, 2H), 7.32 (d, J = 7.6 Hz, 1H), 6.58 (d, J = 7.2 Hz, 1H), 5.38-5.25 (m, 1H), 4.87-4.72 (m, 2H), 3.86-3.73 (m, 4H), 3.63-3.32 (m, 3H), 2.30-2.12 (m, 2H); Calculated (M + H): 422.08, Found (M + H): 422.1. HPLC purity: 98.2% |
| 251 | 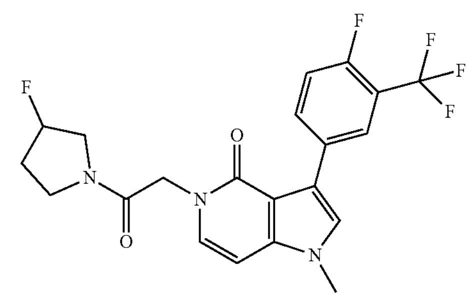 [SMILES: Cn1cc(-c2ccc(F)c(C(F)(F)F)c2)c2c(=O)n(CC(=O)N3CCC(F)C3)ccc21] | 3-(4-fluoro-3-(trifluoromethyl)phenyl)-5-(2-(3-fluoropyrrolidin-1-yl)-2-oxoethyl)-1-methyl-1H-pyrrolo[3,2-c]pyridin-4(5H)-one | $^1$H-NMR (DMSO-d$_6$, 400 MHz) δ (ppm): 8.30 (d, J = 6 Hz, 1H), 8.11 (brs, 1H), 7.53 (s, 1H), 7.43 (t, J = 9.2 Hz, 1H), 7.32 (d, J = 7.2 Hz, 1H), 6.59 (d, J = 7.6 Hz, 1H), 5.5-5.25 (m, 1H), 4.83-4.74 (m, 2H), 3.81-3.33 (m, 7H), 2.38-2.01 (m, 2H). Calculated (M + H): 440.13, Found (M + H): 440.1, HPLC purity: 99.47% |
| 252 | 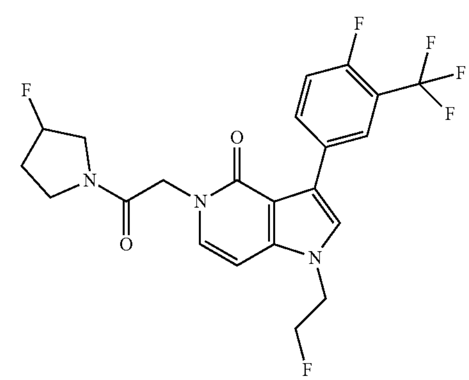 [SMILES: O=C(Cn1ccc2c(c(-c3ccc(F)c(C(F)(F)F)c3)cn2CCF)c1=O)N1CCC(F)C1] | 3-(4-fluoro-3-(trifluoromethyl)phenyl)-1-(2-fluoroethyl)-5-(2-(3-fluoropyrrolidin-1-yl)-2-oxoethyl)-1H-pyrrolo[3,2-c]pyridin-4(5H)-one | $^1$H-NMR (DMSO-d$_6$, 400 MHz) δ (ppm): 8.27 (d, J = 6.4 Hz, 1H), 8.11 (s, 1H), 7.58 (s, 1H), 7.44 (t, J = 9.6 Hz, 1H), 7.32 (d, J = 7.2 Hz, 1H), 6.65 (d, J = 7.2 Hz, 1H), 5.54-5.31 (m, 1H), 4.88-4.45 (m, 4H), 4.42-4.50 (m, 2H), 3.91-3.4 (m, 4H), 2.31-1.99 (m, 2H). Calculated (M + H): 472.14, Found (M + H): 472.1, HPLC purity: 99.87% |

TABLE 21-continued

The following compounds were prepared by the method described above:

| Ex. No. | Structure | Name | Analytical data |
|---|---|---|---|
| 253 | 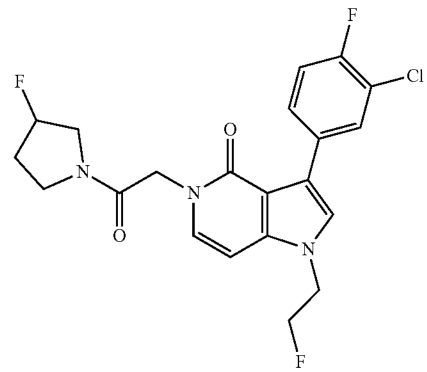 [SMILES: O=C(Cn1ccc2c(c(-c3ccc(F)c(Cl)c3)cn2CCF)c1=O)N1CCC(F)C1] | 3-(3-chloro-4-fluorophenyl)-1-(2-fluoroethyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.13 (dd, J = 2.0 Hz, 7.6 Hz, 1H), 7.74-7.82 (m, 1H), 7.52 (s, 1H), 7.36-7.30 (m, 2H), 6.63 (d, J = 7.6 Hz, 1H), 5.38 (t, J = 49.2 Hz, 1H), 4.87-4.71 (m, 4H), 4.48-4.40 (m, 2H), 3.90-3.48 (m, 4H), 2.30-1.90 (m, 2H). Calculated (M + H): 438.11, found (M + H): 438.1, HPLC purity: 98.20% |
| 254 | 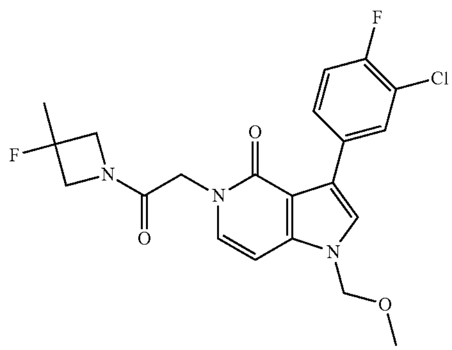 [SMILES: COCn1cc(-c2ccc(F)c(Cl)c2)c2c(=O)n(CC(=O)N3CC(C)(F)C3)ccc21] | 3-(3-chloro-4-fluorophenyl)-5-(2-(3-fluoro-3-methylazetidin-1-yl)-2-oxoethyl)-1-(methoxymethyl)-1,5-dihydro-4H-pyrrolo[3,2-c]pyridin-4-one | $^1$H-NMR (DMSO-$d_6$, 400 MHz) δ (ppm): 8.16-8.14 (m, 1H), 7.80-7.76 (m, 1H), 7.63 (s, 1H), 7.37 (m, 2H), 6.68 (d, J = 7.6 Hz, 1H), 5.43 (s, 2H), 4.60 (s, 2H), 4.40-4.28 (m, 2H), 4.02-3.94 (m, 2H), 3.22 (s, 3H), 1.59 (d, J = 21.6 Hz, 3H). Calculated (M + H): 436.12; Found (M + 1): 436.1. HPLC purity 99.63% |

Example 255: Preparation of 2-(3-(3-chloro-4-fluorophenyl)-4-oxo-1H-pyrrolo[3,2-c]pyridin-5(4H)-yl)acetamide

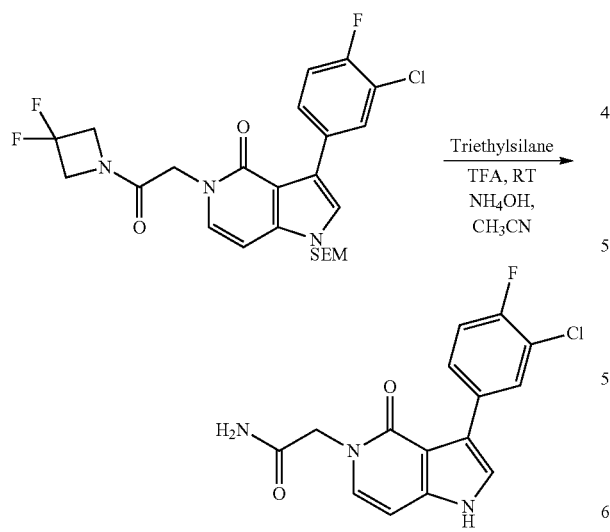

To a stirred suspension of 5-(2-(3,3-difluoroazetidin-1-yl)-2-oxoethyl)-3-(4-fluoro-3-(trifluoromethyl)phenyl)-1-((2-(trimethylsilyl)ethoxy)methyl)-1H-pyrrolo[3,2-c]pyridin-4(5H)-one (0.08 g, 0.143 mmol) in triethylsilane (0.1 mL, 0.429 mmol), was added trifluoroacetic acid (2 mL) at room temperature and stirred for 1 h. After completion of reaction, reaction mixture was evaporated under vacuum and the residue was diluted with 2 mL of acetonitrile and 25 mL of ammonium hydroxide. The resulting mixture was stirred for 24 h at room temperature, and acidified with 2N hydrochloric acid at 0° C. The precipitated product was filtered and dried to afford the title compound 2-(3-(3-chloro-4-fluorophenyl)-4-oxo-1H-pyrrolo[3,2-c]pyridin-5(4H)-yl)acetamide (0.03 g, 25% yield) as an off white solid. $^1$H-NMR (DMSO-$d_6$, 400 MHz) δ (ppm): 11.66 (s, 1H), 8.21 (d, J=7.6 Hz, 1H), 7.81 (s, 1H), 7.46-7.44 (m, 2H), 7.30 (t, J=8.8 Hz, 1H), 7.24 (d, J=7.6 Hz, 1H), 7.02 (s, 1H), 6.39 (d, J=6.8 Hz, 1H), 4.49 (s, 2H). Calculated (M+H): 320.05, Found (M+H): 320.1, HPLC purity: 99.61%.

Example 256: Preparation of 3-(4-fluoro-3-(trifluoromethyl)phenyl)-5-(2-(3-fluoropyrrolidin-1-yl)-2-oxoethyl)-1-(2-hydroxyethyl)-1H-pyrrolo[3,2-c]pyridin-4(5H)-one

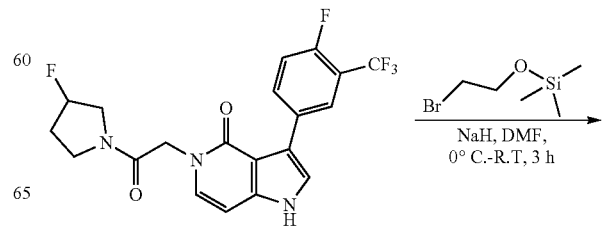

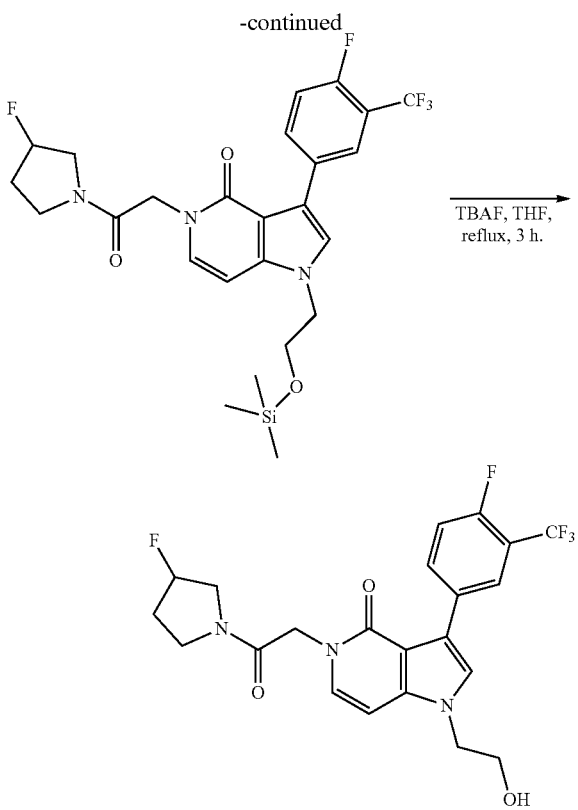

Step-1

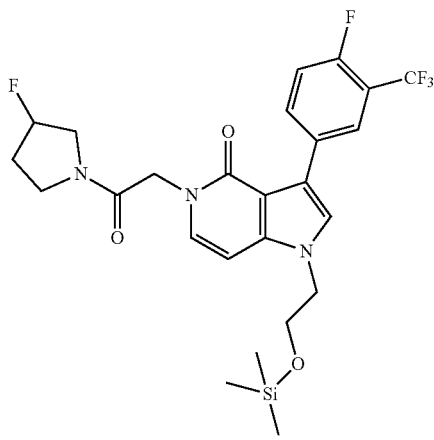 [SMILES: C[Si](C)(C)OCCn1cc(-c2ccc(F)c(C(F)(F)F)c2)c2c(=O)n(CC(=O)N3CCC(F)C3)ccc21]

To a stirred solution of 3-(4-fluoro-3-(trifluoromethyl)phenyl)-5-(2-(3-fluoropyrrolidin-1-yl)-2-oxoethyl)-1-(2-((trimethylsilyl)oxy)ethyl)-1H-pyrrolo[3,2-c]pyridin-4(5H)-one (0.2 g, 0.47 mmol) in N,N-dimethylformamide (10 mL) was added sodium hydride (60% dispersion in mineral oil) (0.04 g, 0.94 mmol) at 0° C. and stirred for 30 min. To the above mixture (2-bromoethoxy) trimethylsilane (0.4 ml, 1.41 mmol) was added at 0° C. and stirred at room temperature for 3 h. After completion of the reaction (monitored by TLC), the mixture was quenched with ice cold water (50 mL) and extracted with ethyl acetate (3×50 mL). The combined organic layer were dried over anhydrous sodium sulfate filtered and concentrated to afford crude product, which was purified by silica gel (60-120) column chromatography using 5% methanol in dichloromethane to afford title compound 3-(4-fluoro-3-(trifluoromethyl)phenyl)-5-(2-(3-fluoropyrrolidin-1-yl)-2-oxoethyl)-1-(2-((trimethylsilyl)oxy)ethyl)-1H-pyrrolo[3,2-c]pyridin-4(5H)-one (0.2 g crude) as brown color semi solid. (The crude was taken as such to next step).

Step 2

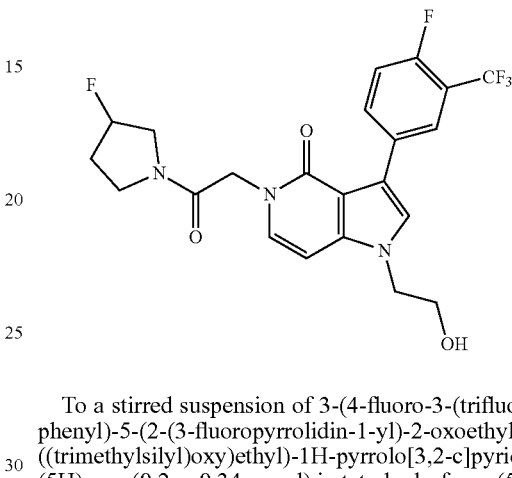

To a stirred suspension of 3-(4-fluoro-3-(trifluoromethyl)phenyl)-5-(2-(3-fluoropyrrolidin-1-yl)-2-oxoethyl)-1-(2-((trimethylsilyl)oxy)ethyl)-1H-pyrrolo[3,2-c]pyridin-4(5H)-one (0.2 g, 0.34 mmol) in tetrahydrofuran (5 mL), was added tetrabutylammoniumfluoride solution (2 mL, 1.0 M in THF), and the reaction mixture was refluxed for 3 h. After completion of reaction, the reaction mixture was diluted with water (50 mL) and extracted with ethyl acetate (2×100 mL), the combined organic layer were dried over anhydrous sodium sulfate, filtered, concentrated under vacuum to afford the crude product. The crude product was purified by preparative HPLC (Column: Chemsil C18 (250 mm×4.6 mm×5μ), mobile phase (A): 0.01% ammonia in water, mobile phase (B): methanol, flow rate: 1.0 mL/minT/% B: 0/20, 10/80, 25/80, 27/20, 30/20) to afford a title compound 3-(4-fluoro-3-(trifluoromethyl)phenyl)-5-(2-(3-fluoropyrrolidin-1-yl)-2-oxoethyl)-1-(2-hydroxyethyl)-1H-pyrrolo[3,2-c]pyridin-4(5H)-one (0.019 g, 11.87% yield) as a white solid. H-NMR (DMSO-$d_6$, 400 MHz) δ (ppm): 8.28 (dd, J=7.2 Hz, J=7.2 Hz, 1H), 8.10 (brs, 1H), 7.52 (s, 1H), 7.44-7.39 (m, 1H), 7.29-7.27 (m, 1H), 6.61 (d, J=7.2 Hz, 1H), 5.49-5.24 (m, 1H), 4.92-4.69 (m, 3H), 4.14-4.12 (m, 2H), 3.90-3.31 (m, 6H), 2.30-1.93 (m, 2H). Calculated (M+H): 470.14, Found (M+H): 470.1, HPLC purity 98.28%.

Example 257: Preparation of 3-(4-fluoro-3-(trifluoromethyl)phenyl)-5-(2-(3-fluoropyrrolidin-1-yl)-2-oxoethyl)-1-(2-hydroxy-2-methylpropyl)-1H-pyrrolo[3,2-c]pyridin-4(5H)-one

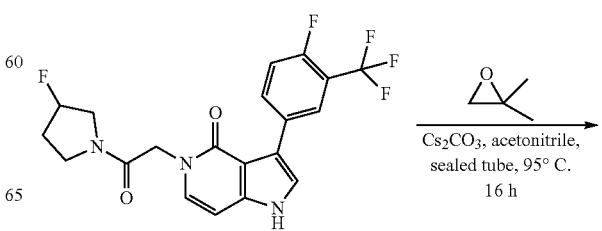

-continued

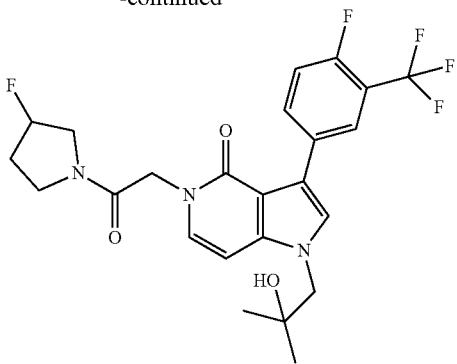

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.05 g, 0.11 mmol) in acetonitrile (3 mL), 2,2-dimethyloxirane and cesium carbonate (0.06 g, 0.17 mmol) were added. The reaction mixture was heated in a sealed tube at 95° C. for 16 h. After completion of the reaction, the reaction mixture was quenched with water (20 mL) and extracted with dichloromethane (3×50 mL). The combined organic layer was washed with brine solution, dried over anhydrous sodium sulfate, filtered and evaporated to afford the crude product which was purified by silica gel column chromatography using 20% ethyl acetate in dichloromethane to afford the title compound 3-(4-fluoro-3-(trifluoromethyl)phenyl)-5-(2-(3-fluoropyrrolidin-1-yl)-2-oxoethyl)-1-(2-hydroxy-2-methylpropyl)-1H-pyrrolo[3,2-c]pyridin-4(5H)-one (0.032 g, 55.2% yield) as off-white solid.
$^1$H-NMR (DMSO-$d_6$, 400 MHz) δ (ppm): 8.26 (d, J=6 Hz, 1H), 8.08 (brs, 1H), 7.45-7.4 (m, 2H), 7.26 (d, J=7.2 Hz, 1H), 6.67 (d, J=7.6 Hz, 1H), 5.5-5.2 (m, 1H), 4.82-4.69 (m, 3H), 3.99 (s, 2H), 3.82-3.57 (m, 4H), 2.3-2 (m, 2H), 1.11 (s, 6H). Calculated (M+H): 498.17, Found (M+H): 498.0. HPLC purity: 98.44%.

TABLE 22

The following compounds were prepared by the method described above:

| Ex. No. | Structure | Name | Analytical data |
|---|---|---|---|
| 258 | 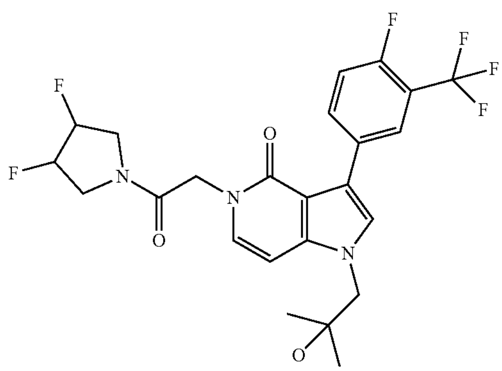 [SMILES: CC(C)(O)Cn1cc(-c2ccc(F)c(C(F)(F)F)c2)c2c(=O)n(CC(=O)N3CC(F)C(F)C3)ccc21] | 5-(2-(3,4-difluoropyrrolidin-1-yl)-2-oxoethyl)-3-(4-fluoro-3-(trifluoromethyl)phenyl)-1-(2-hydroxy-2-methylpropyl)-1H-pyrrolo[3,2-c]pyridin-4(5H)-one | $^1$H-NMR (DMSO-$d_6$, 400 MHz) δ (ppm): 8.27 (d, J = 6.8 Hz, 1H), 8.08 (brs, 1H), 7.45-7.4 (m, 2H), 7.25 (d, J = 7.6 Hz, 1H), 6.68 (d, J = 7.2 Hz, 1H), 5.5-5.2 (m, 2H), 4.82-4.69 (m, 3H), 4.05-3.47 (m, 6H), 1.1 (s, 6H). Calculated (M + H): 516.16, Found (M + H): 516.3, HPLC purity: 99.47% |
| 259 | 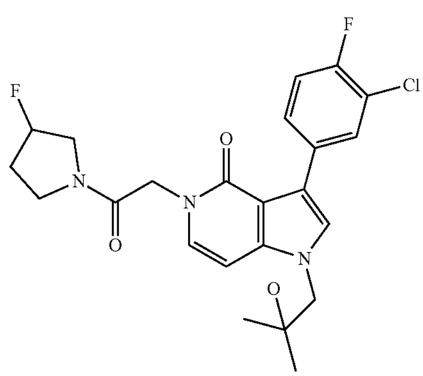 [SMILES: CC(C)(O)Cn1cc(-c2ccc(F)c(Cl)c2)c2c(=O)n(CC(=O)N3CCC(F)C3)ccc21] | 3-(3-chloro-4-fluorophenyl)-5-(2-(3-fluoropyrrolidin-1-yl)-2-oxoethyl)-1-(2-hydroxy-2-methylpropyl)-1H-pyrrolo[3,2-c]pyridin-4(5H)-one | $^1$H-NMR (DMSO-$d_6$, 400 MHz) δ (ppm): 8.12 (d, J = 6.8 Hz, 1H), 7.75 (brs, 1H), 7.39 (s, 1H), 7.32 (t, J = 8.8 Hz, 1H), 7.25 (d, J = 6.8 Hz, 1H), 6.65 (d, J = 7.6 Hz, 1H), 5-5.25 (m, 1H), 4.81-4.68 (m, 3H), 3.98 (s, 2H), 3.79-3.57 (m, 4H), 2.31-2.0 (m, 2H), 1.1 (s, 6H). Calculated (M + H): 464.15, Found (M + H): 464.1, HPLC purity: 97.9% |

Example 260: Preparation of 3-(4-fluoro-3-(trifluoromethyl)phenyl)-5-(2-(3-fluoropyrrolidin-1-yl)-2-oxoethyl)-1-(hydroxymethyl)-1H-pyrrolo[3,2-c]pyridin-4(5H)-one

Example 261: Preparation of 3-(3-chloro-4-fluorophenyl)-5-(2-(3-fluoropyrrolidin-1-yl)-2-oxoethyl)-1-(oxetan-3-yl)-1H-pyrrolo[3,2-c]pyridin-4(5H)-one

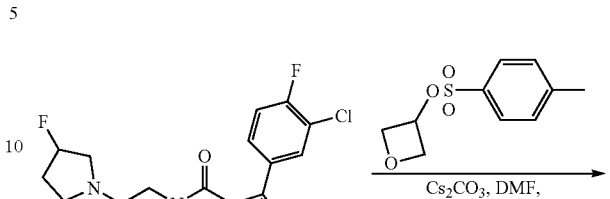

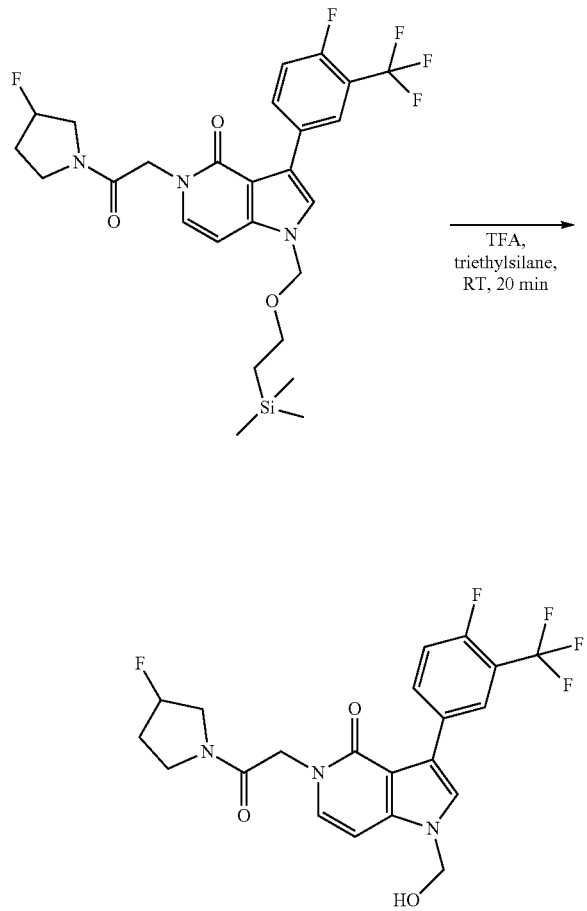 [SMILES: C[Si](C)(C)CCOCn1cc(-c2ccc(F)c(C(F)(F)F)c2)c2c(=O)n(CC(=O)N3CCC(F)C3)ccc21 ; O=C(Cn1ccc2c(c(-c3ccc(F)c(C(F)(F)F)c3)cn2CO)c1=O)N1CCC(F)C1]

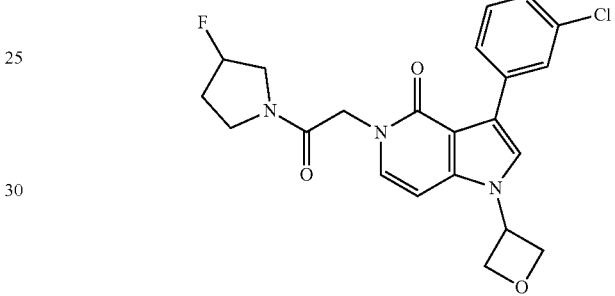

To a stirred suspension of 3-(4-fluoro-3-(trifluoromethyl)phenyl)-5-(2-(3-fluoropyrrolidin-1-yl)-2-oxoethyl)-1-((2-(trimethylsilyl)ethoxy)methyl)-1H-pyrrolo[3,2-c]pyridin-4(5H)-one (0.15 g, 0.27 mmol) in triethylsilane (0.086 mL, 0.54 mmol), trifluoroaceticacid (1.0 mL, 13.51 mmol) was added at room temperature and the reaction mixture was stirred at the same temperature for 20 min. After completion of reaction, the reaction mixture was evaporated under vacuum, the residue was diluted with water (50 mL) and extracted with dichloromethane (2×50 mL). The combined organic layer was dried over anhydrous sodium sulphate, filtered and concentrated. The crude product was purified by prep HPLC (kinetex C18 (100 mm×4.6 mm×2.6 μm), mobile phase (A): 0.01% TFA in water, mobile phase (B): acetonitrile, flow rate: 0.75 ml/min) to afford title compound 3-(4-fluoro-3-(trifluoromethyl)phenyl)-5-(2-(3-fluoropyrrolidin-1-yl)-2-oxoethyl)-1-(hydroxymethyl)-1H-pyrrolo[3,2-c]pyridin-4(5H)-one (0.071 g, 57.72% yield) as off white solid. 1H-NMR (DMSO-d6, 400 MHz) δ (ppm): 8.28 (d, J=6.4 Hz, 1H), 8.09 (brs, 1H), 7.58 (s, 1H), 7.43 (t, J=10 Hz, 1H), 7.33 (d, J=7.2 Hz, 1H), 6.80-6.60 (m, 2H), 5.49-5.25 (m, 3H), 4.87-4.7 (m, 2H), 3.9-3.25 (m, 4H), 2.31-2.07 (m, 2H). Calculated (M+H): 456.13, Found (M+H): 456.1, HPLC purity: 99.97%.

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.1 g, 0.25 mmol) in N,N-dimethylformamide (5 mL), oxetan-3-yl 4-methylbenzenesulfonate (0.14 g, 0.64 mmol) and cesium carbonate (0.25 g, 0.77 mmol) were added. The reaction mixture was heated at 100° C. for 48 h. After completion of the reaction, the reaction mixture was quenched with water (20 mL) and extracted with ethyl acetate (3×50 mL). The combined organic layer was washed with brine solution (50 mL), dried over anhydrous sodium sulfate, filtered and evaporated to afford the crude product which was purified by silica gel column chromatography using 2% methanol in dichloromethane to afford the title compound 3-(3-chloro-4-fluorophenyl)-5-(2-(3-fluoropyrrolidin-1-yl)-2-oxoethyl)-1-(oxetan-3-yl)-1H-pyrrolo[3,2-c]pyridin-4(5H)-one (0.0055 g, 5% yield) as pale yellow solid. 1H-NMR (DMSO-d6, 400 MHz) δ (ppm): 8.19 (dd, J=2 Hz, 7.2 Hz, 1H), 7.95 (s, 1H), 7.9-7.87 (m, 1H), 7.37-7.32 (m, 2H), 6.62 (d, J=7.2 Hz, 1H), 5.69-5.65 (m, 1H), 5.49-5.25 (m, 1H), 4.99-4.71 (m, 6H), 3.89-3.32 (m, 4H), 2.31-1.94 (m, 2H). Calculated (M+H): 448.12, Found (M+H): 448.1, HPLC purity: 97.34%.

TABLE 23

The following compounds were prepared by the method described above:

| Ex. No. | Structure | Name | Analytical data |
|---|---|---|---|
| 262 | 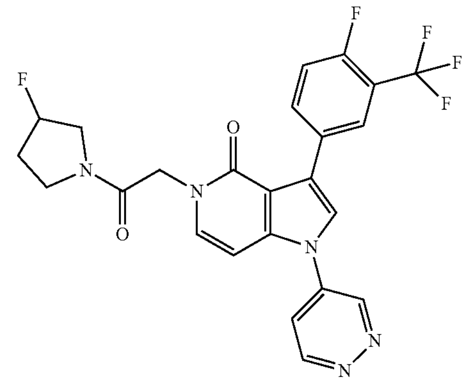 [SMILES: O=C(Cn1ccc2c(c(-c3ccc(F)c(C(F)(F)F)c3)cn2-c2ccnnc2)c1=O)N1CCC(F)C1] | 3-(4-fluoro-3-(trifluoromethyl)phenyl)-5-(2-(3-fluoropyrrolidin-1-yl)-2-oxoethyl)-1-(pyridazin-4-yl)-1H-pyrrolo[3,2-c]pyridin-4(5H)-one | $^1$H-NMR (DMSO-$d_6$, 400 MHz) δ (ppm): 9.7 (s, 1H), 9.4 (d, J = 6 Hz, 1H), 8.3 (d, J = 6.4 Hz, 1H), 8.19 (brs, 1H), 8.08-8.04 (m, 2H), 7.55-7.48 (m, 2H), 6.82 (d, J = 7.6 Hz, 1H), 5.51-5.25 (m, 1H), 4.94-4.76 (m, 2H), 3.91-3.58 (m, 4H), 2.13-1.97 (m, 2H). Calculated (M + H): 504.14, Found (M + H): 504.1, HPLC purity: 99.21% |

Example 263: Preparation of 3-(4-fluoro-3-(trifluoromethyl)phenyl)-5-(2-(3-fluoropyrrolidin-1-yl)-2-oxoethyl)-1-(5-methyl-1,3,4-oxadiazol-2-yl)-1H-pyrrolo[3,2-c]pyridin-4(5H)-one

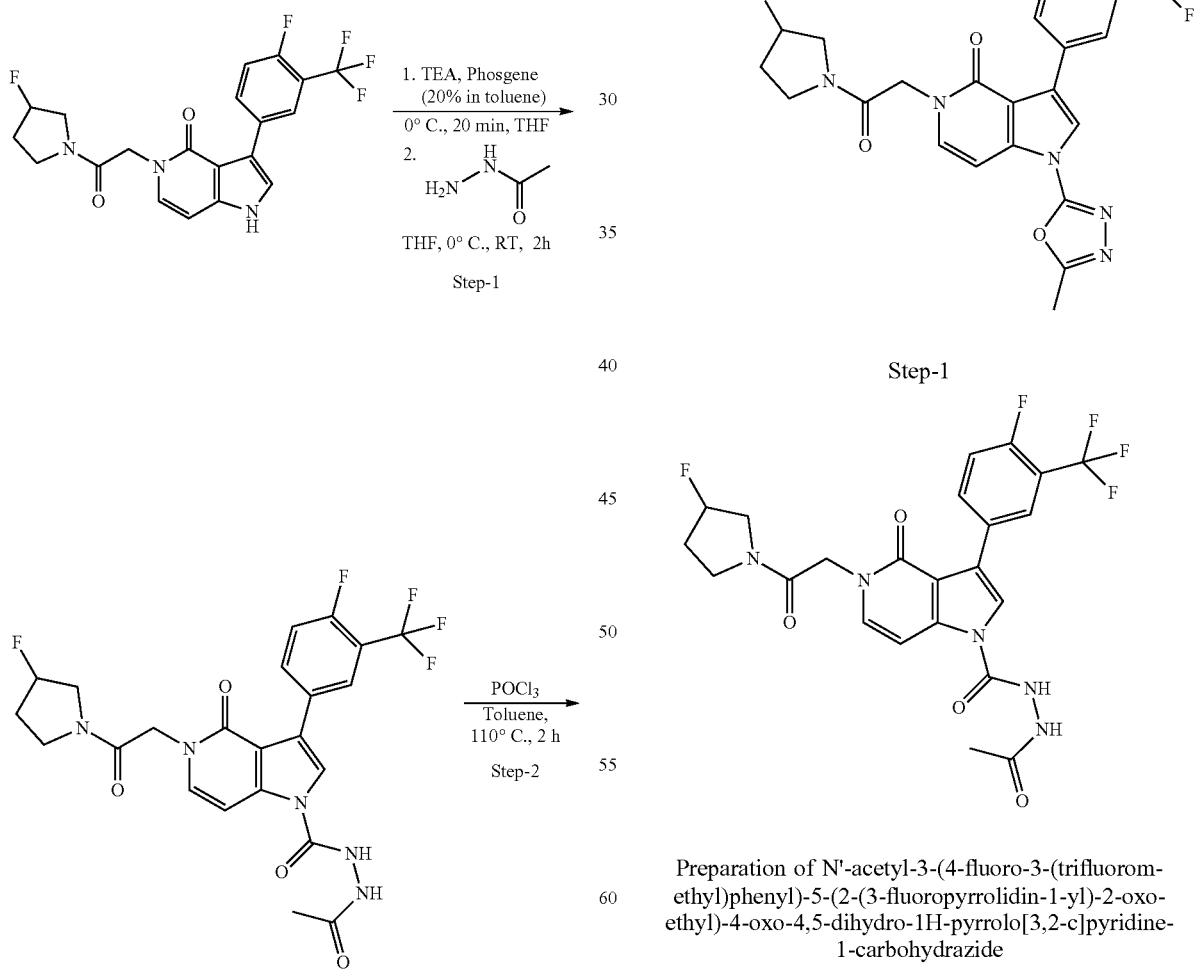

Step-1

Preparation of N'-acetyl-3-(4-fluoro-3-(trifluoromethyl)phenyl)-5-(2-(3-fluoropyrrolidin-1-yl)-2-oxoethyl)-4-oxo-4,5-dihydro-1H-pyrrolo[3,2-c]pyridine-1-carbohydrazide Triethylamine (0.08 mL, 0.587 mmol) and phosgene (0.17 mL, 0.353 mmol) were added sequentially to an ice cold solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.1 g, 0.235 mmol) in tetrahydrofuran (10 mL) and the reaction mixture was stirred at 0° C. for 20 minutes. Then acetohydrazide (0.02 g, 0.28 mmol) in tetrahydrofuran (3 mL) was added and stirring was continued for 1 h at room temperature. The reaction mixture was quenched with cold water (20 mL) and extracted with ethyl acetate (3×50 mL). The combined organic layer was dried over anhydrous sodium sulfate, filtered and evaporated to afford the crude product which was purified by silica gel column chromatography using 8% methanol in dichloromethane to afford the title compound N'-acetyl-3-(4-fluoro-3-(trifluoromethyl)phenyl)-5-(2-(3-fluoropyrrolidin-1-yl)-2-oxoethyl)-4-oxo-4,5-dihydro-1H-pyrrolo[3,2-c]pyridine-1-carbohydrazide (0.04 g, 32% yield) as a white solid. Calculated (M+H): 526.1, Found (M+H): 526.1.

Step-2

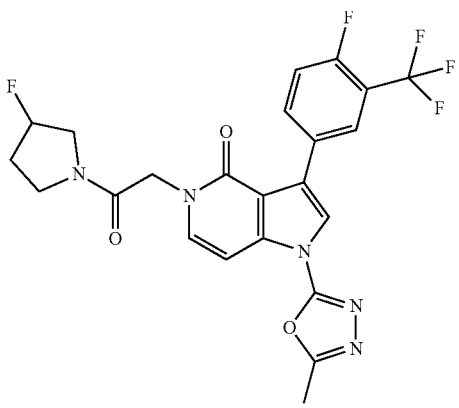 [SMILES: Cc1nnc(-n2cc(-c3ccc(F)c(C(F)(F)F)c3)c3c(=O)n(CC(=O)N4CCC(F)C4)ccc32)o1]

Preparation of 3-(4-fluoro-3-(trifluoromethyl)phenyl)-5-(2-(3-fluoropyrrolidin-1-yl)-2-oxoethyl)-1-(5-methyl-1,3,4-oxadiazol-2-yl)-1H-pyrrolo[3,2-c]pyridin-4(5H)-one To a solution of N'-acetyl-3-(4-fluoro-3-(trifluoromethyl)phenyl)-5-(2-(3-fluoropyrrolidin-1-yl)-2-oxoethyl)-4-oxo-4,5-dihydro-1H-pyrrolo[3,2-c]pyridine-1-carbohydrazide (0.04 g, 0.076 mmol) in toluene (5 mL) was added phosphorus oxychloride (0.007 mL, 0.0761 mmol) and the reaction mixture was stirred at 110° C. for 2 h. The reaction mixture was quenched with cold water (20 mL) and extracted with ethyl acetate (3×50 mL). The combined organic layer was dried over anhydrous sodium sulfate, filtered and evaporated to afford the crude product which was purified by silica gel column chromatography using 4% methanol in dichloromethane to afford 3-(4-fluoro-3-(trifluoromethyl)phenyl)-5-(2-(3-fluoropyrrolidin-1-yl)-2-oxoethyl)-1-(5-methyl-1,3,4-oxadiazol-2-yl)-1H-pyrrolo[3,2-c]pyridin-4(5H)-one (0.004 g, 10% yield) as a white solid. $^1$H-NMR (400 MHz, DMSO-d$_6$) δ (ppm): 8.27 (d, J=6.4 Hz, 1H), 8.15 (brs, 1H), 8.01 (s, 1H), 7.61 (d, J=6.8 Hz, 1H), 7.50 (t, J=9.6 Hz, 1H), 7.21 (d, J=7.2 Hz, 1H), 5.38-5.25 (m, 1H), 4.94-4.81 (m, 2H), 3.82-3.26 (m, 4H), 2.58 (s, 3H), 2.3-2.0 (m, 2H). Calculated (M+H): 508.1, Found (M+H): 508.1, HPLC purity: 97.56%.

TABLE 24

The following compounds were prepared by the method described above:

| Ex. No. | Structure | Name | Analytical data |
|---|---|---|---|
| 264 | 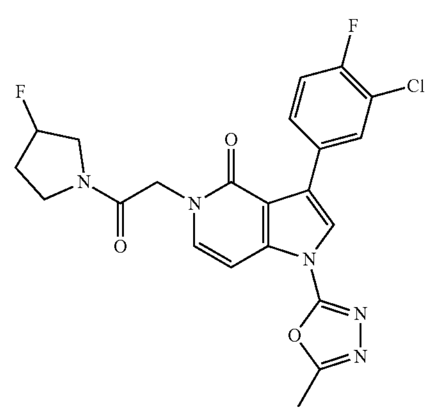 [SMILES: Cc1nnc(-n2cc(-c3ccc(F)c(Cl)c3)c3c(=O)n(CC(=O)N4CCC(F)C4)ccc32)o1] | 3-(3-chloro-4-fluorophenyl)-5-(2-(3-fluoropyrrolidin-1-yl)-2-oxoethyl)-1-(5-methyl-1,3,4-oxadiazol-2-yl)-1H-pyrrolo[3,2-c]pyridin-4(5H)-one | $^1$H-NMR (DMSO-d$_6$, 400 MHz) δ (ppm): 8.11 (d, J = 7.2 Hz, 1H), 7.93 (s, 1H), 7.82 (brs, 1H), 7.60 (d, J = 7.6 Hz, 1H), 7.40 (t, J = 8.8 Hz, 1H), 7.19 (d, J = 7.6 Hz, 1H), 5.51-5.26 (m, 1H), 4.95-4.81 (m, 2H), 3.88-3.35 (m, 4H), 2.58 (s, 3H), 2.26-1.90 (m, 2H). Calculated (M + H): 474.14, Found (M + H): 474.1. HPLC purity: 98.07% |

Example 265: Preparation of 3-(4-fluoro-3-(trifluoromethyl)phenyl)-5-(2-(3-fluoropyrrolidin-1-yl)-2-oxoethyl)-1-(oxetan-3-yl)-1H-pyrrolo[3,2-c]pyridin-4(5H)-one

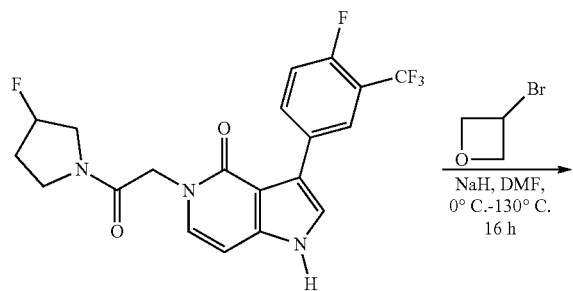

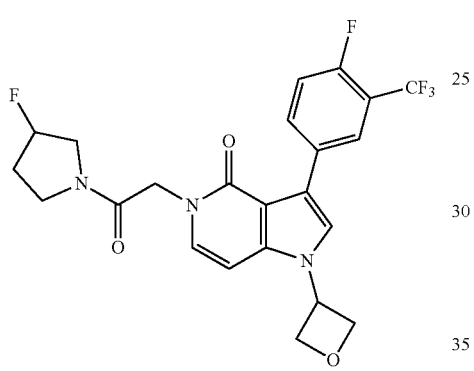

Example 266: Preparation of 3-(4-fluoro-3-(trifluoromethyl)phenyl)-5-(2-(3-fluoropyrrolidin-1-yl)-2-oxoethyl)-1-(1-methyl-1H-1,2,4-triazol-3-yl)-1H-pyrrolo[3,2-c]pyridin-4(5H)-one

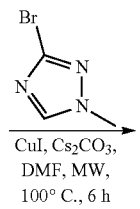

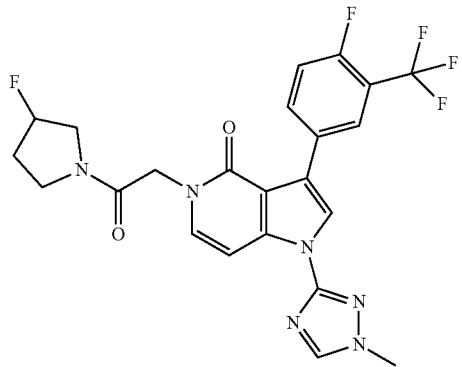

To a stirred suspension of sodium hydride (0.04 g, 1.16 mmol) in N,N-dimethyl formamide was added 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.15 g, 0.35 mmol) at 0° C. and the reaction mixture was stirred at room temperature for 20 min. Then 3-bromooxetane (0.03 mL, 0.70 mmol) was added and the reaction mixture was heated at 130° C. for 16 h. The reaction mixture was quenched with ice cold water (10 mL) and extracted with ethyl acetate (3×25 mL). The combined organic layer was concentrated under vacuum to afford crude product, which was purified by silica gel column chromatography using 4% methanol in dichloromethane to afford title compound 3-(4-fluoro-3-(trifluoromethyl)phenyl)-5-(2-(3-fluoropyrrolidin-1-yl)-2-oxoethyl)-1-(oxetan-3-yl)-1H-pyrrolo[3,2-c]pyridin-4(5H)-one (0.027 g, 16% yield) as white solid. $^1$H-NMR (DMSO-$d_6$, 400 MHz) δ (ppm): 8.35-8.33 (m, 1H), 8.24-8.18 (m, 1H), 8.02 (s, 1H), 7.45 (t, J=10 Hz, 1H), 7.34 (d, J=7.6 Hz, 1H), 6.64 (d, J=7.6 Hz, 1H), 5.74-5.67 (m, 1H), 5.37 (t, J=48.8 Hz, 1H), 5.02-4.94 (m, 4H), 4.87-4.69 (m, 2H), 3.89-3.3 (m, 4H), 2.40-1.90 (m, 2H). Calculated (M+H): 482.14, found (M+H): 482.1. HPLC purity: 99.41%.

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.1 g, 0.23 mmol) in N,N-dimethylformamide (5 mL), 3-bromo-1-methyl-1H-1,2,4-triazole (0.06 g, 0.35 mmol), copper(I) iodide (0.045 g, 0.23 mmol) and cesium carbonate (0.23 g, 0.70 mmol) were added. The reaction mixture was heated at 100° C. for 6 h under microwave conditions. After completion of the reaction, the reaction mixture was quenched with water (20 mL) and extracted with ethyl acetate (3×50 mL). The combined organic layer was washed with brine solution and dried over anhydrous sodium sulfate, filtered and evaporated to afford the crude product which was purified by silica gel column chromatography using 2% methanol in dichloromethane to afford the title compound 3-(4-fluoro-3-(trifluoromethyl)phenyl)-5-(2-(3-fluoropyrrolidin-1-yl)-2-oxoethyl)-1-(1-methyl-1H-1,2,4-triazol-3-yl)-1H-pyrrolo[3,2-c]pyridin-4(5H)-one (0.011 g, 9.2% yield) as off-white solid. $^1$H-NMR (DMSO-$d_6$, 400 MHz) δ (ppm): 8.63 (s, 1H), 8.28 (d, J=6.4 Hz, 1H), 8.14 (brs, 1H), 7.96 (s, 1H), 7.49-7.45 (m, 2H), 7.30 (d, J=7.6 Hz, 1H), 5.5-5.25 (m, 1H), 4.92-4.75 (m, 2H), 3.95 (s, 3H), 3.88-3.38 (m, 4H), 2.31-2.08 (m, 2H). Calculated (M+H): 507.15, Found (M+H): 507.1, HPLC purity: 98.17%.

TABLE 25

The following compounds were prepared by the method described above:

| Ex. No. | Structure | Name | Analytical data |
|---|---|---|---|
| 267 | 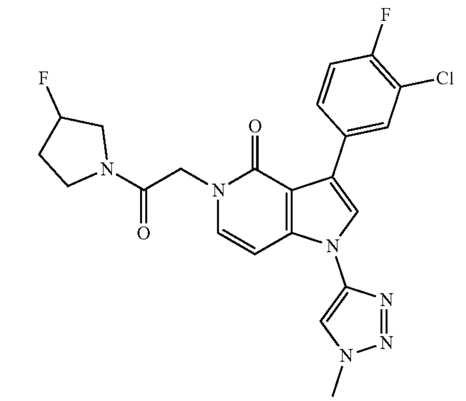 [SMILES: Cn1cc(-n2cc(-c3ccc(F)c(Cl)c3)c3c(=O)n(CC(=O)N4CCC(F)C4)ccc32)nn1] | 3-(3-chloro-4-fluorophenyl)-5-(2-(3-fluoropyrrolidin-1-yl)-2-oxoethyl)-1-(1-methyl-1H-1,2,3-triazol-4-yl)-1H-pyrrolo[3,2-c]pyridin-4(5H)-one | $^1$H-NMR (DMSO-d$_6$, 400 MHz) δ (ppm): 8.58 (s, 1H), 8.19-8.14 (m, 1H), 7.83 (s, 2H), 7.44-7.36 (m, 2H), 6.86 (d, J = 7.6 Hz, 1H), 5.37 (t, J = 50 Hz, 1H), 4.91-4.76 (m, 2H), 4.15 (s, 3H), 3.87-3.29 (m, 4H), 2.30-2.09 (m, 2H). Calculated (M + H): 373.12, found (M + H): 373.1, HPLC purity: 99.18% |
| 268 | 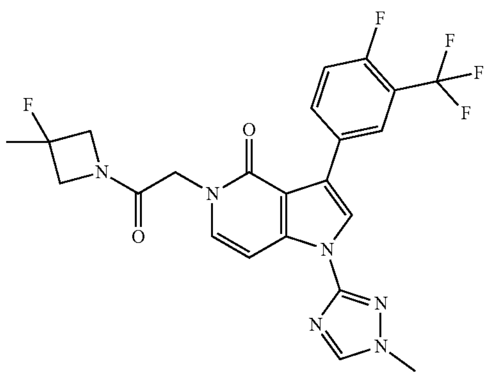 [SMILES: Cn1cnc(-n2cc(-c3ccc(F)c(C(F)(F)F)c3)c3c(=O)n(CC(=O)N4CC(C)(F)C4)ccc32)n1] | 3-(4-fluoro-3-(trifluoromethyl)phenyl)-5-(2-(3-fluoro-3-methylazetidin-1-yl)-2-oxoethyl)-1-(1-methyl-1H-1,2,4-triazol-3-yl)-1H-pyrrolo[3,2-c]pyridin-4(5H)-one | $^1$H-NMR (DMSO-d$_6$, 400 MHz) δ (ppm): 8.63 (s, 1H), 8.31 (d, J = 6.4 Hz, 1H), 8.13 (brs, 1H), 7.97 (s, 1H), 7.49-7.45 (m, 2H), 7.31 (d, J = 7.6 Hz, 1H), 4.64 (s, 2H), 4.39-4.32 (m, 2H), 3.99-3.94 (m, 5H), 1.58 (d, J = 22 Hz, 3H). Calculated (M + H): 507.15, Found (M + H): 507.1, HPLC purity: 94.78% |
| 269 | 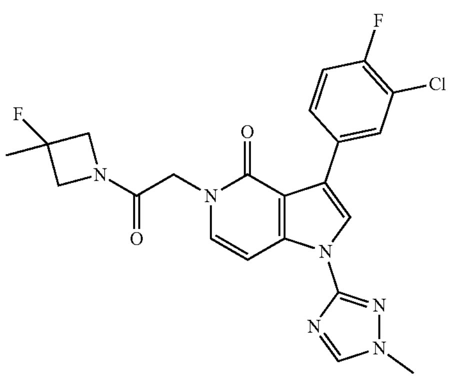 [SMILES: Cn1cnc(-n2cc(-c3ccc(F)c(Cl)c3)c3c(=O)n(CC(=O)N4CC(C)(F)C4)ccc32)n1] | 3-(3-chloro-4-fluorophenyl)-5-(2-(3-fluoro-3-methylazetidin-1-yl)-2-oxoethyl)-1-(1-methyl-1H-1,2,4-triazol-3-yl)-1H-pyrrolo[3,2-c]pyridin-4(5H)-one | $^1$H-NMR (DMSO-d$_6$, 400 MHz) δ (ppm): 8.63 (s, 1H), 8.13 (d, J = 6 Hz, 1H), 7,89 (s, 1H), 7.82-7.76 (m, 1H), 7.47 (d, J = 7.6 Hz, 1H), 7.37 (t, J = 9.2 Hz, 1H), 7.30 (d, J = 7.6 Hz, 1H), 4.64 (s, 2H), 4.41-4.28 (m, 2H), 4.00-3.94 (m, 5H), 1.58 (d, J = 22 Hz, 3H). Calculated (M + H): 507.15, Found (M + H): 507.1, HPLC purity: 94.78% |
| 270 | 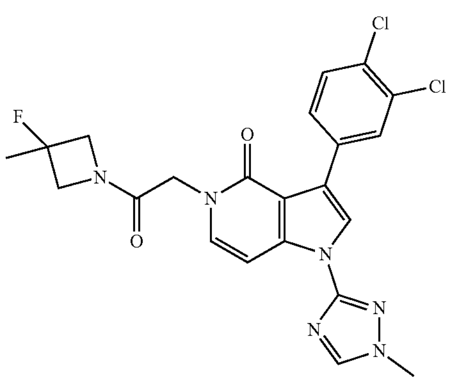 | 3-(3,4-dichlorophenyl)-5-(2-(3-fluoro-3-methylazetidin-1-yl)-2-oxoethyl)-1-(1-methyl-1H-1,2,4-triazol-3-yl)-1H-pyrrolo[3,2-c]pyridin-4(5H)-one | $^1$H-NMR (DMSO-d$_6$, 400 MHz) δ (ppm): 8.63 (s, 1H), 8.22 (d, J = 1.6 Hz, 1H), 7.96 (s, 1H), 7.82 (dd, J = 2.0 Hz, 8.4 Hz, 1H), 7.58 (d, J = 8.8 Hz, 1H), 7.48 (d, J = 7.6 Hz, 1H), 7.3 (d, J = 7.6 Hz, 1H), 4.65 (s, 2H), 4.41-4.29 (m, 2H), 4.0-3.94 (m, 5H) 1.6 (d, J = 22 Hz, 3H). Calculated (M + H): 489.1, Found (M + H): 489.1, HPLC purity: 99.78% |

TABLE 25-continued

The following compounds were prepared by the method described above:

| Ex. No. | Structure | Name | Analytical data |
|---|---|---|---|
| 271 | 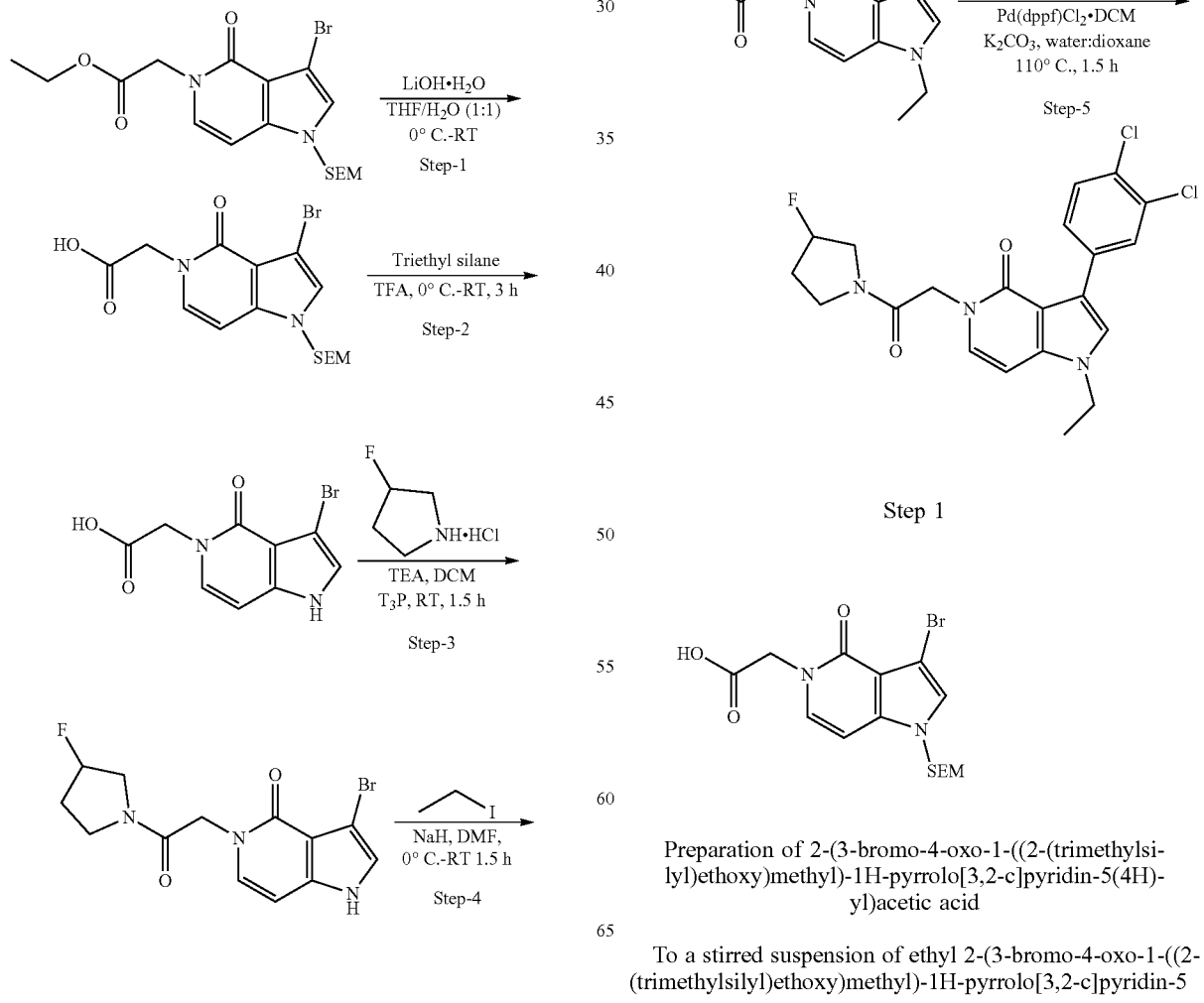 | 3-(3-chloro-4-fluorophenyl)-5-(2-(3-fluoro-3-methylazetidin-1-yl)2-oxoethyl)-1-(1-methyl-1H-1,2,3-triazol-4-yl)-1H-pyrrolo[3,2-c]pyridin-4(5H)-one | $^1$H-NMR (DMSO-$d_6$, 400 MHz) δ (ppm): 8.58 (s, 1H), 8.15 (d, J = 6 Hz, 1H), 7.84 (s, 2H), 7.45-7.37 (m, 2H), 6.87 (d, J = 7.6 Hz, 1H), 4.64 (s, 2H), 4.39-4.32 (m, 2H), 4.15 (s, 3H), 4.0-3.95 (m, 2H), 1.6 (d, J = 22 Hz, 3H). Calculated (M + H): 473.12, Found (M + H): 473.1, HPLC purity: 98.92% |

Example 272: Preparation of 3-(4-chloro-3-(trifluoromethyl)phenyl)-5-(2-(3-fluoropyrrolidin-1-yl)-2-oxoethyl)-1H-pyrrolo[3,2-c]pyridin-4(5H)-one Step 1

Preparation of 2-(3-bromo-4-oxo-1-((2-(trimethylsilyl)ethoxy)methyl)-1H-pyrrolo[3,2-c]pyridin-5(4H)-yl)acetic acid To a stirred suspension of ethyl 2-(3-bromo-4-oxo-1-((2-(trimethylsilyl)ethoxy)methyl)-1H-pyrrolo[3,2-c]pyridin-5

(4H)-yl)acetate (4.0 g, 9.31 mmol) in tetrahydrofuran and water (20 mL, 1:1) at 0° C., was added lithium hydroxide monohydrate (1.95 g, 46.57 mmol). The reaction mixture was stirred at room temperature for 1 h. After completion of the reaction, the reaction mixture was acidified with 1.5 N hydrochloric acid (pH 2~3) and extracted with ethyl acetate (2×100 mL). The combined organic layer was dried over anhydrous sodium sulfate, filtered and evaporated under vacuum to afford the title compound 2-(3-bromo-4-oxo-1-((2-(trimethylsilyl)ethoxy)methyl)-1H-pyrrolo[3,2-c]pyridin-5(4H)-yl)acetic acid (3.2 g, 86.0% yield) as a white solid. Calculated (M+H): 401.05, Found (M+H): 401.2.

Step 2

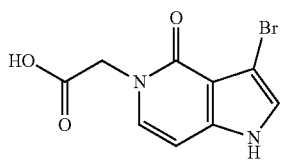 [SMILES: O=C(O)Cn1ccc2[nH]cc(Br)c2c1=O]

Preparation of 2-(3-bromo-4-oxo-1H-pyrrolo[3,2-c]pyridin-5(4H)-yl)acetic acid

To a stirred suspension of 2-(3-bromo-4-oxo-1-((2-(trimethylsilyl)ethoxy)methyl)-1H-pyrrolo[3,2-c]pyridin-5(4H)-yl)acetic acid (2.1 g, 5.23 mmol) in triethylsilane (1.65 mL, 10.47 mmol), was added trifluro acetic acid (20.04 mL, 261.84 mmol) at room temperature and the reaction mixture was stirred at room temperature for 3 h. After completion of reaction, the reaction mixture was evaporated under vacuum and the residue was diluted with 1 mL of acetonitrile and 16 mL of ammonium hydroxide. The resulting mixture was stirred for 2 h at room temperature and acidified with concentrated hydrochloric acid at 0° C. The precipitated product was filtered and dried to afford the title compound 2-(3-bromo-4-oxo-1H-pyrrolo[3,2-c]pyridin-5(4H)-yl)acetic acid (1.0 g, 70% yield) as a pale brown solid. Calculated (M+H): 270.96, Found (M+H): 271.1.

Step 3

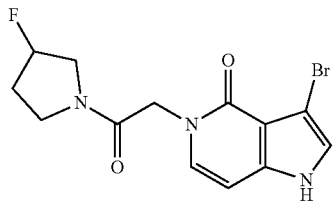 [SMILES: O=C(Cn1ccc2[nH]cc(Br)c2c1=O)N1CCC(F)C1]

Preparation of 3-bromo-5-(2-(3-fluoropyrrolidin-1-yl)-2-oxoethyl)-1H-pyrrolo[3,2-c]pyridin-4(5H)-one To a stirred suspension of 2-(3-bromo-4-oxo-1H-pyrrolo[3,2-c]pyridin-5(4H)-yl)acetic acid (2.1 g, 5.23 mmol) and 3-fluoropyrrolidine hydrochloride (0.34 g, 2.76 mmol) in dichloromethane (10 mL), was added triethylamine (1.28 mL, 9.22 mmol) and the reaction mixture was cooled to 0° C. Then 1-propylphosphonic anhydride (2.19 mL, 3.69 mmol, 50% solution in ethyl acetate) was added and the reaction mixture was stirred at room temperature for 1.5 h. The reaction mixture was diluted with dichloromethane (50 mL), washed with water (20 mL), brine (20 mL), dried over anhydrous sodium sulfate, filtered and concentrated under vacuum to afford crude product, which was purified by silica gel column chromatography using 3% methanol in dichloromethane to afford title compound 3-bromo-5-(2-(3-fluoropyrrolidin-1-yl)-2-oxoethyl)-1H-pyrrolo[3,2-c]pyridin-4(5H)-one (0.75 g, 62% yield) as brownish solid. Calculated (M+H): 342.02, Found (M+H): 342.0.

Step 4

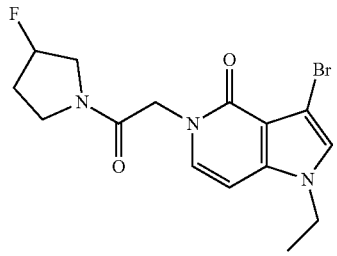 [SMILES: CCn1cc(Br)c2c(=O)n(CC(=O)N3CCC(F)C3)ccc21]

Preparation of 3-bromo-1-ethyl-5-(2-(3-fluoropyrrolidin-1-yl)-2-oxoethyl)-1H-pyrrolo[3,2-c]pyridin-4(5H)-one To a stirred suspension of sodium hydride (0.04 g, 1.16 mmol) in N,N-dimethyl formamide was added 3-bromo-5-(2-(3-fluoropyrrolidin-1-yl)-2-oxoethyl)-1H-pyrrolo[3,2-c]pyridin-4(5H)-one (0.2 g, 0.58 mmol) at 0° C. and the reaction mixture was stirred at room temperature for 20 min. Then ethyl iodide (0.06 mL, 0.87 mmol) was added and the reaction mixture was stirred at room temperature for 1.5 h. The reaction mixture was quenched with ice water (10 mL) and extracted with ethyl acetate (3×25 mL). The combined organic layer was concentrated under vacuum to afford crude product, which was purified by silica gel column chromatography using 3% methanol in dichloromethane to afford title compound 3-bromo-1-ethyl-5-(2-(3-fluoropyrrolidin-1-yl)-2-oxoethyl)-1H-pyrrolo[3,2-c]pyridin-4(5H)-one (0.11 g, 52% yield) as white solid. Calculated (M+H): 370.05, Found (M+H): 370.0.

Step 5

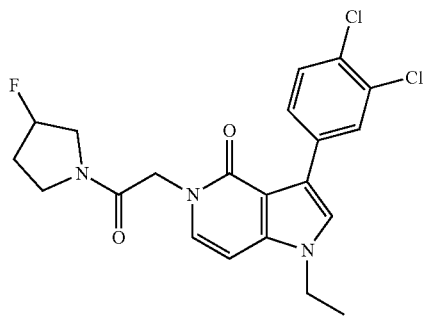 [SMILES: CCn1cc(-c2ccc(Cl)c(Cl)c2)c2c(=O)n(CC(=O)N3CCC(F)C3)ccc21]

Preparation of 3-(3,4-dichlorophenyl)-1-ethyl-5-(2-(3-fluoropyrrolidin-1-yl)-2-oxoethyl)-1H-pyrrolo[3,2-c]pyridin-4(5H)-one To a stirred suspension of 3-bromo-1-ethyl-5-(2-(3-fluoropyrrolidin-1-yl)-2-oxoethyl)-1H-pyrrolo[3,2-c]pyridin-4(5H)-one (0.11 g, 0.30 mmol) in 1,4-dioxane:water mixture (5 mL, 4:1), was added (3,4-dichlorophenyl)boronic acid (0.08 g, 0.45 mmol) at room temperature and the resulting mixture was purged with argon for 10 min. To the above mixture [1,1'-bis(diphenylphosphino)ferrocene]dichloropalladium(II) dichloromethane complex (0.01 g, 0.01 mmol) and potassium carbonate (0.126 g, 0.91 mmol) were added and the reaction mixture was stirred at 110° C. for 1.5 h. After completion of reaction, the mixture was cooled to room temperature, diluted with water (10 mL) and extracted with ethyl acetate (3×25 mL). The combined organic layer was dried over anhydrous sodium sulfate, filtered and concentrated under vacuum to afford crude product, which was purified by silica gel column chromatography using 2.5% methanol in dichloromethane to afford the title compound 3-(3,4-dichlorophenyl)-1-ethyl-5-(2-(3-fluoropyrrolidin-1-yl)-2-oxoethyl)-1H-pyrrolo[3,2-c]pyridin-4(5H)-one (0.03 g, 29%) as a white solid. $^1$H-NMR (DMSO-$d_6$, 400 MHz) δ (ppm): 8.26 (d, J=1.2 Hz, 1H), 7.82 (d, J=9.2 Hz, 1H), 7.62 (s, 1H), 7.52 (d, J=9.2 Hz, 1H), 7.31 (d, J=7.2 Hz, 1H), 6.62 (d, J=7.2 Hz, 1H), 5.37 (t, J=49.6 Hz, 1H), 4.83-4.71 (m, 2H), 4.15-4.09 (m, 2H), 3.86-3.32 (m, 4H), 2.30-1.97 (m, 2H), 1.36 (t, J=6.8 Hz, 3H). Calculated (M+H): 436.09, found (M+H): 436.1, HPLC purity: 96.77%.

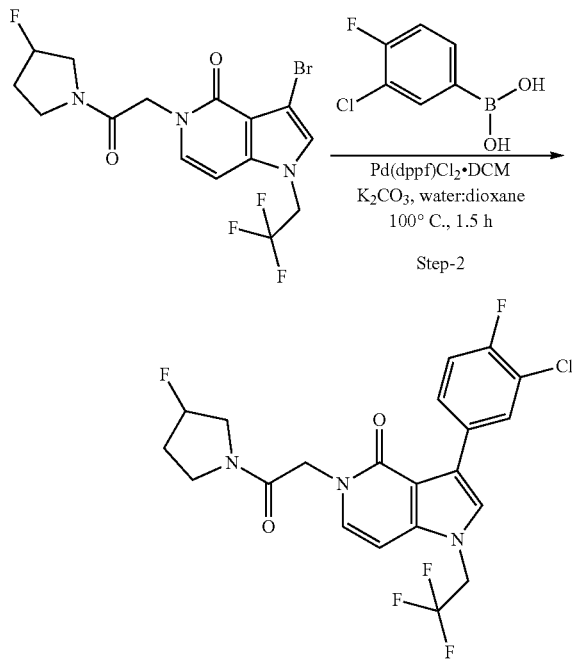

TABLE 26

The following compounds were prepared by the method described above:

| Ex. No. | Structure | Name | Analytical data |
|---|---|---|---|
| 273 | (structure shown) | 3-(3,4-dichlorophenyl)-1-(2-fluoroethyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.24 (s, 1H), 7.79 (d, J = 8.4 Hz, 1H), 7.59 (s, 1H), 7.54 (d, J = 8.4 Hz, 1H), 7.32 (d, J = 7.2 Hz, 1H), 6.64 (d, J = 7.6 Hz, 1H), 5.37 (t, J = 49.6 Hz, 1H), 4.87-4.67 (m, 4H), 4.44 (d, J = 28 Hz, 2H), 3.90-3.37 ((m, 4H), 2.30-1.94 (m, 2H). Calculated (M + H): 454.08, found (M + H): 454.1, HPLC purity: 99.97% |

Example 274: 3-(3-chloro-4-fluorophenyl)-5-(2-(3-fluoropyrrolidin-1-yl)-2-oxoethyl)-1-(2,2,2-trifluoroethyl)-1H-pyrrolo[3,2-c]pyridin-4(5H)-one Step-1

Preparation of 3-bromo-5-(2-(3-fluoropyrrolidin-1-yl)-2-oxoethyl)-1-(2,2,2-trifluoroethyl)-1H-pyrrolo[3,2-c]pyridin-4(5H)-one To a stirred suspension of 3-bromo-5-(2-(3-fluoropyrrolidin-1-yl)-2-oxoethyl)-1H-pyrrolo[3,2-c]pyridin-4(5H)-one (0.2 g, 0.58 mmol) in N,N-dimethylformamide (10 mL), cesium carbonate (0.57 g, 1.75 mmol) and 2,2,2-trifluoroethyl 4-methylbenzenesulfonate (0.22 g, 0.87 mmol) were added and the reaction mixture was heated at 90° C. in a orbital shaker for 16 h. The reaction mixture was diluted with ice water (10 mL) and extracted with ethyl acetate (3×25 mL). The combined organic layer was concentrated under vacuum to afford crude product, which was purified by silica gel column chromatography using 2.5% methanol in dichloromethane to afford the title compound 3-bromo-5-(2-(3-fluoropyrrolidin-1-yl)-2-oxoethyl)-1-(2,2,2-trifluoroethyl)-1H-pyrrolo[3,2-c]pyridin-4(5H)-one (0.08 g, 32% yield) as a white solid. Calculated (M+H): 424.02, Found (M+H): 424.0.

Step-2

Preparation of 3-(3-chloro-4-fluorophenyl)-5-(2-(3-fluoropyrrolidin-1-yl)-2-oxoethyl)-1-(2,2,2-trifluoroethyl)-1H-pyrrolo[3,2-c]pyridin-4(5H)-one To a stirred suspension of 3-bromo-5-(2-(3-fluoropyrrolidin-1-yl)-2-oxoethyl)-1-(2,2,2-trifluoroethyl)-1H-pyrrolo[3,2-c]pyridin-4(5H)-one (0.075 g, 0.17 mmol) in 1,4-dioxane:water mixture (5 mL, 4:1) was added (3-chloro-4-fluorophenyl)boronic acid (0.037 g, 0.21 mmol) at room temperature and the resulting mixture was purged with argon for 10 min. Then [1,1'-bis(diphenylphosphino)ferrocene]dichloropalladium(II) dichloromethane complex (0.007 g, 0.008 mmol) and potassium carbonate (0.073 g, 0.53 mmol) were added and the reaction mixture was stirred at 100° C. for 1.5 h. After completion of reaction, the mixture was cooled to room temperature, diluted with water (10 mL) and extracted with ethyl acetate (3×25 mL). The combined organic layer was dried over anhydrous sodium sulfate, filtered and concentrated under vacuum to afford crude product, which was purified by silica gel column chromatography using 3% methanol in dichloromethane to afford the title compound 3-(3-chloro-4-fluorophenyl)-5-(2-(3-fluoropyrrolidin-1-yl)-2-oxoethyl)-1-(2,2,2-trifluoroethyl)-1H-pyrrolo[3,2-c]pyridin-4(5H)-one (0.016 g, 16% yield) as a white solid. $^1$H-NMR (DMSO-$d_6$, 400 MHz) δ (ppm): 8.08 (dd, J=2.4 Hz, 7.6 Hz, 1H), 7.78-7.70 (m, 1H), 7.51 (s, 1H), 7.40-7.33 (m, 2H), 6.74 (d, J=7.6 Hz, 1H), 5.37 (t, J=49.2 Hz, 1H), 5.20-5.13 (m, 2H), 4.88-4.72 (m, 2H), 3.90-3.38 (m, 4H), 2.31-1.94 (m, 2H). Calculated (M+H): 473.82, found (M+H): 473.82, HPLC purity: 98.74%.

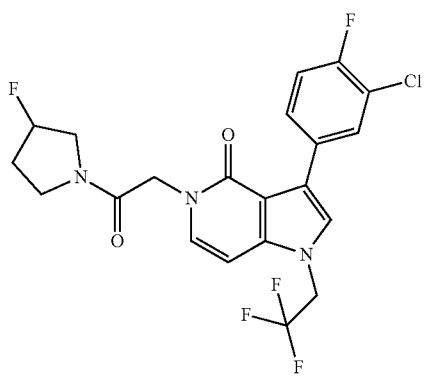 [SMILES: O=C(Cn1ccc2c(c(-c3ccc(F)c(Cl)c3)cn2CC(F)(F)F)c1=O)N1CCC(F)C1]

TABLE 27

The following compounds were prepared by the method described above:

| Ex. No. | Structure | Name | Analytical data |
|---|---|---|---|
| 275 | 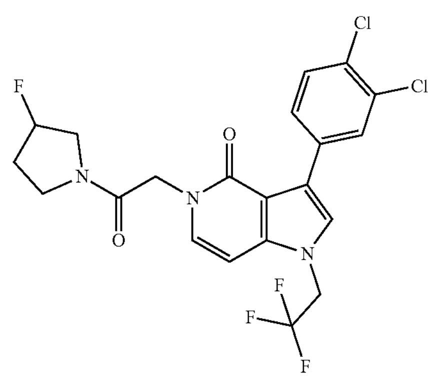 [SMILES: O=C(Cn1ccc2c(c(-c3ccc(Cl)c(Cl)c3)cn2CC(F)(F)F)c1=O)N1CCC(F)C1] | 3-(3,4-dichlorophenyl)-5-(2-(3-fluoropyrrolidin-1-yl)-2-oxoethyl)-1-(2,2,2-trifluoroethyl)-1H-pyrrolo[3,2-c]pyridin-4(5H)-one | $^1$H-NMR (DMSO-$d_6$, 400 MHz) δ (ppm): 8.18 (s, 1H), 7.74 (d, J = 8.4 Hz, 1H), 7.59-7.55 (m, 2H), 7.40 (d, J = 7.2 Hz, 1H), 6.75 (d, J = 7.2 Hz, 1H), 5.37 (t, J = 50.0 Hz, 1H), 5.19-5.14 (m, 2H), 4.88-4.72 (m, 2H), 3.86-3.40 (m, 4H), 2.30-2.09 (m, 2H). Calculated (M + H): 490.06, found (M + H): 490.0, HPLC purity: 98.24% |

TABLE 27-continued

The following compounds were prepared by the method described above:

| Ex. No. | Structure | Name | Analytical data |
|---|---|---|---|
| 276 | (structure shown) | 3-(3,4-dichlorophenyl)-1-(2,2-difluoroethyl)-5-(2-(3-fluoropyrrolidin-1-yl)-2-oxoethyl)-1H-pyrrolo[3,2-c]pyridin-4(5H)-one | $^1$H-NMR (DMSO-$d_6$, 400 MHz) δ (ppm): 8.21 (d, J = 1.6 Hz, 1H), 7.76 (d, J = 8.4 Hz, 1H), 7.57-7.54 (m, 2H), 7.35 (d, J = 7.6 Hz, 1H), 6.68 (d, J = 7.2 Hz, 1H), 6.40 (t, J = 54.8 Hz, 1H), 5.37 (t, J = 49.6 Hz, 1H), 4.88-4.61 (m, 4H), 3.90-3.24 (m, 4H), 2.30-1.91 (m, 2H). Calculated (M + H): 472.07, found (M + H): 472.1, HPLC purity: 99.83% |

Example 277: Preparation of 3-(4-fluoro-3-(trifluoromethyl)phenyl)-5-(2-(3-fluoropyrrolidin-1-yl)-2-oxoethyl)-1-(2,2,2-trifluoroethyl)-1H-pyrrolo[3,2-c]pyridin-4(5H)-one

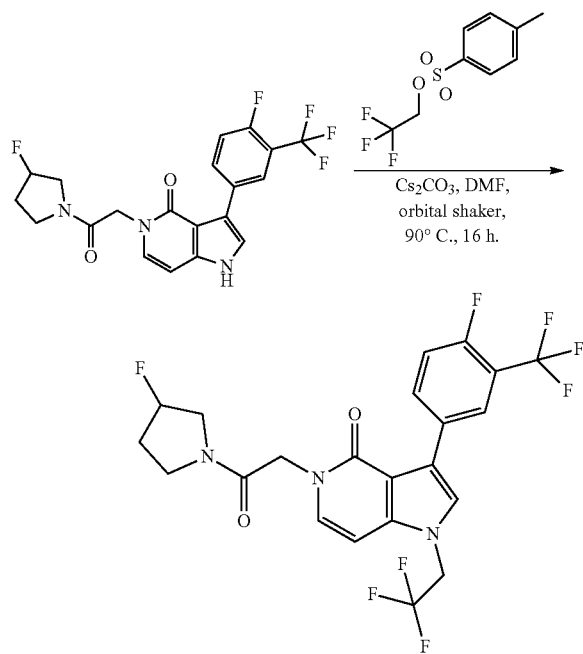

To a solution of 3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one (0.15 g, 0.35 mmol) in N, N-dimethylformamide (3 mL), 2,2,2-trifluoroethyl 4-methylbenzenesulfonate (0.18 g, 0.70 mmol) and cesium carbonate (0.34 g, 1.05 mmol) were added. The reaction mixture was heated in orbital shaker at 90° C. for 16 h. After completion of the reaction, the reaction mixture was quenched with water (20 mL) and extracted with ethyl acetate (3×50 mL). The combined organic layer was washed with brine solution (50 mL), dried over anhydrous sodium sulfate, filtered and evaporated to afford the crude product which was purified by prep HPLC (column: chemsil C18 (250 mm×4.6 mm×5μ), mobile phase (A): 0.1% Ammonia in water, mobile phase (B): acetonitrile, flow rate: 1.0 mL/min, T/% B: 0/20, 10/80, 25/90, 27/20, 30/20) to afford the title compound 3-(4-fluoro-3-(trifluoromethyl)phenyl)-5-(2-(3-fluoropyrrolidin-1-yl)-2-oxoethyl)-1-(2,2,2-trifluoroethyl)-1H-pyrrolo[3,2-c]pyridin-4(5H)-one (0.019 g, 10.6% yield) as a white solid. $^1$H-NMR (DMSO-$d_6$, 400 MHz) δ (ppm): 8.22 (d, J=6 Hz, 1H), 8.1 (s, 1H), 7.58 (s, 1H), 7.47 (t, J=9.6 Hz, 1H), 7.74 (d, J=7.6 Hz, 1H), 6.76 (d, J=7.6 Hz, 1H), 5.5-5.25 (m, 1H), 5.22-5.15 (m, 2H), 4.88-4.71 (m, 2H), 3.90-3.57 (m, 4H), 2.31-1.96 (m, 2H). Calculated (M+H): 508.12, Found (M+H): 508.1, HPLC purity: 99.65%.

TABLE 28

The following compounds were prepared by the method described above:

| Ex. No. | Structure | Name | Analytical data |
|---|---|---|---|
| 278 | 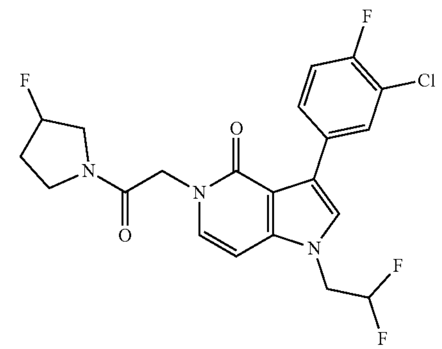 [SMILES: O=C(Cn1ccc2c(c(-c3ccc(F)c(Cl)c3)cn2CC(F)F)c1=O)N1CCC(F)C1] | 3-(3-chloro-4-fluorophenyl)-1-(2,2-difluoroethyl)-5-(2-(3-fluoropyrrolidin-1-yl)-2-oxoethyl)-1H-pyrrolo[3,2-c]pyridin-4(5H)-one | $^1$H-NMR (DMSO-d$_6$, 400 MHz) δ (ppm): 8.10 (d, J = 7.2 Hz, 1H), 7.74 (brs, 1H), 7.50 (s, 1H), 7.38-7.33 (m, 2H), 6.67 (d, J = 7.6 Hz, 1H), 6.54-6.26 (m, 1H), 5.50-5.25 (m, 1H), 4.87-4.61 (m, 4H), 3.89-3.30 (m, 4H), 2.30-1.90 (m, 2H). Calculated (M + H): 456.10, Found (M + H): 456.1. HPLC purity: 99.43% |
| 279 | 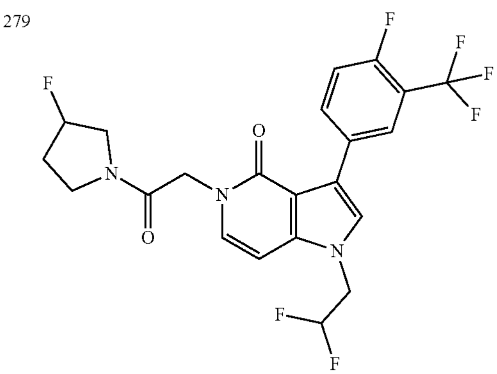 | 1-(2,2-difluoroethyl)-3-(4-fluoro-3-(trifluoromethyl)phenyl)-5-(2-(3-fluoropyrrolidin-1-yl)-2-oxoethyl)-1H-pyrrolo[3,2-c]pyridin-4(5H)-one | $^1$H-NMR (DMSO-d$_6$, 400 MHz) δ (ppm): 8.24 (d, J = 6.8 Hz, 1H), 8.1 (brs, 1H), 7.56 (s, 1H), 7.46 (t, J = 9.2 Hz, 1H), 7.35 (d, J = 7.2 Hz, 1H), 6.69 (d, J = 7.2 Hz, 1H), 6.54-6.27 (m, 1H), 5.5-5.25 (m, 1H), 4.88-4.62 (m, 4H), 3.90-3.39 (m, 4H), 2.31-1.93 (m, 2H). Calculated (M + H): 490.13, Found (M + H): 490.1, HPLC purity: 98.19% |
| 280 | 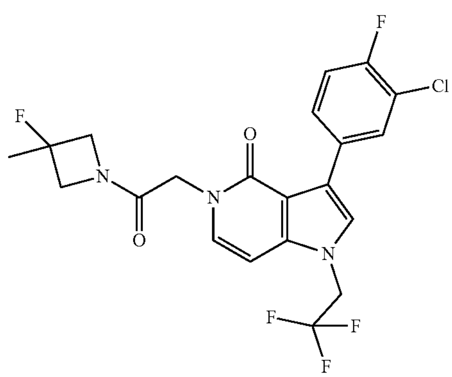 [SMILES: CC1(F)CN(C(=O)Cn2ccc3c(c(-c4ccc(F)c(Cl)c4)cn3CC(F)(F)F)c2=O)C1] | 3-(3-chloro-4-fluorophenyl)-5-(2-(3-fluoro-3-methylazetidin-1-yl)-2-oxoethyl)-1-(2,2,2-trifluoroethyl)-1H-pyrrolo[3,2-c]pyridin-4(5H)-one | $^1$H-NMR (DMSO-d$_6$, 400 MHz) δ (ppm): 8.09 (dd, J = 2.4 Hz, 7.2 Hz, 1H), 7.74-7.71 (m, 1H), 7.52 (s, 1H), 7.41-7.34 (m, 2H), 6.76 (d, J = 7.6 Hz, 1H), 5.17 (m, 2H), 4.6 (s, 2H), 4.41-4.29 (m, 2H), 3.99-3.95 (m, 2H), 1.6 (d, J = 22.4 Hz, 3H). Calculated (M + H): 474.09, Found (M + H): 474.1, HPLC purity: 99.31% |
| 281 | 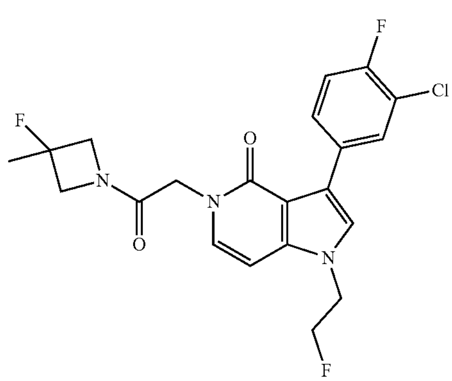 [SMILES: CC1(F)CN(C(=O)Cn2ccc3c(c(-c4ccc(F)c(Cl)c4)cn3CCF)c2=O)C1] | 3-(3-chloro-4-fluorophenyl)-5-(2-(3-fluoro-3-methylazetidin-1-yl)-2-oxoethyl)-1-(2-fluoroethyl)-1H-pyrrolo[3,2-c]pyridin-4(5H)-one | $^1$H-NMR (DMSO-d$_6$, 400 MHz) δ (ppm): 8.14 (dd, J = 2.0 Hz, 7.2 Hz, 1H), 7.78-7.75 (m, 1H), 7.53 (s, 1H), 7.37-7.31 (m, 2H), 6.65 (d, J = 7.2 Hz, 1H), 4.81-4.79 (m, 1H), 4.69-4.67 (m, 1H), 4.59 (s, 2H), 4.48-4.46 (m, 1H), 4.42-4.29 (m, 3H), 3.99-3.95 (m, 2H), 1.6 (d, J = 22.4 Hz, 3H). Calculated (M + H): 438.11, Found (M + H): 438.1, HPLC purity: 98.2% |

TABLE 28-continued

The following compounds were prepared by the method described above:

| Ex. No. | Structure | Name | Analytical data |
|---|---|---|---|
| 282 | 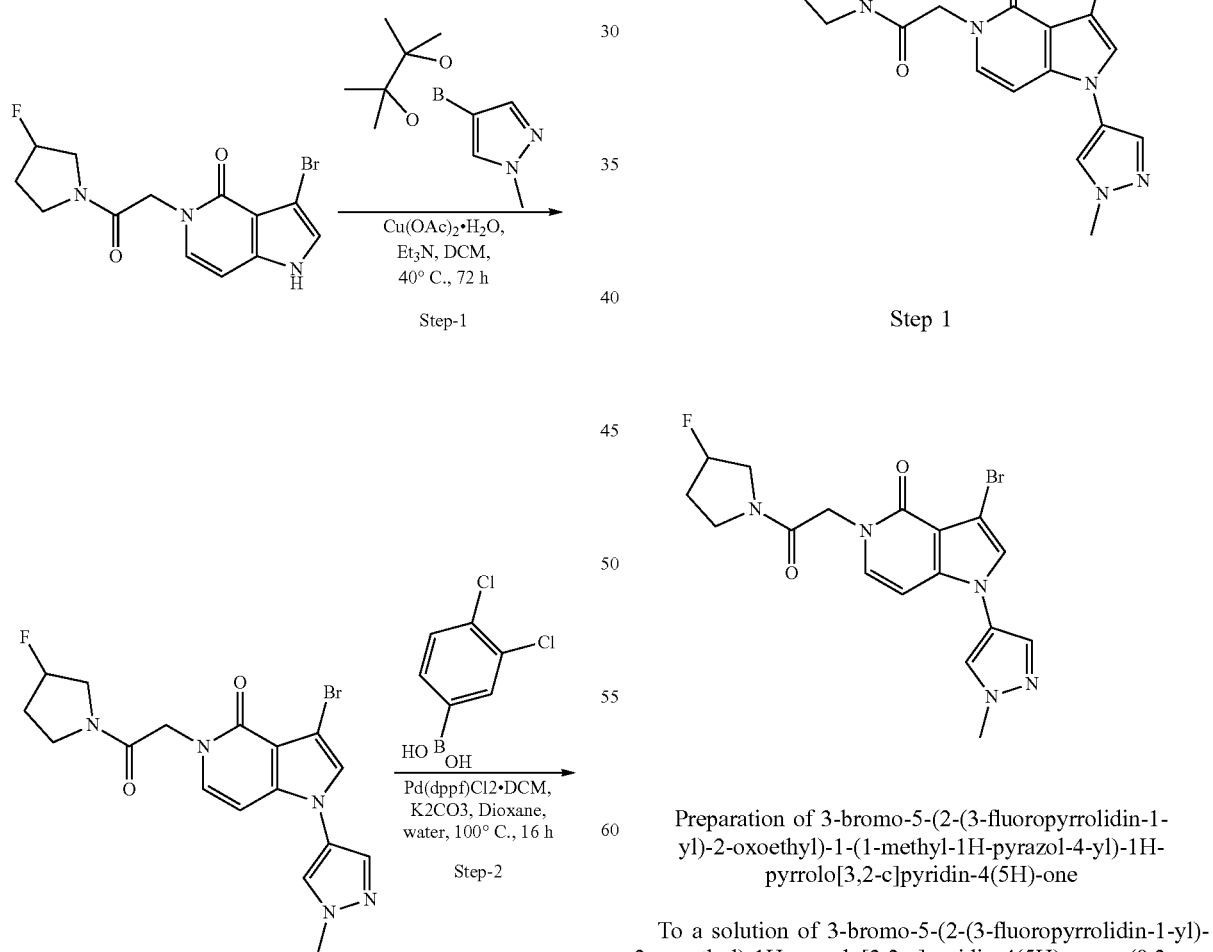 | 3-(3-chloro-4-fluorophenyl)-5-(2-(3-fluoro-3-methylazetidin-1-yl)-2-oxoethyl)-1-(oxetan-3-yl)-1,5-dihydro-4H-pyrrolo[3,2-c]pyridin-4-one | $^1$H-NMR (DMSO-d$_6$, 400 MHz) δ (ppm): 8.21-8.19 (m, 1H), 7.96 (s, 1H), 7.90-7.86 (m, 1H), 7.38-7.32 (m, 2H), 6.64 (d, J = 7.6 Hz, 1H), 5.71-5.65 (m, 1H), 5.01-4.91 (m, 4H), 4.59 (s, 2H), 4.39-4.30 (m, 2H), 3.98-3.94 (m, 2H), 1.59 (d, J = 22 Hz, 3H). Calculated (M + H): 448.12; Found (M + 1): 448.1. HPLC purity 99.64% |

Example 283: Preparation of 3-(3,4-dichlorophenyl)-5-(2-(3-fluoropyrrolidin-1-yl)-2-oxoethyl)-1-(1-methyl-1H-pyrazol-4-yl)-1H-pyrrolo[3,2-c]pyridin-4(5H)-one Preparation of 3-bromo-5-(2-(3-fluoropyrrolidin-1-yl)-2-oxoethyl)-1-(1-methyl-1H-pyrazol-4-yl)-1H-pyrrolo[3,2-c]pyridin-4(5H)-one To a solution of 3-bromo-5-(2-(3-fluoropyrrolidin-1-yl)-2-oxoethyl)-1H-pyrrolo[3,2-c]pyridin-4(5H)-one (0.2 g, 0.58 mmol) in dichloromethane (20 mL), triethylamine (0.25 mL, 1.75 mmol) and copper(II)acetate mono hydrate (0.17 g, 0.87 mmol) were added and the reaction mixture was purged with air for 1 h. Then 1-methyl-4-(4,4,5,5-tetramethyl-1,3,2-dioxaborolan-2-yl)-1H-pyrazole (0.18 g, 0.87 mmol) was added and the reaction mixture was heated at 40° C. for 72 h in the presence of air. The reaction mixture was diluted with dichloromethane, washed with water, dried over anhydrous sodium sulfate, filtered and concentrated under vacuum to afford the crude product, which was purified by silica gel column chromatography using 5% methanol in dichloromethane to afford the title compound 3-bromo-5-(2-(3-fluoropyrrolidin-1-yl)-2-oxoethyl)-1-(1-methyl-1H-pyrazol-4-yl)-1H-pyrrolo[3,2-c]pyridin-4(5H)-one (0.07 g, 31% yield) as off white solid. ¹H-NMR (DMSO-d₆, 400 MHz) δ (ppm): 8.20 (s, 1H), 7.78 (s, 1H), 7.46 (s, 1H), 7.32 (d, J=6.8 Hz, 1H), 6.44 (d, J=7.6 Hz, 1H), 5.51-5.26 (m, 1H), 4.82-4.65 (m, 2H), 3.92-3.40 (m, 7H), 2.30-1.92 (m, 2H).

Step 2

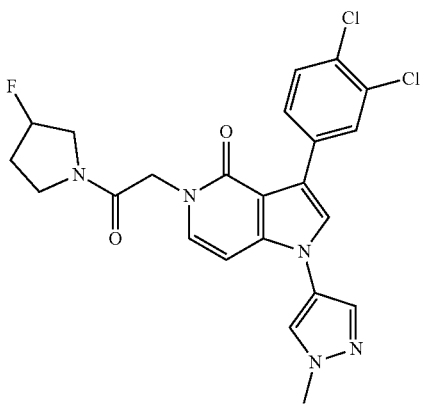 [SMILES: Cn1cc(-n2cc(-c3ccc(Cl)c(Cl)c3)c3c(=O)n(CC(=O)N4CCC(F)C4)ccc32)cn1]

Preparation of 3-(3,4-dichlorophenyl)-5-(2-(3-fluoropyrrolidin-1-yl)-2-oxoethyl)-1-(1-methyl-1H-pyrazol-4-yl)-1H-pyrrolo[3,2-c]pyridin-4(5H)-one To a stirred suspension of 3-bromo-5-(2-(3-fluoropyrrolidin-1-yl)-2-oxoethyl)-1-(1-methyl-1H-pyrazol-4-yl)-1H-pyrrolo[3,2-c]pyridin-4(5H)-one (0.07 g, 0.16 mmol) in 1,4-dioxane:water mixture (10 mL, 4:1) was added (3,4-dichlorophenyl)boronic acid (0.050 g, 0.24 mmol) at room temperature and the resulting mixture was purged with argon for 10 min. Then [1,1'-bis(diphenylphosphino)ferrocene]dichloropalladium(II) dichloromethane complex (0.007 g, 0.008 mmol) and potassium carbonate (0.07 g, 0.49 mmol) were added and the reaction mixture was stirred at 100° C. for 16 h. After completion of reaction, the mixture was cooled to room temperature, diluted with water (10 mL) and extracted with ethyl acetate (3×25 mL). The combined organic layer was dried over anhydrous sodium sulfate, filtered and concentrated under vacuum to afford crude product, which was purified by silica gel column chromatography using 3% methanol in dichloromethane to afford the title compound 3-(3,4-dichlorophenyl)-5-(2-(3-fluoropyrrolidin-1-yl)-2-oxoethyl)-1-(1-methyl-1H-pyrazol-4-yl)-1H-pyrrolo[3,2-c]pyridin-4(5H)-one (0.022 g, 28% yield) as a off white solid. ¹H-NMR (DMSO-d₆, 400 MHz) δ (ppm): 8.27-8.25 (m, 2H), 7.87-7.84 (m, 2H), 7.73 (s, 1H), 7.56 (d, J=8.4 Hz, 1H), 7.38-7.36 (m, 1H), 6.51 (d, J=7.2 Hz, 1H), 5.5-5.25 (m, 1H), 4.91-4.75 (m, 2H), 3.91 (s, 3H), 3.87-3.28 (m, 4H), 2.3-2.6 (m, 2H). Calculated (M+H): 488.1, Found (M+H): 488.1, HPLC purity: 98.48%.

TABLE 29

The following compounds were prepared by the method described above:

| Ex. No. | Structure | Name | Analytical data |
|---|---|---|---|
| 284 | 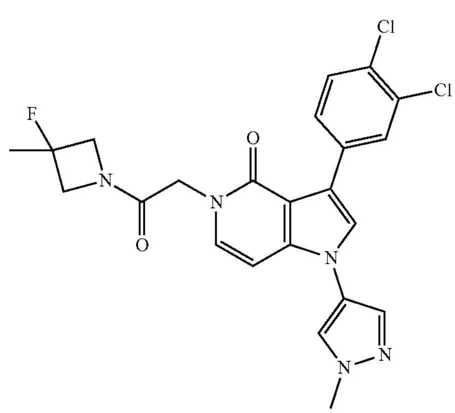 [SMILES: Cn1cc(-n2cc(-c3ccc(Cl)c(Cl)c3)c3c(=O)n(CC(=O)N4CC(C)(F)C4)ccc32)cn1] | 3-(3,4-dichlorophenyl)-5-(2-(3-fluoro-3-methylazetidin-1-yl)-2-oxoethyl)-1-(1-methyl-1H-pyrazol-4-yl)-1H-pyrrolo[3,2-c]pyridin-4(5H)-one | ¹H-NMR (DMSO-d₆, 400 MHz) δ (ppm): 8.26 (d, J = 12.8 Hz, 2H), 7.85 (d, J = 9.6 Hz, 2H), 7.74 (s, 1H), 7.57 (d, J = 8.4 Hz, 1H), 7.37 (d, J = 7.6 Hz, 1H), 6.52 (d, J = 7.6 Hz, 1H), 4.63 (s, 2H), 4.39-4.31 (m, 2H), 3.99-3.91 (m, 5H), 1.6 (d, J = 22 Hz, 3H). Calculated (M + H): 488.1, Found (M + H): 488.1, HPLC purity: 97.50% |

TABLE 29-continued

The following compounds were prepared by the method described above:

| Ex. No. | Structure | Name | Analytical data |
|---|---|---|---|
| 285 | 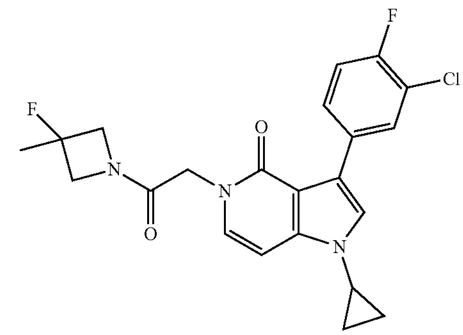 [SMILES: CC1(F)CN(C(=O)Cn2ccc3c(c(-c4ccc(F)c(Cl)c4)cn3C3CC3)c2=O)C1] | 3-(3-chloro-4-fluorophenyl)-1-cyclopropyl-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 8.16 (d, J = 6.4 Hz, 1H), 7.82 (brs, 1H), 7.48 (s, 1H), 7.36-7.3 (m, 2H), 6.65 (d, J = 7.2 Hz, 1H), 4.6 (s, 2H), 4.4-4.28 (m, 2H), 3.99-3.95 (m, 2H), 3.47 (brs, 1H), 1.6 (d, J = 22 Hz, 3H), 1.04-1.01 (m, 4H). Calculated (M + H): 432.12, Found (M + H): 432.1, HPLC purity: 99.94% |
| 286 | 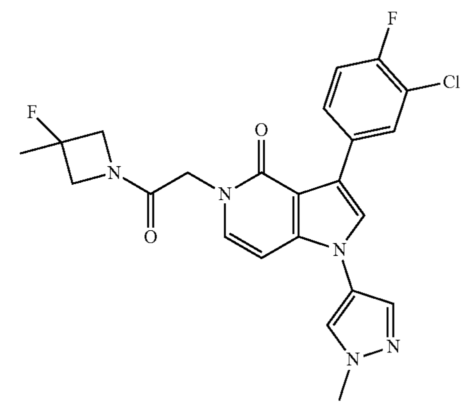 [SMILES: Cn1cc(-n2cc(-c3ccc(F)c(Cl)c3)c3c(=O)n(CC(=O)N4CC(C)(F)C4)ccc32)cn1] | 3-(3-chloro-4-fluorophenyl)-5-(2-(3-fluoro-3-methylazetidin-1-yl)-2-oxoethyl)-1-(1-methyl-1H-pyrazol-4-yl)-1H-pyrrolo[3,2-c]pyridin-4(5H)-one | $^1$H-NMR (DMSO-$d_6$, 400 MHz) δ (ppm): 8.24 (s, 1H), 8.18 (dd, J = 2.0 Hz, 7.6 Hz, 1H), 7.83-7.82 (m, 2H), 7.67 (s, 1H), 7.39-7.35 (m, 2H), 6.52 (d, J = 7.6 Hz, 1H), 4.63 (s, 2H), 4.39-4.31 (m, 2H), 4.0-3.91 (m, 5H), 1.6 (d, J = 22.4 Hz, 3H). Calculated (M + H): 472.13, Found (M + H): 472.1, HPLC purity: 99.5% |
| 287 | 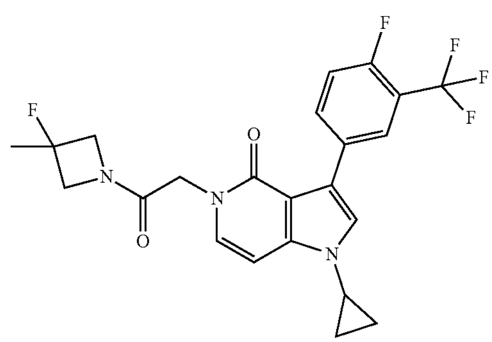 [SMILES: CC1(F)CN(C(=O)Cn2ccc3c(c(-c4ccc(F)c(C(F)(F)F)c4)cn3C3CC3)c2=O)C1] | 1-cyclopropyl-3-(4-fluoro-3-(trifluoromethyl)phenyl)-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 8.35 (d, J = 6.8 Hz, 1H), 8.12 (brs, 1H), 7.53 (s, 1H), 7.42 (t, J = 9.6 Hz, 1H), 7.36 (d, J = 7.2 Hz, 1H), 6.67 (d, J = 7.22 Hz, 1H), 4.59 (s, 2H), 4.40-4.28 (m, 2H), 3.98 (d, J = 19.6 Hz, 2H), 3.48 (s, 1H), 1.61 (d, J = 22 Hz, 3H), 1.04 (d, J = 10.4 Hz, 4H). Calculated (M + H): 466.1; Found (M + H): 466.1. HPLC purity: 99.72% |
| 288 | 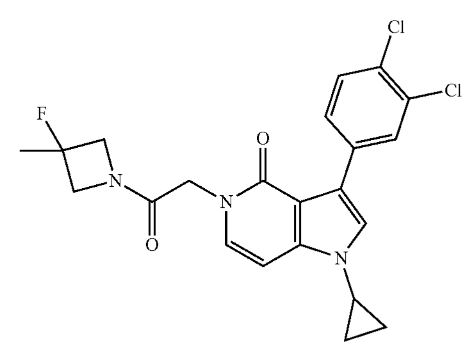 [SMILES: CC1(F)CN(C(=O)Cn2ccc3c(c(-c4ccc(Cl)c(Cl)c4)cn3C3CC3)c2=O)C1] | 1-cyclopropyl-3-(3,4-dichlorophenyl)-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 8.27 (s, 1H), 7.84 (d, J = 8.4 Hz, 1H), 7.55 (s, 1H), 7.53 (d, J = 8.4 Hz, 1H), 7.36 (d, J = 7.6 Hz, 1H), 6.67 (d, J = 6.8 Hz, 1H), 4.60 (s, 2H), 4.40-4.30 (m, 2H), 3.99 (d, J = 19.6 Hz, 2H), 3.47 (s, 1H), 1.62 (d, J = 22 Hz, 3H), 1.03 (d, J = 9.6 Hz, 4 H). Calculated (M + H): 448.0; Found (M + H): 448.1. HPLC purity: 99.87% |

TABLE 29-continued

The following compounds were prepared by the method described above:

| Ex. No. | Structure | Name | Analytical data |
|---|---|---|---|
| 289 | 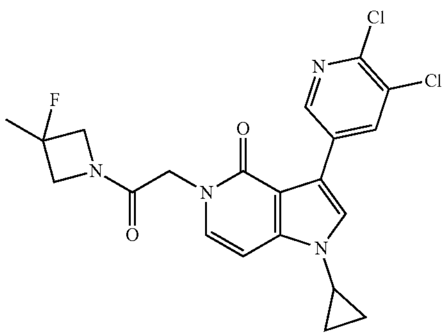 | 1-cyclopropyl-3-(5,6-dichloropyridin-3-yl)-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 8.84 (s, 1H), 8.77 (s, 1H), 7.74 (s, 1H), 7.39 (d, J = 7.2 Hz, 1H), 6.70 (d, J = 7.2 Hz, 1H), 4.62 (s, 2H), 4.41-4.29 (m, 2H), 3.97 (d, J = 19.2 Hz, 2H), 3.52-3.51 (m, 1H), 1.70 (d, J = 22.0 Hz, 3H), 1.15-1.02 (m, 4H). Calculated (M + H): 449.09; Found (M + H): 449.0. HPLC Purity: 98.62% |
| 290 | 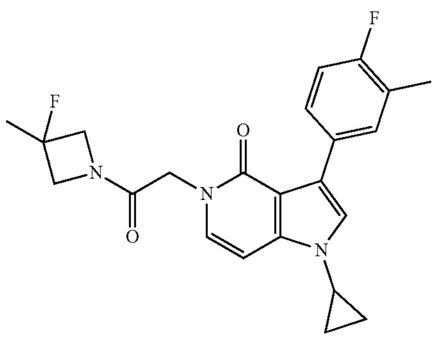 | 1-cyclopropyl-5-(2-(3-fluoro-3-methylazetidin-1-yl)-2-oxoethyl)-3-(4-fluoro-3-methylphenyl)-1H-pyrrolo[3,2-c]pyridin-4(5H)-one | $^1$H-NMR (DMSO-$d_6$, 400 MHz) δ (ppm): 7.68-7.62 (m, 2H), 7.32 (d, J = 7.6 Hz, 1H), 7.28 (s, 1H), 7.027 (t, J = 9.2 Hz, 1H), 6.63 (d, J = 6.8 Hz, 1H), 4.57 (s, 2H), 4.39-4.26 (m, 2H), 3.96 (d, J = 19.6 Hz, 2H), 3.46-3.42 (m, 1H), 2.22 (s, 3H), 1.59 (d, J = 22.0 Hz, 3H), 1.07-0.97 (m, 4H). Calculated (M + H): 412.18; Found (M + H): 412.2. HPLC Purity: 99.78% |
| 291 | 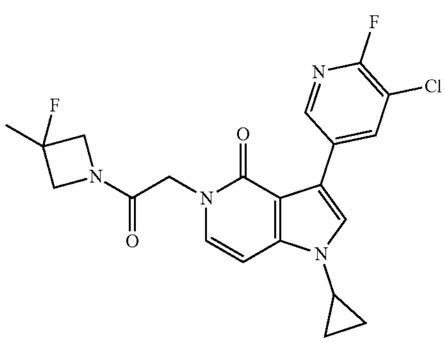 [SMILES: CC1(F)CN(C(=O)Cn2ccc3c(c(-c4cnc(F)c(Cl)c4)cn3C3CC3)c2=O)C1] | 3-(5-chloro-6-fluoropyridin-3-yl)-1-cyclopropyl-5-(2-(3-fluoro-3-methylazetidin-1-yl)-2-oxoethyl)-1H-pyrrolo[3,2-c]pyridin-4(5H)-one | $^1$H-NMR (DMSO-$d_6$, 400 MHz) δ (ppm): 8.74 (dd, J = 1.6 Hz, 9.2 Hz, 1H), 8.61 (s, 1H), 7.66 (s, 1H), 7.38 (d, J = 6.8 Hz, 1H), 6.69 (d, J = 7.2 Hz, 1H), 4.61 (s, 2H), 4.41-4.29 (m, 2H), 3.97 (d, J = 19.2 Hz, 2H), 3.51-3.48 (m, 1H), 1.60 (d, J = 22.0 Hz, 3 H), 1.09-0.99 (m, 4H). Calculated (M + H): 433.12; Found (M + H): 433.1. HPLC Purity: 99.79% |
| 292 | 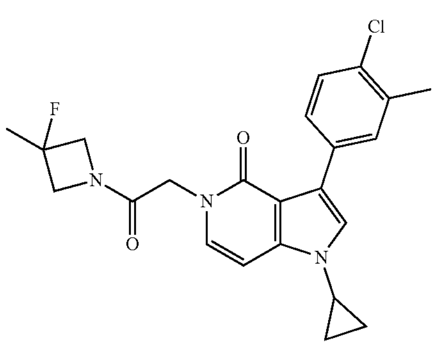 | 3-(4-chloro-3-methylphenyl)-1-cyclopropyl-5-(2-(3-fluoro-3-methylazetidin-1-yl)-2-oxoethyl)-1,5-dihydro-4H-pyrrolo[3,2-c]pyridin-4-one | $^1$H-NMR (DMSO-$d_6$, 400 MHz) δ (ppm): 7.77 (s, 1H), 7.68 (d, J = 8.4 Hz, 1H), 7.36 (s, 1H), 7.33-7.28 (m, 2H), 6.63 (d, J = 7.2 Hz, 1H), 4.57 (s, 2H), 4.38-4.26 (m, 2H), 3.98-3.93 (m, 2H), 3.46-3.45 (m, 1H), 2.31 (s, 3H), 1.58 (d, J = 22 Hz, 3H), 1.07-1.00 (m, 4H). Calculated (M + H): 428.15; Found (M + 1): 428.0. HPLC purity 99.49% |

TABLE 29-continued

The following compounds were prepared by the method described above:

| Ex. No. | Structure | Name | Analytical data |
|---|---|---|---|
| 293 | 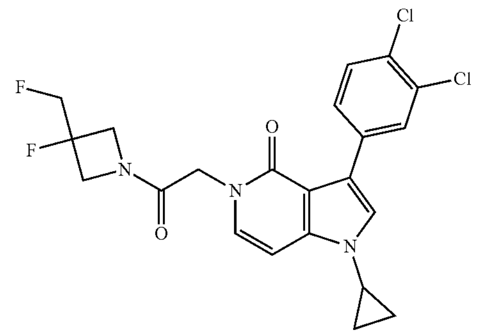 [SMILES: O=C(Cn1ccc2c(c(-c3ccc(Cl)c(Cl)c3)cn2C2CC2)c1=O)N1CC(F)(CF)C1] | 1-cyclopropyl-3-(3,4-dichlorophenyl)-5-(2-(3-fluoro-3-(fluoromethyl)azetidin-1-yl)-2-oxoethyl)-1,5-dihydro-4H-pyrrolo[3,2-c]pyridin-4-one | $^1$H-NMR (DMSO-$d_6$, 400 MHz) δ (ppm): 8.28 (s, 1H), 7.84 (d, J = 6.8 Hz, 1H), 7.56 (s, 1H), 7.52 (d, J = 8.4 Hz, 1H), 7.35 (d, J = 7.6 Hz, 1H), 6.67 (d, J = 7.2 Hz, 1H), 4.90-4.72 (m, 2H), 4.62 (s, 2H), 4.52-4.37 (m, 2H), 4.13-3.96 (m, 2H), 3.49-3.48 (m, 1H), 1.06-1.01 (m, 4H). Calculated (M + H): 466.08; Found (M + 1): 466.1. HPLC purity 99.81% |
| 294 | 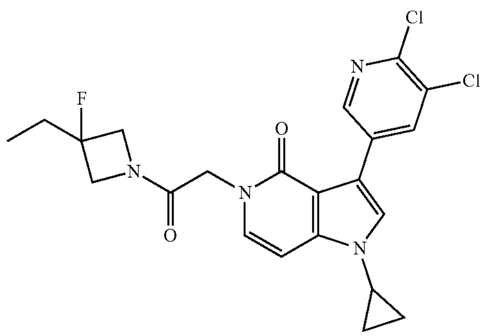 [SMILES: CCC1(F)CN(C(=O)Cn2ccc3c(c(-c4cnc(Cl)c(Cl)c4)cn3C3CC3)c2=O)C1] | 1-cyclopropyl-3-(5,6-dichloropyridin-3-yl)-5-(2-(3-ethyl-3-fluorozetidin-1-yl)-2-oxoethyl)-1,5-dihydro-4H-pyrrolo[3,2-c]pyridin-4-one | $^1$H-NMR (DMSO-$d_6$, 400 MHz) δ (ppm): 8.84 (d, J = 1.6 Hz, 1H), 8.77 (d, J = 2.0 Hz, 1H), 7.74 (s, 1H), 7.39 (d, J = 7.6 Hz, 1H), 6.70 (d, J = 7.2 Hz, 1H), 4.63 (s, 2H), 4.41-4.28 (m, 2H), 4.02-3.88 (m, 2H), 3.51-3.49 (m, 1H), 1.92-1.83 (m, 2H), 1.08-1.02 (m, 4H), 0.90 (t, J = 7.6, 3H). Calculated (M + H): 463.1; Found (M + 1): 463.1. HPLC purity 99.81% |

D. PREPARATION OF QUINAZOLINONES

Example 295: Preparation of 5-(4-chlorophenyl)-3-(2-oxo-2-(pyrrolidin-1-yl)ethyl)quinazolin-4(3H)-one

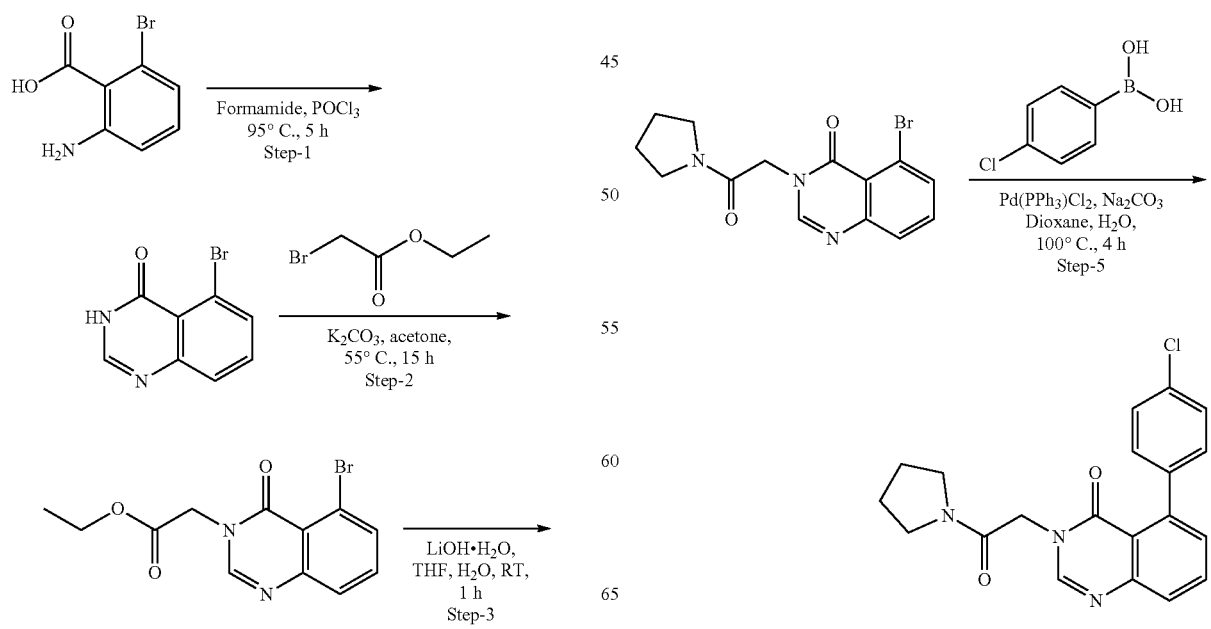

Step-1

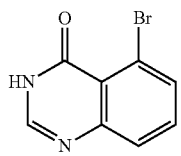

Preparation of 5-bromoquinazolin-4(3H)-one

To a solution of 2-amino-6-bromobenzoic acid (0.5 g, 2.3 mmol) in phosphorousoxychloride (10 mL) was added formamide (0.5 mL) and the reaction mixture was heated at 95° C. for 5 h. The reaction mixture was cooled and evaporated to dryness. The residue was taken in ice-water (25 mL) and adjusted to pH~6 using 1N sodium hydroxide solution. The precipitated solid was filtered, washed with cold water (25 mL) and dried to obtain the title compound 5-bromoquinazolin-4(3H)-one (0.35 g, crude) as off white solid. Calculated (M+H): 224.96; Found (M+H): 225.2.

Step-2

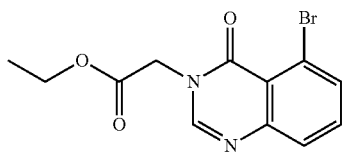 [SMILES: CCOC(=O)Cn1cnc2cccc(Br)c2c1=O]

Preparation of ethyl 2-(5-bromo-4-oxoquinazolin-3(4H)-yl)acetate

To a stirred solution of 5-bromoquinazolin-4(3H)-one (0.35 g, 1.55 mmol) and ethylbromoacetate (0.34 mL, 3.11 mmol) in acetone was added potassium carbonate (0.64 g, 4.66 mmol) and the reaction mixture was heated at 55° C. for 15 h. The reaction mixture was filtered through celite and the filtrate was evaporated. The crude product was purified by silica gel column chromatography using 40% ethyl acetate in hexane to obtain the title compound ethyl 2-(5-bromo-4-oxoquinazolin-3(4H)-yl)acetate (0.4 g, 83% yield) as off white solid. Calculated (M+H): 311; Found (M+H): 311.

Step-3

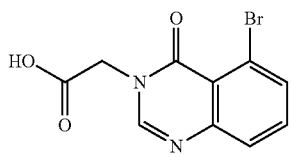 [SMILES: O=C(O)Cn1cnc2cccc(Br)c2c1=O]

Preparation of 2-(5-bromo-4-oxoquinazolin-3(4H)-yl)acetic acid

To a stirred solution of ethyl 2-(5-bromo-4-oxoquinazolin-3(4H)-yl)acetate (0.4 g, 1.29 mmol) in tetrahydrofuran (10 mL) and water (10 mL) mixture, was added lithium hydroxide monohydrate (0.27 g, 6.43 mmol) at 0° C. and the reaction mixture was stirred at room temperature for 1 h. Then the reaction mixture was evaporated, the residue was diluted with water (20 mL) and acidified with 1.5 N hydrochloric acid solution to pH~2. The precipitated solid was filtered, washed with water (50 mL) and dried to obtain the title compound 2-(5-bromo-4-oxoquinazolin-3(4H)-yl)acetic acid (0.28 g, crude) as off white solid. Calculated (M+H): 282.96; Found (M+H): 283.

Step-4

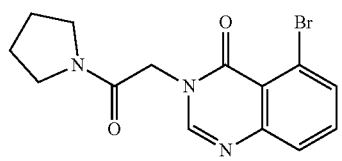 [SMILES: O=C(Cn1cnc2cccc(Br)c2c1=O)N1CCCC1]

Preparation of 5-bromo-3-(2-oxo-2-(pyrrolidin-1-yl) ethyl)quinazolin-4(3H)-one

To a stirred solution of 2-(5-bromo-4-oxoquinazolin-3 (4H)-yl)acetic acid (0.28 g, 0.989 mmol) in dichloromethane (15 mL) was added triethylamine (0.96 mL, 6.92 mmol) and pyrrolidine (0.16 mL, 1.98 mmol) at room temperature. The reaction mixture was cooled to 0° C., 1-propane phosphonic acid cyclic anhydride solution ($T_3P$) (0.94 mL, 1.48 mmol, 50% solution in ethyl acetate) was added dropwise and the reaction mixture was stirred at room temperature for 15 h. The reaction mixture was quenched with water (25 mL) and extracted with dichloromethane (3×25 mL). The combined organic extract was washed with brine (25 mL), dried over anhydrous sodium sulfate, filtered and evaporated. The crude product was purified by silica gel column chromatography using 4% methanol in dichloromethane to obtain the title compound 5-bromo-3-(2-oxo-2-(pyrrolidin-1-yl)ethyl) quinazolin-4(3H)-one (0.28 g, 85% yield) as off-white solid. Calculated (M+H): 336.03; Found (M+H): 336.

Step-5

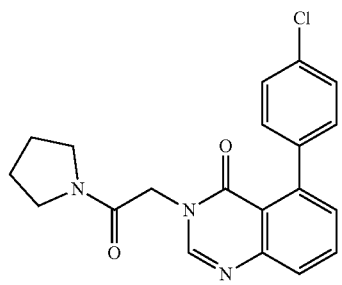 [SMILES: O=C(Cn1cnc2cccc(-c3ccc(Cl)cc3)c2c1=O)N1CCCC1]

Preparation of 5-(4-chlorophenyl)-3-(2-oxo-2-(pyrrolidin-1-yl)ethyl)quinazolin-4(3H)-one To a stirred suspension of 5-bromo-3-(2-oxo-2-(pyrrolidin-1-yl)ethyl)quinazolin-4(3H)-one (0.1 g, 0.29 mmol) and (4-chlorophenyl)boronic acid (0.06 g, 0.38 mmol) in 1,4- dioxane (10 mL) and water (3 mL) mixture, was added sodium carbonate (0.095 g, 0.89 mmol) and the resulting mixture was purged with argon for 30 minutes. Then bis(triphenylphosphine)palladium(II) dichloride [Pd(PPh$_3$)$_2$Cl$_2$] (0.02 g, 0.02 mmol) was added and the reaction mixture was heated at 100° C. for 4 h. Then the reaction mixture was cooled to room temperature, diluted with water (25 mL) and extracted with ethyl acetate (3×25 mL). The combined organic extract was washed with brine (25 mL), dried over anhydrous sodium sulfate, filtered and evaporated. The crude product was purified by silica gel column chromatography using 4% methanol in dichloromethane to obtain the title compound 5-(4-chlorophenyl)-3-(2-oxo-2-(pyrrolidin-1-yl)ethyl)quinazolin-4(3H)-one (0.105 g, 95% yield) as white solid. $^1$H NMR (400 MHz, DMSO-d$_6$) δ (ppm): 8.24 (s, 1H), 7.84-7.80 (m, 1H), 7.71 (d, J=8.0 Hz, 1H), 7.38 (d, J=8.4 Hz, 2H), 7.27-7.24 (m, 3H), 4.68 (s, 2H), 3.45 (t, J=6.4 Hz, 2H), 3.27 (t, J=6.8 Hz, 2H), 1.93-1.87 (m, 2H), 1.75-1.72 (m, 2H). Calculated (M+H): 368.1; Found (M+H): 368.1. HPLC Purity: 99.13%.

Example 296: Preparation of 5-(4-chlorophenyl)-3-(2-(3,3-difluoroazetidin-1-yl)-2-oxoethyl)quinazolin-4(3H)-one

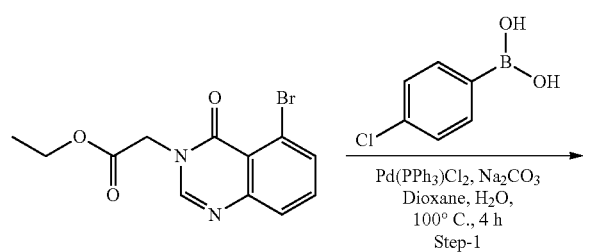

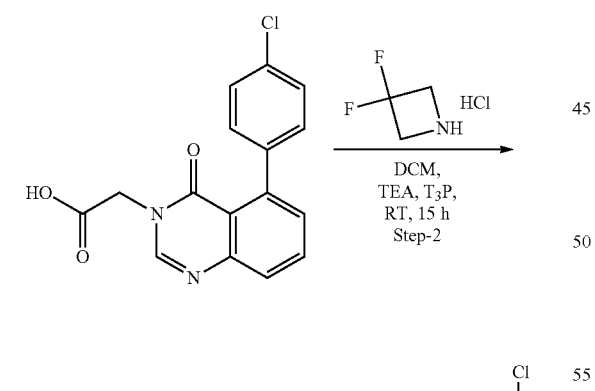

Step-1

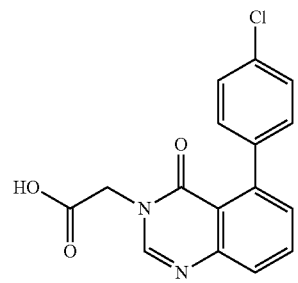 [SMILES: O=C(O)Cn1cnc2cccc(-c3ccc(Cl)cc3)c2c1=O]

Preparation of 2-(5-(4-chlorophenyl)-4-oxoquinazolin-3(4H)-yl)acetic acid

To a stirred suspension of ethyl 2-(5-bromo-4-oxoquinazolin-3(4H)-yl)acetate (0.1 g, 0.32 mmol) and (4-chlorophenyl)boronic acid (0.065 g, 0.42 mmol) in 1,4-dioxane (6 mL) and water (2 mL) mixture, was added sodium carbonate (0.1 g, 0.96 mmol) and the resulting mixture was purged with argon for 30 minutes. Then bis(triphenylphosphine)palladium(II) dichloride [Pd(PPh$_3$)$_2$Cl$_2$] (0.022 g, 0.03 mmol) was added and the reaction mixture was heated at 100° C. for 4 h. Then the reaction mixture was cooled to room temperature and filtered through celite. The filtrate was diluted with water (25 mL) and extracted with ethyl acetate (3×25 mL) and the organic extract was discarded. The aqueous layer was acidified with 1.5N hydrochloric acid solution and was extracted with ethyl acetate (3×25 mL). The combined organic extract was washed with brine (25 mL), dried over anhydrous sodium sulfate, filtered and evaporated to obtain the title compound 2-(5-(4-chlorophenyl)-4-oxoquinazolin-3(4H)-yl)acetic acid (0.1 g, crude) as white solid. Calculated (M+H): 315.05; Found (M+H): 315.1.

Step-2

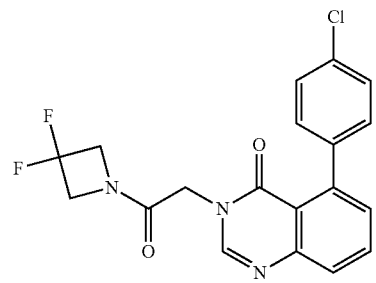 [SMILES: O=C(Cn1cnc2cccc(-c3ccc(Cl)cc3)c2c1=O)N1CC(F)(F)C1]

Preparation of 5-(4-chlorophenyl)-3-(2-(3,3-difluoroazetidin-1-yl)-2-oxoethyl)quinazolin-4(3H)-one To a stirred solution of 2-(5-(4-chlorophenyl)-4-oxoquinazolin-3(4H)-yl)acetic acid (0.1 g, 0.31 mmol) in dichloromethane (10 mL) were added triethylamine (0.265 mL, 1.9 mmol) and 3,3-difluoroazetidine hydrochloride (0.062 mL, 0.47 mmol) at room temperature. The reaction mixture was cooled to 0° C., 1-propane phosphonic acid cyclic

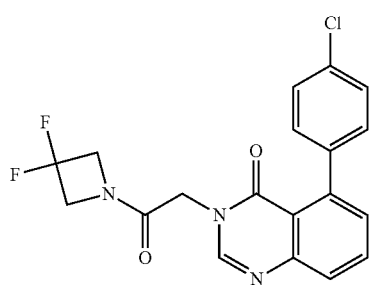

anhydride solution (T₃P) (0.3 mL, 0.47 mmol, 50% solution in ethyl acetate) was added dropwise and the reaction mixture was stirred at room temperature for 15 h. The reaction mixture was quenched with water (25 mL) and extracted with dichloromethane (3×25 mL). The combined organic extract was washed with brine (25 mL), dried over anhydrous sodium sulfate, filtered and evaporated. The crude product was purified by silica gel column chromatography using 4% methanol in dichloromethane to obtain the title compound 5-(4-chlorophenyl)-3-(2-(3,3-difluoroazetidin-1-yl)-2-oxoethyl)quinazolin-4(3H)-one (0.075 g, 60%) as white solid. $^1$H NMR (400 MHz, DMSO-$d_6$) δ (ppm): 8.24 (s, 1H), 7.85-7.81 (m, 1H), 7.72 (d, J=8 Hz, 1H), 7.39 (d, J=8.4 Hz, 2H), 7.29-7.24 (m, 3H), 4.69 (t, J=12 Hz, 2H), 4.64 (s, 2H), 4.32 (t, J=12.4 Hz, 2H). Calculated (M+H): 390.07; Found (M+H): 390.01. HPLC Purity: 98.49%.

TABLE 30

The following compounds were prepared by the method described above:

| Ex. No. | Structure | IUPAC Name | Analytical Data |
|---|---|---|---|
| 297 | (structure) | 5-(4-chlorophenyl)-3-(2-oxo-2-(2-(trifluoromethyl)pyrrolidin-1-yl)ethyl)quinazolin-4(3H)-one | $^1$H NMR (400 MHz, DMSO-$d_6$) δ (ppm): 8.28-8.25 (m, 1H), 7.85-7.81 (m, 1H), 7.72 (d, J = 8 Hz, 1H), 7.38 (d, J = 8.0 Hz, 2H), 7.29-7.25 (m, 3H), 4.86-4.77 (m, 2H), 4.71-4.67 (m, 1H), 3.63 (bs, 2H), 2.12-1.89 (m, 4H). Calculated (M + H): 436.1; Found (M + H): 436.1, HPLC purity: 98.88% |
| 298 | (structure) | 5-(4-chlorophenyl)-3-(2-(2-fluoropyrrolidin-1-yl)-2-oxoethyl)quinazolin-4(3H)-one | $^1$H NMR (400 MHz, DMSO-$d_6$) δ (ppm): 8.26 (s, 1H), 7.84-7.80 (m, 1H), 7.73-7.71 (m, 1H), 7.38 (d, J = 8.0 Hz, 2H), 7.28-7.24 (m, 3H), 5.37 (t, J = 52.4 Hz, 1H), 4.82-4.64 (m, 2H), 3.84-3.28 (m, 4H), 2.24-1.92 (m, 2H). Calculated (M + H): 386.1; Found (M + H): 386.1. HPLC Purity: 98.24% |

E. PREPARATION OF ISOQUINOLINONES

Example 299: Preparation of 8-(4-chloro-3-(trifluoromethyl)phenyl)-2-(2-(3-fluoropyrrolidin-1-yl)-2-oxoethyl)isoquinolin-1(2H)-one

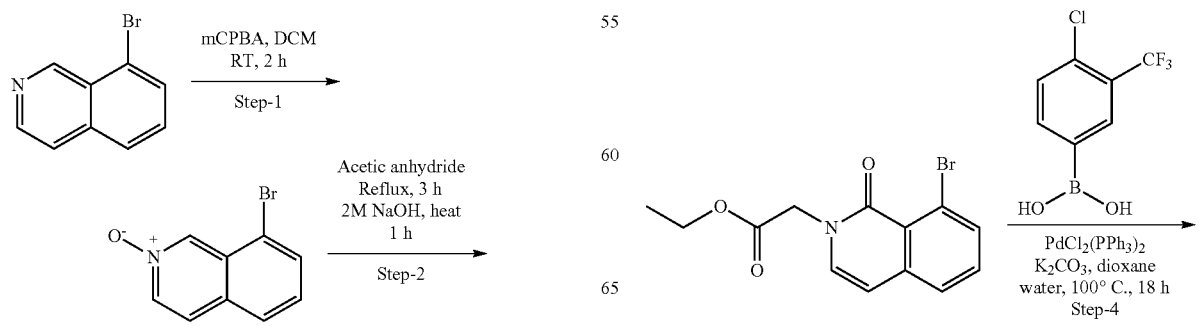

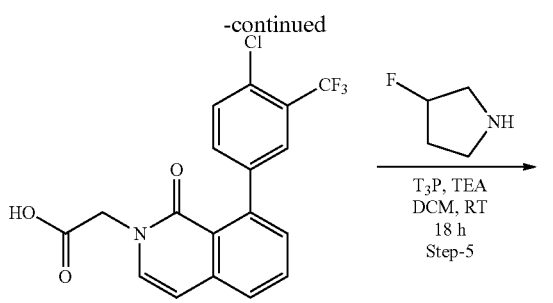

T₃P, TEA
DCM, RT
18 h
Step-5

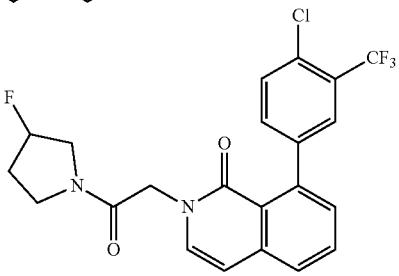

Step-1

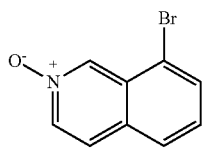

Preparation of 8-bromoisoquinoline 2-oxide

To a solution of 8-bromoisoquinoline (1 g, 4.806 mmol) in dichloromethane (30 mL) was added meta-chloroperbenzoic acid (mCPBA) (0.995 g, 5.76 mmol) and the reaction mixture was stirred at room temperature for 2 h. After completion of the reaction (monitored by TLC), the reaction mixture was diluted with dichloromethane (30 mL) and washed with 2M sodium hydroxide solution (2×30 mL). The aqueous layer was again extracted with dichloromethane (60 mL) and combined organic layer was dried over anhydrous sodium sulphate, filtered and concentrated to afford the title compound 8-bromoisoquinoline 2-oxide (1.1 g, crude) as a brownish solid. Calculated (M+H): 223.96; Found (M+H): 223.9.

Step-2

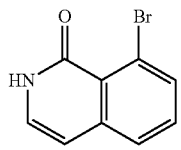

Preparation of 8-bromoisoquinolin-1(2H)-one

A solution of 8-bromoisoquinoline 2-oxide (0.35 g) and acetic anhydride (5 mL) was refluxed for 3 h. The solution was concentrated, the residue was dissolved in 2M sodium hydroxide solution (10 mL) and heated at 85° C. for 1 h. The mixture was acidified to pH 6 using 5% aqueous citric acid solution and extracted with dichloromethane (2×30 mL). The combined organic layer was dried over anhydrous sodium sulphate, filtered and concentrated. The obtained residue was triturated with ether to afford the title compound 8-bromoisoquinolin-1(2H)-one (0.18 g, 51% yield) as a brownish solid. Calculated (M+H): 223.96; Found (M+H): 223.9.

Step-3

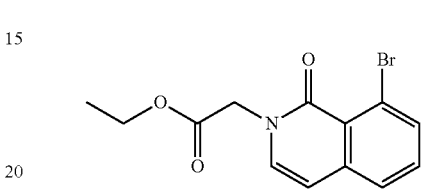

Preparation of ethyl 2-(8-bromo-1-oxoisoquinolin-2(1H)-yl)acetate

A mixture of 8-bromoisoquinolin-1(2H)-one (2.5 g, 11.15 mmol), ethyl 2-bromoacetate (2.5 mL, 22.31 mmol) and potassium carbonate (4.62 g, 33.47 mmol) in acetone (100 mL) was heated at 60° C. for 2 h. The reaction mixture was filtered and the filtrate was concentrated. The crude product was purified by column chromatography using 30% ethyl acetate in hexane to afford the title compound ethyl 2-(8-bromo-1-oxoisoquinolin-2(1H)-yl)acetate (2.1 g, 61% yield) as a brownish solid. Calculated (M+H): 310.00; Found (M+H): 310.0.

Step-4

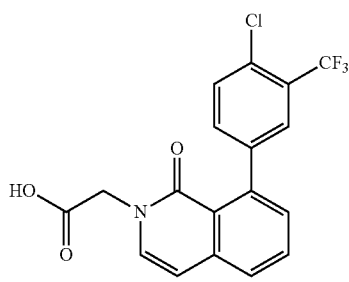 [SMILES: O=C(O)Cn1ccc2cccc(-c3ccc(Cl)c(C(F)(F)F)c3)c2c1=O]

Preparation of 2-(8-(4-chloro-3-(trifluoromethyl)phenyl)-1-oxoisoquinolin-2(1H)-yl)acetic acid A mixture of ethyl 2-(8-bromo-1-oxoisoquinolin-2(1H)-yl)acetate (0.65 g, 2.09 mmol), (4-chloro-3-(trifluoromethyl)phenyl)boronic acid (0.705 g, 3.14 mmol) and potassium carbonate (0.868 g, 6.28 mmol) in dioxane:water mixture (50 mL, 4:1) was purged with argon for 15 minutes. Then bis(triphenylphosphine)palladium(II) dichloride (0.171 g, 0.209 mmol) was added and the reaction mixture was heated at 100° C. for 18 h. The reaction mixture was diluted with water (50 mL) and extracted with ethyl acetate (30 mL). The aqueous layer was cooled, acidified with 1.5N hydrochloric acid, extracted with ethyl acetate (100 mL×2)

and the combined organic layer was dried over anhydrous sodium sulphate, filtered and concentrated to afford the title compound 2-(8-(4-chloro-3-(trifluoromethyl)phenyl)-1-oxoisoquinolin-2(1H)-yl)acetic acid (0.6 g, 75% yield) as a brownish solid. Calculated (M+H): 382.04; Found (M+H): 382.0.

Step-5

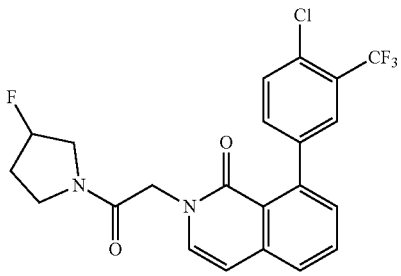 [SMILES: O=C(Cn1ccc2cccc(-c3ccc(Cl)c(C(F)(F)F)c3)c2c1=O)N1CCC(F)C1]

Preparation of 8-(4-chloro-3-(trifluoromethyl)phenyl)-2-(2-(3-fluoropyrrolidin-1-yl)-2-oxoethyl)isoquinolin-1(2H)-one To a solution of 2-(8-(4-chloro-3-(trifluoromethyl)phenyl)-1-oxoisoquinolin-2(1H)-yl)acetic acid (0.06 g, 0.15 mmol), 3-fluoropyrrolidine hydrochloride (0.039 g, 0.31 mmol) and triethylamine (0.12 mL, 0.86 mmol) in dichloromethane (10 mL) cooled to 0° C., was added 1-propane phosphonic acid cyclic anhydride ($T_3P$) (0.15 mL, 0.23 mmol, 50% in ethyl acetate) dropwise and the reaction mixture was stirred at room temperature for 18 h. The reaction mixture was diluted with dichloromethane (30 mL) and washed with water (30 mL×2). The organic layer dried over anhydrous sodium sulphate, filtered and concentrated. The crude was purified by column chromatography using 2% methanol in dichloromethane to afford the title compound 8-(4-chloro-3-(trifluoromethyl)phenyl)-2-(2-(3-fluoropyrrolidin-1-yl)-2-oxoethyl)isoquinolin-1(2H)-one (0.03 g, 42% yield) as a off white solid. Calculated (M+H): 453.09; Found (M+H): 453.0. $^1$H NMR (400 MHz, DMSO-$d_6$) δ (ppm): 7.72-7.69 (m, 2H), 7.62 (t, J=8.4 Hz, 2H), 7.48 (d, J=8 Hz, 1H), 7.38-7.37 (m, 1H), 7.25-7.23 (dd, J=2.8 Hz, 5.6 Hz, 1H), 6.66 (d, J=7.2 Hz, 1H), 5.45-5.21 (m, 1H), 4.77-4.58 (m, 2H), 3.80-3.20 (m, 4H), 3.21-2.04 (m, 2H). HPLC purity: 98.72%.

TABLE 31

The following compounds were prepared by the method described above:

| Ex. No. | Structure | IUPAC Name | Analytical Data |
|---|---|---|---|
| 300 | 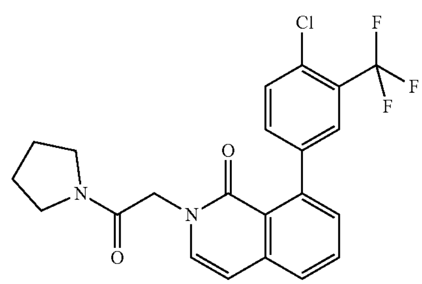 [SMILES: O=C(Cn1ccc2cccc(-c3ccc(Cl)c(C(F)(F)F)c3)c2c1=O)N1CCCC1] | 8-(4-chloro-3-(trifluoromethyl) phenyl)-2-(2-oxo-2-(pyrrolidin-1-yl)ethyl)isoquinolin-1(2H)-one | $^1$H NMR (400 MHz, DMSO-$d_6$) δ (ppm): 7.71-7.68 (m, 2H), 7.64-7.60 (m, 2H), 7.48 (d, J = 8 Hz, 1H), 7.36 (d, J = 7.2 Hz, 1H), 7.24-7.22 (dd, J = 2.4 Hz, 6 Hz, 1H), 6.65 (d, J = 7.2 Hz, 1H), 4.61 (s, 2H), 3.41 (t, J = 6.4 Hz, 2H), 3.27-3.22 (m, 2H), 1.90-1.83 (m, 2H), 1.76-1.70 (m, 2H). Calculated (M + H): 435.10; Found (M + H): 435.0. HPLC purity: 99.69% |
| 301 | 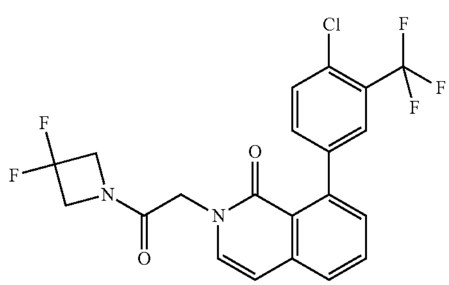 [SMILES: O=C(Cn1ccc2cccc(-c3ccc(Cl)c(C(F)(F)F)c3)c2c1=O)N1CC(F)(F)C1] | 8-(4-chloro-3-(trifluoromethyl) phenyl)-2-(2-(3,3-difluoroazetidin-1-yl)-2-oxoethyl)isoquinolin-1(2H)-one | $^1$H NMR (400 MHz, DMSO-$d_6$) δ (ppm): 7.73-7.69 (m, 2H), 7.65-7.60 (m, 2H), 7.49 (d, J = 8.4 Hz, 1H), 7.37 (d, J = 7.2 Hz, 1H), 7.26-7.24 (m, 1H), 6.68 (d, J = 7.6 Hz, 1H), 4.64 (t, J = 11.6 Hz, 2H), 4.56 (s, 2H), 4.27 (t, J = 12 Hz, 2H). Calculated (M + H): 457.07; Found (M + H): 457.0. HPLC purity: 99.25% |

TABLE 31-continued

The following compounds were prepared by the method described above:

| Ex. No. | Structure | IUPAC Name | Analytical Data |
|---|---|---|---|
| 302 | 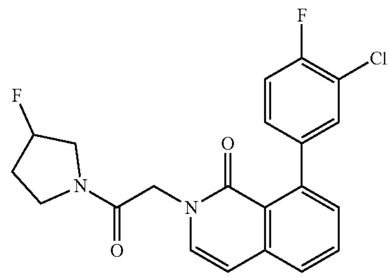 | 8-(3-chloro-4-fluorophenyl)-2-(2-(3-fluoropyrrolidin-1-yl)-2-oxoethyl)isoquinolin-1(2H)-one | $^1$H NMR (400 MHz, DMSO-d$_6$) δ (ppm): 7.68-7.65 (m, 2H), 7.36-77.29 (m, 3H), 7.20-7.14 (m, 2H), 6.63 (d, J = 7.6 Hz, 1H), 5.46-5.21 (m, 1H), 4.77-460 (m, 2H), 3.81-3.24 (m, 4H), 2.30-1.87 (m, 2H). Calculated (M + H): 403.09; Found (M + H): 403.0. HPLC purity: 98.96% |
| 303 | 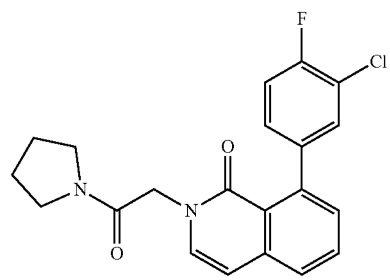 [SMILES: O=C(Cn1ccc2cccc(-c3ccc(F)c(Cl)c3)c2c1=O)N1CCCC1] | 8-(3-chloro-4-fluorophenyl)-2-(2-oxo-2-(pyrrolidin-1-yl)ethyl)isoquinolin-1(2H)-one | $^1$H NMR (400 MHz, DMSO-d$_6$) δ (ppm): 7.68-7.65 (m, 2H), 7.36-7.29 (m, 3H), 7.21-7.13 (m, 2H), 6.62 (d, J = 6.8 Hz, 1H), 4.61 (s, 2H), 3.42 (t, J = 6.4 Hz, 2H), 3.24 (t, J = 6.4 Hz, 2H), 1.91-1.84 (m, 2H), 1.77-1.70 (m, 2H). Calculated (M + H): 385.10; Found M + H: 385.0. HPLC purity: 99.35% |
| 304 | 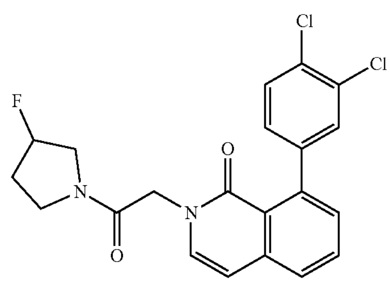 [SMILES: O=C(Cn1ccc2cccc(-c3ccc(Cl)c(Cl)c3)c2c1=O)N1CCC(F)C1] | 8-(3,4-dichlorophenyl)-2-(2-(3-fluoropyrrolidin-1-yl)-2-oxoethyl)isoquinolin-1(2H)-one | $^1$H NMR (400 MHz, DMSO-d$_6$) δ (ppm): 7.70-7.66 (m, 2H), 7.53 (d, J = 8.4 Hz, 1H) 7.41 (d, J = 1.6 Hz, 1H), 7.37-7.35 (m, 1H), 7.21-7.18 (m, 1H), 7.16-7.14 (m, 1H), 6.64 (d, J = 7.2 Hz, 1H), 5.46-5.21 (m, 1H), 4.77-4.60 (m, 2H), 3.80-3.21 (m, 4H), 2.30-1.89 (m, 2H). Calculated (M + H): 419.07; Found (M + H): 419.0. HPLC purity: 99.47% |
| 305 | 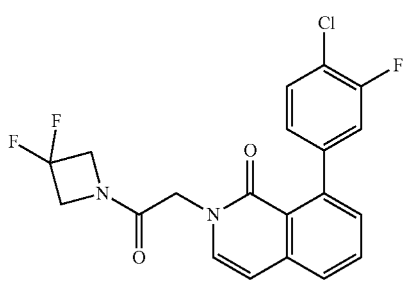 [SMILES: O=C(Cn1ccc2cccc(-c3ccc(Cl)c(F)c3)c2c1=O)N1CC(F)(F)C1] | 8-(4-chloro-3-fluorophenyl)-2-(2-(3,3-difluoroazetidin-1-yl)-2-oxoethyl)isoquinolin-1(2H)-one | $^1$H NMR (400 MHz, DMSO-d$_6$) δ (ppm): 7.69 (d, J = 4.4 Hz, 2H), 7.48 (t, J = 8.0 Hz, 1H), 7.35 (d, J = 7.2 Hz, 1H), 7.23-7.20 (m, 2H), 7.03 (d, J = 8.0 Hz, 1H), 6.66 (d, J = 7.6 Hz, 1H), 4.67-4.62 (m, 2H), 4.57 (s, 2H), 4.32-4.26 (m, 2H). Calculated (M + H): 407.07, Found (M + H): 407.0, HPLC purity: 99.23% |
| 306 | 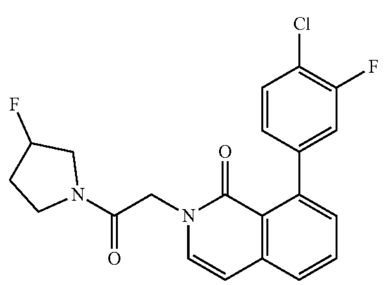 [SMILES: O=C(Cn1ccc2cccc(-c3ccc(Cl)c(F)c3)c2c1=O)N1CCC(F)C1] | 8-(4-chloro-3-fluorophenyl)-2-(2-(3-fluoropyrrolidin-1-yl)-2-oxoethyl)isoquinolin-1(2H)-one | $^1$H NMR (400 MHz, DMSO-d$_6$) δ (ppm): 7.69 (d, J = 4.0 Hz, 2H), 7.48 (t, J = 8.0 Hz, 1H), 7.37 (d, J = 7.2 Hz, 1H), 7.22-7.19 (m, 2H), 7.03 (d, J = 8.4 Hz, 1H), 6.64 (d, J = 7.6 Hz, 1H), 5.46-5.22 (m, 1H), 4.77-4.61 (m, 2H), 3.81-3.21 (m, 4H), 2.22-2.15 (m, 1H), 2.12-1.96 (m, 1H); (Calculated (M + H): 403.09, Found (M + H): 403.3, HPLC purity: 99.52% |

TABLE 31-continued

The following compounds were prepared by the method described above:

| Ex. No. | Structure | IUPAC Name | Analytical Data |
|---|---|---|---|
| 307 | 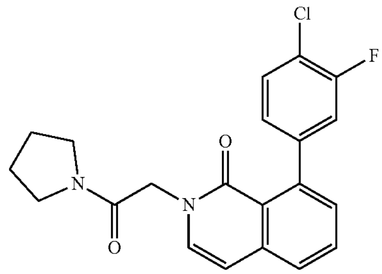 [SMILES: O=C(Cn1ccc2cccc(-c3ccc(Cl)c(F)c3)c2c1=O)N1CCCC1] | 8-(4-chloro-3-fluorophenyl)-2-(2-oxo-2-(pyrrolidin-1-yl)ethyl)isoquinolin-1(2H)-one | $^1$H NMR (400 MHz, DMSO-$d_6$) δ (ppm): 7.69 (d, J = 4.0 Hz, 2H), 7.48 (t, J = 8.0 Hz, 1H), 7.35 (d, J = 7.6 Hz, 1H), 7.21-7.19 (m, 2H), 7.02 (d, J = 7.6 Hz, 1H), 6.63 (d, J = 7.2 Hz, 1H), 4.61 (s, 2 H), 3.43-3.40 (m, 2H), 3.27-3.23 (m, 2H), 1.91-1.85 (m, 2H), 1.77-1.71 (m, 2H); (Calculated (M + 1): 385.1, Found (M + H): 385.1, HPLC purity: 99.68% |
| 308 | 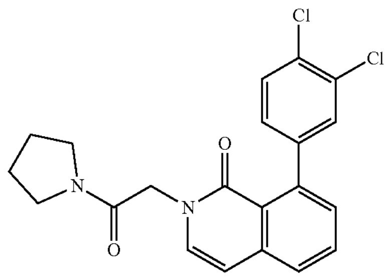 [SMILES: O=C(Cn1ccc2cccc(-c3ccc(Cl)c(Cl)c3)c2c1=O)N1CCCC1] | 8-(3,4-dichlorophenyl)-2-(2-oxo-2-(pyrrolidin-1-yl)ethyl)isoquinolin-1(2H)-one | $^1$H NMR (400 MHz, DMSO-$d_6$) δ (ppm): 7.69-7.66 (m, 2H), 7.53 (d, J = 8 Hz, 1H), 7.40 (d, J = 1.2 Hz, 1H), 7.35 (d, J = 7.6 Hz, 1H), 7.21-7.19 (m, 1H), 7.16-7.13 (m, 1H), 6.63 (d, J = 7.2 Hz, 1H), 4.61 (s, 2H), 3.42 (t, J = 6.8 Hz, 2H), 3.24 (t, J = 7.2 Hz, 2H), 1.91-1.84 (m, 2H), 1.77-1.70 (m, 2H). Calculated (M + H): 401.07; Found (M + H): 401.0. HPLC purity: 99.33% |
| 309 | 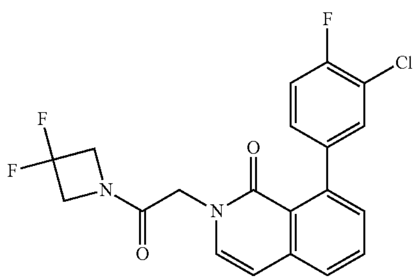 [SMILES: O=C(Cn1ccc2cccc(-c3ccc(F)c(Cl)c3)c2c1=O)N1CC(F)(F)C1] | 8-(3-chloro-4-fluorophenyl)-2-(2-(3,3-difluoroazetidin-1-yl)-2-oxoethyl)isoquinolin-1(2H)-one | $^1$H NMR (400 MHz, DMSO-$d_6$) δ (ppm): 7.69 (d, J = 4 Hz, 2H), 7.36-7.30 (m, 3H), 7.21 (t, J = 4 Hz, 1H), 7.18-7.15 (m, 1H), 6.65 (d, J = 7.6 Hz, 1H), 4.64 (t, J = 11.6 Hz, 2H), 4.57 (s, 2H), 4.29 (t, J = 12 Hz, 2H). Calculated (M + H): 407.07; Found (M + H): 407.0. HPLC purity: 99.28% |

Example 310: Preparation of 7-(4-chloro-3-(trifluoromethyl)phenyl)-2-(2-oxo-2-(pyrrolidin-1-yl)ethyl)isoquinolin-1(2H)-one

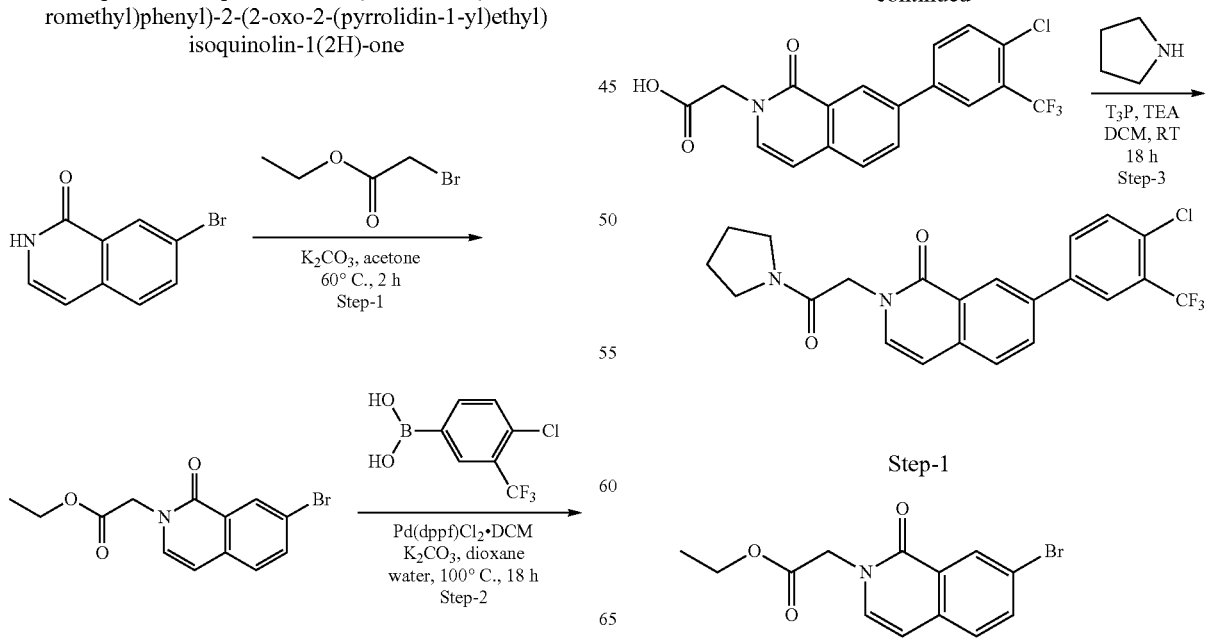

Preparation of ethyl 2-(7-bromo-1-oxoisoquinolin-2(1H)-yl)acetate

A mixture of 7-bromoisoquinolin-1(2H)-one (1.8 g, 8.03 mmol), ethyl 2-bromoacetate (1.8 mL, 16.06 mmol) and potassium carbonate (3.33 g, 24.10 mmol) in acetone (50 mL) was heated at 60° C. for 2 h. The reaction mixture was filtered and the filtrate was concentrated. The crude product was purified by column chromatography using 30% ethyl acetate in hexane to afford the title compound ethyl 2-(7-bromo-1-oxoisoquinolin-2(1H)-yl)acetate (2.1 g, 84% yield) as off white solid. Calculated (M+H): 310.00; Found (M+H): 310.0.

Step-2

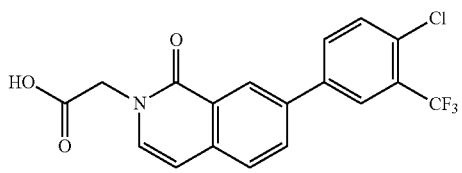 [SMILES: O=C(O)Cn1ccc2ccc(-c3ccc(Cl)c(C(F)(F)F)c3)cc2c1=O]

Preparation of 2-(7-(4-chloro-3-(trifluoromethyl)phenyl)-1-oxoisoquinolin-2(1H)-yl)acetic acid A mixture of 2-(7-bromo-1-oxoisoquinolin-2(1H)-yl)acetate (0.2 g, 0.64 mmol), (4-chloro-3-(trifluoromethyl)phenyl)boronic acid (0.14 g, 0.64 mmol) and potassium carbonate (0.26 g, 1.93 mmol) in dioxane:water mixture (10 mL, 4:1) was purged with argon for 15 minutes. Then [1,1'-Bis(diphenylphosphino)ferrocene]dichloropalladium (II) dichloromethane complex (Pd(dppf)Cl$_2$.DCM)(0.026 g, 0.03 mmol) was added and the reaction mixture was heated at 100° C. for 18 h. The reaction mixture was diluted with water (25 mL) and extracted with ethyl acetate (30 mL). The aqueous layer was cooled, acidified with 1.5N hydrochloric acid, extracted with ethyl acetate (100 mL×2) and the combined organic layer was dried over anhydrous sodium sulphate, filtered and concentrated to afford the title compound 2-(7-(4-chloro-3-(trifluoromethyl)phenyl)-1-oxoisoquinolin-2(1H)-yl)acetic acid (0.21 g, crude) as a brownish solid. Calculated (M+H): 382.04; Found (M+H): 382.0.

Step-3

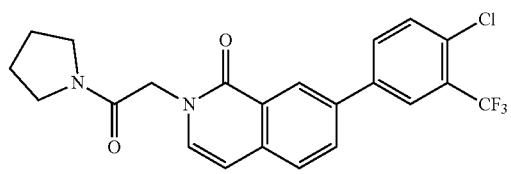 [SMILES: O=C(Cn1ccc2ccc(-c3ccc(Cl)c(C(F)(F)F)c3)cc2c1=O)N1CCCC1]

Preparation of 7-(4-chloro-3-(trifluoromethyl)phenyl)-2-(2-oxo-2-(pyrrolidin-1-yl)ethyl)isoquinolin-1(2H)-one To a solution of 2-(7-(4-chloro-3-(trifluoromethyl)phenyl)-1-oxoisoquinolin-2(1H)-yl)acetic acid (0.07 g, 0.16 mmol), pyrrolidine (0.011 g, 0.16 mmol) and triethylamine (0.18 mL, 1.33 mmol) in dichloromethane (10 mL) cooled to 0° C., was added 1-propane phosphonic acid cyclic anhydride (T$_3$P) (0.21 mL, 0.33 mmol, 50% in ethyl acetate) dropwise and the reaction mixture was stirred at room temperature for 18 h. The reaction mixture was diluted with dichloromethane (30 mL) and washed with water (30 mL×2). The organic layer dried over anhydrous sodium sulphate, filtered and concentrated. The crude was purified by column chromatography using 2% methanol in dichloromethane to afford the title compound 7-(4-chloro-3-(trifluoromethyl)phenyl)-2-(2-oxo-2-(pyrrolidin-1-yl)ethyl)isoquinolin-1(2H)-one (0.03 g, 42% yield) as off white solid. $^1$H NMR (400 MHz, DMSO-d$_6$) δ (ppm): 8.44 (s, 1H), 8.10 (s, 2H), 8.06 (d, J=8.4 Hz, 1H), 7.82 (d, J=8.4 Hz, 1H), 7.78 (d, J=8.4 Hz, 1H), 7.39 (d, J=7.6 Hz, 1H), 6.65 (d, J=7.2 Hz, 1H), 4.78 (s, 2H), 3.54 (d, J=6.4 Hz, 2H), 3.32-3.26 (m, 2H), 1.95-1.90 (m, 2H), 1.82-1.77 (m, 2H); Calculated (M+H): 435.1, Found (M+H): 435.1; HPLC purity: 99.59%.

TABLE 32

The following compounds were prepared by the method described above:

| Ex. No. | Structure | IUPAC Name | Analytical data |
|---|---|---|---|
| 311 | (structure: 7-(4-chloro-3-(trifluoromethyl)phenyl) isoquinolin-1(2H)-one with 2-(3-fluoropyrrolidin-1-yl)-2-oxoethyl substituent) | 7-(4-chloro-3-(trifluoromethyl)phenyl)-2-(2-(3-fluoropyrrolidin-1-yl)-2-oxoethyl)isoquinolin-1(2H)-one | $^1$H NMR (400 MHz, DMSO-d$_6$) δ (ppm): 8.44 (s, 1H), 8.10 (s, 2H), 8.06 (d, J = 8.4 Hz, 1H), 7.82 (d, J = 8.8 Hz, 1H), 7.78 (d, J = 8.4 Hz, 1H), 7.40 (d, J = 6.8 Hz, 1H), 6.66 (d, J = 7.2 Hz, 1H), 5.39 (t, J = 50.4 Hz, 1H), 4.91-4.73 (m, 2 H), 3.94-3.31 (m, 4H), 2.30-1.96 (m, 2H). Calculated (M + H): 453.09, Found (M + H): 453.1, HPLC purity: 96.54% |

TABLE 32-continued

The following compounds were prepared by the method described above:

| Ex. No. | Structure | IUPAC Name | Analytical data |
|---|---|---|---|
| 312 | 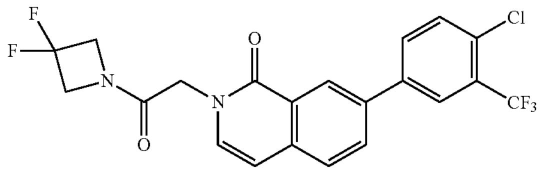 [SMILES: O=C(Cn1ccc2ccc(-c3ccc(Cl)c(C(F)(F)F)c3)cc2c1=O)N1CC(F)(F)C1] | 7-(4-chloro-3-(trifluoromethyl)phenyl)-2-(2-(3,3-difluoroazetidin-1-yl)-2-oxoethyl)isoquinolin-1(2H)-one | $^1$H NMR (400 MHz, DMSO-$d_6$) δ (ppm): 8.45 (s, 1H), 8.13-8.07 (m, 3H), 7.83-7.78 (m, 2H), 7.42 (d, J = 7.6 Hz, 1H), 6.69 (d, J = 7.2 Hz, 1H), 4.78 (t, J = 12 Hz, 2H), 4.70 (s, 2H), 4.35 (t, J = 12 Hz, 2H). Calculated (M + H): 457.07, Found (M + H): 457.0. HPLC purity: 99.57% |
| 313 | 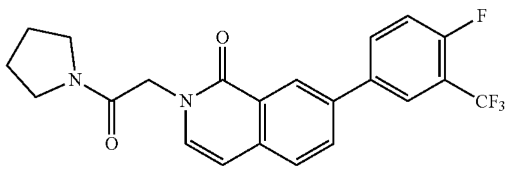 | 7-(4-fluoro-3-(trifluoromethyl)phenyl)-2-(2-oxo-2-(pyrrolidin-1-yl)ethyl)isoquinolin-1(2H)-one | $^1$H NMR (400 MHz, DMSO-$d_6$) δ (ppm): 8.41 (d, J = 1.6 Hz, 1H), 8.12-8.03 (m, 3H), 7.77 (d, J = 8.4 Hz, 1H), 7.62 (t, J = 10 Hz, 1H), 7.38 (d, J = 7.2 Hz, 1H), 6.65 (d, J = 4.4 Hz, 1H), 4.78 (s, 2H), 3.54 (t, J = 6.8 Hz, 2H), 3.32-3.28 (m, 2H), 1.97-1.90 (m, 2H), 1.82-1.75 (m, 2H). Calculated (M + H): 419.13, Found (M + H): 419.1. HPLC purity: 98.83% |
| 314 | 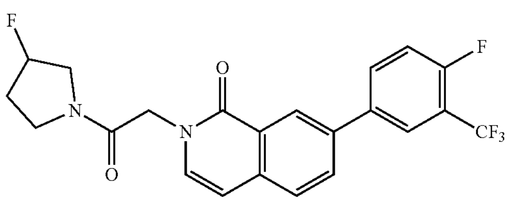 [SMILES: O=C(Cn1ccc2ccc(-c3ccc(F)c(C(F)(F)F)c3)cc2c1=O)N1CCC(F)C1] | 7-(4-fluoro-3-(trifluoromethyl)phenyl)-2-(2-(3-fluoropyrrolidin-1-yl)-2-oxoethyl)isoquinolin-1(2H)-one | $^1$H NMR (400 MHz, DMSO-$d_6$) δ (ppm): 8.41 (s, 1H), 8.09-8.03 (m, 3H), 7.77 (d, J = 8 Hz, 1H), 7.62 (t, J = 9.6 Hz, 1H), 7.40 (d, J = 6.8 Hz, 1H), 6.66 (d, J = 7.2 Hz, 1H), 5.39 (t, J = 50 Hz, 1H), 4.90-4.73 (m, 2H), 3.94-3.34 (m, 4H), 2.30-1.96 (m, 2H). Calculated (M + H): 437.12, Found (M + H): 437.1. HPLC purity: 96.69% |
| 315 | 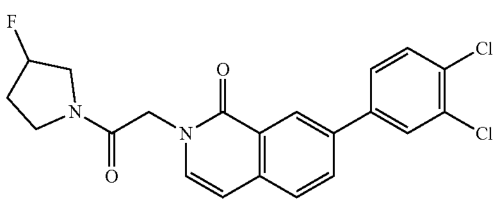 [SMILES: O=C(Cn1ccc2ccc(-c3ccc(Cl)c(Cl)c3)cc2c1=O)N1CCC(F)C1] | 7-(3,4-dichlorophenyl)-2-(2-(3-fluoropyrrolidin-1-yl)-2-oxoethyl)isoquinolin-1(2H)-one | $^1$H NMR (400 MHz, DMSO-$d_6$) δ (ppm): 8.40 (s, 1H), 8.05 (d, J = 7.6 Hz, 1H), 8.00 (s, 1H), 7.68-7.73 (m, 3H), 7.38 (d, J = 6.0 Hz, 1H), 6.64 (d, J = 7.2 Hz, 1 H), 5.38 (t, J = 49.2 Hz, 1H), 4.90-4.73 (m, 2 H), 3.93-3.42 (m, 4H), 2.29-1.97 (m, 2H). Calculated (M + H): 419.07, Found (M + H): 419.0. HPLC purity: 97.89% |
| 316 | 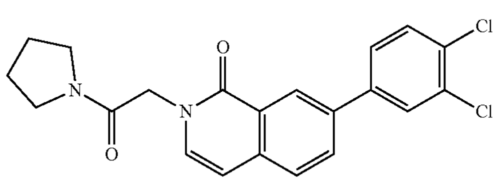 [SMILES: O=C(Cn1ccc2ccc(-c3ccc(Cl)c(Cl)c3)cc2c1=O)N1CCCC1] | 7-(3,4-dichlorophenyl)-2-(2-oxo-2-(pyrrolidin-1-yl)ethyl)isoquinolin-1(2H)-one | $^1$H NMR (400 MHz, DMSO-$d_6$) δ (ppm): 8.41 (s, 1H), 8.06 (d, J = 8.4 Hz, 1H), 8.00 (s, 1H), 7.76-7.71 (m, 3H), 7.37 (d, J = 7.2 Hz, 1H), 6.64 (d, J = 7.2 Hz, 1H), 4.77 (s, 2H), 3.54 (t, J = 6.4 Hz, 2H), 3.32-3.26 (m, 2H), 1.95-1.90 (m, 2H), 1.82-1.75 (m, 2H). Calculated (M + H): 401.07, Found (M + H): 401.1. HPLC purity: 98.38% |

F. PREPARATION OF PYRAZOLOPYRIMIDINONES

Example 317: Preparation of 3-(4-chloro-3-(trifluoromethyl)phenyl)-5-(2-oxo-2-(pyrrolidin-1-yl)ethyl)-1H-pyrazolo[3,4-d]pyrimidin-4(5H)-one

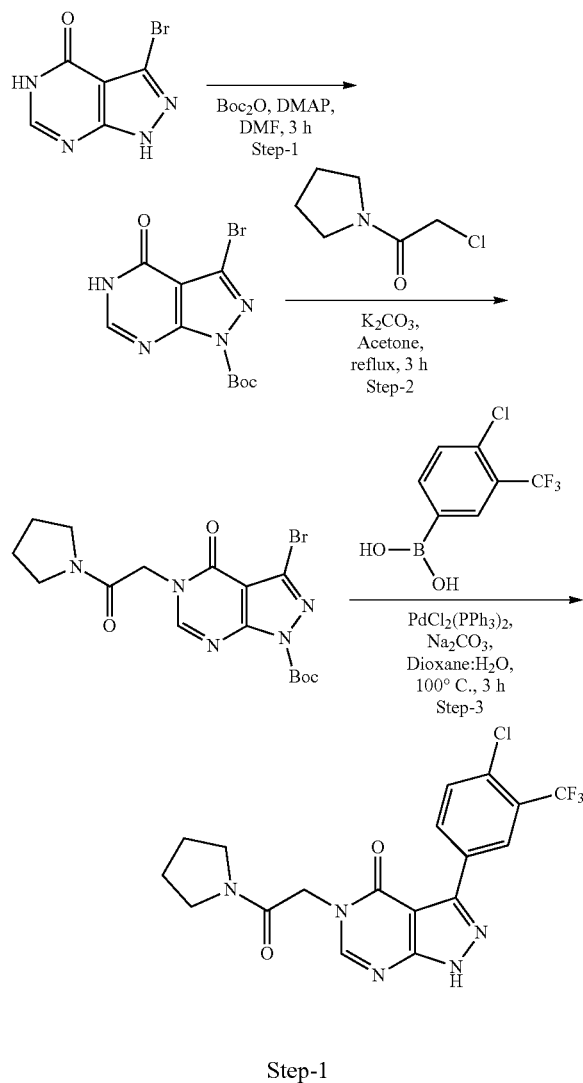

Step-1

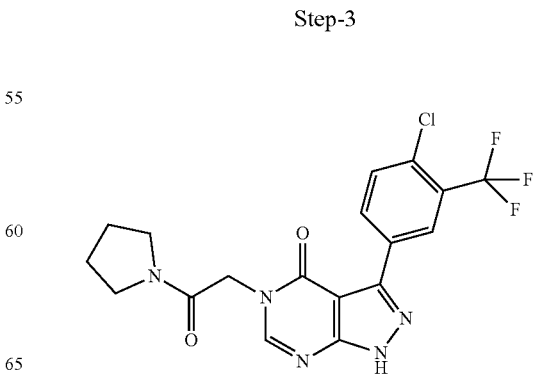

Preparation of tert-butyl 3-bromo-4-oxo-4,5-dihydro-1H-pyrazolo[3,4-d]pyrimidine-1-carboxylate To a stirred solution of 3-bromo-1H-pyrazolo[3,4-d]pyrimidin-4(5H)-one (0.1 g, 0.465 mmol) and N,N-dimethylpyridin-4-amine (0.005 g, 0.0465 mmol) in N,N-dimethyl formamide (6 mL) cooled to 0° C. was added di-tert-butyl dicarbonate (0.1 mL, 0.465 mmol) and then the reaction mixture was stirred at room temperature for 3 h. The reaction mixture was diluted with ice cold water (30 mL) with 1-2 mL of diethyl ether and stirred for 1 h at 0° C. The solid formed was filtered, washed with ether (2×5 mL) and dried under vacuum to get the title compound tert-butyl 3-bromo-4-oxo-4,5-dihydro-1H-pyrazolo[3,4-d]pyrimidine-1-carboxylate (0.13 g, crude) as white solid, which was used for next step without further purification. Calculated (M+H): 315; Found (M+H): 315.

Step-2

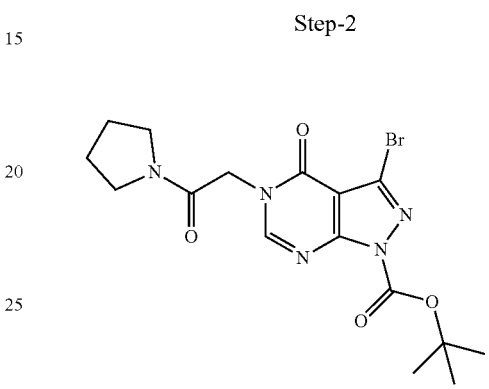

Preparation of tert-butyl 3-bromo-4-oxo-5-(2-oxo-2-(pyrrolidin-1-yl)ethyl)-4,5-dihydro-1H-pyrazolo[3,4-d]pyrimidine-1-carboxylate To a stirred solution of tert-butyl 3-bromo-4-oxo-4,5-dihydro-1H-pyrazolo[3,4-d]pyrimidine-1-carboxylate (0.13 g, 0.412 mmol) in dry acetone (4 mL) was added potassium carbonate (1.7 g, 1.23 mmol) followed by 2-chloro-1-(pyrrolidin-1-yl)ethanone (0.09 g, 0.619 mmol) at room temperature and the reaction mixture was heated at reflux for 3 h. The reaction mixture was concentrated, diluted with water and extracted with ethyl acetate (3×10 mL). The combined organic layer was dried over anhydrous sodium sulfate, filtered and concentrated to get crude compound which was washed with pentane (2×20 mL) to get the title compound tert-butyl 3-bromo-4-oxo-5-(2-oxo-2-(pyrrolidin-1-yl)ethyl)-4,5-dihydro-1H-pyrazolo[3,4-d]pyrimidine-1-carboxylate (0.085 g, 48.6% yield) as off white solid. Calculated (M+H): 426.07; Found (M+H): 326 (de-Boc mass observed).

Step-3

Preparation of tert-butyl 3-(4-chloro-3-(trifluoromethyl)phenyl)-4-oxo-5-(2-oxo-2-(pyrrolidin-1-yl)ethyl)-4,5-dihydro-1H-pyrazolo[3,4-d]pyrimidine-1-carboxylate To a stirred solution of tert-butyl 3-bromo-4-oxo-5-(2-oxo-2-(pyrrolidin-1-yl)ethyl)-4,5-dihydro-1H-pyrazolo[3,4-d]pyrimidine-1-carboxylate (0.085 g, 0.199 mmol) and (4-chloro-3-(trifluoromethyl)phenyl)boronic acid in dioxane:water mixture (5 mL, 4:1) was added sodium carbonate (0.064 g, 0.597 mmol) and the reaction mixture was purged with argon for 15 minutes. Then Bis(triphenylphosphine)palladium(II) dichloride (0.014 g, 0.019 mmol) was added and the reaction mixture heated at 100° C. for 2 h. The reaction mixture was cooled to room temperature, diluted with water and extracted with ethyl acetate (4×25 mL). The combined organic layer was dried over anhydrous sodium sulfate, filtered and concentrated to get crude compound which was purified by silica gel column chromatography using 4% methanol in dichloromethane to get the title compound tert-butyl 3-(4-chloro-3-(trifluoromethyl)phenyl)-4-oxo-5-(2-oxo-2-(pyrrolidin-1-yl)ethyl)-4,5-dihydro-1H-pyrazolo[3,4-d]pyrimidine-1-carboxylate (0.01 g, 11.90% yield) as white solid. $^1$H NMR (400 MHz, DMSO-$d_6$) δ (ppm): 14.2 (s, 1H), 9.90 (s, 1H), 8.61 (d, J=8.4 Hz, 1H), 8.25 (s, 1H), 7.80 (d, J=8.8 Hz, 1H), 4.84 (s, 2H), 3.55-3.52 (m, 2H), 3.32-3.22 (m, 2H), 2.04-1.91 (m, 2H), 1.82-1.76 (m, 2H). Calculated (M+H): 426.09; Found (M+H): 426. HPLC purity: 99.83%.

Example 318: Preparation of 3-(4-chloro-3-(trifluoromethyl)phenyl)-5-(2-(3-fluoropyrrolidin-1-yl)-2-oxoethyl)-1H-pyrazolo[3,4-d]pyrimidin-4(5H)-one

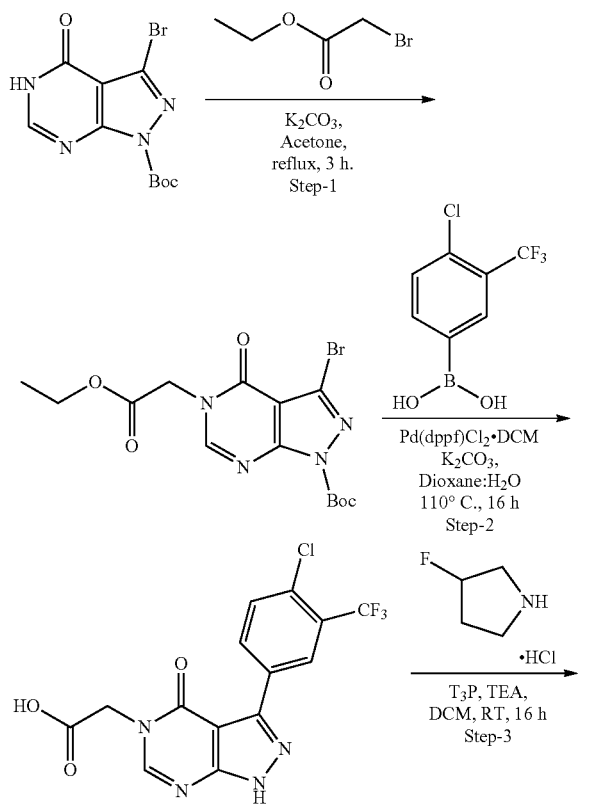

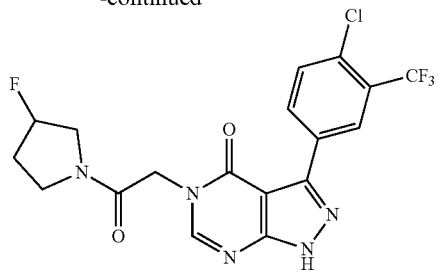

Step-1

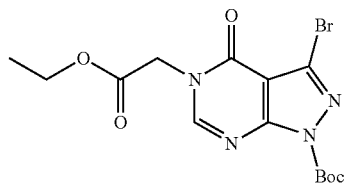 [SMILES: CCOC(=O)Cn1cnc2c(c(Br)nn2C(=O)OC(C)(C)C)c1=O]

Preparation of tert-butyl 3-bromo-5-(2-ethoxy-2-oxoethyl)-4-oxo-4,5-dihydro-1H-pyrazolo[3,4-d]pyrimidine-1-carboxylate To a stirred solution of tert-butyl 3-bromo-4-oxo-4,5-dihydro-1H-pyrazolo[3,4-d]pyrimidine-1-carboxylate (1.1 g, 3.49 mmol) in dry acetone (15 ml) at room temperature was added potassium carbonate (1.44 g, 10.47 mmol) followed by ethyl-2-bromoacetate (0.58 mL, 5.23 mmol) and the reaction mixture was heated at reflux for 3 h. The reaction mixture concentrated, diluted with water and extracted with ethyl acetate (4×50 mL). The combined organic layer was dried over anhydrous sodium sulfate, filtered and concentrated to get the crude compound which was purified by silica gel column chromatography using 100% dichloromethane to get the title compound tert-butyl 3-bromo-5-(2-ethoxy-2-oxoethyl)-4-oxo-4,5-dihydro-1H-pyrazolo[3,4-d]pyrimidine-1-carboxylate (0.67 g, 47.85% yield) as yellow solid. Calculated (M+H): 401.04; Found (M+H): 301.2 (de-Boc mass observed).

Step-2

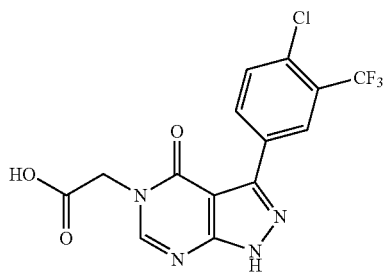 [SMILES: O=C(O)Cn1cnc2[nH]nc(-c3ccc(Cl)c(C(F)(F)F)c3)c2c1=O]

Preparation of 2-(3-(4-chloro-3-(trifluoromethyl)phenyl)-4-oxo-1H-pyrazolo[3,4-d]pyrimidin-5(4H)-yl)acetic acid To a stirred solution of tert-butyl 3-bromo-5-(2-ethoxy-2-oxoethyl)-4-oxo-4,5-dihydro-1H-pyrazolo[3,4-d]pyrimidine-1-carboxylate (0.67 g, 1.67 mmol) and (4-chloro-3-(trifluoromethyl) phenyl)boronic acid (0.449 g, 2.00 mmol) in dioxane:water mixture (10 mL, 4:1) was added potassium carbonate (0.69 g, 5.01 mmol) and the reaction mixture was purged with argon for 15 minutes. Then [1,1'-Bis(diphenylphosphino)ferrocene]dichloropalladium(II). dichloromethane complex (pd(dppf)Cl$_2$.CH$_2$Cl$_2$) (0.068 g, 0.083 mmol) was added and the reaction mixture was heated at 110° C. for 16 h. The reaction mixture was concentrated, the residue was diluted with water (30 mL) and extracted with ethyl acetate (30 mL). The aqueous layer was acidified to pH~2 with 1.5N hydrochloric acid solution under cooling to get precipitation. The precipitate was filtered, washed with pentane (2×10 mL), diethyl ether (2×10 mL) and dried under vacuum to get the title compound 2-(3-(4-chloro-3-(trifluoromethyl)phenyl)-4-oxo-1H-pyrazolo[3,4-d]pyrimidin-5(4H)-yl)acetic acid (0.32 g, 47.8% yield) as brown solid. Calculated (M+H): 373.02; Found (M+H): 373.

Step-3

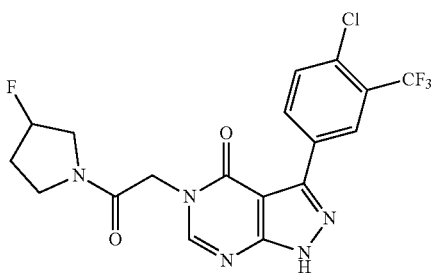 [SMILES: O=C(Cn1cnc2[nH]nc(-c3ccc(Cl)c(C(F)(F)F)c3)c2c1=O)N1CCC(F)C1]

Preparation of 3-(4-chloro-3-(trifluoromethyl)phenyl)-5-(2-(3-fluoropyrrolidin-1-yl)-2-oxoethyl)-1H-pyrazolo[3,4-d]pyrimidin-4(5H)-one To a stirred solution of 2-(3-(4-chloro-3-(trifluoromethyl)phenyl)-4-oxo-1H-pyrazolo[3,4-d]pyrimidin-5(4H)-yl)acetic acid (0.12 g, 0.322 mmol) in dichloromethane (10 mL) was added triethylamine (0.08 mL, 0.644 mmol) at room temperature and stirred for 10 minutes. Then 3-fluoropyrrolidine hydrochloride salt (0.048 g, 0.388 mmol) was added. Then the reaction mixture was cooled to 0° C., 1-Propanephosphonic anhydride solution (T$_3$P) (0.3 mL, 0.483 mmol, 50% in ethyl acetate) was added and stirred at room temperature for 16 h. The solution was diluted with water and extracted with dichloromethane (4×50 mL). The combined organic layer was dried over anhydrous sodium sulfate, filtered and concentrated to get crude compound which was purified by silica gel column chromatography using 3% methanol in dichloromethane to afford the title compound 3-(4-chloro-3-(trifluoromethyl)phenyl)-5-(2-(3-fluoropyrrolidin-1-yl)-2-oxoethyl)-1H-pyrazolo[3,4-d]pyrimidin-4(5H)-one (0.015 g, 10.4% yield) as off-white solid. $^1$H NMR (400 MHz, DMSO-d$_6$) δ (ppm) 14.20 (s, 1H), 8.99 (s, 1H), 8.60 (d, J=8.4 Hz, 1H), 8.28 (s, 1H), 7.80 (d, J=8.4 Hz, 1H), 5.52-5.26 (m, 1H), 4.98-4.80 (m, 2H), 3.90-3.27 (m, 4H), 2.23-2.11 (m, 2H). Calculated (M+H): 444.08; Found (M+H): 444. HPLC purity: 99.36%.

| Ex. No. | Structure | Name | Analytical data |
|---|---|---|---|
| 319 | 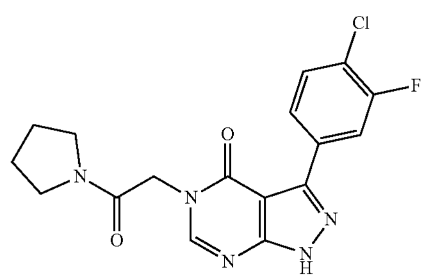 [SMILES: O=C(Cn1cnc2[nH]nc(-c3ccc(Cl)c(F)c3)c2c1=O)N1CCCC1] | 3-(4-chloro-3-fluorophenyl)-5-(2-oxo-2-(pyrrolidin-1-yl)ethyl)-1H-pyrazolo[3,4-d]pyrimidin-4(5H)-one | $^1$H-NMR (DMSO-d$_6$, 400 MHz) δ (ppm): 14.12 (s, 1H), 8.49 (d, 11.2 Hz, 1H), 8.26 (s, 1H), 8.21 (d, 8.4 Hz, 1H), 7.65 (t, 7.6 Hz, 1H), 4.82 (s, 2H), 3.53 (t, 6.8 Hz, 2H), 3.30 (t, 6.4 Hz, 2H), 1.96-1.92 (m, 2H), 1.81-1.70 (m, 2H); Calculated (M − H): 374.09, Found (M − H): 374.0. HPLC purity: 99.31% |
| 320 | 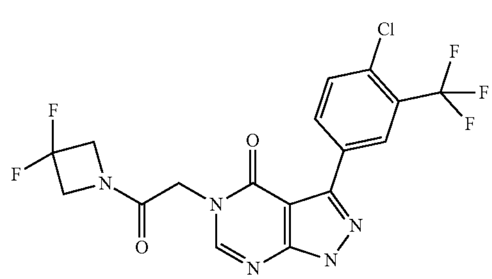 [SMILES: O=C(Cn1cnc2[nH]nc(-c3ccc(Cl)c(C(F)(F)F)c3)c2c1=O)N1CC(F)(F)C1] | 3-(4-Chloro-3-trifluoromethyl-phenyl)-5-[2-(3,3-difluoro-azetidin-1-yl)-2-oxo-ethyl]-1,5-dihydro-pyrazolo[3,4-d]pyrimidin-4-one | $^1$H-NMR (DMSO-d$_6$, 400 MHz) δ (ppm): 14.22 (s, 1H), 9.00 (s, 1H), 8.58 (d, J = 8 Hz, 1H), 8.27 (s, 1H), 7.81 (d, J = 8.4 Hz, 1H), 4.78 (s, 4H), 4.36 (m, 2H). Calculated (M + H): 448.05; Found (M + H): 448.0. HPLC purity: 97.49% |

G. PREPARATION OF PYRAZOLOPYRAZINONES

Example 321: Preparation of 3-(4-fluoro-3-(trifluoromethyl) phenyl)-5-(2-(3-fluoropyrrolidin-1-yl)-2-oxoethyl) pyrazolo [1, 5-a]pyrazin-4(5H)-one

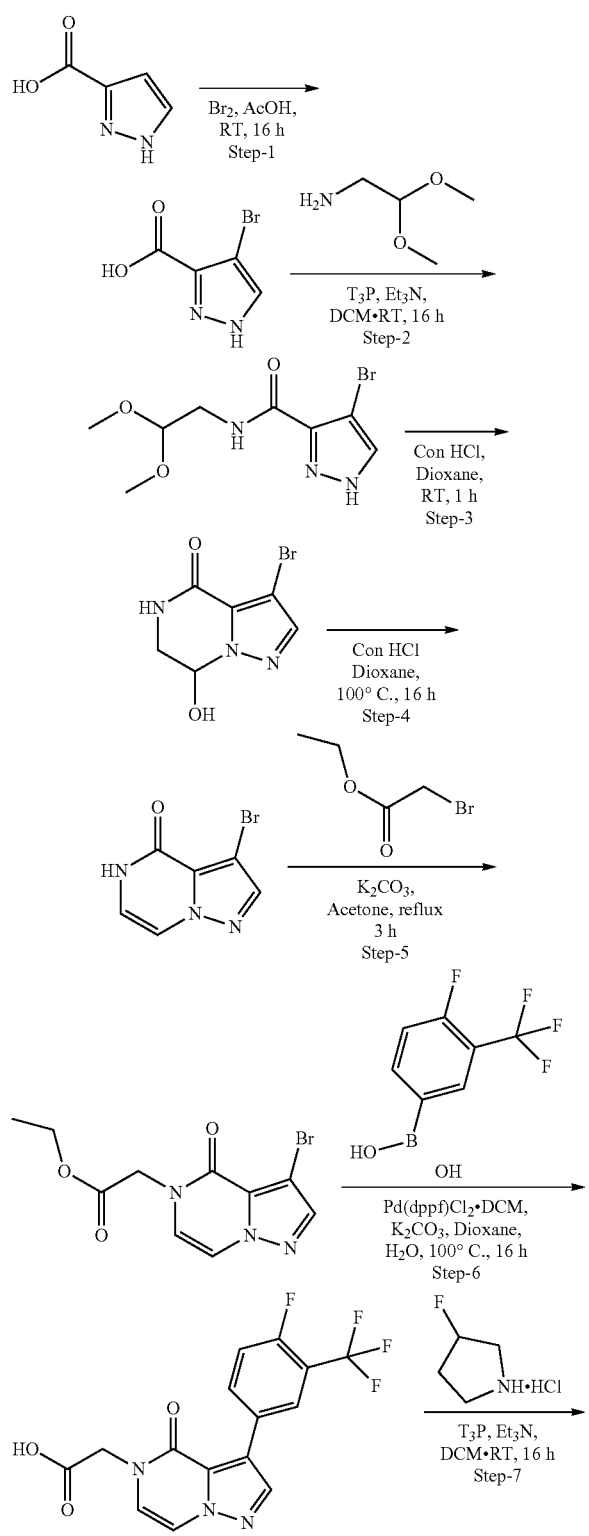

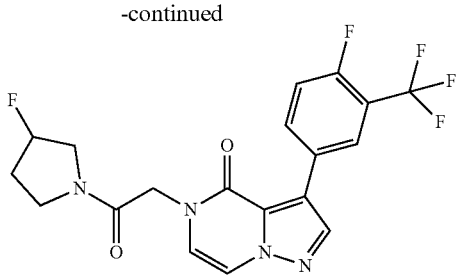

Step 1

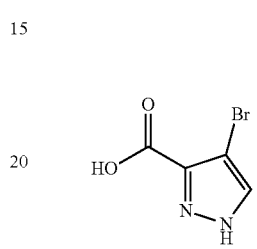

Preparation of 4-bromo-1H-pyrazole-3-carboxylic acid

To a stirred solution of 1H-pyrazole-3-carboxylic acid (2.0 g, 17.85 mmol) in acetic acid (50 mL), bromine (1.2 mL, 23.21 mmol) was added at 0° C. and the reaction mixture was stirred at room temperature for 16 h. The reaction mixture was diluted with water (150 mL) and extracted with ethyl acetate (3×100 mL). The combined organic layer was washed with brine solution, dried over anhydrous sodium sulfate, filtered and concentrated to afford the title compound 4-bromo-1H-pyrazole-3-carboxylic acid (3.4 g, crude) as off-white solid. Calculated (M+H): 190.94; Found (M+H): 191.0.

Step 2

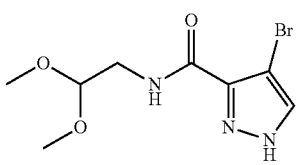

Preparation of 4-bromo-N-(2,2-dimethoxyethyl)-1H-pyrazole-3-carboxamide

To a stirred solution of 4-bromo-1H-pyrazole-3-carboxylic acid (3.4 g, 17.8 mmol) in dichloromethane (100 mL) were added triethylamine (12.42 mL, 89.00 mmol) and 2,2-dimethoxyethanamine (2.9 mL, 26.70 mmol) at room temperature. The reaction mixture was cooled to 0° C. and 1-propanephosphonic anhydride solution (T₃P) (15.89 mL, 26.70 mmol, 50% in ethyl acetate) was added and the reaction mixture was stirred at room temperature for 16 h. The reaction mixture was diluted with water (200 mL) and extract with dichloromethane (3×100 mL). The combined organic layer was dried over anhydrous sodium sulfate, filtered and concentrated to afford the title compound 4-bromo-N-(2,2-dimethoxyethyl)-1H-pyrazole-3-carboxamide (3.6 g, crude) as a white solid. Calculated (M−H): 276.01; Found (M−H): 276.0.

Step 3

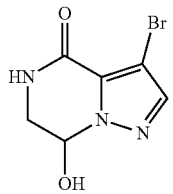 [SMILES: O=C1NCC(O)n2ncc(Br)c21]

Preparation of 3-bromo-7-hydroxy-6, 7-dihydropyrazolo [1, 5-a]pyrazin-4(5H)-one

To a stirred solution of 4-bromo-N-(2,2-dimethoxyethyl)-1H-pyrazole-3-carboxamide (3.6 g, 12.94 mmol) in 1,4-dioxane (100 mL), concentrated hydrochloric acid was added slowly and solution was stirred at room temperature for 1 h. The reaction mixture was quenched with ice water (200 mL), extracted with ethyl acetate (3×100 mL) and the combined organic layer was dried over anhydrous sodium sulfate, filtered and concentrated to afford the title compound 3-bromo-7-hydroxy-6, 7-dihydropyrazolo [1, 5-a]pyrazin-4(5H)-one (3.0 g, crude) as a white solid. Calculated (M+H): 231.96; Found (M+H): 232.0.

Step 4

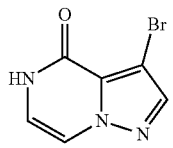

Preparation of 3-bromopyrazolo[1, 5-a]pyrazin-4(5H)-one

To a stirred solution of 3-bromo-7-hydroxy-6,7-dihydropyrazolo[1,5-a]pyrazin-4(5H)-one (3.0 g, 12.94 mmol) in 1,4-dioxane (60 mL), concentrated hydrochloric acid was added slowly and the reaction mixture was heated at 100° C. for 16 h. After completion of the reaction (monitored by TLC), the reaction mixture was diluted with ice water (200 mL) and extracted with ethyl acetate (3×100 mL). The combined organic layer was dried over anhydrous sodium sulfate, filtered and concentrated to afford the crude compound which was triturated with ether:n-pentane mixture to afford the title compound 3-bromopyrazolo [1, 5-a]pyrazin-4(5H)-one as a off-white solid (0.7 g, crude). Calculated (M+H): 213.96; Found (M+H): 214.0.

Step 5

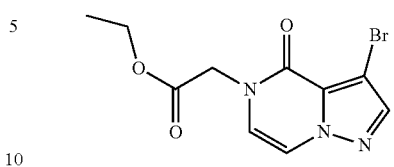

Preparation of ethyl 2-(3-bromo-4-oxopyrazolo [1, 5-a]pyrazin-5(4H)-yl) acetate

To a solution of 3-bromopyrazolo [1, 5-a]pyrazin-4(5H)-one (0.5 g, 2.33 mmol) in acetone (20 mL) was added potassium carbonate (0.97 g, 7.00 mmol) followed by ethylbromoacetate (0.51 mL, 4.67 mmol). The reaction mixture was heated at 55° C. for 16 h. After completion of the reaction (monitored by TLC), the reaction mixture was filtered and the filtrate was concentrated under vacuum. The crude product was purified by silica gel column chromatography using 2% methanol in dichloromethane to afford the title compound ethyl 2-(3-bromo-4-oxopyrazolo[1,5-a]pyrazin-5(4H)-yl)acetate (0.7 g, 100% yield) as a off-white solid. Calculated (M+H): 299.99; Found (M+H): 300.0.

Step 6

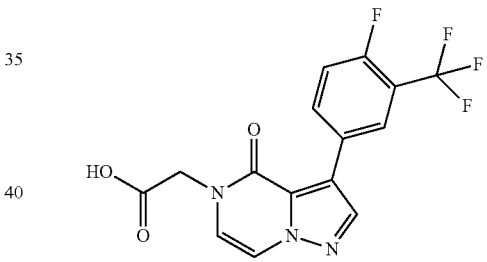

Preparation of 2-(3-(4-fluoro-3-(trifluoromethyl) phenyl)-4-oxopyrazolo[1,5-a]pyrazin-5(4H)-yl)acetic acid To a solution of 2-(3-bromo-4-oxopyrazolo [1, 5-a] pyrazin-5(4H)-yl) acetate (0.5 g, 1.66 mmol) in 1,4-dioxane: water mixture (4:1, 30 mL), potassium carbonate (0.69 g, 4.99 mmol) and (4-fluoro-3-(trifluoromethyl)phenyl)boronic acid (0.52 g, 2.49 mmol) were added and the reaction mixture was purged with argon for 10 min. Then [1,1'-bis (diphenylphosphino)ferrocene]dichloropalladium(II), complex with dichloromethane (Pd(dppf)Cl$_2$.DCM) (0.14 g, 0.166 mmol) was added and the reaction mixture was heated at 100° C. for 16 h. The reaction mixture was diluted with water (50 mL) and it was washed with ethyl acetate (2×30 mL). The aqueous layer pH was adjusted to acidic by using 1.5N hydrochloric acid solution and extracted with ethyl acetate (2×100 mL). The combined organic layer was dried over anhydrous sodium sulphate, filtered and concentrated. The crude was purified by silica gel column chromatography using 5% methanol in dichloromethane to afford 2-(3-(4-fluoro-3-(trifluoromethyl)phenyl)-4-oxopyrazolo[1,5-a]

pyrazin-5(4H)-yl)acetic acid (0.48 g, 81.35% yield) as a off-white solid. Calculated (M+H): 356.06; Found (M+H): 356.0.

Step 7

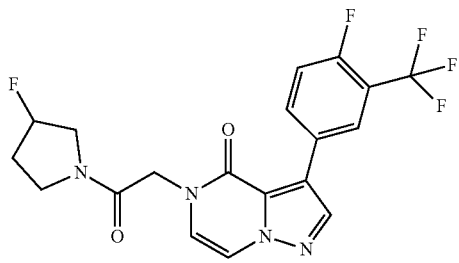 [SMILES: O=C(Cn1ccn2ncc(-c3ccc(F)c(C(F)(F)F)c3)c2c1=O)N1CCC(F)C1]

Preparation of 3-(4-fluoro-3-(trifluoromethyl)phenyl)-5-(2-(3-fluoropyrrolidin-1-yl)-2-oxoethyl)pyrazolo[1,5-a]pyrazin-4(5H)-one To a stirred solution of 2-(3-(4-fluoro-3-(trifluoromethyl)phenyl)-4-oxopyrazolo[1,5-a]pyrazin-5(4H)-yl)acetic acid (0.12 g, 0.33 mmol) in dichloromethane (10 mL) was added triethylamine (0.23 ml, 1.69 mmol) at room temperature followed by 3-fluoropyrrolidine hydrochloride (0.063 g, 0.50 mmol). The reaction mixture was cooled to 0° C., 1-propanephosphonic anhydride solution (T$_3$P) (0.4 ml, 0.676 mmol, 50% in ethyl acetate) was added and stirred at room temperature for 16 h. The reaction mixture was diluted with water (50 mL) and extracted with dichloromethane (2×50 mL). The combined organic layer was dried over anhydrous sodium sulfate, filtered and concentrated. The crude product was purified by silica gel column chromatography using 3% methanol in dichloromethane to afford 3-(4-fluoro-3-(trifluoromethyl)phenyl)-5-(2-(3-fluoropyrrolidin-1-yl)-2-oxoethyl)pyrazolo[1,5-a]pyrazin-4(5H)-one (0.065 g, 45% yield) as a off-white solid. $^1$H NMR (400 MHz, DMSO-d$_6$) δ (ppm): 8.33 (s, 1H), 8.30 (d, J=5.6 Hz, 1H), 8.12-8.15 (m, 1H), 7.808 (d, J=6 Hz, 1H), 7.53 (t, J=9.2 Hz, 1H), 7.09-7.11 (m, 1H), 5.38 (m, 1H), 4.69-4.88 (m, 2H), 3.31-3.88 (m, 4H), 1.99-2.30 (m, 2H). Calculated M+H: 427.11; Found M+H: 427.1. HPLC purity: 99.7%.

TABLE 33

The following compounds were prepared by the method described above:

| Ex. No. | Structure | IUPAC Name | Analytical Data |
|---|---|---|---|
| 322 | 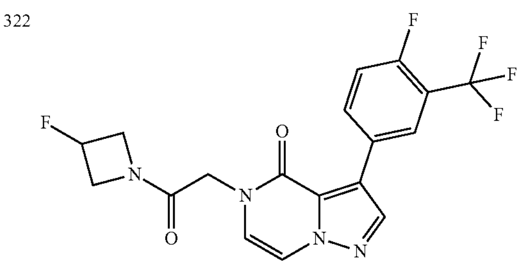 | 3-(4-fluoro-3-(trifluoromethyl)phenyl)-5-(2-(3-fluoroazetidin-1-yl)-2-oxoethyl)pyrazolo[1,5-a]pyrazin-4(5H)-one | $^1$H NMR (400 MHz, DMSO-d$_6$) δ (ppm): 8.33 (s, 1H), 8.30-8.29 (m, 1H), 8.15-8.122 (m, 1H), 7.813 (d, J = 5.6 Hz, 1H), 7.53 (t, J = 10.4 Hz, 1H), 7.09 (d, J = 5.6 Hz, 1H), 5.525-5.35 (m, 1H), 4.61 (s, 2H), 4.57-3.89 (m, 4H). Calculated M + H: 413.1; Found M + H: 413.1; HPLC purity: 99.58% |
| 323 | 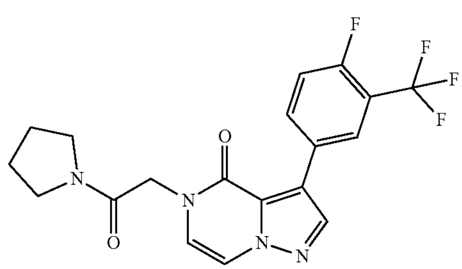 [SMILES: O=C(Cn1ccn2ncc(-c3ccc(F)c(C(F)(F)F)c3)c2c1=O)N1CCCC1] | 3-(4-fluoro-3-(trifluoromethyl)phenyl)-5-(2-oxo-2-(pyrrolidin-1-yl)ethyl)pyrazolo[1,5-a]pyrazin-4(5H)-one | $^1$H NMR (400 MHz, DMSO-d$_6$) δ (ppm): 8.29 (s, 1H), 8.31-8.29 (m, 1H), 8.152-8.125 (m, 1H), 7.79 (d, J = 5.2 Hz, 1H), 7.53 (t, J = 9.6 Hz, 1H), 7.09 (d, J = 6.0 Hz, 1H), 4.72 (s, 2H), 3.49 (t, J = 7.2 Hz, 2H), 3.29 (t, J = 6.8 Hz, 2H), 1.88-1.95 (m, 2H), 1.74-1.807 (m, 2H) Calculated (M + H): 409.12; Found (M + H): 409.1; HPLC purity: 99.88% |
| 324 | 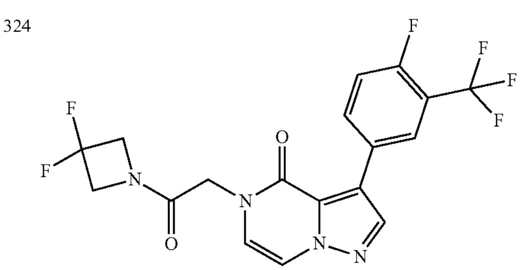 | 5-(2-(3,3-difluoroazetidin-1-yl)-2-oxoethyl)-3-(4-fluoro-3-(trifluoromethyl)phenyl)pyrazolo[1,5-a]pyrazin-4(5H)-one | $^1$H NMR (400 MHz, DMSO-d$_6$) δ (ppm): 8.34 (s, 1H), 8.31 (d, J = 7.2 Hz, 1H), 8.14-8.12 (m, 1H), 7.82 (d, J = 6 Hz, 1H), 7.53 (t, J = 10.0 Hz, 1H), 7.09 (d, J = 5.6 Hz, 1H), 4.74 (t, J = 11.6 Hz, 2H), 4.68 (s, 2H), 4.34 (t, J = 12 Hz, 2H). Calculated (M + H): 431.09; Found (M + H): 431.1; HPLC purity: 99.78% |

TABLE 33-continued

The following compounds were prepared by the method described above:

| Ex. No. | Structure | IUPAC Name | Analytical Data |
|---|---|---|---|
| 325 | 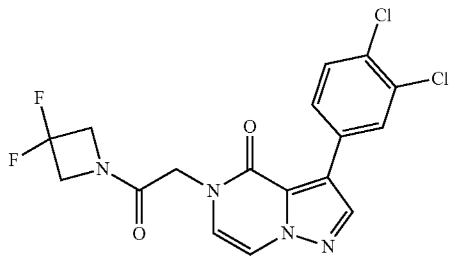 [SMILES: O=C(Cn1ccn2ncc(-c3ccc(Cl)c(Cl)c3)c2c1=O)N1CC(F)(F)C1] | 3-(3,4-dichlorophenyl)-5-(2-(3,3-difluoroazetidin-1-yl)-2-oxoethyl)pyrazolo[1,5-a]pyrazin-4(5H)-one | $^{1}$H NMR (400 MHz, DMSO-d$_6$) δ (ppm): 8.33 (s, 1H), 8.20 (d, J = 2.4 Hz, 1H), 7.84-7.81 (m, 2H), 7.63 (d, J = 8.4 Hz, 1H), 7.09 (d, J = 6.4 Hz, 1H), 4.74 (t, J = 12.4 Hz, 2H), 4.68 (s, 2H), 4.35 (t, J = 12.4 Hz, 2H). Calculated (M + H): 413.03; Found (M + H): 413.0; HPLC purity: 97.39% |
| 326 | 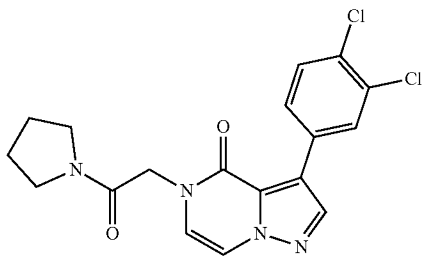 [SMILES: O=C(Cn1ccn2ncc(-c3ccc(Cl)c(Cl)c3)c2c1=O)N1CCCC1] | 3-(3,4-dichlorophenyl)-5-(2-oxo-2-(pyrrolidin-1-yl)ethyl)pyrazolo[1,5-a]pyrazin-4(5H)-one | $^{1}$H NMR (400 MHz, DMSO-d$_6$) δ (ppm): 8.32 (s, 1H), 8.21 (d, J = 1.6 Hz, 1H), 7.84 (dd, J = 2.4 Hz, 8.0 Hz, 1H), 7.79 (d, J = 5.6 Hz, 1H), 7.63 (d, J = 8.4 Hz, 1H), 7.09 (d, J = 6.0 Hz, 1H), 4.72 (s, 2H), 3.49 (t, J = 6.8 Hz, 2H), 3.29 (t, J = 10 Hz, 2H), 1.95-1.89 (m, 2H), 1.74-1.81 (m, 2H) Calculated (M + H): 391.07; Found (M + H): 391.0; HPLC purity: 98.52% |
| 327 | 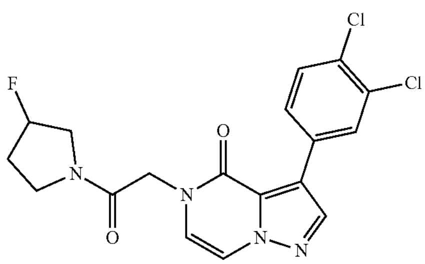 [SMILES: O=C(Cn1ccn2ncc(-c3ccc(Cl)c(Cl)c3)c2c1=O)N1CCC(F)C1] | 3-(3,4-dichlorophenyl)-5-(2-(3-fluoropyrrolidin-1-yl)-2-oxoethyl)pyrazolo[1,5-a]pyrazin-4(5H)-one | $^{1}$H NMR (400 MHz, DMSO-d$_6$) δ (ppm): 8.33 (s, 1H), 8.21 (d, J = 1.6 Hz, 1H), 7.84-7.79 (m, 2H), 7.63 (d, J = 8.4 Hz, 1H), 7.12-7.09 (m, 1H), 5.37 (m, 1H), 4.87-4.69 (m, 2 H), 3.88-3.39 (m, 4H), 1.89-1.69 (m, 2H). Calculated (M + H): 409.06; Found (M + H): 409.0; HPLC purity: 97.40% |
| 328 | 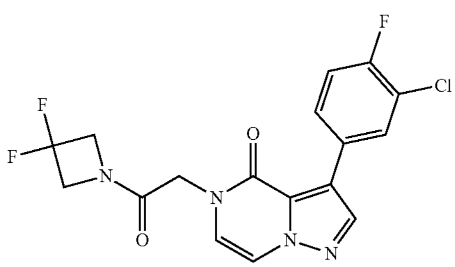 [SMILES: O=C(Cn1ccn2ncc(-c3ccc(F)c(Cl)c3)c2c1=O)N1CC(F)(F)C1] | 3-(3-chloro-4-fluorophenyl)-5-(2-(3,3-difluoroazetidin-1-yl)-2-oxoethyl)pyrazolo[1,5-a]pyrazin-4(5H)-one | $^{1}$H NMR (400 MHz, DMSO-d$_6$) δ (ppm): 8.29 (s, 1H), 8.14-8.12 (m, 1H), 7.83-7.80 (m, 2H), 7.46-7.41 (m, 1H), 7.08 (d, J = 6.4 Hz, 1H), 4.74 (t, J = 12.4 Hz, 2H), 4.68 (s, 2H), 4.35 (t, J = 12.0 Hz, 2H). Calculated (M + H): 397.06; Found (M + 1): 397.0. HPLC purity 99.88% |
| 329 | 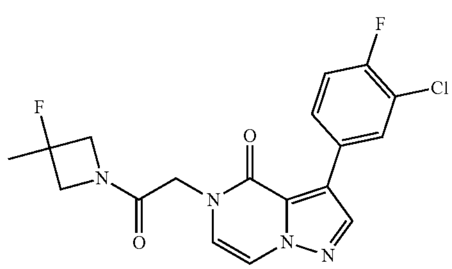 [SMILES: CC1(F)CN(C(=O)Cn2ccn3ncc(-c4ccc(F)c(Cl)c4)c3c2=O)C1] | 3-(3-chloro-4-fluorophenyl)-5-(2-(3-fluoro-3-methylazetidin-1-yl)-2-oxoethyl)pyrazolo[1,5-a]pyrazin-4(5H)-one | $^{1}$H NMR (400 MHz, DMSO-d$_6$) δ (ppm): 8.28 (s, 1H), 8.13 (d, J = 7.6 Hz, 1H), 7.80-7.79 (m, 2H), 7.45-7.41 (m, 1H), 7.08 (d, J = 6.0 Hz, 1H), 4.61 (s, 2H), 4.41-4.28 (m, 2H), 3.99 (d, J = 20.0 Hz, 2H), 1.59 (d, J = 21.6 Hz, 3H). Calculated (M + H): 393.09; Found (M + 1): 393.1. HPLC purity 99.21% |

H. PREPARATION OF THIOENOTRIAZINONES

Example 330: Preparation of 5-(3-chloro-4-fluorophenyl)-3-(2-oxo-2-(pyrrolidin-1-yl)ethyl)thieno[2,3-d][1,2,3]triazin-4(3H)-one

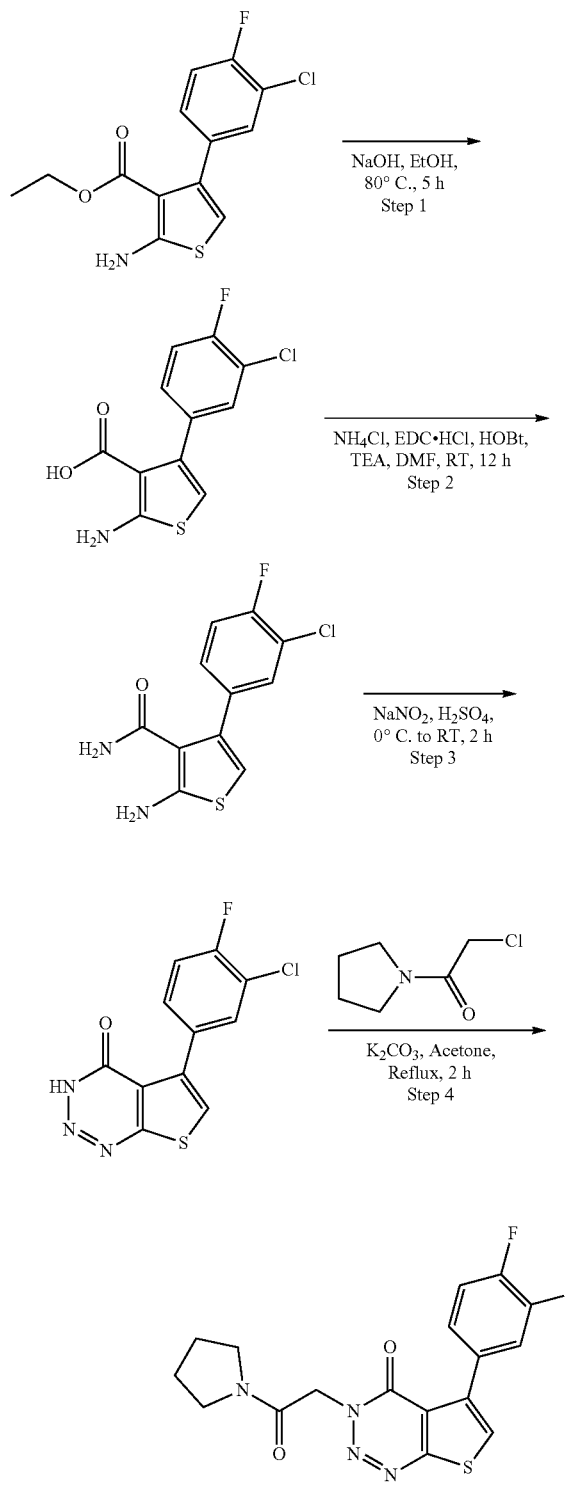

Step-1

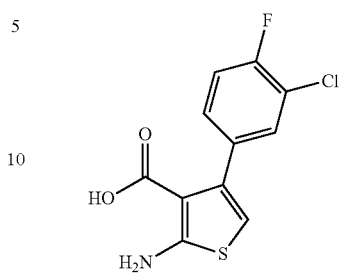

Preparation of 2-amino-4-(3-chloro-4-fluorophenyl)thiophene-3-carboxylic acid

To a solution of ethyl 2-amino-4-(3-chloro-4-fluorophenyl)thiophene-3-carboxylate (0.6 g, 4.81 mmol) in ethanol (5 mL) was added 3N sodium hydroxide solution (0.5 mL) and the reaction mixture was stirred at 80° C. for 2 h. After completion of the reaction (monitored by TLC), the reaction mixture was evaporated, diluted with water (30 ml) and acidified with 1.5M hydrochloric acid to pH 2-4. The precipitated solid was filtered, washed with water, and dried to afford the title compound 2-amino-4-(3-chloro-4-fluorophenyl)thiophene-3-carboxylic acid (0.45 g, 82% yield) as a brownish solid. Calculated M+H: 271.99; Found M+H: 272.0.

Step-2

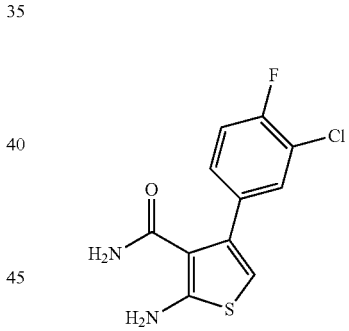

Preparation of 2-amino-4-(3-chloro-4-fluorophenyl)thiophene-3-carboxamide

To a solution of 2-amino-4-(3-chloro-4-fluorophenyl)thiophene-3-carboxylic acid (0.45 g, 1.66 mmol) in dimethylformamide (DMF) was added 1-Ethyl-3-(3-dimethylaminopropyl)carbodiimide (EDCI.HCl) (0.47 g, 2.49 mmol), 1-hydroxybenzotriazole (HOBt) (0.38 g, 2.49 mmol), triethylamine (0.69 mL, 4.98 mmol) and ammonium chloride (0.18 g, 3.32 mmol) and stirred at room temperature for 12 h. After completion of the reaction (monitored by TLC), the reaction mixture was diluted with water and extracted with ethyl acetate (2×30 mL). The combined organic layers were dried over anhydrous sodium sulphate, filtered and concentrated to afford the crude product, which was purified by silica gel (60-120) column chromatography using 40% ethyl acetate in hexane to afford the title compound 2-amino-4-(3-chloro-4-fluorophenyl)thiophene-3-carboxamide (0.3 g, 65% yield) as a brownish solid. $^1$H-NMR (DMSO-$d_6$, 400 MHz) δ (ppm): 8.00 (s, 2H), 7.46 (d, J=7.2 Hz, 1H), 7.28 (s, 1H), 7.17 (t, J=8.4 Hz, 1H), 6.36 (s, 2H).

Step-3

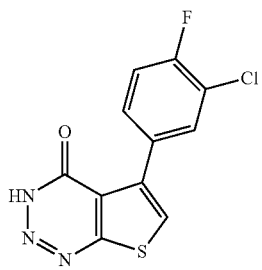 [SMILES: O=c1[nH]nnc2scc(-c3ccc(F)c(Cl)c3)c12]

Preparation of 5-(3-chloro-4-fluorophenyl)thieno[2,3-d][1,2,3]triazin-4(3H)-one

To a solution of 2-amino-4-(3-chloro-4-fluorophenyl)thiophene-3-carboxamide (0.3 g, 1.11 mmol), in concentrated sulfuric acid (3 mL) was added a solution of sodium nitrite (0.15 g, 2.22 mmol) in concentrated sulfuric acid (2 mL) slowly at 0° C. and stirred at 0° C. for 2 h. The reaction mixture was diluted with water, the precipitated solid was filtered, washed with water and dried under vacuum to afford the title compound 5-(3-chloro-4-fluorophenyl)thieno[2,3-d][1,2,3]triazin-4(3H)-one (0.15 g, 48% yield) as a brownish solid. Calculated M−H: 279.98; Found M−H: 280.0.

Step-4

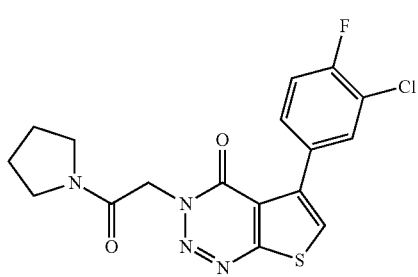 [SMILES: O=C(Cn1nnc2scc(-c3ccc(F)c(Cl)c3)c2c1=O)N1CCCC1]

Preparation of 5-(3-chloro-4-fluorophenyl)-3-(2-oxo-2-(pyrrolidin-1-yl)ethyl)thieno[2,3-d][1,2,3]triazin-4(3H)-one To a solution of 5-(3-chloro-4-fluorophenyl)thieno[2,3-d][1,2,3]triazin-4(3H)-one (0.1 g, 0.36 mmol) in acetone (4 mL) was added 2-chloro-1-(pyrrolidin-1-yl)ethanone (0.1 g, 0.71 mmol) and potassium carbonate (0.14 g, 1.07 mmol) at room temperature and heated to reflux for 2 h. After completion of the reaction (monitored by TLC), the reaction mixture was evaporated, diluted with water (30 mL), extracted with ethyl acetate (2×30 mL). The combined organic layers were washed with water, dried over anhydrous sodium sulfate, filtered and concentrated. The crude was purified by silica gel (60-120) column chromatography using 40% ethyl acetate in hexane to afford the title compound 5-(3-chloro-4-fluorophenyl)-3-(2-oxo-2-(pyrrolidin-1-yl)ethyl)thieno[2,3-d][1,2,3]triazin-4(3H)-one (0.02 g, 14% yield) as a brownish solid. $^1$H-NMR (DMSO-$d_6$, 400 MHz) δ (ppm): 8.27 (s, 1H), 7.82 (d, J=5.2 Hz, 1H), 7.58 (s, 1H), 7.47 (t, J=9.2 Hz, 1H), 5.24 (s, 2H), 3.56 (t, J=6.8 Hz, 2H), 1.91 (t, J=6.8 Hz, 2H), 1.77 (t, J=6.8 Hz, 2H) (Two protons are merged with solvent peak). Calculated (M+H): 393.05, Found (M+H): 393.0, HPLC purity: 99.35%.

TABLE 34

The following compounds were prepared by the method described above:

| Ex. No. | Structure | Name | Analytical data |
|---|---|---|---|
| 331 | (structure shown) | 5-(4-chloro-3-(trifluoromethyl)phenyl)-3-(2-oxo-2-(pyrrolidin-1-yl)ethyl)thieno[2,3-d][1,2,3]triazin-4(3H)-one | $^1$H-NMR (DMSO-$d_6$, 400 MHz) δ (ppm): 8.38 (s, 1H), 8.07 (s, 1H), 7.88 (d, J = 7.2 Hz, 1H), 7.79 (d, J = 8.0 Hz, 1H), 5.24 (s, 2H), 3.56 (m, 2H), 1.91 (m, 2H), 1.77 (m, 2H) (Two protons are merged with solvent peak). Calculated (M + H): 443.05, Found (M + H): 443.3, HPLC purity: 99.35%. |

Example 332: Preparation of 5-(4-chloro-3-(trifluoromethyl)phenyl)-3-(2-(3-fluoropyrrolidin-1-yl)-2-oxoethyl)thieno[2,3-d][1,2,3]triazin-4(3H)-one

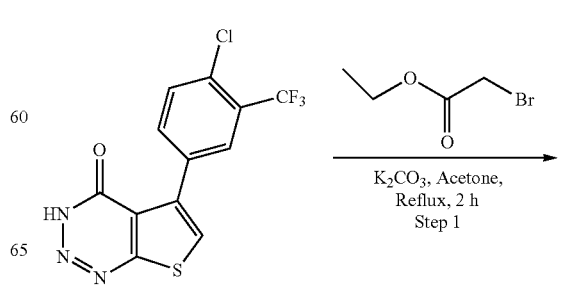

K$_2$CO$_3$, Acetone, Reflux, 2 h
Step 1

259

-continued

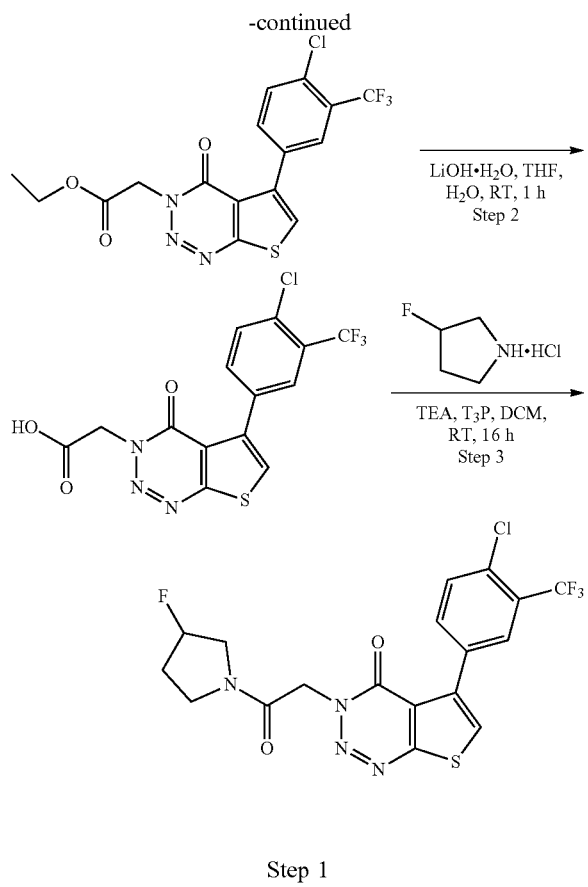

Step 1

Preparation of ethyl 2-(5-(4-chloro-3-(trifluoromethyl)phenyl)-4-oxothieno[2,3-d][1,2,3]triazin-3(4H)-yl)acetate To a solution of 5-(4-chloro-3-(trifluoromethyl)phenyl)thieno[2,3-d][1,2,3]triazin-4(3H)-one (0.35 g, 1.06 mmol) in acetone (10 mL) was added ethyl 2-bromoacetate (0.35 g, 2.12 mmol) and potassium carbonate (0.43 g, 3.18 mmol) at room temperature and the reaction mixture was heated to 55° C. for 30 min. The reaction mixture was cooled to room temperature, filtered through celite bed, washed with acetone. The filtrate was concentrated under vacuum and crude was purified by silica gel (60-120) column chromatography using 30% ethyl acetate in hexane to afford title product ethyl 2-(5-(4-chloro-3-(trifluoromethyl)phenyl)-4-oxothieno[2,3-d][1,2,3]triazin-3(4H)-yl)acetate (0.35 g, 79% yield) as off-white solid. Calculated (M+H): 418.02; Found (M+H): 418.0.

260

Step 2

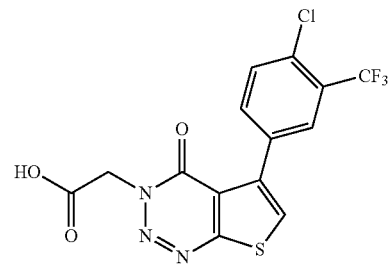 [SMILES: O=C(O)Cn1nnc2scc(-c3ccc(Cl)c(C(F)(F)F)c3)c2c1=O]

Preparation of 2-(5-(4-chloro-3-(trifluoromethyl)phenyl)-4-oxothieno[2,3-d][1,2,3]triazin-3(4H)-yl)acetic acid To a mixture of 5 ethyl 2-(5-(4-chloro-3-(trifluoromethyl)phenyl)-4-oxothieno[2,3-d][1,2,3]triazin-3(4H)-yl)acetate (0.35 g, 0.84 mmol) in tetrahydrofuran (4 mL) and water (2 mL) was added lithium hydroxide monohydrate (0.1 g, 2.58 mmol) at 0° C. and the reaction mixture was stirred at room temperature for 1 h. The reaction mixture was diluted with water, acidified with 1.5M hydrochloric acid to pH 2 to 3, the precipitated solid was filtered, washed with water and dried under vacuum to afford the title compound 2-(5-(4-chloro-3-(trifluoromethyl)phenyl)-4-oxothieno[2,3-d][1,2,3]triazin-3(4H)-yl)acetic acid (0.3 g, 92% yield) as off-white solid. Calculated M+H: 389.98, Found M+H: 389.9.

Step 3

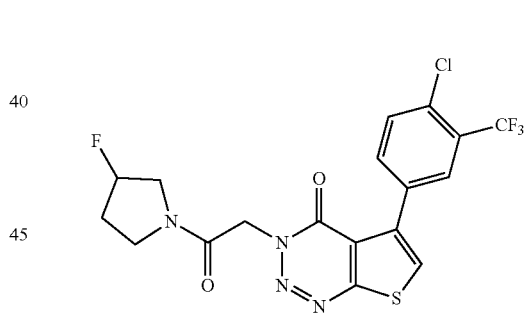

Preparation of 5-(4-chloro-3-(trifluoromethyl)phenyl)-3-(2-(3-fluoropyrrolidin-1-yl)-2-oxoethyl)thieno[2,3-d][1,2,3]triazin-4(3H)-one To a stirred solution of 2-(5-(4-chloro-3-(trifluoromethyl)phenyl)-4-oxothieno[2,3-d][1,2,3]triazin-3(4H)-yl)acetic acid (0.07 g, 0.18 mmol) in dichloromethane (3 mL) was added triethylamine (0.07 mL, 0.54 mmol), 3-fluoropyrrolidine hydrochloride (0.05 g, 0.36 mmol) at room temperature, The reaction mixture was allowed to cool to 0° C., was added 1-propanephosphonic anhydride (50% solution in ethyl acetate) (0.22 mL, 0.36 mmol) and stirred at room temperature for 16 h. The reaction mixture was diluted with dichloromethane, washed with water (2×25 mL), dried over anhydrous sodium sulfate, filtered, concentrated under vacuum to afford the crude compound, which was purified by silica gel (60-120) column chromatography using 50% ethyl acetate in hexane to afford the title compound 5-(4-chloro-3-(trifluoromethyl)phenyl)-3-(2-(3-fluoropyrrolidin-1-yl)-2-oxoethyl)thieno[2,3-d][1,2,3]triazin-4(3H)-one (0.03 g, 36% yield) as off white solid. $^1$H-NMR (DMSO-$d_6$, 400 MHz) δ (ppm): 8.39 (s, 1H), 8.07 (s, 1H), 7.88 (d, J=8.4 Hz, 1H), 7.79 (d, J=8.4 Hz, 1H), 5.49-5.18 (m, 3H), 4.0-3.59 (m, 4H), 2.30-1.96 (m, 2H). Calculated (M+H): 461.04, Found (M+H): 461.0, HPLC purity 99.82%.

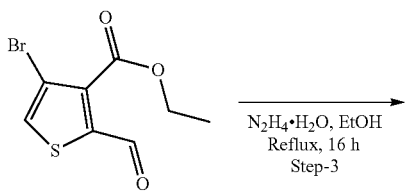

TABLE 35

The following compounds were prepared by the method described above:

| Ex. No. | Structure | Name | Analytical data |
|---|---|---|---|
| 333 | 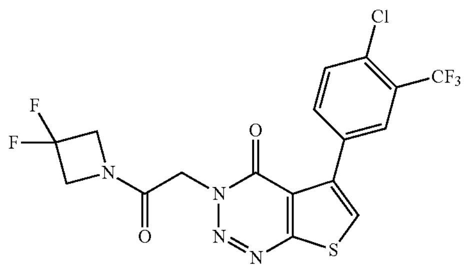 [SMILES: O=C(Cn1nnc2scc(-c3ccc(Cl)c(C(F)(F)F)c3)c2c1=O)N1CC(F)(F)C1] | 5-(4-chloro-3-(trifluoromethyl)phenyl)-3-(2-(3,3-difluoroazetidin-1-yl)-2-oxoethyl)thieno[2,3-d][1,2,3]triazin-4(3H)-one | $^1$H-NMR (DMSO-$d_6$, 400 MHz) δ (ppm): 8.40 (s, 1H), 8.07 (s, 1H), 7.88 (d, J = 8.0 Hz, 1H), 7.79 (d, J = 8.4 Hz, 1H), 5.22 (s, 2H), 4.81 (t, J = 12.4 Hz, 2H), 4.35 (t, J = 12.4 Hz, 2H). Calculated (M + H): 465.01, Found (M + H): 464.9, HPLC purity 99.68%. |
| 334 | 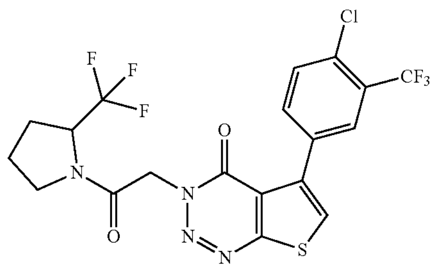 [SMILES: O=C(Cn1nnc2scc(-c3ccc(Cl)c(C(F)(F)F)c3)c2c1=O)N1CCCC1C(F)(F)F] | 5-(4-chloro-3-(trifluoromethyl)phenyl)-3-(2-oxo-2-(2-(trifluoromethyl)pyrrolidin-1-yl)ethyl)thieno[2,3-d][1,2,3]triazin-4(3H)-one | $^1$H-NMR (DMSO-$d_6$, 400 MHz) δ (ppm): 8.40 (s, 1H), 8.07 (s, 1H), 7.88 (d, J = 8.4 Hz, 1H), 7.79 (d, J = 8.4 Hz, 1H), 5.62-5.18 (m, 3H), 4.69 (m, 1H), 3.75 (m, 2H), 2.22-1.92 (m, 3H). Calculated (M + H): 511.04, Found (M + H): 511.0, HPLC purity: 99.29%. |

I. PREPARATION OF THIENOPYRIDAZINONES

Example 335: Preparation of 3-(4-chloro-3-(trifluoromethyl)phenyl)-5-(2-oxo-2-(pyrrolidin-1-yl)ethyl)thieno[2,3-d]pyridazin-4(5H)-one

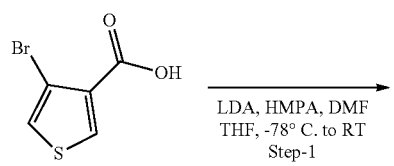

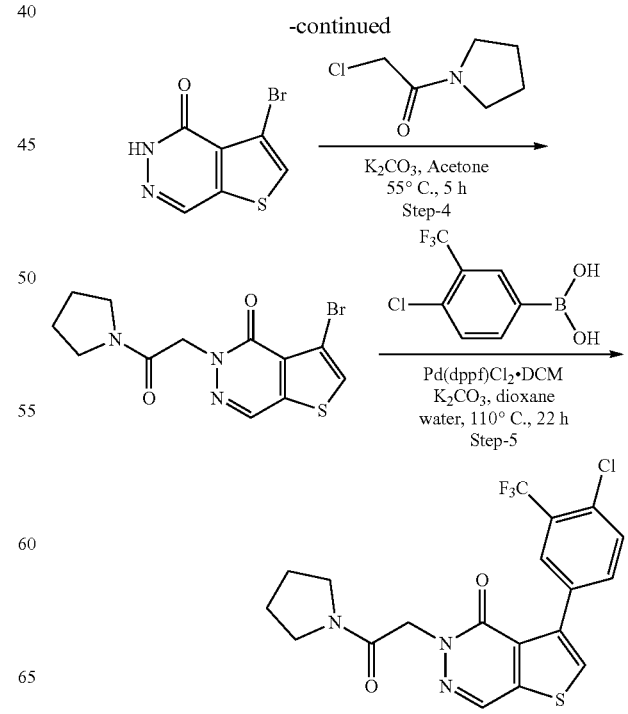

Step 1

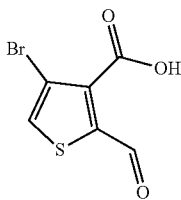

Preparation of
4-bromo-2-formylthiophene-3-carboxylic acid

To a mixture of diisopropylamine (4.58 mL, 32.60 mmol) in tetrahydrofuran (20 mL) was added n-butyl lithium (1.6 M in hexane) (24.1 mL, 36.22 mmol) at −30° C. and stirred for 45 min at −10° C. to −30° C. The reaction mixture was allowed cool to −78° C., added slowly a mixture of 4-bromothiophene-3-carboxylic acid (3.0 g, 14.49 mmol) and hexamethylphosphoramide (0.25 g, 1.45 mmol) in tetrahydrofuran and stirred for 1 h at −78° C. After 1 h, dimethylformamide was added slowly to above reaction mixture at −78° C. The mixture was gradually allowed to warm to room temperature and stirred for 1 h. The reaction was quenched with water (100 mL), acidified with 5M hydrochloric acid and filtered through celite, the filtrate was extracted with dichloromethane (3×250 mL). The combined organic layers were dried over anhydrous sodium sulfate, filtered and concentrated under vacuum to afford crude product. The crude product was purified by silica gel (60-120) column chromatography using 4% methanol in dichloromethane to obtain title compound 4-bromo-2-formylthiophene-3-carboxylic acid (2.8 g, 76% LCMS purity) as a red gummy. Calculated (M+H): 234.90; Found (M+H): 235.0.

Step 2

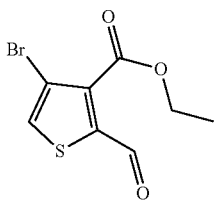

Preparation of ethyl
4-bromo-2-formylthiophene-3-carboxylate

To a stirred mixture of 4-bromo-2-formylthiophene-3-carboxylic acid (2.8 g, 11.91 mmol) (crude), potassium carbonate (4.1 g, 29.79 mmol) in dimethylformamide was added ethyl iodide at room temperature. The resulting mixture was heated to 55° C. and stirred for 5 h. The reaction mixture was allowed to cool to room temperature, diluted with water (100 mL) and extracted with ethyl acetate (3×250 mL). The combined organic layers were washed with water, brine solution, dried over anhydrous sodium sulfate, filtered and concentrated under vacuum to afford crude product which was purified by silica gel (60-120) column chromatography using 10% ethyl acetate in hexane to obtain title compound ethyl 4-bromo-2-formylthiophene-3-carboxylate (1.7 g) as pale yellow solid. $^1$H NMR (400 MHz, DMSO-d$_6$) δ (ppm) 10.28 (s, 1H), 7.64 (s, 1H), 4.50-4.45 (m, 2H), 1.44 (t, J=6.8 Hz, 3H).

Step 3

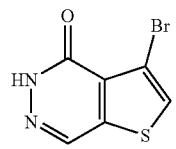

Preparation of
3-bromothieno[2,3-d]pyridazin-4(5H)-one

To a solution of ethyl 4-bromo-2-formylthiophene-3-carboxylate (1.56 g, 5.93 mmol) in ethanol (10 mL) was added hydrazine solution (1M in tetrahydofuran solution). The reaction mixture was heated to 80° C. and stirred for 2 h. The mixture was allowed to cool to room temperature, the precipitated product was filtered, washed with dichloromethane and dried to obtain title compound 3-bromothieno[2,3-d]pyridazin-4(5H)-one (0.81 g, 59% yield) as a white solid. Calculated (M+H): 230.91; Found (M+H): 230.9.

Step 4

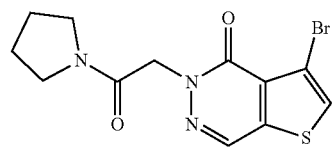 [SMILES: O=C(Cn1ncc2scc(Br)c2c1=O)N1CCCC1]

Preparation of 3-bromo-5-(2-oxo-2-(pyrrolidin-1-yl)
ethyl)thieno[2,3-d]pyridazin-4(5H)-one To a mixture of 3-bromothieno[2,3-d]pyridazin-4(5H)-one (0.2 g, 0.87 mmol) and potassium carbonate (0.29 g, 2.16 mmol) in dry acetone was added 2-chloro-1-(pyrrolidin-1-yl)ethanone (0.15 g, 1.04 mmol). The resulting mixture was heated to 55° C. and stirred for 5 h. The reaction mixture was allowed to cool to room temperature, filtered the solid, and washed with ethyl acetate. The filtrate was concentrated under vacuum to afford crude product, which was purified by silica gel (60-120) column chromatography using 5% methanol in dichloromethane to afford the title compound 3-bromo-5-(2-oxo-2-(pyrrolidin-1-yl)ethyl)thieno[2,3-d]pyridazin-4(5H)-one (0.23 g, 79.3% yield) as a white solid. Calculated (M+H): 341.98; Found (M+H): 341.9.

Step 5

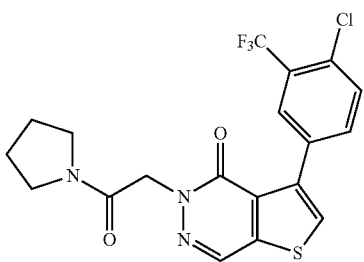 [SMILES: O=C(Cn1ncc2scc(-c3ccc(Cl)c(C(F)(F)F)c3)c2c1=O)N1CCCC1]

Preparation of 3-(4-chloro-3-(trifluoromethyl)phenyl)-5-(2-oxo-2-(pyrrolidin-1-yl)ethyl)thieno[2,3-d]pyridazin-4(5H)-one A mixture of 3-bromo-5-(2-oxo-2-(pyrrolidin-1-yl)ethyl)thieno[2,3-d]pyridazin-4(5H)-one (0.075 g, 0.22 mmol) and (4-chloro-3-(trifluoromethyl)phenyl)boronic acid (0.049 g, 0.22 mmol) in a mixture of 1,4-dioxane (5 mL) and water (2 mL) was purged with argon for 10 min. Then Pd(dppf)Cl$_2$.DCM (0.017 g, 0.02 mmol) and potassium carbonate (0.09 g, 066 mmol) was added under argon and mixture was heated to 100° C. and stirred for 2 h. The mixture was allowed to cool to room temperature, filtered through celite pad and thoroughly washed with ethyl acetate. The filtrate was washed with water, brine, dried over sodium sulfate, concentrated under vacuum to afford the crude compound, which was purified by silica gel (60-120) column chromatography using 5% methanol in dichloromethane to afford the title compound 3-(4-chloro-3-(trifluoromethyl)phenyl)-5-(2-oxo-2-(pyrrolidin-1-yl)ethyl)thieno[2,3-d]pyridazin-4(5H)-one (0.068 g, 70.8%, yield). $^1$H NMR (400 MHz, DMSO-d$_6$) δ (ppm): 8.64 (s, 1H), 8.20 (s, 1H), 7.97 (s, 1H), 7.80 (d, J=8.4 Hz, 1H), 7.74 (d, J=8.4 Hz, 1H), 4.90 (s, 2H), 3.48 (t, J=6.8 Hz, 2H), 3.27 (t, J=6.8 Hz, 2H), 1.90-1.85 (m, 2H), 1.78-1.73 (m, 2H). Calculated (M+H): 442.05; Found (M+1): 442.0, HPLC purity 97.6%.

TABLE 35

The following compounds were prepared by the method described above:

| Ex. No. | Structure | IUPAC Name | Analytical data |
|---|---|---|---|
| 336 | 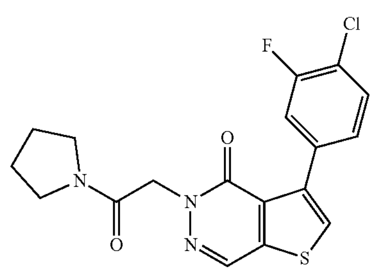 [SMILES: O=C(Cn1ncc2scc(-c3ccc(Cl)c(F)c3)c2c1=O)N1CCCC1] | 3-(4-chloro-3-fluorophenyl)-5-(2-oxo-2-(pyrrolidin-1-yl)ethyl)thieno[2,3-d]pyridazin-4(5H)-one | $^1$H NMR (400 MHz, DMSO-d$_6$) δ (ppm); 8.62 (s, 1H), 8.13 (s, 1H), 7.61-7.55 (m, 2H), 7.37 (d, J = 7.6 Hz, 1H), 4.89 (s, 2H), 3.48 (t, J = 6.8 Hz, 2H), 3.24 (t, J = 6.8 Hz, 2H), 2.04-1.87 (m, 2H), 1.78-1.74 (m, 2H). Calculated (M + H): 392.06, Found (M + H): 392.0, HPLC purity 99.27%. |
| 337 | 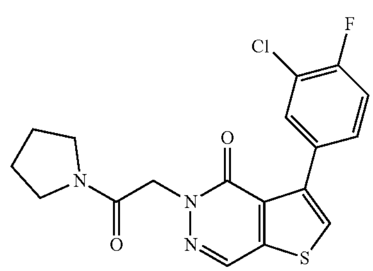 [SMILES: O=C(Cn1ncc2scc(-c3ccc(F)c(Cl)c3)c2c1=O)N1CCCC1] | 3-(3-chloro-4-fluorophenyl)-5-(2-oxo-2-(pyrrolidin-1-yl)ethyl)thieno[2,3-d]pyridazin-4(5H)-one | $^1$H NMR (400 MHz, DMSO-d$_6$) δ (ppm): 8.61 (s, 1H), 8.09 (s, 1H), 7.32 (d, J = 6.4 Hz, 1H), 7.50 (brs, 1H), 7.44-7.00 (m, 1H), 4.89 (s, 2H), 3.48 (t, J = 6.8 Hz, 2H), 3.26 (t, J = 6.8 Hz, 2H), 1.91-1.87 (m, 2H), 1.77-1.73 (m, 2H). Calculated (M + H): 392.06, Found (M + H): 392.0, HPLC purity 99.14%. |
| 338 | 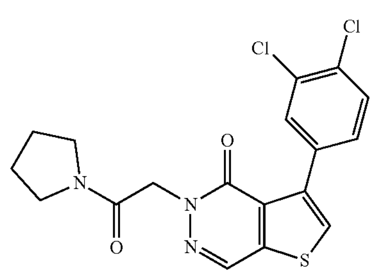 [SMILES: O=C(Cn1ncc2scc(-c3ccc(Cl)c(Cl)c3)c2c1=O)N1CCCC1] | 3-(3,4-dichlorophenyl)-5-(2-oxo-2-(pyrrolidin-1-yl)ethyl)thieno[2,3-d]pyridazin-4(5H)-one | $^1$H NMR (400 MHz, DMSO-d6) δ (ppm): 8.62 (s, 1H), 8.14 (s, 1H), 7.77 (d, J = 1.6 Hz, 1H), 7.64 (d, J = 8.4 Hz, 1H), 7.77 (dd, J = 2.0 Hz, J = 8.4 Hz, 1H), 4.90 (s, 2 H), 3.48 (t, J = 6.8 Hz, 2H), 3.27 (t, J = 6.8 Hz, 2H), 1.92-1.86 (m, 2H), 1.78-1.72 (m, 2H). Calculated (M + H): 408.03, Found (M + H): 408.0; HPLC purity 99.51%. |

Example 339: Preparation of 3-(4-chloro-3-(trifluoromethyl)phenyl)-5-(2-(3,3-difluoroazetidin-1-yl)-2-oxoethyl)thieno[2,3-d]pyridazin-4(5H)-one

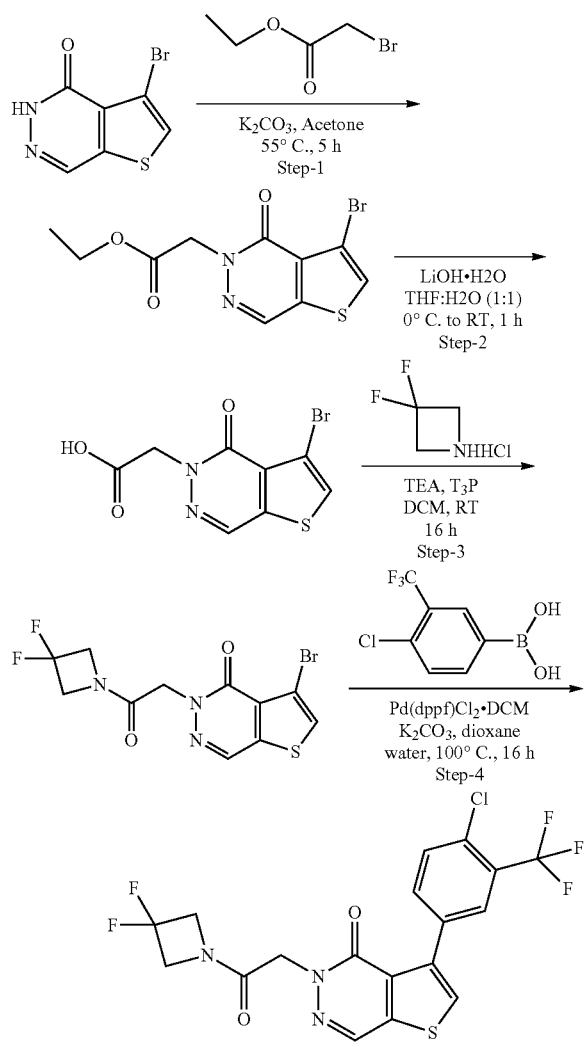

Step 1

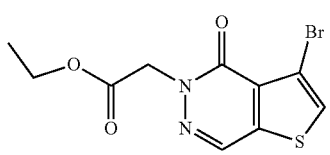 [SMILES: CCOC(=O)Cn1ncc2scc(Br)c2c1=O]

Preparation of ethyl 2-(3-bromo-4-oxothieno[2,3-d]pyridazin-5(4H)-yl)acetate

To a mixture of 3-bromothieno[2,3-d]pyridazin-4(5H)-one (0.65 g, 2.81 mmol) and potassium carbonate (1.16 g, 8.44 mmol) in dry acetone was added ethyl 2-bromoacetate (0.62 mL, 5.63 mmol). The resulting mixture was heated to 55° C. and stirred for 5 h. The reaction mixture was allowed to cool to room temperature, filtered the solid, and washed with ethyl acetate. The filtrate was concentrated under vacuum to afford crude product, which was purified by silica gel (60-120) column chromatography using 30% ethyl acetate in hexane to afford the title compound ethyl 2-(3-bromo-4-oxothieno[2,3-d]pyridazin-5(4H)-yl)acetate (0.78 g, 87% yield) as a white solid. Calculated (M+H): 316.95, Found (M+H): 316.9.

Step 2

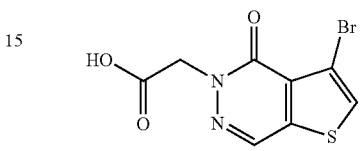

Preparation of 2-(3-bromo-4-oxothieno[2,3-d]pyridazin-5(4H)-yl)acetic acid

To a suspension of ethyl 2-(3-bromo-4-oxothieno[2,3-d]pyridazin-5(4H)-yl)acetate (0.68 g, 2.14 mmol) in a mixture of tetrahydrofuran and water (10 mL: 10 mL) was added lithium hydroxide mono hydrate (0.27 g, 6.43 mmol) at 0° C. The resulting suspension was gradually allowed to warm to room temperature and stirred for 3 h. The reaction mixture was allowed to cool to 0° C. and acidified with 1.5M hydrochloric acid solution to pH 2 to 3, the precipitated product was filtered and dried to obtain the title compound 2-(3-bromo-4-oxothieno[2,3-d]pyridazin-5(4H)-yl)acetic acid (0.58 g, 93% yield) as a colorless solid. Calculated (M+H): 288.9, Found (M+H): 288.9.

Step 3

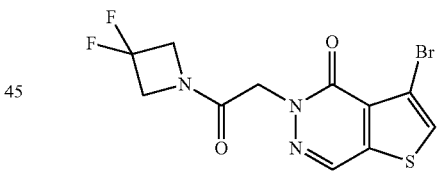

Preparation of 3-bromo-5-(2-(3,3-difluoroazetidin-1-yl)-2-oxoethyl)thieno[2,3-d]pyridazin-4(5H)-one To a solution of 2-(3-bromo-4-oxothieno[2,3-d]pyridazin-5(4H)-yl)acetic acid (0.3 g, 1.08 mmol) in dichloromethane (20 mL) was added 3,3-difluoroazetidine hydrochloride (0.13 g, 1.04 mmol) and triethylamine (1.16 mL, 8.30 mmol). The reaction mixture was allowed to cool to 0° C. and 1-propanephosphonic anhydride (50% solution in ethyl acetate) (1.31 mL, 2.07 mmol) was added, the mixture was allowed to warm to room temperature and stirred for 16 h. The reaction mixture was diluted with dichloromethane (100 mL), washed with water (2×50 mL), brine, dried over anhydrous sodium sulfate, filtered and concentrated under vacuum to afford crude product, which was purified by silica gel (60-120) column chromatography using 5% methanol in dichloromethane as eluent to afford the title compound 3-bromo-5-(2-(3,3-difluoroazetidin-1-yl)-2-oxoethyl)thieno[2,3-d]pyridazin-4(5H)-one (0.34 g, 90% yield) as off white solid. Calculated (M+H): 363.95, Found (M+1): 363.9.

Step 4

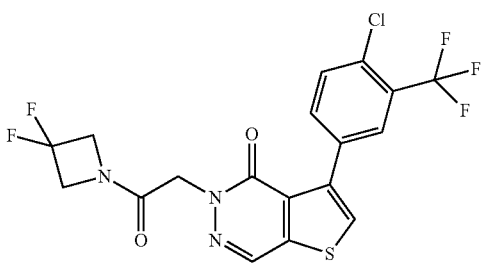 [SMILES: O=C(Cn1ncc2scc(-c3ccc(Cl)c(C(F)(F)F)c3)c2c1=O)N1CC(F)(F)C1]

Preparation of 3-(4-chloro-3-(trifluoromethyl)phenyl)-5-(2-(3,3-difluoroazetidin-1-yl)-2-oxoethyl)thieno[2,3-d]pyridazin-4(5H)-one To a stirred solution of 3-bromo-5-(2-(3,3-difluoroazetidin-1-yl)-2-oxoethyl)thieno[2,3-d]pyridazin-4(5H)-one (0.075 g, 0.21 mmol) and (4-chloro-3-(trifluoromethyl)phenyl)boronic acid (0.046 g, 0.21 mmol) in a mixture of 1,4-dioxane (5 mL) and water (2 mL) and the mixture was purged with argon for 10 min. Then Pd(dppf)Cl$_2$.DCM (0.008 g, 0.010 mmol) and potassium carbonate (0.08 g, 0.62 mmol) was added under argon atmosphere. The reaction mixture was heated to 100° C. and stirred for 2 h. The reaction mixture was allowed to cool to room temperature, filtered through celite pad and washed with ethyl acetate. The filtrate was washed with water, brine, dried over anhydrous sodium sulfate, concentrated to afford the crude compound, which was purified by silica gel (60-120) column chromatography using 5% methanol in dichloromethane to afford the title compound 3-(4-chloro-3-(trifluoromethyl)phenyl)-5-(2-(3,3-difluoroazetidin-1-yl)-2-oxoethyl)thieno[2,3-d]pyridazin-4(5H)-one (0.052 g, 54.7%, yield) as off white solid. $^1$H NMR (400 MHz, DMSO-d$_6$) δ (ppm): 8.66 (s, 1H), 8.22 (s, 1H), 7.98 (s, 1H), 7.81 (d, J=7.6 Hz, 1H), 7.74 (d, J=8.4 Hz, 1H), 4.87 (s, 2H), 4.72 (t, J=12 Hz, 2H), 4.30 (t, J=12 Hz, 2H). Calculated (M+H): 464.02; Found (M+1): 464.0, HPLC purity 99.7%.

TABLE 36

The following compounds were prepared by the method described above:

| Ex. No. | Structure | IUPAC Name | Analytical data |
|---|---|---|---|
| 340 | 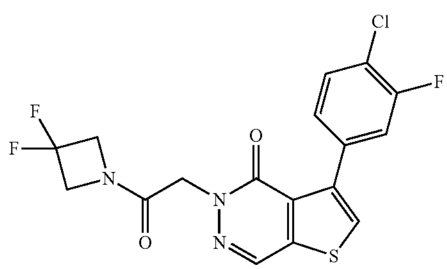 [SMILES: O=C(Cn1ncc2scc(-c3ccc(Cl)c(F)c3)c2c1=O)N1CC(F)(F)C1] | 3-(4-chloro-3-fluorophenyl)-5-(2-(3,3-difluoroazetidin-1-yl)-2-oxoethyl)thieno[2,3-d]pyridazin-4(5H)-one | $^1$H NMR (400 MHz, DMSO-d$_6$) δ (ppm); 8.65 (s, 1H), 8.14 (s, 1H), 7.61-7.56(m, 2H), 7.38 (d, J = 8.4 Hz, 1H), 4.87 (s, 2H), 4.71 (t, J = 12.4 Hz, 2H), 4.31 (t, J = 12.4 Hz, 2H), Calculated (M + H): 414.02, Found (M + H): 414.0, HPLC purity 99.7%. |
| 341 | 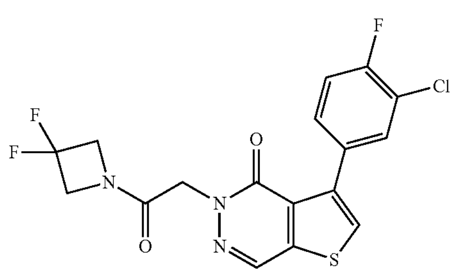 [SMILES: O=C(Cn1ncc2scc(-c3ccc(F)c(Cl)c3)c2c1=O)N1CC(F)(F)C1] | 3-(3-chloro-4-fluorophenyl)-5-(2-(3,3-difluoroazetidin-1-yl)-2-oxoethyl)thieno[2,3-d]pyridazin-4(5H)-one | $^1$H NMR (400 MHz, DMSO-d$_6$) δ (ppm); 8.64 (s, 1H), 8.11 (s, 1H), 7.73 (d, J = 6.0 Hz, 1H), 7.50 (brs, 1H), 7.44-7.40 (m, 1H), 4.87 (s, 2 H), 4.72 (brs, 2H), 4.3 (brs, 2H); Calculated (M + H): 414.02, Found (M + H): 414.0, HPLC purity 99.3%. |
| 342 | 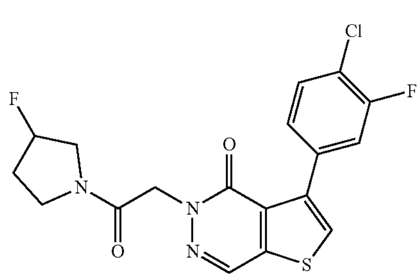 [SMILES: O=C(Cn1ncc2scc(-c3ccc(Cl)c(F)c3)c2c1=O)N1CCC(F)C1] | 3-(4-chloro-3-fluorophenyl)-5-(2-(3-fluoropyrrolidin-1-yl)-2-oxoethyl)thieno[2,3-d]pyridazin-4(5H)-one | $^1$H NMR (400 MHz, DMSO-d$_6$) δ (ppm); 8.63 (s, 1H), 8.13 (s, 1H), 7.61-7.56 (m, 2H), 7.38 (d, J = 8.0 Hz, 1H), 5.47-5.23 (m, 1H), 5.02-4.84 (m, 2H), 3.90-3.39 (m, 4H), 2.23-2.06 (m, 2H); Calculated (M + H): 410.05, Found (M + H): 410.3, HPLC purity 99.21%. |

TABLE 36-continued

The following compounds were prepared by the method described above:

| Ex. No. | Structure | IUPAC Name | Analytical data |
|---|---|---|---|
| 343 | 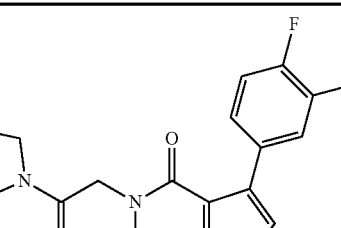 | 3-(3-chloro-4-fluorophenyl)-5-(2-(3-fluoropyrrolidin-1-yl)-2-oxoethyl)thieno[2,3-d]pyridazin-4(5H)-one | $^1$H NMR (400 MHz, DMSO-$d_6$) δ (ppm); 8.63 (s, 1H), 8.10 (s, 1H), 7.74-7.71 (dd, J = 2.8 Hz, J = 7.2 Hz, 1H), 7.53-7.49 (m, 1H), 7.44-7.40 (m, 1H), 5.47-5.23 (m, 1H), 5.02-4.84 (m, 2H), 3.90-3.35 (m, 4H), 2.22-2.05 (m, 2H). Calculated (M + H): 410.05, Found (M + H): 410.3, HPLC purity 99.82%. |
| 344 | 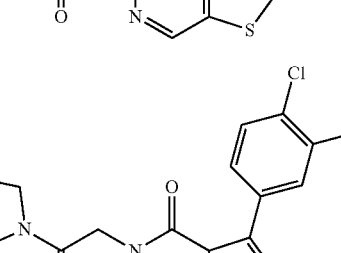 | 3-(4-chloro-3-(trifluoromethyl)phenyl)-5-(2-(3-fluoropyrrolidin-1-yl)-2-oxoethyl)thieno[2,3-d]pyridazin-4(5H)-one | $^1$H NMR (400 MHz, DMSO-$d_6$) δ (ppm); 8.65 (s, 1H), 8.21 (s, 1H), 7.97 (s, 1H), 7.81(d, J = 8.0 Hz, 1H), 7.74 (d, J = 8.8 Hz, 1H), 5.47-5.22 (m, 1H), 5.03-4.84 (m, 2H), 3.90-3.38 (m, 4H), 2.22-2.05 (m, 2H). Calculated (M + H): 460.04, Found (M + H): 460.0, HPLC purity 99.42%. |

J. PREPARATION OF ISOTHIENOPYRIMIDINONES

Example 345: Preparation of 5-(4-chlorophenyl)-3-(2-(3-fluoropyrrolidin-1-yl)-2-oxoethyl)thieno[3,4-d]pyrimidin-4(3H)-one

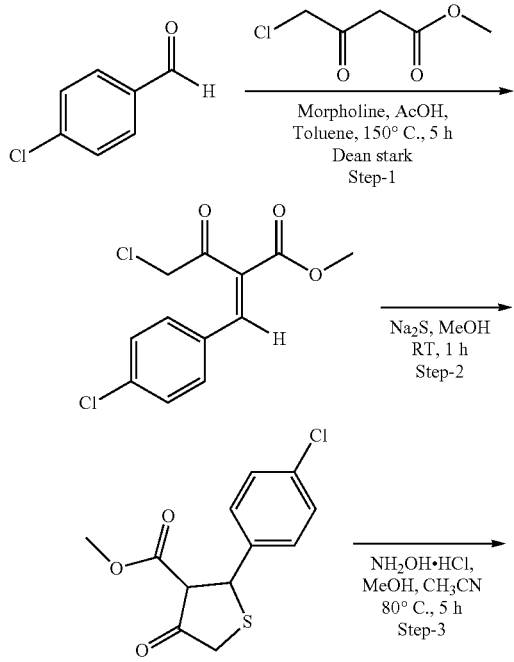

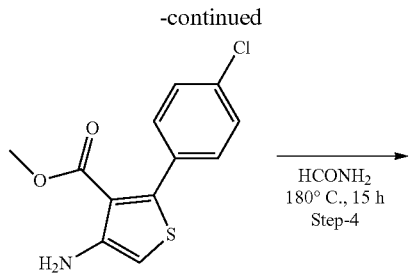

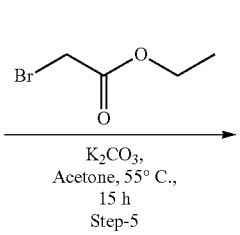

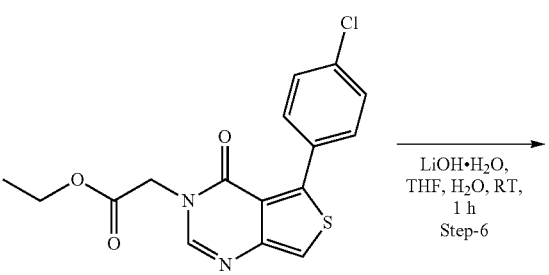

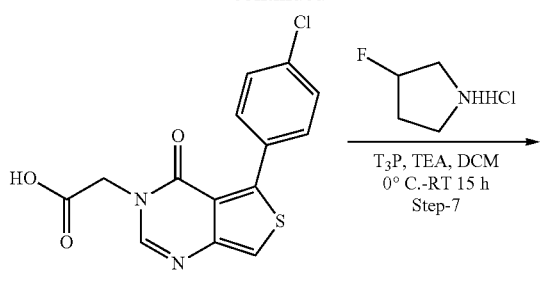

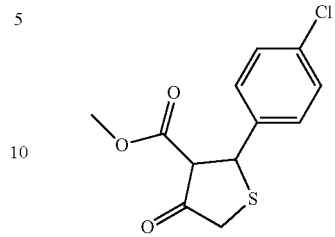

Step-2

Preparation of methyl 2-(4-chlorophenyl)-4-oxotetrahydrothiophene-3-carboxylate To a stirred solution of (E)-methyl 4-chloro-2-(4-chlorobenzylidene)-3-oxobutanoate (8.0 g, 29.41 mmol) in methanol (100 mL) was added sodium sulfide (8.34 g, 58.82 mmol) at room temperature and stirred for 1 h. The reaction mixture was poured on to cold 1N hydrochloric acid solution (250 mL) and extracted with dichloromethane (3×100 mL). The combined organic extract was washed with brine (50 mL), dried over anhydrous sodium sulfate, filtered and concentrated under vacuum to afford the crude product, which was purified by silica gel column chromatography using 15% ethyl acetate in hexane to obtain the title compound methyl 2-(4-chlorophenyl)-4-oxotetrahydrothiophene-3-carboxylate (5.8 g, 73.0% yield) as brown solid. Calculated (M−H): 269.01, found (M−H): 269.0.

Step-1

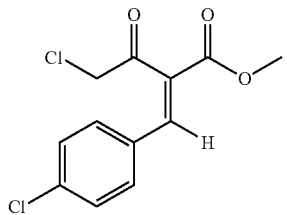 [SMILES: COC(=O)/C(=C/c1ccc(Cl)cc1)C(=O)CCl]

Step-3

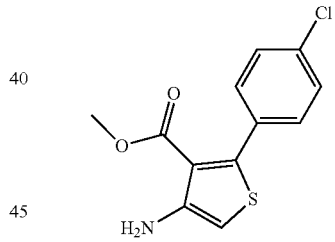

Preparation of (E)-methyl 4-chloro-2-(4-chlorobenzylidene)-3-oxobutanoate

To a stirred solution of 1-(4-chlorophenyl)ethanone (10.0 g, 71.13 mmol) and methyl 4-chloro-3-oxobutanoate (8.2 mL, 71.13 mmol) in toluene (200 mL) was added morpholine (0.3 mL, 3.55 mmol) and acetic acid (0.22 mL, 3.91 mmol) at room temperature and the mixture was heated to 150° C. with azeotropic removal of water using Dean-stark apparatus for 5 h. The reaction mixture was cooled room temperature, diluted with ethyl acetate (200 mL), washed with water (100 mL), brine (100 mL), dried over anhydrous sodium sulfate, filtered and concentrated under vacuum to afford the crude product, which was purified by silica gel column chromatography using 10% ethyl acetate in hexane to obtain the title compound (E)-methyl 4-chloro-2-(4-chlorobenzylidene)-3-oxobutanoate (9.0 g, 47% yield) as white solid. Calculated (M+H): 273.0, found (M+H): 273.0.

Preparation of methyl 4-amino-2-(4-chlorophenyl)thiophene-3-carboxylate

To a stirred solution of methyl 2-(4-chlorophenyl)-4-oxotetrahydrothiophene-3-carboxylate (5.8 g, 21.48 mmol) in methanol:acetonitrile mixture (100 mL, 7:3) was added hydroxylamine hydrochloride (1.86 g, 26.85 mmol) at room temperature and the reaction mixture was heated to 80° C. for 5 h. The reaction mixture was cooled to room temperature and poured on to saturated sodium bicarbonate solution (100 mL) and extracted with ethyl acetate (3×50 mL). The combined organic layer was washed with brine (50 mL), dried over anhydrous sodium sulfate and concentrated under vacuum to afford the crude product, which was purified by silica gel column chromatography using 12% ethyl acetate in hexane to obtain the title compound methyl 4-amino-2-(4-chlorophenyl)thiophene-3-carboxylate (3.0 g, 55% yield) as off white solid. Calculated (M+H): 268.0, found (M+H): 268.0.

Step-4

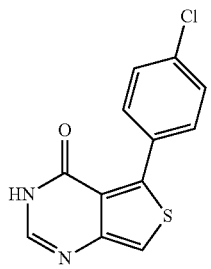 [SMILES: O=c1[nH]cnc2csc(-c3ccc(Cl)cc3)c12]

Preparation of 5-(4-chlorophenyl)thieno[3,4-d]pyrimidin-4(3H)-one

A solution of methyl 4-amino-2-(4-chlorophenyl)thiophene-3-carboxylate (3.0 g, 11.23 mmol) in formamide (25 mL) was heated at 180° C. for 15 h. The reaction mixture was poured on to ice-water (100 mL), the precipitated product was filtered, washed with water (100 mL) and dried to obtain the title compound 5-(4-chloro-phenyl)thieno[3,4-d]pyrimidin-4(3H)-one (3.0 g, crude) as off white solid. Calculated (M+H): 263.0, Found (M+H): 263.0.

Step-5

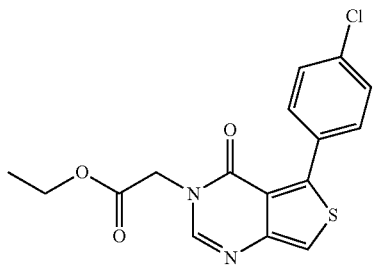 [SMILES: CCOC(=O)Cn1cnc2csc(-c3ccc(Cl)cc3)c2c1=O]

Preparation of ethyl 2-(5-(4-chlorophenyl)-4-oxothieno[3,4-d]pyrimidin-3(4H)-yl)acetate To a stirred solution of 5-(4-chloro-3-fluorophenyl)thieno[3,4-d]pyrimidin-4(3H)-one (1.5 g, 5.7 mmol) and ethyl-2-bromoacetate (1.26 mL, 11.42 mmol) in acetone (50 mL) was added potassium carbonate (2.36 g, 17.12 mmol) and the mixture was heated to 55° C. for 15 h. The reaction mixture was filtered through the celite and the filtrate was evaporated. The crude material was purified by silica gel column chromatography using 40% ethyl acetate in hexane to obtain the title compound ethyl 2-(5-(4-chlorophenyl)-4-oxothieno[3,4-d]pyrimidin-3(4H)-yl)acetate (1.5 g, 75% yield) as gummy material. Calculated (M+H): 349.03, Found (M+H): 349.0.

Step-6

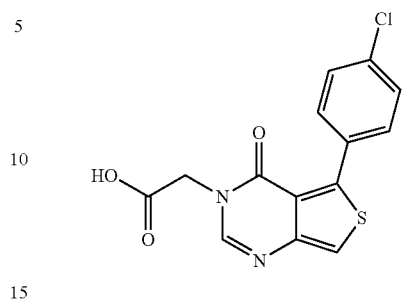

Preparation of 2-(5-(4-chlorophenyl)-4-oxothieno[3,4-d]pyrimidin-3(4H)-yl)acetic acid To a stirred solution of ethyl 2-(5-(4-chlorophenyl)-4-oxothieno[3,4-d]pyrimidin-3(4H)-yl)acetate (1.5 g, 4.3 mmol) in tetrahydrofuran:water mixture (20 mL, 1:1) was added lithium hydroxide monohydrate (0.9 g, 21.5 mmol) at 0° C. and the reaction mixture was stirred at room temperature for 1 h. After completion of the reaction, mixture was concentrated, the residue was diluted with water (50 mL) and acidified with 1.5 N hydrochloric acid solution to pH~2. The precipitated solid was filtered, washed with water (50 mL) and dried to obtain the title compound 2-(5-(4-chlorophenyl)-4-oxothieno[3,4-d]pyrimidin-3(4H)-yl)acetic acid (1.1 g, crude) as off white solid. Calculated (M+H): 321, found (M+H): 321.0.

Step-7

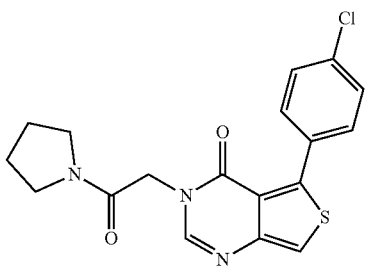 [SMILES: O=C(Cn1cnc2csc(-c3ccc(Cl)cc3)c2c1=O)N1CCCC1]

Preparation of 5-(4-chlorophenyl)-3-(2-oxo-2-(pyrrolidin-1-yl)ethyl)thieno[3,4-d]pyrimidin-4(3H)-one To a stirred solution of 2-(5-(4-chlorophenyl)-4-oxothieno[3,4-d]pyrimidin-3(4H)-yl)acetic acid (0.1 g, 0.31 mmol) in dichloromethane (10 mL) was added triethylamine (0.26 mL, 1.87 mmol) and pyrrolidine (0.051 mL, 0.62 mmol) at room temperature and the reaction mixture was cooled to 0° C. Then 1-propanephosphonic anhydride ($T_3P$) (0.3 mL, 0.46 mmol, 50% solution in ethyl acetate) was added dropwise and the reaction mixture was stirred at room temperature for 15 h. The reaction mixture was quenched with water (25 mL) and extracted with dichloromethane (3×25 mL). The combined organic layer was washed with brine (25 mL), dried over anhydrous sodium sulfate, filtered and concentrated under vacuum to afford the crude product, which was purified by silica gel column chromatography using 4% methanol in dichloromethane to obtain the title compound 5-(4-chlorophenyl)-3-(2-oxo-2-(pyrrolidin-1-yl) ethyl)thieno[3,4-d]pyrimidin-4(3H)-one (0.075 g, 65% yield) as off-white solid. ¹H NMR (400 MHz, DMSO-d₆) δ (ppm): 7.93 (s, 1H), 7.87 (s, 1H), 7.66 (d, J=8.4 Hz, 2H), 7.5 (d, J=8.4 Hz, 2H), 4.68 (s, 2H), 3.47 (t, J=7.2 Hz, 2H), 3.30 (brs, 2H), 1.94-1.89 (m, 2H), 1.81-1.76 (m, 2H). Calculated (M+H): 374.07, Found (M+H): 374.1. HPLC Purity: 99.34%.

TABLE 37

The following compounds were prepared by the method described above:

| Ex. No. | Structure | IUPAC Name | Analytical Data |
|---|---|---|---|
| 346 | 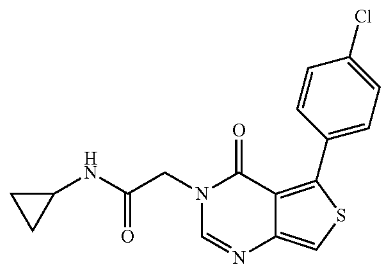 [SMILES: O=C(Cn1cnc2csc(-c3ccc(Cl)cc3)c2c1=O)NC1CC1] | 2-(5-(4-chlorophenyl)-4-oxothieno[3,4-d]pyrimidin-3(4H)-yl)-N-cyclopropylacetamide | ¹H NMR (400 MHz, DMSO-d₆) δ (ppm): 8.26 (brs, 1H), 7.96 (s, 1H), 7.87 (s, 1H), 7.67 (d, J = 7.6 Hz, 2H), 7.51 (d, J = 7.6 Hz, 2H), 4.43 (s, 2H), 2.66-2.61 (m, 1H), 0.6 (d, J = 6.4 Hz, 2H), 0.39 (brs, 2H). Calculated (M + H): 360.05, Found (M + H): 360.1, HPLC purity: 99.06%. |
| 347 | 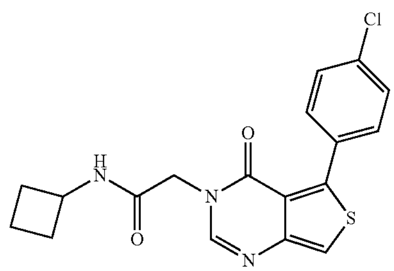 [SMILES: O=C(Cn1cnc2csc(-c3ccc(Cl)cc3)c2c1=O)NC1CCC1] | 2-(5-(4-chlorophenyl)-4-oxothieno[3,4-d]pyrimidin-3(4H)-yl)-N-cyclobutylacetamide | ¹H NMR (400 MHz, DMSO-d₆) δ (ppm): 8.26 (d, J = 6.8 Hz, 1H), 7.96 (s, 1H), 7.86 (s, 1H), 7.65 (d, J = 8.4 Hz, 2H), 7.50 (d, J = 8.4 Hz, 2H), 4.45 (s, 2H), 4.19-4.13 (m, 1H), 2.13-2.11 (m, 2H), 1.90-1.85 (m, 2H), 1.63-1.55 (m, 2H). Calculated (M + H): 374.07, Found (M + H): 374.1, HPLC purity: 99.44%. |
| 348 | 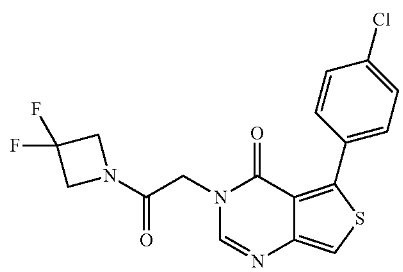 [SMILES: O=C(Cn1cnc2csc(-c3ccc(Cl)cc3)c2c1=O)N1CC(F)(F)C1] | 5-(4-chlorophenyl)-3-(2-(3,3-difluoroazetidin-1-yl)-2-oxoethyl)thieno[3,4-d]pyrimidin-4(3H)-one | ¹H NMR (400 MHz, DMSO-d₆) δ (ppm): 7.94 (s, 1H), 7.89 (s, 1H), 7.67 (d, J = 7.6 Hz, 2H), 7.51 (d, J = 8.0 Hz, 2H), 4.73 (t, J = 11.2 Hz, 2H), 4.63 (s, 2H), 4.35 (t, J = 11.6 Hz, 2H). Calculated (M + H): 396.03, Found (M + H): 396.0, HPLC purity: 98.56%. |
| 349 | 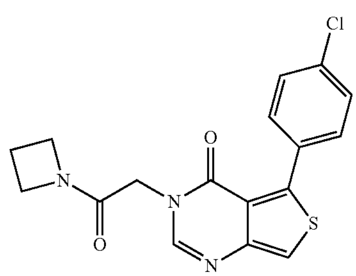 [SMILES: O=C(Cn1cnc2csc(-c3ccc(Cl)cc3)c2c1=O)N1CCC1] | 3-(2-(azetidin-1-yl)-2-oxoethyl)-5-(4-chlorophenyl)thieno[3,4-d]pyrimidin-4(3H)-one | ¹H NMR (400 MHz, DMSO-d₆) δ (ppm): 7.94 (s, 1H), 7.87 (s, 1H), 7.66 (d, J = 8.4 Hz, 2H), 7.51 (d, J = 8.4 Hz, 2H), 4.49 (s, 2H), 4.21 (t, J = 7.6 Hz, 2H), 3.87 (t, J = 7.6 Hz, 2H), 2.31-2.22 (m, 2H). Calculated (M + H): 360.05, Found (M + H): 360.1; HPLC purity: 99.46%. |
| 350 | 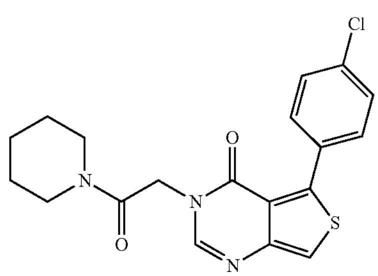 [SMILES: O=C(Cn1cnc2csc(-c3ccc(Cl)cc3)c2c1=O)N1CCCCC1] | 5-(4-chlorophenyl)-3-(2-oxo-2-(piperidin-1-yl)ethyl)thieno[3,4-d]pyrimidin-4(3H)-one | ¹H NMR (400 MHz, DMSO-d₆) δ (ppm): 7.93 (s, 1H), 7.87 (s, 1H), 7.65 (d, J = 8.4 Hz, 2H), 7.5 (d, J = 8.4 Hz, 2H), 4.77 (s, 2H), 3.44-3.28 (m, 4H), 1.57 (brs, 4H), 1.42 (brs, 2H). Calculated (M + H): 388.1, Found (M + H): 388.1, HPLC purity: 99.74%. |

TABLE 37-continued

The following compounds were prepared by the method described above:

| Ex. No. | Structure | IUPAC Name | Analytical Data |
|---|---|---|---|
| 351 | 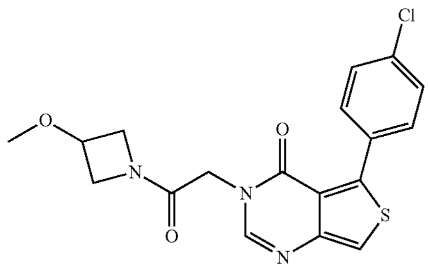 [SMILES: COC1CN(C(=O)Cn2cnc3csc(-c4ccc(Cl)cc4)c3c2=O)C1] | 5-(4-chlorophenyl)-3-(2-(3-methoxyazetidin-1-yl)-2-oxoethyl)thieno[3,4-d]pyrimidin-4(3H)-one | $^1$H NMR (400 MHz, DMSO-$d_6$) δ (ppm): 7.94 (s, 1H), 7.87 (s, 1H), 7.66 (d, J = 8.4 Hz, 2H), 7.51 (d, J = 8.4 Hz, 2H), 4.53 (s, 2H), 4.41-4.37(m, 1H), 4.25-4.24 (m, 1H), 4.07-4.03 (m, 2H), 3.69-3.66 (m, 1H), 3.21 (s, 3H). Calculated (M + H): 390.06, Found (M + H): 390.1; HPLC purity: 99.52%. |
| 352 | 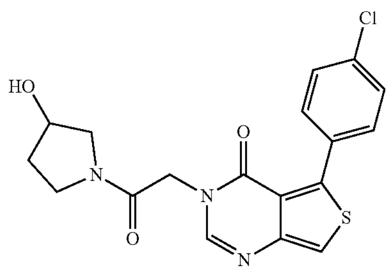 [SMILES: O=C(Cn1cnc2csc(-c3ccc(Cl)cc3)c2c1=O)N1CCC(O)C1] | 5-(4-chlorophenyl)-3-(2-(3-hydroxypyrrolidin-1-yl)-2-oxoethyl)thieno[3,4-d]pyrimidin-4(3H)-one | $^1$H NMR (400 MHz, CDCl$_3$) δ (ppm): 7.75 (d, J = 3.2 Hz, 1H), 7.61 (d, J = 7.2 Hz, 2H), 7.54 (s, 1H), 7.39 (d, J = 8.4 Hz, 2H), 4.76-4.45 (m, 3H), 3.78-3.51 (m, 5H), 2.10-1.97 (m, 2H). Calculated (M + H): 390.06, Found (M + H): 390.1, HPLC purity: 99.85%. |
| 353 | 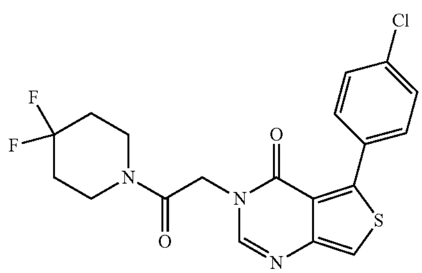 [SMILES: O=C(Cn1cnc2csc(-c3ccc(Cl)cc3)c2c1=O)N1CCC(F)(F)CC1] | 5-(4-chlorophenyl)-3-(2-(4,4-difluoropiperidin-1-yl)-2-oxoethyl)thieno[3,4-d]pyrimidin-4(3H)-one | $^1$H NMR (400 MHz, DMSO-$d_6$) δ (ppm): 7.92 (s, 1H), 7.88 (s, 1H), 7.66 (d, J = 8.4 Hz, 2H), 7.50 (d, J = 8.4 Hz, 2H), 4.86 (s, 2H), 3.61 (brs, 2H), 3.55 (brs, 2H) 2.09-1.92 (m, 4H). Calculated (M + H): 424.06, Found (M + H): 424.1, HPLC purity: 99.70%. |
| 354 | 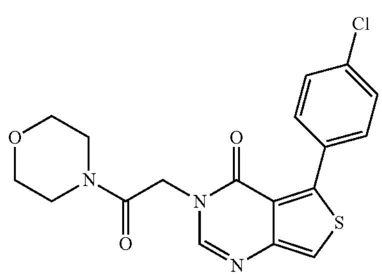 [SMILES: O=C(Cn1cnc2csc(-c3ccc(Cl)cc3)c2c1=O)N1CCOCC1] | 5-(4-chlorophenyl)-3-(2-morpholino-2-oxoethyl)thieno[3,4-d]pyrimidin-4(3H)-one | $^1$H NMR (400 MHz, DMSO-$d_6$) δ (ppm): 7.93 (s, 1H), 7.87 (s, 1H), 7.65 (d, J = 8.4 Hz, 2H), 7.5 (d, J = 8.4 Hz, 2H), 4.81 (s, 2H), 3.63 (brs, 2H), 3.56 (brs, 2H), 3.52 (brs, 2H), 3.42 (brs, 2H). Calculated (M + H): 390.06, Found (M + H): 390.4, HPLC purity: 99.4%. |
| 355 | 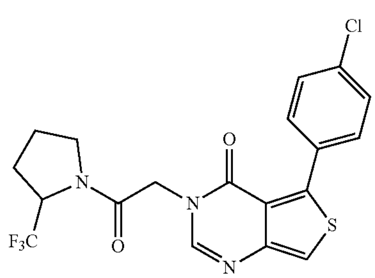 | 5-(4-chlorophenyl)-3-(2-oxo-2-(2-(trifluoromethyl)pyrrolidin-1-yl)ethyl)thieno[3,4-d]pyrimidin-4(3H)-one | $^1$H NMR (400 MHz, DMSO-$d_6$) δ (ppm): 7.96-7.94 (m, 1H), 7.89 (s, 1H), 7.67-7.65 (m, 2H), 7.51-7.49 (m, 2H), 4.81 (s, 2H), 4.75-4.71 (m, 1H), 3.67 (brs, 2H), 2.15-1.90 (m, 4H). Calculated (M + H): 442.85; Found (M + H): 442.2, HPLC purity: 99.45%. |

TABLE 37-continued

The following compounds were prepared by the method described above:

| Ex. No. | Structure | IUPAC Name | Analytical Data |
|---|---|---|---|
| 356 | 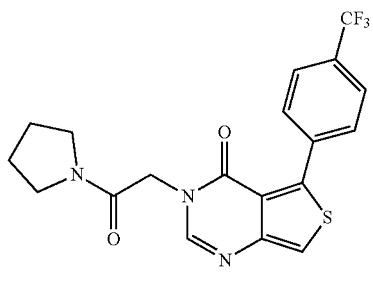 [SMILES: O=C(Cn1cnc2csc(-c3ccc(C(F)(F)F)cc3)c2c1=O)N1CCCC1] | 3-(2-oxo-2-(pyrrolidin-1-yl)ethyl)-5-(4-(trifluoromethyl)phenyl)thieno[3,4-d]pyrimidin-4(3H)-one | $^1$H NMR (400 MHz, DMSO-$d_6$) δ (ppm): 7.96 (brs, 2H), 7.86 (d, J = 8.4 Hz, 2H), 7.80 (d, J = 8.0 Hz, 2H), 4.69 (s, 2H), 3.48 (t, J = 6.4 Hz, 2H), 3.28 (brs, 2H), 1.93-1.89 (m, 2H), 1.80-1.75 (m, 2H). Calculated (M + H): 408.41, Found (M + H): 408.0, HPLC purity: 99.28%. |
| 357 | 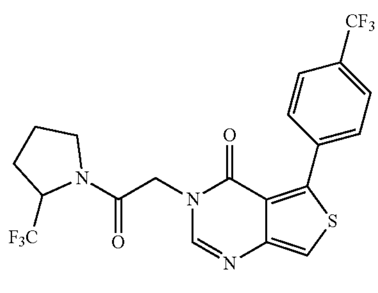 [SMILES: O=C(Cn1cnc2csc(-c3ccc(C(F)(F)F)cc3)c2c1=O)N1CCCC1C(F)(F)F] | 3-(2-oxo-2-(2-(trifluoromethyl)pyrrolidin-1-yl)ethyl)-5-(4-(trifluoromethyl)phenyl)thieno[3,4-d]pyrimidin-4(3H)-one | $^1$H NMR (400 MHz, DMSO-$d_6$) δ (ppm): 7.98 (brs, 2H), 7.86 (d, J = 8.0 Hz, 2H), 7.80 (d, J = 8.0 Hz, 2H), 5.1-4.8 (m, 2H), 4.72-4.71 (m, 1H), 3.66 (brs, 2H), 2.14-1.9 (m, 4H). Calculated (M + H): 476.08, Found (M + H): 476.1, HPLC purity: 99.54%. |
| 358 | 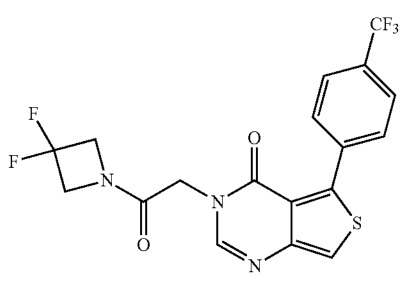 [SMILES: O=C(Cn1cnc2csc(-c3ccc(C(F)(F)F)cc3)c2c1=O)N1CC(F)(F)C1] | 3-(2-(3,3-difluoroazetidin-1-yl)-2-oxoethyl)-5-(4-(trifluoromethyl)phenyl)thieno[3,4-d]pyrimidin-4(3H)-one | $^1$H NMR (400 MHz, DMSO-$d_6$) δ (ppm): 7.96 (s, 2H), 7.86-7.84 (m, 2H), 7.80-7.78 (m, 2H), 4.72 (t, J = 12 Hz, 2H), 4.63 (s, 2H), 4.33 (t, J = 12 Hz, 2H). Calculated (M + H): 414.02, Found (M + H): 392, HPLC purity: 99.51%. |
| 359 | 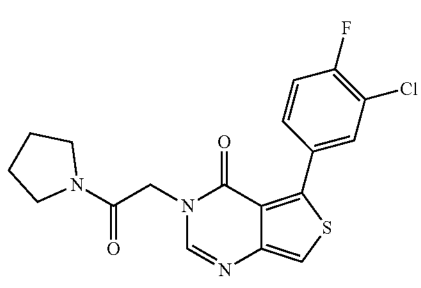 [SMILES: O=C(Cn1cnc2csc(-c3ccc(F)c(Cl)c3)c2c1=O)N1CCCC1] | 5-(3-chloro-4-fluorophenyl)-3-(2-oxo-2-(pyrrolidin-1-yl)ethyl)thieno[3,4-d]pyrimidin-4(3H)-one | $^1$H NMR (400 MHz, DMSO-$d_6$) δ (ppm): 7.92-7.88 (m, 3H), 7.61 (brs, 1H), 7.50-7.45 (m, 1H), 4.69 (s, 2H), 3.48 (t, J = 7.2 Hz, 2H), 3.27 (brs, 2H), 1.92-1.89 (m, 2H), 1.79-1.74 (m, 2H). Calculated (M + H): 392.06, Found (M + H): 392, HPLC Purity: 99.51%. |
| 360 | 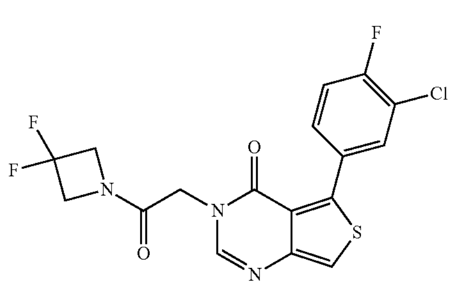 [SMILES: O=C(Cn1cnc2csc(-c3ccc(F)c(Cl)c3)c2c1=O)N1CC(F)(F)C1] | 5-(3-chloro-4-fluorophenyl)-3-(2-(3,3-difluoroazetidin-1-yl)-2-oxoethyl)thieno[3,4-d]pyrimidin-4(3H)-one | $^1$H NMR (400 MHz, DMSO-$d_6$) δ (ppm): 7.93-7.87 (m, 3H), 7.63-7.60 (m, 1H), 7.50-7.46 (m, 1H), 4.72 (t, J = 12.4 Hz, 2H), 4.64 (s, 2H), 4.33 (t, J = 12.4 Hz, 2H). Calculated (M + H): 414.8, Found (M + H): 414.0, HPLC Purity: 98.27%. |

TABLE 37-continued

The following compounds were prepared by the method described above:

| Ex. No. | Structure | IUPAC Name | Analytical Data |
| --- | --- | --- | --- |
| 361 | 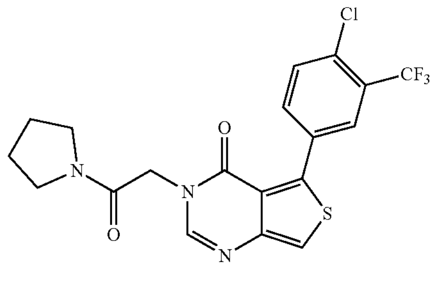 [SMILES: O=C(Cn1cnc2csc(-c3ccc(Cl)c(C(F)(F)F)c3)c2c1=O)N1CCCC1] | 5-(4-chloro-3-(trifluoromethyl)phenyl)-3-(2-oxo-2-(pyrrolidin-1-yl)ethyl)thieno[3,4-d]pyrimidin-4(3H)-one | $^1$H NMR (400 MHz, DMSO-$d_6$) δ (ppm): 8.10 (s, 1H), 7.94-7.89 (m, 3H), 7.79-7.77 (m, 1H), 4.69 (s, 2H), 3.47 (brs, 2H), 3.26 (brs, 2H) 1.91 (brs, 2H), 1.77 (brs, 2H). Calculated (M + H): 442.05, Found (M + H): 442.3, HPLC purity: 99.69%. |
| 362 | 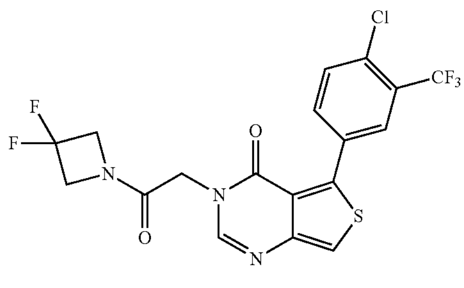 [SMILES: O=C(Cn1cnc2csc(-c3ccc(Cl)c(C(F)(F)F)c3)c2c1=O)N1CC(F)(F)C1] | 5-(4-chloro-3-(trifluoromethyl)phenyl)-3-(2-(3,3-difluoroazetidin-1-yl)-2-oxoethyl)thieno[3,4-d]pyrimidin-4(3H)-one | $^1$H NMR (400 MHz, DMSO-$d_6$) δ (ppm): 8.13 (s, 1H), 7.97-7.95 (m, 2H), 7.90 (d, J = 7.6 Hz, 1H), 7.79 (d, J = 8.4 Hz, 1H), 4.72 (t, J = 12 Hz, 2H), 4.65 (s, 2H), 4.32 (t, J = 12 Hz, 2H). Calculated (M + H): 464.02, Found (M + H): 464.3, HPLC purity: 99.80%. |
| 363 | 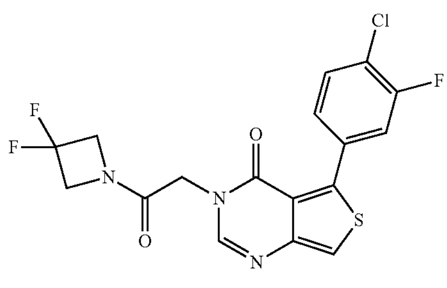 [SMILES: O=C(Cn1cnc2csc(-c3ccc(Cl)c(F)c3)c2c1=O)N1CC(F)(F)C1] | 5-(4-chloro-3-fluorophenyl)-3-(2-(3,3-difluoroazetidin-1-yl)-2-oxoethyl)thieno[3,4-d]pyrimidin-4(3H)-one | $^1$H NMR (400 MHz, DMSO-$d_6$) δ (ppm): 7.94 (s, 1H), 7.93 (s, 1H), 7.74-7.72 (m, 1H), 7.65 (t, J = 8.0 Hz, 1H), 7.48 (d, J = 8.4 Hz, 1H), 4.72 (t, J = 12 Hz, 2H), 4.63 (s, 2H), 4.33 (t, J = 12.4 Hz, 2H). Calculated (M + H): 414.2, Found (M + H): 414.0, HPLC purity: 99.72%. |
| 364 | 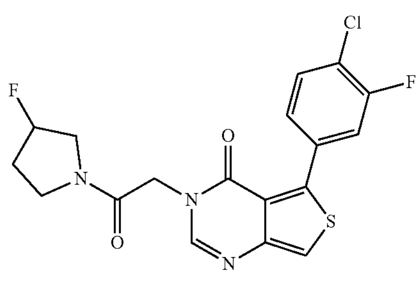 [SMILES: O=C(Cn1cnc2csc(-c3ccc(Cl)c(F)c3)c2c1=O)N1CCC(F)C1] | 5-(4-chloro-3-fluorophenyl)-3-(2-(3-fluoropyrrolidin-1-yl)-2-oxoethyl)thieno[3,4-d]pyrimidin-4(3H)-one | $^1$H NMR (400 MHz, DMSO-$d_6$) δ (ppm): 7.95 (s, 1H), 7.92 (s, 1H), 7.73 (d, J = 10.0 Hz, 1H), 7.66-7.62 (m, 1H), 7.48 (d, J = 7.6 Hz, 1H), 5.49-5.24 (m, 1H), 4.82-4.64 (m, 2 H), 3.87-3.36 (m, 4H), 2.25-2.07 (m, 2H). Calculated (M + H): 410.04, Found (M + H): 410.0, HPLC purity: 96.50%. |
| 365 | 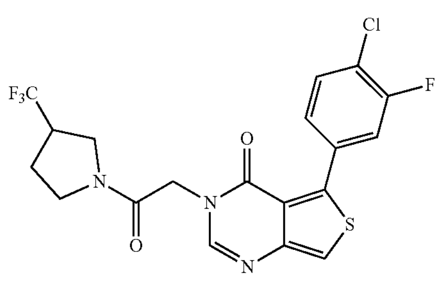 [SMILES: O=C(Cn1cnc2csc(-c3ccc(Cl)c(F)c3)c2c1=O)N1CCC(C(F)(F)F)C1] | 5-(4-chloro-3-fluorophenyl)-3-(2-oxo-2-(3-(trifluoromethyl)pyrrolidin-1-yl)ethyl)thieno[3,4-d]pyrimidin-4(3H)-one | $^1$H NMR (400 MHz, DMSO-$d_6$) δ (ppm): 7.97-7.93 (m, 2H), 7.74-7.71 (m, 1H), 7.67-7.63 (m, 1H), 7.48 (d, J = 7.6 Hz, 1H), 5.03-4.69 (m, 2H), 3.65 (s, 2H), 2.13-1.91(m, 5H). Calculated (M + H): 360.04; Found (M + H): 460.0, HPLC purity: 99.95%. |

Example 366: 5-(4-chloro-3-(trifluoromethyl)phenyl)-3-(2-oxo-2-(pyrrolidin-1-yl)ethyl)thieno[3,4-d]pyrimidin-4(3H)-one

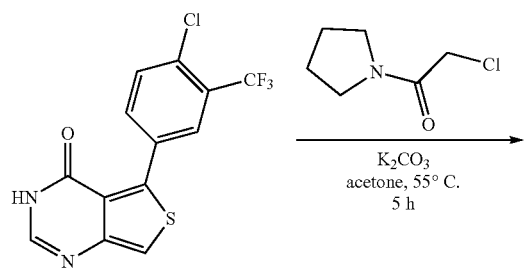

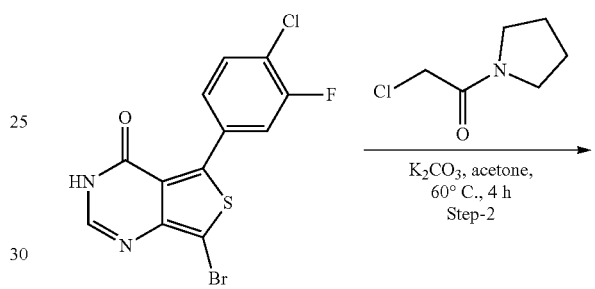

A mixture of 7-bromo-5-(4-chloro-3-fluorophenyl)thieno[3,4-d]pyrimidin-4(3H)-one (0.08 g, 0.24 mmol), 2-chloro-1-(pyrrolidin-1-yl)ethanone (0.071 g, 0.48 mmol) and potassium carbonate (0.11 g, 0.85 mmol) in acetone (10 mL) was heated at 55° C. for 5 h. The reaction mixture was filtered and the filtrate was concentrated. The crude was purified by silica gel column chromatography using 4% methanol in dichloromethane to afford the title compound 5-(4-chloro-3-(trifluoromethyl)phenyl)-3-(2-oxo-2-(pyrrolidin-1-yl)ethyl)thieno[3,4-d]pyrimidin-4(3H)-one (0.02 g, 20% yield) as a white solid. $^1$H NMR (400 MHz, DMSO-$d_6$) δ (ppm): 8.10 (s, 1H), 7.94-7.89 (m, 3H), 7.79-7.77 (m, 1H), 4.69 (s, 2H), 3.47 (brs, 2H), 3.26 (brs, 2H) 1.91 (brs, 2H), 1.77 (brs, 2H). Calculated (M+H): 442.05, Found (M+H): 442.3. HPLC purity: 99.69%.

Examples 368 and 369: Preparation of 5-(4-chloro-3-fluorophenyl)-7-methyl-3-(2-oxo-2-(pyrrolidin-1-yl)ethyl)thieno[3,4-d]pyrimidin-4(3H)-one

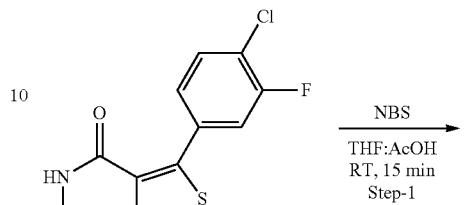

NBS
THF:AcOH
RT, 15 min
Step-1

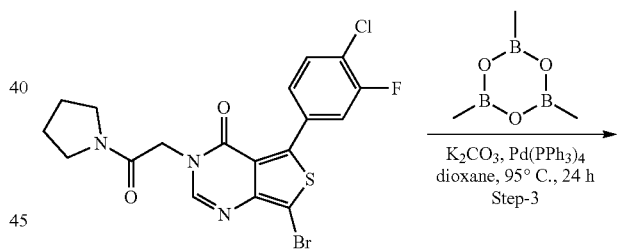

$K_2CO_3$, Pd(PPh$_3$)$_4$
dioxane, 95° C., 24 h
Step-3

TABLE 38

The following compound was prepared by the method described above:

| Ex. No. | Structure | IUPAC Name | Analytical Data |
|---|---|---|---|
| 367 | (structure) | 5-(4-chloro-3-fluorophenyl)-3-(2-oxo-2-(pyrrolidin-1-yl)ethyl)thieno[3,4-d]pyrimidin-4(3H)-one | $^1$H NMR (400 MHz, DMSO-$d_6$) δ (ppm): 7.93 (s, 1H), 7.91 (s, 1H), 7.75-7.71 (dd, J = 2.4 Hz, J = 2.0 Hz, 2H), 7.66-7.62 (m, 1H), 7.49-7.46 (m, 1H), 4.69 (s, 2H), 3.48 (t, J = 6.8 Hz, 2H), 3.27 (brs, 1H), 1.94-1.87 (m, 2H), 1.79-1.73 (m, 2H). Calculated (M + H): 392.06; Found (M + H): 392.0, HPLC purity: 99.68%. |

-continued

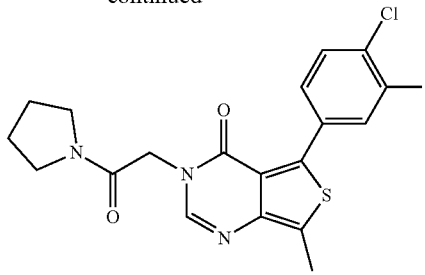

Step-1

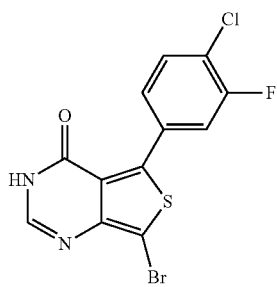 [SMILES: O=c1[nH]cnc2c(Br)sc(-c3ccc(Cl)c(F)c3)c12]

Preparation of 7-bromo-5-(4-chloro-3-fluorophenyl)thieno[3,4-d]pyrimidin-4(3H)-one To a solution of 5-(4-chloro-3-fluorophenyl)thieno[3,4-d]pyrimidin-4(3H)-one (0.07 g, 0.25 mmol) in tetrahydrofuran:acetic acid mixture (17.5 mL, 6:1), was added N-bromosuccinimide and the reaction mixture was stirred at room temperature for 15 min. The reaction mixture was concentrated and the crude was purified by column chromatography using 80% ethyl acetate in hexane to afford the title compound 7-bromo-5-(4-chloro-3-fluorophenyl)thieno[3,4-d]pyrimidin-4(3H)-one (0.065 crude). Calculated (M+H): 358.90, Found M+H: 358.9.

Step-2

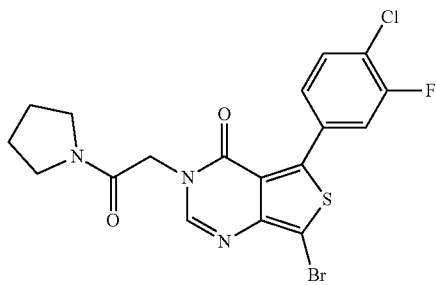 [SMILES: O=C(Cn1cnc2c(Br)sc(-c3ccc(Cl)c(F)c3)c2c1=O)N1CCCC1]

Preparation of 7-bromo-5-(4-chloro-3-fluorophenyl)-3-(2-oxo-2-(pyrrolidin-1-yl)ethyl)thieno[3,4-d]pyrimidin-4(3H)-one A mixture of 7-bromo-5-(4-chloro-3-fluorophenyl)thieno[3,4-d]pyrimidin-4(3H)-one (0.9 g, 2.50 mmol), 2-chloro-1-(pyrrolidin-1-yl)ethanone (0.738 g, 5.00 mmol) and potassium carbonate (1.037 g, 7.51 mmol) in acetone (40 mL) was heated at 60° C. for 4 h. The reaction mixture was filtered and the filtrate was concentrated. The crude was purified by column chromatography using 70% ethyl acetate in hexane to afford the title compound 7-bromo-5-(4-chloro-3-fluorophenyl)-3-(2-oxo-2-(pyrrolidin-1-yl)ethyl)thieno[3,4-d]pyrimidin-4(3H)-one (0.65 g, 55% yield) as a brownish solid. $^1$H NMR (400 MHz, DMSO-d$_6$) δ (ppm): 8.05 (s, 1H), 7.74-7.71 (m, 1H), 7.66 (t, J=7.6 Hz, 1H), 7.47 (d, J=7.2 Hz, 1H), 4.69 (s, 2H), 3.47 (t, J=6.4 Hz, 2H), 3.29-3.27 (m, 2H), 1.96-1.87 (m, 2H), 1.79-1.73 (m, 2H). Calculated (M+H): 469.97, Found M+H: 469.9, HPLC purity: 99.07%.

Step-3

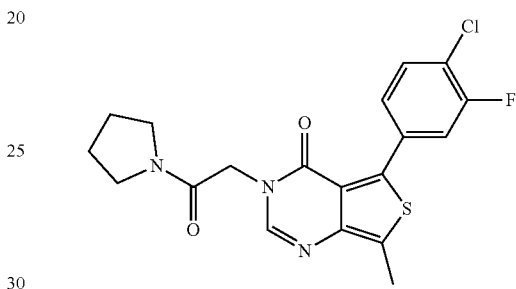

Preparation of 5-(4-chloro-3-fluorophenyl)-7-methyl-3-(2-oxo-2-(pyrrolidin-1-yl)ethyl)thieno[3,4-d]pyrimidin-4(3H)-one To a solution of 7-bromo-5-(4-chloro-3-fluorophenyl)-3-(2-oxo-2-(pyrrolidin-1-yl)ethyl)thieno[3,4-d]pyrimidin-4(3H)-one (0.25 g, 0.53 mmol) in dioxane (50 mL) potassium carbonate (0.367 g, 2.66 mmol) was added and the reaction mixture was purged with argon for 20 minutes. Then trimethylboroxine (0.074 ml, 0.53 mmol) and tetrakis(triphenylphosphine) palladium(0) (0.092 g, 0.08 mmol) were added and the reaction mixture was heated at 95° C. for 24 h. The reaction mixture was filtered through celite and filtrate was concentrated. The crude was purified by column chromatography followed by preparative HPLC (analytical conditions: column: Inertsil ODS 3V (250 mm×4.6 mm×5μ), mobile phase (A): 0.01% ammonia in water, mobile phase (B): methanol, flow rate: 1.0 mL/min, T/% B: 0/20, 8/80, 25/90, 27/20, 30/20, wavelength: 220 nm) to afford the title compound 5-(4-chloro-3-fluorophenyl)-7-methyl-3-(2-oxo-2-(pyrrolidin-1-yl)ethyl)thieno[3,4-d]pyrimidin-4(3H)-one (0.040 g, 18% yield) as a off-white solid. $^1$H NMR (400 MHz, DMSO-d$_6$) δ (ppm): 7.90 (s, 1H), 7.72-7.68 (dd, J=2.4 Hz, J=10.8 Hz, 1H), 7.63-7.61 (m, 1H), 7.45-7.43 (dd, J=1.2 Hz, J=8.4 Hz, 1H), 4.68 (s, 2H), 3.48 (t, J=6.8 Hz, 2H), 3.29-3.25 (m, 2H), 2.62 (s, 3H), 1.92-1.87 (m, 2H), 1.79-1.74 (m, 2H). Calculated (M+H): 406.07; Found (M+H): 406.0, HPLC purity: 99.90%.

K. PREPARATION OF ISOPYRROLOPYRIMIDINONES

Example 370: Preparation of 3-(2-(azetidin-1-yl)-2-oxoethyl)-5-(4-chlorophenyl)-3H-pyrrolo[3,2-d]pyrimidin-4(5H)-one

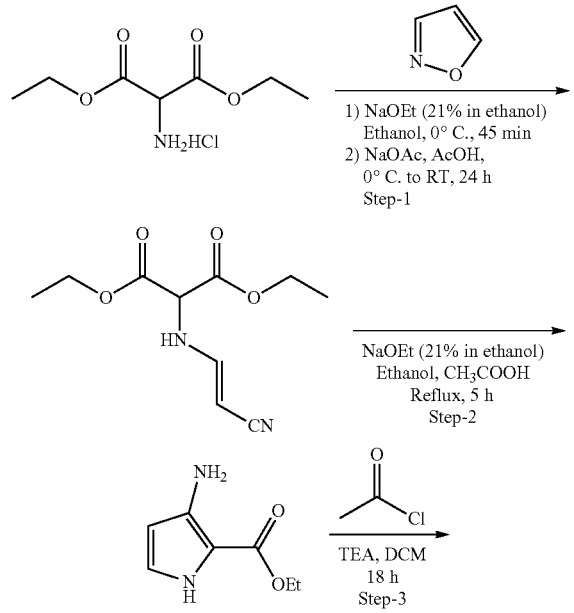

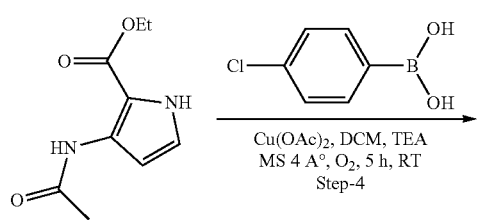

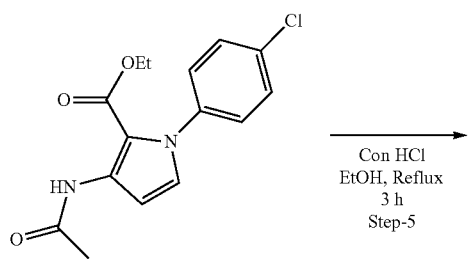

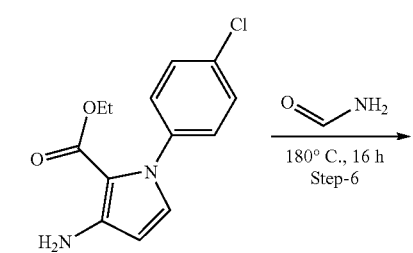

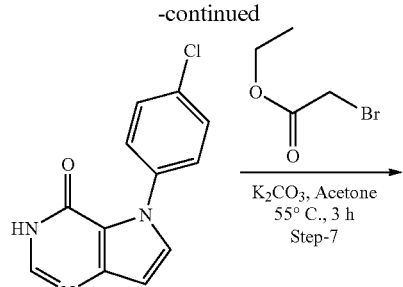

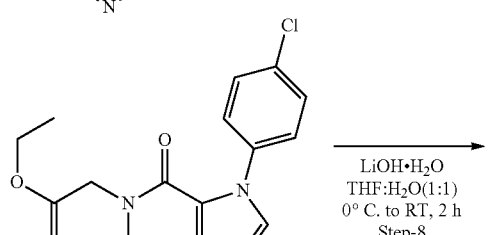

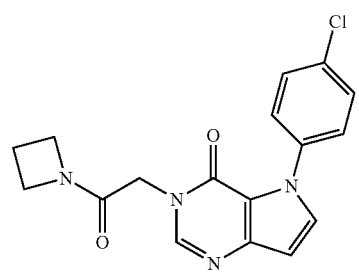

Step 1

Preparation of (E)-diethyl 2-((2-cyanovinyl)amino)malonate

To a mixture of isoxazole (5.0 g, 72.40 mmol) in ethanol (20 mL) was added a solution of sodium ethoxide in ethanol (21% in ethanol) (5.9 g, 86.88 mmol) at 0° C. slowly (maintaining the temperature<8° C. while addition) and stirred for 45 min at 0° C. To the above reaction mixture, acetic acid (1.4 mL), diethyl 2-aminodimalonate hydrochloride (10.72 g, 50.68 mmol), and sodium acetate (4.15 g, 50.68 mmol) were sequentially added at 0° C., the mixture was allowed to warm to room temperature and stirred for 24 h. After completion of reaction, the reaction mixture was concentrated under reduced pressure, the residue was dissolved with dichloromethane (500 mL), washed with water, dried over anhydrous sodium sulfate, filtered and concentrated under vacuum to obtain title compound (E)-diethyl 2-((2-cyanovinyl)amino)malonate (10.2 g, crude) as orange gummy liquid, which was taken for next step without further purification. Calculated (M+H): 227.10; Found (M+1): 227.1.

Step 2

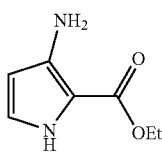

Preparation of ethyl 3-amino-1H-pyrrole-2-carboxylate

To a mixture of (E)-diethyl 2-((2-cyanovinyl)amino)malonate (10.2 g crude, 45.09 mmol), in ethanol (25 mL) was added a solution of 21% sodium ethoxide in ethanol (22 mL) at room temperature. The resulting mixture was heated to reflux and stirred for 4 h. After 4 h, the mixture was allowed to cool to room temperature and acetic acid (3 mL) was added. The solvent was removed under vacuum, the residue was dissolved with dichloromethane (500 mL), washed with an aqueous solution of saturated sodium bicarbonate, water, and brine, dried over anhydrous sodium sulfate, filtered and concentrated under vacuum to afford the crude product. The crude material was purified by silica gel (60-120) column chromatography using 2.5% methanol in dichloromethane to afford ethyl 3-amino-1H-pyrrole-2-carboxylate (2.0 g, impure) as a yellow solid. Calculated (M+H): 155.07; Found (M+1): 155.1.

Step 3

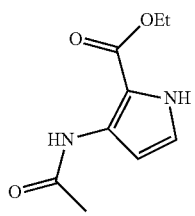

Preparation of ethyl 3-acetamido-1H-pyrrole-2-carboxylate

To a mixture of ethyl 3-amino-1H-pyrrole-2-carboxylate (2.0 g, 12.97 mmol) and triethyl amine (5.4 mL, 38.92 mmol) in dichloromethane (100 mL) was added acetyl chloride (1.1 mL, 15.57 mmol) at 0° C. The reaction mixture was allowed to warm to room temperature and stirred for 18 h. The progress of the reaction was monitored by TLC. The reaction mixture was diluted with dichloromethane (100 mL), washed with a saturated aqueous solution of sodium bicarbonate, water, and brine, dried over anhydrous sodium sulfate, filtered and concentrated under vacuum to afford the crude product. The crude product was purified by silica gel (60-120) column chromatography using 3% methanol in dichloromethane to afford ethyl 3-acetamido-1H-pyrrole-2-carboxylate (2.08 g, 83.2% yield) as a yellow solid. Calculated (M+H): 197.08; Found (M+1): 197.1.

Step 4

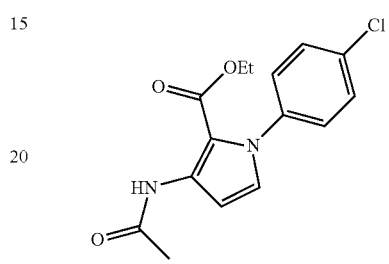

Preparation of ethyl 3-acetamido-1-(4-chlorophenyl)-1H-pyrrole-2-carboxylate

To a mixture of ethyl 3-acetamido-1H-pyrrole-2-carboxylate (2.0 g, 10.19 mmol) in dichloromethane (100 mL) was added triethylamine (6.4 mL, 45.87 mmol), (4-chlorophenyl)boronic acid (3.18 g, 20.39 mmol), 4 Å molecular sieves (20 g) and copper(II)acetate (3.7 g, 20.39 mmol), at room temperature. The resulting mixture was stirred at room temperature in the presence of air for 5 h. The progress of the reaction was monitored by TLC. The reaction mixture was filtered and washed with dichloromethane. The filtrate was washed with 1M aqueous hydrochloric acid (100 mL×2) and the organic layer was dried over anhydrous sodium sulfate, filtered, concentrated under vacuum to afford the crude product. The crude material was purified by silica gel (60-120) column chromatography using 30% ethyl acetate in hexane to afford ethyl 3-acetamido-1-(4-chlorophenyl)-1H-pyrrole-2-carboxylate (2.9 g, 93% yield) as orange yellow solid. Calculated (M+H): 307.08; Found (M+1): 307.1.

Step 5

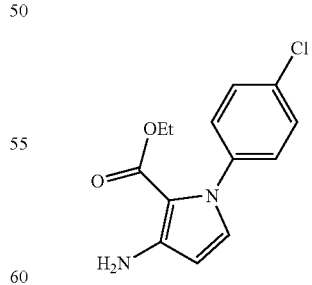

Preparation of ethyl 3-amino-1-(4-chlorophenyl)-1H-pyrrole-2-carboxylate

To a solution of ethyl 3-acetamido-1-(4-chlorophenyl)-1H-pyrrole-2-carboxylate (2.9 g, 9.454 mmol) in ethanol (100 mL) was added concentrated hydrochloric acid (10 mL) at room temperature. The resulting mixture was heated to reflux and stirred for 3 h. After 3 h, the mixture was allowed to cool to room temperature and the solvent was removed under vacuum. The residue was dissolved with ethyl acetate, washed with aqueous solution of saturated sodium bicarbonate, water, brine, dried over anhydrous sodium sulfate, filtered and concentrated under vacuum to afford the title compound ethyl 3-amino-1-(4-chlorophenyl)-1H-pyrrole-2-carboxylate (4.7 g, crude) as a pale brown solid, which was taken for next step without further purification. Calculated (M+H): 265.07; Found (M+1): 265.1.

Step 6

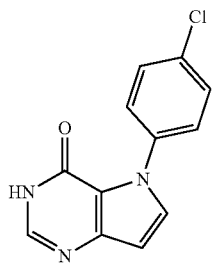 [SMILES: O=c1[nH]cnc2ccn(-c3ccc(Cl)cc3)c12]

Preparation of 5-(4-chlorophenyl)-3H-pyrrolo[3,2-d] pyrimidin-4(5H)-one

A mixture of 3-amino-1-(4-chlorophenyl)-1H-pyrrole-2-carboxylate (4.7 g, 17.79 mmol) and formamide (40 mL) was heated to 180° C. and stirred for 16 h. The reaction was monitored by TLC. The mixture was allowed to cool to room temperature and diluted with water (150 mL), the precipitated solid was filtered, washed with water, dried under vacuum to afford the title compound 5-(4-chlorophenyl)-3H-pyrrolo[3,2-d]pyrimidin-4(5H)-one (4.0 g, 91.4% yield) as a brown solid. Calculated (M+H): 246.04; Found (M+H): 246.1.

Step 7

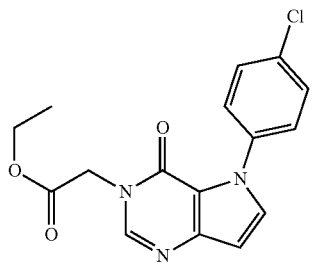 [SMILES: CCOC(=O)Cn1cnc2ccn(-c3ccc(Cl)cc3)c2c1=O]

Preparation of ethyl 2-(5-(4-chlorophenyl)-4-oxo-4,5-dihydro-3H-pyrrolo[3,2-d]pyrimidin-3-yl)acetate To a mixture of 5-(4-chlorophenyl)-3H-pyrrolo[3,2-d]pyrimidin-4(5H)-one (2.0 g, 8.14 mmol) and potassium carbonate (3.37 g, 24.42 mmol) in dry acetone was added ethyl 2-bromoacetate (1.81 mL, 16.28 mmol). The resulting mixture was heated to 55° C. and stirred for 5 h. The mixture was allowed to cool to room temperature, filtered the solid, and washed with ethyl acetate. The filtrate was concentrated under vacuum to afford crude product, which was purified by silica gel (60-120) column chromatography using 25% ethyl acetate in hexane to afford the title compound ethyl 2-(5-(4-chlorophenyl)-4-oxo-4,5-dihydro-3H-pyrrolo[3,2-d]pyrimidin-3-yl)acetate (2.3 g, 85% yield) as an orange gummy compound. Calculated (M+H): 332.07; Found (M+H): 332.1.

Step 8

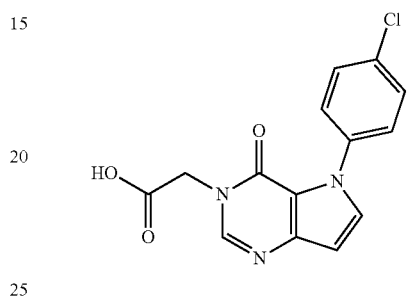

Preparation of 2-(5-(4-chlorophenyl)-4-oxo-4,5-dihydro-3H-pyrrolo[3,2-d]pyrimidin-3-yl)acetic acid To a suspension of ethyl 2-(5-(4-chlorophenyl)-4-oxo-4,5-dihydro-3H-pyrrolo[3,2-d]pyrimidin-3-yl)acetate (2.3 g, 6.93 mmol) in a mixture of tetrahydrofuran and water (25 mL: 25 mL) was added lithium hydroxide monohydrate (1.45 g, 34.66 mmol) at 0° C. The resulting suspension was gradually allowed to warm to room temperature and stirred for 2 h. After 2 h, the reaction mixture was allowed to cool to 0° C. and acidified with 1.5M hydrochloric acid solution to pH 2 to 3, the precipitated solid was filtered, washed with water, dried under vacuum to afford the title compound 2-(5-(4-chlorophenyl)-4-oxo-4,5-dihydro-3H-pyrrolo[3,2-d]pyrimidin-3-yl)acetic acid (1.7 g, 80% yield) as a colorless solid. Calculated (M+H): 304.04; Found (M+H): 304.1.

Step 9

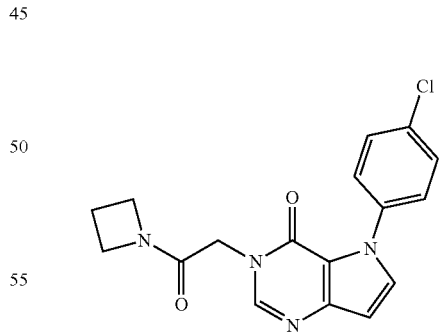

Preparation of 3-(2-(azetidin-1-yl)-2-oxoethyl)-5-(4-chlorophenyl)-3H-pyrrolo[3,2-d]pyrimidin-4(5H)-one To a solution of 2-(5-(4-chlorophenyl)-4-oxo-4,5-dihydro-3H-pyrrolo[3,2-d]pyrimidin-3-yl)acetic acid (0.1 g, 0.329 mmol) in dichloromethane (15 mL) was added azetidine hydrochloride (0.03 g, 0.033 mmol) and triethylamine (0.14 mL, 0.99 mmol) at room temperature. The reaction mixture was allowed to cool to 0° C. and 1-Propanephosphonic anhydride solution (50% solution in ethyl acetate) (0.42 mL, 0.66 mmol) was added. The resulting mixture was allowed to warm to room temperature and stirred for 16 h, after completion of reaction, the reaction mixture was diluted with dichloromethane (25 mL), washed with water (2×25 mL), and brine, dried over anhydrous sodium sulfate, filtered and concentrated under reduced pressure to afford crude product. The crude product was purified by silica gel (60-120) column chromatography using 3% methanol in dichloromethane as eluent to afford the title compound 3-(2-(azetidin-1-yl)-2-oxoethyl)-5-(4-chlorophenyl)-3H-pyrrolo[3,2-d]pyrimidin-4(5H)-one (0.046 g, 42% yield) as white solid. $^1$H NMR (400 MHz, DMSO-$d_6$) δ (ppm): 8.08 (s, 1H), 7.69 (d, J=3.2 Hz, 1H), 7.53 (d, J=8.8 Hz, 2H), 7.47 (d, J=8.8 Hz, 2H), 6.61 (d, J=2.4 Hz, 1H), 4.56 (s, 2H), 4.21 (t, J=7.6 Hz, 2H), 3.86 (t, J=7.6 Hz, 2H), 2.25 (t, J=7.6 Hz, 2H). Calculated (M+H): 343.09; Found (M+1): 343.3. HPLC purity: 98.12%.

TABLE 39

The following compounds were prepared by the method described above:

| Ex. No. | Structure | IUPAC Name | Analytical data |
|---|---|---|---|
| 371 | 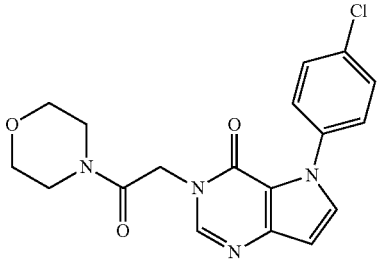 [SMILES: O=C(Cn1cnc2ccn(-c3ccc(Cl)cc3)c2c1=O)N1CCOCC1] | 5-(4-chlorophenyl)-3-(2-morpholino-2-oxoethyl)-3H-pyrrolo[3,2-d]pyrimidin-4(5H)-one | $^1$H NMR (400 MHz, DMSO-$d_6$) δ (ppm); 8.07 (s, 1H), 7.69 (d, J = 2.4 Hz, 1H), 7.52 (d, J = 8.4 Hz, 2H), 7.47 (d, J = 8.4 Hz, 2H), 6.62 (d, J = 2.8 Hz, 1H), 4.88 (s, 2H), 3.63 (brs, 2H), 3.54 (brs, 4H), 3.41 (brs, 2H). Calculated (M + H): 373.10; Found (M + 1): 373.1. HPLC purity 99.19%. |
| 372 | 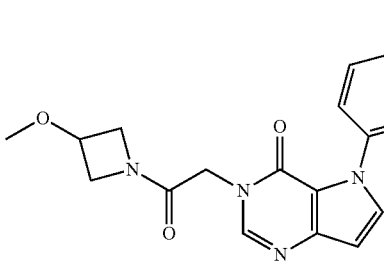 | 5-(4-chlorophenyl)-3-(2-(3-methoxyazetidin-1-yl)-2-oxoethyl)-3H-pyrrolo[3,2-d]pyrimidin-4(5H)-one | $^1$H NMR (400 MHz, DMSO-$d_6$) δ (ppm); 8.09 (s, 1H), 7.69 (d, J = 2.4 Hz, 1H), 7.53 (d, J = 8.8 Hz, 2H), 7.47 (d, J = 8.8 Hz, 2H), 6.61 (d, J = 3.2 Hz, 1H), 4.60 (s, 2H), 4.41-4.37 (m, 1H), 4.27-4.22 (m, 1H), 4.06-4.02 (m, 2H), 3.69-3.66 (m, 1H), 3.21 (s, 3H). Calculated (M + H): 373.10; Found (M + 1): 373.1. HPLC purity 99.34%. |
| 373 | 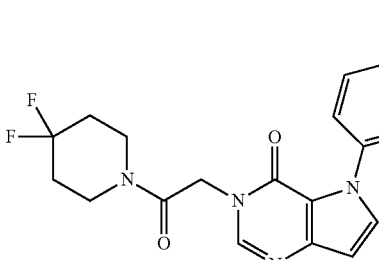 | 5-(4-chlorophenyl)-3-(2-(4,4-difluoropiperidin-1-yl)-2-oxoethyl)-3H-pyrrolo[3,2-d]pyrimidin-4(5H)-one | $^1$H NMR (400 MHz, DMSO-$d_6$) δ (ppm); 8.07 (s, 1H), 7.69 (d, J = 3.2 Hz, 1H), 7.52 (d, J = 8.8 Hz, 2H), 7.47 (d, J = 8.8 Hz, 2H), 6.62 (d, J = 2.8 Hz, 1H), 4.94 (s, 2H), 3.63 (brs, 2H), 3.54 (brs, 2H), 2.09 (brs, 2H), 1.92 (brs, 2H). Calculated (M + H): 407.10; Found (M + 1): 407.1. HPLC purity 99.37%. |
| 374 | 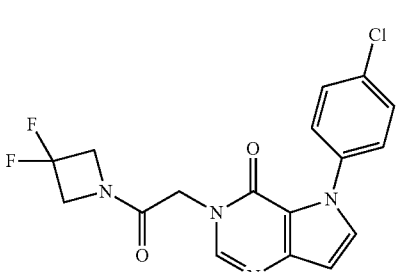 | 5-(4-chlorophenyl)-3-(2-(3,3-difluoroazetidin-1-yl)-2-oxoethyl)-3H-pyrrolo[3,2-d]pyrimidin-4(5H)-one | $^1$H NMR (400 MHz, DMSO-$d_6$) δ (ppm); 8.10 (s, 1H), 7.71 (d, J = 3.2 Hz, 1H), 7.53 (d, J = 8.8 Hz, 2H), 7.47 (d, J = 8.8 Hz, 2H), 6.61 (d, J = 3.2 Hz, 1H), 4.76-4.70 (m, 4H), 4.33 (t, J = 12.4 Hz, 2H). Calculated (M + H): 379.07; Found (M + 1): 379.4. HPLC purity 99.05%. |

TABLE 39-continued

The following compounds were prepared by the method described above:

| Ex. No. | Structure | IUPAC Name | Analytical data |
|---|---|---|---|
| 375 | 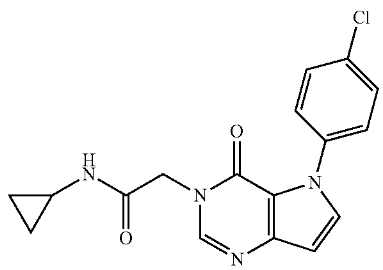 [SMILES: O=C(Cn1cnc2ccn(-c3ccc(Cl)cc3)c2c1=O)NC1CC1] | 2-(5-(4-chlorophenyl)-4-oxo-4,5-dihydro-3H-pyrrolo[3,2-d]pyrimidin-3-yl)-N-cyclopropylacetamide | $^1$H NMR (400 MHz, DMSO-$d_6$) δ (ppm): 8.25 (d, J = 4 Hz, 1H), 8.10 (s, 1H), 7.68 (d, J = 3.2 Hz, 1H), 7.53-7.46 (m, 4H), 6.61 (d, J = 2.8 Hz, 1H), 4.52 (s, 2H), 2.62-2.58 (m, 1H), 0.60 (brs, 2H), 0.39 (brs, 2H). Calculated (M + H): 343.09, Found (M + H): 343.1. HPLC purity 99.39%. |
| 376 | 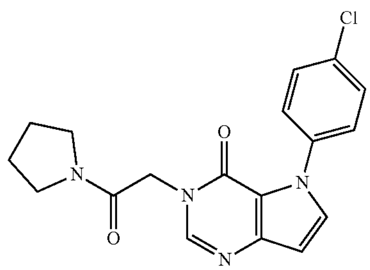 [SMILES: O=C(Cn1cnc2ccn(-c3ccc(Cl)cc3)c2c1=O)N1CCCC1] | 5-(4-chlorophenyl)-3-(2-oxo-2-(pyrrolidin-1-yl)ethyl)-3H-pyrrolo[3,2-d]pyrimidin-4(5H)-one | $^1$H NMR (400 MHz, DMSO-$d_6$) δ (ppm): 8.08 (s, 1H), 7.69 (d, J = 2.8 Hz, 1H), 7.53-7.46 (m, 4H), 6.62 (d, J = 3.2 Hz, 1H), 4.76 (s, 2H), 3.5 (d, J = 6.8 Hz, 2H), 1.95-1.89 (m, 2H), 1.80-1.74 (m, 2H). (Two protons are merged with DMSO water peak) Calculated (M + H): 357.1, Found (M + H): 357.1. HPLC purity99.05%. |
| 377 | 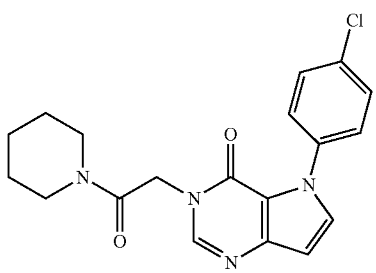 [SMILES: O=C(Cn1cnc2ccn(-c3ccc(Cl)cc3)c2c1=O)N1CCCCC1] | 5-(4-chlorophenyl)-3-(2-oxo-2-(piperidin-1-yl)ethyl)-3H-pyrrolo[3,2-d]pyrimidin-4(5H)-one | $^1$H NMR (400 MHz, DMSO-$d_6$) δ (ppm): 8.07 (s, 1H), 7.68 (d, J = 3.2 Hz, 1H), 7.521 (d, J = 8.4 Hz, 2H), 7.47 (d, J = 8.8 Hz, 2H), 6.613 (d, J = 2.4 Hz, 1H), 4.86 (s, 2H), 3.45 (m, 2H), 3.39 (m, 2H), 1.57 (m, 4H), 1.42 (m, 2H). Calculated M + H: 370.12; Found M + H: 371.4; HPLC: 99.31% |
| 378 | 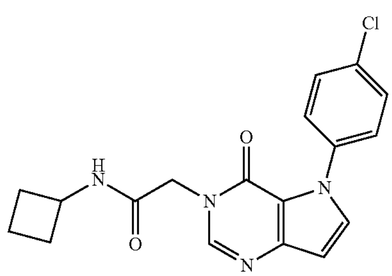 [SMILES: O=C(Cn1cnc2ccn(-c3ccc(Cl)cc3)c2c1=O)NC1CCC1] | 2-(5-(4-chlorophenyl)-4-oxo-4,5,6,7-tetrahydro-3H-pyrrolo[3,2-d]pyrimidin-3-yl)-N-cyclobutylacetamide | $^1$H NMR (400 MHz, DMSO-$d_6$) δ 8.40 (d, J = 7.2 Hz, 1H), 8.1 (s, 1H), 7.68 (s, 1H), 7.46-7.53 (m, 4H), 6.61 (s, 1H), 4.56 (s, 2H), 4.13-4.19 (m, 1H), 2.12-2.13 (m, 2H), 1.88 (t, J = 9.1 Hz, 2H), 1.55-1.63 (m, 2H). Calculated M + H: 190.94; Found M + H: 191.0; HPLC: 99.27% |
| 379 | 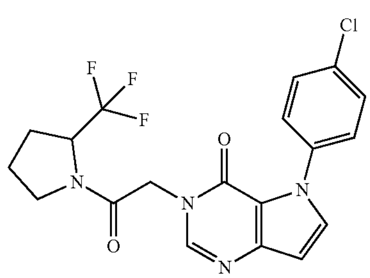 [SMILES: O=C(Cn1cnc2ccn(-c3ccc(Cl)cc3)c2c1=O)N1CCCC1C(F)(F)F] | 5-(4-chlorophenyl)-3-(2-oxo-2-(2-(trifluoromethyl)pyrrolidin-1-yl)ethyl)-3H-pyrrolo[3,2-d]pyrimidin-4(5H)-one | $^1$H NMR (400 MHz, DMSO-$d_6$) δ (ppm): 8.09 (s, 1H), 7.70 (d, J = 2.4 Hz, 1H), 7.53-7.46 (m, 4H), 6.63 (d, J = 2.8 Hz, 1H), 5.04-4.79 (m, 2H), 4.70 (brs, 1H), 3.67 (brs, 1H), 2.15-1.90 (m, 4H). Calculated (M + H): 425.09, Found (M + H): 425.1. HPLC purity 99.64%. |

L. PREPARATION OF THIAZOLOPYRIMIDINONES

Example 380: Preparation of 3-(4-chlorophenyl)-5-(2-oxo-2-(pyrrolidin-1-yl)ethyl)isothiazolo[5,4-d]pyrimidin-4(5H)-one

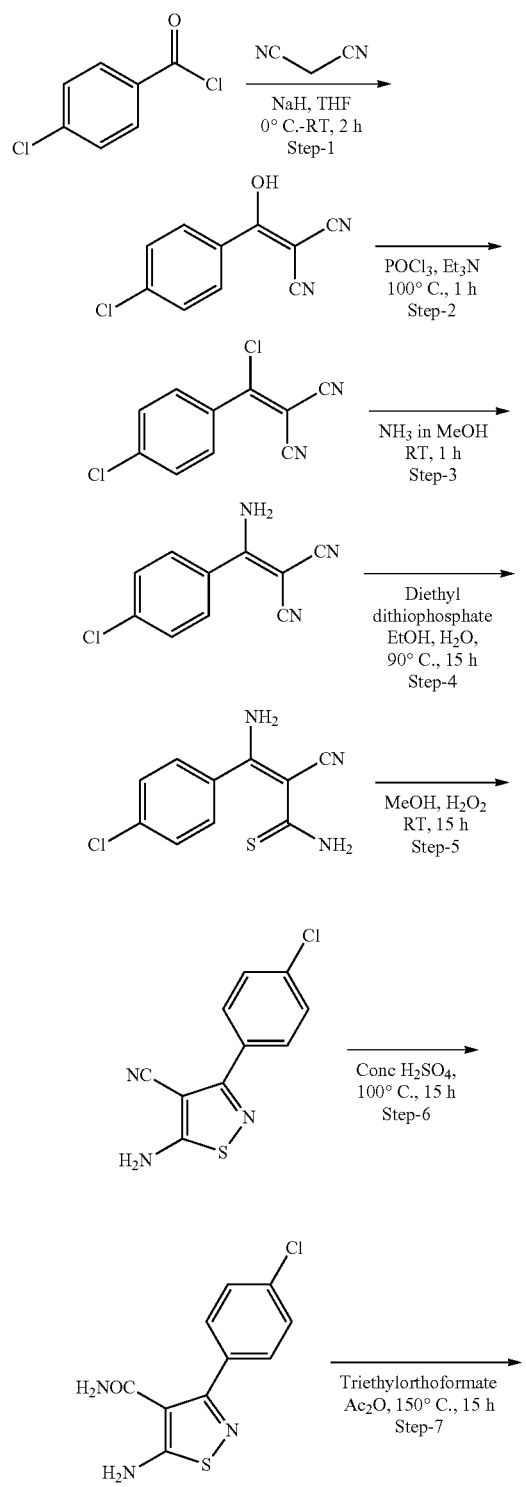

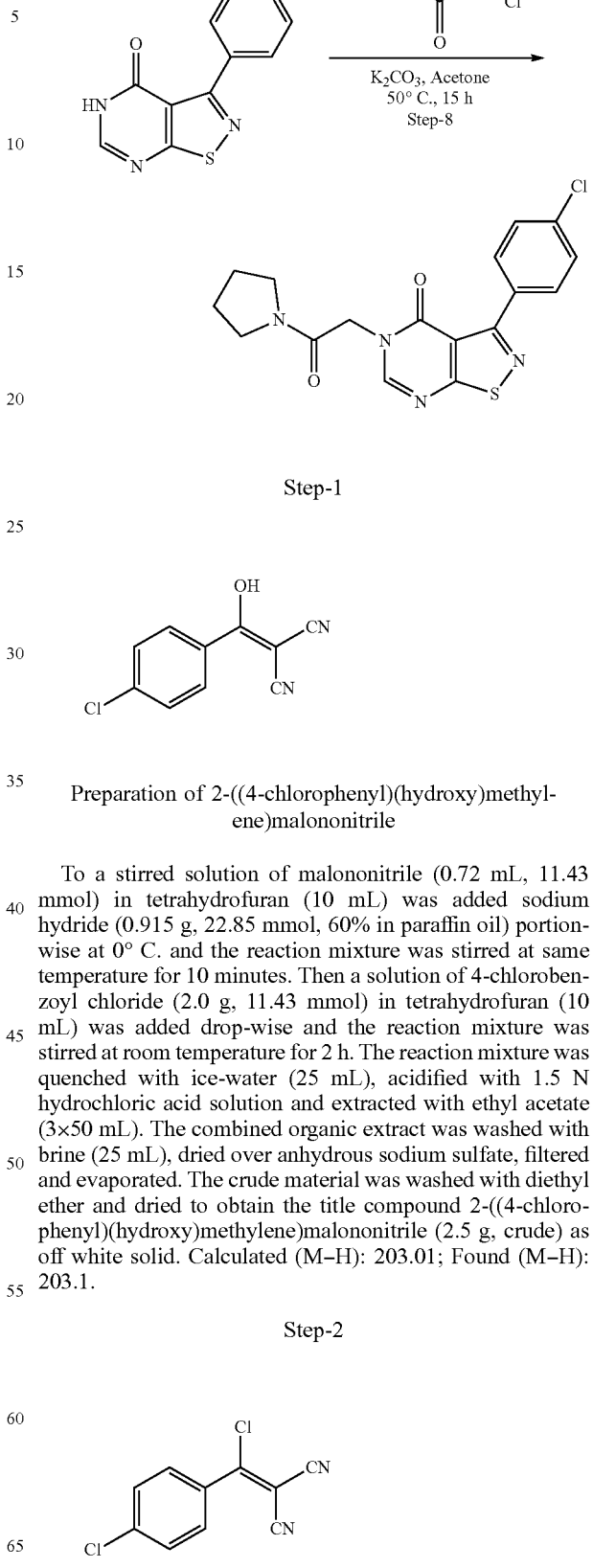

Step-1

Preparation of 2-((4-chlorophenyl)(hydroxy)methylene)malononitrile

To a stirred solution of malononitrile (0.72 mL, 11.43 mmol) in tetrahydrofuran (10 mL) was added sodium hydride (0.915 g, 22.85 mmol, 60% in paraffin oil) portion-wise at 0° C. and the reaction mixture was stirred at same temperature for 10 minutes. Then a solution of 4-chlorobenzoyl chloride (2.0 g, 11.43 mmol) in tetrahydrofuran (10 mL) was added drop-wise and the reaction mixture was stirred at room temperature for 2 h. The reaction mixture was quenched with ice-water (25 mL), acidified with 1.5 N hydrochloric acid solution and extracted with ethyl acetate (3×50 mL). The combined organic extract was washed with brine (25 mL), dried over anhydrous sodium sulfate, filtered and evaporated. The crude material was washed with diethyl ether and dried to obtain the title compound 2-((4-chlorophenyl)(hydroxy)methylene)malononitrile (2.5 g, crude) as off white solid. Calculated (M−H): 203.01; Found (M−H): 203.1.

Step-2

Preparation of 2-(chloro(4-chlorophenyl)methylene)malononitrile

To a stirred solution of 2-((4-chlorophenyl)(hydroxy)methylene)malononitrile (1.0 g, 4.88 mmol) in phosphorous oxychloride (10 mL) was added triethylamine (0.68 mL, 4.88 mmol) and the reaction mixture was heated at 100° C. for 1 h. The reaction mixture was cooled and evaporated. The residue was quenched with ice-water (25 mL) and extracted with ethyl acetate (3×50 mL). The combined organic extract was washed with brine (25 mL), dried over anhydrous sodium sulfate, filtered and evaporated. The crude material was purified by silica gel column chromatography using 5% ethyl acetate in hexane to obtain the title compound 2-(chloro(4-chlorophenyl)methylene)malononitrile (0.85 g, crude) as yellow solid. $^1$H NMR (400 MHz, DMSO-d$_6$) δ (ppm): 7.58 (d, J=8.4 Hz, 2H), 7.43 (d, J=8.4 Hz, 2H).

Step-3

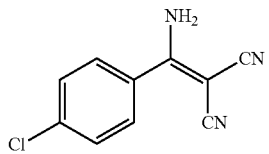 [SMILES: N#CC(C#N)=C(N)c1ccc(Cl)cc1]

Preparation of 2-(amino(4-chlorophenyl)methylene)malononitrile

A solution of 2-(chloro(4-chlorophenyl)methylene)malononitrile (0.85 g, 3.81 mmol) and ammonia in methanol (15 mL) was stirred at room temperature for 1 h. The reaction mixture was evaporated to dryness. The residue was washed with diethyl ether and dried to obtain the title compound 2-(amino(4-chlorophenyl)methylene)malononitrile (1.0 g, crude) as off white solid. Calculated (M−H): 202.03; Found (M−H): 202.

Step-4

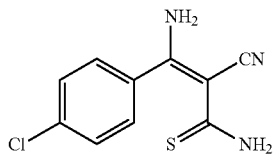 [SMILES: N#C/C(C(N)=S)=C(\N)c1ccc(Cl)cc1]

Preparation of (E)-3-amino-3-(4-chlorophenyl)-2-cyanoprop-2-enethioamide

To a stirred solution of 2-(amino(4-chlorophenyl)methylene)malononitrile (1.0 g, 4.91 mmol) in ethanol: water (12.5 mL, 4:1) mixture, was added diethyl dithiophosphate (1.24 mL, 7.36 mmol) and the reaction mixture was heated at 90° C. for 15 h. The reaction mixture was evaporated to dryness. The residue was washed with diethyl ether and dried to obtain the title compound (E)-3-amino-3-(4-chlorophenyl)-2-cyanoprop-2-enethioamide (1.3 g, crude) as yellow solid. Calculated (M+H): 238.01; Found (M+H): 238.

Step-5

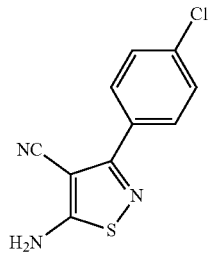 [SMILES: N#Cc1c(-c2ccc(Cl)cc2)nsc1N]

Preparation of 5-amino-3-(4-chlorophenyl)isothiazole-4-carbonitrile

To a stirred solution of (E)-3-amino-3-(4-chlorophenyl)-2-cyanoprop-2-enethioamide (0.9 g, 3.78 mmol) in methanol (20 mL) was added hydrogen peroxide (0.86 mL, 7.57 mmol, 30% aqueous solution) and the reaction mixture was stirred at room temperature for 15 h. The reaction mixture was carefully evaporated to dryness. The residue was washed with diethyl ether and dried to obtain the title compound 5-amino-3-(4-chlorophenyl)isothiazole-4-carbonitrile (0.85 g, crude) as white solid. Calculated (M+H): 236; Found (M+H): 236.

Step-6

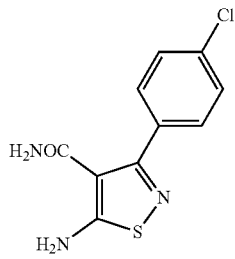 [SMILES: NC(=O)c1c(-c2ccc(Cl)cc2)nsc1N]

Preparation of 5-amino-3-(4-chlorophenyl)isothiazole-4-carboxamide

A solution of 5-amino-3-(4-chlorophenyl)isothiazole-4-carbonitrile (0.65 g, 2.56 mmol) in concentrated sulfuric acid (20 mL) was heated at 100° C. for 15 h. The reaction mixture was cooled and poured into ice-water (25 mL) and extracted with ethyl acetate (3×50 mL). The combined organic extract was washed with brine (25 mL), dried over anhydrous sodium sulfate and evaporated to obtain the title compound 5-amino-3-(4-chlorophenyl)isothiazole-4-carboxamide (0.65 g, crude) as off white solid. Calculated (M+H): 254.01; Found (M+H): 254.1.

Step-7

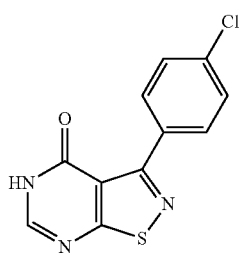 [SMILES: O=c1[nH]cnc2snc(-c3ccc(Cl)cc3)c12]

Preparation of 3-(4-chlorophenyl)isothiazolo[5,4-d]pyrimidin-4(5H)-one

To a solution of 5-amino-3-(4-chlorophenyl)isothiazole-4-carboxamide (0.65 g, 2.56 mmol) in acetic anhydride (7 mL) was added triethylorthoformate (7 mL) and the reaction mixture was heated at 150° C. for 15 h. The reaction mixture was cooled and poured into ice-water (25 mL). The precipitated solid was filtered, washed with cold water (25 mL) and dried to obtain the title compound 3-(4-chlorophenyl)isothiazolo[5,4-d]pyrimidin-4(5H)-one (0.65 g, 97% yield) as off white solid. Calculated (M−H): 262; Found (M−H): 262.

Step-8

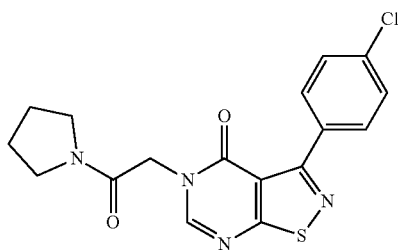 [SMILES: O=C(Cn1cnc2snc(-c3ccc(Cl)cc3)c2c1=O)N1CCCC1]

Preparation of 3-(4-chlorophenyl)-5-(2-oxo-2-(pyrrolidin-1-yl)ethyl)isothiazolo[5,4-d]pyrimidin-4(5H)-one To a stirred solution of 3-(4-chlorophenyl)isothiazolo[5,4-d]pyrimidin-4(5H)-one (0.1 g, 0.371 mmol) and 2-chloro-1-(pyrrolidin-1-yl)ethanone (0.072 g, 0.493 mmol) in acetone was added potassium carbonate (0.156 g, 1.13 mmol) and the reaction mixture was heated at 50° C. for 15 h. The reaction mixture was filtered and the filtrate was evaporated. The crude material was purified by silica gel column chromatography using 2% methanol in dichloromethane to obtain the title compound 3-(4-chlorophenyl)-5-(2-oxo-2-(pyrrolidin-1-yl)ethyl)isothiazolo[5,4-d]pyrimidin-4(5H)-one (0.03 g, 22% yield) as off white solid. $^1$H NMR (400 MHz, DMSO-$d_6$) δ (ppm): 8.53 (s, 1H), 7.85 (d, J=8.4 Hz, 2H), 7.57 (d, J=8.4 Hz, 2H), 4.85 (s, 2H), 3.50 (t, J=6.8 Hz, 2H), 3.29 (t, J=6.4 Hz, 2H), 1.95-1.89 (m, 2H), 1.81-1.74 (m, 2H). Calculated (M+H): 375.06; Found (M+H): 375.1, HPLC Purity: 99.89%.

Example 381: Preparation of 3-(4-chlorophenyl)-5-(2-(3,3-difluoroazetidin-1-yl)-2-oxoethyl)isothiazolo[5,4-d]pyrimidin-4(5H)-one

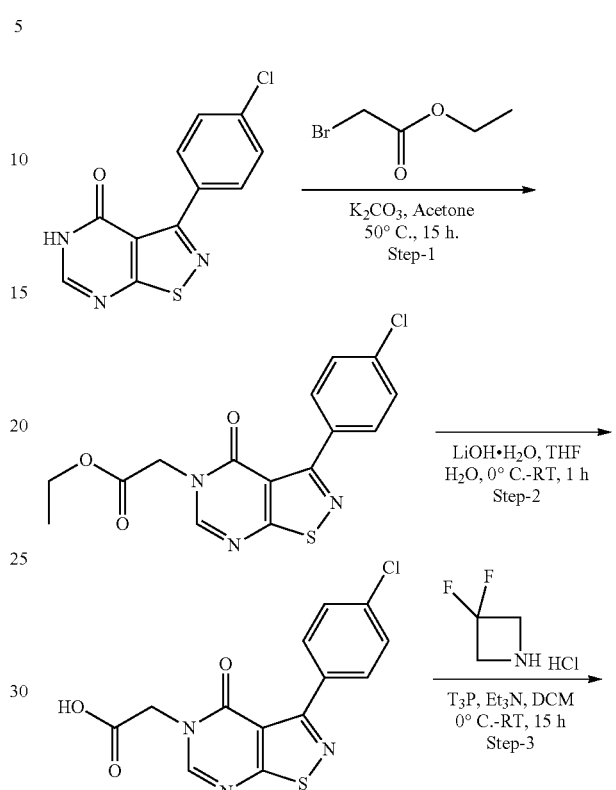

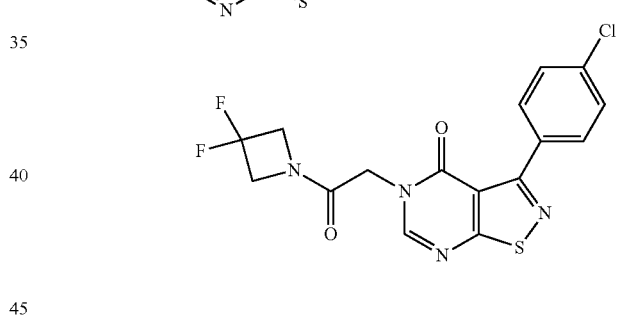

Step-1

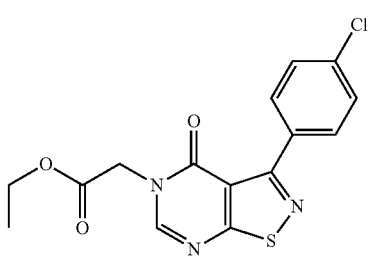 [SMILES: CCOC(=O)Cn1cnc2snc(-c3ccc(Cl)cc3)c2c1=O]

Preparation of ethyl 2-(3-(4-chlorophenyl)-4-oxoisothiazolo[5,4-d]pyrimidin-5(4H)-yl)acetate To a stirred solution of 3-(4-chlorophenyl)isothiazolo[5,4-d]pyrimidin-4(5H)-one (0.54 g, 2.05 mmol) and ethyl bromoacetate (0.453 mL, 4.09 mmol) in acetone (20 mL)

was added potassium carbonate (0.848 g, 6.14 mmol) and the reaction mixture was heated at 50° C. for 15 h. The reaction mixture was filtered and the filtrate was evaporated. The crude material was purified by silica gel column chromatography using 3% methanol in dichloromethane to obtain the title compound ethyl 2-(3-(4-chlorophenyl)-4-oxoisothiazolo[5,4-d]pyrimidin-5(4H)-yl)acetate (0.25 g, 35% yield) as off white solid. Calculated (M+H): 350.03; Found (M+H): 350.

Step-2

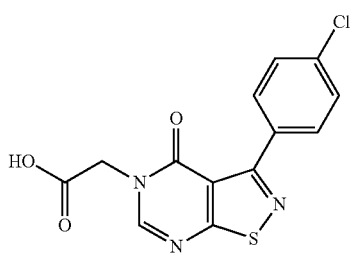 [SMILES: O=C(O)Cn1cnc2snc(-c3ccc(Cl)cc3)c2c1=O]

Preparation of 2-(3-(4-chlorophenyl)-4-oxoisothiazolo[5,4-d]pyrimidin-5(4H)-yl)acetic acid To a stirred solution of ethyl 2-(3-(4-chlorophenyl)-4-oxoisothiazolo[5,4-d]pyrimidin-5(4H)-yl)acetate (0.23 g, 65 mmol) in acetic acid (10 mL) was added hydrochloric acid (10 mL) and the reaction mixture was heated at 100° C. for 15 h. Then the reaction mixture was cooled and quenched with ice-water. The precipitated solid was filtered, washed with water (50 mL) and dried to obtain the title compound 2-(3-(4-chlorophenyl)-4-oxoisothiazolo[5,4-d]pyrimidin-5(4H)-yl)acetic acid (0.15 g, crude) as off white solid. Calculated (M+H): 322; Found (M+H): 322.2.

Step-3

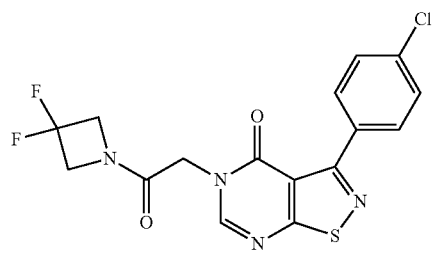 [SMILES: O=C(Cn1cnc2snc(-c3ccc(Cl)cc3)c2c1=O)N1CC(F)(F)C1]

Preparation of 3-(4-chlorophenyl)-5-(2-(3,3-difluoroazetidin-1-yl)-2-oxoethyl)isothiazolo[5,4-d]pyrimidin-4(5H)-one To a stirred solution of 2-(3-(4-chlorophenyl)-4-oxoisothiazolo[5,4-d]pyrimidin-5(4H)-yl)acetic acid (0.075 g, 0.23 mmol) in dichloromethane (10 mL) was added triethylamine (0.228 mL, 1.63 mmol) and 3,3-difluoroazitidine hydrochloride (0.036 g, 0.28 mmol) at room temperature and the reaction mixture was cooled to 0° C. Then 1-propanephosphonic anhydride (T$_3$P) (0.22 mL, 0.35 mmol, 50% solution in ethyl acetate) was added dropwise and the reaction mixture was stirred at room temperature for 15 h. The reaction mixture was quenched with water (25 mL) and extracted with dichloromethane (3×25 mL). The combined organic extract was washed with brine (25 mL), dried over anhydrous sodium sulfate, filtered and evaporated. The crude material was purified by silica gel column chromatography 2% methanol in dichloromethane to obtain the title compound 3-(4-chlorophenyl)-5-(2-(3,3-difluoroazetidin-1-yl)-2-oxoethyl)isothiazolo[5,4-d]pyrimidin-4(5H)-one (0.08 g, 80% yield) as white solid. $^1$H NMR (400 MHz, DMSO-d$_6$) δ (ppm): 8.53 (s, 1H), 7.86 (d, J=8.8 Hz, 2H), 7.53 (d, J=8.4 Hz, 2H), 4.79-4.73 (m, 4H), 4.35 (t, J=8.0 Hz, 2H). Calculated (M+H): 397.03, Found (M+H): 397.2. HPLC Purity: 99.81%.

TABLE 40

The following compound was prepared by the method described above:

| Ex. No. | Structure | IUPAC Name | Analytical Data |
|---|---|---|---|
| 382 | ![structure] | 3-(4-chlorophenyl)-5-(2-oxo-2-(2-(trifluoromethyl)pyrrolidin-1-yl)ethyp)isothiazolo[5,4-d]pyrimidin-4(5H)-one | $^1$H NMR (400 MHz, DMSO-d$_6$) δ (ppm): 8.54 (s, 1H), 7.86 (d, J = 8.4 Hz, 2H), 7.52 (d, J = 8.4 Hz, 2H), 4.98 (s, 2H), 4.69-4.73 (m, 1H), 3.68 (bs, 2H), 1.99-2.05 (m, 4H). Calculated (M + H): 443.05; Found (M + H): 443.3. HPLC Purity: 99.55% |

M. PREPARATION OF OXAZOLOPYRIMIDINONES

Example 383: Preparation of 3-(4-chlorophenyl)-5-(2-oxo-2-(pyrrolidin-1-yl)ethyl)isoxazolo[5,4-d]pyrimidin-4(5H)-one

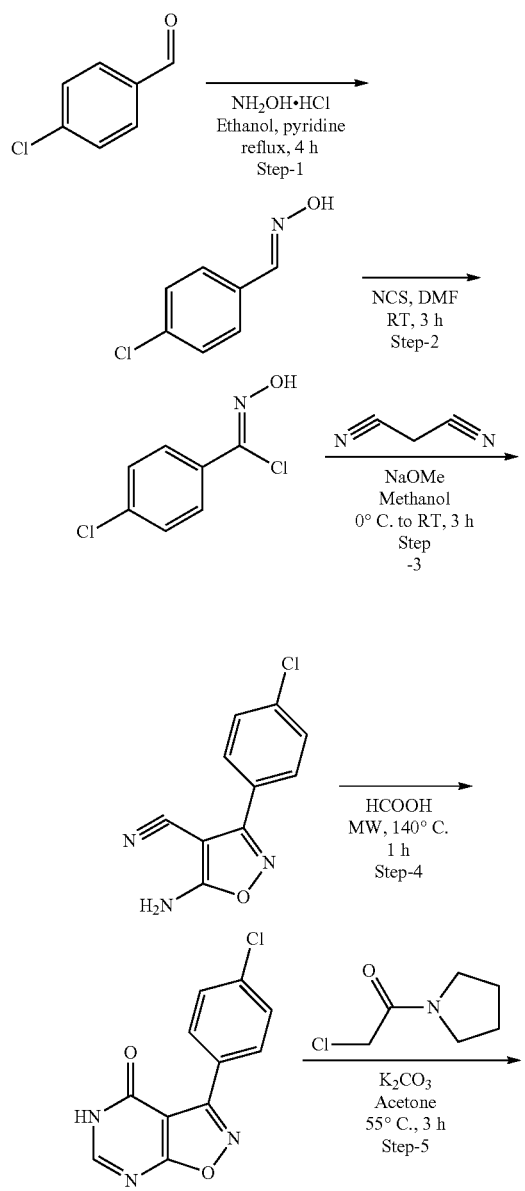

Step 1

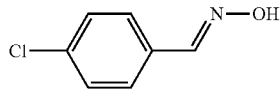

Preparation of (E)-4-chlorobenzaldehyde oxime

To a solution of 4-chlorobenzaldehyde (20.0 g, 142.27 mmol) in ethanol (200 mL) were added pyridine (17.2 mL, 213.46 mmol) and hydroxylamine hydrochloride (12.85 g, 184.96 mmol) at room temperature. The resulting mixture was heated to 80° C. and stirred for 4 h. The progress of the reaction was monitored by TLC. The mixture was allowed to cool to room temperature and the solvent was removed under reduced pressure. The residue was diluted with cold water and stirred for 30 min. The precipitated solid was filtered, washed with water and dried under vacuum to obtain title compound (E)-4-chlorobenzaldehyde oxime (21.3 g, 95% yield) as off white solid. Calculated (M+H): 156.01; Found (M+1): 156.1.

Step 2

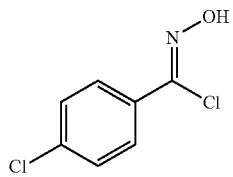 [SMILES: O/N=C(\Cl)c1ccc(Cl)cc1]

Preparation of (Z)-4-chloro-N-hydroxybenzimidoyl chloride

To a solution of (E)-4-chlorobenzaldehyde oxime (21.3 g, 137.08 mmol) in N, N-dimethylformamide (100 mL) was added N-chlorosuccinimide (23.70 g, 178.20 mmol) at room temperature and the reaction mixture was stirred at room temperature for 3 h. After completion of reaction, the solvent was removed under reduced pressure. The residue was diluted with cold water and stirred for 30 min. The precipitated solid filtered, washed with water and dried under vacuum to obtain title compound (Z)-4-chloro-N-hydroxybenzimidoyl chloride (17.8 g, 68% yield) as off white solid. $^1$H NMR (400 MHz, DMSO-$d_6$) δ (ppm): 12.94 (s, 1H), 7.79 (d, J=8.8 Hz, 2H), 7.53 (d, J=8.8 Hz, 2H).

Step 3

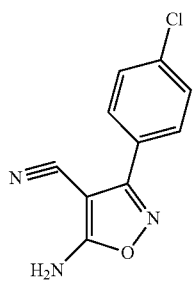 [SMILES: N#Cc1c(-c2ccc(Cl)cc2)noc1N]

Preparation of 5-amino-3-(4-chlorophenyl)isoxazole-4-carbonitrile

To a suspension of (Z)-4-chloro-N-hydroxybenzimidoyl chloride (2.5 g, 13.14 mmol) in methanol was added malononitrile (0.86 g, 13.14 mmol) at room temperature and stirred for 30 min. The reaction mixture was cooled to 0° C. and sodium methoxide was added portion wise. The resulting mixture was slowly allowed to warm to room temperature and stirred for 3 h. Methanol was removed under vacuum, the residue was diluted with cold water and stirred for 30 min. The precipitated solid was filtered, washed with water and dried under vacuum to afford the title compound 5-amino-3-(4-chlorophenyl)isoxazole-4-carbonitrile (2.3 g, 79% yield) as pale brown solid. Calculated (M+H): 220.02; Found (M+1): 220.3.

Step 4

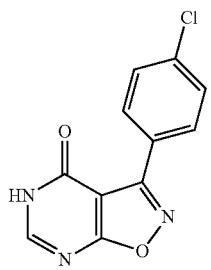 [SMILES: O=c1[nH]cnc2onc(-c3ccc(Cl)cc3)c12]

Preparation of 3-(4-chlorophenyl)isoxazolo[5,4-d]pyrimidin-4(5H)-one

A mixture of 5-amino-3-(4-chlorophenyl)isoxazole-4-carbonitrile (1.25 g, 5.69 mmol) and formamide (10 mL) was taken in microwave vial and subjected to microwave irradiation at 140° C. for 1 h. The reaction mixture was allowed to cool to room temperature and diluted with water (15 mL). The precipitated solid was filtered, washed with water and dried under vacuum to afford the title compound 3-(4-chlorophenyl)isoxazolo[5,4-d]pyrimidin-4(5H)-one (1.0 g, crude) as a pale brown solid which was as such taken for next step without further purification. Calculated (M+H): 248.01; Found (M+H): 248.1.

Step 5

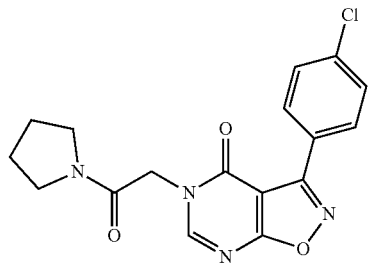 [SMILES: O=C(Cn1cnc2onc(-c3ccc(Cl)cc3)c2c1=O)N1CCCC1]

Preparation of 3-(4-chlorophenyl)-5-(2-oxo-2-(pyrrolidin-1-yl)ethyl)isoxazolo[5,4-d]pyrimidin-4(5H)-one To a mixture of 3-(4-chlorophenyl)isoxazolo[5,4-d]pyrimidin-4(5H)-one (0.2 g, 0.80 mmol) and potassium carbonate (0.33 g, 2.42 mmol) in dry acetone was added 2-chloro-1-(pyrrolidin-1-yl)ethanone (0.23 g, 1.61 mmol). The resulting mixture was heated at 55° C. for 3 h. After completion of the reaction (monitored by TLC), the mixture was allowed to cool to room temperature and filtered. The solid was washed with ethyl acetate and the combined filtrate was concentrated under vacuum to afford crude product which was purified by silica gel (60-120) column chromatography using 3% methanol in dichloromethane to afford the title compound 3-(4-chlorophenyl)-5-(2-oxo-2-(pyrrolidin-1-yl)ethyl)isoxazolo[5,4-d]pyrimidin-4(5H)-one (0.15 g, 53% yield) as white solid. $^1$H NMR (400 MHz, DMSO-$d_6$) δ (ppm): 8.65 (s, 1H), 8.27 (d, J=8.4 Hz, 2H), 7.63 (d, J=8.4 Hz, 2H), 4.89 (s, 2H), 3.53 (t, J=6.4 Hz, 2H), 3.31 (t, J=6.4 Hz, 2H), 1.94-1.90 (m, 2H), 1.82-1.76 (m, 2H). Calculated (M+H): 359.08; Found (M+1): 359.1; HPLC purity: 99.72%.

TABLE 41

The following compound was prepared by the method described above:

| Ex. No. | Structure | IUPAC Name | Analytical data |
|---|---|---|---|
| 384 | 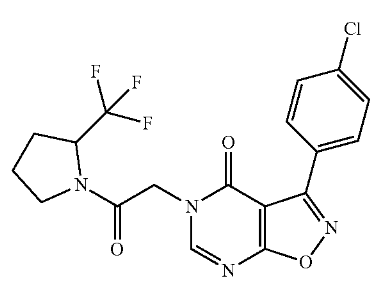 [SMILES: O=C(Cn1cnc2onc(-c3ccc(Cl)cc3)c2c1=O)N1CCCC1C(F)(F)F] | 3-(4-chlorophenyl)-5-(2-oxo-2-(2-(trifluoromethyl)pyrrolidin-1-yl)ethyl)isoxazolo[5,4-d]pyrimidin-4(5H)-one | $^1$H NMR (400 MHz, DMSO-$d_6$) δ (ppm): 8.67 (s, 1H), 8.26 (d, J = 8.4 Hz, 2H), 7.63 (d, J = 8.4 Hz, 2H), 5.17-4.91 (m, 2H), 4.73 (brs, 1H), 3.7 (brs, 2H), 2.18-1.93 (m, 4H). Calculated (M + H): 427.07, Found (M + H): 427.1. HPLC purity: 99.62%. |

Example 385: Preparation of 3-(4-chlorophenyl)-5-(2-(3,3-difluoroazetidin-1-yl)-2-oxoethyl)isoxazolo[5,4-d]pyrimidin-4(5H)-one

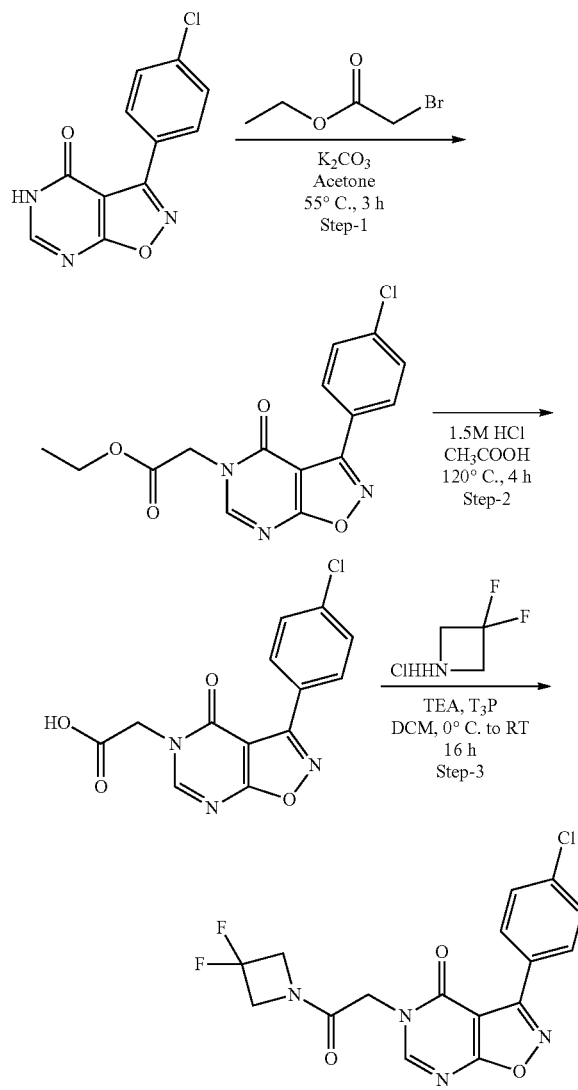

Step 1

Preparation of ethyl 2-(3-(4-chlorophenyl)-4-oxoisoxazolo[5,4-d]pyrimidin-5(4H)-yl)acetate To a mixture of 3-(4-chlorophenyl)isoxazolo[5,4-d]pyrimidin-4(5H)-one (0.8 g, 3.23 mmol) and potassium carbonate (1.34 g, 9.71 mmol) in dry acetone (80 mL) was added ethyl 2-bromoacetate (0.72 g, 6.46 mmol). The resulting mixture was heated to 55° C. and stirred for 3 h. The reaction mixture was allowed to cool to room temperature and filtered. The solid was washed with ethyl acetate and the combined filtrate was concentrated under vacuum to afford crude product which was purified by silica gel (60-120) column chromatography using 35% ethyl acetate in hexane to afford the title compound ethyl 2-(3-(4-chlorophenyl)-4-oxoisoxazolo[5,4-d]pyrimidin-5(4H)-yl)acetate (0.62 g, 62% yield) as white solid. Calculated (M+H): 334.05; Found (M+1): 334.1.

Step 2

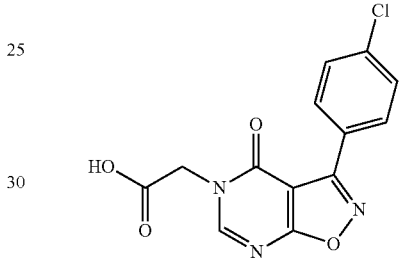

Preparation of 2-(3-(4-chlorophenyl)-4-oxoisoxazolo[5,4-d]pyrimidin-5(4H)-yl)acetic acid A suspension of ethyl 2-(3-(4-chlorophenyl)-4-oxoisoxazolo[5,4-d]pyrimidin-5(4H)-yl)acetate (0.25 g, 0.75 mmol) in a mixture of 1.5 N hydrochloric acid (5 mL) and acetic acid (5 mL) was heated to 120° C. and stirred for 4 h. The reaction mixture was gradually allowed to warm to room temperature and diluted with cold water. The precipitated solid was filtered, washed with water and dried under vacuum to obtain the title compound 2-(3-(4-chlorophenyl)-4-oxoisoxazolo[5,4-d]pyrimidin-5(4H)-yl)acetic acid (0.2 g, 87% yield) as a white solid. Calculated (M+H): 306.02; Found (M+H): 306.0.

Step 3

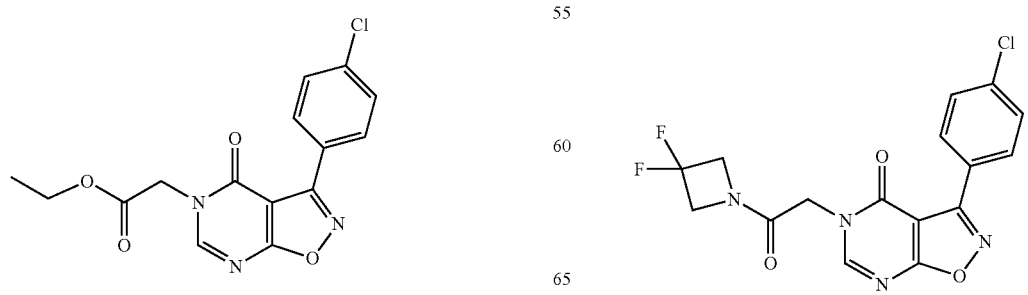

Preparation of 3-(4-chlorophenyl)-5-(2-(3,3-difluoroazetidin-1-yl)-2-oxoethyl)isoxazolo[5,4-d]pyrimidin-4(5H)-one To a solution of 2-(3-(4-chlorophenyl)-4-oxoisoxazolo[5,4-d]pyrimidin-5(4H)-yl)acetic acid (0.1 g, 0.32 mmol) in dichloromethane (15 mL), were added 3,3-difluoroazetidine hydrochloride (0.04 g, 0.32 mmol) and triethylamine (0.22 mL, 1.63 mmol). The reaction mixture was cooled to room temperature and 1-propanephosphonic anhydride (T$_3$P) (0.41 mL, 0.65 mmol, 50% solution in ethyl acetate) was added and mixture was allowed to warm to room temperature and stirred for 16 h. The reaction mixture was diluted with dichloromethane (25 mL), washed with water (2×50 mL), brine, dried over anhydrous sodium sulfate, filtered and concentrated under reduced pressure to afford crude product which was purified by silica gel column chromatography using 3% methanol in dichloromethane as eluent to afford the title compound 3-(4-chlorophenyl)-5-(2-(3,3-difluoroazetidin-1-yl)-2-oxoethyl)isoxazolo[5,4-d]pyrimidin-4(5H)-one (0.057 g, 47.5% yield) as white solid. $^1$H NMR (400 MHz, DMSO-d6) δ (ppm): 8.67 (s, 1H), 8.25 (d, J=8.4 Hz, 2H), 7.63 (d, J=8.4 Hz, 2H), 4.82-4.75 (m, 4H), 4.37 (t, J=12 Hz, 2H). Calculated (M+H): 381.05; Found (M+1): 381.3. HPLC purity: 99.87%.

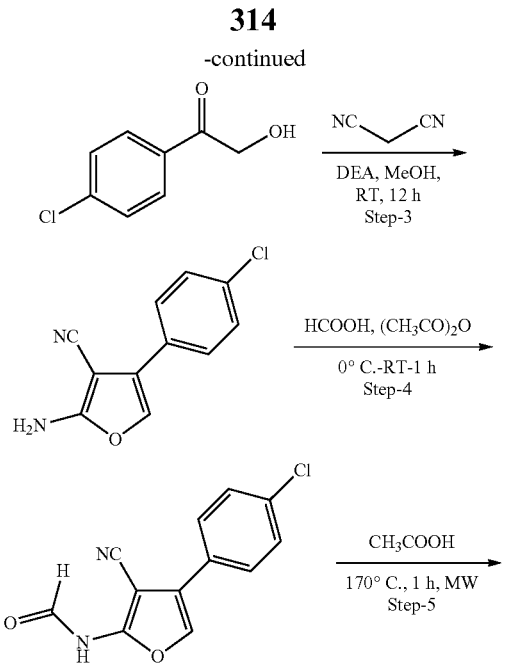

TABLE 42

The following compound was prepared by the method described above:

| Ex. No. | Structure | IUPAC Name | Analytical data |
|---|---|---|---|
| 386 | (structure shown) | 3-(4-chlorophenyl)-5-(2-(3-fluoropyrrolidin-1-yl)-2-oxoethyl)isoxazolo[5,4-d]pyrimidin-4(5H)-one | $^1$H NMR (400 MHz, DMSO-d$_6$) δ (ppm): 8.67 (d, J = 2.4 Hz, 1H), 8.27 (d, J = 8.4 Hz, 2H), 7.63 (d, J = 8.4 Hz, 2H), 5.39 (t, J = 49.6 Hz,1H), 5.01-4.83 (m, 2H), 3.93-3.40 (m, 4H), 2.25-1.96 (m, 2H); Calculated (M + H): 377.07, Found (M + H): 377.4; HPLC purity: 99.76% |

Example 387: Preparation of 5-(4-chlorophenyl)-3-(2-oxo-2-(3-(trifluoromethyl)cyclopentyl)ethyl)furo[2,3-d]pyrimidin-4(3H)-one

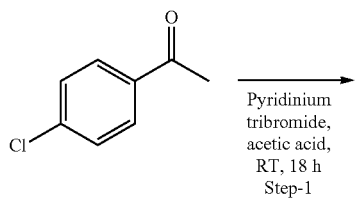

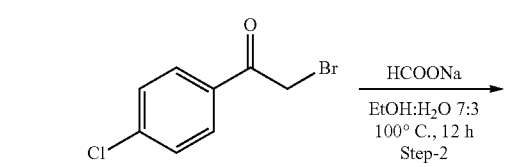

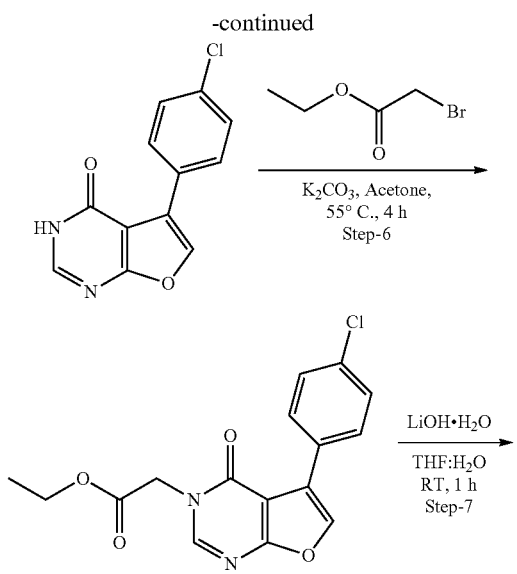

315

-continued

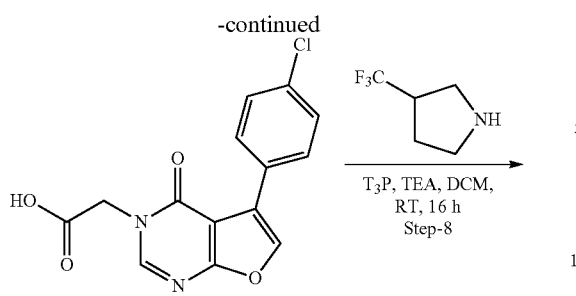

T₃P, TEA, DCM,
RT, 16 h
Step-8

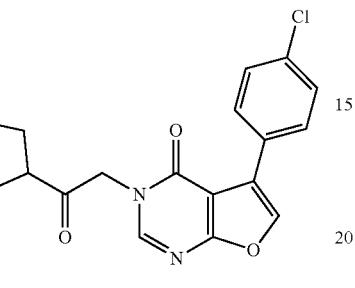

Step-1

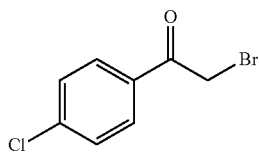 [SMILES: O=C(CBr)c1ccc(Cl)cc1]

Preparation of 2-bromo-1-(4-chlorophenyl)ethanone

To a stirred solution of 1-(4-chlorophenyl)ethanone (6.0 g, 38.96 mmol) in acetic acid (15 mL) at room temperature was added pyridinium tribromide (13.67 g, 42.85 mmol) and stirred at RT for 18 h. Reaction mixture was diluted with ice water (100 mL) and the precipitate was filtered through the sintered glass funnel, washed with water (50 mL) and dried by using high vacuum to afford compound 2-bromo-1-(4-chlorophenyl)ethanone (9.0 g, 99.0% yield) as off white solid. ¹H NMR (400 MHz, CDCl₃) δ (ppm): 7.93 (d, J=8.4 Hz, 2H), 7.47 (d, J=8.4 Hz, 2H), 4.40 (s, 2H).

Step-2

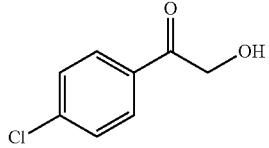 [SMILES: O=C(CO)c1ccc(Cl)cc1]

Preparation of 1-(4-chlorophenyl)-2-hydroxyethanone

To a stirred solution of 2-bromo-1-(4-chlorophenyl)ethanone (9.0 g, 38.96 mmol) in mixture of ethanol and water (7:3) 180 (mL), sodium formate (16.4 g, 241.15 mmol) was added at room temperature and stirred at 100° C. for 12 h.

316

The solvent was removed under vacuum and the resulting crude product was diluted with water (100 mL) and the precipitate was filtered through the sintered funnel and was washed with water (50 mL) and the solid was dried under high vacuum to afford compound 1-(4-chlorophenyl)-2-hydroxyethanone (5.5 g, 80.0% yield) as yellow solid. ¹H NMR (400 MHz, DMSO-d₆): δ (ppm): 7.93 (d, J=8.0 Hz, 2H), 7.58 (d, J=8.4 Hz, 2H), 5.11 (t, J=5.2 Hz, 1H), 4.76 (d, J=5.6 Hz, 2H).

Step-3

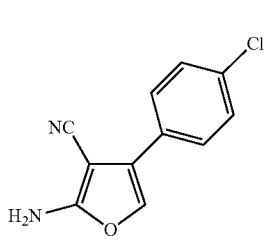 [SMILES: N#Cc1c(-c2ccc(Cl)cc2)coc1N]

Preparation of 2-amino-4-(4-chlorophenyl)furan-3-carbonitrile

To a stirred solution of 1-(4-chlorophenyl)-2-hydroxyethanone (5.0 g, 29.41 mmol) in methanol (50 mL), diethyl amine (1.25 mL, 11.76 mmol) was added at room temperature and followed by malononitrile (2.1 g, 32.45 mmol). Reaction mixture was stirred at room temperature for 3 h. The solvent was removed under vacuum and the resulting crude material was diluted with water (100 mL) and extracted with ethyl acetate (3×50 mL). The combined organic layer was dried over anhydrous sodium sulfate and concentrated to get crude compound which was purified by column chromatography using 50% ethyl acetate in hexane to afford title compound 2-amino-4-(4-chlorophenyl)furan-3-carbonitrile (4.1 g, 66.0% yield) as off white solid. ¹H NMR (400 MHz, CDCl₃), δ (ppm): 7.48 (d, J=8.4 Hz, 2H), 7.39 (d, J=8.8 Hz, 2H), 6.99 (s, 1H), 4.85 (s, 2H). Calculated M+H: 219.02; Found M+H: 219.1.

Step-4

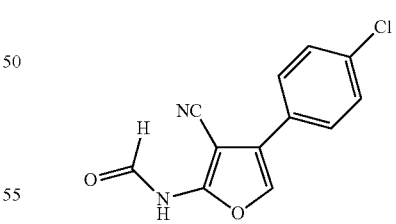

Preparation of N-(4-(4-chlorophenyl)-3-cyanofuran-2-yl)formamide

To a stirred solution of 2-amino-4-(4-chlorophenyl)furan-3-carbonitrile (10.0 g, 45.87 mmol) in formic acid (120 mL) at 0⁰ was added acetic anhydride (120 mL). The reaction mixture was stirred at room temperature for 1 h. The reaction mixture was diluted with ice cold water (50 mL) and the precipitate was filtered through the sintered funnel and washed with water (150 mL) and the solid was dried under high vacuum to afford the title compound N-(4-(4-chlorophenyl)-3-cyanofuran-2-yl)formamide (5.0 g, 42.0% yield) as pale pink solid. $^1$H NMR (400 MHz, DMSO-d$_6$), δ (ppm): 11.63 (s, 1H), 8.32 (s, 1H), 8.05 (s, 1H), 7.63 (d, J=8.4 Hz, 2H), 7.56 (d, J=8.8 Hz, 2H). Calculated M+H: 247.02; Found M+H: 247.1.

Step-5

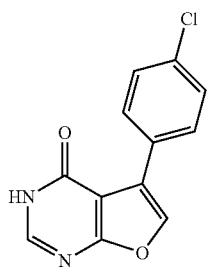 [SMILES: O=c1[nH]cnc2occ(-c3ccc(Cl)cc3)c12]

Preparation of 5-(4-chlorophenyl)furo[2,3-d]pyrimidin-4(3H)-one

The solution of N-(4-(4-chlorophenyl)-3-cyanofuran-2-yl)formamide (1.5 g, 60.72 mmol) in acetic acid (3.0 mL) was taken in microwave vial and it was heated at 170° C. in CEM microwave for 1 h, The reaction mixture was diluted with ice cold water (50 mL) and the precipitate was filtered through the sintered funnel, washed with water (150 mL) and dried under high vacuum to afford compound 5-(4-chlorophenyl)furo[2,3-d]pyrimidin-4(3H)-one (1.4 g, 66.0% yield) as off white solid. $^1$H NMR (400 MHz, DMSO-d$_6$) δ (ppm): 12.71 (s, 1H), 8.29 (s, 1H), 8.15 (s, 1H), 8.02 (d, J=8.4 Hz, 2H), 7.47 (d, J=8 Hz, 2H). Calculated M+H: 247.02; Found M+H: 247.0.

Step-6

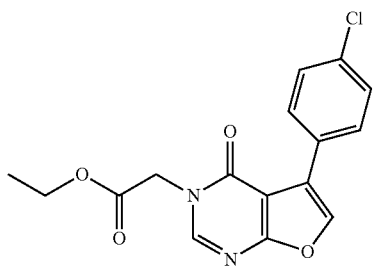 [SMILES: CCOC(=O)Cn1cnc2occ(-c3ccc(Cl)cc3)c2c1=O]

Preparation of ethyl ethyl 2-(5-(4-chlorophenyl)-4-oxofuro[2,3-d]pyrimidin-3(4H)-yl)acetate To a stirred solution of 5-(4-chlorophenyl)furo[2,3-d]pyrimidin-4(3H)-one (1.0 g, 4.04 mmol) in acetone (20 mL) at room temperature was added potassium carbonate (1.6 g, 12.14 mmol) followed by ethyl bromoacetate (1.47 mL, 8.09 mmol). The reaction mixture was heated to 55° C. for 4 h. The reaction mixture was filtered through the sintered funnel and washed with 10% methanol in dichloromethane (50 mL). The filtrate was concentrated to yield the crude compound which was purified by column chromatography using 30% ethyl acetate in hexane to get the title compound— ethyl 2-(5-(4-chlorophenyl)-4-oxofuro[2,3-d]pyrimidin-3(4H)-yl)acetate (1.2 g, 92.0% yield) as off white solid. Calculated M+H: 333.06; Found M+H: 333.1.

Step-7

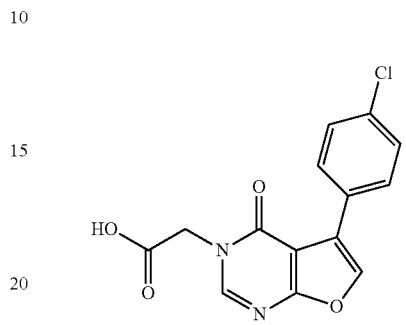

Preparation of 2-(5-(4-chlorophenyl)-4-oxofuro[2,3-d]pyrimidin-3(4H)-yl)acetic acid To a stirred solution of ethyl 2-(5-(4-chlorophenyl)-4-oxofuro[2,3-d]pyrimidin-3(4H)-yl)acetate (1.2 g, 3.60 mmol) in tetrahydrofuran and water (1:1) (20 mL) at room temperature was added lithium hydroxide monohydrate (18.01, 1.08 g). Reaction mixture was stirred at room temperature for 1 h. The reaction mixture was evaporated and the resulting crude material was acidified with 1.5 N HCl (pH 2~3). The precipitate was filtered through the sintered funnel and washed with water (20 mL) and dried under vacuum to give the title compound 2-(5-(4-chlorophenyl)-4-oxofuro[2,3-d]pyrimidin-3(4H)-yl)acetic acid (0.8 g, 73.0% yield) as off white solid. $^1$H NMR (400 MHz, DMSO-d$_6$), δ (ppm): 13.25 (s, 1H), 8.50 (s, 1H), 8.34 (s, 1H), 7.98 (d, J=8.4 Hz, 2H), 7.48 (d, J=8.8 Hz, 2H), 4.76 (s, 2H).

Step-8

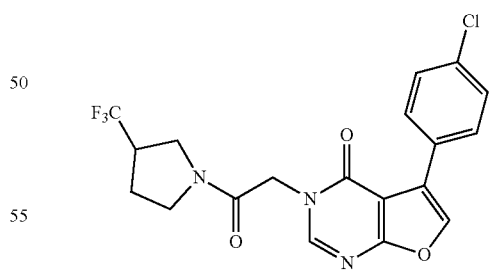

Preparation of 5-(4-chlorophenyl)-3-(2-oxo-2-(3-(trifluoromethyl)pyrrolidin-1-yl)ethyl)furo[2,3-d]pyrimidin-4(3H)-one To a stirred solution of 2-(5-(4-chlorophenyl)-4-oxofuro[2,3-d]pyrimidin-3(4H)-yl)acetic acid (0.15 g, 0.49 mmol) in dichloromethane (20 mL) at room temperature was added triethylamine (0.21 mL, 2.96 mmol) stirred for 10 min and 3-(trifluoromethyl)pyrrolidine (0.082 g, 0.59 mmol) was added. Finally propyl phosphonic anhydride (50% solution) (0.21 mL, 0.74 mmol) was added and stirred at room temperature for 16 h. Reaction mixture was diluted with water (50 mL) and extracted with dichloromethane (3×50 mL). Combined organic layers were dried over anhydrous sodium sulfate and concentrated to get the crude compound. The crude material was purified by silica gel column chromatography using 5% methanol in dichloromethane to afford the title compound 5-(4-chlorophenyl)-3-(2-oxo-2-(3-(trifluoromethyl)cyclopentyl)ethyl)furo[2,3-d]pyrimidin-4(3H)-one (0.033 g, 7.0% yield) as off white solid. $^1$H NMR (400 MHz, DMSO-$d_6$) δ (ppm): 8.40 (s, 1H), 8.34 (s, 1H), 7.98 (d, J=8.4 Hz, 2H), 7.48 (d, J=8.4 Hz, 2H), 5.14-4.72 (m, 4H), 3.71 (s, 2H), 2.31-1.93 (m, 4H). Calculated (M+H): 426.08; Found (M+H): 426.3; HPLC purity: 99.72%.

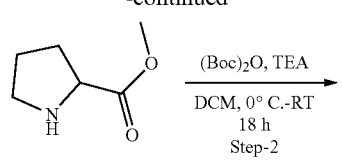

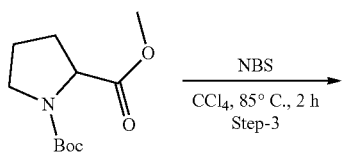

TABLE 43

The following compounds were prepared by the method described above:

| Ex. No. | Structure | IUPAC Name | Analytical Data |
|---|---|---|---|
| 388 | 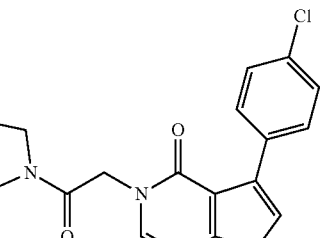 | 5-(4-chlorophenyl)-3-(2-oxo-2-(pyrrolidin-1-yl)ethyl)furo[2,3-d]pyrimidin-4(3H)-one | $^1$H NMR (400 MHz, DMSO-$d_6$) δ (ppm): 8.38 (s, 1H), 8.33 (s, 1H), 7.99 (d, J = 8.4 Hz, 2H), 7.47 (d, J = 8.4 Hz, 2H), 4.86 (s, 2 H), 3.54 (t, J = 6.4 Hz, 2H), 3.31(t, J = 6.8 Hz, 2H), 1.97-1.922 (m, 2H), 1.83-1.78 (m, 2H). Calculated M + H: 358.09; Found M + H: 358.0 HPLC purity: 99.21%. |
| 389 | 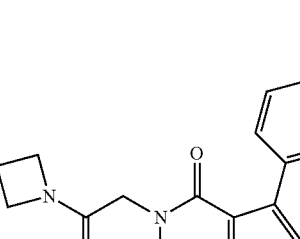 | 5-(4-chlorophenyl)-3-(2-(3,3-difluoroazetidin-1-yl)-2-oxoethyl)furo[2,3-d]pyrimidin-4(3H)-one | $^1$H NMR (400 MHz, DMSO-$d_6$) δ (ppm): 8.40 (s, 1H), 8.33 (s, 1H), 7.97 (d, J = 8.0 Hz, 2H), 7.48 (s, J = 8.4 Hz, 2H), 4.78 (s, 4 H), 4.38 (t, J = 12.0 Hz, 2H). Calculated M + H: 380.05; Found M + H: 380.01 HPLC purity: 99.42%. |

N. PREPARATION OF PYRROLOPYRAZINONES

Example 390: Preparation of 8-(4-fluoro-3-(trifluoromethyl)phenyl)-2-(2-(3-fluoropyrrolidin-1-yl)-2-oxoethyl)pyrrolo[1,2-a]pyrazin-1(2H)-one

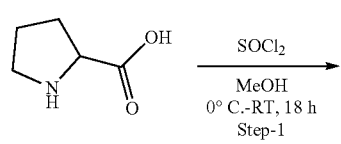

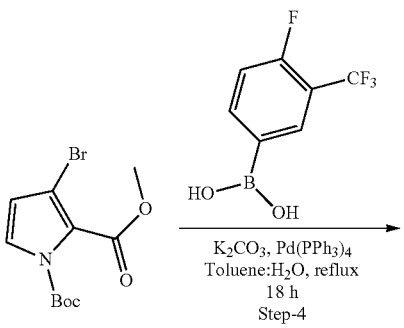

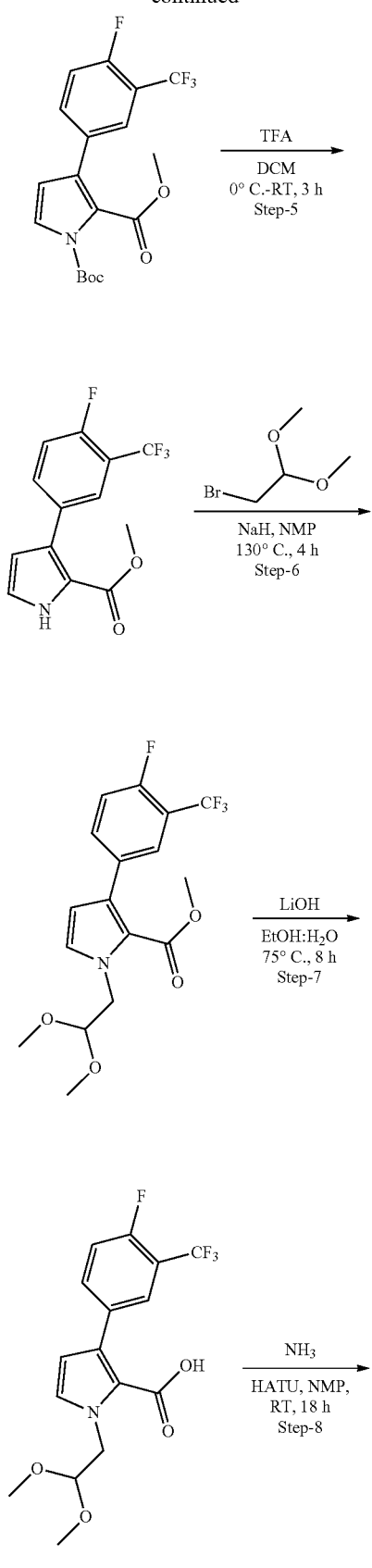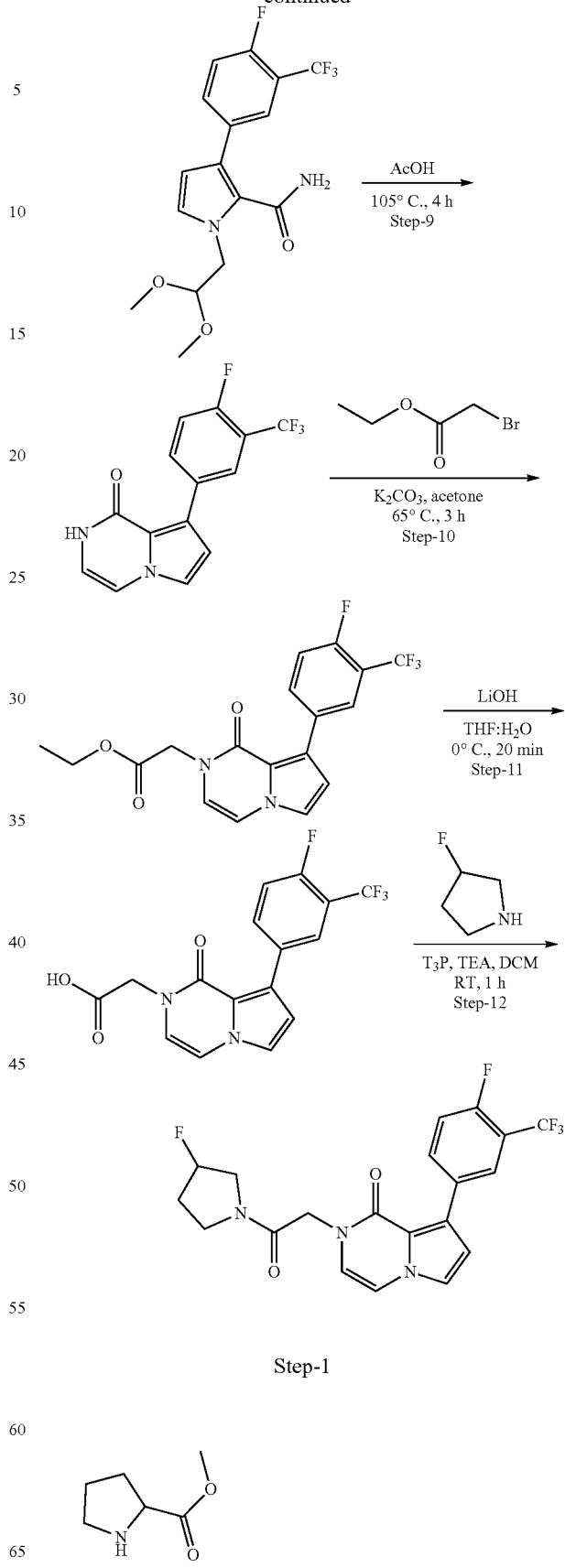

Preparation of methyl pyrrolidine-2-carboxylate

To a solution of L-proline (6 g, 52.11 mmol) in methanol (50 mL) cooled to 0° C., was added thionyl chloride (4.92 mL, 67.74 mmol) drop-wise and the reaction mixture was stirred at room temperature for 18 h. The reaction mixture was concentrated to afford the title compound methyl pyrrolidine-2-carboxylate (9.6 g, crude) as a colourless liquid. Calculated (M+H): 130.08; Found (M+H): 130.2.

Step-2

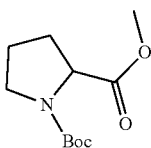

Preparation of 1-tert-butyl 2-methyl pyrrolidine-1,2-dicarboxylate

To a solution of methyl pyrrolidine-2-carboxylate (9.6 g, 74.41 mmol) and triethylamine (15.55 mL, 111.62 mmol) in dichloromethane (200 mL) cooled to 0° C., was added Boc anhydride (20.5 mL, 89.30 mmol) drop-wise and the reaction mixture was stirred at room temperature for 18 h. The reaction mixture was diluted with dichloromethane (200 mL) and washed with water (2×200 mL). The organic layer was dried over anhydrous sodium sulphate, filtered and concentrated. The crude product was purified by silica gel column chromatography using 20% ethyl acetate in hexane to afford the title compound 1-tert-butyl 2-methyl pyrrolidine-1,2-dicarboxylate (11 g, 93% yield) as a colourless liquid. Calculated (M+H): 230.13; Found (M+H): 130.2 [Boc deprotected mass observed].

Step-3

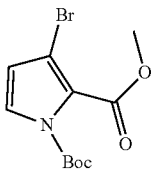 [SMILES: COC(=O)c1c(Br)ccn1C(=O)OC(C)(C)C]

Preparation of 1-tert-butyl 2-methyl 3-bromo-1H-pyrrole-1,2-dicarboxylate

To a solution of 1-tert-butyl 2-methyl pyrrolidine-1,2-dicarboxylate (2.5 g, 10.90 mmol) in carbon tetrachloride (1.25 L), was added N-bromosuccinimide (6.87 g, 38.60 mmol) and the reaction mixture was heated at 85° C. for 2 h (observed succinimide precipitation and bromine vapours after completion of reaction). The reaction mixture was cooled to 0° C. and stirred for 15 minutes. The precipitated solid was filtered off and the filtrate was concentrated. The crude product was purified by silica gel column chromatography using 10% ethyl acetate in hexane to afford the title compound 1-tert-butyl 2-methyl 3-bromo-1H-pyrrole-1,2-dicarboxylate (1.7 g, 51% yield) as a brownish liquid. $^1$H NMR (400 MHz, CDCl3) δ (ppm): 7.21 (d, J=3.2 Hz, 1H), 6.22 (d, J=3.6 Hz, 1H), 3.89 (s, 3H), 1.54 (s, 9H).

Step-4

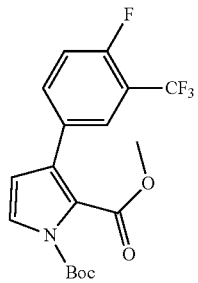 [SMILES: COC(=O)c1c(-c2ccc(F)c(C(F)(F)F)c2)ccn1C(=O)OC(C)(C)C]

Preparation of 1-tert-butyl 2-methyl 3-(4-fluoro-3-(trifluoromethyl)phenyl)-1H-pyrrole-1,2-dicarboxylate To a solution of 1-tert-butyl 2-methyl 3-bromo-1H-pyrrole-1,2-dicarboxylate (2.5 g, 8.21 mmol), (4-fluoro-3-(trifluoromethyl)phenyl)boronic acid (3.59 g, 17.26 mmol) and potassium carbonate (9.08 g, 65.75 mmol) in toluene:water mixture (70 mL, 1:1), tetrabutyl ammonium bromide (0.23 g, 0.73 mmol) was added and the reaction mixture was purged with argon for 15 minutes. Then tetrakis(triphenylphosphine)palladium (0) (0.189 g, 0.16 mmol) was added and the reaction mixture was heated at 110° C. for 18 h. The reaction mixture was diluted with ethyl acetate (100 mL) and washed with water (2×50 mL). The organic layer was dried over anhydrous sodium sulphate, filtered and concentrated. The crude product was purified by silica gel column chromatography using 15% ethyl acetate in hexane to afford the title compound 1-tert-butyl 2-methyl 3-(4-fluoro-3-(trifluoromethyl)phenyl)-1H-pyrrole-1,2-dicarboxylate (1.7 g, 53% yield) as a brownish gum. $^1$H NMR (400 MHz, DMSO-d$_6$) δ (ppm): 7.80-7.78 (m, 2H), 7.54 (t, J=10 Hz, 1H), 7.44 (d, J=3.2 Hz, 1H), 6.62 (d, J=3.6 Hz, 1H), 3.74 (s, 3H), 1.51 (s, 9H).

Step-5

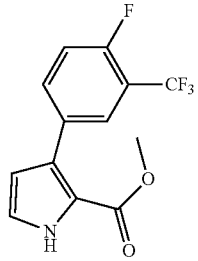 [SMILES: COC(=O)c1[nH]ccc1-c1ccc(F)c(C(F)(F)F)c1]

Preparation of methyl 3-(4-fluoro-3-(trifluoromethyl)phenyl)-1H-pyrrole-2-carboxylate To a solution of 1-tert-butyl 2-methyl 3-(4-fluoro-3-(trifluoromethyl)phenyl)-1H-pyrrole-1,2-dicarboxylate (1.7 g)

in dichloromethane (20 mL) cooled to 0° C., was added trifluoroacetic acid (2 ml) and the reaction mixture was stirred at room temperature for 3 h. After completion of the reaction (as monitored by TLC), the reaction mixture was concentrated, the residue was basified with saturated sodium bicarbonate solution (30 mL) and extracted with dichloromethane (2×50 mL). The combined organic layer was dried over anhydrous sodium sulphate, filtered and concentrated. The crude product was purified by silica gel column chromatography using 60% ethyl acetate in hexane to afford the title compound methyl 3-(4-fluoro-3-(trifluoromethyl) phenyl)-1H-pyrrole-2-carboxylate (1.15 g, 91% yield) as a brownish gum. Calculated (M–H): 286.06; Found (M–H): 286.

Step-6

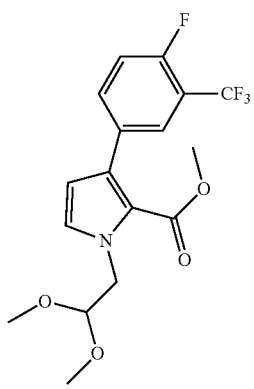 [SMILES: COC(=O)c1c(-c2ccc(F)c(C(F)(F)F)c2)ccn1CC(OC)OC]

Preparation of methyl 1-(2,2-dimethoxyethyl)-3-(4-fluoro-3-(trifluoromethyl)phenyl)-1H-pyrrole-2-carboxylate To a suspension of sodium hydride (0.022 g, 0.54 mmol, 60% dispersion in mineral oil) in N-methyl pyrrolidine (5 mL) cooled to 0° C., was added a solution of methyl 3-(4-fluoro-3-(trifluoromethyl)phenyl)-1H-pyrrole-2-carboxylate (0.15 g, 0.52 mmol) in N-methyl pyrrolidine (5 mL) drop-wise and the reaction mixture was stirred at room temperature for 1 h. Then 2-bromo-1,1-dimethoxyethane (0.097 g, 0.57 mmol) was added and the reaction mixture was heated at 130° C. for 4 h. The reaction mixture was diluted with ice water (30 mL) and extracted with ethyl acetate (2×60 mL). The combined organic layer was dried over anhydrous sodium sulphate, filtered and concentrated. The crude product was purified by silica gel column chromatography using 40% ethyl acetate in hexane to afford the title compound methyl 1-(2,2-dimethoxyethyl)-3-(4-fluoro-3-(trifluoromethyl)phenyl)-1H-pyrrole-2-carboxylate (0.13 g, 66% yield) as a colourless liquid. $^1$H NMR (400 MHz, CDCl3) δ (ppm): 7.60 (d, J=6 Hz, 1H), 7.52 (bs, 1H), 7.15 (t, J=9.2 Hz, 1H), 6.91 (d, J=2 Hz, 1H), 6.15 (d, J=2 Hz, 1H), 4.58 (t, J=5.6 Hz, 1H), 4.39 (d, J=5.6 Hz, 2H), 3.64 (s, 3H), 3.40 (s, 6H).

Step-7

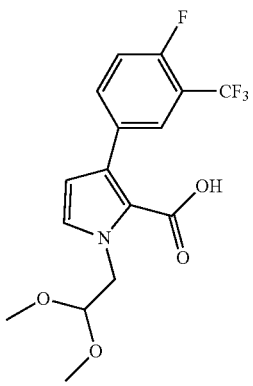 [SMILES: COC(Cn1ccc(-c2ccc(F)c(C(F)(F)F)c2)c1C(=O)O)OC]

Preparation of 1-(2,2-dimethoxyethyl)-3-(4-fluoro-3-(trifluoromethyl)phenyl)-1H-pyrrole-2-carboxylic acid To a solution of methyl 1-(2,2-dimethoxyethyl)-3-(4-fluoro-3-(trifluoromethyl)phenyl)-1H-pyrrole-2-carboxylate (0.17 g, 0.45 mmol) in ethanol:water mixture (10 mL, 1:1), lithium hydroxide monohydrate was added and the reaction mixture was heated at 75° C. for 8 h. The reaction mixture was concentrated to remove ethanol. The residue was diluted with water (15 mL), neutralized with acetic acid and extracted with ethyl acetate (2×50 mL). The combined organic layer was dried over anhydrous sodium sulphate, filtered and concentrated to afford the title compound 1-(2,2-dimethoxyethyl)-3-(4-fluoro-3-(trifluoromethyl)phenyl)-1H-pyrrole-2-carboxylic acid (0.15 g, 92% yield) as a brownish solid. Calculated (M–H): 360.09; Found (M–H): 360.1.

Step-8

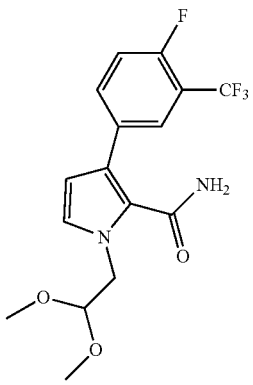 [SMILES: COC(Cn1ccc(-c2ccc(F)c(C(F)(F)F)c2)c1C(N)=O)OC]

Preparation of 1-(2,2-dimethoxyethyl)-3-(4-fluoro-3-(trifluoromethyl)phenyl)-1H-pyrrole-2-carboxamide To a solution of 1-(2,2-dimethoxyethyl)-3-(4-fluoro-3-(trifluoromethyl)phenyl)-1H-pyrrole-2-carboxylic acid (0.15 g, 0.41 mmol) in a mixture of N-methyl pyrrolidine (1.5 mL) and ammonia in dioxane (4 mL, 0.5M), HATU (0.31 g, 0.83 mmol) was added and the reaction mixture was stirred at room temperature for 18 h. Additional 1 equivalent of HATU and N-methyl pyrrolidine (5 mL) were added and the reaction mixture was purged with ammonia gas until the completion of the reaction (20 minutes). The reaction mixture was diluted with brine solution (20 mL) and extracted with ethyl acetate (2×50 mL). The combined organic layer was dried over anhydrous sodium sulphate, filtered and concentrated. The crude product was purified by silica gel column chromatography using 3% methanol in dichloromethane to afford the title compound 1-(2,2-dimethoxyethyl)-3-(4-fluoro-3-(trifluoromethyl)phenyl)-1H-pyrrole-2-carboxamide (0.12 g, 80% yield) as off-white solid. $^1$H NMR (400 MHz, DMSO-d$_6$) δ (ppm): 7.68-7.65 (m, 2H), 7.45 (t, J=10 Hz, 1H), 7.38 (bs, 1H), 7.30 (bs, 1H), 6.89 (d, J=2.4 Hz, 1H), 6.24 (d, J=2.8 Hz, 1H), 4.52 (t, J=5.2 Hz, 1H), 4.15 (d, J=5.2 Hz, 2H), 3.23 (s, 6H).

Step-9

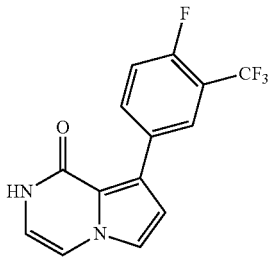

Preparation of 8-(4-fluoro-3-(trifluoromethyl)phenyl)pyrrolo[1,2-a]pyrazin-1(2H)-one A mixture of 1-(2,2-dimethoxyethyl)-3-(4-fluoro-3-(trifluoromethyl)phenyl)-1H-pyrrole-2-carboxamide (0.12 g) and acetic acid (6 mL) was heated at 105° C. for 4 h. The reaction mixture was concentrated, the residue was diluted with water (20 mL), basified with aqueous ammonia and extracted with ethyl acetate (2×50 mL). The combined organic layer was dried over anhydrous sodium sulphate, filtered and concentrated to afford the title compound 8-(4-fluoro-3-(trifluoromethyl)phenyl)pyrrolo[1,2-a]pyrazin-1(2H)-one (0.1 g, crude) as a brownish solid. Calculated (M+H): 297.06; Found (M+H): 297.1.

Step-10

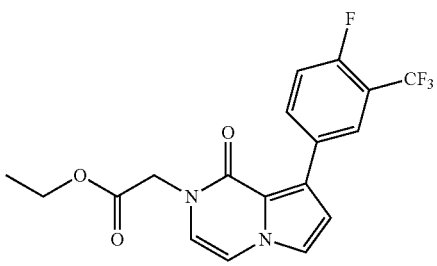 [SMILES: CCOC(=O)Cn1ccn2ccc(-c3ccc(F)c(C(F)(F)F)c3)c2c1=O]

Preparation of ethyl 2-(8-(4-fluoro-3-(trifluoromethyl)phenyl)-1-oxopyrrolo[1,2-a]pyrazin-2(1H)-yl)acetate A mixture of 8-(4-fluoro-3-(trifluoromethyl)phenyl)pyrrolo[1,2-a]pyrazin-1(2H)-one (0.097 g, 0.32 mmol), ethyl 2-bromoacetate (0.07 mL, 0.65 mmol) and potassium carbonate (0.135 g, 0.98 mmol) in acetone (10 mL) was heated at 65° C. for 3 h. The reaction mixture was filtered and the filtrate was concentrated. The crude product was purified by silica gel column chromatography using 15% ethyl acetate in hexane to afford the title compound ethyl 2-(8-(4-fluoro-3-(trifluoromethyl)phenyl)-1-oxopyrrolo[1,2-a]pyrazin-2(1H)-yl)acetate (0.09 g, 72% yield) as a brownish gum. Calculated (M+H): 383.09; Found (M+H): 383.1.

Step-11

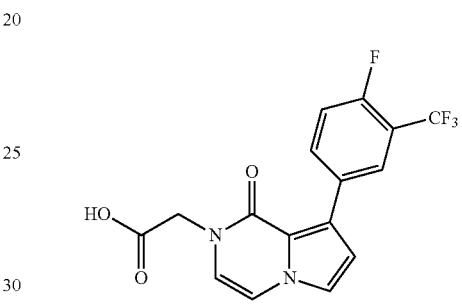

Preparation of 2-(8-(4-fluoro-3-(trifluoromethyl)phenyl)-1-oxopyrrolo[1,2-a]pyrazin-2(1H)-yl)acetic acid To a stirred solution of ethyl 2-(8-(4-fluoro-3-(trifluoromethyl)phenyl)-1-oxopyrrolo[1,2-a]pyrazin-2(1H)-yl)acetate (0.09 g, 0.23 mmol) in tetrahydrofuran:water mixture (10 mL, 1:1) cooled to 0° C., was added lithium hydroxide monohydrate (0.049 g, 1.17 mmol) and the reaction mixture was stirred at the same temperature for 20 minutes. The reaction mixture was diluted with water (15 mL), acidified with 1.5N hydrochloric acid and extracted with ethyl acetate (2×35 mL). The combined organic layer was dried over anhydrous sodium sulphate, filtered and concentrated to afford the title compound 2-(8-(4-fluoro-3-(trifluoromethyl)phenyl)-1-oxopyrrolo[1,2-a]pyrazin-2(1H)-yl)acetic acid (0.08 g, crude) as a brownish solid. Calculated (M+H): 355.06; Found (M+H): 355.1.

Step-12

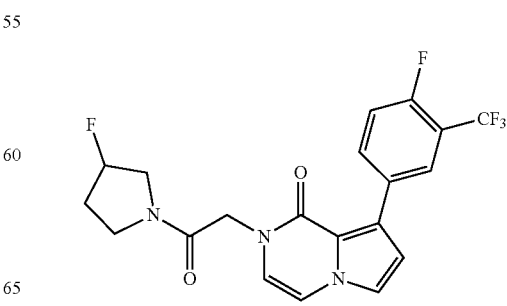

Preparation of 8-(4-fluoro-3-(trifluoromethyl)phenyl)-2-(2-(3-fluoropyrrolidin-1-yl)-2-oxoethyl)pyrrolo[1,2-a]pyrazin-1(2H)-one To a stirred solution of 2-(8-(4-fluoro-3-(trifluoromethyl) phenyl)-1-oxopyrrolo[1,2-a]pyrazin-2(1H)-yl)acetic acid (0.08 g, 0.22 mmol) in dichloromethane (20 mL) was added triethylamine (0.25 mL, 1.80 mmol) at room temperature and stirred for 10 minutes. 3-fluoropyrrolidine hydrochloride (0.043 g, 0.33 mmol) was added and the reaction mixture was cooled to 0° C. Then 1-propanephosphonic anhydride solution (T$_3$P) (0.21 mL, 0.33 mmol, 50% in ethyl acetate) was added and the reaction mixture was stirred at room temperature for 1 h. The solution was diluted with dichloromethane (50 mL) and washed with water (2×30 mL). The organic layer was dried over anhydrous sodium sulfate, filtered and concentrated to get the crude compound which was purified by silica gel column chromatography using 3% methanol in dichloromethane to afford the title compound 8-(4-fluoro-3-(trifluoromethyl)phenyl)-2-(2-(3-fluoropyrrolidin-1-yl)-2-oxoethyl)pyrrolo[1,2-a]pyrazin-1 (2H)-one (0.055 g, 57% yield) as white solid. Calculated (M+H): 426.12; Found (M+H): 426.1. $^1$H NMR (400 MHz, DMSO-d$_6$) δ (ppm): 8.10 (d, J=5.6 Hz, 1H), 7.97 (t, J=5.6 Hz, 1H), 7.52 (d, J=2.8 Hz, 1H), 7.45 (t, J=10.8 Hz, 1H), 7.39 (d, J=6 Hz, 1H), 6.84 (d, J=2.8 Hz, 1H), 6.78-6.76 (m, 1H), 5.48-5.24 (m, 1H), 4.75-4.57 (m, 2H), 3.86-3.20 (m, 4H), 2.30-1.92 (m, 2H). HPLC purity: 99.99%.

TABLE 44

The following compounds were prepared by the method described above:

| Ex. No. | Structure | IUPAC Name | Analytical Data |
|---|---|---|---|
| 391 | 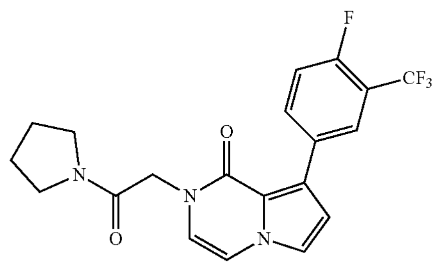 [SMILES: O=C(Cn1ccn2ccc(-c3ccc(F)c(C(F)(F)F)c3)c2c1=O)N1CCCC1] | 8-(4-fluoro-3-(trifluoromethyl) phenyl)-2-(2-oxo-2-(pyrrolidin-1-yl)ethyl)pyrrolo[1,2-a]pyrazin-1(2H)-one | $^1$H NMR (400 MHz, DMSO-d$_6$) δ (ppm): 8.10 (d, J = 6.8 Hz, 1H), 7.97 (bs, 1H), 7.51 (s, 1H), 7.45 (t, J = 9.6 Hz, 1H), 7.38 (d, J = 6 Hz, 1H), 6.84 (s, 1H), 6.75 (d, J = 6 Hz, 1H), 4.60 (s, 2H), 3.47 (t, J = 6.8 Hz, 2H), 1.92-1.84 (m, 2H), 1.80-1.72 (m, 2H). 2H were merged with DMSO water peak. Calculated (M + H): 408.13; Found (M + H): 408.1. HPLC purity: 99.48% |
| 392 | 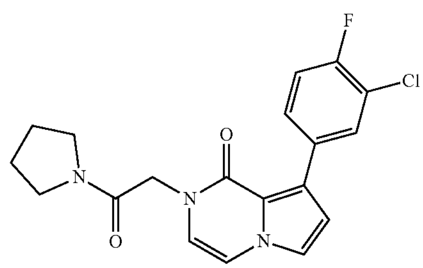 | 8-(3-chloro-4-fluorophenyl)-2-(2-oxo-2-(pyrrolidin-1-yl)ethyl)pyrrolo[1,2-a]pyrazin-1(2H)-one | $^1$H-NMR (DMSO-d$_6$, 400 MHz) δ (ppm): 7.93 (dd, J$_1$ = 1.6 Hz, 7.6 Hz, 1H), 7.62-7.68 (m, 1H), 7.49 (d, J = 2.8 Hz, 1H), 7.37-7.33 (m, 2H), 6.79 (d, J = 2.8 Hz, 1H), 6.74 (d, J = 6.0 Hz, 1H), 4.59 (s, 2H), 3.47 (t, J = 6.8 Hz, 2H), 3.32-3.22 (m, 2H), 1.79-1.73 (m, 2H). 2H merged with DMSO water peak. Calculated (M + H): 374.10, found (M + H): 374.1, HPLC purity: 99.64% |
| 393 | 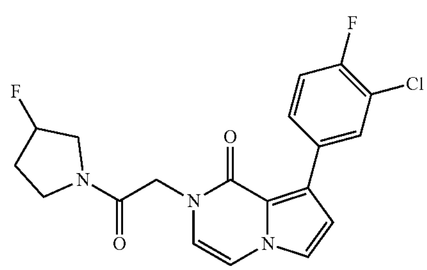 | 8-(3-chloro-4-fluorophenyl)-2-(2-(3-fluoropyrrolidin-1-yl)-2-oxoethyl)pyrrolo[1,2-a]pyrazin-1(2H)-one | 1H-NMR (DMSO-d$_6$, 400 MHz) δ (ppm): 7.93 (d, J = 5.6 Hz, 1H), 7.62-7.69 (m, 1H), 7.50 (d, J = 2.8 Hz, 1H), 7.38-7.33 (m, 2H), 6.79 (d, J = 2.0 Hz, 1H), 6.76 (d, J = 5.6 Hz, 1H), 5.40-5.50 (m, 1H), 4.74-4.58 (m, 2H), 3.75-3.27 (m, 4H), 2.30-2.07 (m, 2H). Calculated (M + H): 392.09, found (M + H): 392.1, HPLC purity: 95.15% |
| 394 | 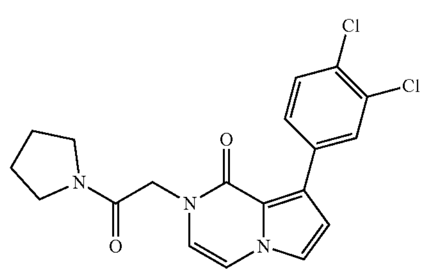 [SMILES: O=C(Cn1ccn2ccc(-c3ccc(F)c(Cl)c3)c2c1=O)N1CCCC1] | 8-(3,4-dichlorophenyl)-2-(2-oxo-2-(pyrrolidin-1-yl)ethyl)pyrrolo[1,2-a]pyrazin-1(2H)-one | $^1$H NMR (400 MHz, DMSO-d$_6$) δ (ppm): 8.02 (d, J = 1.6 Hz, 1H), 7.66 (dd, J = 2.0 Hz, 8.4 Hz, 1H), 7.56 (d, J = 8.8 Hz, 1H), 7.51 (d, J = 2.8 Hz, 1H), 7.38 (d, J = 5.6 Hz, 1H), 6.83 (d, J = 2.8 Hz, 1H), 6.76 (d, J = 6.0 Hz, 1H), 4.61 (s, 2H), 3.47 (t, J = 6.4 Hz, 2H), 3.32-3.22 (m, 2H), 1.95-1.88 (m, 2H), 1.80-1.73 (m, 2H). Calculated (M + H): 390.07; Found (M + H): 390.0. HPLC Purity: 99.77% |

TABLE 44-continued

The following compounds were prepared by the method described above:

| Ex. No. | Structure | IUPAC Name | Analytical Data |
|---|---|---|---|
| 395 | 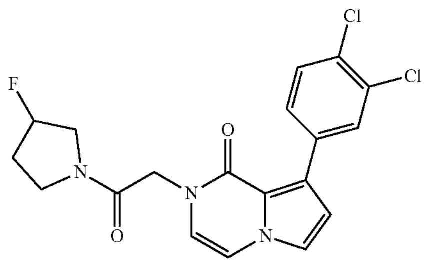 [SMILES: O=C(Cn1ccn2ccc(-c3ccc(F)c(Cl)c3)c2c1=O)N1CCC(F)C1] | 8-(3,4-dichlorophenyl)-2-(2-(3-fluoropyrrolidin-1-yl)-2-oxoethyl)pyrrolo[1,2-a]pyrazin-1(2H)-one | $^1$H NMR (400 MHz, DMSO-$d_6$) δ (ppm): 8.02 (d, J = 1.6 Hz, 1H), 7.66 (dd, J = 1.2 Hz, 8.4 Hz, 1H), 7.56 (d, J = 8.4 Hz, 1H), 7.52 (d, J = 2.8 Hz, 1H), 7.39 (d, J = 5.6 Hz, 1H), 6.84 (d, J = 2.4 Hz, 1H), 6.78 (dd, J = 2.0 Hz, 5.6 Hz, 1H), 5.49-5.24 (m, 1H), 4.76-4.58 (m, 2H), 3.87-3.22 (m, 4H), 2.30-1.93 (m, 2H). Calculated (M + H): 408.06; Found (M + H): 408.1. HPLC Purity: 99.52% |
| 396 | 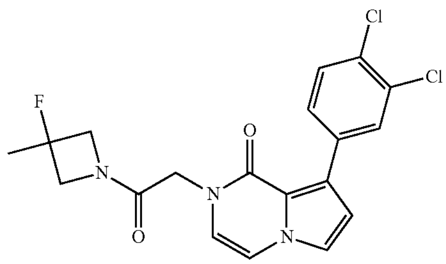 | 8-(3,4-dichlorophenyl)-2-(2-(3-fluoro-3-methylazetidin-1-yl)-2-oxoethyl)pyrrolo[1,2-a]pyrazin-1(2H)-one | $^1$H NMR (400 MHz, DMSO-$d_6$) δ (ppm): 8.02 (s, 1H), 7.65 (d, J = 8.4 Hz, 1H), 7.57 (d, J = 8.4 Hz, 1H), 7.52 (d, J = 2 Hz, 1H), 7.41 (d, J = 5.6 Hz, 1H), 6.84 (d, J = 1.6 Hz, 1H), 6.77 (d, J = 6 Hz, 1H), 4.49 (s, 2H), 4.39-4.26 (m, 2H), 3.96 (d, J = 20.4 Hz, 2H), 1.58 (d, J = 22 Hz, 3H). Calculated (M + H): 408.06; Found (M + H): 408.0. HPLC purity: 99.07%. |
| 397 | 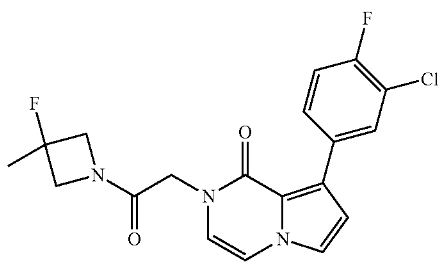 [SMILES: CC1(F)CN(C(=O)Cn2ccn3ccc(-c4ccc(F)c(Cl)c4)c3c2=O)C1] | 8-(3-chloro-4-fluorophenyl)-2-(2-(3-fluoro-3-methylazetidin-1-yl)-2-oxoethyl)pyrrolo[1,2-a]pyrazin-1(2H)-one | $^1$H-NMR (DMSO-$d_6$, 400 MHz) δ (ppm): 7.94 (dd, J = 2.0, 7.2 Hz, 1H), 7.66-7.62 (m, 1H), 7.50 (d, J = 2.8 Hz, 1H), 7.39-7.33 (m, 2H), 6.80 (d, J = 2.8 Hz, 1H), 6.75 (d, J = 6 Hz, 1H), 4.48 (s, 2H), 4.38-4.25 (m, 2H), 4.02-3.94 (m, 2H), 1.58 (d, J = 22 Hz, 3H). Calculated (M + H): 392.09, found (M + H): 392.2, HPLC purity: 99.89%. |
| 398 | 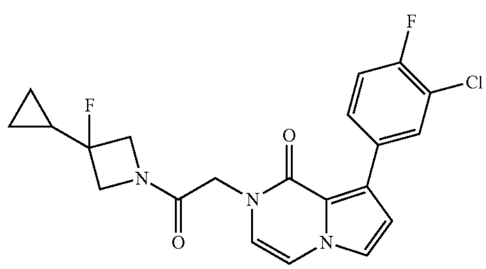 [SMILES: O=C(Cn1ccn2ccc(-c3ccc(F)c(Cl)c3)c2c1=O)N1CC(F)(C2CC2)C1] | 8-(3-chloro-4-fluorophenyl)-2-(2-(3-cyclopropyl-3-fluoroazetidin-1-yl)-2-oxoethyl)pyrrolo[1,2-a]pyrazin-1(2H)-one | $^1$H NMR (400 MHz, DMSO-$d_6$) δ (ppm): 7.96-7.94 (m, 1H), 7.66-7.64 (m, 1H), 7.50 (d, J = 2.8 Hz, 1H), 7.39-7.34 (m, 2H), 6.80-6.76 (m, 2H), 4.53-4.43 (m, 2H), 4.29-4.17 (m, 2H), 3.93-3.82 (m, 2H), 1.40-1.34 (m, 1H), 0.62-0.42 (m, 4H). Calculated (M + H): 418.11; Found (M + H): 418.1. HPLC Purity: 99.09% |
| 399 | 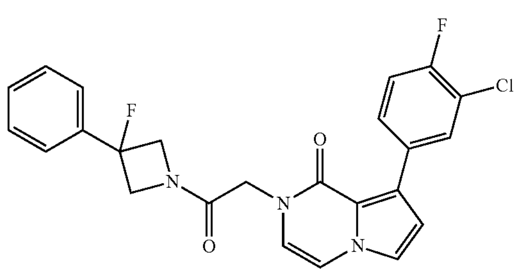 [SMILES: O=C(Cn1ccn2ccc(-c3ccc(F)c(Cl)c3)c2c1=O)N1CC(F)(c2ccccc2)C1] | 8-(3-chloro-4-fluorophenyl)-2-(2-(3-fluoro-3-phenylazetidin-1-yl)-2-oxoethyl)pyrrolo[1,2-a]pyrazin-1(2H)-one | $^1$H NMR (400 MHz, DMSO-$d_6$) δ (ppm): 7.96-7.94 (m, 1H), 7.67-7.65 (m, 1H), 7.55-7.51 (m, 3H), 7.48-7.34 (m, 5H), 6.81-6.79 (m, 2H), 4.81-4.68 (m, 2H), 4.58 (s, 2H), 4.35 (d, J = 20.0 Hz, 2H). Calculated (M + H): 454.11; Found (M + H): 454.1. HPLC Purity: 97.38% |

TABLE 44-continued

The following compounds were prepared by the method described above:

| Ex. No. | Structure | IUPAC Name | Analytical Data |
|---|---|---|---|
| 400 | 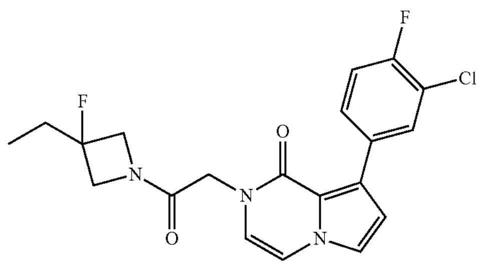 [SMILES: CCC1(F)CN(C(=O)Cn2ccn3ccc(-c4ccc(F)c(Cl)c4)c3c2=O)C1] | 8-(3-chloro-4-fluorophenyl)-2-(2-(3-ethyl-3-fluoroazetidin-1-yl)-2-oxoethyl)pyrrolo[1,2-a]pyrazin-1(2H)-one | $^1$H NMR (400 MHz, DMSO-$d_6$) δ (ppm): 7.94 (dd, J = 1.6 Hz, 7.2 Hz, 1H), 7.66-7.62 (m, 1H), 7.51 (d, J = 2.8 Hz, 1H), 7.39-7.34 (m, 2H), 6.80 (d, J = 2.4 Hz, 1H), 6.76 (d, J = 5.6 Hz, 1H), 4.54-4.45 (m, 2H), 4.37-4.25 (m, 2H), 4.02-3.88 (m, 2H), 1.93-1.82 (m, 2H), 0.91 (t, J = 7.2 Hz, 3H). Calculated (M + H): 406.11; Found (M + H): 406.1. HPLC Purity: 99.84% |
| 401 | 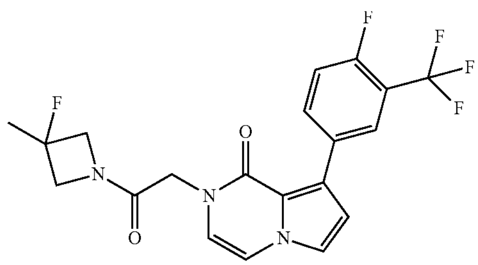 [SMILES: CC1(F)CN(C(=O)Cn2ccn3ccc(-c4ccc(F)c(C(F)(F)F)c4)c3c2=O)C1] | 8-(4-fluoro-3-(trifluoromethyl)phenyl)-2-(2-(3-fluoro-3-methylazetidin-1-yl)-2-oxoethyl)pyrrolo[1,2-a]pyrazin-1(2H)-one | $^1$H NMR (400 MHz, DMSO-$d_6$) δ (ppm): 8.13 (d, J = 6.4 Hz, 1H), 7.97 (brs, 1H), 7.53 (d, J = 2 Hz, 1H), 7.46 (t, J = 10 Hz, 1H), 7.41 (d, J = 6 Hz, 1H), 6.85 (d, J = 2 Hz, 1H), 6.78 (d, J = 6 Hz, 1H), 4.52 (s, 2H), 4.48 (m, 2H), 3.98 (d, J = 18.8 Hz, 2H), 1.60 (d, J = 22 Hz, 3H). Calculated (M + H): 426.1; Found (M + H): 426.1. HPLC purity: 99.86% |
| 402 | 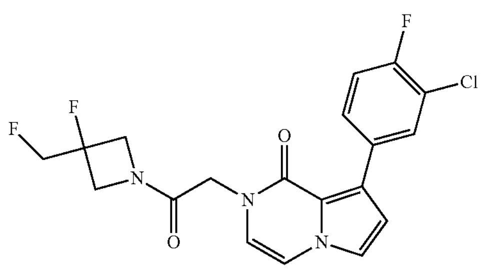 [SMILES: O=C(Cn1ccn2ccc(-c3ccc(F)c(Cl)c3)c2c1=O)N1CC(F)(CF)C1] | 8-(3-chloro-4-fluorophenyl)-2-(2-(3-fluoro-3-(fluoromethyl)azetidin-1-yl)-2-oxoethyl)pyrrolo[1,2-a]pyrazin-1(2H)-one | $^1$H NMR (400 MHz, DMSO-$d_6$) δ (ppm); 7.94 (d, J = 5.6 Hz, 1H), 7.64 (brs, 1H), 7.50 (d, J = 2.4 Hz, 1H), 7.39-7.33 (m, 2H), 6.80 (d, J = 2.4 Hz, 1H), 6.75 (d, J = 5.6 Hz, 1H), 4.88-4.71 (m, 2H), 4.50 (s, 2H), 4.46-4.35 (m, 2H), 4.13-3.96 (m, 2H). Calculated (M + H): 410.08; Found (M + 1): 410.1. HPLC purity 98.01%. |
| 403 | 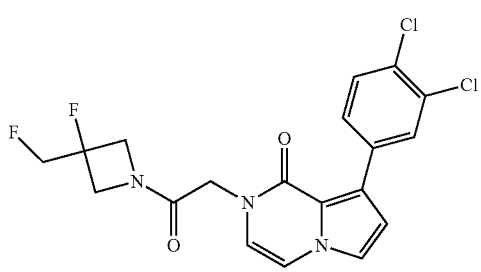 | 8-(3,4-dichlorophenyl)-2-(2-(3-fluoro-3-(fluoromethyl)azetidin-1-yl)-2-oxoethyl)pyrrolo[1,2-a]pyrazin-1(2H)-one | $^1$H NMR (400 MHz, DMSO-$d_6$) δ (ppm); 8.02 (d, J = 2 Hz, 1H), 7.71-7.41 (m, 3H), 7.38 (d, J = 10.4 Hz, 1H), 6.84 (d, J = 2.8 Hz, 1H), 6.77 (d, J = 6.0 Hz, 1H), 4.89-4.71 (m, 2H), 4.51-4.35 (m, 4H), 4.13-3.96 (m, 2H). Calculated (M + H): 426.05; Found (M + 1): 426.0. HPLC purity 98.10% |
| 404 | 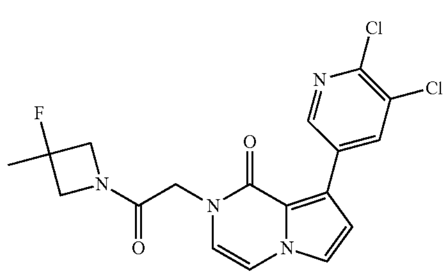 [SMILES: CC1(F)CN(C(=O)Cn2ccn3ccc(-c4cnc(Cl)c(Cl)c4)c3c2=O)C1] | 8-(5,6-dichloropyridin-3-yl)-2-(2-(3-fluoro-3-methylazetidin-1-yl)-2-oxoethyl)pyrrolo[1,2-a]pyrazin-1(2H)-one | $^1$H NMR (400 MHz, DMSO-$d_6$) δ (ppm): 8.66 (s, 1H), 8.50 (s, 1H), 7.57 (d, J = 2.4 Hz, 1H), 7.44 (d, J = 5.6 Hz, 1H), 6.97 (d, J = 2.0 Hz, 1H), 6.82 (d, J = 5.6 Hz, 1H), 4.51 (s, 2H), 4.37-4.26 (m, 2H), 3.96 (d, J = 20 Hz, 2H), 1.58 (d, J = 22 Hz, 3H). Calculated (M + H): 409.06; Found (M + H): 409.0. HPLC purity: 99.20%. |

TABLE 44-continued

The following compounds were prepared by the method described above:

| Ex. No. | Structure | IUPAC Name | Analytical Data |
|---|---|---|---|
| 405 | 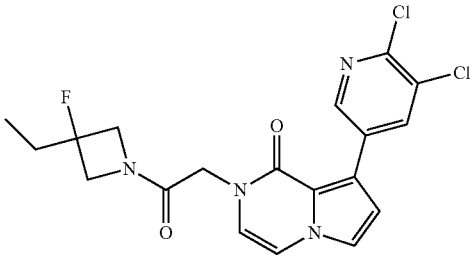 [SMILES: CCC1(F)CN(C(=O)Cn2ccn3ccc(-c4cnc(Cl)c(Cl)c4)c3c2=O)C1] | 8-(5,6-dichloropyridin-3-yl)-2-(2-(3-ethyl-3-fluoroazetidin-1-yl)-2-oxoethyl)pyrrolo[1,2-a]pyrazin-1(2H)-one | $^1$H NMR (400 MHz, DMSO-$d_6$) δ (ppm): 8.66 (s, 1H), 8.50 (s, 1H), 7.57 (d, J = 2 Hz, 1H), 7.44 (d, J = 5.6 Hz, 1H), 6.97 (s, 1H), 6.82 (d, J = 5.6 Hz, 1H), 4.56 (s, 2H), 4.52-4.28 (m, 2H), 4.02-3.88 (m, 2H), 1.91-1.83 (m, 2H), 0.91 (t, J = 7.2 Hz, 3H). Calculated (M + H): 423.07; Found (M + H): 423.1. HPLC purity: 99.53%. |
| 406 | 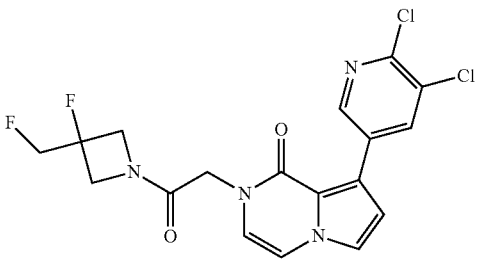 [SMILES: O=C(Cn1ccn2ccc(-c3cnc(Cl)c(Cl)c3)c2c1=O)N1CC(F)(CF)C1] | 8-(5,6-dichloropyridin-3-yl)-2-(2-(3-fluoro-3-(fluoromethyl)azetidin-1-yl)-2-oxoethyl)pyrrolo[1,2-a]pyrazin-1(2H)-one | $^1$H NMR (400 MHz, DMSO-$d_6$) δ (ppm): 8.66 (d, J = 2 Hz, 1H), 8.50 (d, J = 1.6 Hz, 1H), 7.58 (d, J = 2 Hz, 1H), 7.44 (d, J = 5.6 Hz, 1H), 6.97 (d, J = 2 Hz, 1H), 6.82 (d, J = 6 Hz, 1H), 4.89-4.71 (m, 2H), 4.53 (s, 2H), 4.50-4.36 (m, 2H), 4.13-3.96 (m, 2H). Calculated (M + H): 427.05; Found (M + H): 427.2. HPLC purity: 99.91%. |
| 407 | 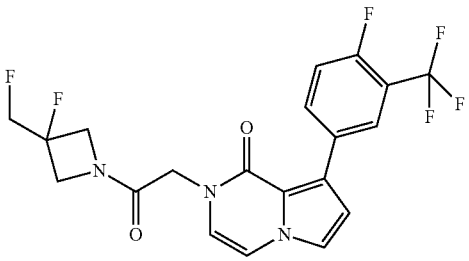 [SMILES: O=C(Cn1ccn2ccc(-c3ccc(F)c(C(F)(F)F)c3)c2c1=O)N1CC(F)(CF)C1] | 2-(2-(3-fluoro-3-(fluoromethyl)azetidin-1-yl)-2-oxoethyl)-8-(4-fluoro-3-(trifluoromethyl)phenyl)pyrrolo[1,2-a]pyrazin-1(2H)-one | $^1$H NMR (400 MHz, DMSO-$d_6$) δ (ppm): 8.13 (d, J = 6.4 Hz, 1H), 7.97 (brs, 1H), 7.53 (d, J = 2.0 Hz, 1H), 7.47 (t, J = 9.6 Hz, 1H), 7.41 (d, J = 5.6 Hz, 1H), 6.86 (s, 1H), 6.76 (d, J = 6.0 Hz, 1H), 4.88-4.70 (m, 2H), 4.51-4.36 (m, 4H), 4.13-3.96 (m, 2H). Calculated (M + H): 444.11; Found (M + H): 444.1. HPLC Purity: 98.77% |
| 408 | 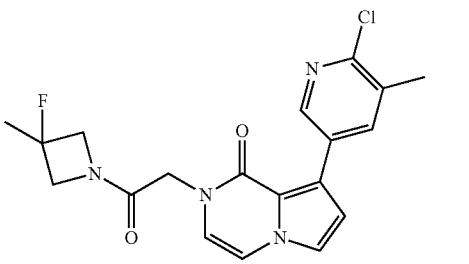 | 8-(6-chloro-5-methylpyridin-3-yl)-2-(2-(3-fluoro-3-methylazetidin-1-yl)-2-oxoethyl)pyrrolo[1,2-a]pyrazin-1(2H)-one | $^1$H NMR (400 MHz, DMSO-$d_6$) δ (ppm); 8.48 (d, J = 2.0 Hz, 1H), 8.06 (d, J = 2.0 Hz, 1H), 7.54 (d, J = 2.8 Hz, 1H), 7.41 (d, J = 5.6 Hz, 1H), 6.83 (d, J = 2.4 Hz, 1H), 6.78 (d, J = 5.6 Hz, 1H), 4.48 (s, 2H), 4.39-4.25 (m, 2H), 3.99-3.94 (m, 2H), 2.33 (s, 3H), 1.58 (d, J = 22.4 Hz, 3H). Calculated (M + H): 389.11; Found (M + 1): 389.1. HPLC purity 99.03% |
| 409 | 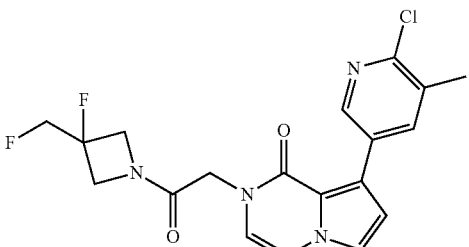 | 8-(6-chloro-5-methylpyridin-3-yl)-2-(2-(3-fluoro-3-(fluoromethyl)azetidin-1-yl)-2-oxoethyl)pyrrolo[1,2-a]pyrazin-1(2H)-one | $^1$H NMR (400 MHz, DMSO-$d_6$) δ (ppm); 8.48 (d, J = 2.4 Hz, 1H), 8.06 (d, J = 1.6 Hz, 1H), 7.55 (d, J = 2.8 Hz, 1H), 7.42 (d, J = 5.6 Hz, 1H), 6.84 (d, J = 2.8 Hz, 1H), 6.77 (d, J = 5.6 Hz, 1H), 4.88-4.71 (m, 2H), 4.51 (s, 2H), 4.47-4.38 (m, 2H), 4.13-3.99 (m, 2H), 2.33 (s, 3H). Calculated (M + H): 407.10; Found (M + 1): 407.1. HPLC purity 99.22% |

TABLE 44-continued

The following compounds were prepared by the method described above:

| Ex. No. | Structure | IUPAC Name | Analytical Data |
|---|---|---|---|
| 410 | 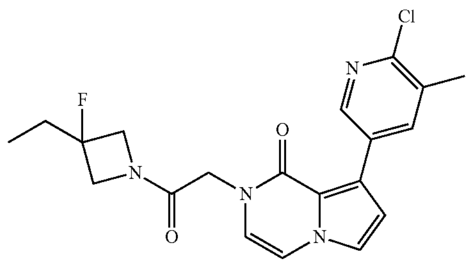 [SMILES: CCC1(F)CN(C(=O)Cn2ccn3ccc(-c4cnc(Cl)c(C)c4)c3c2=O)C1] | 8-(6-chloro-5-methylpyridin-3-yl)-2-(2-(3-ethyl-3-fluoroazetidin-1-yl)-2-oxoethyl)pyrrolo[1,2-a]pyrazin-1(2H)-one | $^1$H NMR (400 MHz, DMSO-$d_6$) δ (ppm); 8.48 (d, J = 2.4 Hz, 1H), 8.06 (s, 1H), 7.54 (d, J = 2.4 Hz, 1H), 7.41 (d, J = 6.0 Hz, 1H), 6.83 (d, J = 2.4 Hz, 1H), 6.78 (d, J = 5.6 Hz, 1H), 4.49 (s, 2H), 4.34-4.25 (m, 2H), 4.01-3.87 (m, 2H), 2.34 (s, 3H), 1.93-1.81 (m, 2H), 0.91 (t, J = 7.6 Hz, 3H). Calculated (M + H): 403.13; Found (M + 1): 403.1. HPLC purity 99.21% |

Examples 411 and 412: Preparation of 8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one and 6-bromo-8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one

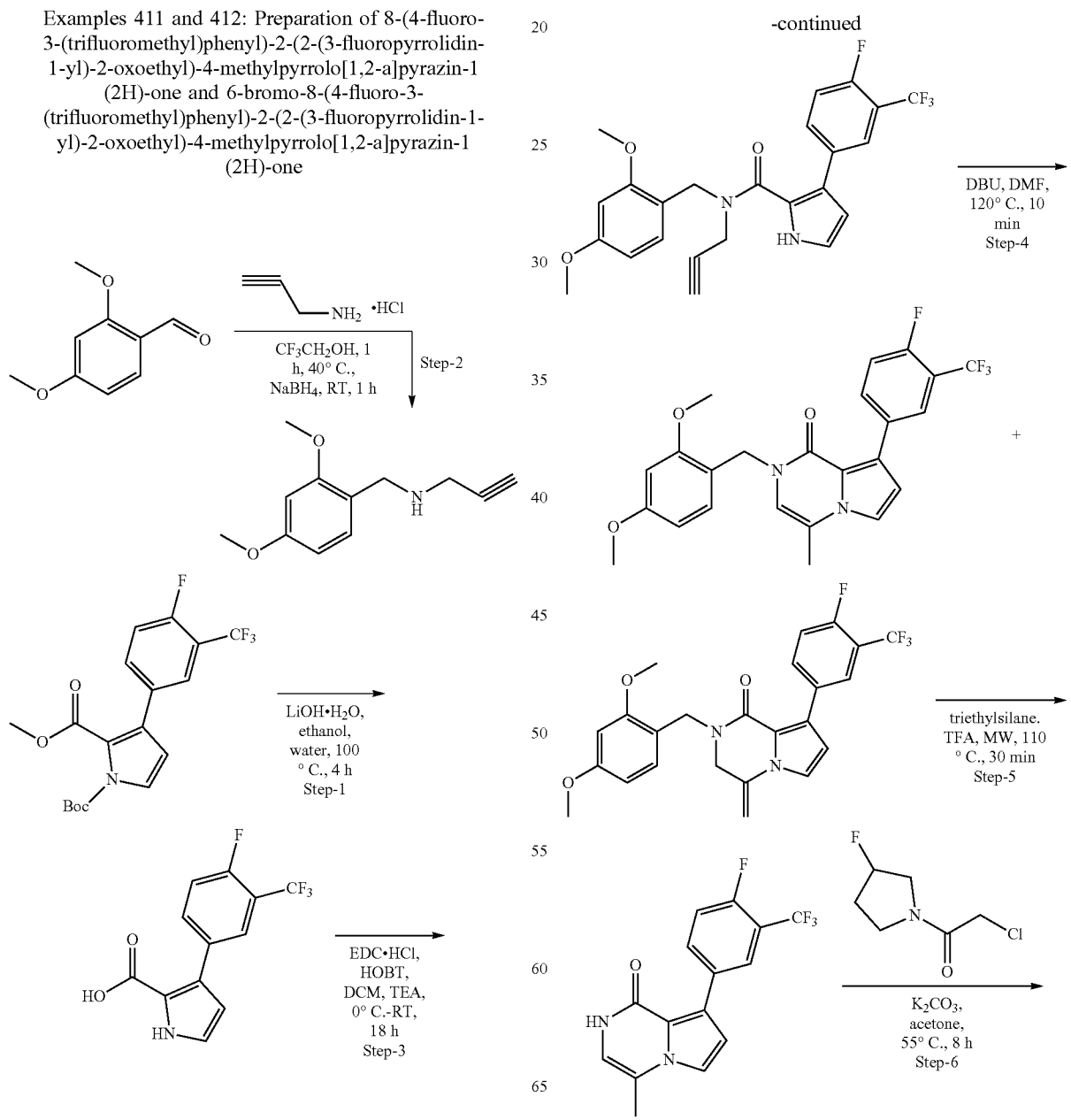

-continued

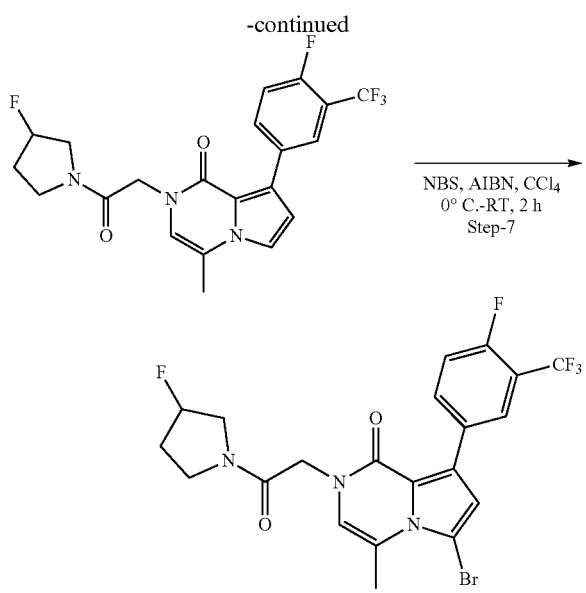

Step 1

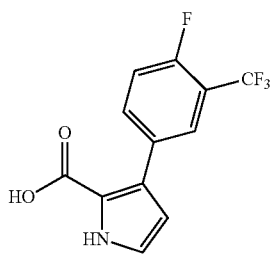 [SMILES: O=C(O)c1[nH]ccc1-c1ccc(F)c(C(F)(F)F)c1]

Preparation of 3-(4-fluoro-3-(trifluoromethyl)phenyl)-1H-pyrrole-2-carboxylic acid To a solution of 1-tert-butyl 2-methyl 3-(4-fluoro-3-(trifluoromethyl)phenyl)-1H-pyrrole-1,2-dicarboxylate (1.0 g, 2.58 mmol) in ethanol:water mixture (20 mL, 1:1) was added lithium hydroxide monohydrate (1.08 g, 25.82 mmol) the reaction mixture was stirred at 100° C. for 4 h. Ethanol present in the reaction mixture was evaporated, the resulting solution was diluted with water (20 mL) and neutralized with glacial acetic acid at 0° C. The obtained solid was filtered and dried to afford the title compound 3-(4-fluoro-3-(trifluoromethyl)phenyl)-1H-pyrrole-2-carboxylic acid (0.69 g, 97.9% yield) as off-white solid. Calculated (M−H): 272.04; Found (M−H): 272.0

Step 2

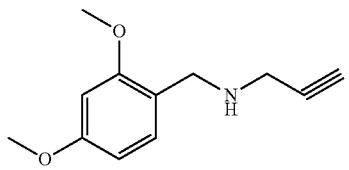

Preparation of N-(2,4-dimethoxybenzyl)prop-2-yn-1-amine

To a solution of 2,4-dimethoxybenzaldehyde (1.0 g, 2.58 mmol) in 2,2,2-trifluoroethanol (20 mL), prop-2-yn-1-amine hydrochloride (0.33 g, 3.61 mmol) was added at 40° C. and the resulting solution was stirred at 40° C. for 1 h. Then sodium borohydride (0.171 g, 4.52 mmol) was added at room temperature and reaction mixture was stirred at room temperature for 1 h. The reaction mixture was evaporated, the resulting residue was dissolved in water (40 mL) and extracted with dichloromethane (2×100 mL). The combined organic layer was dried over anhydrous sodium sulfate, filtered and concentrated to get the crude product which was purified by silica gel column chromatography using 30% ethyl acetate in hexane to afford the title compound N-(2,4-dimethoxybenzyl)prop-2-yn-1-amine (0.98 g, 79.7% yield) as pale yellow liquid. Calculated (M+H): 206.11; Found (M+1): 206.1

Step-3

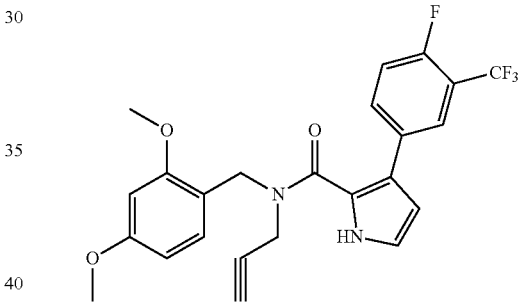

Preparation of N-(2,4-dimethoxybenzyl)-3-(4-fluoro-3-(trifluoromethyl)phenyl)-N-(prop-2-yn-1-yl)-1H-pyrrole-2-carboxamide To a solution of 3-(4-fluoro-3-(trifluoromethyl)phenyl)-1H-pyrrole-2-carboxylic acid (0.4 g, 1.46 mmol) in dichloromethane (35 mL), triethylamine (0.444 g, 4.39 mmol), N-(3-dimethylaminopropyl)-N'-ethylcarbodiimide hydrochloride (0.42 g, 2.19 mmol) and N-hydroxybenzotriazole (0.22 g, 1.46 mmol) were added at 0° C. and the reaction mixture was stirred at 0° C. for 30 min. Then N-(2,4-dimethoxybenzyl)prop-2-yn-1-amine (0.45 g, 2.19 mmol) was added and the reaction mixture was stirred at room temperature for 18 h. The reaction mixture was quenched with water (30 mL) and extracted with dichloromethane (2×100 mL). The combined organic layer was dried over anhydrous sodium sulfate, filtered and concentrated to get crude product, which was purified by silica gel column chromatography using 30% ethyl acetate in hexane to afford the title compound N-(2,4-dimethoxybenzyl)-3-(4-fluoro-3-(trifluoromethyl)phenyl)-N-(prop-2-yn-1-yl)-1H-pyrrole-2-carboxamide (0.60 g, 89.5% yield) as yellowish gum. Calculated (M+H): 461.14; Found (M+1): 461.1.

Step-4

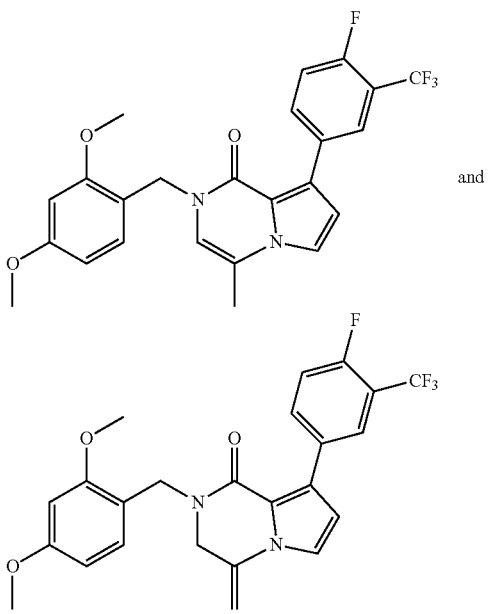

and

Preparation of 2-(2,4-dimethoxybenzyl)-8-(4-fluoro-3-(trifluoromethyl)phenyl)-4-methylpyrrolo[1,2-a]pyrazin-1(2H)-one and 2-(2,4-dimethoxybenzyl)-8-(4-fluoro-3-(trifluoromethyl)phenyl)-4-methylene-3,4-dihydropyrrolo[1,2-a]pyrazin-1(2H)-one To a solution of N-(2,4-dimethoxybenzyl)-3-(4-fluoro-3-(trifluoromethyl)phenyl)-N-(prop-2-yn-1-yl)-1H-pyrrole-2-carboxamide (0.6 g, 1.30 mmol) in N,N-dimethylformamide (4 mL), 1,8-diazabicycloundec-7-ene (0.19 mL, 1.30 mmol) was added and the reaction mixture was stirred under microwave irradiation at 120° C. for 10 min. The reaction mixture was diluted with ethyl acetate (60 mL) and washed with ice cold water (2×50 mL). The organic layer was dried over anhydrous sodium sulfate, filtered and evaporated to get crude mixture (0.6 g). The crude mixture was as such taken for next step without purification. Calculated (M+H): 461.14; Found (M+1): 461.1.

Step-5

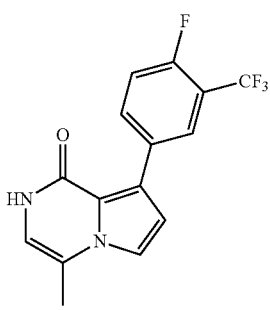 [SMILES: Cc1c[nH]c(=O)c2c(-c3ccc(F)c(C(F)(F)F)c3)ccn12]

Preparation of 8-(4-fluoro-3-(trifluoromethyl)phenyl)-4-methylpyrrolo[1,2-a]pyrazin-1(2H)-one To a solution of crude mixture of 2-(2,4-dimethoxybenzyl)-8-(4-fluoro-3-(trifluoromethyl)phenyl)-4-methylpyrrolo[1,2-a]pyrazin-1(2H)-one and 2-(2,4-dimethoxybenzyl)-8-(4-fluoro-3-(trifluoromethyl)phenyl)-4-methylene-3,4-dihydropyrrolo[1,2-a]pyrazin-1(2H)-one (0.6 g, 1.30 mmol) in trifluoroacetic acid (4 mL), triethylsilane (1.25 mL, 7.82 mmol) was added and the reaction mixture was stirred under microwave irradiation at 120° C. for 30 minutes. The reaction mixture was evaporated to get the crude compound which was purified by silica gel column chromatography using 50% ethyl acetate in hexane to afford the title compound 8-(4-fluoro-3-(trifluoromethyl)phenyl)-4-methylpyrrolo[1,2-a]pyrazin-1(2H)-one as off-white solid (0.25 g, 62.5% yield). Calculated (M+H): 311.07; Found (M+1): 311.1.

Step-6

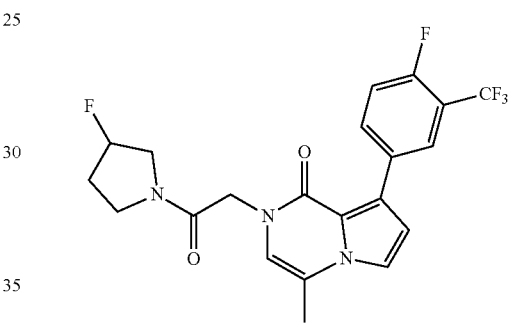

Preparation of 8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one To a suspension of 8-(4-fluoro-3-(trifluoromethyl)phenyl)-4-methylpyrrolo[1,2-a]pyrazin-1(2H)-one (0.25 g, 0.81 mmol) in acetone (20 mL), potassium carbonate (0.33 g, 2.42 mmol) and 2-chloro-1-(3-fluoropyrrolidin-1-yl)ethanone (0.20 g, 1.21 mmol) were added and the reaction mixture was stirred at 55° C. for 8 h. The reaction mixture was filtered and the filtrate was evaporated to get crude product which was purified by silica gel column chromatography using 3% methanol in dichloromethane to afford title compound 8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one (0.29 g, 81.9% yield) as off-white solid. $^1$H NMR (400 MHz, DMSO-$d_6$) δ (ppm): 8.11 (d, J=6.0 Hz, 1H), 7.98-7.97 (m, 1H), 7.49-7.44 (m, 2H), 6.91 (d, J=2.8 Hz, 1H), 6.65 (s, 1H), 5.49-5.24 (m, 1H), 4.75-4.57 (m, 2H), 3.84-3.45 (m, 4H), 2.30 (s, 3H), 2.26-2.05 (n, 2H). Calculated (M+H): 440.13; Found (M+H): 440.1. HPLC Purity: 99.08%.

Step-7

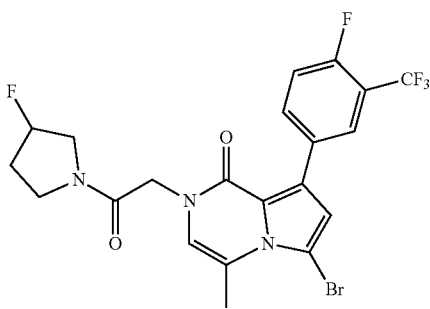 [SMILES: Cc1cn(CC(=O)N2CCC(F)C2)c(=O)c2c(-c3ccc(F)c(C(F)(F)F)c3)cc(Br)n12]

Preparation of 6-bromo-8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one To a stirred solution of 8-(4-fluoro-3-(trifluoromethyl)phenyl)-2-(2-(3-fluoropyrrolidin-1-yl)-2-oxoethyl)-4-methylpyrrolo[1,2-a]pyrazin-1(2H)-one (0.14 g, 0.32 mmol) in carbon tetrachloride (50 mL), azobisisobutyronitrile (0.005 g, 0.032 mmol) and N-bromosuccinimide were added at 0° C. The reaction mixture was slowly warmed to room temperature and stirred for 2 h. The reaction mixture was diluted with dichloromethane (50 mL) and washed with water (2×30 mL). The organic layer was dried over anhydrous sodium sulfate, filtered and evaporated to get crude product which was purified by silica gel column chromatography using 70% ethyl acetate in hexane and further purified by preparative HPLC (analytical conditions: column: chemsil C18 (250 mm×4.6 mm×5µ), mobile phase (A): 0.1% ammonia in water, mobile phase (B): acetonitrile, flow rate: 1.0 mL/min, T/% B: 0/20, 10/80, 25/90, 27/20, 30/20) to afford title compound 6-bromo-8-(4-fluoro-3-(trifluoromethyl)phenyl)-2-(2-(3-fluoropyrrolidin-1-yl)-2-oxoethyl)-4 methylpyrrolo[1,2-a]pyrazin-1(2H)-one (0.015 g, 9.1% yield) as off-white solid. $^1$H NMR (400 MHz, DMSO-$d_6$) δ (ppm): 7.92 (d, J=6.8 Hz, 1H), 7.85 (brs, 1H), 7.47 (t, J=9.6 Hz, 1H), 6.98 (s, 1H), 6.60 (s, 1H), 5.50-5.20 (m, 1H), 4.66-4.51 (m, 2H), 3.76-3.31 (m, 4H), 2.62 (s, 3H), 2.30-1.90 (m, 2H). Calculated (M+H): 518.04; Found (M+H): 518.0. HPLC Purity: 99.32%.

TABLE 45

The following compounds were prepared by the method described above:

| Ex. No. | Structure | IUPAC name | Analytical data |
| --- | --- | --- | --- |
| 413 | 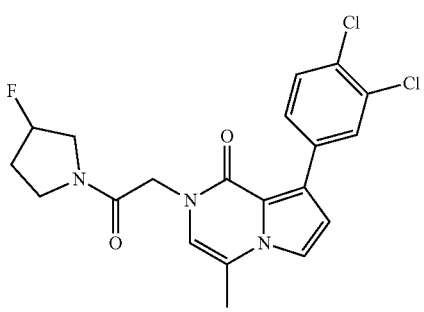 [SMILES: Cc1cn(CC(=O)N2CCC(F)C2)c(=O)c2c(-c3ccc(Cl)c(Cl)c3)ccn12] | 8-(3,4-dichlorophenyl)-2-(2-(3-fluoropyrrolidin-1-yl)-2-oxoethyl)-4-methylpyrrolo[1,2-a]pyrazin-1(2H)-one | $^1$H NMR (400 MHz, DMSO-$d_6$) δ (ppm): 8.01 (s, 1H), 7.66 (d, J = 8.4 Hz, 1H), 7.57 (d, J = 8.4 Hz, 1H), 7.48 (d, J = 1.6 Hz, 1H), 6.90 (d, J = 1.6 Hz, 1H), 6.66 (s, 1H), 5.49-5.24 (m, 1H), 4.75-4.57 (m, 2H), 3.87-3.39 (m, 4H), 2.29 (s, 3H), 2.21-1.95 (m, 2H). Calculated (M + H): 422.08; Found (M + H): 422.2. HPLC Purity: 98.57% |
| 414 | 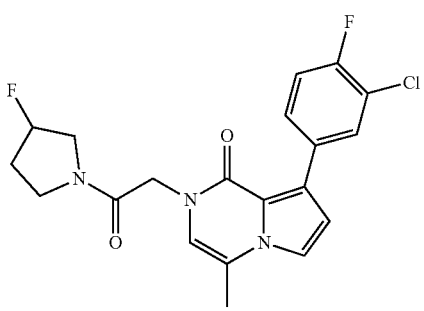 [SMILES: Cc1cn(CC(=O)N2CCC(F)C2)c(=O)c2c(-c3ccc(F)c(Cl)c3)ccn12] | 8-(3-chloro-4-fluorophenyl)-2-(2-(3-fluoropyrrolidin-1-yl)-2-oxoethyl)-4-methylpyrrolo[1,2-a]pyrazin-1(2H)-one | $^1$H NMR (400 MHz, DMSO-$d_6$) δ (ppm): 7.94 (dd, 1.6 Hz, J = 7.6 Hz, 1H), 7.66-7.63 (m, 1H), 7.46 (d, J = 4.2 Hz, 1H), 7.36 (t, J = 8.8 Hz, 1H), 6.86 (d, J = 4.2 Hz, 1H), 6.65 (s, 1H), 5.49-5.24 (m, 1H), 4.75-4.56 (m, 2H), 3.84-3.23 (m, 4H), 2.28 (s, 3H), 2.21-2.05 (m, 2H). Calculated (M + H): 406.11; Found (M + H): 406.1. HPLC Purity: 99.23% |

TABLE 45-continued

The following compounds were prepared by the method described above:

| Ex. No. | Structure | IUPAC name | Analytical data |
|---|---|---|---|
| 415 | 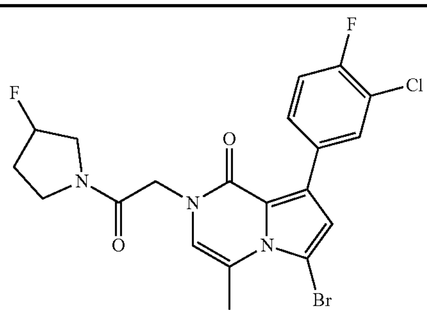 | 6-bromo-8-(3-chloro-4-fluorophenyl)-2-(2-(3-fluoropyrrolidin-1-yl)-2-oxoethyl)-4-methylpyrrolo[1,2-a]pyrazin-1(2H)-one | $^1$H NMR (400 MHz, DMSO-$d_6$) δ (ppm): 7.75 (dd, J = 2.4 Hz, 7.6 Hz, 1H), 7.53-7.49 (m, 1H), 7.36 (t, J = 8.8 Hz, 1H), 6.92 (s, 1H), 6.60 (s, 1H), 5.48-5.24 (m, 1H), 4.69-4.51 (m, 2H), 3.81-3.23 (m, 4H), 2.62 (s, 3H), 2.31-2.05 (m, 2H). Calculated (M + H): 484.02; Found (M + H): 484.0. HPLC Purity: 100.0% |
| 416 | 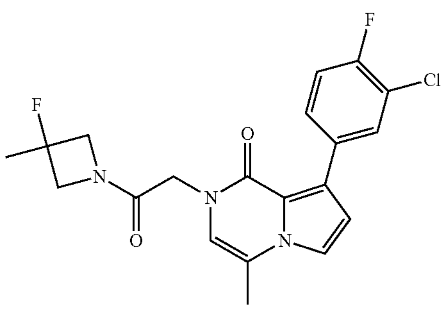 [SMILES: Cc1cn(CC(=O)N2CC(C)(F)C2)c(=O)c2c(-c3ccc(F)c(Cl)c3)ccn12] | 8-(3-chloro-4-fluorophenyl)-2-(2-(3-fluoro-3-methylazetidin-1-yl)-2-oxoethyl)-4-methylpyrrolo[1,2-a]pyrazin-1(2H)-one | $^1$H NMR (400 MHz, DMSO-$d_6$) δ (ppm): 7.93 (dd, J = 2 Hz, 7.2 Hz, 1H), 7.67-7.63 (m, 1H), 7.46 (d, J = 2.8 Hz, 1H), 7.36 (t, J = 8.8 Hz, 1H), 6.86 (d, J = 3.2 Hz, 1H), 6.63 (s, 1H), 4.47 (s, 2H), 4.39-4.26 (m, 2H), 3.96 (d, J = 19.6 2H), 2.28 (s, 3H), 1.58 (d, J = 22 Hz, 3H). Calculated (M + H): 406.11; Found (M + H): 406.1. HPLC purity: 99.89% |
| 417 | 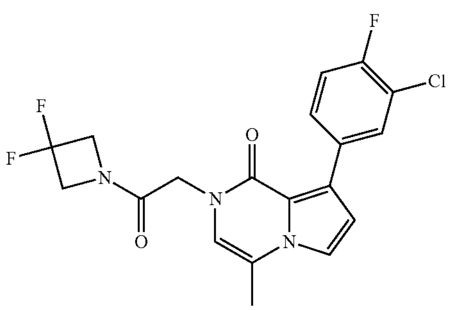 [SMILES: Cc1cn(CC(=O)N2CC(F)(F)C2)c(=O)c2c(-c3ccc(F)c(Cl)c3)ccn12] | 8-(3-chloro-4-fluorophenyl)-2-(2-(3,3-difluoroazetidin-1-yl)-2-oxoethyl)-4-methylpyrrolo[1,2-a]pyrazin-1(2H)-one | $^1$H NMR (400 MHz, DMSO-$d_6$) δ (ppm): 7.93 (d, J = 7.2 Hz, 1H), 7.65 (brs, 1H), 7.46 (s, 1H), 7.36 (t, J = 9.2 Hz, 1H), 6.86 (s, 1H), 6.63 (s, 1H), 4.71-4.68 (m, 2H), 4.53 (s, 2H), 4.35-4.32 (m, 2H), 2.29 (s, 3H). Calculated (M + H): 410.08; Found (M + H): 410.1. HPLC purity: 99.05% |
| 418 | 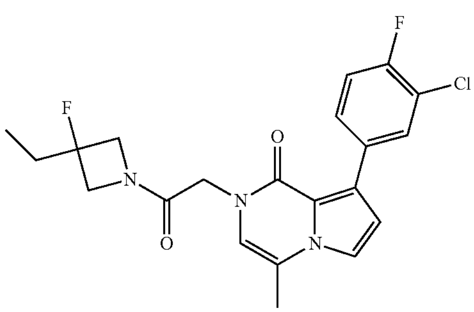 [SMILES: CCC1(F)CN(C(=O)Cn2cc(C)n3ccc(-c4ccc(F)c(Cl)c4)c3c2=O)C1] | 8-(3-chloro-4-fluorophenyl)-2-(2-(3-ethyl-3-fluoroazetidin-1-yl)-2-oxoethyl)-4-methylpyrrolo[1,2-a]pyrazin-1(2H)-one | $^1$H NMR (400 MHz, DMSO-$d_6$) δ (ppm): 7.93 (dd, J = 2.4 Hz, 7.6 Hz, 1H), 7.66-7.62 (m, 1H), 7.45 (d, J = 2.8 Hz, 1H), 7.36 (t, J = 9.2 Hz, 1H), 6.85 (d, J = 2.4 Hz, 1H), 6.63 (s, 1H), 4.51-4.42 (m, 2H), 4.37-4.25 (m, 2H), 4.01-3.87 (m, 2H), 2.28 (s, 3H), 1.92-1.81 (m, 2H), 0.91 (t, J = 7.6 Hz, 3H). Calculated (M + H): 420.12; Found (M + H): 420.1. HPLC purity: 99.20% |
| 419 | 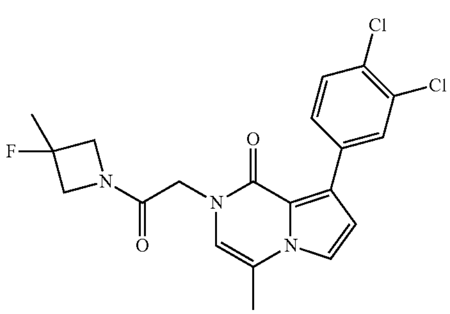 [SMILES: Cc1cn(CC(=O)N2CC(C)(F)C2)c(=O)c2c(-c3ccc(Cl)c(Cl)c3)ccn12] | 8-(3,4-dichlorophenyl)-2-(2-(3-fluoro-3-methylazetidin-1-yl)-2-oxoethyl)-4-methylpyrrolo[1,2-a]pyrazin-1(2H)-one | $^1$H NMR (DMSO-$d_6$, 400 MHz) δ (ppm): 8.01 (s, 1H), 7.65 (d, J = 8.0 Hz, 1H), 7.57 (d, J = 8.0 Hz, 1H), 7.47 (s, 1H), 6.89 (s. 1H), 6.65 (s, 1H), 4.47 (s, 2H), 4.39-4.26 (m, 2H), 3.96 (d, J = 19.6 Hz, 2H), 2.29 (s, 3H), 1.59 (d, J = 22.4 Hz, 3H). Calculated (M + H): 422.28, Found (M + H): 422.1, HPLC purity: 99.85% |

TABLE 45-continued

The following compounds were prepared by the method described above:

| Ex. No. | Structure | IUPAC name | Analytical data |
|---|---|---|---|
| 420 | 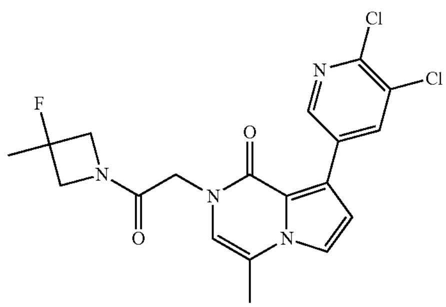 | 8-(5,6-dichloropyridin-3-yl)-2-(2-(3-fluoro-3-methylazetidin-1-yl)-2-oxoethyl)-4-methylpyrrolo[1,2-a]pyrazin-1(2H)-one | $^1$H NMR (400 MHz, DMSO-$d_6$) δ (ppm); 8.66 (d, J = 2.4 Hz, 1H), 8.49 (d, J = 2.0 Hz, 1H), 7.54 (d, J = 2.8 Hz, 1H), 7.03 (d, J = 2.4 Hz, 1H), 6.69 (s, 1H), 4.53-4.48 (m, 2H), 4.45-4.29 (m, 2H), 4.02-3.94 (m, 2H), 2.30 (s, 3H), 1.58 (d, J = 22 Hz, 3H). Calculated (M + H): 423.07; Found (M + 1): 423.0. HPLC purity 99.55% |
| 421 | 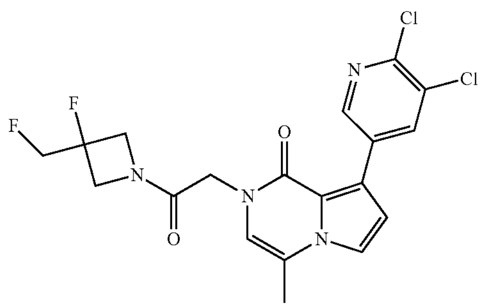 [SMILES: Cc1cn(CC(=O)N2CC(F)(CF)C2)c(=O)c2c(-c3cnc(Cl)c(Cl)c3)ccn12] | 8-(5,6-dichloropyridin-3-yl)-2-(2-(3-fluoro-3-(fluoromethyl)azetidin-1-yl)-2-oxoethyl)-4-methylpyrrolo[1,2-a]pyrazin-1(2H)-one | $^1$H NMR (400 MHz, DMSO-$d_6$) δ (ppm); 8.66 (d, J = 2.4 Hz, 1H), 8.50 (d, J = 1.6 Hz, 1H), 7.54 (d, J = 3.2 Hz, 1H), 7.03 (d, J = 3.2 Hz, 1H), 6.69 (s, 1H), 4.89-4.71 (m, 2H), 4.52-4.36 (m, 4H), 4.13-3.96 (m, 2H), 2.30 (s, 3H). Calculated (M + H): 441.06; Found (M + 1): 437.0. HPLC purity 99.52% |
| 422 | 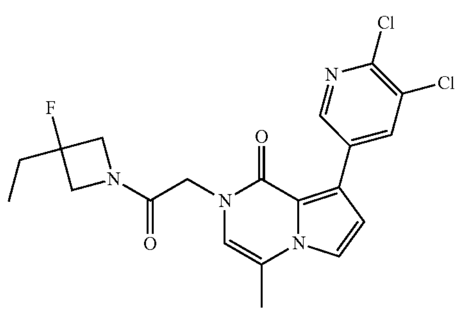 [SMILES: CCC1(F)CN(C(=O)Cn2cc(C)n3ccc(-c4cnc(Cl)c(Cl)c4)c3c2=O)C1] | 8-(5,6-dichloropyridin-3-yl)-2-(2-(3-ethyl-3-fluoroazetidin-1-yl)-2-oxoethyl)-4-methylpyrrolo[1,2-a]pyrazin-1(2H)-one | $^1$H NMR (400 MHz, DMSO-$d_6$) δ (ppm); 8.66 (d, J = 1.6 Hz, 1H), 8.49 (d, J = 2.0 Hz, 1H), 7.54 (d, J = 2.8 Hz, 1H), 7.03 (d, J = 2.4 Hz, 1H), 6.70 (s, 1H), 4.54-4.45 (m, 2H), 4.35-4.26 (m, 2H), 4.02-3.87 (m, 2H), 2.30 (s, 3H), 1.93-1.81 (m, 2H), 0.91 (t, J = 7.6 Hz, 3H). Calculated (M + H): 437.09; Found (M + 1): 437.0. HPLC purity 99.52% |

Example 423: Preparation of 6-bromo-8-(4-fluoro-3-(trifluoromethyl)phenyl)-2-(2-(3-fluoropyrrolidin-1-yl)-2-oxoethyl)pyrrolo[1,2-a]pyrazin-1(2H)-one

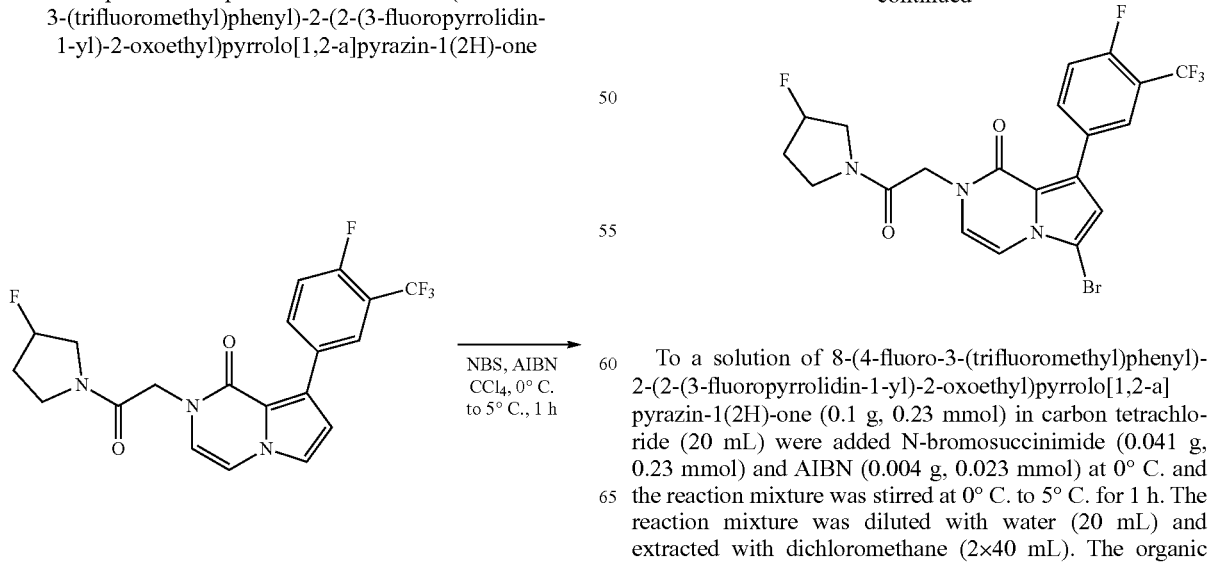

To a solution of 8-(4-fluoro-3-(trifluoromethyl)phenyl)-2-(2-(3-fluoropyrrolidin-1-yl)-2-oxoethyl)pyrrolo[1,2-a]pyrazin-1(2H)-one (0.1 g, 0.23 mmol) in carbon tetrachloride (20 mL) were added N-bromosuccinimide (0.041 g, 0.23 mmol) and AIBN (0.004 g, 0.023 mmol) at 0° C. and the reaction mixture was stirred at 0° C. to 5° C. for 1 h. The reaction mixture was diluted with water (20 mL) and extracted with dichloromethane (2×40 mL). The organic layer was dried over anhydrous sodium sulfate, filtered and concentrated to get the crude compound which was purified by preparative HPLC (column: chemsil C18 (250 mm×4.6 mm×5µ), mobile phase (A): 0.1% ammonia in water, mobile phase (B): acetonitrile, flow rate: 1.0 mL/min, T/% B: 0/20, 10/80, 25/90, 27/20, 30/20) to afford the title compound 6-bromo-8-(4-fluoro-3-(trifluoromethyl)phenyl)-2-(2-(3-fluoropyrrolidin-1-yl)-2-oxoethyl)pyrrolo[1,2-a]pyrazin-1(2H)-one (0.015 g, 13% yield) as white solid. Calculated (M+H): 504.03; Found (M+H): 504.0. $^1$H NMR (400 MHz, DMSO-d$_6$) δ (ppm): $^1$H NMR (400 MHz, DMSO-d$_6$) δ (ppm): 8.06 (d, J=6.4 Hz, 1H), 7.96 (bs, 1H), 7.48 (t, J=10 Hz, 1H), 7.29 (d, J=5.6 Hz, 1H), 7.09 (s, 1H), 6.95-6.94 (m, 1H), 5.48-5.24 (m, 1H), 4.79-4.60 (m, 2H), 3.86-3.27 (m, 4H), 2.30-1.95 (m, 2H). HPLC purity: 97.37%.

O. PREPARATION OF IMIDOTRIAZINONES

Example 424: Preparation of 5-(3-chloro-4-fluorophenyl)-3-(2-(3-fluoro-3-methylazetidin-1-yl)-2-oxoethyl)imidazo[5,1-f][1,2,4]triazin-4(3H)-one

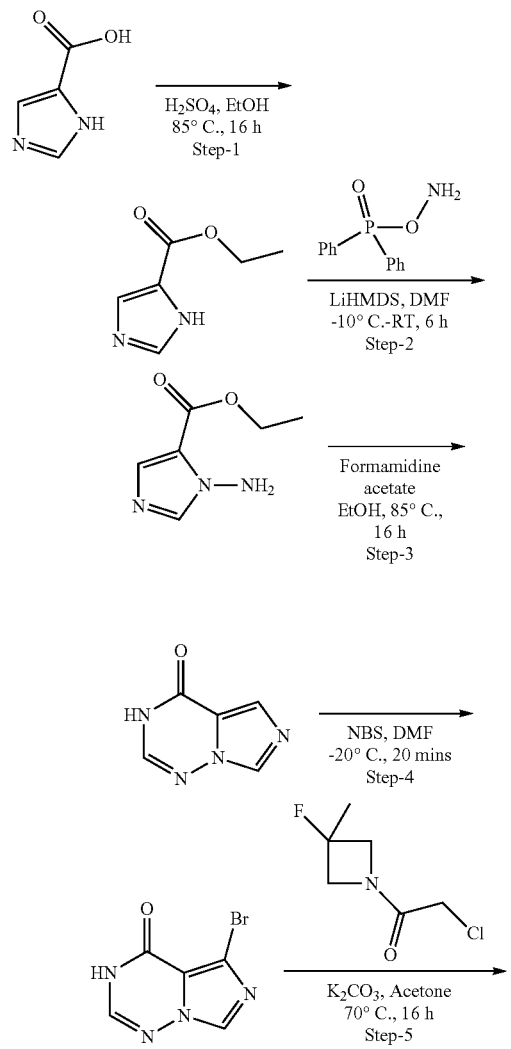

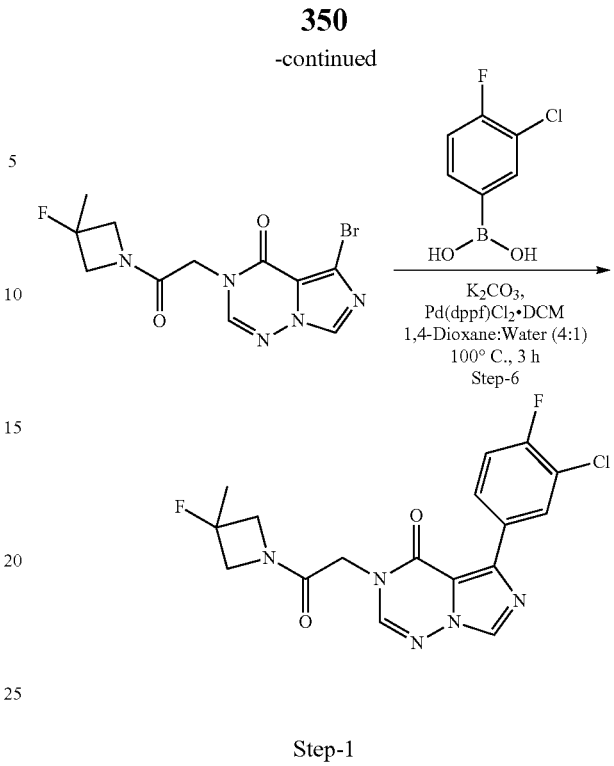

Step-1

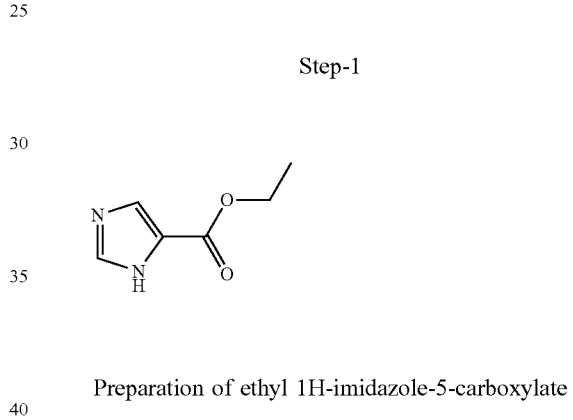

Preparation of ethyl 1H-imidazole-5-carboxylate

To a stirred solution of 1H-imidazole-5-carboxylic acid (0.2 g, 1.78 mmol) in ethanol (10 mL) was added sulfuric acid (0.48 mL, 8.92 mmol) and the reaction mixture was refluxed for 16 h. The reaction mixture concentrated under reduced pressure. The residue was diluted with water, neutralized using saturated sodium bicarbonate solution and extracted using ethyl acetate (2×50 mL). The combined organic layer was dried over anhydrous sodium sulfate, filtered and concentrated. The crude product was purified by silica gel column chromatography using 5% methanol in dichloromethane to afford title compound ethyl 1H-imidazole-5-carboxylate (0.08 g, 32.0% yield) as an off-white solid. Calculated (M+H): 141.06, Found (M+H): 141.0.

Step-2

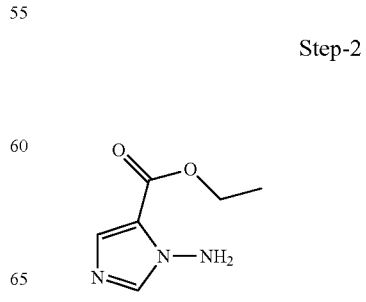

Preparation of ethyl 1-amino-1H-imidazole-5-carboxylate

To stirred solution of ethyl 1H-imidazole-5-carboxylate (0.1 g, 0.71 mmol) in N,N-dimethylformamide (10 mL) cooled to −10° C., was added lithium bis(trimethylsilyl) amide (0.78 mL, 0.78 mmol) drop wise and the reaction mixture was stirred at −10° C. for 15 min. Then (aminooxy) diphenylphosphine oxide (0.199 g, 0.85 mmol) was added at −10° C. and the reaction mixture was stirred at room temperature for 6 h. The reaction mixture was quenched by slow addition of water until the precipitate formed was dissolved to become clear solution. Then it was extracted using ethyl acetate (2×50 mL). The combined organic layer was dried over anhydrous sodium sulfate, filtered and concentrated to afford the title compound ethyl 1-amino-1H-imidazole-5-carboxylate as off white solid (0.1 g, crude). Calculated (M+H): 156.07; Found (M+H): 156.1.

Step-3

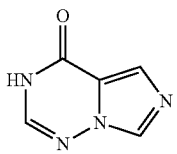

Preparation of imidazo[5,1-f][1,2,4]triazin-4(3H)-one

To a solution of ethyl 1-amino-1H-imidazole-5-carboxylate (0.38 g, 2.44 mmol) in ethanol (20 mL) was added formamidine acetate (1.27 g, 12.25 mmol) and the reaction mixture was heated at 85° C. for 16 h. After completion of the reaction, the reaction mixture was cooled to room temperature and the solid obtained was filtered, washed with hexane and dried under high vacuum to afford the title compound imidazo[5,1-f][1,2,4]triazin-4(3H)-one (0.17 g, crude) as a off-white solid. Calculated (M+H): 137.04; Found (M+H): 137.1.

Step-4

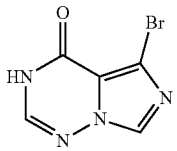

Preparation of 5-bromoimidazo[5,1-f][1,2,4]triazin-4(3H)-one

To a solution of imidazo[5,1-f][1,2,4]triazin-4(3H)-one (0.1 g, 0.73 mmol) in N,N-dimethylformamide (25 mL), was added N-bromosuccinimide (0.131 g, 0.7347 mmol) at −20° C. and the reaction was stirred at the same temperature for 20 min. After completion of the reaction, the reaction mixture was diluted with water (50 mL) and extracted with ethyl acetate (2×60 mL). The combined organic layer was dried over anhydrous sodium sulfate, filtered and concentrated to afford the crude compound. Addition of ethyl acetate (10 mL) to the crude compound resulted in the precipitation of the product. The precipitated product was filtered, washed with ethyl acetate and dried under high vacuum to afford 5-bromoimidazo[5,1-f][1,2,4]triazin-4(3H)-one (0.07 g, 44.3% yield) as off white solid. Calculated (M+H): 214.95; Found (M+H): 215.0.

Step-5

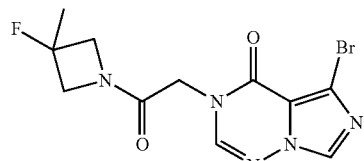

Preparation of 5-bromo-3-(2-(3-fluoro-3-methylazetidin-1-yl)-2-oxoethyl)imidazo[5,1-f][1,2,4]triazin-4(3H)-one To a stirred solution of 2-(5-bromoimidazo[5,1-f][1,2,4]triazin-4(3H)-one (0.25 g, 1.18 mmol) in acetone (30 mL) were added potassium carbonate (0.492 g, 2.37 mmol) and 2-chloro-1-(3-fluoro-3-methylazetidin-1-yl)ethanone (0.393 g, 3.56 mmol) at room temperature. The reaction mixture was heated at 70° C. for 16 h. After the completion of the reaction, the reaction mixture was filtered and the filtrate was concentrated. The crude product was purified by silica gel column chromatography using 80% ethyl acetate in hexane to afford the title compound 5-bromo-3-(2-(3-fluoro-3-methylazetidin-1-yl)-2-oxoethyl)imidazo[5,1-f][1,2,4]triazin-4(3H)-one (0.07 g, 25.7% yield) as off white solid. Calculated (M+H): 344.01, Found (M+H): 344.0.

Step-6

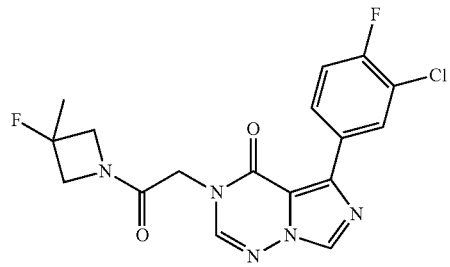 [SMILES: CC1(F)CN(C(=O)Cn2cnn3cnc(-c4ccc(F)c(Cl)c4)c3c2=O)C1]

Preparation of 5-(3-chloro-4-fluorophenyl)-3-(2-(3-fluoro-3-methylazetidin-1-yl)-2-oxoethyl)imidazo[5,1-f][1,2,4]triazin-4(3H)-one To a stirred solution of 5-bromo-3-(2-(3-fluoro-3-methylazetidin-1-yl)-2-oxoethyl)imidazo[5,1-f][1,2,4]triazin-4(3H)-one (0.07 g, 0.20 mmol) in 1,4-dioxane:water mixture (25 mL, 4:1), were added (3-chloro-4-fluorophenyl)boronic acid (0.043 g, 0.24 mmol) and potassium carbonate (0.084 g, 0.610 mmol) and the reaction mixture was purged with argon for 20 min. Then 1,1'-Bis(diphenylphosphino)ferrocene-palladium(II)dichloride dichloromethane complex (0.008 g, 0.010 mmol) was added at room temperature and the reaction mixture was heated at 100° C. for 3 h. After the completion of the reaction, the reaction mixture was cooled to room temperature, filtered and the filtrate was concentrated. The crude product was purified by silica gel column chromatography using 90% ethyl acetate in hexane to afford the title compound 5-(3-chloro-4-fluorophenyl)-3-(2-(3-fluoro-3-methylazetidin-1-yl)-2-oxoethyl)imidazo[5,1-f][1,2,4]triazin-4(3H)-one (0.02 g, 25.3% yield) as off white solid. $^1$H NMR (400 MHz, DMSO-d$_6$) δ (ppm): 8.61 (s, 1H), 8.58 (d, J=7.6 Hz, 1H), 8.31-8.28 (m, 1H), 8.09 (s, 1H), 7.49 (t, J=9.2 Hz, 1H), 4.63 (s, 2H), 4.45-4.31 (m, 2H), 4.07-3.99 (m, 2H), 1.61 (d, J=22.0 Hz, 3H). Calculated (M+H): 394.08; Found (M+H): 394.1; HPLC purity: 99.42%.

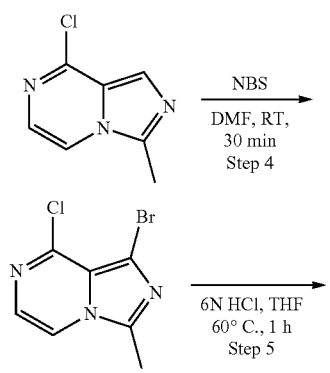

TABLE 46

The following compounds were prepared by the method described above:

| Ex. No. | Structure | Name | Analytical data |
|---|---|---|---|
| 425 | (structure) | 5-(3,4-dichlorophenyl)-3-(2-(3-fluoro-3-methylazetidin-1-yl)-2-oxoethyl)imidazo[5,1-f][1,2,4]triazin-4(3H)-one | $^1$H NMR (400 MHz, DMSO-d$_6$) δ (ppm); 8.63 (s, 2H), 8.29-8.27 (m, 1H), 8.10 (s, 1H), 7.71 (d, J = 8.4 Hz, 1H), 4.64 (s, 2H), 4.47-4.31 (m, 2H), 4.07-3.99 (m, 2H), 1.61 (d, J = 22 Hz, 3H). Calculated (M + H): 410.05; Found (M + 1): 410.0. HPLC purity 98.23% |

P. PREPARATION OF IMIDAZOPYRAZINONES

Example 426: Preparation of 1-(3-chloro-4-fluorophenyl)-7-(2-(3-fluoro-3-methylazetidin-1-yl)-2-oxoethyl)-3-methylimidazo[1,5-a]pyrazin-8(7H)-one

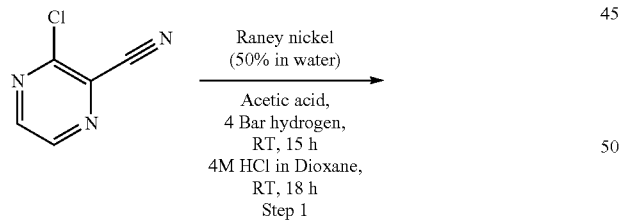

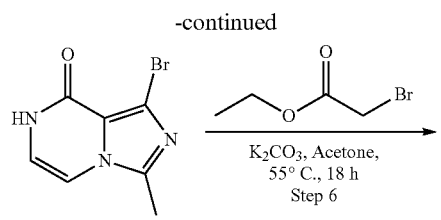

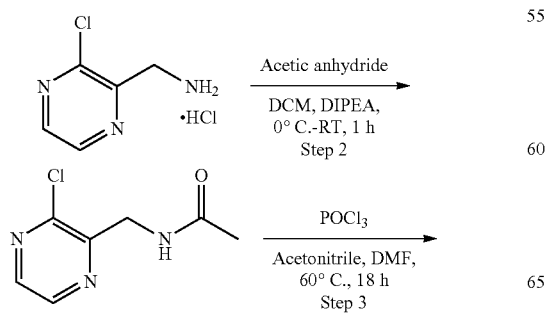

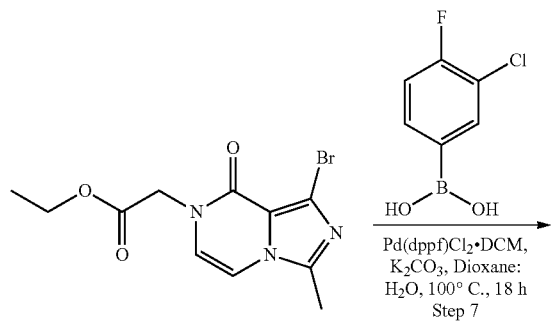

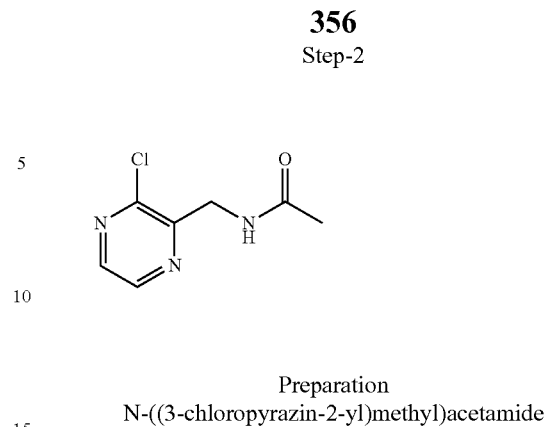

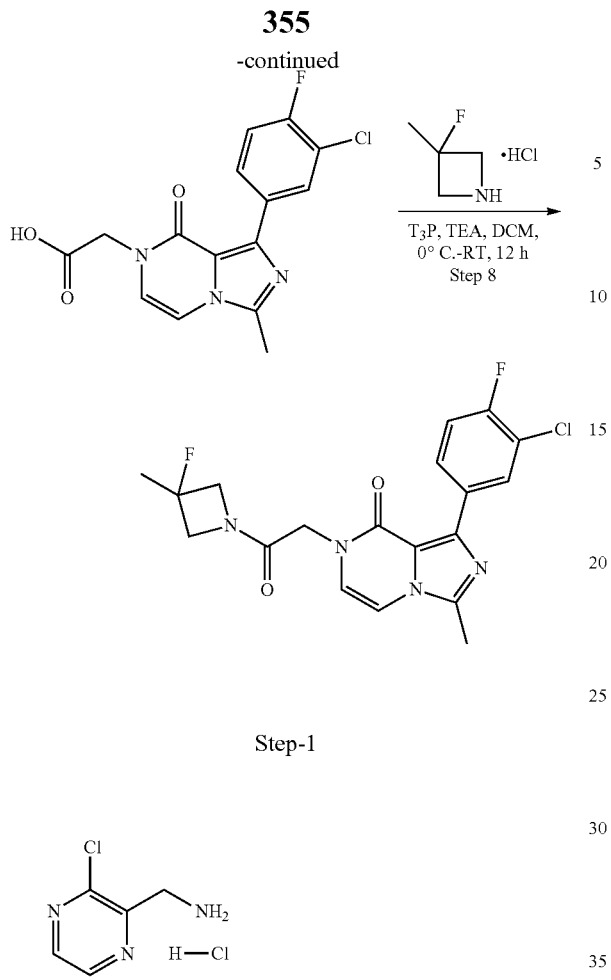

Step-1

Preparation of (3-chloropyrazin-2-yl)methanamine hydrochloride

To a solution of 3-chloropyrazine-2-carbonitrile (10 g) in acetic acid (100 mL) was added Raney Nickel (50% slurry in water, 10 g). The resulting mixture was stirred under 4 bar hydrogen pressure at room temperature for 15 h. The reaction mixture was filtered through celite and the filtrate was concentrated under reduced pressure and co-evaporated with toluene. The remaining brown solid was dissolved in ethyl acetate at 50° C. and cooled on an ice-bath. 4M hydrochloric acid in dioxane (50 mL) was added and the reaction mixture was allowed to stir at room temperature for 18 h. The precipitate formed was collected by filtration, washed with diethyl ether and dried under reduced pressure. The product brown solid obtained was dissolved in methanol at 60° C. and filtered. The filtrate was partially concentrated, cooled to room temperature and diethyl ether (500 mL) was added. The mixture was allowed to stir at room temperature 18 h. The solids formed were collected by filtration, washed with diethyl ether and dried under reduced pressure to afford the title compound (3-chloropyrazin-2-yl)methanamine hydrochloride (7.67 g, crude) as a brown solid. Calculated (M+H): 144.03; Found (M+H): 144.0.

Step-2

Preparation N-((3-chloropyrazin-2-yl)methyl)acetamide

To a solution of (3-chloropyrazin-2-yl)methanamine hydrochloride (3.5 g, 19.49 mmol) in dichloromethane (100 mL) was added diisopropylethylamine (10.18 mL, 38.99 mmol) followed by acetic anhydride (3.67 mL, 38.9 mmol) at room temperature. Then the reaction mixture was stirred at room temperature for 1 h. The reaction mixture was diluted with ice water (100 mL), basified with saturated sodium bicarbonate solution and extracted with ethyl acetate (3×200 mL). The combined organic layer was dried over anhydrous sodium sulphate, filtered and concentrated. The crude product was purified by silica gel column chromatography using 3% methanol in dichloromethane to afford the title compound N-((3-chloropyrazin-2-yl)methyl)acetamide (1.66 g, 46% yield) as a brown solid. Calculated (M+H): 186.0; Found (M+H): 186.1.

Step-3

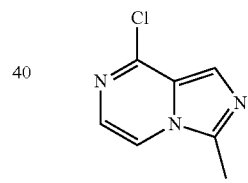

Preparation of 8-chloro-3-methylimidazo[1,5-a]pyrazine

To a solution of N-((3-chloropyrazin-2-yl)methyl)acetamide (1.66 g, 8.97 mmol) in acetonitrile (30 mL) and N,N-dimethylformamide (0.6 mL), was added phosphorous oxychloride (2.5 mL, 26.9 mmol) and the reaction mixture was stirred at 60° C. for 18 h. Then the solvent was removed under pressure, the resulting residue was basified with saturated sodium bicarbonate solution and extracted with ethyl acetate (3×100 mL). The combined organic layer was dried over anhydrous sodium sulphate, filtered and concentrated. The crude product was purified by silica gel column chromatography using 4% methanol in dichloromethane to afford the title compound 8-chloro-3-methylimidazo[1,5-a]pyrazine (1.45 g, 97% yield) as a yellow solid. Calculated (M+H): 168.0; Found (M+H): 168.1.

Step-4

Preparation of 1-bromo-8-chloro-3-methylimidazo[1,5-a]pyrazine

To a solution of 8-chloro-3-methylimidazo[1,5-a]pyrazine (1.45 g, 8.68 mmol) in N,N-dimethylformamide (30 mL), was added N-bromosuccinimide (1.54 g, 8.68 mmol) and the reaction mixture was stirred at room temperature for 30 min. Then the reaction mixture was diluted with water (50 mL) and extracted with ethyl acetate (3×50 mL). The combined organic layer was dried over anhydrous sodium sulphate, filtered and concentrated. The crude product was purified by silica gel column chromatography using 1% methanol in dichloromethane to afford the title compound 1-bromo-8-chloro-3-methylimidazo[1,5-a]pyrazine (1.06 g, 79% yield) as a yellow solid. Calculated (M+H): 245.9; Found (M+H): 246.0.

Step-5

Preparation of 1-bromo-3-methylimidazo[1,5-a]pyrazin-8(7H)-one

To a solution of 1-bromo-8-chloro-3-methylimidazo[1,5-a]pyrazine (1.06 g) in tetrahydrofuran (10 mL), was added 6N aqueous hydrochloric acid (25 mL) and the reaction mixture was stirred at 60° C. for 1 h. Then the reaction mixture was concentrated and dried to afford the title compound 1-bromo-3-methylimidazo[1,5-a]pyrazin-8(7H)-one (0.82 g, 83% yield) as a white solid. Calculated (M+H): 227.9; Found (M+H): 228.0.

Step-6

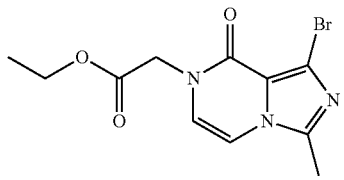 [SMILES: CCOC(=O)Cn1ccn2c(C)nc(Br)c2c1=O]

Preparation of ethyl 2-(1-bromo-3-methyl-8-oxoimidazo[1,5-a]pyrazin-7(8H)-yl)acetate To a stirred solution 1-bromo-3-methylimidazo[1,5-a]pyrazin-8(7H)-one (0.3 g, 1.32 mmol) in dry acetone (15 mL) was added potassium carbonate (0.54 g, 3.96 mmol) followed by ethyl 2-bromoacetate (0.29 mL, 2.64 mmol) at room temperature and the reaction mixture was heated at reflux for 18 h. The reaction mixture was filtered and the filtrate was concentrated. The crude product was purified by silica gel column chromatography using 2% methanol in dichloromethane to afford the title compound ethyl 2-(1-bromo-3-methyl-8-oxoimidazo[1,5-a]pyrazin-7(8H)-yl)acetate (0.37 g, 89% yield) as a white solid. Calculated (M+H): 314.0; Found (M+H): 314.0.

Step-7

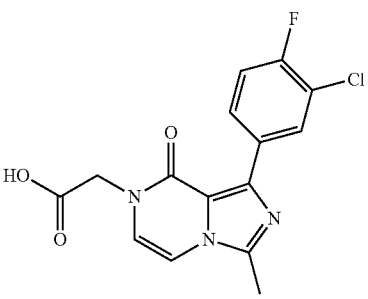 [SMILES: Cc1nc(-c2ccc(F)c(Cl)c2)c2c(=O)n(CC(=O)O)ccn12]

Preparation of 2-(1-(3-chloro-4-fluorophenyl)-3-methyl-8-oxoimidazo[1,5-a]pyrazin-7(8H)-yl)acetic acid To a solution of ethyl 2-(1-bromo-3-methyl-8-oxoimidazo[1,5-a]pyrazin-7(8H)-yl)acetate (0.37 g, 1.18 mmol) and (3-chloro-3-fluro-phenyl)boronic acid (0.267 g, 1.53 mmol) in 1,4-dioxane:water mixture (20 mL, 4:1), potassium carbonate (0.49 g, 3.54 mmol) was added. The reaction mixture was purged with argon for 15 min, 1,1'-bis(diphenylphosphino)ferrocene-palladium(II)dichloride dichloromethane complex [Pd(dppf)Cl₂.DCM] (0.048 g, 0.059 mmol) was added and the reaction mixture was stirred at 100° C. for 18 h. The reaction mixture was diluted with water (60 mL) and washed with ethyl acetate (2×30 mL). The aqueous layer was separated, acidified with 1.5M hydrochloric acid solution and extracted with ethyl acetate (3×60 mL). The combined organic layer was dried over anhydrous sodium sulphate, filtered and concentrated to afford the title compound 2-(1-(3-chloro-4-fluorophenyl)-3-methyl-8-oxoimidazo[1,5-a]pyrazin-7(8H)-yl)acetic acid (0.22 g, 55% yield) as off-white solid. Calculated (M+H): 336.0; Found (M+H): 336.1.

Step-8

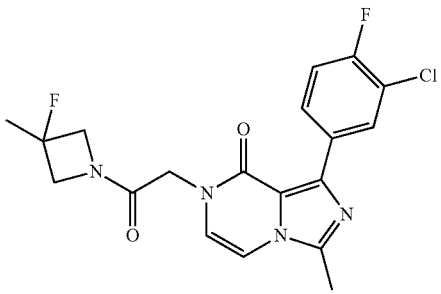 [SMILES: Cc1nc(-c2ccc(F)c(Cl)c2)c2c(=O)n(CC(=O)N3CC(C)(F)C3)ccn12]

Preparation 1-(3-chloro-4-fluorophenyl)-7-(2-(3-fluoro-3-methylazetidin-1-yl)-2-oxoethyl)-3-methyl-imidazo[1,5-a]pyrazin-8(7H)-one To a stirred solution of 2-(1-(3-chloro-4-fluorophenyl)-3-methyl-8-oxoimidazo[1,5-a]pyrazin-7(8H)-yl)acetic acid (0.11 g, 0.32 mmol) and 3-fluoro-3-methylazetidine hydrochloride (0.082 g, 0.65 mmol) in dichloromethane (15 mL) was added triethylamine (0.36 mL, 2.62 mmol) and the reaction mixture was cooled to 0° C. Then 1-propanephosphonic anhydride solution ($T_3P$) (0.35 mL, 0.55 mmol, 50% in ethyl acetate) was added and the reaction mixture was stirred at room temperature for 12 h. The solution was diluted with water and extracted with dichloromethane (3×30 mL). The combined organic layer was dried over anhydrous sodium sulfate, filtered and concentrated to get the crude compound. The crude product was purified by preparative HPLC (analytical conditions: column: chemsil $C_{18}$ (250 mm×4.6 mm×5 mic), mobile phase (A): 0.1% ammonia in water, mobile phase (B): acetonitrile, flow rate: 1.0 mL/min, T/% B: 0/20, 10/80, 25/90, 27/20, 30/20) to afford the title compound 1-(3-chloro-4-fluorophenyl)-7-(2-(3-fluoro-3-methylazetidin-1-yl)-2-oxoethyl)-3-methylimidazo[1,5-a]pyrazin-8(7H)-one (0.022 g, 16% yield) as a white solid. $^1$H NMR (400 MHz, DMSO-$d_6$) δ (ppm): 8.59 (dd, $J_1$=2 Hz, 7.6 Hz, 1H), 8.29-8.25 (m, 1H), 7.42 (t, J=9.2 Hz, 1H), 7.35 (d, J=6 Hz, 1H), 6.86 (d, J=6 Hz, 1H), 4.53 (s, 2H); 4.38-4.30 (m, 2H), 4.01 (d, J=19.2 Hz, 2H), 2.55 (s, 3H), 1.63 (d, J=22 Hz, 3H). Calculated (M+H): 407.1, Found (M+H): 407.1. HPLC purity: 99.71%.

The following compounds were prepared by the method described above:

| Ex. No. | Structure | IUPAC Name | Analytical Data |
|---|---|---|---|
| 427 | 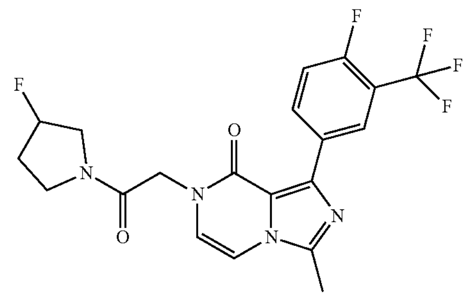 [SMILES: Cc1nc(-c2ccc(F)c(C(F)(F)F)c2)c2c(=O)n(CC(=O)N3CCC(F)C3)ccn12] | 1-(4-fluoro-3-(trifluoromethyl)phenyl)-7-(2-(3-fluoropyrrolidin-1-yl)-2-oxoethyl)-3-methylimidazo[1,5-a]pyrazin-8(7H)-one | $^1$H NMR (400 MHz, DMSO-$d_6$) δ (ppm): 8.80 (d, J = 6.8 Hz, 1H), 8.62 (s , 1H), 7.52 (t, J = 10 Hz, 1H), 7.36 (d, J = 6 Hz, 1H), 6.87 (s, 1H), 5.38-5.2 (m, 1H), 4.77-4.63 (m, 2H), 3.79-3.58 (m, 4H), 2.56 (s, 3H), 2.30-1.96 (m, 2H), Calculated (M + H): 441.1; Found (M + H): 441.1. HPLC purity: 99.13% |
| 428 | 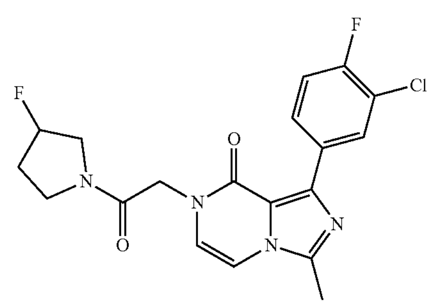 [SMILES: Cc1nc(-c2ccc(F)c(Cl)c2)c2c(=O)n(CC(=O)N3CCC(F)C3)ccn12] | 1-(3-chloro-4-fluorophenyl)-7-(2-(3-fluoropyrrolidin-1-yl)-2-oxoethyl)-3-methylimidazo[1,5-a]pyrazin-8(7H)-one | $^1$H NMR (400 MHz, DMSO-$d_6$) δ (ppm): 8.60 (d, J = 7.6 Hz, 1H), 8.28-8.25 (m, 1H), 7.41 (t, J = 12 Hz, 1H), 7.35 (d, J = 6 Hz, 1H), 6.87 (t, J = 2.8 Hz, 1H), 5.50-5.25 (m, 1H), 4.80-4.61 (m, 2H), 3.87-3.48 (m, 4H), 2.54 (s, 3H), 2.30-1.96 (m, 2H), Calculated (M + H): 407.1; Found (M + H): 407.1. HPLC purity: 99.36% |
| 429 | 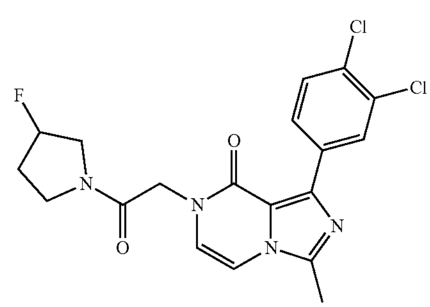 [SMILES: Cc1nc(-c2ccc(Cl)c(Cl)c2)c2c(=O)n(CC(=O)N3CCC(F)C3)ccn12] | 1-(3,4-dichlorophenyl)-7-(2-(3-fluoropyrrolidin-1-yl)-2-oxoethyl)-3-methylimidazo[1,5-a]pyrazin-8(7H)-one | $^1$H NMR (400 MHz, DMSO-$d_6$) δ (ppm): 8.67 (s, 1H), 8.28 (d, J = 8.4 Hz, 1H), 7.64 (d, J = 8.4 Hz, 1H), 7.36 (d, J = 5 .6 Hz, 1H), 6.89-6.87 (m, 1H), 5.51-5.25 (m, 1H), 4.81-4.61 (m, 2H), 3.88-3.49 (m, 4H), 2.55 (s, 3H), 2.30-2.08 (m, 2H). Calculated (M + H): 423.0; Found (M + H): 423.1. HPLC purity: 99.05% |

| Ex. No. | Structure | IUPAC Name | Analytical Data |
|---|---|---|---|
| 430 | 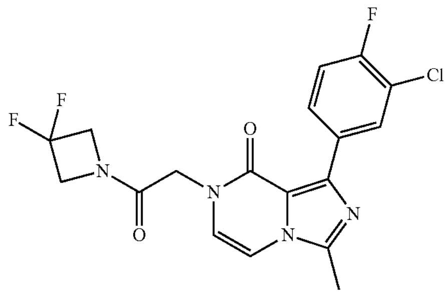 [SMILES: Cc1nc(-c2ccc(F)c(Cl)c2)c2c(=O)n(CC(=O)N3CC(F)(F)C3)ccn12] | 1-(3-chloro-4-fluorophenyl)-7-(2-(3,3-difluoroazetidin-1-yl)-2-oxoethyl)-3-methylimidazo[1,5-a]pyrazin-8(7H)-one | $^1$H NMR (400 MHz, DMSO-$d_6$) δ (ppm): 8.59 (d, J = 7.6 Hz, 1H), 8.28-8.25 (m, 1H), 7.42 (t, J = 8.8 Hz, 1H), 7.35 (d, J = 6 Hz 1H), 6.85 (d, J = 5.6 Hz, 1H), 4.73 (t, J = 11.2 Hz, 2H), 4.60 (s, 2H), 4.35 (t, J = 12 Hz, 2H), 2.55 (s, 3H), Calculated (M + H): 411.0; Found (M + H): 411.1. HPLC purity: 96.7% |
| 431 | 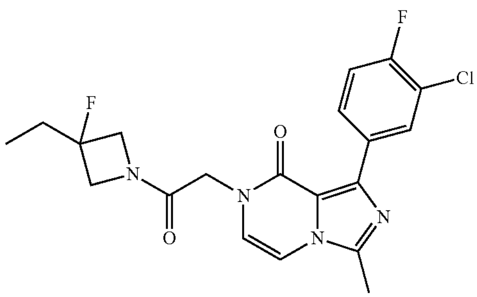 [SMILES: CCC1(F)CN(C(=O)Cn2ccn3c(C)nc(-c4ccc(F)c(Cl)c4)c3c2=O)C1] | 1-(3-chloro-4-fluorophenyl)-7-(2-(3-ethyl-3-fluoroazetidin-1-yl)-2-oxoethyl)-3-methylimidazo[1,5-a]pyrazin-8(7H)-one | $^1$H NMR (400 MHz, DMSO-$d_6$) δ (ppm): 8.59 (d, J = 6.8 Hz, 1H), 8.26 (brs, 1H), 7.41 (t, J = 9.2 Hz, 1H), 7.34 (d, J = 5.6 Hz, 1H), 6.85 (d, J = 6.4 Hz, 1H), 4.53 (s, 2H), 4.36-4.30 (m, 2H), 4.01-3.92 (m, 2H), 2.54(s, 3H), 1.92-1.85 (m, 2H), 0.92 (t, J = 7.2 Hz, 3H), Calculated (M + H): 421.1; Found (M + H): 421.1. HPLC purity: 96.71% |

Example 432: Preparation of 1-(3-chloro-4-fluorophenyl)-3-cyclopropyl-7-(2-(3-fluoropyrrolidin-1-yl)-2-oxoethyl)imidazo[1,5-a]pyrazin-8(7H)-one

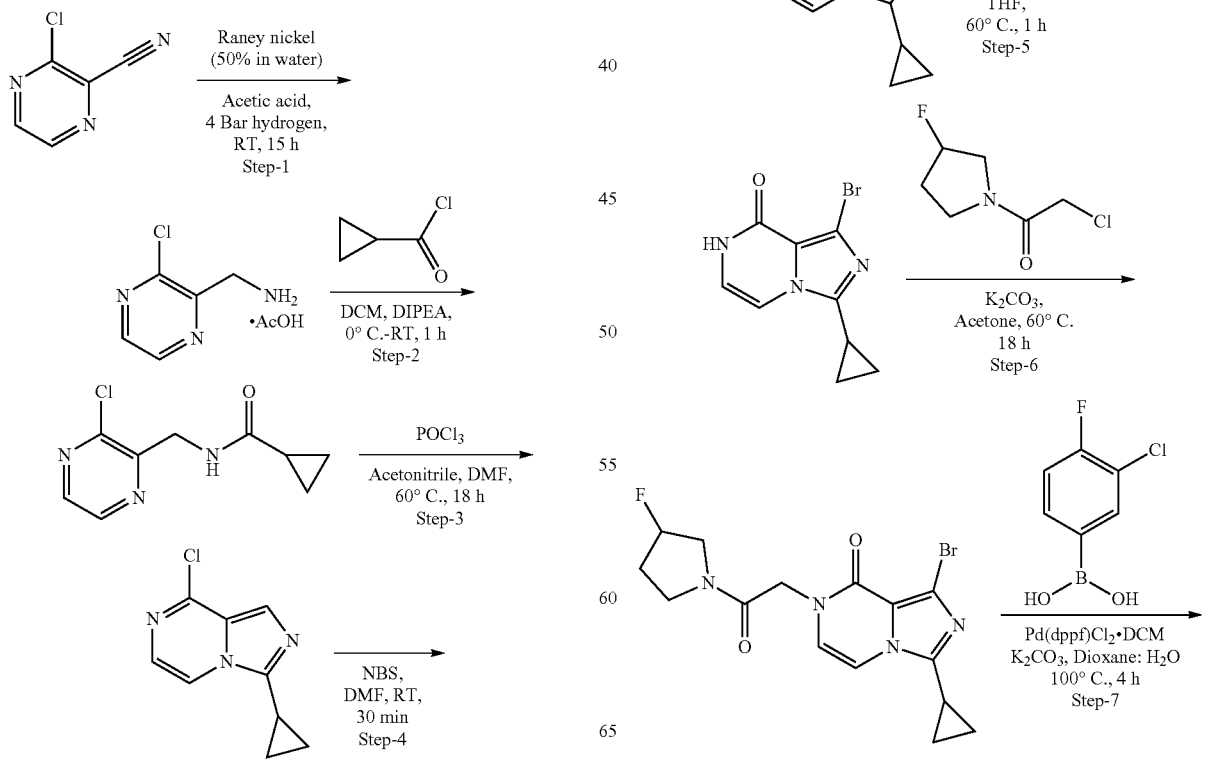

-continued

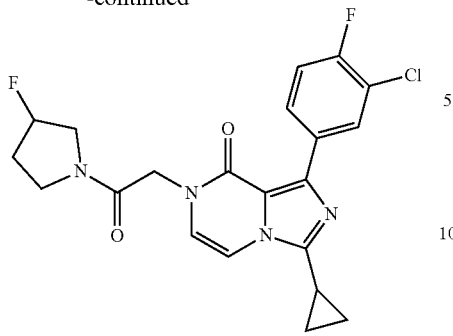

Step-1

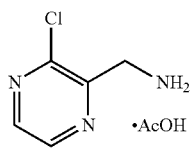

Preparation of (3-chloropyrazin-2-yl)methanamine

To a solution of 3-chloropyrazine-2-carbonitrile (2 g) in acetic acid (20 mL) was added Raney nickel (50% slurry in water, 1.6 g). The resulting mixture was stirred under 4 bar hydrogen pressure at room temperature for 15 h. The reaction mixture was filtered through celite and the filtrate was concentrated under reduced pressure and co-evaporated with toluene to afford the title compound (3-chloropyrazin-2-yl) methanamine acetate (2.9 g, crude) as brown solid. Calculated (M+H): 144.03; Found (M+H): 144.0.

Step-2

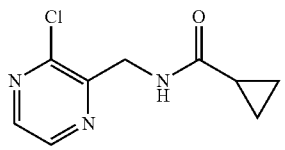 [SMILES: O=C(NCc1nccnc1Cl)C1CC1]

Preparation of N-((3-chloropyrazin-2-yl)methyl) cyclopropanecarboxamide

To a solution of (3-chloropyrazin-2-yl)methanamine (5.0 g, 24.63 mmol) in dichloromethane (50 mL) was added diisopropylethylamine (13.26 mL, 73.89 mmol) followed by cyclopropanecarbonyl chloride (4.46 mL, 49.26 mmol). Then the reaction mixture was stirred at room temperature for 1 h. The reaction mixture was diluted with ice water (100 mL), basified with sodium bicarbonate solution and extracted with ethyl acetate (3×100 mL). The combined organic layer was dried over anhydrous sodium sulphate, filtered and concentrated. The crude product was purified by silica gel column chromatography using 2% methanol in dichloromethane to afford the title compound N-((3-chloro-pyrazin-2-yl)methyl)cyclopropanecarboxamide (2.5 g, 47% yield) as brown solid. Calculated (M+H): 212.05; Found (M+H): 212.1.

Step-3

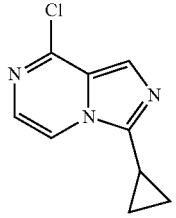 [SMILES: Clc1nccn2c(C3CC3)ncc12]

Preparation of 8-chloro-3-cyclopropylimidazo[1,5-a]pyrazine

To a solution of N-((3-chloropyrazin-2-yl)methyl)cyclo-propanecarboxamide (2.5 g, 12.32 mmol) in acetonitrile (80 mL) and N,N-dimethylformamide (0.5 mL), was added phosphorous oxychloride (3.4 mL, 36.96 mmol) and the reaction mixture was stirred at 60° C. for 2 h. Then the solvent was removed under pressure, the resulting crude mixture was basified with sodium bicarbonate solution and extracted with ethyl acetate (3×100 mL). The combined organic layer was dried over anhydrous sodium sulphate, filtered and concentrated. The crude product was purified by silica gel column chromatography using 3% methanol in dichloromethane to afford the title compound 8-chloro-3-cyclopropylimidazo[1,5-a]pyrazine (1.65 g, 68% yield) as pale yellow solid. Calculated (M+H): 194.04; Found (M+H): 194.1.

Step-4

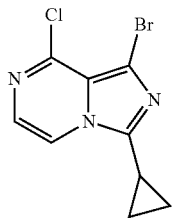 [SMILES: Clc1nccn2c(C3CC3)nc(Br)c12]

Preparation of 1-bromo-8-chloro-3-cyclopropylimi-dazo[1,5-a]pyrazine

To a solution of 8-chloro-3-cyclopropylimidazo[1,5-a] pyrazine (1.65 g, 8.54 mmol) in N,N-dimethylformamide (50 mL), was added N-bromosuccinimide (1.54 g, 8.54 mmol) and the reaction mixture was stirred at room temperature for 30 min. Then the reaction mixture was diluted with water (50 mL) and extracted with ethyl acetate (3×50 mL). The combined organic layer was dried over anhydrous sodium sulphate, filtered and concentrated. The crude product was purified by silica gel column chromatography using 30% ethyl acetate in hexane afford the title compound 1-bromo-8-chloro-3-cyclopropylimidazo[1,5-a]pyrazine (1.6 g, 69.0% yield) as white solid. Calculated (M+H): 271.95; Found (M+H): 272.0.

Step-5

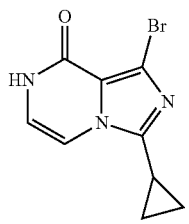 [SMILES: O=c1[nH]ccn2c(C3CC3)nc(Br)c12]

Preparation of 1-bromo-3-cyclopropylimidazo[1,5-a]pyrazin-8(7H)-one

To a solution of 1-bromo-8-chloro-3-cyclopropylimidazo[1,5-a]pyrazine (1.6 g, 5.90 mmol) in tetrahydrofuran (15 mL), was added 6N hydrochloric acid (50 mL) and the reaction mixture was stirred at 60° C. for 2 h. Then the reaction mixture was diluted with water (50 mL), basified with sodium bicarbonate solution and extracted with ethyl acetate (3×70 mL). The combined organic layer was dried over anhydrous sodium sulphate, filtered and concentrated to afford the title compound 1-bromo-3-cyclopropylimidazo[1,5-a]pyrazin-8(7H)-one (1.62 g, 99% yield) as brown solid. Calculated (M+H): 253.9; Found (M+H): 254.1.

Step-6

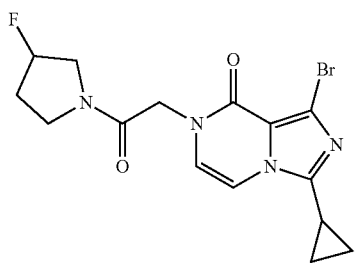 [SMILES: O=C(Cn1ccn2c(C3CC3)nc(Br)c2c1=O)N1CCC(F)C1]

Preparation of 1-bromo-3-cyclopropyl-7-(2-(3-fluoropyrrolidin-1-yl)-2-oxoethyl)imidazo[1,5-a]pyrazin-8(7H)-one To a stirred solution of 1-bromo-3-cyclopropylimidazo[1,5-a]pyrazin-8(7H)-one (0.35 g, 1.35 mmol) in dry acetone (30 mL) was added potassium carbonate (0.57 g, 4.18 mmol) followed by 2-chloro-1-(pyrrolidin-1-yl)ethanone (0.27 g, 1.67 mmol) at room temperature and the reaction mixture was heated at 60° C. for 18 h. The reaction mixture was filtered and the filtrate was concentrated under vacuum. The crude product was purified by silica gel column chromatography using 2% methanol in dichloromethane to afford the title compound 1-bromo-3-cyclopropyl-7-(2-(3-fluoropyrrolidin-1-yl)-2-oxoethyl)imidazo[1,5-a]pyrazin-8(7H)-one (045 g, 84% yield) as pale yellow solid. Calculated (M+H): 383.04; Found (M+H): 383.2.

Step-7

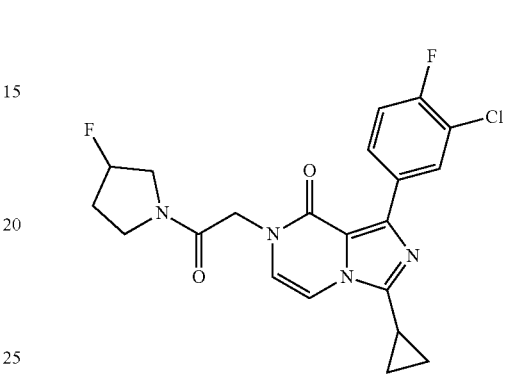

Preparation of 1-(3-chloro-4-fluorophenyl)-3-cyclopropyl-7-(2-(3-fluoropyrrolidin-1-yl)-2-oxoethyl)imidazo[1,5-a]pyrazin-8(7H)-one To a solution of 1-bromo-3-cyclopropyl-7-(2-(3-fluoropyrrolidin-1-yl)-2-oxoethyl)imidazo[1,5-a]pyrazin-8(7H)-one (015 g, 0.9 mmol) and (3-chloro-3-fluro-phenyl)boronic acid (0.09 g, 0509 mmol) in 1,4-dioxane:water mixture (20 mL, 4:1), potassium carbonate (0.16 g, 1.17 mmol) was added. The reaction mixture was purged with argon for 15 min and 1,1'-Bis(diphenylphosphino)ferrocene-palladium (II)dichloride dichloromethane complex (Pd(dppf)Cl$_2$.DCM) (0.03 g, 0.039 mmol) was added. Then the reaction mixture was stirred at 100° C. for 4 h. The reaction mixture was diluted with water (30 mL) and extracted with ethyl acetate (3×50 mL). The combined organic layer was dried over anhydrous sodium sulphate, filtered and concentrated. The crude product was purified by silica gel column chromatography using 2% methanol in dichloromethane to afford the title compound 1-(3-chloro-4-fluorophenyl)-3-cyclopropyl-7-(2-(3-fluoropyrrolidin-1-yl)-2-oxoethyl)imidazo[1,5-a]pyrazin-8(7H)-one (0.041 g, 24% yield) as off-white solid. $^1$H NMR (400 MHz, DMSO-d$_6$) δ (ppm): 8.54 (d, J=6.8 Hz, 1H), 8.23-8.23 (m, 1H), 7.57 (d, J=6.0 Hz, 1H), 7.40 (t, J=9.2 Hz, 1H), 6.89-6.87 (m, 1H), 5.50-4.79 (m, 1H), 4.79-4.61 (m, 2H), 3.87-3.30 (m, 4H), 2.40-1.94 (m, 3H), 1.08-1.03 (m, 4H). Calculated (M+H): 433.12; Found (M+H): 433.1. HPLC purity: 99.7%.

| Ex. No. | Structure | IUPAC Name | Analytical Data |
|---|---|---|---|
| 433 | 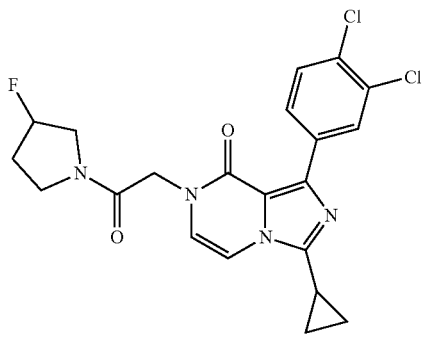 [SMILES: O=C(Cn1ccn2c(C3CC3)nc(-c3ccc(Cl)c(Cl)c3)c2c1=O)N1CCC(F)C1] | 3-cyclopropyl-1-(3,4-dichlorophenyl)-7-(2-(3-fluoropyrrolidin-1-yl)-2-oxoethyl)imidazo[1,5-a]pyrazin-8(7H)-one | $^1$H NMR (400 MHz, DMSO-$d_6$) δ (ppm): 8.62 (s, 1H), 8.22 (d, J = 8.4 Hz, 1H), 7.62-7.58 (m, 2H), 6.90-6.88 (m, 1H), 5.51-5.25 (m, 1H), 4.80-4.65 (m, 2H), 3.88-3.39 (m, 4H), 2.36-1.97 (m, 3H), 1.08-1.03 (m, 4H). (M + H): 449.09; Found (M + H): 449.1:, HPLC purity: 98.68% |
| 434 | 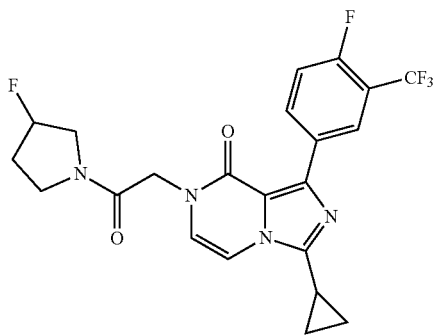 [SMILES: O=C(Cn1ccn2c(C3CC3)nc(-c3ccc(F)c(C(F)(F)F)c3)c2c1=O)N1CCC(F)C1] | 3-cyclopropyl-1-(4-fluoro-3-(trifluoromethyl)phenyl)-7-(2-(3-fluoropyrrolidin-1-yl)-2-oxoethyl)imidazo[1,5-a]pyrazin-8(7H)-one | $^1$H NMR (400 MHz, DMSO-$d_6$) δ (ppm): 8.75 (d, J = 6.8 Hz, 1H), 8.53 (s, 1H), 7.59 (d, J = 5.6 Hz, 1H), 7.51 (t, J = 10.4 Hz, 1H), 6.90-6.88 (m, 1H), 5.50-5.25 (m, 1H), 4.81-4.61 (m, 2H), 3.88-3.38 (m, 4H), 2.35-1.96 (m, 3H), 1.21-1.04 (m, 4H), (M + H): 467.14; Found (M + H): 467.1:, HPLC purity: 98.03% |
| 435 | 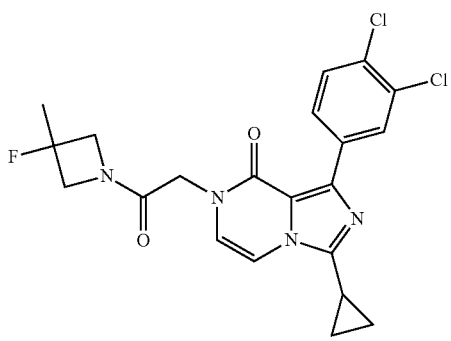 [SMILES: CC1(F)CN(C(=O)Cn2ccn3c(C4CC4)nc(-c4ccc(Cl)c(Cl)c4)c3c2=O)C1] | 3-cyclopropyl-1-(3,4-dichlorophenyl)-7-(2-(3-fluoro-3-methylazetidin-1-yl)-2-oxoethyl)imidazo[1,5-a]pyrazin-8(7H)-one | $^1$H-NMR (DMSO-$d_6$, 400 MHz) δ (ppm): 8.61 (s, 1H), 8.21 (d, J = 8 Hz, 1H), 7.63-7.57 (m, 2H), 6.87 (d, J = 6 Hz, 1H), 4.54 (s, 2H), 4.41-4.28 (m, 2H), 4.02-3.97 (m, 2H), 2.32 (brs, 1H), 1.6 (d, J = 22 Hz, 3H), 1.08-1.03 (m, 4H). Calculated (M + H): 449.09, Found (M + H): 449.0, HPLC purity: 98.33%. |
| 436 | 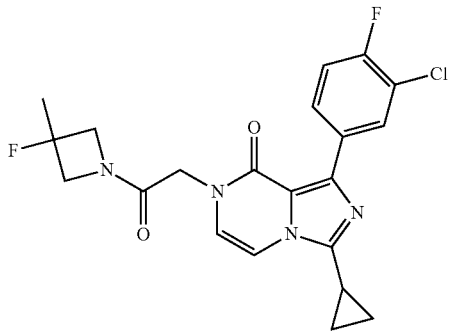 [SMILES: CC1(F)CN(C(=O)Cn2ccn3c(C4CC4)nc(-c4ccc(F)c(Cl)c4)c3c2=O)C1] | 1-(3-chloro-4-fluorophenyl)-3-cyclopropyl-7-(2-(3-fluoro-3-methylazetidin-1-yl)-2-oxoethyl)imidazo[1,5-a]pyrazin-8(7H)-one | $^1$H-NMR (DMSO-$d_6$, 400 MHz) δ (ppm): 8.53 (d, J = 7.6 Hz, 1H), 8.23-8.2 (m, 1H), 7.56 (d, J = 5.6 Hz, 1H), 7.4 (t, J = 8.8 Hz, 1H), 6.86 (d, J = 6 Hz, 1H), 4.53 (s, 2H), 4.41-4.28 (m, 2H), 4.01-3.96 (m, 2H), 2.33-2.3 (m, 1H), 1.6 (d, J = 22 Hz, 3H), 1.08-1.03 (m, 4H). Calculated (M + H): 433.12, Found (M + H): 433.1, HPLC purity: 99.52%. |

| Ex. No. | Structure | IUPAC Name | Analytical Data |
|---|---|---|---|
| 437 | 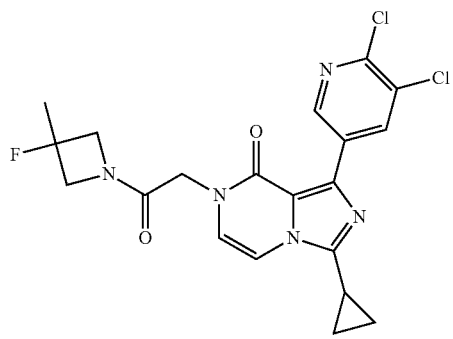 [SMILES: CC1(F)CN(C(=O)Cn2ccn3c(C4CC4)nc(-c4cnc(Cl)c(Cl)c4)c3c2=O)C1] | 3-cyclopropyl-1-(5,6-dichloropyridin-3-yl)-7-(2-(3-fluoro-3-methylazetidin-1-yl)-2-oxoethyl)imidazo[1,5-a]pyrazin-8(7H)-one | $^1$H-NMR (DMSO-$d_6$, 400 MHz) δ (ppm): 9.1 (s, 1H), 8.95 (s, 1H), 7.63 (d, J = 5.6 Hz, 1H), 6.92 (d, J = 5.6 Hz, 1H), 4.56 (s, 2H), 4.42-4.29 (m, 2H), 4.02-3.97 (m, 2H), 2.34-2.31 (m, 1H), 1.6 (d, J = 22 Hz, 3H), 1.09-1.05 (m, 4H). Calculated (M + H): 450.08, Found (M + H): 450.2, HPLC purity: 99.12%. |
| 438 | 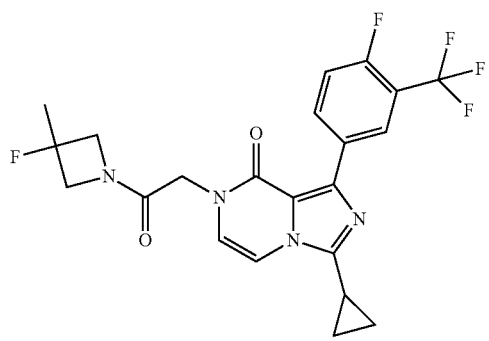 [SMILES: CC1(F)CN(C(=O)Cn2ccn3c(C4CC4)nc(-c4ccc(F)c(C(F)(F)F)c4)c3c2=O)C1] | 3-cyclopropyl-1-(4-fluoro-3-(trifluoromethyl)phenyl)-7-(2-(3-fluoro-3-methylazetidin-1-yl)-2-oxoethyl)imidazo[1,5-a]pyrazin-8(7H)-one | $^1$H-NMR (DMSO-$d_6$, 400 MHz) δ (ppm): 8.76 (d, J = 6.8 Hz, 1H), 8.52 (brs, 1H), 7.58 (d, J = 6 Hz, 1H), 7.51 (t, J = 10 Hz, 1H), 6.87 (d, J = 6.4 Hz, 1H), 4.54 (s, 2H), 4.42-4.28 (m, 2H), 4.01-3.96 (m, 2H), 2.33-2.31 (m, 1H), 1.59 (d, J = 22 Hz, 3H), 1.08-1.04 (m, 4H). Calculated (M + H): 467.14, Found (M + H): 467.3, HPLC purity: 99.63%. |
| 439 | 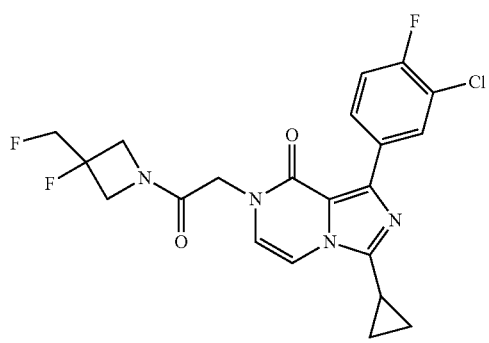 | 1-(3-chloro-4-fluorophenyl)-3-cyclopropyl-7-(2-(3-fluoro-3-(fluoromethyl)azetidin-1-yl)-2-oxoethyl)imidazo[1,5-a]pyrazin-8(7H)-one | $^1$H NMR (400 MHz, DMSO-$d_6$) δ (ppm); 8.53 (d, J = 6.0 Hz, 1H), 8.21 (s, 1H), 7.57 (d, J = 5.6 Hz, 1H), 7.40 (t, J = 8.8 Hz, 1H), 6.85 (d, J = 5.6 Hz, 1H), 4.90-4.72 (m, 2H), 4.55 (s, 2H), 4.51-4.40 (m, 2H), 4.15-4.01 (m, 2H), 1.08-1.03 (m, 4H). 1H was merged with DMSO residual peak. Calculated (M + H): 451.11; Found (M + 1): 451.0. HPLC purity 99.09% |
| 440 | 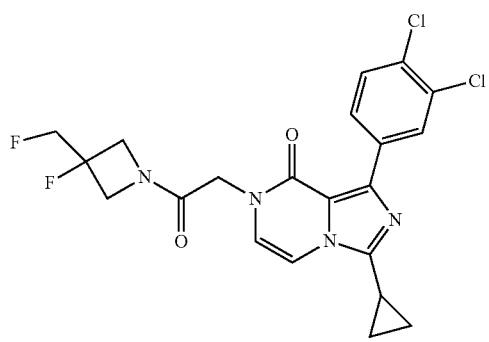 [SMILES: O=C(Cn1ccn2c(C3CC3)nc(-c3ccc(F)c(Cl)c3)c2c1=O)N1CC(F)(CF)C1] | 3-cyclopropyl-1-(3,4-dichlorophenyl)-7-(2-(3-fluoro-3-(fluoromethyl)azetidin-1-yl)-2-oxoethyl)imidazo[1,5-a]pyrazin-8(7H)-one | $^1$H NMR (400 MHz, DMSO-$d_6$) δ (ppm); 8.61 (s, 1H), 8.21 (d, J = 8.8 Hz, 1H), 7.63-7.58 (m, 2H), 6.87 (d, J = 6 Hz, 1H), 4.90-4.72 (m, 2H), 4.56 (s, 2H), 4.51-4.37 (m, 2H), 4.15-3.98 (m, 2H), 2.33-2.31 (m, 1H), 1.08-1.03 (m, 4H). Calculated (M + H): 467.08; Found (M + 1): 467.1. HPLC purity 99.64% |

-continued

| Ex. No. | Structure | IUPAC Name | Analytical Data |
|---|---|---|---|
| 441 | 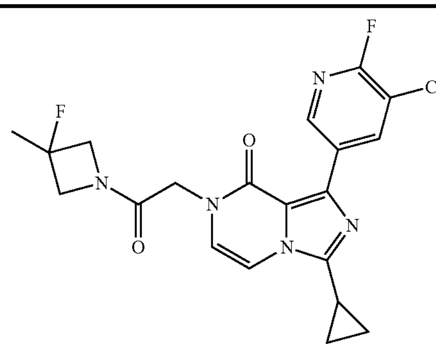 | 1-(5-chloro-6-fluoropyridin-3-yl)-3-cyclopropyl-7-(2-(3-fluoro-3-methylazetidin-1-yl)-2-oxoethyl)imidazo[1,5-a]pyrazin-8(7H)-one | $^1$H NMR (400 MHz, DMSO-d$_6$) δ (ppm): 8.96 (d, J = 7.6 Hz, 1H), 8.89 (s, 1H), 7.62 (d, J = 6.4 Hz, 1H), 6.91 (d, J = 6 Hz, 1H), 4.54 (s, 2H), 4.41-4.28 (m, 2H), 4.04 (d, J = 12 Hz, 2H), 2.48-2.30 (m, 1H), 1.62 (d, J = 22 Hz, 3H), 1.09-1.04 (m, 4H). Calculated (M + H): 434.1; Found (M + H): 434.0. HPLC purity: 97.07% |
| 442 | 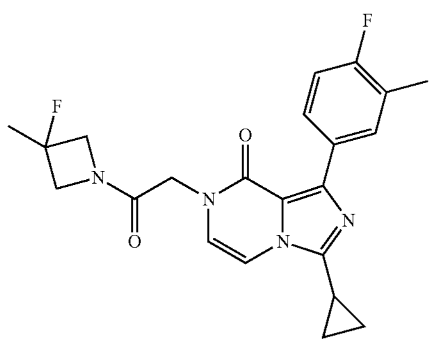 | 3-cyclopropyl-7-(2-(3-fluoro-3-methylazetidin-1-yl)-2-oxoethyl)-1-(4-fluoro-3-methylphenyl)imidazo[1,5-a]pyrazin-8(7H)-one | $^1$H NMR (400 MHz, DMSO-d$_6$) δ (ppm): 8.08-8.02 (m, 2H), 7.53 (d, J = 6 Hz, 1H), 7.10 (t, J = 8.8 Hz, 1H), 6.82 (d, J = 5.6 Hz, 1H), 4.50 (s, 2H), 4.40-4.26 (m, 2H), 4.00 (d, J = 19.6 Hz, 2H), 2.48-2.27(m, 1H), 2.24 (s, 3H), 1.62 (d, J = 22 Hz, 3H), 1.06-1.01 (m, 4H). Calculated (M + H): 413.1; Found (M + H): 413.0. HPLC purity: 99.51% |
| 443 | 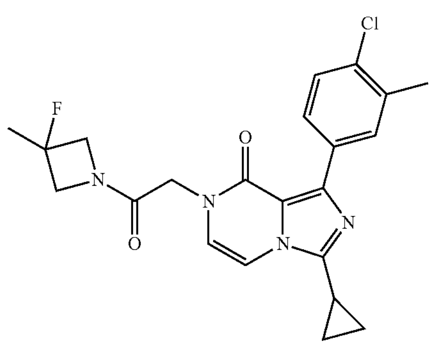 | 1-(4-chloro-3-methylphenyl)-3-cyclopropyl-7-(2-(3-fluoro-3-methylazetidin-1-yl)-2-oxoethyl)imidazo[1,5-a]pyrazin-8(7H)-one | $^1$H NMR (400 MHz, DMSO-d$_6$) δ (ppm): 8.16 (s, 1H), 8.06 (d, J = 8.4 Hz, 1H), 7.55 (d, J = 6.4 Hz, 1H), 7.38 (d, J = 9.2 Hz, 1H), 6.84 (d, J = 6 Hz, 1H) 4.51 (s, 2H), 4.40-4.26 (m, 2H), 4.04 (d, J = 12.8 Hz, 2H), 2.33-2.27(m, 4H), 1.62 (d, J = 22 Hz, 3H), 1.06-1.02 (m, 4H). Calculated (M + H): 429.1; Found (M + H): 429.0. HPLC purity: 98.99% |

Example 444: Preparation of 1-(3-chloro-4-fluorophenyl)-7-(2-(3-fluoro-3-methylazetidin-1-yl)-2-oxoethyl)imidazo[1,5-a]pyrazin-8(7H)-one

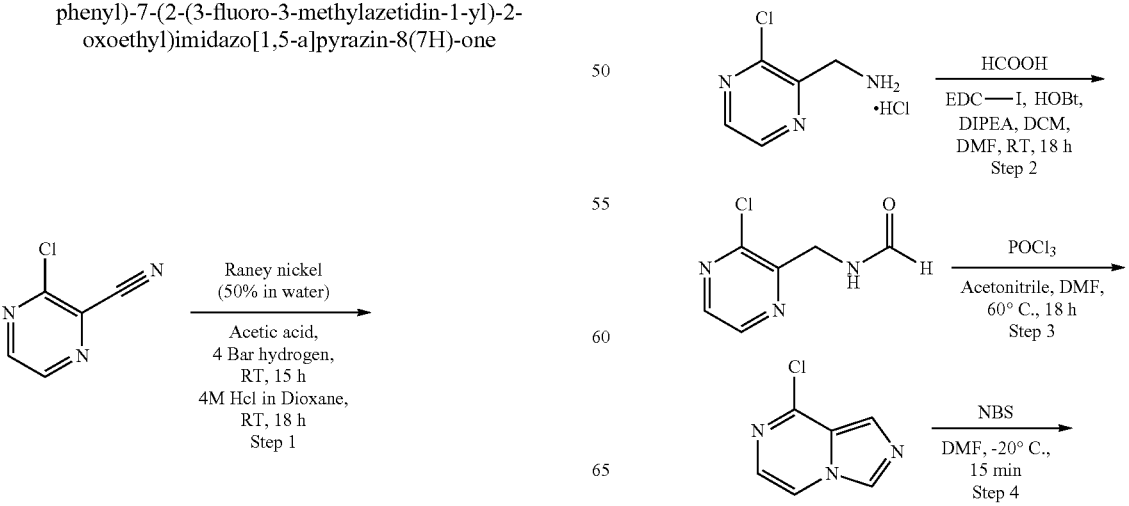

Step 2

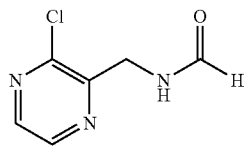 [SMILES: O=CNCc1nccnc1Cl]

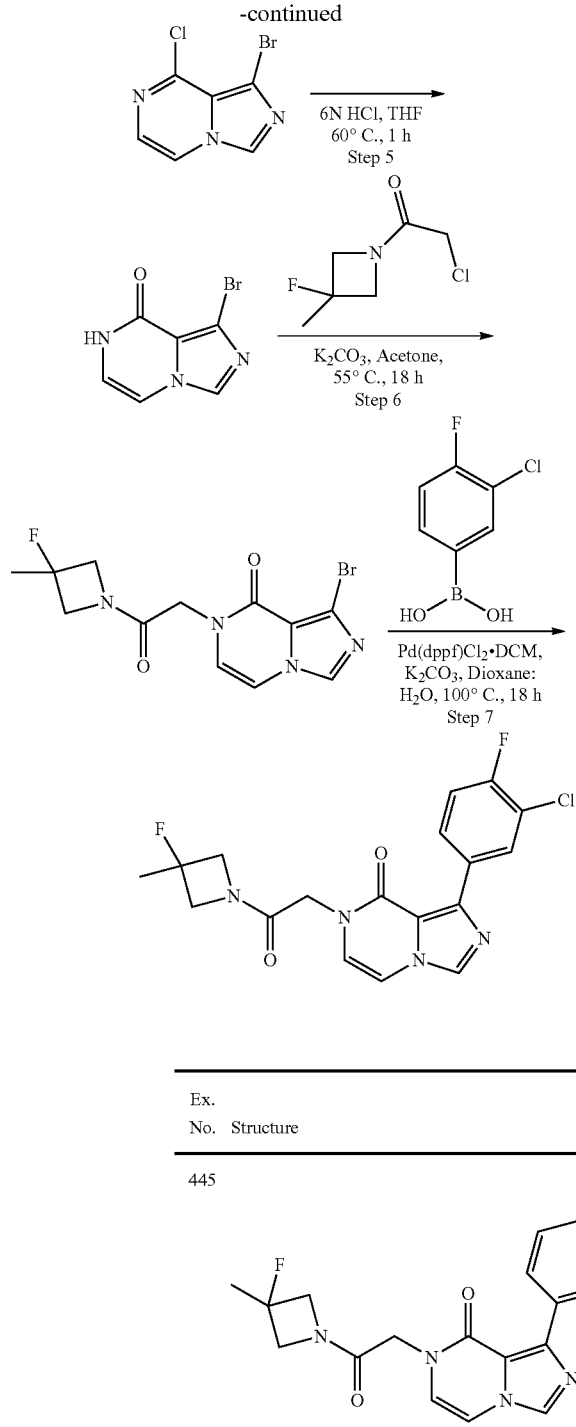

Preparation of
N-((3-chloropyrazin-2-yl)methyl)formamide

To a stirred solution (3-chloropyrazin-2-yl)methanamine hydrochloride (0.5 g, 2.77 mmol) in dichloromethane (20 mL) and N,N-dimethyl formamide (4 mL) were added N,N-diisopropylethylamine (0.72 mL, 4.16 mmol), 1-Ethyl-3-(3-dimethylaminopropyl)carbodiimide (0.79 g, 4.16 mmol), 1-hydroxybenzotriazole (0.37 g, 2.77 mmol), formic acid (0.135 mL, 3.60 mmol) and the reaction mixture was stirred at room temperature for 18 h. After completion of the reaction, the reaction mixture was quenched with water (50 mL) and extracted with dichloromethane (3×80 mL). The combined organic layer was washed with brine (40 mL), dried over anhydrous sodium sulfate and evaporated to get the crude product. The crude product was purified by silica gel column chromatography using 2% methanol in dichloromethane to afford the title compound N-((3-chloropyrazin-2-yl)methyl)formamide (0.21 g, 44% yield) as a yellow solid. Calculated (M+H): 172.0; Found (M+H): 172.1.

| Ex. No. | Structure | IUPAC Name | Analytical Data |
|---|---|---|---|
| 445 | 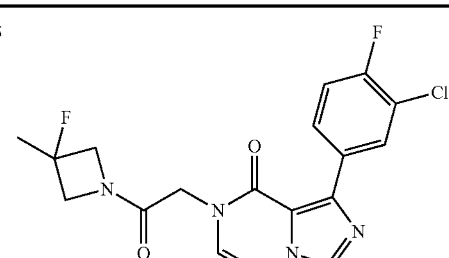 | 1-(3-chloro-4-fluorophenyl)-7-(2-(3-fluoro-3-methylazetidin-1-yl)-2-oxoethyl)imidazo[1,5-a]pyrazin-8(7H)-one | $^1$H NMR (400 MHz, DMSO-$d_6$) δ (ppm): 8.59 (dd, J = 1.6 Hz, 7.6 Hz, 1H), 8.36 (s, 1H), 8.29-8.25 (m, 1H), 7.49-7.41 (m, 2H), 6.85 (d, J = 6 Hz, 1H), 4.54 (s, 2H), 4.41-4.28 (m, 2H), 4.04-3.96 (m, 2H), 1.62 (d, J = 22 Hz, 3H), Calculated (M + H): 393.0; Found (M + H): 393.0. HPLC purity: 98.71% |
| 446 | 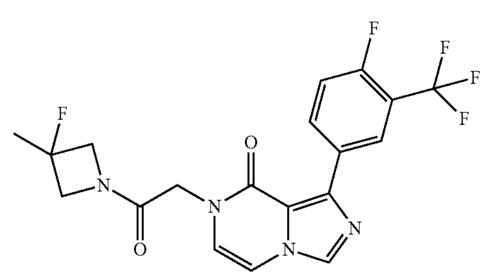 [SMILES: CC1(F)CN(C(=O)Cn2ccn3cnc(-c4ccc(F)c(C(F)(F)F)c4)c3c2=O)C1] | 1-(4-fluoro-3-(trifluoromethyl)phenyl)-7-(2-(3-fluoro-3-methylazetidin-1-yl)-2-oxoethyl)imidazo[1,5-a]pyrazin-8(7H)-one | $^1$H NMR (400 MHz, DMSO-$d_6$) δ (ppm): 8.82 (d, J = 6.8 Hz, 1H), 8.61 (brs, 1H), 8.39 (s, 1H), 7.57-7.50 (m, 2H), 6.86 (d, J = 6 Hz, 1H), 4.54 (s, 2H), 4.42-4.28 (m, 2H), 4.01 (d, J = 20 Hz, 2H), 1.62 (d, J = 22 Hz, 3H). Calculated (M + H): 427.1; Found (M + H): 427.1. HPLC purity: 99.36% |

| Ex. No. | Structure | IUPAC Name | Analytical Data |
|---|---|---|---|
| 447 | 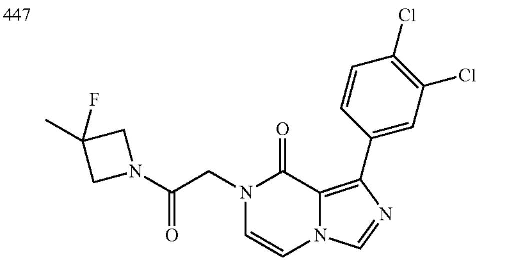 | 1-(3,4-dichlorophenyl)-7-(2-(3-fluoro-3-methylazetidin-1-yl)-2-oxoethyl)imidazo[1,5-a]pyrazin-8(7H)-one | $^1$H NMR (400 MHz, DMSO-d$_6$) δ (ppm): 8.67 (s, 1H), 8.38 (s, 1H), 8.28 (d, J = 8.4 Hz, 1H), 7.66 (d, J = 8.4 Hz, 1H), 7.51 (d, J = 5.6 Hz, 1H), 6.86 (d, J = 6 Hz, 1H), 4.54 (s, 2H), 4.41-4.28 (m, 2H), 4.01 (d, J = 19.6 Hz, 2H), 1.63 (d, J = 22 Hz, 3 H), Calculated (M + H): 409.0; Found (M + H): 409.0. HPLC purity: 97.88% |

Q. PREPARATION OF IMIDAZOPYRIMIDINONES

Example 448: Preparation of 3-(4-fluoro-3-(trifluoromethyl)phenyl)-6-(2-(3-fluoropyrrolidin-1-yl)-2-oxoethyl)imidazo[1,2-c]pyrimidin-5(6H)-one

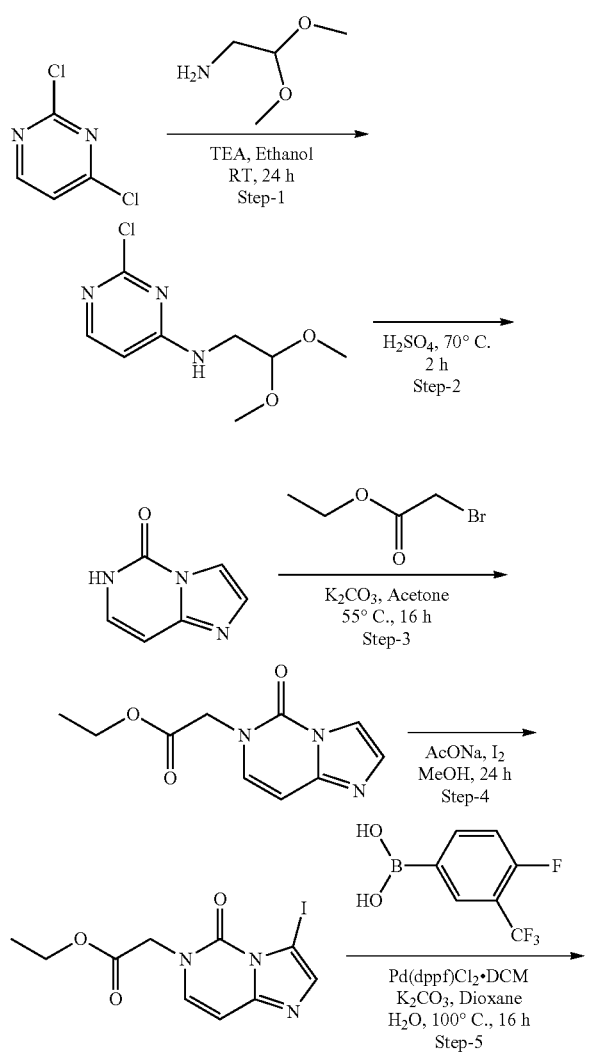

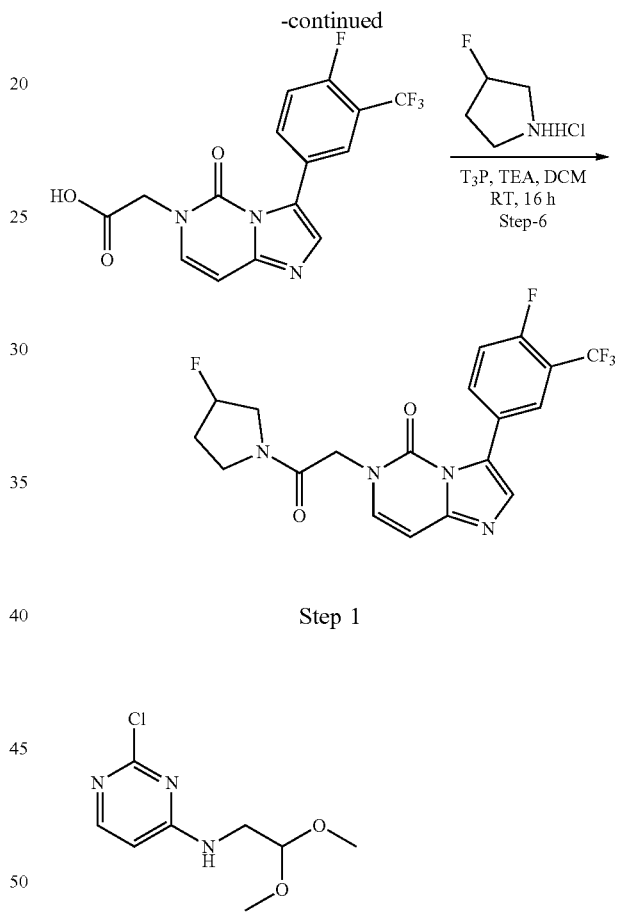

Step 1

Preparation of 2-chloro-N-(2,2-dimethoxyethyl)pyrimidin-4-amine

To a solution of 2,4-dichloropyrimidine (1.0 g, 6.71 mmol) in ethanol (10 mL) were added triethylamine (1.13 mL, 8.05 mmol), 2,2-dimethoxyethanamine (0.87 mL, 8.05 mmol) at room temperature and the reaction mixture was stirred for 24 h. After completion of reaction, the reaction mixture was concentrated under reduced pressure to obtain crude product which was purified by silica gel column chromatography using 40% ethyl acetate in hexane as eluent to obtain title compound 2-chloro-N-(2,2-dimethoxyethyl)pyrimidin-4-amine (7.2 g, 76% yield) as white solid. Calculated (M+H): 218.06; Found (M+1): 218.1.

Step 2

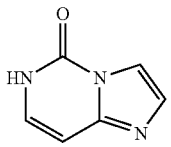

Preparation of imidazo[1,2-c]pyrimidin-5(6H)-one

To concentrated sulfuric acid (0.66 mL, 12.43 mmol), 2-chloro-N-(2,2-dimethoxyethyl)pyrimidin-4-amine (0.9 g, 4.14 mmol) was added at 0° C. and the resulting mixture was heated at 70° C. for 2 h. The reaction mixture was allowed to cool to room temperature, poured on to ice water and basified with solid sodium bicarbonate. The precipitated product was filtered, washed with cold water and dried to obtain the title compound imidazo[1,2-c]pyrimidin-5(6H)-one (0.27 g, 48% yield) as a yellow solid. Calculated (M+H): 136.04; Found (M+1): 136.2.

Step 3

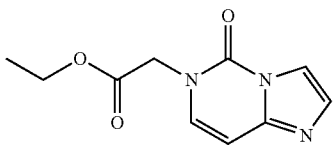 [SMILES: CCOC(=O)Cn1ccc2nccn2c1=O]

Preparation of ethyl 2-(5-oxoimidazo[1,2-c]pyrimidin-6(5H)-yl)acetate

To a mixture of imidazo[1,2-c]pyrimidin-5(6H)-one (3.8 g, 28.12 mmol) and potassium carbonate (11.66 g, 84.36 mmol) in dry acetone was added ethyl 2-bromoacetate (6.22 mL, 56.24 mmol). The resulting mixture was heated at 55° C. for 16 h. The mixture was allowed to cool to room temperature and filtered. The filtrate was concentrated under vacuum to afford crude product, which was purified by silica gel column chromatography using 3.5% methanol in dichloromethane to afford the title compound ethyl 2-(5-oxoimidazo[1,2-c]pyrimidin-6(5H)-yl)acetate (4.3 g, 69% yield) as a pale yellow solid. Calculated (M+H): 222.08; Found (M+H): 222.1.

Step 4

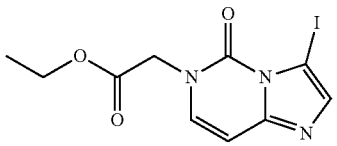 [SMILES: CCOC(=O)Cn1ccc2ncc(I)n2c1=O]

Preparation of ethyl 2-(3-iodo-5-oxoimidazo[1,2-c]pyrimidin-6(5H)-yl)acetate

To a mixture of ethyl 2-(5-oxoimidazo[1,2-c]pyrimidin-6(5H)-yl)acetate (2.0 g, 9.05 mmol) and sodium acetate (2.22 g, 27.14 mmol) in methanol (50 mL) was added iodine (6.9 g, 27.14 mmol) at 0° C. The reaction mixture was allowed to warm to room temperature and stirred for 5 h. The reaction showed the presence of starting material. Again (6.9 g, 27.14 mmol) of iodine was added and stirred for 19 h. The progress of the reaction was monitored by TLC. The reaction mixture was concentrated under vacuum. The residue was diluted with ethyl acetate (500 mL), washed with saturated solution of sodium thiosulfate (200 mL), water (200 mL), brine (100 mL), dried over anhydrous sodium sulfate, filtered and concentrated under vacuum to afford the crude product, which was purified by silica gel column chromatography using 6% methanol in dichloromethane to afford the title compound ethyl 2-(3-iodo-5-oxoimidazo[1,2-c]pyrimidin-6(5H)-yl)acetate (1.48 g, 47% yield) as pale yellow solid. Calculated (M+H): 347.98; Found (M+1): 348.0.

Step 5

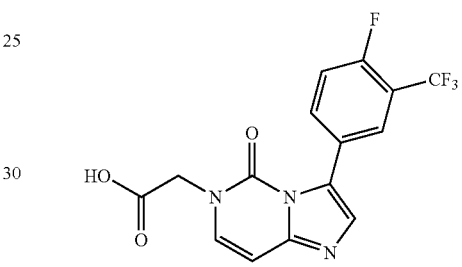

Preparation of 2-(3-(4-fluoro-3-(trifluoromethyl)phenyl)-5-oxoimidazo[1,2-c]pyrimidin-6(5H)-yl)acetic acid To a solution of ethyl 2-(3-iodo-5-oxoimidazo[1,2-c]pyrimidin-6(5H)-yl)acetate (0.2 g, 0.58 mmol) and (4-fluoro-3-(trifluoromethyl)phenyl)boronic acid (0.12 g, 0.58 mmol) in 1,4-dioxane:water mixture (5 mL:2 mL) potassium carbonate (0.24 g, 1.73 mmol) was added. The reaction mixture was purged with argon for 10 min. Then 1,1'-bis(diphenylphosphino)ferrocene-palladium(II)dichloride dichloromethane complex [Pd(dppf)Cl$_2$.DCM] (0.05 g, 0.06 mmol) was added and the reaction mixture was heated at 100° C. for 16 h. The reaction mixture was allowed to cool to room temperature, filtered through celite and the filtrate was concentrated. The residue was diluted with water (25 mL) and washed with ethyl acetate (20 mL). The aqueous layer was acidified with concentrated hydrochloric acid (pH~4) and extracted with ethyl acetate (3×50 mL). The combined organic layer was dried over anhydrous sodium sulfate, filtered and concentrated to afford the crude compound, which was triturated with 50% diethyl ether in n-pentane to afford the title compound 2-(3-(4-fluoro-3-(trifluoromethyl)phenyl)-5-oxoimidazo[1,2-c]pyrimidin-6(5H)-yl)acetic acid (0.11 g, 55% yield) as pale yellow solid. Calculated (M+H): 356.06; Found (M+H): 356.1.

Step 6

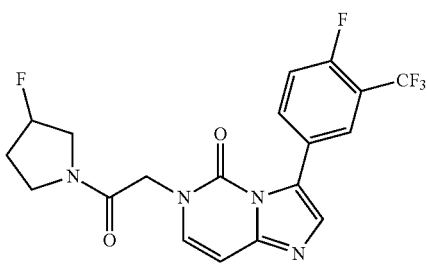 [SMILES: O=C(Cn1ccc2ncc(-c3ccc(F)c(C(F)(F)F)c3)n2c1=O)N1CCC(F)C1]

Preparation of 3-(4-fluoro-3-(trifluoromethyl)phenyl)-6-(2-(3-fluoropyrrolidin-1-yl)-2-oxoethyl)imidazo[1,2-c]pyrimidin-5(6H)-one To a solution of 2-(3-(4-fluoro-3-(trifluoromethyl)phenyl)-5-oxoimidazo[1,2-c]pyrimidin-6(5H)-yl)acetic acid (0.08 g, 0.23 mmol) in dichloromethane (10 mL) were added 3-fluoropyrrolidine hydrochloride (0.05 g, 0.45 mmol) and triethylamine (0.25 mL, 1.80 mmol) at room temperature. The reaction mixture was cooled to 0° C. and 1-propanephosphonic anhydride solution (0.3 mL, 0.45 mmol, 50% solution in ethyl acetate) was added. The resulting mixture was allowed to warm to room temperature and stirred for 16 h. After completion of reaction (monitored by TLC), the reaction mixture was diluted with dichloromethane (25 mL), washed with water (2×25 mL), brine (20 mL), dried over anhydrous sodium sulfate, filtered and concentrated under reduced pressure to afford crude product, which was purified by silica gel column chromatography using 3% methanol in dichloromethane as eluent to afford the title compound 3-(4-fluoro-3-(trifluoromethyl)phenyl)-6-(2-(3-fluoropyrrolidin-1-yl)-2-oxoethyl)imidazo[1,2-c]pyrimidin-5(6H)-one (0.025 g, 27% yield) as white solid. $^1$H NMR (400 MHz, DMSO-$d_6$) δ (ppm): 7.85-7.78 (m, 2H), 7.54-7.49 (m, 2H), 7.42-7.39 (m, 1H), 6.70 (d, J=8.0 Hz, 1H), 5.48-5.23 (m, 1H), 4.86-4.67 (m, 2H), 3.85-3.32 (m, 4H), 2.24-2.06 (m, 2H). Calculated (M+H): 427.11; Found (M+1): 427.1. HPLC purity: 99.83%.

TABLE 47

The following compounds were prepared by the method described above:

| Ex. No. | Structure | IUPAC Name | Analytical data |
|---|---|---|---|
| 449 | 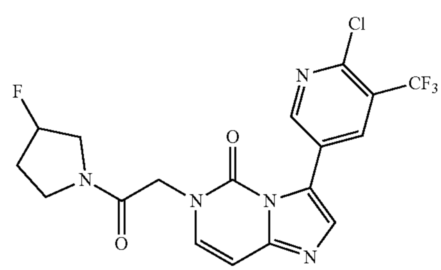 [SMILES: O=C(Cn1ccc2ncc(-c3cnc(Cl)c(C(F)(F)F)c3)n2c1=O)N1CCC(F)C1] | 3-(6-chloro-5-(trifluoromethyl)pyridin-3-yl)-6-(2-(3-fluoropyrrolidin-1-yl)-2-oxoethyl)imidazo[1,2-c]pyrimidin-5(6H)-one | $^1$H NMR (400 MHz, DMSO-$d_6$) δ (ppm); 8.77(d, J = 3.2 Hz, 1H), 8.43 (d, J = 3.0 Hz, 1H), 7.70 (s, 1H), 7.48-7.45 (m, 1H), 6.76 (d, J = 7.6 Hz, 1H), 5.48-5.23 (m, 1H), 4.89-4.70 (m, 2H), 3.84-3.30 (m, 4H), 2.24-1.91 (m, 2H). Calculated (M + H): 444.08; Found (M + 1): 444.1. HPLC purity 97.24% |
| 450 | 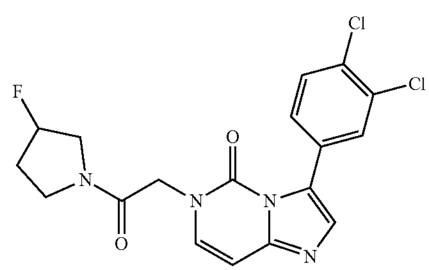 [SMILES: O=C(Cn1ccc2ncc(-c3ccc(F)c(Cl)c3)n2c1=O)N1CCC(F)C1] | 3-(3,4-dichlorophenyl)-6-(2-(3-fluoropyrrolidin-1-yl)-2-oxoethyl)imidazo[1,2-c]pyrimidin-5(6H)-one | $^1$H NMR (400 MHz, DMSO-$d_6$) δ (ppm); 7.72 (s, 1H), 7.61 (d, J = 8.0 Hz, 1H), 7.50 (s, 1H), 7.44-7.40 (m, 2H), 6.70 (d, J = 7.6 Hz, 1H), 5.48-5.23 (m, 1H), 4.86-4.67 (m, 2H), 3.86-3.36 (m, 4H), 2.24-2.06 (m, 2H). Calculated (M + H): 409.06; Found (M + H): 409.2. HPLC purity 99.37% |
| 451 | 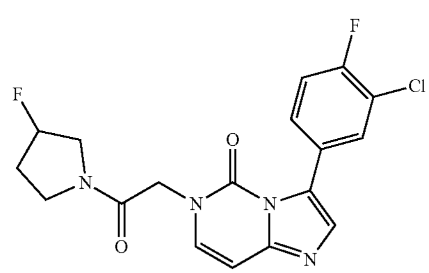 | 3-(3-chloro-4-fluorophenyl)-6-(2-(3-fluoropyrrolidin-1-yl)-2-oxoethyl)imidazo[1,2-c]pyrimidin-5(6H)-one | $^1$H NMR (400 MHz, DMSO-$d_6$) δ (ppm); 7.67 (d, J = 6.8 Hz, 1H), 7.45-7.38 (m, 4H), 6.69 (d, J = 7.6 Hz, 1H), 5.48-5.23 (m, 1H), 4.86-4.67 (m, 2H), 3.85-3.27 (m, 4H), 2.24-2.06 (m, 2H). Calculated (M + H): 393.09; Found (M + 1): 393.2.2. HPLC purity 99.94% |

Example 452: Preparation of 3-(3-chloro-4-fluorophenyl)-6-(2-(3-fluoropyrrolidin-1-yl)-2-oxoethyl)-8 methylimidazo[1,2-c]pyrimidin-5(6H)-one

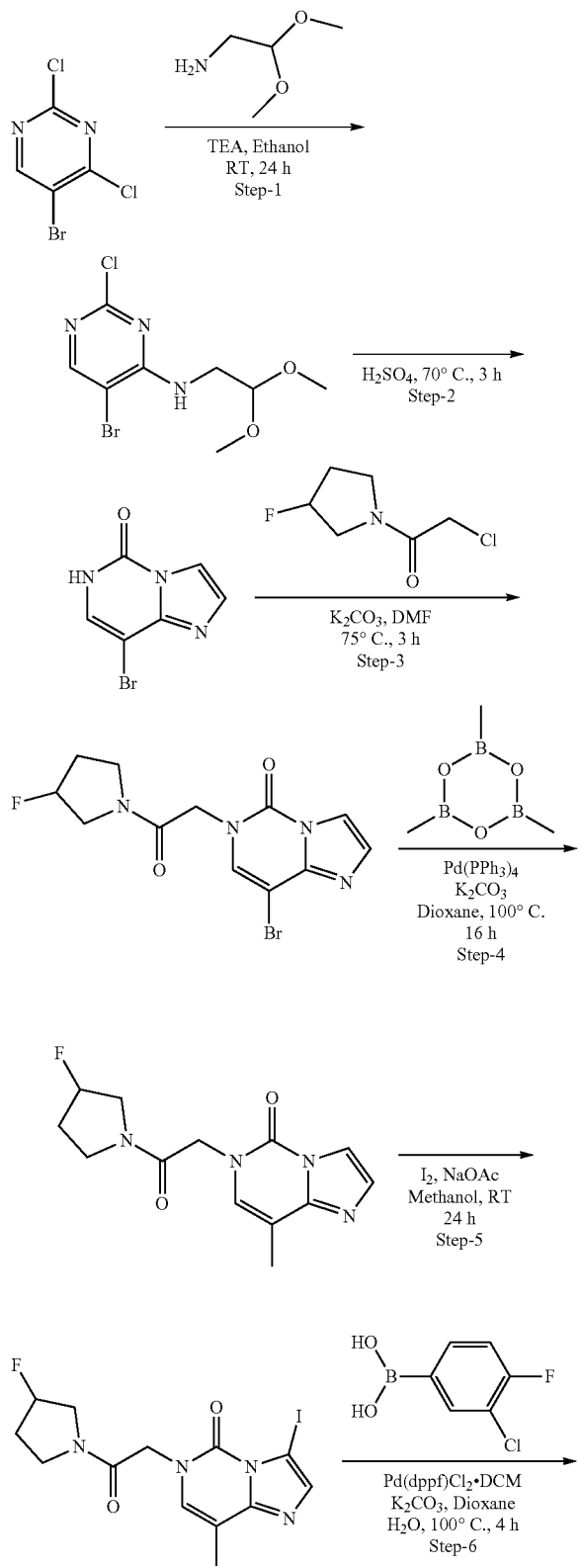

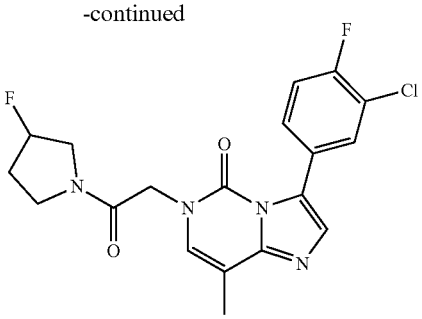

Step 1

Preparation of 5-bromo-2-chloro-N-(2,2-dimethoxyethyl)pyrimidin-4-amine

To a solution of 5-bromo-2,4-dichloropyrimidine (5.0 g, 21.94 mmol) in ethanol (100 mL) were added triethylamine (3.7 mL, 26.33 mmol) and 2,2-dimethoxyethanamine (2.53 mL, 24.14 mmol) at room temperature and the reaction mixture was stirred for 24 h. After completion of reaction, the reaction mixture was concentrated under reduced pressure. The residue was diluted with ethyl acetate (100 mL), washed with water (50 mL), brine (50 mL), dried over anhydrous sodium sulfate, filtered and concentrated under vacuum to obtain crude product, which was purified by silica gel column chromatography using 20% ethyl acetate in hexane as eluent to obtain title compound 5-bromo-2-chloro-N-(2,2-dimethoxyethyl)pyrimidin-4-amine (5.4 g, 83% yield) as white solid. Calculated (M+H): 295.97; Found (M+H): 296.0.

Step 2

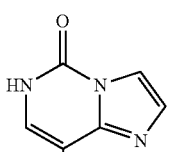

Preparation of 8-bromoimidazo[1,2-c]pyrimidin-5(6H)-one

To concentrated sulfuric acid (2 mL), 5-bromo-2-chloro-N-(2,2-dimethoxyethyl)pyrimidin-4-amine (1.0 g, 3.37 mmol) was added at 0° C. and the resulting mixture was heated at 70° C. for 3 h. The reaction mixture was allowed to cool to room temperature, poured on to ice water and the pH was adjusted 6 to 7 using 2N sodium hydroxide solution. The precipitated product was filtered, washed with cold water and dried to obtain the title compound 8-bromoimidazo[1,2-c]pyrimidin-5(6H)-one (0.25 g, 34% yield) as a yellow solid. Calculated (M+H): 213.95; Found (M+1): 214.0.

Step 3

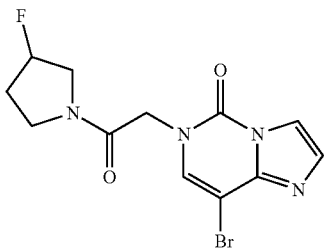 [SMILES: O=C(Cn1cc(Br)c2nccn2c1=O)N1CCC(F)C1]

Preparation of 8-bromo-6-(2-(3-fluoropyrrolidin-1-yl)-2-oxoethyl)imidazo[1,2-c]pyrimidin-5(6H)-one To a mixture of 8-bromoimidazo[1,2-c]pyrimidin-5(6H)-one (2.0 g, 9.344 mmol) and potassium carbonate (3.87 g, 28.03 mmol) in dry N, N dimethyl formamide, was added 2-chloro-1-(3-fluoropyrrolidin-1-yl)ethanone (1.85 g, 11.21 mmol). The resulting mixture was heated at 75° C. for 3 h. The reaction mixture was allowed to cool to room temperature, diluted with cold water (75 mL) and extracted with ethyl acetate (3×250 mL). The combined organic layer was dried over anhydrous sodium sulphate, filtered and concentrated under vacuum to afford crude product, which was purified by silica gel (60-120) column chromatography using 3% methanol in dichloromethane to afford the title compound 8-bromo-6-(2-(3-fluoropyrrolidin-1-yl)-2-oxoethyl)imidazo[1,2-c]pyrimidin-5(6H)-one (1.0 g, 46% yield) as off white solid. Calculated (M+H): 343.01; Found (M+H): 343.0.

Step 4

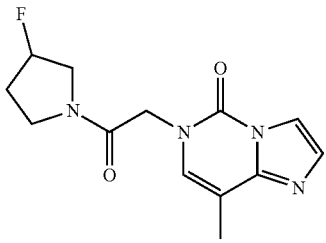 [SMILES: Cc1cn(CC(=O)N2CCC(F)C2)c(=O)n2ccnc12]

Preparation of ethyl 6-(2-(3-fluoropyrrolidin-1-yl)-2-oxoethyl)-8-methylimidazo[1,2-c]pyrimidin-5(6H)-one To a solution of 8-bromo-6-(2-(3-fluoropyrrolidin-1-yl)-2-oxoethyl)imidazo[1,2-c]pyrimidin-5(6H)-one (0.87 g, 2.54 mmol)) in 1,4-dioxane (10 mL) was added 2,4,6-trimethyl-1,3,5,2,4,6-trioxatriborinane (1.07 mL, 7.61 mmol). The reaction mixture was purged with argon for 10 minutes. Then tetrakis(triphenylphosphine)palladium [Pd (pph$_3$)$_4$] (0.3 g, 0.25 mmol) and potassium carbonate (1.75 g, 12.77 mmol) were added under argon atmosphere and the reaction mixture was heated at 100° C. for 16 h. After completion of the reaction (monitored by TLC), the reaction mixture was allowed to cool to room temperature, filtered through celite pad and washed with ethyl acetate. The filtrate was concentrated to afford the crude product, which was purified by silica gel column chromatography using 4% methanol in dichloromethane to afford the title compound ethyl 6-(2-(3-fluoropyrrolidin-1-yl)-2-oxoethyl)-8-methylimidazo[1,2-c]pyrimidin-5(6H)-one (0.36 g, 51% yield) as off white solid. Calculated (M+H): 279.12; Found (M+H): 279.2.

Step 5

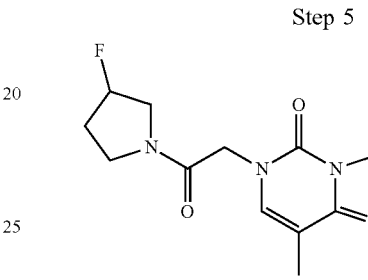

Preparation of 6-(2-(3-fluoropyrrolidin-1-yl)-2-oxoethyl)-3-iodo-8-methylimidazo[1,2-c]pyrimidin-5(6H)-one To a mixture of ethyl 6-(2-(3-fluoropyrrolidin-1-yl)-2-oxoethyl)-8-methylimidazo[1,2-c]pyrimidin-5(6H)-one (0.36 g, 1.29 mmol) and sodium acetate (0.53 g, 6.47 mmol) in methanol (20 mL) was added iodine (1.6 g, 6.47 mmol) at 0° C. The reaction mixture was allowed to warm to room temperature and stirred for 24 h. The reaction mixture was concentrated under vacuum, the residue was diluted 5M sodium thiosulphate solution (100 mL) and extracted with ethyl acetate (3×250 mL). The combined organic layer was dried over anhydrous sodium sulfate, filtered, concentrated under vacuum to afford the crude product, which was purified by silica gel column chromatography using 4% methanol in dichloromethane to afford the title compound 6-(2-(3-fluoropyrrolidin-1-yl)-2-oxoethyl)-3-iodo-8-methylimidazo[1,2-c]pyrimidin-5(6H)-one (0.26 g, 50% yield) as white solid. Calculated (M+H): 405.01; Found (M+1): 405.0.

Step 6

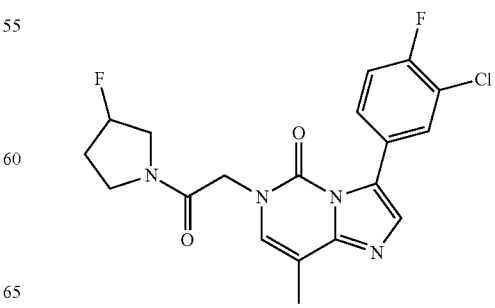

Preparation of 3-(3-chloro-4-fluorophenyl)-6-(2-(3-fluoropyrrolidin-1-yl)-2-oxoethyl)-8-methylimidazo[1,2-c]pyrimidin-5(6H)-one To a solution of 6-(2-(3-fluoropyrrolidin-1-yl)-2-oxoethyl)-3-iodo-8-methylimidazo[1,2-c]pyrimidin-5(6H)-one (0.18 g, 0.45 mmol) and (4-fluoro-3-(trifluoromethyl)phenyl)boronic acid (0.08 g, 0.45 mmol) in 1,4-dioxane:water mixture (20 mL, 1:1), potassium carbonate (0.18 g, 1.33 mmol) was added. The reaction mixture was purged with argon for 10 min. Then 1,1'-bis(diphenylphosphino)ferrocene-palladium(II)dichloride dichloromethane complex [Pd(dppf)Cl$_2$.DCM] (0.04 g, 0.05 mmol) was added the reaction mixture was heated at 100° C. for 4 h. The reaction mixture was allowed to cool to room temperature, filtered through celite and washed with ethyl acetate. The filtrate was washed with water (20 mL), brine (20 mL), dried over anhydrous sodium sulfate, filtered and concentrated to afford the crude compound, which was purified by silica gel column chromatography using 4% methanol in dichloromethane as eluent to afford the title compound 3-(3-chloro-4-fluorophenyl)-6-(2-(3-fluoropyrrolidin-1-yl)-2-oxoethyl)-8-methylimidazo[1,2-c]pyrimidin-5(6H)-one (0.072 g, 40% yield) as pale brown solid. H NMR (400 MHz, DMSO-d$_6$) δ (ppm): 7.66 (d, J=5.6 Hz, 1H), 7.46-7.38 (m, 3H), 7.24 (s, 1H), 5.48-5.23 (m, 1H), 4.82-4.62 (m, 2H), 3.85-3.38 (m, 4H), 2.30-1.96 (m, 5H). Calculated (M+H): 407.1; Found (M+H): 407.1. HPLC purity: 99.57%.

5% CO$_2$. NR2B expression is induced by overnight incubation with 0.3-0.4 μg/ml tetracycline in the presence of 2.5 mM ARL-15896 at 37° C., followed by moving to 30° C. for 3-5 hours. Cells are next harvested using TripleExpress™ (Life Technologies, Carlsbad, Calif.) according to the manufacturer's instructions, first removing culture medium, rinsing with Dulbecco's phosphate buffered saline (Ca$^{2+}$ and Mg$^{2+}$-free), and then adding the TripleExpress™ reagent. Harvested cells are spun down, washed twice in Ca$^{2+}$- and Mg$^{2+}$-free Hank's Balanced Salt Solution with 20 mM HEPES and 10 mM glucose, pH 7.4 (HHnoCa solution), and counted with viability assessed using Trypan Blue. Cells are loaded with fluo-8 Ca$^{2+}$-sensitive dye in HHnoCa solution according to the manufacturer's directions (AAT Bioquest, Sunnyvale, Calif.), incubating at 37° C. for 20 minutes followed by 25 minutes at 22-25° C. After a wash in HHnoCa to remove extracellular dye, cells are resuspended in HHnoCa and plated at 2×10$^7$-3×10$^7$ cells per well in a volume of 25 μl/well in 384 well black-wall, clear bottom plates (Hamamatsu, Middlesex, N.J.). Plates are then centrifuged to create a monolayer in the wells and stored in the dark until used.

Prior to analysis, compound plates are prepared with each compound at 6× the final desired concentration. From stock solutions at 10 mM in 100% DMSO, compounds are spotted in the desired amounts using an ECHO liquid handler (Labcyte, Sunnyvale, Calif.) into wells of a 384-well plate and then diluted with 50 μl of HHnoCa containing 750 nM

TABLE 48

The following compounds were prepared by the method described above:

| Ex. No. | Structure | IUPAC Name | Analytical data |
|---|---|---|---|
| 453 | (structure shown) | 3-(3,4-dichlorophenyl)-6-(2-(3-fluoropyrrolidin-1-yl)-2-oxoethyl)-8-methylimidazo[1,2-c]pyrimidin-5(6H)-one | $^1$H NMR (400 MHz, DMSO-d$_6$) δ (ppm); 7.71(s, 1H), 7.61 (d, J = 8.4 Hz, 1H), 7.51 (s, 1H), 7.43 (d, J = 7.2 Hz, 1H), 7.26 (s, 1H), 5.48-5.23 (m, 1H), 4.82-4.63 (m, 2H), 3.85-3.45 (m, 4H), 2.23-1.94 (m, 5H). Calculated (M + H): 423.07; Found (M + 1): 423.1. HPLC purity 95.82% |
| 454 | (structure shown) | 3-(4-fluoro-3-(trifluoromethyl)phenyl)-6-(2-(3-fluoropyrrolidin-1-yl)-2-oxoethyl)-8-methylimidazo[1,2-c]pyrimidin-5(6H)-one | $^1$H NMR (400 MHz, DMSO-d$_6$) δ (ppm); 7.85-7.80 (m, 2H), 7.54-7.49 (m, 2H), 7.25 (s, 1H), 5.48-5.23 (m, 1H), 4.82-4.67 (m, 2H), 3.76-3.54 (m, 4H), 2.30-2.07 (m, 5H). Calculated (M + H): 441.13; Found (M + 1): 441.1. HPLC purity 99.03% |

R. BIOLOGICAL EXAMPLE

HEK293 cells with constructs conferring stable expression of the GRIN1 gene and tetracycline-inducible expression of the GRIN2B gene (Chantest, Cleveland, Ohio) are grown to ~75% confluence in tissue culture flasks at 37° C., Ro 25-6981 and 120 μM 5,7-dichlorokynurenic acid (both purchased from Tocris Bioscience (Bristol, England) and maintained as 10 mM stock solutions in 100% DMSO). To insure complete compound dissolution, these plates are then placed in an orbital shaker for at least one hour. Also prepared prior to the assay is a co-agonist plate containing HHnoCa with 240 μM glutamate, 2.4 mM glycine, and 7.2 mM CaCl$_2$, which is 2.4× the desired final concentration of each reagent. Both the compound plate and co-agonist plate are 384-well polypropylene plates from Thermo Fisher Scientific, Waltham, Mass.

The assay is performed by first adding 10 μl solution from each well of the compound plate described above to the cell plate using a CyBiWell liquid handler (Analytik Jena AG, Jena, Germany), followed by 10 minutes pre-incubation in the dark. Cell plates are then loaded onto a Hamamatsu FDSS 6000 plate reader. After a 30-second baseline, 25 μl is added to each well from the co-agonist plate, and the fluorescence signal is recorded for another 2 minutes. FDSS software applies shading and autofluorescence correction, and resultant raw fluorescence measurements are exported in the form of a fluorescence ratio for each well to its own reading at time zero in the experiment. In each plate, negative control wells consist of wells where Ro 25-6981 and 5,7 dichlorokynurenic acid are present and co-agonist is applied in the absence of any added assay compound. Under these conditions, the Ca$^{2+}$ response to co-agonist is suppressed. Positive control wells also present in each plate contain 5,7 dichlorokynurenic acid but no Ro 25-6981, so that co-agonist addition results in a large Ca$^{2+}$ response. Compounds tested are evaluated on the basis of their ability to reverse the suppression of the Ca$^{2+}$ response mediated by Ro 25-6981, which is quantified as % reversal=100*(R−R$_{neg}$)/(R$_{pos}$−R$_{neg}$) where R is the fluorescence ratio for the test compound at the end of the experiment and R$_{neg}$ and R$_{pos}$ are the end ratios for the negative and positive controls, respectively. Using this equation, a compound would return 0% if it had no effect on the Ro 25-6981-mediated suppression of Ca$^{2+}$ flux, whereas a compound that entirely reversed the effect of Ro 25-6981 (to the level of co-agonist stimulation) would return 100%.

The results of the above assay are shown in Table 49.

TABLE 49

| Ex. No. | IUPAC Name | Response Recovered (%) |
| --- | --- | --- |
| 345 | 5-(4-chlorophenyl)-3-[2-oxo-2-(pyrrolidin-1-yl)ethyl]-3H,4H-thieno[3,4-d]pyrimidin-4-one | 18 |
| 346 | 2-[5-(4-chlorophenyl)-4-oxo-3H,4H-thieno[3,4-d]pyrimidin-3-yl]-N-cyclopropylacetamide | 0 |
| 347 | 2-[5-(4-chlorophenyl)-4-oxo-3H,4H-thieno[3,4-d]pyrimidin-3-yl]-N-cyclobutylacetamide | 2 |
| 348 | 5-(4-chlorophenyl)-3-[2-(3,3-difluoroazetidin-1-yl)-2-oxoethyl]-3H,4H-thieno[3,4-d]pyrimidin-4-one | 26 |
| 349 | 3-[2-(azetidin-1-yl)-2-oxoethyl]-5-(4-chlorophenyl)-3H,4H-thieno[3,4-d]pyrimidin-4-one | 3 |
| 370 | 3-[2-(azetidin-1-yl)-2-oxoethyl]-5-(4-chlorophenyl)-3H,4H,5H-pyrrolo[3,2-d]pyrimidin-4-one | 4 |
| 371 | 5-(4-chlorophenyl)-3-[2-(morpholin-4-yl)-2-oxoethyl]-3H,4H,5H-pyrrolo[3,2-d]pyrimidin-4-one | 1 |
| 372 | 5-(4-chlorophenyl)-3-[2-(3-methoxyazetidin-1-yl)-2-oxoethyl]-3H,4H,5H-pyrrolo[3,2-d]pyrimidin-4-one | 1 |
| 373 | 5-(4-chlorophenyl)-3-[2-(4,4-difluoropiperidin-1-yl)-2-oxoethyl]-3H,4H,5H-pyrrolo[3,2-d]pyrimidin-4-one | 3 |
| 350 | 5-(4-chlorophenyl)-3-[2-oxo-2-(piperidin-1-yl)ethyl]-3H,4H-thieno[3,4-d]pyrimidin-4-one | 0 |
| 351 | 5-(4-chlorophenyl)-3-[2-(3-methoxyazetidin-1-yl)-2-oxoethyl]-3H,4H-thieno[3,4-d]pyrimidin-4-one | 1 |
| 352 | 5-(4-chlorophenyl)-3-[2-(3-hydroxypyrrolidin-1-yl)-2-oxoethyl]-3H,4H-thieno[3,4-d]pyrimidin-4-one | 7 |
| 353 | 5-(4-chlorophenyl)-3-[2-(4,4-difluoropiperidin-1-yl)-2-oxoethyl]-3H,4H-thieno[3,4-d]pyrimidin-4-one | 1 |
| 374 | 5-(4-chlorophenyl)-3-[2-(3,3-difluoroazetidin-1-yl)-2-oxoethyl]-3H,4H,5H-pyrrolo[3,2-d]pyrimidin-4-one | 4 |
| 375 | 2-[5-(4-chlorophenyl)-4-oxo-3H,4H,5H-pyrrolo[3,2-d]pyrimidin-3-yl]-N-cyclopropylacetamide | 0 |
| 376 | 5-(4-chlorophenyl)-3-[2-oxo-2-(pyrrolidin-1-yl)ethyl]-3H,4H,5H-pyrrolo[3,2-d]pyrimidin-4-one | 3 |
| 354 | 5-(4-chlorophenyl)-3-[2-(morpholin-4-yl)-2-oxoethyl]-3H,4H-thieno[3,4-d]pyrimidin-4-one | 1 |
| 377 | 5-(4-chlorophenyl)-3-[2-oxo-2-(piperidin-1-yl)ethyl]-3H,4H,5H-pyrrolo[3,2-d]pyrimidin-4-one | 1 |
| 378 | 2-[5-(4-chlorophenyl)-4-oxo-3H,4H,5H-pyrrolo[3,2-d]pyrimidin-3-yl]-N-cyclobutylacetamide | 1 |
| 379 | 5-(4-chlorophenyl)-3-{2-oxo-2-[2-(trifluoromethyl)pyrrolidin-1-yl]ethyl}-3H,4H,5H-pyrrolo[3,2-d]pyrimidin-4-one | 5 |
| 355 | 5-(4-chlorophenyl)-3-{2-oxo-2-[2-(trifluoromethyl)pyrrolidin-1-yl]ethyl}-3H,4H-thieno[3,4-d]pyrimidin-4-one | 10 |
| 295 | 5-(4-chlorophenyl)-3-[2-oxo-2-(pyrrolidin-1-yl)ethyl]-3,4-dihydroquinazolin-4-one | 1 |
| 296 | 5-(4-chlorophenyl)-3-[2-(3,3-difluoroazetidin-1-yl)-2-oxoethyl]-3,4-dihydroquinazolin-4-one | 9 |
| 297 | 5-(4-chlorophenyl)-3-{2-oxo-2-[2-(trifluoromethyl)pyrrolidin-1-yl]ethyl}-3,4-dihydroquinazolin-4-one | 3 |
| 298 | 5-(4-chlorophenyl)-3-[2-(3-fluoropyrrolidin-1-yl)-2-oxoethyl]-3,4-dihydroquinazolin-4-one | 9 |
| 356 | 3-[2-oxo-2-(pyrrolidin-1-yl)ethyl]-5-[4-(trifluoromethyl)phenyl]-3H,4H-thieno[3,4-d]pyrimidin-4-one | 11 |

TABLE 49-continued

| Ex. No. | IUPAC Name | Response Recovered (%) |
|---|---|---|
| 388 | 5-(4-chlorophenyl)-3-[2-oxo-2-(pyrrolidin-1-yl)ethyl]-3H,4H-furo[2,3-d]pyrimidin-4-one | 8 |
| 389 | 5-(4-chlorophenyl)-3-[2-(3,3-difluoroazetidin-1-yl)-2-oxoethyl]-3H,4H-furo[2,3-d]pyrimidin-4-one | 8 |
| 387 | 5-(4-chlorophenyl)-3-{2-oxo-2-[2-(trifluoromethyl)pyrrolidin-1-yl]ethyl}-3H,4H-furo[2,3-d]pyrimidin-4-one | 7 |
| 357 | 3-{2-oxo-2-[2-(trifluoromethyl)pyrrolidin-1-yl]ethyl}-5-[4-(trifluoromethyl)phenyl]-3H,4H-thieno[3,4-d]pyrimidin-4-one | 2 |
| 358 | 3-[2-(3,3-difluoroazetidin-1-yl)-2-oxoethyl]-5-[4-(trifluoromethyl)phenyl]-3H,4H-thieno[3,4-d]pyrimidin-4-one | 12 |
| 383 | 3-(4-chlorophenyl)-5-[2-oxo-2-(pyrrolidin-1-yl)ethyl]-4H,5H-[1,2]oxazolo[5,4-d]pyrimidin-4-one | 1 |
| 384 | 3-(4-chlorophenyl)-5-{2-oxo-2-[2-(trifluoromethyl)pyrrolidin-1-yl]ethyl}-4H,5H-[1,2]oxazolo[5,4-d]pyrimidin-4-one | 2 |
| 385 | 3-(4-chlorophenyl)-5-[2-(3,3-difluoroazetidin-1-yl)-2-oxoethyl]-4H,5H-[1,2]oxazolo[5,4-d]pyrimidin-4-one | 4 |
| 386 | 3-(4-chlorophenyl)-5-[2-(3-fluoropyrrolidin-1-yl)-2-oxoethyl]-4H,5H-[1,2]oxazolo[5,4-d]pyrimidin-4-one | 4 |
| 380 | 3-(4-chlorophenyl)-5-[2-oxo-2-(pyrrolidin-1-yl)ethyl]-4H,5H-[1,2]thiazolo[5,4-d]pyrimidin-4-one | 6 |
| 150 | 5-(4-chlorophenyl)-3-[2-oxo-2-(pyrrolidin-1-yl)ethyl]-3H,4H,7H-pyrrolo[2,3-d]pyrimidin-4-one | 31 |
| 151 | 5-(4-chlorophenyl)-7-methyl-3-[2-oxo-2-(pyrrolidin-1-yl)ethyl]-3H,4H,7H-pyrrolo[2,3-d]pyrimidin-4-one | 17 |
| 152 | 5-(4-chlorophenyl)-3-{2-oxo-2-[2-(trifluoromethyl)pyrrolidin-1-yl]ethyl}-3H,4H,7H-pyrrolo[2,3-d]pyrimidin-4-one | 10 |
| 153 | 5-(4-chlorophenyl)-7-methyl-3-{2-oxo-2-[2-(trifluoromethyl)pyrrolidin-1-yl]ethyl}-3H,4H,7H-pyrrolo[2,3-d]pyrimidin-4-one | 35 |
| 154 | 5-(4-chlorophenyl)-3-[2-(3,3-difluoroazetidin-1-yl)-2-oxoethyl]-3H,4H,7H-pyrrolo[2,3-d]pyrimidin-4-one | 36 |
| 381 | 3-(4-chlorophenyl)-5-[2-(3,3-difluoroazetidin-1-yl)-2-oxoethyl]-4H,5H-[1,2]thiazolo[5,4-d]pyrimidin-4-one | 2 |
| 382 | 3-(4-chlorophenyl)-5-{2-oxo-2-[2-(trifluoromethyl)pyrrolidin-1-yl]ethyl}-4H,5H-[1,2]thiazolo[5,4-d]pyrimidin-4-one | 9 |
| 155 | 5-(4-chlorophenyl)-3-[2-(3,3-difluoroazetidin-1-yl)-2-oxoethyl]-7-methyl-3H,4H,7H-pyrrolo[2,3-d]pyrimidin-4-one | 24 |
| 359 | 5-(3-chloro-4-fluorophenyl)-3-[2-oxo-2-(pyrrolidin-1-yl)ethyl]-3H,4H-thieno[3,4-d]pyrimidin-4-one | 35 |
| 360 | 5-(3-chloro-4-fluorophenyl)-3-[2-(3,3-difluoroazetidin-1-yl)-2-oxoethyl]-3H,4H-thieno[3,4-d]pyrimidin-4-one | 39 |
| 366 | 5-[4-chloro-3-(trifluoromethyl)phenyl]-3-[2-oxo-2-(pyrrolidin-1-yl)ethyl]-3H,4H-thieno[3,4-d]pyrimidin-4-one | 34 |
| 156 | 5-(3-chloro-4-fluorophenyl)-3-[2-oxo-2-(pyrrolidin-1-yl)ethyl]-3H,4H,7H-pyrrolo[2,3-d]pyrimidin-4-one | 36 |
| 148 | 5-[4-chloro-3-(trifluoromethyl)phenyl]-3-[2-oxo-2-(pyrrolidin-1-yl)ethyl]-3H,4H,7H-pyrrolo[2,3-d]pyrimidin-4-one | 66 |
| 157 | 5-[4-chloro-3-(trifluoromethyl)phenyl]-7-ethyl-3-[2-oxo-2-(pyrrolidin-1-yl)ethyl]-3H,4H,7H-pyrrolo[2,3-d]pyrimidin-4-one | 70 |
| 158 | 5-[4-chloro-3-(trifluoromethyl)phenyl]-7-methyl-3-[2-oxo-2-(pyrrolidin-1-yl)ethyl]-3H,4H,7H-pyrrolo[2,3-d]pyrimidin-4-one | 72 |
| 362 | 5-[4-chloro-3-(trifluoromethyl)phenyl]-3-[2-(3,3-difluoroazetidin-1-yl)-2-oxoethyl]-3H,4H-thieno[3,4-d]pyrimidin-4-one | 39 |
| 335 | 3-[4-chloro-3-(trifluoromethyl)phenyl]-5-[2-oxo-2-(pyrrolidin-1-yl)ethyl]-4H,5H-thieno[2,3-d]pyridazin-4-one | 23 |
| 159 | 5-(3-chloro-4-fluorophenyl)-7-methyl-3-[2-oxo-2-(pyrrolidin-1-yl)ethyl]-3H,4H,7H-pyrrolo[2,3-d]pyrimidin-4-one | 25 |
| 160 | 5-(3-chloro-4-fluorophenyl)-7-ethyl-3-[2-oxo-2-(pyrrolidin-1-yl)ethyl]-3H,4H,7H-pyrrolo[2,3-d]pyrimidin-4-one | 42 |
| 161 | 5-(3-chloro-4-fluorophenyl)-3-[2-(3,3-difluoroazetidin-1-yl)-2-oxoethyl]-3H,4H,7H-pyrrolo[2,3-d]pyrimidin-4-one | 58 |
| 162 | 5-(3-chloro-4-fluorophenyl)-3-[2-(3,3-difluoroazetidin-1-yl)-2-oxoethyl]-7-methyl-3H,4H,7H-pyrrolo[2,3-d]pyrimidin-4-one | 40 |
| 163 | 5-(3-chloro-4-fluorophenyl)-3-[2-(3,3-difluoroazetidin-1-yl)-2-oxoethyl]-7-ethyl-3H,4H,7H-pyrrolo[2,3-d]pyrimidin-4-one | 48 |
| 164 | 5-(4-chloro-3-fluorophenyl)-3-[2-oxo-2-(pyrrolidin-1-yl)ethyl]-3H,4H,7H-pyrrolo[2,3-d]pyrimidin-4-one | 48 |
| 165 | 5-(4-chloro-3-fluorophenyl)-7-methyl-3-[2-oxo-2-(pyrrolidin-1-yl)ethyl]-3H,4H,7H-pyrrolo[2,3-d]pyrimidin-4-one | 25 |
| 166 | 5-[4-chloro-3-(trifluoromethyl)phenyl]-3-[2-(3,3-difluoroazetidin-1-yl)-2-oxoethyl]-3H,4H,7H-pyrrolo[2,3-d]pyrimidin-4-one | 65 |
| 331 | 5-[4-chloro-3-(trifluoromethyl)phenyl]-3-[2-oxo-2-(pyrrolidin-1-yl)ethyl]-3H,4H-thieno[2,3-d][1,2,3]triazin-4-one | 8 |
| 336 | 3-(4-chloro-3-fluorophenyl)-5-[2-oxo-2-(pyrrolidin-1-yl)ethyl]-4H,5H-thieno[2,3-d]pyridazin-4-one | 3 |

TABLE 49-continued

| Ex. No. | IUPAC Name | Response Recovered (%) |
|---|---|---|
| 337 | 3-(3-chloro-4-fluorophenyl)-5-[2-oxo-2-(pyrrolidin-1-yl)ethyl]-4H,5H-thieno[2,3-d]pyridazin-4-one | 7 |
| 338 | 3-(3,4-dichlorophenyl)-5-[2-oxo-2-(pyrrolidin-1-yl)ethyl]-4H,5H-thieno[2,3-d]pyridazin-4-one | 15 |
| 1 | 3-[4-chloro-3-(trifluoromethyl)phenyl]-5-[2-oxo-2-(pyrrolidin-1-yl)ethyl]-4H,5H-thieno[3,2-c]pyridin-4-one | 83 |
| 5 | 3-[4-chloro-3-(trifluoromethyl)phenyl]-5-[2-(3,3-difluoroazetidin-1-yl)-2-oxoethyl]-4H,5H-thieno[3,2-c]pyridin-4-one | 139 |
| 4 | 3-[4-chloro-3-(trifluoromethyl)phenyl]-5-[2-(3-fluoropyrrolidin-1-yl)-2-oxoethyl]-4H,5H-thieno[3,2-c]pyridin-4-one | 107 |
| 2 | 3-(4-chloro-3-fluorophenyl)-5-[2-oxo-2-(pyrrolidin-1-yl)ethyl]-4H,5H-thieno[3,2-c]pyridin-4-one | 34 |
| 6 | 3-(4-chloro-3-fluorophenyl)-5-[2-(3,3-difluoroazetidin-1-yl)-2-oxoethyl]-4H,5H-thieno[3,2-c]pyridin-4-one | 41 |
| 7 | 3-(4-chloro-3-fluorophenyl)-5-[2-(3-fluoropyrrolidin-1-yl)-2-oxoethyl]-4H,5H-thieno[3,2-c]pyridin-4-one | 49 |
| 333 | 5-[4-chloro-3-(trifluoromethyl)phenyl]-3-[2-(3,3-difluoroazetidin-1-yl)-2-oxoethyl]-3H,4H-thieno[2,3-d][1,2,3]triazin-4-one | 13 |
| 332 | 5-[4-chloro-3-(trifluoromethyl)phenyl]-3-[2-(3-fluoropyrrolidin-1-yl)-2-oxoethyl]-3H,4H-thieno[2,3-d][1,2,3]triazin-4-one | 20 |
| 334 | 5-[4-chloro-3-(trifluoromethyl)phenyl]-3-{2-oxo-2-[2-(trifluoromethyl)pyrrolidin-1-yl]ethyl}-3H,4H-thieno[2,3-d][1,2,3]triazin-4-one | 2 |
| 167 | 5-(4-chloro-3-fluorophenyl)-3-[2-(3,3-difluoroazetidin-1-yl)-2-oxoethyl]-3H,4H,7H-pyrrolo[2,3-d]pyrimidin-4-one | 35 |
| 168 | 5-[4-chloro-3-(trifluoromethyl)phenyl]-3-[2-(3,3-difluoroazetidin-1-yl)-2-oxoethyl]-7-methyl-3H,4H,7H-pyrrolo[2,3-d]pyrimidin-4-one | 55 |
| 169 | 5-[4-chloro-3-(trifluoromethyl)phenyl]-3-[2-(3,3-difluoroazetidin-1-yl)-2-oxoethyl]-7-ethyl-3H,4H,7H-pyrrolo[2,3-d]pyrimidin-4-one | 57 |
| 170 | 5-(4-chloro-3-fluorophenyl)-3-[2-(3,3-difluoroazetidin-1-yl)-2-oxoethyl]-7-methyl-3H,4H,7H-pyrrolo[2,3-d]pyrimidin-4-one | 18 |
| 171 | 5-(4-chloro-3-fluorophenyl)-3-[2-(3,3-difluoroazetidin-1-yl)-2-oxoethyl]-7-ethyl-3H,4H,7H-pyrrolo[2,3-d]pyrimidin-4-one | 15 |
| 3 | 3-(3-chloro-4-fluorophenyl)-5-[2-oxo-2-(pyrrolidin-1-yl)ethyl]-4H,5H-thieno[3,2-c]pyridin-4-one | 60 |
| 339 | 3-[4-chloro-3-(trifluoromethyl)phenyl]-5-[2-(3,3-difluoroazetidin-1-yl)-2-oxoethyl]-4H,5H-thieno[2,3-d]pyridazin-4-one | 20 |
| 340 | 3-(4-chloro-3-fluorophenyl)-5-[2-(3,3-difluoroazetidin-1-yl)-2-oxoethyl]-4H,5H-thieno[2,3-d]pyridazin-4-one | 3 |
| 341 | 3-(3-chloro-4-fluorophenyl)-5-[2-(3,3-difluoroazetidin-1-yl)-2-oxoethyl]-4H,5H-thieno[2,3-d]pyridazin-4-one | 8 |
| 342 | 3-(4-chloro-3-fluorophenyl)-5-[2-(3-fluoropyrrolidin-1-yl)-2-oxoethyl]-4H,5H-thieno[2,3-d]pyridazin-4-one | 4 |
| 343 | 3-(3-chloro-4-fluorophenyl)-5-[2-(3-fluoropyrrolidin-1-yl)-2-oxoethyl]-4H,5H-thieno[2,3-d]pyridazin-4-one | 15 |
| 8 | 3-(3-chloro-4-fluorophenyl)-5-[2-(3,3-difluoroazetidin-1-yl)-2-oxoethyl]-4H,5H-thieno[3,2-c]pyridin-4-one | 66 |
| 9 | 3-(3-chloro-4-fluorophenyl)-5-[2-(3-fluoropyrrolidin-1-yl)-2-oxoethyl]-4H,5H-thieno[3,2-c]pyridin-4-one | 81 |
| 172 | 5-(3-chloro-4-fluorophenyl)-7-(2-fluoroethyl)-3-[2-oxo-2-(pyrrolidin-1-yl)ethyl]-3H,4H,7H-pyrrolo[2,3-d]pyrimidin-4-one | 40 |
| 344 | 3-[4-chloro-3-(trifluoromethyl)phenyl]-5-[2-(3-fluoropyrrolidin-1-yl)-2-oxoethyl]-4H,5H-thieno[2,3-d]pyridazin-4-one | −1 |
| 363 | 5-(4-chloro-3-fluorophenyl)-3-[2-(3,3-difluoroazetidin-1-yl)-2-oxoethyl]-3H,4H-thieno[3,4-d]pyrimidin-4-one | 16 |
| 173 | 5-(4-chloro-3-fluorophenyl)-7-(2-fluoroethyl)-3-[2-oxo-2-(pyrrolidin-1-yl)ethyl]-3H,4H,7H-pyrrolo[2,3-d]pyrimidin-4-one | 32 |
| 367 | 5-(4-chloro-3-fluorophenyl)-3-[2-oxo-2-(pyrrolidin-1-yl)ethyl]-3H,4H-thieno[3,4-d]pyrimidin-4-one | 15 |
| 364 | 5-(4-chloro-3-fluorophenyl)-3-[2-(3-fluoropyrrolidin-1-yl)-2-oxoethyl]-3H,4H-thieno[3,4-d]pyrimidin-4-one | 35 |
| 149 | 5-[4-chloro-3-(trifluoromethyl)phenyl]-7-(2-fluoroethyl)-3-[2-oxo-2-(pyrrolidin-1-yl)ethyl]-3H,4H,7H-pyrrolo[2,3-d]pyrimidin-4-one | 64 |
| 330 | 5-(3-chloro-4-fluorophenyl)-3-[2-oxo-2-(pyrrolidin-1-yl)ethyl]-3H,4H-thieno[2,3-d][1,2,3]triazin-4-one | 6 |
| 368 | 7-bromo-5-(4-chloro-3-fluorophenyl)-3-[2-oxo-2-(pyrrolidin-1-yl)ethyl]-3H,4H-thieno[3,4-d]pyrimidin-4-one | 41 |
| 369 | 5-(4-chloro-3-fluorophenyl)-7-methyl-3-[2-oxo-2-(pyrrolidin-1-yl)ethyl]-3H,4H-thieno[3,4-d]pyrimidin-4-one | 33 |
| 317 | 3-[4-chloro-3-(trifluoromethyl)phenyl]-5-[2-oxo-2-(pyrrolidin-1-yl)ethyl]-1H,4H,5H-pyrazolo[3,4-d]pyrimidin-4-one | 8 |
| 365 | 5-(4-chloro-3-fluorophenyl)-3-{2-oxo-2-[2-(trifluoromethyl)pyrrolidin-1-yl]ethyl}-3H,4H-thieno[3,4-d]pyrimidin-4-one | 4 |
| 10 | 3-(3,4-dichlorophenyl)-5-[2-(3-fluoropyrrolidin-1-yl)-2-oxoethyl]-4H,5H-thieno[3,2-c]pyridin-4-one | 102 |

TABLE 49-continued

| Ex. No. | IUPAC Name | Response Recovered (%) |
|---|---|---|
| 11 | 3-[4-fluoro-3-(trifluoromethyl)phenyl]-5-[2-(3-fluoropyrrolidin-1-yl)-2-oxoethyl]-4H,5H-thieno[3,2-c]pyridin-4-one | 99 |
| 185 | 5-[4-chloro-3-(trifluoromethyl)phenyl]-7-(2-methoxyethyl)-3-[2-oxo-2-(pyrrolidin-1-yl)ethyl]-3H,4H,7H-pyrrolo[2,3-d]pyrimidin-4-one | 76 |
| 186 | 5-(3-chloro-4-fluorophenyl)-7-(2-methoxyethyl)-3-[2-oxo-2-(pyrrolidin-1-yl)ethyl]-3H,4H,7H-pyrrolo[2,3-d]pyrimidin-4-one | 18 |
| 190 | 5-[4-chloro-3-(trifluoromethyl)phenyl]-7-cyclopropyl-3-[2-oxo-2-(pyrrolidin-1-yl)ethyl]-3H,4H,7H-pyrrolo[2,3-d]pyrimidin-4-one | 71 |
| 187 | 5-(4-chloro-3-fluorophenyl)-7-(2-methoxyethyl)-3-[2-oxo-2-(pyrrolidin-1-yl)ethyl]-3H,4H,7H-pyrrolo[2,3-d]pyrimidin-4-one | 9 |
| 24 | 3-[4-chloro-3-(trifluoromethyl)phenyl]-5-[3-(3-fluoropyrrolidin-1-yl)-3-oxopropyl]-4H,5H-thieno[3,2-c]pyridin-4-one | 3 |
| 174 | 5-[4-fluoro-3-(trifluoromethyl)phenyl]-3-[2-(3-fluoropyrrolidin-1-yl)-2-oxoethyl]-3H,4H,7H-pyrrolo[2,3-d]pyrimidin-4-one | 91 |
| 175 | 5-(3,4-dichlorophenyl)-3-[2-(3-fluoropyrrolidin-1-yl)-2-oxoethyl]-3H,4H,7H-pyrrolo[2,3-d]pyrimidin-4-one | 77 |
| 176 | 5-[3-chloro-4-(trifluoromethyl)phenyl]-3-[2-(3-fluoropyrrolidin-1-yl)-2-oxoethyl]-3H,4H,7H-pyrrolo[2,3-d]pyrimidin-4-one | 63 |
| 319 | 3-(4-chloro-3-fluorophenyl)-5-[2-oxo-2-(pyrrolidin-1-yl)ethyl]-1H,4H,5H-pyrazolo[3,4-d]pyrimidin-4-one | 4 |
| 177 | 5-[4-chloro-3-(trifluoromethyl)phenyl]-3-[2-(3-fluoropyrrolidin-1-yl)-2-oxoethyl]-3H,4H,7H-pyrrolo[2,3-d]pyrimidin-4-one | 85 |
| 178 | 5-(3-chloro-4-fluorophenyl)-3-[2-(3-fluoropyrrolidin-1-yl)-2-oxoethyl]-3H,4H,7H-pyrrolo[2,3-d]pyrimidin-4-one | 54 |
| 197 | 5-(4-chloro-3-fluorophenyl)-7-(2-hydroxyethyl)-3-[2-oxo-2-(pyrrolidin-1-yl)ethyl]-3H,4H,7H-pyrrolo[2,3-d]pyrimidin-4-one | 7 |
| 191 | 5-(4-chloro-3-fluorophenyl)-7-cyclopropyl-3-[2-oxo-2-(pyrrolidin-1-yl)ethyl]-3H,4H,7H-pyrrolo[2,3-d]pyrimidin-4-one | 36 |
| 179 | 5-(4-chloro-3-fluorophenyl)-3-[2-(3-fluoropyrrolidin-1-yl)-2-oxoethyl]-3H,4H,7H-pyrrolo[2,3-d]pyrimidin-4-one | 37 |
| 194 | 5-[4-chloro-3-(trifluoromethyl)phenyl]-7-(2-hydroxyethyl)-3-[2-oxo-2-(pyrrolidin-1-yl)ethyl]-3H,4H,7H-pyrrolo[2,3-d]pyrimidin-4-one | 2 |
| 192 | 5-(3-chloro-4-fluorophenyl)-7-cyclopropyl-3-[2-oxo-2-(pyrrolidin-1-yl)ethyl]-3H,4H,7H-pyrrolo[2,3-d]pyrimidin-4-one | 42 |
| 320 | 3-[4-chloro-3-(trifluoromethyl)phenyl]-5-[2-(3,3-difluoroazetidin-1-yl)-2-oxoethyl]-1H,4H,5H-pyrazolo[3,4-d]pyrimidin-4-one | 9 |
| 318 | 3-[4-chloro-3-(trifluoromethyl)phenyl]-5-[2-(3-fluoropyrrolidin-1-yl)-2-oxoethyl]-1H,4H,5H-pyrazolo[3,4-d]pyrimidin-4-one | 26 |
| 195 | 5-(3-chloro-4-fluorophenyl)-7-(2-hydroxyethyl)-3-[2-oxo-2-(pyrrolidin-1-yl)ethyl]-3H,4H,7H-pyrrolo[2,3-d]pyrimidin-4-one | 21 |
| 12 | 3-(5,6-dichloropyridin-3-yl)-5-[2-(3-fluoropyrrolidin-1-yl)-2-oxoethyl]-4H,5H-thieno[3,2-c]pyridin-4-one | 35 |
| 180 | 5-(5,6-dichloropyridin-3-yl)-3-[2-(3-fluoropyrrolidin-1-yl)-2-oxoethyl]-3H,4H,7H-pyrrolo[2,3-d]pyrimidin-4-one | 15 |
| 299 | 8-[4-chloro-3-(trifluoromethyl)phenyl]-2-[2-(3-fluoropyrrolidin-1-yl)-2-oxoethyl]-1,2-dihydroisoquinolin-1-one | 32 |
| 300 | 8-[4-chloro-3-(trifluoromethyl)phenyl]-2-[2-oxo-2-(pyrrolidin-1-yl)ethyl]-1,2-dihydroisoquinolin-1-one | 37 |
| 301 | 8-[4-chloro-3-(trifluoromethyl)phenyl]-2-[2-(3,3-difluoroazetidin-1-yl)-2-oxoethyl]-1,2-dihydroisoquinolin-1-one | 28 |
| 13 | 3-[3-chloro-4-(trifluoromethyl)phenyl]-5-[2-(3-fluoropyrrolidin-1-yl)-2-oxoethyl]-4H,5H-thieno[3,2-c]pyridin-4-one | 90 |
| 198 | 3-[4-chloro-3-(trifluoromethyl)phenyl]-5-[2-oxo-2-(pyrrolidin-1-yl)ethyl]-1H,4H,5H-pyrrolo[3,2-c]pyridin-4-one | 104 |
| 199 | 3-[4-chloro-3-(trifluoromethyl)phenyl]-5-[2-(3-fluoropyrrolidin-1-yl)-2-oxoethyl]-1-{[2-(trimethylsilyl)ethoxy]methyl}-1H,4H,5H-pyrrolo[3,2-c]pyridin-4-one | 47 |
| 200 | 3-[4-chloro-3-(trifluoromethyl)phenyl]-5-[2-(3,3-difluoroazetidin-1-yl)-2-oxoethyl]-1-{[2-(trimethylsilyl)ethoxy]methyl}-1H,4H,5H-pyrrolo[3,2-c]pyridin-4-one | 18 |
| 201 | 3-(4-chloro-3-fluorophenyl)-5-[2-oxo-2-(pyrrolidin-1-yl)ethyl]-1-{[2-(trimethylsilyl)ethoxy]methyl}-1H,4H,5H-pyrrolo[3,2-c]pyridin-4-one | 62 |
| 202 | 3-(4-chloro-3-fluorophenyl)-5-[2-(3-fluoropyrrolidin-1-yl)-2-oxoethyl]-1-{[2-(trimethylsilyl)ethoxy]methyl}-1H,4H,5H-pyrrolo[3,2-c]pyridin-4-one | 32 |
| 212 | 3-[4-chloro-3-(trifluoromethyl)phenyl]-5-[2-(3,3-difluoroazetidin-1-yl)-2-oxoethyl]-1H,4H,5H-pyrrolo[3,2-c]pyridin-4-one | 107 |
| 181 | 5-[4-chloro-3-(trifluoromethyl)phenyl]-3-{2-[(3R,4S)-3,4-difluoropyrrolidin-1-yl]-2-oxoethyl}-3H,4H,7H-pyrrolo[2,3-d]pyrimidin-4-one | 69 |
| 203 | 3-[4-chloro-3-(trifluoromethyl)phenyl]-5-[2-(3-fluoropyrrolidin-1-yl)-2-oxoethyl]-1H,4H,5H-pyrrolo[3,2-c]pyridin-4-one | 42 |
| 204 | 3-(4-chloro-3-fluorophenyl)-5-[2-(3-fluoropyrrolidin-1-yl)-2-oxoethyl]-1H,4H,5H-pyrrolo[3,2-c]pyridin-4-one | 47 |
| 211 | 3-(4-chloro-3-fluorophenyl)-5-[2-oxo-2-(pyrrolidin-1-yl)ethyl]-1H,4H,5H-pyrrolo[3,2-c]pyridin-4-one | 55 |

TABLE 49-continued

| Ex. No. | IUPAC Name | Response Recovered (%) |
|---|---|---|
| 213 | 3-(4-chloro-3-fluorophenyl)-5-[2-(3,3-difluoroazetidin-1-yl)-2-oxoethyl]-1H,4H,5H-pyrrolo[3,2-c]pyridin-4-one | 109 |
| 14 | 3-[4-chloro-3-(trifluoromethyl)phenyl]-5-{2-[(3R,4S)-3,4-difluoropyrrolidin-1-yl]-2-oxoethyl}-4H,5H-thieno[3,2-c]pyridin-4-one | 99 |
| 15 | 3-[4-chloro-3-(trifluoromethyl)phenyl]-5-{2-[(3S)-3-fluoropyrrolidin-1-yl]-2-oxoethyl}-4H,5H-thieno[3,2-c]pyridin-4-one | 95 |
| 16 | 3-(3,4-dichlorophenyl)-5-{2-[(3R,4S)-3,4-difluoropyrrolidin-1-yl]-2-oxoethyl}-4H,5H-thieno[3,2-c]pyridin-4-one | 107 |
| 25 | 3-[6-chloro-5-(trifluoromethyl)pyridin-3-yl]-5-[2-(3-fluoropyrrolidin-1-yl)-2-oxoethyl]-4H,5H-thieno[3,2-c]pyridin-4-one | 28 |
| 302 | 8-(3-chloro-4-fluorophenyl)-2-[2-(3-fluoropyrrolidin-1-yl)-2-oxoethyl]-1,2-dihydroisoquinolin-1-one | 40 |
| 303 | 8-(3-chloro-4-fluorophenyl)-2-[2-oxo-2-(pyrrolidin-1-yl)ethyl]-1,2-dihydroisoquinolin-1-one | 46 |
| 304 | 8-(3,4-dichlorophenyl)-2-[2-(3-fluoropyrrolidin-1-yl)-2-oxoethyl]-1,2-dihydroisoquinolin-1-one | 60 |
| 205 | 3-(3-chloro-4-fluorophenyl)-5-[2-oxo-2-(pyrrolidin-1-yl)ethyl]-1-{[2-(trimethylsilyl)ethoxy]methyl}-1H,4H,5H-pyrrolo[3,2-c]pyridin-4-one | 59 |
| 206 | 3-(3-chloro-4-fluorophenyl)-5-[2-(3-fluoropyrrolidin-1-yl)-2-oxoethyl]-1-{[2-(trimethylsilyl)ethoxy]methyl}-1H,4H,5H-pyrrolo[3,2-c]pyridin-4-one | 107 |
| 17 | 3-[4-chloro-3-(trifluoromethyl)phenyl]-5-{2-[(3R)-3-fluoropyrrolidin-1-yl]-2-oxoethyl}-4H,5H-thieno[3,2-c]pyridin-4-one | 99 |
| 26 | 3-[4-fluoro-3-(trifluoromethyl)phenyl]-5-{2-[(3S)-3-fluoropyrrolidin-1-yl]-2-oxoethyl}-4H,5H-thieno[3,2-c]pyridin-4-one | 103 |
| 27 | 3-[4-fluoro-3-(trifluoromethyl)phenyl]-5-{2-[(3R)-3-fluoropyrrolidin-1-yl]-2-oxoethyl}-4H,5H-thieno[3,2-c]pyridin-4-one | 81 |
| 28 | 5-{2-[(3R,4S)-3,4-difluoropyrrolidin-1-yl]-2-oxoethyl}-3-[4-fluoro-3-(trifluoromethyl)phenyl]-4H,5H-thieno[3,2-c]pyridin-4-one | 94 |
| 307 | 8-(4-chloro-3-fluorophenyl)-2-[2-oxo-2-(pyrrolidin-1-yl)ethyl]-1,2-dihydroisoquinolin-1-one | 24 |
| 306 | 8-(4-chloro-3-fluorophenyl)-2-[2-(3-fluoropyrrolidin-1-yl)-2-oxoethyl]-1,2-dihydroisoquinolin-1-one | 25 |
| 305 | 8-(4-chloro-3-fluorophenyl)-2-[2-(3,3-difluoroazetidin-1-yl)-2-oxoethyl]-1,2-dihydroisoquinolin-1-one | 23 |
| 308 | 8-(3,4-dichlorophenyl)-2-[2-oxo-2-(pyrrolidin-1-yl)ethyl]-1,2-dihydroisoquinolin-1-one | 78 |
| 309 | 8-(3-chloro-4-fluorophenyl)-2-[2-(3,3-difluoroazetidin-1-yl)-2-oxoethyl]-1,2-dihydroisoquinolin-1-one | 41 |
| 29 | 3-(3,4-dichlorophenyl)-5-{2-[(3R)-3-fluoropyrrolidin-1-yl]-2-oxoethyl}-4H,5H-thieno[3,2-c]pyridin-4-one | 104 |
| 30 | 3-(3,4-dichlorophenyl)-5-{2-[(3S)-3-fluoropyrrolidin-1-yl]-2-oxoethyl}-4H,5H-thieno[3,2-c]pyridin-4-one | 96 |
| 31 | 3-(5-chlorothiophen-2-yl)-5-[2-(3-fluoropyrrolidin-1-yl)-2-oxoethyl]-4H,5H-thieno[3,2-c]pyridin-4-one | 34 |
| 182 | 5-[6-chloro-5-(trifluoromethyl)pyridin-3-yl]-3-[2-(3,3-difluoroazetidin-1-yl)-2-oxoethyl]-3H,4H,7H-pyrrolo[2,3-d]pyrimidin-4-one | 18 |
| 207 | 3-(3-chloro-4-fluorophenyl)-5-[2-(3,3-difluoroazetidin-1-yl)-2-oxoethyl]-1-{[2-(trimethylsilyl)ethoxy]methyl}-1H,4H,5H-pyrrolo[3,2-c]pyridin-4-one | 69 |
| 208 | 3-(3-chloro-4-fluorophenyl)-5-[2-oxo-2-(pyrrolidin-1-yl)ethyl]-1H,4H,5H-pyrrolo[3,2-c]pyridin-4-one | 60 |
| 209 | 3-(3-chloro-4-fluorophenyl)-5-[2-(3-fluoropyrrolidin-1-yl)-2-oxoethyl]-1H,4H,5H-pyrrolo[3,2-c]pyridin-4-one | 53 |
| 214 | 3-(3,4-dichlorophenyl)-5-[2-(3-fluoropyrrolidin-1-yl)-2-oxoethyl]-1H,4H,5H-pyrrolo[3,2-c]pyridin-4-one | 84 |
| 215 | 3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 89 |
| 216 | 5-[2-(3,3-difluoroazetidin-1-yl)-2-oxoethyl]-3-[4-fluoro-3-(trifluoromethyl)phenyl]-1H,4H,5H-pyrrolo[3,2-c]pyridin-4-one | 101 |
| 98 | 7-bromo-3-[4-chloro-3-(trifluoromethyl)phenyl]-5-[2-oxo-2-(pyrrolidin-1-yl)ethyl]-4H,5H-thieno[3,2-c]pyridin-4-one | 40 |
| 255 | 2-[3-(3-chloro-4-fluorophenyl)-4-oxo-1H,4H,5H-pyrrolo[3,2-c]pyridin-5-yl]acetamide | −1 |
| 217 | 3-(3,4-dichlorophenyl)-5-[2-oxo-2-(pyrrolidin-1-yl)ethyl]-1H,4H,5H-pyrrolo[3,2-c]pyridin-4-one | 70 |
| 99 | 3-[4-chloro-3-(trifluoromethyl)phenyl]-4-oxo-5-[2-oxo-2-(pyrrolidin-1-yl)ethyl]-4H,5H-thieno[3,2-c]pyridine-7-carbonitrile | 37 |
| 101 | 3-[4-chloro-3-(trifluoromethyl)phenyl]-7-cyclopropyl-5-[2-oxo-2-(pyrrolidin-1-yl)ethyl]-4H,5H-thieno[3,2-c]pyridin-4-one | 29 |
| 183 | 5-[6-chloro-5-(trifluoromethyl)pyridin-3-yl]-3-[2-(3-fluoropyrrolidin-1-yl)-2-oxoethyl]-3H,4H,7H-pyrrolo[2,3-d]pyrimidin-4-one | 14 |
| 218 | 3-(3-chloro-4-fluorophenyl)-5-[2-(3,3-difluoroazetidin-1-yl)-2-oxoethyl]-1H,4H,5H-pyrrolo[3,2-c]pyridin-4-one | 71 |

TABLE 49-continued

| Ex. No. | IUPAC Name | Response Recovered (%) |
|---|---|---|
| 188 | 5-[4-fluoro-3-(trifluoromethyl)phenyl]-3-[2-(3-fluoropyrrolidin-1-yl)-2-oxoethyl]-7-(2-methoxyethyl)-3H,4H,7H-pyrrolo[2,3-d]pyrimidin-4-one | 53 |
| 219 | 3-[4-fluoro-3-(trifluoromethyl)phenyl]-5-[2-oxo-2-(pyrrolidin-1-yl)ethyl]-1H,4H,5H-pyrrolo[3,2-c]pyridin-4-one | 91 |
| 310 | 7-[4-chloro-3-(trifluoromethyl)phenyl]-2-[2-oxo-2-(pyrrolidin-1-yl)ethyl]-1,2-dihydroisoquinolin-1-one | 3 |
| 311 | 7-[4-chloro-3-(trifluoromethyl)phenyl]-2-[2-(3-fluoropyrrolidin-1-yl)-2-oxoethyl]-1,2-dihydroisoquinolin-1-one | 6 |
| 312 | 7-[4-chloro-3-(trifluoromethyl)phenyl]-2-[2-(3,3-difluoroazetidin-1-yl)-2-oxoethyl]-1,2-dihydroisoquinolin-1-one | 3 |
| 313 | 7-cyclopropyl-5-[4-fluoro-3-(trifluoromethyl)phenyl]-3-[2-(3-fluoropyrrolidin-1-yl)-2-oxoethyl]-3H,4H,7H-pyrrolo[2,3-d]pyrimidin-4-one | 88 |
| 184 | 7-ethyl-5-[4-fluoro-3-(trifluoromethyl)phenyl]-3-[2-(3-fluoropyrrolidin-1-yl)-2-oxoethyl]-3H,4H,7H-pyrrolo[2,3-d]pyrimidin-4-one | 66 |
| 196 | 5-[4-fluoro-3-(trifluoromethyl)phenyl]-3-[2-(3-fluoropyrrolidin-1-yl)-2-oxoethyl]-7-(2-hydroxyethyl)-3H,4H,7H-pyrrolo[2,3-d]pyrimidin-4-one | 34 |
| 106 | 3-[4-chloro-3-(trifluoromethyl)phenyl]-7-methyl-5-[2-oxo-2-(pyrrolidin-1-yl)ethyl]-4H,5H-thieno[3,2-c]pyridin-4-one | 76 |
| 102 | 3-[4-chloro-3-(trifluoromethyl)phenyl]-5-[2-oxo-2-(pyrrolidin-1-yl)ethyl]-7-phenyl-4H,5H-thieno[3,2-c]pyridin-4-one | 23 |
| 32 | 3-[4-fluoro-3-(trifluoromethyl)phenyl]-5-[2-(3-fluoroazetidin-1-yl)-2-oxoethyl]-4H,5H-thieno[3,2-c]pyridin-4-one | 60 |
| 327 | 3-(3,4-dichlorophenyl)-5-[2-(3-fluoropyrrolidin-1-yl)-2-oxoethyl]-4H,5H-pyrazolo[1,5-a]pyrazin-4-one | 54 |
| 326 | 3-(3,4-dichlorophenyl)-5-[2-oxo-2-(pyrrolidin-1-yl)ethyl]-4H,5H-pyrazolo[1,5-a]pyrazin-4-one | 29 |
| 313 | 7-[4-fluoro-3-(trifluoromethyl)phenyl]-2-[2-oxo-2-(pyrrolidin-1-yl)ethyl]-1,2-dihydroisoquinolin-1-one | 5 |
| 314 | 7-[4-fluoro-3-(trifluoromethyl)phenyl]-2-[2-(3-fluoropyrrolidin-1-yl)-2-oxoethyl]-1,2-dihydroisoquinolin-1-one | 8 |
| 315 | 7-(3,4-dichlorophenyl)-2-[2-(3-fluoropyrrolidin-1-yl)-2-oxoethyl]-1,2-dihydroisoquinolin-1-one | 2 |
| 238 | 3-[4-fluoro-3-(trifluoromethyl)phenyl]-5-[2-(3-fluoropyrrolidin-1-yl)-2-oxoethyl]-1-(methoxymethyl)-1H,4H,5H-pyrrolo[3,2-c]pyridin-4-one | 65 |
| 103 | 3-[4-chloro-3-(trifluoromethyl)phenyl]-5-[2-oxo-2-(pyrrolidin-1-yl)ethyl]-7-(pyridin-4-yl)-4H,5H-thieno[3,2-c]pyridin-4-one | 32 |
| 189 | 5-[4-fluoro-3-(trifluoromethyl)phenyl]-3-[2-(3-fluoropyrrolidin-1-yl)-2-oxoethyl]-7-(methoxymethyl)-3H,4H,7H-pyrrolo[2,3-d]pyrimidin-4-one | 39 |
| 239 | 1-ethyl-3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 86 |
| 325 | 3-(3,4-dichlorophenyl)-5-[2-(3,3-difluoroazetidin-1-yl)-2-oxoethyl]-4H,5H-pyrazolo[1,5-a]pyrazin-4-one | 50 |
| 321 | 3-[4-fluoro-3-(trifluoromethyl)phenyl]-5-[2-(3-fluoropyrrolidin-1-yl)-2-oxoethyl]-4H,5H-pyrazolo[1,5-a]pyrazin-4-one | 46 |
| 324 | 5-[2-(3,3-difluoroazetidin-1-yl)-2-oxoethyl]-3-[4-fluoro-3-(trifluoromethyl)phenyl]-4H,5H-pyrazolo[1,5-a]pyrazin-4-one | 51 |
| 323 | 3-[4-fluoro-3-(trifluoromethyl)phenyl]-5-[2-oxo-2-(pyrrolidin-1-yl)ethyl]-4H,5H-pyrazolo[1,5-a]pyrazin-4-one | 40 |
| 322 | 3-[4-fluoro-3-(trifluoromethyl)phenyl]-5-[2-(3-fluoroazetidin-1-yl)-2-oxoethyl]-4H,5H-pyrazolo[1,5-a]pyrazin-4-one | 33 |
| 100 | 3-[4-fluoro-3-(trifluoromethyl)phenyl]-4-oxo-5-[2-oxo-2-(pyrrolidin-1-yl)ethyl]-4H,5H-thieno[3,2-c]pyridine-7-carbonitrile | 34 |
| 108 | 3-[4-fluoro-3-(trifluoromethyl)phenyl]-N-hydroxy-4-oxo-5-[2-oxo-2-(pyrrolidin-1-yl)ethyl]-4H,5H-thieno[3,2-c]pyridine-7-carboximidamide | 64 |
| 230 | 3-[4-fluoro-3-(trifluoromethyl)phenyl]-5-[2-(3-fluoropyrrolidin-1-yl)-2-oxoethyl]-1-phenyl-1H,4H,5H-pyrrolo[3,2-c]pyridin-4-one | 109 |
| 225 | 3-[4-fluoro-3-(trifluoromethyl)phenyl]-5-[2-(3-fluoropyrrolidin-1-yl)-2-oxoethyl]-1-(pyridin-2-yl)-1H,4H,5H-pyrrolo[3,2-c]pyridin-4-one | 83 |
| 316 | 7-(3,4-dichlorophenyl)-2-[2-oxo-2-(pyrrolidin-1-yl)ethyl]-1,2-dihydroisoquinolin-1-one | 2 |
| 33 | 3-(3,4-dichlorophenyl)-5-[2-(3-fluoroazetidin-1-yl)-2-oxoethyl]-4H,5H-thieno[3,2-c]pyridin-4-one | 54 |
| 34 | 3-[4-chloro-3-(trifluoromethyl)phenyl]-5-[2-(3-fluoroazetidin-1-yl)-2-oxoethyl]-4H,5H-thieno[3,2-c]pyridin-4-one | 79 |
| 107 | 3-[4-fluoro-3-(trifluoromethyl)phenyl]-7-methyl-5-[2-oxo-2-(pyrrolidin-1-yl)ethyl]-4H,5H-thieno[3,2-c]pyridin-4-one | 63 |
| 104 | 3-[4-fluoro-3-(trifluoromethyl)phenyl]-5-[2-oxo-2-(pyrrolidin-1-yl)ethyl]-7-phenyl-4H,5H-thieno[3,2-c]pyridin-4-one | 22 |

TABLE 49-continued

| Ex. No. | IUPAC Name | Response Recovered (%) |
|---|---|---|
| 105 | 3-[4-fluoro-3-(trifluoromethyl)phenyl]-5-[2-oxo-2-(pyrrolidin-1-yl)ethyl]-7-(pyridin-4-yl)-4H,5H-thieno[3,2-c]pyridin-4-one | 22 |
| 111 | 3-[4-fluoro-3-(trifluoromethyl)phenyl]-5-[2-(3-fluoropyrrolidin-1-yl)-2-oxoethyl]-7-(hydroxymethyl)-4H,5H-thieno[3,2-c]pyridin-4-one | 97 |
| 35 | 3-(5,6-dichloropyridin-3-yl)-5-[2-(3,4-difluoropyrrolidin-1-yl)-2-oxoethyl]-4H,5H-thieno[3,2-c]pyridin-4-one | 28 |
| 36 | 3-[6-chloro-5-(trifluoromethyl)pyridin-3-yl]-5-[2-(3,4-difluoropyrrolidin-1-yl)-2-oxoethyl]-4H,5H-thieno[3,2-c]pyridin-4-one | 54 |
| 109 | 3-[4-fluoro-3-(trifluoromethyl)phenyl]-7-(1,2,4-oxadiazol-3-yl)-5-[2-oxo-2-(pyrrolidin-1-yl)ethyl]-4H,5H-thieno[3,2-c]pyridin-4-one | 14 |
| 256 | 3-[4-fluoro-3-(trifluoromethyl)phenyl]-5-[2-(3-fluoropyrrolidin-1-yl)-2-oxoethyl]-1-(2-hydroxyethyl)-1H,4H,5H-pyrrolo[3,2-c]pyridin-4-one | 54 |
| 224 | 3-[4-chloro-3-(trifluoromethyl)phenyl]-5-[2-(3-fluoropyrrolidin-1-yl)-2-oxoethyl]-1-(pyridin-2-yl)-1H,4H,5H-pyrrolo[3,2-c]pyridin-4-one | 109 |
| 112 | 3-[4-fluoro-3-(trifluoromethyl)phenyl]-5-[2-(3-fluoropyrrolidin-1-yl)-2-oxoethyl]-7-(pyrrolidin-1-ylmethyl)-4H,5H-thieno[3,2-c]pyridin-4-one | 89 |
| 226 | 3-[4-fluoro-3-(trifluoromethyl)phenyl]-5-[2-(3-fluoropyrrolidin-1-yl)-2-oxoethyl]-1-(pyridin-3-yl)-1H,4H,5H-pyrrolo[3,2-c]pyridin-4-one | 69 |
| 113 | 3-[4-fluoro-3-(trifluoromethyl)phenyl]-4-oxo-5-[2-oxo-2-(pyrrolidin-1-yl)ethyl]-4H,5H-thieno[3,2-c]pyridine-7-carboximidamide | 47 |
| 448 | 3-[4-fluoro-3-(trifluoromethyl)phenyl]-6-[2-(3-fluoropyrrolidin-1-yl)-2-oxoethyl]-5H,6H-imidazo[1,2-c]pyrimidin-5-one | 14 |
| 449 | 3-[6-chloro-5-(trifluoromethyl)pyridin-3-yl]-6-[2-(3-fluoropyrrolidin-1-yl)-2-oxoethyl]-5H,6H-imidazo[1,2-c]pyrimidin-5-one | 5.2 |
| 240 | 1-[2-(dimethylamino)ethyl]-3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 29 |
| 257 | 3-[4-fluoro-3-(trifluoromethyl)phenyl]-5-[2-(3-fluoropyrrolidin-1-yl)-2-oxoethyl]-1-(2-hydroxy-2-methylpropyl)-1H,4H,5H-pyrrolo[3,2-c]pyridin-4-one | 20 |
| 241 | 1-(ethoxymethyl)-3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 61 |
| 110 | 3-[4-fluoro-3-(trifluoromethyl)phenyl]-5-[2-(3-fluoropyrrolidin-1-yl)-2-oxoethyl]-N-hydroxy-4-oxo-4H,5H-thieno[3,2-c]pyridine-7-carboximidamide | 33 |
| 391 | 8-[4-fluoro-3-(trifluoromethyl)phenyl]-2-[2-oxo-2-(pyrrolidin-1-yl)ethyl]-1H,2H-pyrrolo[1,2-a]pyrazin-1-one | 77 |
| 390 | 8-[4-fluoro-3-(trifluoromethyl)phenyl]-2-[2-(3-fluoropyrrolidin-1-yl)-2-oxoethyl]-1H,2H-pyrrolo[1,2-a]pyrazin-1-one | 51 |
| 231 | 1-cyclopropyl-3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 90 |
| 37 | 3-(5-chloro-6-fluoropyridin-3-yl)-5-[2-(3-fluoropyrrolidin-1-yl)-2-oxoethyl]-4H,5H-thieno[3,2-c]pyridin-4-one | 22 |
| 227 | 3-[4-chloro-3-(trifluoromethyl)phenyl]-5-[2-(3-fluoropyrrolidin-1-yl)-2-oxoethyl]-1-(pyridin-3-yl)-1H,4H,5H-pyrrolo[3,2-c]pyridin-4-one | 42 |
| 114 | 3-[4-fluoro-3-(trifluoromethyl)phenyl]-5-[2-oxo-2-(pyrrolidin-1-yl)ethyl]-7-(pyrrolidin-1-yl)-4H,5H-thieno[3,2-c]pyridin-4-one | 15 |
| 118 | 7-(azetidin-1-ylmethyl)-3-[4-fluoro-3-(trifluoromethyl)phenyl]-5-[2-(3-fluoropyrrolidin-1-yl)-2-oxoethyl]-4H,5H-thieno[3,2-c]pyridin-4-one | 77 |
| 220 | 5-[2-(3,4-difluoropyrrolidin-1-yl)-2-oxoethyl]-3-[4-fluoro-3-(trifluoromethyl)phenyl]-1H,4H,5H-pyrrolo[3,2-c]pyridin-4-one | 120 |
| 258 | 5-[2-(3,4-difluoropyrrolidin-1-yl)-2-oxoethyl]-3-[4-fluoro-3-(trifluoromethyl)phenyl]-1-(2-hydroxy-2-methylpropyl)-1H,4H,5H-pyrrolo[3,2-c]pyridin-4-one | 13 |
| 242 | 5-[2-(3,4-difluoropyrrolidin-1-yl)-2-oxoethyl]-3-[4-fluoro-3-(trifluoromethyl)phenyl]-1-(methoxymethyl)-1H,4H,5H-pyrrolo[3,2-c]pyridin-4-one | 110 |
| 221 | 3-[6-chloro-5-(trifluoromethyl)pyridin-3-yl]-5-[2-(3,4-difluoropyrrolidin-1-yl)-2-oxoethyl]-1H,4H,5H-pyrrolo[3,2-c]pyridin-4-one | 43 |
| 117 | 7-[(diethylamino)methyl]-3-[4-fluoro-3-(trifluoromethyl)phenyl]-5-[2-(3-fluoropyrrolidin-1-yl)-2-oxoethyl]-4H,5H-thieno[3,2-c]pyridin-4-one | 30 |
| 116 | 7-[(dimethylamino)methyl]-3-[4-fluoro-3-(trifluoromethyl)phenyl]-5-[2-(3-fluoropyrrolidin-1-yl)-2-oxoethyl]-4H,5H-thieno[3,2-c]pyridin-4-one | 70 |
| 126 | 3-[4-fluoro-3-(trifluoromethyl)phenyl]-5-[2-(3-fluoropyrrolidin-1-yl)-2-oxoethyl]-7-(methoxymethyl)-4H,5H-thieno[3,2-c]pyridin-4-one | 46 |
| 38 | 3-(5-chloro-6-fluoropyridin-3-yl)-5-[2-(3,4-difluoropyrrolidin-1-yl)-2-oxoethyl]-4H,5H-thieno[3,2-c]pyridin-4-one | 18 |

TABLE 49-continued

| Ex. No. | IUPAC Name | Response Recovered (%) |
|---|---|---|
| 228 | 3-(3-chloro-4-fluorophenyl)-5-[2-(3-fluoropyrrolidin-1-yl)-2-oxoethyl]-1-(pyridin-2-yl)-1H,4H,5H-pyrrolo[3,2-c]pyridin-4-one | 39 |
| 127 | 7-(ethoxymethyl)-3-[4-fluoro-3-(trifluoromethyl)phenyl]-5-[2-(3-fluoropyrrolidin-1-yl)-2-oxoethyl]-4H,5H-thieno[3,2-c]pyridin-4-one | 48 |
| 210 | 3-(5,6-dichloropyridin-3-yl)-5-[2-(3,4-difluoropyrrolidin-1-yl)-2-oxoethyl]-1H,4H,5H-pyrrolo[3,2-c]pyridin-4-one | 26 |
| 134 | 3-[4-fluoro-3-(trifluoromethyl)phenyl]-5-[2-(3-fluoropyrrolidin-1-yl)-2-oxoethyl]-7-[(1E)-(hydroxyimino)methyl]-4H,5H-thieno[3,2-c]pyridin-4-one | 130 |
| 450 | 3-(3,4-dichlorophenyl)-6-[2-(3-fluoropyrrolidin-1-yl)-2-oxoethyl]-5H,6H-imidazo[1,2-c]pyrimidin-5-one | 33 |
| 451 | 3-(3-chloro-4-fluorophenyl)-6-[2-(3-fluoropyrrolidin-1-yl)-2-oxoethyl]-5H,6H-imidazo[1,2-c]pyrimidin-5-one | 23 |
| 115 | 7-(azetidin-1-yl)-3-[4-fluoro-3-(trifluoromethyl)phenyl]-5-[2-(3-fluoropyrrolidin-1-yl)-2-oxoethyl]-4H,5H-thieno[3,2-c]pyridin-4-one | 8.3 |
| 243 | 3-[4-fluoro-3-(trifluoromethyl)phenyl]-5-[2-(3-fluoropyrrolidin-1-yl)-2-oxoethyl]-1-(pyrimidin-2-yl)-1H,4H,5H-pyrrolo[3,2-c]pyridin-4-one | 96 |
| 244 | 3-[4-fluoro-3-(trifluoromethyl)phenyl]-5-[2-(3-fluoropyrrolidin-1-yl)-2-oxoethyl]-1-(pyrimidin-4-yl)-1H,4H,5H-pyrrolo[3,2-c]pyridin-4-one | 110 |
| 128 | 3-(3-chloro-4-fluorophenyl)-5-[2-(3-fluoropyrrolidin-1-yl)-2-oxoethyl]-7-(methoxymethyl)-4H,5H-thieno[3,2-c]pyridin-4-one | 23 |
| 129 | 3-(3-chloro-4-fluorophenyl)-5-[2-(3-fluoropyrrolidin-1-yl)-2-oxoethyl]-7-(hydroxymethyl)-4H,5H-thieno[3,2-c]pyridin-4-one | 39 |
| 130 | 3-(3-chloro-4-fluorophenyl)-7-(ethoxymethyl)-5-[2-(3-fluoropyrrolidin-1-yl)-2-oxoethyl]-4H,5H-thieno[3,2-c]pyridin-4-one | 42 |
| 260 | 3-[4-fluoro-3-(trifluoromethyl)phenyl]-5-[2-(3-fluoropyrrolidin-1-yl)-2-oxoethyl]-1-(hydroxymethyl)-1H,4H,5H-pyrrolo[3,2-c]pyridin-4-one | 68 |
| 245 | 3-(3-chloro-4-fluorophenyl)-1-[2-(dimethylamino)ethyl]-5-[2-(3-fluoropyrrolidin-1-yl)-2-oxoethyl]-1H,4H,5H-pyrrolo[3,2-c]pyridin-4-one | 14 |
| 259 | 3-(3-chloro-4-fluorophenyl)-5-[2-(3-fluoropyrrolidin-1-yl)-2-oxoethyl]-1-(2-hydroxy-2-methylpropyl)-1H,4H,5H-pyrrolo[3,2-c]pyridin-4-one | 35 |
| 246 | 3-(3-chloro-4-fluorophenyl)-5-[2-(3-fluoropyrrolidin-1-yl)-2-oxoethyl]-1-(methoxymethyl)-1H,4H,5H-pyrrolo[3,2-c]pyridin-4-one | 34 |
| 247 | 3-(3-chloro-4-fluorophenyl)-5-[2-(3-fluoropyrrolidin-1-yl)-2-oxoethyl]-1-methyl-1H,4H,5H-pyrrolo[3,2-c]pyridin-4-one | 51 |
| 229 | 3-(3,4-dichlorophenyl)-5-[2-(3-fluoropyrrolidin-1-yl)-2-oxoethyl]-1-(pyridin-2-yl)-1H,4H,5H-pyrrolo[3,2-c]pyridin-4-one | 78 |
| 135 | 3-[4-fluoro-3-(trifluoromethyl)phenyl]-5-[2-(3-fluoropyrrolidin-1-yl)-2-oxoethyl]-7-[(1Z)-1-(hydroxyimino)ethyl]-4H,5H-thieno[3,2-c]pyridin-4-one | 11 |
| 131 | 3-(3,4-dichlorophenyl)-5-[2-(3-fluoropyrrolidin-1-yl)-2-oxoethyl]-7-(hydroxymethyl)-4H,5H-thieno[3,2-c]pyridin-4-one | 72 |
| 132 | 3-(3,4-dichlorophenyl)-5-[2-(3-fluoropyrrolidin-1-yl)-2-oxoethyl]-7-(methoxymethyl)-4H,5H-thieno[3,2-c]pyridin-4-one | 20 |
| 133 | 3-[4-fluoro-3-(trifluoromethyl)phenyl]-5-[2-(3-fluoropyrrolidin-1-yl)-2-oxoethyl]-7-(2-hydroxypropan-2-yl)-4H,5H-thieno[3,2-c]pyridin-4-one | 9.9 |
| 248 | 3-(3-chloro-4-fluorophenyl)-5-[2-(3-fluoropyrrolidin-1-yl)-2-oxoethyl]-1-(pyrimidin-4-yl)-1H,4H,5H-pyrrolo[3,2-c]pyridin-4-one | 59 |
| 232 | 3-(3-chloro-4-fluorophenyl)-1-cyclopropyl-5-[2-(3-fluoropyrrolidin-1-yl)-2-oxoethyl]-1H,4H,5H-pyrrolo[3,2-c]pyridin-4-one | 66 |
| 261 | 3-(3-chloro-4-fluorophenyl)-5-[2-(3-fluoropyrrolidin-1-yl)-2-oxoethyl]-1-(oxetan-3-yl)-1H,4H,5H-pyrrolo[3,2-c]pyridin-4-one | 29 |
| 233 | 1-cyclopropyl-3-(3,4-dichlorophenyl)-5-[2-(3-fluoropyrrolidin-1-yl)-2-oxoethyl]-1H,4H,5H-pyrrolo[3,2-c]pyridin-4-one | 85 |
| 392 | 8-(3-chloro-4-fluorophenyl)-2-[2-oxo-2-(pyrrolidin-1-yl)ethyl]-1H,2H-pyrrolo[1,2-a]pyrazin-1-one | 118 |
| 393 | 8-(3-chloro-4-fluorophenyl)-2-[2-(3-fluoropyrrolidin-1-yl)-2-oxoethyl]-1H,2H-pyrrolo[1,2-a]pyrazin-1-one | 49 |
| 119 | 3-(3-chloro-4-fluorophenyl)-5-[2-(3-fluoropyrrolidin-1-yl)-2-oxoethyl]-7-(pyrrolidin-1-ylmethyl)-4H,5H-thieno[3,2-c]pyridin-4-one | 75 |
| 120 | 3-(3-chloro-4-fluorophenyl)-7-[(dimethylamino)methyl]-5-[2-(3-fluoropyrrolidin-1-yl)-2-oxoethyl]-4H,5H-thieno[3,2-c]pyridin-4-one | 61 |
| 394 | 8-(3,4-dichlorophenyl)-2-[2-oxo-2-(pyrrolidin-1-yl)ethyl]-1H,2H-pyrrolo[1,2-a]pyrazin-1-one | 62 |
| 395 | 8-(3,4-dichlorophenyl)-2-[2-(3-fluoropyrrolidin-1-yl)-2-oxoethyl]-1H,2H-pyrrolo[1,2-a]pyrazin-1-one | 58 |
| 121 | 3-(3,4-dichlorophenyl)-5-[2-(3-fluoropyrrolidin-1-yl)-2-oxoethyl]-7-(pyrrolidin-1-ylmethyl)-4H,5H-thieno[3,2-c]pyridin-4-one | 59 |
| 122 | 7-(azetidin-1-ylmethyl)-3-(3,4-dichlorophenyl)-5-[2-(3-fluoropyrrolidin-1-yl)-2-oxoethyl]-4H,5H-thieno[3,2-c]pyridin-4-one | 27 |
| 123 | 3-(3,4-dichlorophenyl)-7-[(dimethylamino)methyl]-5-[2-(3-fluoropyrrolidin-1-yl)-2-oxoethyl]-4H,5H-thieno[3,2-c]pyridin-4-one | 70 |

TABLE 49-continued

| Ex. No. | IUPAC Name | Response Recovered (%) |
|---|---|---|
| 249 | 3-(3,4-dichlorophenyl)-5-[2-(3-fluoropyrrolidin-1-yl)-2-oxoethyl]-1-(methoxymethyl)-1H,4H,5H-pyrrolo[3,2-c]pyridin-4-one | 70 |
| 124 | 7-(azetidin-1-ylmethyl)-3-(3-chloro-4-fluorophenyl)-5-[2-(3-fluoropyrrolidin-1-yl)-2-oxoethyl]-4H,5H-thieno[3,2-c]pyridin-4-one | 76 |
| 262 | 3-[4-fluoro-3-(trifluoromethyl)phenyl]-5-[2-(3-fluoropyrrolidin-1-yl)-2-oxoethyl]-1-(pyridazin-4-yl)-1H,4H,5H-pyrrolo[3,2-c]pyridin-4-one | 44 |
| 250 | 3-(3,4-dichlorophenyl)-5-[2-(3-fluoropyrrolidin-1-yl)-2-oxoethyl]-1-methyl-1H,4H,5H-pyrrolo[3,2-c]pyridin-4-one | 62 |
| 263 | 3-[4-fluoro-3-(trifluoromethyl)phenyl]-5-[2-(3-fluoropyrrolidin-1-yl)-2-oxoethyl]-1-(5-methyl-1,3,4-oxadiazol-2-yl)-1H,4H,5H-pyrrolo[3,2-c]pyridin-4-one | 72 |
| 265 | 3-[4-fluoro-3-(trifluoromethyl)phenyl]-5-[2-(3-fluoropyrrolidin-1-yl)-2-oxoethyl]-1-(oxetan-3-yl)-1H,4H,5H-pyrrolo[3,2-c]pyridin-4-one | 61 |
| 264 | 3-(3-chloro-4-fluorophenyl)-5-[2-(3-fluoropyrrolidin-1-yl)-2-oxoethyl]-1-(5-methyl-1,3,4-oxadiazol-2-yl)-1H,4H,5H-pyrrolo[3,2-c]pyridin-4-one | 49 |
| 251 | 3-[4-fluoro-3-(trifluoromethyl)phenyl]-5-[2-(3-fluoropyrrolidin-1-yl)-2-oxoethyl]-1-methyl-1H,4H,5H-pyrrolo[3,2-c]pyridin-4-one | 61 |
| 234 | 3-[4-fluoro-3-(trifluoromethyl)phenyl]-5-[2-(3-fluoropyrrolidin-1-yl)-2-oxoethyl]-1-(1-methyl-1H-pyrazol-4-yl)-1H,4H,5H-pyrrolo[3,2-c]pyridin-4-one | 80 |
| 266 | 3-[4-fluoro-3-(trifluoromethyl)phenyl]-5-[2-(3-fluoropyrrolidin-1-yl)-2-oxoethyl]-1-(1-methyl-1H-1,2,4-triazol-3-yl)-1H,4H,5H-pyrrolo[3,2-c]pyridin-4-one | 95 |
| 272 | 3-(3,4-dichlorophenyl)-1-ethyl-5-[2-(3-fluoropyrrolidin-1-yl)-2-oxoethyl]-1H,4H,5H-pyrrolo[3,2-c]pyridin-4-one | 33 |
| 39 | 3-(3-chloro-4-fluorophenyl)-5-[2-(3-fluoro-3-methylazetidin-1-yl)-2-oxoethyl]-4H,5H-thieno[3,2-c]pyridin-4-one | 140 |
| 252 | 3-[4-fluoro-3-(trifluoromethyl)phenyl]-1-(2-fluoroethyl)-5-[2-(3-fluoropyrrolidin-1-yl)-2-oxoethyl]-1H,4H,5H-pyrrolo[3,2-c]pyridin-4-one | 96 |
| 40 | 3-(3-chloro-4-fluorophenyl)-5-{2-[(3S)-3-fluoropyrrolidin-1-yl]-2-oxoethyl}-4H,5H-thieno[3,2-c]pyridin-4-one | 46 |
| 41 | 3-(3-chloro-4-fluorophenyl)-5-{2-[(3R)-3-fluoropyrrolidin-1-yl]-2-oxoethyl}-4H,5H-thieno[3,2-c]pyridin-4-one | 77 |
| 253 | 3-(3-chloro-4-fluorophenyl)-1-(2-fluoroethyl)-5-[2-(3-fluoropyrrolidin-1-yl)-2-oxoethyl]-1H,4H,5H-pyrrolo[3,2-c]pyridin-4-one | 66 |
| 274 | 3-(3-chloro-4-fluorophenyl)-5-[2-(3-fluoropyrrolidin-1-yl)-2-oxoethyl]-1-(2,2,2-trifluoroethyl)-1H,4H,5H-pyrrolo[3,2-c]pyridin-4-one | 94 |
| 411 | 8-[4-fluoro-3-(trifluoromethyl)phenyl]-2-[2-(3-fluoropyrrolidin-1-yl)-2-oxoethyl]-4-methyl-1H,2H-pyrrolo[1,2-a]pyrazin-1-one | 59 |
| 453 | 3-(3,4-dichlorophenyl)-6-[2-(3-fluoropyrrolidin-1-yl)-2-oxoethyl]-8-methyl-5H,6H-imidazo[1,2-c]pyrimidin-5-one | 26 |
| 452 | 3-(3-chloro-4-fluorophenyl)-6-[2-(3-fluoropyrrolidin-1-yl)-2-oxoethyl]-8-methyl-5H,6H-imidazo[1,2-c]pyrimidin-5-one | 7.5 |
| 454 | 3-[4-fluoro-3-(trifluoromethyl)phenyl]-6-[2-(3-fluoropyrrolidin-1-yl)-2-oxoethyl]-8-methyl-5H,6H-imidazo[1,2-c]pyrimidin-5-one | 35 |
| 427 | 1-[4-fluoro-3-(trifluoromethyl)phenyl]-7-[2-(3-fluoropyrrolidin-1-yl)-2-oxoethyl]-3-methyl-7H,8H-imidazo[1,5-a]pyrazin-8-one | 19 |
| 428 | 1-(3-chloro-4-fluorophenyl)-7-[2-(3-fluoropyrrolidin-1-yl)-2-oxoethyl]-3-methyl-7H,8H-imidazo[1,5-a]pyrazin-8-one | 18 |
| 429 | 1-(3,4-dichlorophenyl)-7-[2-(3-fluoropyrrolidin-1-yl)-2-oxoethyl]-3-methyl-7H,8H-imidazo[1,5-a]pyrazin-8-one | 11 |
| 275 | 3-(3,4-dichlorophenyl)-5-[2-(3-fluoropyrrolidin-1-yl)-2-oxoethyl]-1-(2,2,2-trifluoroethyl)-1H,4H,5H-pyrrolo[3,2-c]pyridin-4-one | 100 |
| 276 | 3-(3-chloro-4-fluorophenyl)-1-(2,2-difluoroethyl)-5-[2-(3-fluoropyrrolidin-1-yl)-2-oxoethyl]-1H,4H,5H-pyrrolo[3,2-c]pyridin-4-one | 50 |
| 277 | 3-[4-fluoro-3-(trifluoromethyl)phenyl]-5-[2-(3-fluoropyrrolidin-1-yl)-2-oxoethyl]-1-(2,2,2-trifluoroethyl)-1H,4H,5H-pyrrolo[3,2-c]pyridin-4-one | 78 |
| 235 | 3-(3-chloro-4-fluorophenyl)-5-[2-(3-fluoropyrrolidin-1-yl)-2-oxoethyl]-1-(1-methyl-1H-pyrazol-4-yl)-1H,4H,5H-pyrrolo[3,2-c]pyridin-4-one | 40 |
| 279 | 1-(2,2-difluoroethyl)-3-[4-fluoro-3-(trifluoromethyl)phenyl]-5-[2-(3-fluoropyrrolidin-1-yl)-2-oxoethyl]-1H,4H,5H-pyrrolo[3,2-c]pyridin-4-one | 71 |
| 432 | 1-(3-chloro-4-fluorophenyl)-3-cyclopropyl-7-[2-(3-fluoropyrrolidin-1-yl)-2-oxoethyl]-7H,8H-imidazo[1,5-a]pyrazin-8-one | 19 |
| 413 | 8-(3,4-dichlorophenyl)-2-[2-(3-fluoropyrrolidin-1-yl)-2-oxoethyl]-4-methyl-1H,2H-pyrrolo[1,2-a]pyrazin-1-one | 43 |
| 42 | 3-(3,4-dichlorophenyl)-5-[2-(3-fluoro-3-methylazetidin-1-yl)-2-oxoethyl]-4H,5H-thieno[3,2-c]pyridin-4-one | 150 |

TABLE 49-continued

| Ex. No. | IUPAC Name | Response Recovered (%) |
|---|---|---|
| 43 | 3-[4-fluoro-3-(trifluoromethyl)phenyl]-5-[2-(3-fluoro-3-methylazetidin-1-yl)-2-oxoethyl]-4H,5H-thieno[3,2-c]pyridin-4-one | 160 |
| 433 | 3-cyclopropyl-1-(3,4-dichlorophenyl)-7-[2-(3-fluoropyrrolidin-1-yl)-2-oxoethyl]-7H,8H-imidazo[1,5-a]pyrazin-8-one | 68 |
| 434 | 3-cyclopropyl-1-[4-fluoro-3-(trifluoromethyl)phenyl]-7-[2-(3-fluoropyrrolidin-1-yl)-2-oxoethyl]-7H,8H-imidazo[1,5-a]pyrazin-8-one | 40 |
| 276 | 3-(3,4-dichlorophenyl)-1-(2,2-difluoroethyl)-5-[2-(3-fluoropyrrolidin-1-yl)-2-oxoethyl]-1H,4H,5H-pyrrolo[3,2-c]pyridin-4-one | 78 |
| 414 | 8-(3-chloro-4-fluorophenyl)-2-[2-(3-fluoropyrrolidin-1-yl)-2-oxoethyl]-4-methyl-1H,2H-pyrrolo[1,2-a]pyrazin-1-one | 112 |
| 412 | 6-bromo-8-[4-fluoro-3-(trifluoromethyl)phenyl]-2-[2-(3-fluoropyrrolidin-1-yl)-2-oxoethyl]-4-methyl-1H,2H-pyrrolo[1,2-a]pyrazin-1-one | 38 |
| 415 | 6-bromo-8-(3-chloro-4-fluorophenyl)-2-[2-(3-fluoropyrrolidin-1-yl)-2-oxoethyl]-4-methyl-1H,2H-pyrrolo[1,2-a]pyrazin-1-one | 52 |
| 423 | 6-bromo-8-[4-fluoro-3-(trifluoromethyl)phenyl]-2-[2-(3-fluoropyrrolidin-1-yl)-2-oxoethyl]-1H,2H-pyrrolo[1,2-a]pyrazin-1-one | 72 |
| 396 | 8-(3,4-dichlorophenyl)-2-[2-(3-fluoro-3-methylazetidin-1-yl)-2-oxoethyl]-1H,2H-pyrrolo[1,2-a]pyrazin-1-one | 140 |
| 44 | 3-(3-chloro-4-fluorophenyl)-5-[2-(3-cyclopropyl-3-fluoroazetidin-1-yl)-2-oxoethyl]-4H,5H-thieno[3,2-c]pyridin-4-one | 63 |
| 45 | 5-[2-(3-cyclopropyl-3-fluoroazetidin-1-yl)-2-oxoethyl]-3-[4-fluoro-3-(trifluoromethyl)phenyl]-4H,5H-thieno[3,2-c]pyridin-4-one | 12 |
| 283 | 3-(3,4-dichlorophenyl)-5-[2-(3-fluoropyrrolidin-1-yl)-2-oxoethyl]-1-(1-methyl-1H-pyrazol-4-yl)-1H,4H,5H-pyrrolo[3,2-c]pyridin-4-one | 82 |
| 222 | 3-[4-fluoro-3-(trifluoromethyl)phenyl]-5-[2-(3-fluoro-3-methylazetidin-1-yl)-2-oxoethyl]-1H,4H,5H-pyrrolo[3,2-c]pyridin-4-one | 86 |
| 46 | 5-[2-(azetidin-1-yl)-2-oxoethyl]-3-(3-chloro-4-fluorophenyl)-4H,5H-thieno[3,2-c]pyridin-4-one | 26 |
| 47 | 3-(3-chloro-4-fluorophenyl)-5-[2-(3-fluoroazetidin-1-yl)-2-oxoethyl]-4H,5H-thieno[3,2-c]pyridin-4-one | 23 |
| 48 | 3-(3-chloro-4-fluorophenyl)-5-[2-(3-methylazetidin-1-yl)-2-oxoethyl]-4H,5H-thieno[3,2-c]pyridin-4-one | 67 |
| 125 | 3-(3-chloro-4-fluorophenyl)-7-[(3-fluoroazetidin-1-yl)methyl]-5-[2-(3-fluoropyrrolidin-1-yl)-2-oxoethyl]-4H,5H-thieno[3,2-c]pyridin-4-one | 53 |
| 273 | 3-(3,4-dichlorophenyl)-1-(2-fluoroethyl)-5-[2-(3-fluoropyrrolidin-1-yl)-2-oxoethyl]-1H,4H,5H-pyrrolo[3,2-c]pyridin-4-one | 93 |
| 267 | 3-(3-chloro-4-fluorophenyl)-5-[2-(3-fluoropyrrolidin-1-yl)-2-oxoethyl]-1-(1-methyl-1H-1,2,3-triazol-4-yl)-1H,4H,5H-pyrrolo[3,2-c]pyridin-4-one | 27 |
| 397 | 8-(3-chloro-4-fluorophenyl)-2-[2-(3-fluoro-3-methylazetidin-1-yl)-2-oxoethyl]-1H,2H-pyrrolo[1,2-a]pyrazin-1-one | 140 |
| 49 | 5-[2-(3-cyclopropyl-3-fluoroazetidin-1-yl)-2-oxoethyl]-3-(3,4-dichlorophenyl)-4H,5H-thieno[3,2-c]pyridin-4-one | 26 |
| 50 | 3-(3,4-dichlorophenyl)-5-[2-(3-ethyl-3-fluoroazetidin-1-yl)-2-oxoethyl]-4H,5H-thieno[3,2-c]pyridin-4-one | 96 |
| 51 | 5-[2-(3-ethyl-3-fluoroazetidin-1-yl)-2-oxoethyl]-3-[4-fluoro-3-(trifluoromethyl)phenyl]-4H,5H-thieno[3,2-c]pyridin-4-one | 57 |
| 52 | 3-(3-chloro-4-fluorophenyl)-5-[2-(3-ethyl-3-fluoroazetidin-1-yl)-2-oxoethyl]-4H,5H-thieno[3,2-c]pyridin-4-one | 130 |
| 53 | 3-(3,4-dichlorophenyl)-5-[2-(3-fluoro-3-phenylazetidin-1-yl)-2-oxoethyl]-4H,5H-thieno[3,2-c]pyridin-4-one | 24 |
| 54 | 3-[4-fluoro-3-(trifluoromethyl)phenyl]-5-[2-(3-fluoro-3-phenylazetidin-1-yl)-2-oxoethyl]-4H,5H-thieno[3,2-c]pyridin-4-one | 17 |
| 55 | 3-[4-fluoro-3-(trifluoromethyl)phenyl]-5-[2-(3-hydroxy-3-methylazetidin-1-yl)-2-oxoethyl]-4H,5H-thieno[3,2-c]pyridin-4-one | 14 |
| 223 | 3-(3-chloro-4-fluorophenyl)-5-[2-(3-fluoro-3-methylazetidin-1-yl)-2-oxoethyl]-1H,4H,5H-pyrrolo[3,2-c]pyridin-4-one | |
| 56 | 2-[3-(3-chloro-4-fluorophenyl)-4-oxo-4H,5H-thieno[3,2-c]pyridin-5-yl]-N-(2,2,2-trifluoroethyl)acetamide | 7.3 |
| 398 | 8-(3-chloro-4-fluorophenyl)-2-[2-(3-cyclopropyl-3-fluoroazetidin-1-yl)-2-oxoethyl]-1H,2H-pyrrolo[1,2-a]pyrazin-1-one | 43 |
| 399 | 8-(3-chloro-4-fluorophenyl)-2-[2-(3-fluoro-3-phenylazetidin-1-yl)-2-oxoethyl]-1H,2H-pyrrolo[1,2-a]pyrazin-1-one | 1.5 |
| 268 | 3-[4-fluoro-3-(trifluoromethyl)phenyl]-5-[2-(3-fluoro-3-methylazetidin-1-yl)-2-oxoethyl]-1-(1-methyl-1H-1,2,4-triazol-3-yl)-1H,4H,5H-pyrrolo[3,2-c]pyridin-4-one | 52 |
| 57 | 3-(3-chloro-4-fluorophenyl)-5-[2-(3-fluoro-3-phenylazetidin-1-yl)-2-oxoethyl]-4H,5H-thieno[3,2-c]pyridin-4-one | 15 |
| 58 | 3-(3-chloro-4-fluorophenyl)-5-[2-(3-hydroxy-3-methylazetidin-1-yl)-2-oxoethyl]-4H,5H-thieno[3,2-c]pyridin-4-one | 10 |
| 59 | 3-(3,4-dichlorophenyl)-5-[2-(3-methylazetidin-1-yl)-2-oxoethyl]-4H,5H-thieno[3,2-c]pyridin-4-one | 110 |

TABLE 49-continued

| Ex. No. | IUPAC Name | Response Recovered (%) |
|---|---|---|
| 60 | 3-[4-fluoro-3-(trifluoromethyl)phenyl]-5-[2-(3-methylazetidin-1-yl)-2-oxoethyl]-4H,5H-thieno[3,2-c]pyridin-4-one | 76 |
| 61 | 3-(3,4-dichlorophenyl)-5-[2-(3-hydroxy-3-methylazetidin-1-yl)-2-oxoethyl]-4H,5H-thieno[3,2-c]pyridin-4-one | 16 |
| 62 | 3-(3-chloro-4-fluorophenyl)-5-[2-(3-methoxy-3-methylazetidin-1-yl)-2-oxoethyl]-4H,5H-thieno[3,2-c]pyridin-4-one | 11 |
| 400 | 8-(3-chloro-4-fluorophenyl)-2-[2-(3-ethyl-3-fluoroazetidin-1-yl)-2-oxoethyl]-1H,2H-pyrrolo[1,2-a]pyrazin-1-one | 97 |
| 63 | 3-(3,4-dichlorophenyl)-5-[2-(3-methoxy-3-methylazetidin-1-yl)-2-oxoethyl]-4H,5H-thieno[3,2-c]pyridin-4-one | 16 |
| 64 | 3-[4-fluoro-3-(trifluoromethyl)phenyl]-5-[2-(3-methoxy-3-methylazetidin-1-yl)-2-oxoethyl]-4H,5H-thieno[3,2-c]pyridin-4-one | 22 |
| 65 | 3-(3-chloro-4-fluorophenyl)-5-(2-{6,6-difluoro-3-azabicyclo[3.1.0]hexan-3-yl}-2-oxoethyl)-4H,5H-thieno[3,2-c]pyridin-4-one | 13 |
| 66 | 3-(3,4-dichlorophenyl)-5-(2-{6,6-difluoro-3-azabicyclo[3.1.0]hexan-3-yl}-2-oxoethyl)-4H,5H-thieno[3,2-c]pyridin-4-one | 26 |
| 67 | 3-(3-chloro-4-fluorophenyl)-5-(2-{2-oxa-6-azaspiro[3.3]heptan-6-yl}-2-oxoethyl)-4H,5H-thieno[3,2-c]pyridin-4-one | 4.4 |
| 68 | 3-(3,4-dichlorophenyl)-5-(2-{2-oxa-6-azaspiro[3.3]heptan-6-yl}-2-oxoethyl)-4H,5H-thieno[3,2-c]pyridin-4-one | 13 |
| 69 | 3-[4-fluoro-3-(trifluoromethyl)phenyl]-5-(2-{2-oxa-6-azaspiro[3.3]heptan-6-yl}-2-oxoethyl)-4H,5H-thieno[3,2-c]pyridin-4-one | 16 |
| 269 | 3-(3-chloro-4-fluorophenyl)-5-[2-(3-fluoro-3-methylazetidin-1-yl)-2-oxoethyl]-1-(1-methyl-1H-1,2,4-triazol-3-yl)-1H,4H,5H-pyrrolo[3,2-c]pyridin-4-one | 130 |
| 93 | 2-[3-(3-chloro-4-fluorophenyl)-4-oxo-4H,5H-thieno[3,2-c]pyridin-5-yl]-N-methyl-N-(2,2,2-trifluoroethyl)acetamide | 4.1 |
| 70 | 5-[2-(3-cyclopropyl-3-fluoroazetidin-1-yl)-2-oxoethyl]-3-(5,6-dichloropyridin-3-yl)-4H,5H-thieno[3,2-c]pyridin-4-one | 64 |
| 71 | 5-(2-{5-azaspiro[2.3]hexan-5-yl}-2-oxoethyl)-3-(3-chloro-4-fluorophenyl)-4H,5H-thieno[3,2-c]pyridin-4-one | 46 |
| 72 | 5-(2-{6,6-difluoro-3-azabicyclo[3.1.0]hexan-3-yl}-2-oxoethyl)-3-[4-fluoro-3-(trifluoromethyl)phenyl]-4H,5H-thieno[3,2-c]pyridin-4-one | 37 |
| 284 | 3-(3,4-dichlorophenyl)-5-[2-(3-fluoro-3-methylazetidin-1-yl)-2-oxoethyl]-1-(1-methyl-1H-pyrazol-4-yl)-1H,4H,5H-pyrrolo[3,2-c]pyridin-4-one | 5.2 |
| 73 | tert-butyl N-(1-{2-[3-(3,4-dichlorophenyl)-4-oxo-4H,5H-thieno[3,2-c]pyridin-5-yl]acetyl}-3-methylazetidin-3-yl)carbamate | 9.8 |
| 94 | 5-[2-(3-amino-3-methylazetidin-1-yl)-2-oxoethyl]-3-(3,4-dichlorophenyl)-4H,5H-thieno[3,2-c]pyridin-4-one | 3.1 |
| 401 | 8-[4-fluoro-3-(trifluoromethyl)phenyl]-2-[2-(3-fluoro-3-methylazetidin-1-yl)-2-oxoethyl]-1H,2H-pyrrolo[1,2-a]pyrazin-1-one | 160 |
| 74 | tert-butyl N-(1-{2-[3-(3-chloro-4-fluorophenyl)-4-oxo-4H,5H-thieno[3,2-c]pyridin-5-yl]acetyl}-3-methylazetidin-3-yl)carbamate | 4.7 |
| 95 | 5-[2-(3-amino-3-methylazetidin-1-yl)-2-oxoethyl]-3-(3-chloro-4-fluorophenyl)-4H,5H-thieno[3,2-c]pyridin-4-one | 1 |
| 75 | 3-(5,6-dichloropyridin-3-yl)-5-[2-(3-ethyl-3-fluoroazetidin-1-yl)-2-oxoethyl]-4H,5H-thieno[3,2-c]pyridin-4-one | 78 |
| 76 | 3-(5,6-dichloropyridin-3-yl)-5-[2-(3-fluoro-3-methylazetidin-1-yl)-2-oxoethyl]-4H,5H-thieno[3,2-c]pyridin-4-one | 77 |
| 77 | tert-butyl N-[1-(2-{3-[4-fluoro-3-(trifluoromethyl)phenyl]-4-oxo-4H,5H-thieno[3,2-c]pyridin-5-yl}acetyl)-3-methylazetidin-3-yl]carbamate | −6.4 |
| 96 | 5-[2-(3-amino-3-methylazetidin-1-yl)-2-oxoethyl]-3-[4-fluoro-3-(trifluoromethyl)phenyl]-4H,5H-thieno[3,2-c]pyridin-4-one | 4.3 |
| 270 | 3-(3,4-dichlorophenyl)-5-[2-(3-fluoro-3-methylazetidin-1-yl)-2-oxoethyl]-1-(1-methyl-1H-1,2,4-triazol-3-yl)-1H,4H,5H-pyrrolo[3,2-c]pyridin-4-one | 130 |
| 236 | 3-[4-fluoro-3-(trifluoromethyl)phenyl]-5-[2-(3-fluoro-3-methylazetidin-1-yl)-2-oxoethyl]-1-(1-methyl-1H-pyrazol-4-yl)-1H,4H,5H-pyrrolo[3,2-c]pyridin-4-one | 140 |
| 78 | 5-(2-{5-azaspiro[2.3]hexan-5-yl}-2-oxoethyl)-3-(3,4-dichlorophenyl)-4H,5H-thieno[3,2-c]pyridin-4-one | 53 |
| 79 | tert-butyl 6-{2-[3-(3-chloro-4-fluorophenyl)-4-oxo-4H,5H-thieno[3,2-c]pyridin-5-yl]acetyl}-1,6-diazaspiro[3.3]heptane-1-carboxylate | 18 |
| 271 | 3-(3-chloro-4-fluorophenyl)-5-[2-(3-fluoro-3-methylazetidin-1-yl)-2-oxoethyl]-1-(1-methyl-1H-1,2,3-triazol-4-yl)-1H,4H,5H-pyrrolo[3,2-c]pyridin-4-one | 140 |
| 285 | 3-(3-chloro-4-fluorophenyl)-1-cyclopropyl-5-[2-(3-fluoro-3-methylazetidin-1-yl)-2-oxoethyl]-1H,4H,5H-pyrrolo[3,2-c]pyridin-4-one | 140 |
| 80 | 5-(2-{5-azaspiro[2.3]hexan-5-yl}-2-oxoethyl)-3-[4-fluoro-3-(trifluoromethyl)phenyl]-4H,5H-thieno[3,2-c]pyridin-4-one | 64 |

TABLE 49-continued

| Ex. No. | IUPAC Name | Response Recovered (%) |
|---|---|---|
| 286 | 3-(3-chloro-4-fluorophenyl)-5-[2-(3-fluoro-3-methylazetidin-1-yl)-2-oxoethyl]-1-(1-methyl-1H-pyrazol-4-yl)-1H,4H,5H-pyrrolo[3,2-c]pyridin-4-one | 130 |
| 280 | 3-(3-chloro-4-fluorophenyl)-5-[2-(3-fluoro-3-methylazetidin-1-yl)-2-oxoethyl]-1-(2,2,2-trifluoroethyl)-1H,4H,5H-pyrrolo[3,2-c]pyridin-4-one | 73 |
| 281 | 3-(3-chloro-4-fluorophenyl)-5-[2-(3-fluoro-3-methylazetidin-1-yl)-2-oxoethyl]-1-(2-fluoroethyl)-1H,4H,5H-pyrrolo[3,2-c]pyridin-4-one | 150 |
| 18 | 3-(4-chloro-3-fluorophenyl)-5-[2-(3-fluoro-3-methylazetidin-1-yl)-2-oxoethyl]-4H,5H-thieno[3,2-c]pyridin-4-one | 120 |
| 19 | 3-(5-chloro-6-fluoropyridin-3-yl)-5-[2-(3-fluoro-3-methylazetidin-1-yl)-2-oxoethyl]-4H,5H-thieno[3,2-c]pyridin-4-one | 35 |
| 97 | 3-(3-chloro-4-fluorophenyl)-5-(2-{1,6-diazaspiro[3.3]heptan-6-yl}-2-oxoethyl)-4H,5H-thieno[3,2-c]pyridin-4-one | 2.8 |
| 20 | 3-(3,4-difluorophenyl)-5-[2-(3-fluoro-3-methylazetidin-1-yl)-2-oxoethyl]-4H,5H-thieno[3,2-c]pyridin-4-one | 41 |
| 21 | 3-[4-chloro-3-(trifluoromethyl)phenyl]-5-[2-(3-fluoro-3-methylazetidin-1-yl)-2-oxoethyl]-4H,5H-thieno[3,2-c]pyridin-4-one | 120 |
| 426 | 1-(3-chloro-4-fluorophenyl)-7-[2-(3-fluoro-3-methylazetidin-1-yl)-2-oxoethyl]-3-methyl-7H,8H-imidazo[1,5-a]pyrazin-8-one | 30 |
| 430 | 1-(3-chloro-4-fluorophenyl)-7-[2-(3,3-difluoroazetidin-1-yl)-2-oxoethyl]-3-methyl-7H,8H-imidazo[1,5-a]pyrazin-8-one | 7.3 |
| 416 | 8-(3-chloro-4-fluorophenyl)-2-[2-(3-fluoro-3-methylazetidin-1-yl)-2-oxoethyl]-4-methyl-1H,2H-pyrrolo[1,2-a]pyrazin-1-one | 110 |
| 417 | 8-(3-chloro-4-fluorophenyl)-2-[2-(3,3-difluoroazetidin-1-yl)-2-oxoethyl]-4-methyl-1H,2H-pyrrolo[1,2-a]pyrazin-1-one | 20 |
| 328 | 3-(3-chloro-4-fluorophenyl)-5-[2-(3,3-difluoroazetidin-1-yl)-2-oxoethyl]-4H,5H-pyrazolo[1,5-a]pyrazin-4-one | 29 |
| 22 | 3-(4-chloro-3-methylphenyl)-5-[2-(3-fluoro-3-methylazetidin-1-yl)-2-oxoethyl]-4H,5H-thieno[3,2-c]pyridin-4-one | 130 |
| 23 | 5-[2-(3-fluoro-3-methylazetidin-1-yl)-2-oxoethyl]-3-(4-fluoro-3-methylphenyl)-4H,5H-thieno[3,2-c]pyridin-4-one | 100 |
| 329 | 3-(3-chloro-4-fluorophenyl)-5-[2-(3-fluoro-3-methylazetidin-1-yl)-2-oxoethyl]-4H,5H-pyrazolo[1,5-a]pyrazin-4-one | 110 |
| 81 | 3-(3-chloro-4-fluorophenyl)-5-{2-[3-fluoro-3-(fluoromethyl)azetidin-1-yl]-2-oxoethyl}-4H,5H-thieno[3,2-c]pyridin-4-one | 140 |
| 237 | 3-(3-chloro-4-fluorophenyl)-1-cyclopropyl-5-[2-(3-ethyl-3-fluoroazetidin-1-yl)-2-oxoethyl]-1H,4H,5H-pyrrolo[3,2-c]pyridin-4-one | 79 |
| 445 | 1-(3-chloro-4-fluorophenyl)-7-[2-(3-fluoro-3-methylazetidin-1-yl)-2-oxoethyl]-7H,8H-imidazo[1,5-a]pyrazin-8-one | 34 |
| 446 | 1-[4-fluoro-3-(trifluoromethyl)phenyl]-7-[2-(3-fluoro-3-methylazetidin-1-yl)-2-oxoethyl]-7H,8H-imidazo[1,5-a]pyrazin-8-one | 68 |
| 447 | 1-(3,4-dichlorophenyl)-7-[2-(3-fluoro-3-methylazetidin-1-yl)-2-oxoethyl]-7H,8H-imidazo[1,5-a]pyrazin-8-one | 58 |
| 82 | 3-(3,4-dichlorophenyl)-5-{2-[3-fluoro-3-(fluoromethyl)azetidin-1-yl]-2-oxoethyl}-4H,5H-thieno[3,2-c]pyridin-4-one | 140 |
| 83 | 5-{2-[3-fluoro-3-(fluoromethyl)azetidin-1-yl]-2-oxoethyl}-3-[4-fluoro-3-(trifluoromethyl)phenyl]-4H,5H-thieno[3,2-c]pyridin-4-one | 140 |
| 402 | 8-(3-chloro-4-fluorophenyl)-2-{2-[3-fluoro-3-(fluoromethyl)azetidin-1-yl]-2-oxoethyl}-1H,2H-pyrrolo[1,2-a]pyrazin-1-one | 130 |
| 435 | 3-cyclopropyl-1-(3,4-dichlorophenyl)-7-[2-(3-fluoro-3-methylazetidin-1-yl)-2-oxoethyl]-7H,8H-imidazo[1,5-a]pyrazin-8-one | 120 |
| 403 | 8-(3,4-dichlorophenyl)-2-{2-[3-fluoro-3-(fluoromethyl)azetidin-1-yl]-2-oxoethyl}-1H,2H-pyrrolo[1,2-a]pyrazin-1-one | 130 |
| 418 | 8-(3-chloro-4-fluorophenyl)-2-[2-(3-ethyl-3-fluoroazetidin-1-yl)-2-oxoethyl]-4-methyl-1H,2H-pyrrolo[1,2-a]pyrazin-1-one | 74 |
| 404 | 8-(5,6-dichloropyridin-3-yl)-2-[2-(3-fluoro-3-methylazetidin-1-yl)-2-oxoethyl]-1H,2H-pyrrolo[1,2-a]pyrazin-1-one | 58 |
| 436 | 1-(3-chloro-4-fluorophenyl)-3-cyclopropyl-7-[2-(3-fluoro-3-methylazetidin-1-yl)-2-oxoethyl]-7H,8H-imidazo[1,5-a]pyrazin-8-one | 100 |
| 437 | 3-cyclopropyl-1-(5,6-dichloropyridin-3-yl)-7-[2-(3-fluoro-3-methylazetidin-1-yl)-2-oxoethyl]-7H,8H-imidazo[1,5-a]pyrazin-8-one | 65 |
| 438 | 3-cyclopropyl-1-[4-fluoro-3-(trifluoromethyl)phenyl]-7-[2-(3-fluoro-3-methylazetidin-1-yl)-2-oxoethyl]-7H,8H-imidazo[1,5-a]pyrazin-8-one | 79 |
| 431 | 1-(3-chloro-4-fluorophenyl)-7-[2-(3-ethyl-3-fluoroazetidin-1-yl)-2-oxoethyl]-3-methyl-7H,8H-imidazo[1,5-a]pyrazin-8-one | −3.9 |
| 405 | 8-(5,6-dichloropyridin-3-yl)-2-[2-(3-ethyl-3-fluoroazetidin-1-yl)-2-oxoethyl]-1H,2H-pyrrolo[1,2-a]pyrazin-1-one | 61 |
| 406 | 8-(5,6-dichloropyridin-3-yl)-2-{2-[3-fluoro-3-(fluoromethyl)azetidin-1-yl]-2-oxoethyl}-1H,2H-pyrrolo[1,2-a]pyrazin-1-one | 85 |
| 287 | 1-cyclopropyl-3-[4-fluoro-3-(trifluoromethyl)phenyl]-5-[2-(3-fluoro-3-methylazetidin-1-yl)-2-oxoethyl]-1H,4H,5H-pyrrolo[3,2-c]pyridin-4-one | 140 |
| 288 | 1-cyclopropyl-3-(3,4-dichlorophenyl)-5-[2-(3-fluoro-3-methylazetidin-1-yl)-2-oxoethyl]-1H,4H,5H-pyrrolo[3,2-c]pyridin-4-one | 130 |

TABLE 49-continued

| Ex. No. | IUPAC Name | Response Recovered (%) |
|---|---|---|
| 419 | 8-(3,4-dichlorophenyl)-2-[2-(3-fluoro-3-methylazetidin-1-yl)-2-oxoethyl]-4-methyl-1H,2H-pyrrolo[1,2-a]pyrazin-1-one | 110 |
| 424 | 5-(3-chloro-4-fluorophenyl)-3-[2-(3-fluoro-3-methylazetidin-1-yl)-2-oxoethyl]-3H,4H-imidazo[4,3-f][1,2,4]triazin-4-one | 0.55 |
| 407 | 2-{2-[3-fluoro-3-(fluoromethyl)azetidin-1-yl]-2-oxoethyl}-8-[4-fluoro-3-(trifluoromethyl)phenyl]-1H,2H-pyrrolo[1,2-a]pyrazin-1-one | 130 |
| 289 | 1-cyclopropyl-3-(5,6-dichloropyridin-3-yl)-5-[2-(3-fluoro-3-methylazetidin-1-yl)-2-oxoethyl]-1H,4H,5H-pyrrolo[3,2-c]pyridin-4-one | 120 |
| 290 | 1-cyclopropyl-5-[2-(3-fluoro-3-methylazetidin-1-yl)-2-oxoethyl]-3-(4-fluoro-3-methylphenyl)-1H,4H,5H-pyrrolo[3,2-c]pyridin-4-one | 120 |
| 291 | 3-(5-chloro-6-fluoropyridin-3-yl)-1-cyclopropyl-5-[2-(3-fluoro-3-methylazetidin-1-yl)-2-oxoethyl]-1H,4H,5H-pyrrolo[3,2-c]pyridin-4-one | 80 |
| 292 | 3-(4-chloro-3-methylphenyl)-1-cyclopropyl-5-[2-(3-fluoro-3-methylazetidin-1-yl)-2-oxoethyl]-1H,4H,5H-pyrrolo[3,2-c]pyridin-4-one | 140 |
| 439 | 1-(3-chloro-4-fluorophenyl)-3-cyclopropyl-7-{2-[3-fluoro-3-(fluoromethyl)azetidin-1-yl]-2-oxoethyl}-7H,8H-imidazo[1,5-a]pyrazin-8-one | 120 |
| 440 | 3-cyclopropyl-1-(3,4-dichlorophenyl)-7-{2-[3-fluoro-3-(fluoromethyl)azetidin-1-yl]-2-oxoethyl}-7H,8H-imidazo[1,5-a]pyrazin-8-one | 110 |
| 441 | 1-(5-chloro-6-fluoropyridin-3-yl)-3-cyclopropyl-7-[2-(3-fluoro-3-methylazetidin-1-yl)-2-oxoethyl]-7H,8H-imidazo[1,5-a]pyrazin-8-one | 46 |
| 442 | 3-cyclopropyl-7-[2-(3-fluoro-3-methylazetidin-1-yl)-2-oxoethyl]-1-(4-fluoro-3-methylphenyl)-7H,8H-imidazo[1,5-a]pyrazin-8-one | 65 |
| 443 | 1-(4-chloro-3-methylphenyl)-3-cyclopropyl-7-[2-(3-fluoro-3-methylazetidin-1-yl)-2-oxoethyl]-7H,8H-imidazo[1,5-a]pyrazin-8-one | 120 |
| 293 | 1-cyclopropyl-3-(3,4-dichlorophenyl)-5-{2-[3-fluoro-3-(fluoromethyl)azetidin-1-yl]-2-oxoethyl}-1H,4H,5H-pyrrolo[3,2-c]pyridin-4-one | 160 |
| 425 | 5-(3,4-dichlorophenyl)-3-[2-(3-fluoro-3-methylazetidin-1-yl)-2-oxoethyl]-3H,4H-imidazo[4,3-f][1,2,4]triazin-4-one | 27 |
| 282 | 3-(3-chloro-4-fluorophenyl)-5-[2-(3-fluoro-3-methylazetidin-1-yl)-2-oxoethyl]-1-(oxetan-3-yl)-1H,4H,5H-pyrrolo[3,2-c]pyridin-4-one | 120 |
| 254 | 3-(3-chloro-4-fluorophenyl)-5-[2-(3-fluoro-3-methylazetidin-1-yl)-2-oxoethyl]-1-(methoxymethyl)-1H,4H,5H-pyrrolo[3,2-c]pyridin-4-one | 140 |
| 84 | 3-(6-chloro-5-methylpyridin-3-yl)-5-[2-(3-fluoro-3-methylazetidin-1-yl)-2-oxoethyl]-4H,5H-thieno[3,2-c]pyridin-4-one | 39 |
| 85 | 3-(6-chloro-5-methylpyridin-3-yl)-5-[2-(3-ethyl-3-fluoroazetidin-1-yl)-2-oxoethyl]-4H,5H-thieno[3,2-c]pyridin-4-one | 16 |
| 86 | 3-(6-chloro-5-methylpyridin-3-yl)-5-{2-[3-fluoro-3-(fluoromethyl)azetidin-1-yl]-2-oxoethyl}-4H,5H-thieno[3,2-c]pyridin-4-one | 17 |
| 87 | 5-[2-(3-fluoro-3-methylazetidin-1-yl)-2-oxoethyl]-3-(6-fluoro-5-methylpyridin-3-yl)-4H,5H-thieno[3,2-c]pyridin-4-one | −4.2 |
| 88 | 5-[2-(3-ethyl-3-fluoroazetidin-1-yl)-2-oxoethyl]-3-(6-fluoro-5-methylpyridin-3-yl)-4H,5H-thieno[3,2-c]pyridin-4-one | 20 |
| 89 | 5-{2-[3-fluoro-3-(fluoromethyl)azetidin-1-yl]-2-oxoethyl}-3-(6-fluoro-5-methylpyridin-3-yl)-4H,5H-thieno[3,2-c]pyridin-4-one | 16 |
| 408 | 8-(6-chloro-5-methylpyridin-3-yl)-2-[2-(3-fluoro-3-methylazetidin-1-yl)-2-oxoethyl]-1H,2H-pyrrolo[1,2-a]pyrazin-1-one | 51 |
| 409 | 8-(6-chloro-5-methylpyridin-3-yl)-2-{2-[3-fluoro-3-(fluoromethyl)azetidin-1-yl]-2-oxoethyl}-1H,2H-pyrrolo[1,2-a]pyrazin-1-one | 33 |
| 410 | 8-(6-chloro-5-methylpyridin-3-yl)-2-[2-(3-ethyl-3-fluoroazetidin-1-yl)-2-oxoethyl]-1H,2H-pyrrolo[1,2-a]pyrazin-1-one | 34 |
| 294 | 1-cyclopropyl-3-(5,6-dichloropyridin-3-yl)-5-[2-(3-ethyl-3-fluoroazetidin-1-yl)-2-oxoethyl]-1H,4H,5H-pyrrolo[3,2-c]pyridin-4-one | 88 |
| 90 | 3-(5-chloro-6-methylpyridin-3-yl)-5-[2-(3-fluoro-3-methylazetidin-1-yl)-2-oxoethyl]-4H,5H-thieno[3,2-c]pyridin-4-one | 75 |
| 91 | 3-(5-chloro-6-methylpyridin-3-yl)-5-[2-(3-ethyl-3-fluoroazetidin-1-yl)-2-oxoethyl]-4H,5H-thieno[3,2-c]pyridin-4-one | 74 |
| 92 | 3-(5-chloro-6-methylpyridin-3-yl)-5-{2-[3-fluoro-3-(fluoromethyl)azetidin-1-yl]-2-oxoethyl}-4H,5H-thieno[3,2-c]pyridin-4-one | 70 |
| 136 | 3-chloro-5-{5-[2-(3-fluoro-3-methylazetidin-1-yl)-2-oxoethyl]-4-oxo-4H,5H-thieno[3,2-c]pyridin-3-yl}pyridine-2-carbonitrile | 17 |
| 137 | 3-chloro-5-{5-[2-(3-ethyl-3-fluoroazetidin-1-yl)-2-oxoethyl]-4-oxo-4H,5H-thieno[3,2-c]pyridin-3-yl}pyridine-2-carbonitrile | 22 |
| 138 | 3-chloro-5-(5-{2-[3-fluoro-3-(fluoromethyl)azetidin-1-yl]-2-oxoethyl}-4-oxo-4H,5H-thieno[3,2-c]pyridin-3-yl)pyridine-2-carbonitrile | 10 |

TABLE 49-continued

| Ex. No. | IUPAC Name | Response Recovered (%) |
|---|---|---|
| 420 | 8-(5,6-dichloropyridin-3-yl)-2-[2-(3-fluoro-3-methylazetidin-1-yl)-2-oxoethyl]-4-methyl-1H,2H-pyrrolo[1,2-a]pyrazin-1-one | 69 |
| 421 | 8-(5,6-dichloropyridin-3-yl)-2-{2-[3-fluoro-3-(fluoromethyl)azetidin-1-yl]-2-oxoethyl}-4-methyl-1H,2H-pyrrolo[1,2-a]pyrazin-1-one | 92 |
| 422 | 8-(5,6-dichloropyridin-3-yl)-2-[2-(3-ethyl-3-fluoroazetidin-1-yl)-2-oxoethyl]-4-methyl-1H,2H-pyrrolo[1,2-a]pyrazin-1-one | 29 |
| 139 | 3-(5,6-difluoropyridin-3-yl)-5-[2-(3-fluoro-3-methylazetidin-1-yl)-2-oxoethyl]-4H,5H-thieno[3,2-c]pyridin-4-one | 11 |
| 140 | 3-(2-chloropyrimidin-5-yl)-5-[2-(3-fluoro-3-methylazetidin-1-yl)-2-oxoethyl]-4H,5H-thieno[3,2-c]pyridin-4-one | 3.1 |
| 141 | 3-(2-chloropyrimidin-5-yl)-5-[2-(3-ethyl-3-fluoroazetidin-1-yl)-2-oxoethyl]-4H,5H-thieno[3,2-c]pyridin-4-one | −4.1 |
| 142 | 3-(2-chloropyrimidin-5-yl)-5-{2-[3-fluoro-3-(fluoromethyl)azetidin-1-yl]-2-oxoethyl}-4H,5H-thieno[3,2-c]pyridin-4-one | −4.2 |
| 143 | 3-(5,6-difluoropyridin-3-yl)-5-[2-(3-ethyl-3-fluoroazetidin-1-yl)-2-oxoethyl]-4H,5H-thieno[3,2-c]pyridin-4-one | 15 |
| 144 | 3-(5,6-difluoropyridin-3-yl)-5-{2-[3-fluoro-3-(fluoromethyl)azetidin-1-yl]-2-oxoethyl}-4H,5H-thieno[3,2-c]pyridin-4-one | 9.8 |
| 145 | 3-(6-chloropyrazin-2-yl)-5-[2-(3-fluoro-3-methylazetidin-1-yl)-2-oxoethyl]-4H,5H-thieno[3,2-c]pyridin-4-one | 3 |
| 146 | 3-(6-chloropyrazin-2-yl)-5-{2-[3-fluoro-3-(fluoromethyl)azetidin-1-yl]-2-oxoethyl}-4H,5H-thieno[3,2-c]pyridin-4-one | −3.8 |
| 147 | 3-(6-chloropyrazin-2-yl)-5-[2-(3-ethyl-3-fluoroazetidin-1-yl)-2-oxoethyl]-4H,5H-thieno[3,2-c]pyridin-4-one | −0.39 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound represented by Formula I

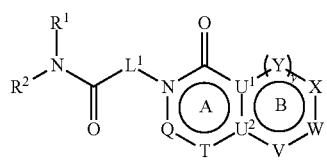

or a pharmaceutically acceptable salt or stereoisomer thereof, wherein:

rings A and B are a fused [5,6] or [6,6] heteroaromatic system;

Q is N or $CR^6$;

T is N or $CR^6$; and y is 0 or 1 wherein when y is 1, $U^1$ and $U^2$ are C; W and V are each independently selected from $CR^6$; one of Y and X is $CR^3$ and one of Y and X is $CR^6$; and when y is 0:

X is $CR^3$ or $NR^{33}$;

W is selected from the group consisting of $CR^6$, N or S;

V is selected from the group consisting of N, $NR^7$, $CR^6$, S and O;

$U^1$ and $U^2$ may each be C or N; wherein when one of $U^1$ and $U^2$ is N the other is C; and when Q is $CR^6$, T is N, W is $CR^6$ and X is $CR^3$; V is not S;

$L^1$ is a bond or $C_{1-4}$alkylene optionally interrupted by O, and optionally substituted on a carbon not bound to the ring nitrogen with one, two, or three substituents each independently selected from the group consisting of halogen, OH, cyano and $—NR^aR^b$;

$R^1$ and $R^2$, together with the nitrogen to which they are attached, form a 4-6 membered monocyclic heterocyclic ring optionally substituted on a carbon by one, two or more substituents each selected from the group consisting of halogen, cyano, oxo, hydroxyl and $C_{1-6}$alkyl, wherein said $C_{1-6}$alkyl is optionally substituted by one, two or three halogens;

$R^3$ is selected from the group consisting of phenyl and monocyclic heteroaryl, wherein said phenyl and monocyclic heteroaryl for $R^3$ are optionally substituted with one, two or three substituents each independently selected from the group consisting of $C_{1-4}$alkyl, halogen, hydroxyl, $C_{1-4}$alkoxy, $C_{2-6}$alkenyl, $C_{2-6}$alkynyl, $C_{3-6}$cycloalkyl, $C_{1-6}$alkyl-$S(O)_2—$, $C_{1-6}$alkylcarbonyl, $R^aR^bN—SO_2—$, $NR^aR^b$, C(O)

OH, C₁₋₄alkoxycarbonyl, and NRᵃRᵇcarbonyl, and wherein C₁₋₆alkyl, C₂₋₆alkenyl, C₂₋₆alkynyl, C₃₋₆cycloalkyl, C₁₋₆alkyl-S(O)₂—, and C₁₋₆alkylcarbonyl may be optionally substituted by one or more substituents each independently selected from the group consisting of halogen, hydroxyl, cyano, and NRᵃRᵇ;

R³³ is selected from the group consisting of phenyl, naphthyl, heteroaryl, heterocyclyl and C₃₋₆cycloalkyl, wherein R³³ is optionally substituted with one, two or three substituents each independently selected from the group consisting of C₁₋₄alkyl, halogen, hydroxyl, C₁₋₄alkoxy, C₂₋₆alkenyl, C₂₋₆alkynyl, C₃₋₆cycloalkyl, C₁₋₆alkyl-S(O)₂—, C₁₋₆alkylcarbonyl, RᵃRᵇN—SO₂—, NRᵃRᵇ, C(O) OH, C₁₋₄alkoxycarbonyl, and NRᵃRᵇcarbonyl; wherein C₁₋₆alkyl, C₂₋₆alkenyl, C₂₋₆alkynyl, C₃₋₆cycloalkyl, C₁₋₆alkyl-S(O)₂— and C₁₋₆alkylcarbonyl may be optionally substituted by one or more substituents each selected from the group consisting of halogen, hydroxyl, cyano, and NRᵃRᵇ;

R⁶ is independently selected for each occurrence from the group consisting of hydrogen, halogen, cyano, C₁₋₄ alkyl, C(O)OH, C(O)H, —C(=NH)—NRᵃRᶜ, phenyl, pyridinyl and pyrimidinyl, wherein said C₁₋₄ alkyl for R⁶ is optionally substituted by one or two substituents each selected from the group consisting of —NRᵃRᵇ, C₁₋₄alkoxy, halogen, cyano, hydroxyl, C(O)H, and =NRᵃ, and wherein said phenyl for R⁶ is optionally substituted by one or two substituents each selected from the group consisting of NRᵃRᵇ, C₁₋₄alkoxy, halogen, cyano, hydroxyl, C(O)H, and =NRᵃ);

R⁷ is selected from the group consisting of hydrogen, C₁₋₆alkyl, C₂₋₆alkynyl, C₃₋₆cycloalkyl, heterocyclyl, heteroaryl, and phenyl; wherein C₁₋₆alkyl, C₂₋₆alkenyl and C₃₋₆cycloalkyl may optionally be substituted by one or more substituents each selected from the group consisting of halogen, hydroxyl, C₁₋₄alkoxy (optionally substituted by halogen or —Si(Rₛ)₀₋₃(wherein Rₛ is H or C₁₋₆alkyl)), cyano, —Si(Rₛ)₀₋₃(wherein Rₛ is H or C₁₋₆alkyl), —O—Si (Rₛ)₀₋₃(wherein Rₛ is H or C₁₋₆alkyl), and NRᵃRᵇ;

Rᶜ is selected from the group consisting of hydrogen, C₁₋₃alkyl, and hydroxyl; and Rᵃ and Rᵇ are independently selected, for each occurrence, from the group consisting of hydrogen, C₁₋₄ alkylcarbonyl, —C(O)—O—C₁₋₄alkyl, C₃₋₆cycloalkyl and C₁₋₃alkyl; wherein C₁₋₃alkyl and C₃₋₆cycloalkyl may optionally be substituted on a carbon not bound to the nitrogen by one or more substituents each selected from the group consisting of fluorine, cyano, oxo and hydroxyl; or Rᵃ and Rᵇ, together with the nitrogen to which they are attached, form a 4-6 membered heterocyclic ring which may have an additional heteroatom selected from O, S, or N; and wherein the 4-6 membered heterocyclic ring may optionally be substituted on a carbon not bound to the nitrogen by one or more substituents selected from the group consisting of fluorine, methyl, cyano, oxo and hydroxyl.

2. The compound of claim 1, wherein the fused [5,6] or [6,6] heteroaromatic system is selected from the group consisting of:

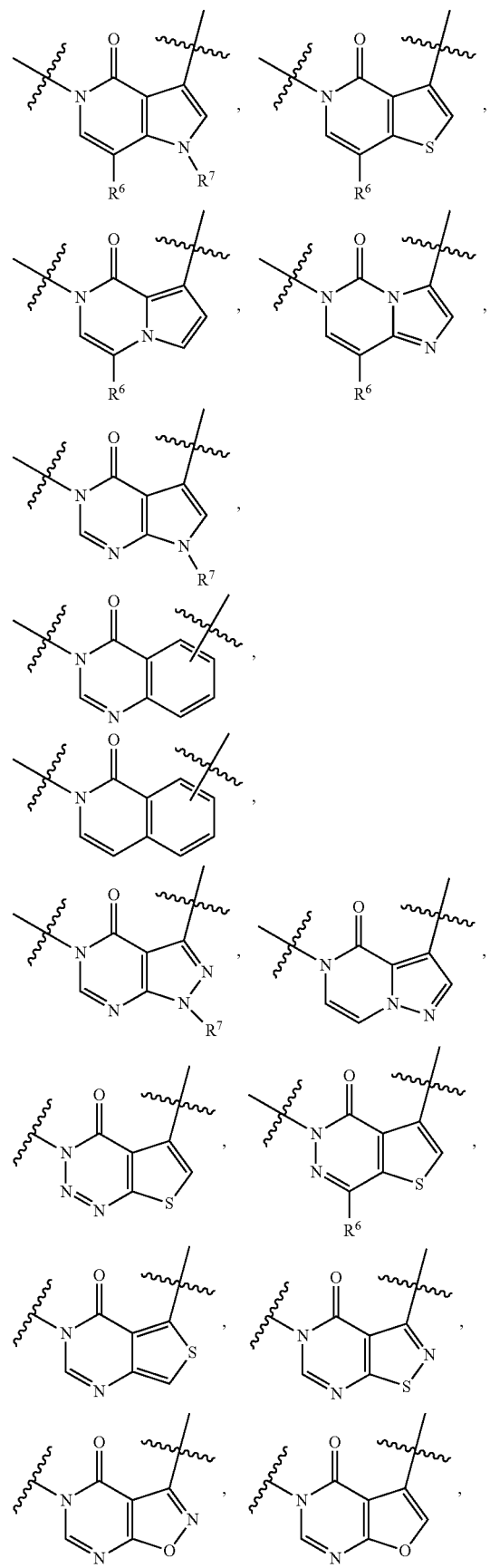

-continued

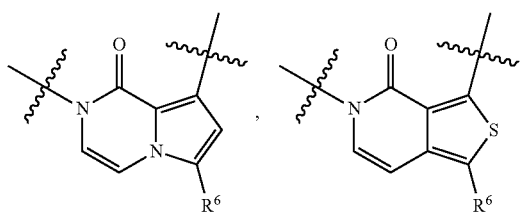

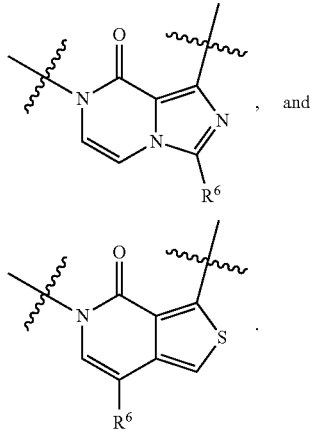

3. The compound of claim 1, wherein the rings A and B are a fused [5,6] heteroaromatic system.

4. The compound of claim 1, wherein the rings A and B are a fused [5,6] heteroaromatic system selected from the group consisting of:

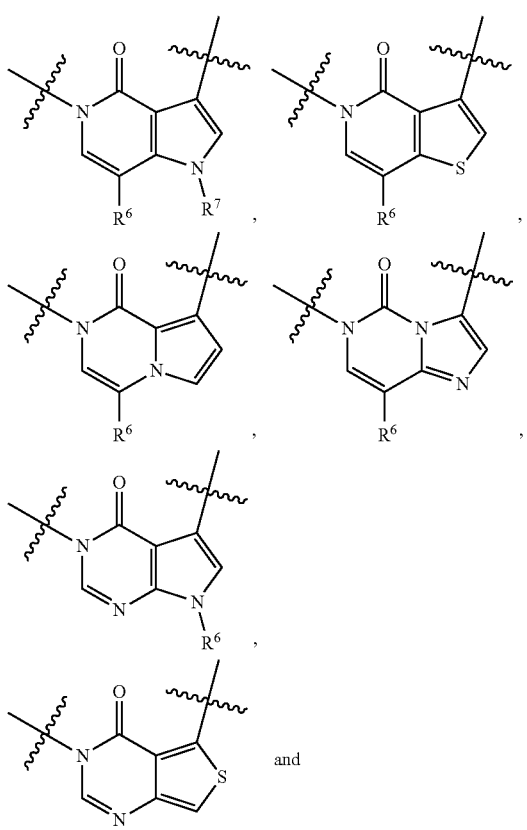

-continued

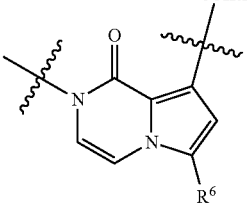

5. The compound of claim 1, wherein the rings A and B represent the following fused [5,6] heteroaromatic system:

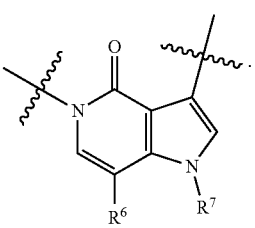

6. The compound of claim 1, wherein $L^1$ is —$CH_2$—.

7. The compound of claim 1, wherein $R^3$ is phenyl, thiophenyl, pyrimidinyl, pyrazinyl or pyridinyl, each optionally substituted by one or two substituents each independently selected from the group consisting of halogen and $C_{1-3}$alkyl, wherein said $C_{1-3}$alkyl is optionally substituted by one, two or three halogens.

8. The compound of claim 1, wherein $R^3$ is phenyl, optionally substituted by one or two substituents each independently selected from the group consisting of Cl, F, Br, and $CF_3$.

9. The compound of claim 1, wherein the compound is represented by:

Formula II

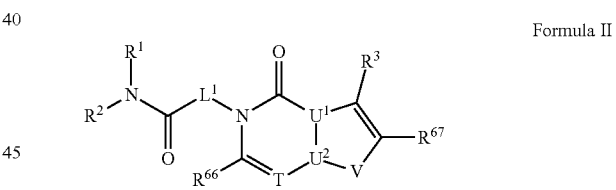

wherein
$U^1$ and $U^2$ may each be C or N; wherein when one of $U^1$ and $U^2$ is N the other is C;
T is N or $CR^6$;
$R^{66}$ and $R^{67}$ are each independently selected from the group consisting of halogen and $C_{1-4}$ alkyl, wherein said $C_{1-4}$ alkyl is optionally substituted by one, two, three substituents selected from halogen, hydroxyl, cyano and $NR^aR^b$; and
V is selected from the group consisting of N, $NR^7$, $CR^{66}$ and S.

10. The compound of claim 9, wherein $U^1$ is N and $U^2$ is C.

11. The compound of claim 1, wherein V is $NR^7$.

12. The compound of claim 1, wherein $U^1$ is C and $U^2$ is N.

13. The compound of claim 1, wherein V is N.

14. The compound of claim 9, wherein the compound is represented by:

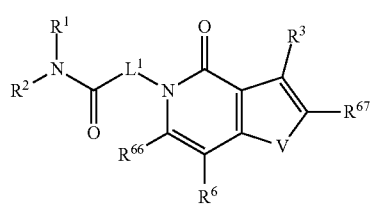

Formula III wherein V is $NR^7$ or S.

15. The compound of claim 14, wherein $R^7$ is selected from the group consisting of hydrogen, $C_{1-6}$alkyl, pyridyl, and phenyl; wherein $C_{1-6}$alkyl is optionally substituted by one or more substituents each selected from the group consisting of halogen, hydroxyl, and $C_{1-4}$ alkoxy.

16. A pharmaceutically acceptable composition comprising a compound of claim 1, or a pharmaceutically acceptable salt or stereoisomer thereof and a pharmaceutically acceptable excipient.

* * * * *